(12) United States Patent
Edens et al.

(10) Patent No.: US 7,323,327 B2
(45) Date of Patent: Jan. 29, 2008

(54) GENES ENCODING NOVEL PROTEOLYTIC ENZYMES

(75) Inventors: Luppo Edens, JI Rotterdam (NL); Albertus Van Dijk, Pb Vlaardingen (NL); Philipp Krubasik, Martinsried (DE); Kaj Albermann, Martinsried (DE); Alexander Stock, Martinsried (DE); Erik Kimpel, Munich (DE); Sabine Klugbauer, Munich (DE); Christian Wagner, Martinsried (DE); Andreas Fritz, Martinsried (DE); Wilk Von Gustedt, Planegg (DE); Oliver Heinrich, Martinsried (DE); Dieter Maier, Martinsried (DE); Fabio Spreafico, Martinsried (DE); Ulrike Folkers, Munich (DE); Sylvia Hopper, Munich (DE); Wolfram Kemmner, Munich (DE); Pamela Tan, Martinsried (DE); Josephine Stiebler, Munich (DE); Richard Albang, Martinsried (DE)

(73) Assignee: DSM IP Assets B.V., TE Heerlen (NL)

( * ) Notice: Subject to any disclaimer, the term of this patent is extended or adjusted under 35 U.S.C. 154(b) by 38 days.

(21) Appl. No.: 10/469,204

(22) PCT Filed: Feb. 22, 2002
(Under 37 CFR 1.47)

(86) PCT No.: PCT/EP02/01984

§ 371 (c)(1),
(2), (4) Date: Oct. 21, 2004

(87) PCT Pub. No.: WO02/068623

PCT Pub. Date: Sep. 6, 2002

(65) Prior Publication Data

US 2005/0064403 A1    Mar. 24, 2005

(51) Int. Cl.
*C12N 9/62* (2006.01)
*C12N 15/00* (2006.01)
*C12N 1/00* (2006.01)
*C07H 21/04* (2006.01)

(52) U.S. Cl. .............. 435/225; 435/320.1; 435/254.3; 435/212; 435/252.3; 536/23.2

(58) Field of Classification Search ............... 435/225, 435/212, 320.1, 252.3, 254.3; 536/23.2
See application file for complete search history.

(56) References Cited

U.S. PATENT DOCUMENTS

| | | | |
|---|---|---|---|
| 5,674,728 A | | 10/1997 | Buxton et al. |
| 5,821,104 A | * | 10/1998 | Holm et al. ............... 435/225 |
| 2004/0115306 A1 | | 6/2004 | Lopez et al. |
| 2004/0241664 A1 | | 12/2004 | Dekker et al. |
| 2004/0241791 A1 | | 12/2004 | Edens et al. |
| 2005/0064403 A1 | | 3/2005 | Edens et al. |

FOREIGN PATENT DOCUMENTS

| | | |
|---|---|---|
| WO | 02/45523 A2 | 6/2002 |
| WO | 02/45524 A2 | 6/2002 |
| WO | 02/46381 A2 | 6/2002 |
| WO | 02/68623 A2 | 9/2002 |
| WO | 02/45524 A3 | 10/2002 |
| WO | 02/46381 A3 | 11/2002 |
| WO | 02/68623 A3 | 12/2002 |
| WO | 02/45523 A3 | 1/2003 |

OTHER PUBLICATIONS

International Preliminary Examination Report for PCT/EP02/01984, completed on Jul. 18, 2003, 9 pages.
International Search Report for PCT/EP02/01984, mailed on Sep. 18, 2002, 3 pages.
Jarai et al., Current Genetics (1994) 26:238-244.
U36471, EMBL, EBI, "Neurospora crassa vacuolar protease A (pep-4) gene, complete cds" (Oct. 25, 1995).
Van Den Hombergh et al., Gene (1994) 151:73-79.

* cited by examiner

*Primary Examiner*—Rebecca Prouty
*Assistant Examiner*—M. A. Walicka
(74) *Attorney, Agent, or Firm*—Nixon & Vanderhye P.C.

(57) ABSTRACT

The invention relates to newly identified gene sequences that encode novel proteases obtainable from *Aspergillus niger*. The invention features the full length gene sequence of the novel genes, their cDNA sequences as well as the full-length functional protein and fragments thereof. The invention also relates to methods of using these enzymes in industrial processes and methods of diagnosing fungal infections. Also included in the invention are cells transformed with DNA according to the invention and cells wherein a protease according to the invention is genetically modified to enhance or reduce its activity and/or level of expression.

25 Claims, No Drawings

SEQUENCE LISTING

<160> NUMBER OF SEQ ID NOS: 171

<210> SEQ ID NO 1
<211> LENGTH: 2520
<212> TYPE: DNA
<213> ORGANISM: Aspergillus niger

<400> SEQUENCE: 1

```
cgcaggcgtc cgttgcgccg cgaaaacctg ccgagtgggc cgtttaggct ttgggtctcc      60
ccacgatgta agcataatca ttctgtgcct gagtgtgaat tctcctgttg gaggctgcat     120
cttaattctt aactgcatga aaagcacttg ggtgctattt tcttttccct ttctttcttt     180
tccgtgttca tttccattcc cttgctcttc ttctttgtgt cgacatttac aaatcacatt     240
tttcttatac tttcttttct tcacctcgtt tcttcctatt cactctctgt gttcagcatt     300
cgttatcagc actttatctt ttgctcgtct cttttatctt cacttgtttg tgcctttcca     360
ctagcaatct atcgtttgat cttctagag cattgtcttg attgtgtcat tctgtcattg     420
actccggcta tgaaatatta ttctcaatct gcctaaaacc aaattctact ctatcactac     480
acatttgtat cacctgatct ggctgagata ggagagtccg gcatctcatc gtctgcatca     540
gacaattgcg ataaattcat tgcttgcacc tgttattgat tcttccaagt tatgcatctc     600
ccacagcgtc tcgttacagc agcgtgtctt tgcgccagtc ccacggcttt catcccatac     660
accatcaaac tcgatacgtc ggacgacatc tcagcccgtg attcattagc tcgtcgtttc     720
ctgccagtac caaaaccaag cgatgctcta gcagacgatt ccacctcatc tgccagcgat     780
gagtccctgt cactgaacat caaaaggatt cccgttcgtc gtgacaatga tttcaagatt     840
gtggtagcgg aaactccctc ttggtctaac accgccgctc tcgatcaaga tggtagcgac     900
atttcataca tctctgtcgt caacattggg tctgatgaga aatctatgta catgttgctc     960
gacacaggcg gctctgatac ctgggttttc ggttccaact gcacgtccac accctgcacg    1020
atgcacaata ccttcggttc ggacgattct tcgacccttg aaatgacatc ggaagagtgg    1080
agtgtgggct atggaactgg gtctgtcagc ggcttgctag gaaaagacaa gctcacgatt    1140
```

-continued

```
gcaaatgtca ctgtacgcat gactttcgga cttgcttcca acgcatcgga taacttcgag    1200
tcgtacccaa tggacggcat tctcggtctc ggtcgaacca acgatagttc ctacgacaac    1260
ccaacattca tggatgccgt tgcagaaagt aacgttttca agtcgaatat cgttggcttc    1320
gcccttttca gtagccccgc caaggatggc acggtcagct ttggcactac tgacaaggac    1380
aagtacaccg gcgatatcac ctacaccgat accgtcggat cggacagcta ttggcgcatt    1440
cccgtggacg atgtctatgt tggcggcact tcatgcgatt tctccaacaa atcagccatc    1500
atcgataccg gaacttctta tgctatgctg ccttcaagcg actcgaagac gctgcacagt    1560
ctcattcccg gcgccaaatc ttcggggagc taccacatta ttccgtgcaa cacaactact    1620
aagctacaag tggcattctc tggtgtgaat tacaccatct cgccgaagga ctacgtggga    1680
gcaacttcag gttctggatg cgtttcgaac attatcagct acgacttatt tggtgatgac    1740
atctggctcc tgggtgacac gtttctcaaa aatgtgtatg ctgtgtttga ctacgatgag    1800
ttacgggtcg gatttgcaga gcgttcctcg aacaccacct ctgcgtcgaa ctctacgagc    1860
tctggaacaa gcagcacctc gggatccact acaacgggca gctcaacgac tacgacgagc    1920
tctgctagct ctagtagttc atctgatgct gaatcaggaa gtagcatgac cattcccgct    1980
cctcagtatt tcttctctgc tctggcgatt gcttccttca tgctttggct ctagttaacc    2040
gcatcttact cgacgcctga acctcgggaa acatatgcat tatttacaca tgctgctgat    2100
ttgtatttgc atatattctt cgagcctgga cggcgtgcgg gtcatattac cttacattcg    2160
aagtccttct ctaatcaatc aacatttatt cttactccac cagttctggc tcgcaattaa    2220
ccctgtctaa gaaaaagttg gtatagaaca tggcatccac tacctggaac attcaaagaa    2280
ccttgtccgg gatcagtgtg tatgacttcg ggtacgattc tgacatgaca gttagcgtcc    2340
atcctgagga ttcatcctga tctccttacc tagtatggac ttatcaaagt ccttgacgct    2400 attgtacccct cccacagcca tcaggatatc gaaatcggcc aacagcgact tcatcacatg    2460
gcgaacaccc tcctcaccca tgatactgag gccccagatc cagagccggc cgacgaaaac    2520
```

<210> SEQ ID NO 2
<211> LENGTH: 5001
<212> TYPE: DNA
<213> ORGANISM: Aspergillus niger

<400> SEQUENCE: 2

```
taggaaaatc agaggcgaca atttgctccg atactggata agtaccatcg gtcacgaaat     60
tcagcaccga ctggcttatg tcctgctccg ataccttagc ggacattatg ttagtagttc    120
taagcaagag cccttggttc ttggtaatcg gcggatcaaa aacgtaaaga agacaaacag    180
aagcgccaca ctaggctctg cctccctctt acagaagatc tgccaggtat cgatccacaa    240
agatatacca aggactccaa tgcagcagat cgcaaccgaa agggaaggcg agctgtcaac    300
accgccatgt gacttcaccg ctcaccgcct tagctgcgat gggcaagacc acgaacgatc    360
tcgctcttcc ccagggccag actgaggccg attatatgat tttttctttt cttttccgtg    420
tgtctcgtct gctgctatat tcttattttt ctgttcggta aagatacctc ctaagaatag    480 acacggggttg ttttttttgtg aattatctgt tggtgtggtg ctctctatcg aaccggaaac    540
ctgaactcca ctctgaaccg ttacagttgg agggtaacct tcgttcagcg gccaactgtg    600
tgacctcaaa attcctgaaa catcataatc ggcgtcaagc agagcccatc gtgttgtctc    660
agttactatt gagaagcctg attcgggcaa acgcttctcg atccatgtga gtcatgcttg    720
taccagccct gaactccatt gaataaaaaa aaagcaagaa aagagattgc ccctccgtcg    780
```

```
ttttctgtat taaacatcca atcctcaacc ggcagcctta cattggctgc cacagatttg    840
tgcctccata cagcatgctt cgtggtcttc gtgatgtcgt attattacaa tttgcaatcc    900
ccttgttctt gctattggta tttcaaacat ggaatgggtg cttttcccgt ttcaattccc    960
cgcaccctga acctcaagca ttgctagctt ctctaaaatg aataaaactg ttatacttgc   1020
ttcctaaaag tttgcgcttc tggcctatgg attactaaca gcattttaga ttatcgctac   1080
ggggtgtgat cacaggattt ggttctaaat cacatttcca gagaccattg agcaaaatgt   1140
catctactca aaagagccat ttcaagctac tccagaagtt caaaccggag tactcgccta   1200
gcgagtttgc tcagtatgag tcggagagaa caggcatgag ggtagtggtc attgaccaaa   1260
aaggacccaa agtcacaggt tattttgttc tagccacaga gattctcgat gattcaggtg   1320
ctcctcacac gttggagcac ttgtgcttta tgggctcgcg gaactataga tataagggct   1380
tccttgacaa gctagcaaca cgtgtttatt cgagcaccaa tgcctggacg gccacagacc   1440
acacggccta caccttggac acagcaggct gggaagggtt cgctcaaatc ttgcccgtgt   1500
acctagagca tgttatagct ccaacactga cagatgaagg gtgctatacc gaagtgcatc   1560
atattgatgg cgctggagac gacgctggag tcgtctactc ggagatgcag ggtgtgcaga   1620
ataactctgc agagttaatc gatctaaccg ctcgtcgatt gacttacccg catggtgtag   1680
gttttcgcta cgagacaggc ggtatgatgg agcagctccg cgtcctcacc gcggaccgta   1740
tccgagcgtt ccatcgtgag atgtaccagc ccaagaactt atgcctaatc atcacaggcg   1800
aagtagatca ccagaacatg ctggagacct ggacaagtt cgaagatact attctagatg   1860
tcattcccag tcctgattca ccttttcaaga ggccgtgggt agattccaag caggcgccgc   1920
cattggagaa gtccattgtc cagactgtgg aatttccgga agaagatgaa tctttcgggg   1980
agatagaaat tagattcctc ggtccggact gtaccgaccc tgttcaaagt gagtgttccg   2040
ctgtcctcat ttcgaagata tacttactct gttatagccg gggctgtcaa tgttgcattg   2100
ctgtatctgg ccggttcatc tgcttctcta ttggataaca tcctggttga aaggagcag    2160 ctcgccagtg ctgtctatta tgctaccgaa gatcatccca gcattgagat ccgcttcaca   2220
ttaaccagtg tggagacaga gaaactcgcg aaggtagagc aacggttttt cgaagtgctc   2280
aaggacgcta tggagaaaga tttagacatg aggtatatca aggagtgcat tgaccggcaa   2340
agacggacct ggaagttctc taccgaaagc tccgcctctt cctttgcgga gtacgtgatc   2400
tcggattttc ttttcggaaa gagagacgga tcgactatgc ttgatgttgc gaccttgcaa   2460
gagtacgacg tgctggagaa gtggagtgaa gaacagtggc gcagttttat caaaacatgg   2520
atttctgatg ccaaccatgt cactatcctt ggtgttccgt ccgttaagat gtctgacaca   2580
ttaaagaagg aggaggaagc tagagtcgca gagcaaaaga agcgcttggg tgatgagggg   2640
ctgaagaagt tggccgacaa gctggaaaaa gctaaagctg aaaatgacaa ggagatcccc   2700
aaggagatgc tggagaggtt ccaaatccct ggaatagagt ctatccattt cgtggacact   2760
actacagcca ggtctggtgc agccctcgat gccgggcgcc atcccacaa ggcgcaaaaa   2820 ctggtggatg ctgatggctc tgatctgccc ttgttcatcc atttcgagca tatccccagt   2880
agcttcgtgc agctctccct cctcatctcg gcacaggccg tacctgtgca gcttcgtcca   2940
ctgctgtctg tgtatactga ggcattcttc aacctgcctg tcaaccggaa cggggaaacc   3000
atcaactttg agcaggtggt tgtcgagttg gaaagggata ctgttggcta ctccatggaa   3060
ggagctagaa gcctaggaaa ctcggagatg ttgcggatct cattccaggt ggagcttgag   3120
```

```
aagtatcaca cggcgatcgc atggatccag gaactttcct ggaactcgat tttcgatgtc   3180
gagcgactcc gagcgattac cagtcgactg ctctccgatg tgcccgattc caagcgtagt   3240
ggcgacgaca tgctcgcggc tgttcatgtg atggtccact atgcagcaga gtctattgtt   3300
cgggctcgga gcaccttggt gaaggcgcgt tatttgaaac ggatcaagaa gcaattagca   3360
gaagagccga agtctgtcgt tgcgcggatg aagaaatca gagatgcgct tttccgtttc    3420
gagaacatgc gagtcttagt tatcgctgac ctggagaaac ttcaaaaccc tgtgtcagca   3480
tggaaaccat tgctgagcg tttgggtgca ggtgcccctc tacagcctat cacgactaga    3540
agaccgttgc tcagtgaggc aggccagaag ttgggcggta agtcgtatgt ggttcctatg   3600
ccgacgattg attcatcgtt cgcatatgct accgcacgtg gtttggattc ttatgatgat   3660
ccaagacttc ctgccttaat ggttgcaatt gcatacatga acgcggttga gggtcccctc   3720
tgggttgcag ttcgaggcaa gggtttggca tatggcacga actttgccta acattgat    3780 accggattcg tcaacttcga cgtttaccgc tcccccaacg cccataaagc cttcgactcc   3840
agcaagcaga ttgttgagga tcacctctct ggtgcgatgc ccttcgatcc cttgatgctg   3900
gagggttcca ttagcagcat tgtggtaagc tttgcgaatg aacagtcgac aattggtagc   3960
gcagcctcag gcagtttcat ccgacaggtg attcggcgcc tgcctagcga ctacaaggag   4020
cgggtgctca gcaggtgcg ggctactagc gttgatgacg tgaaaggcgc tctgaaggac    4080
atcattctgc ctttgtttaa cccgtccacg gccaatatcg tggttacctg cgctacagtg   4140
cttgaggagg tttgtcattc catgaagaaa ttatgatctt cttgtgtatc atttactaac   4200
tgtcggttta gactatcaag gaaggtctcc aggcatcggg attcacgcct gcggtgcagc   4260
cactcaaaga attcgaagat gactatgggc tgaaggtcgg cgatgacgag gacgaggagt   4320
ccgacgatga cgacgatgag tatgaaaccg gatctgaaga tgaagatgac agtgatgaag   4380
acatggagga tgacgaagat gatgagtgat gcaatctata cgacaacctc tagacatgac   4440
aagatttatc tgagccagtt cctggataac acctaggtcg aaagaccagc taccctggg    4500 ggcccagata tgccgacccg tgtgatctgt attgttagag atgtctccaa ctagcagacg   4560
cgcaatgatt tttgatgtta atgatatatc gtacaacata agtggttaac caccacaaat   4620
ctgcacctaa atcttagttg tgattatcgg tacctaccaa acccgagtaa acgttgccag   4680
aagtttatga aaaagctctc gttcttctta tttcattgaa tgttgtaata aaaagtgcta   4740
gcagatgctt tcgctatcgg gcccactact atgattaacc tgaagcttag tctcttaggt   4800
gacataacct gttctacaca ggctgccatt atatttgcaa cacacagctt ctatctctga   4860
cctttgtgag aataatacaa ttactagaaa ccccaggaga tataaataca ctctactcct   4920
accgaactaa cacccagatc gacaaattat aaaccaaacc acgtgacaat atgatatcta   4980
tatatgaata tgtataaggt a                                             5001
```

<210> SEQ ID NO 3
<211> LENGTH: 3850
<212> TYPE: DNA
<213> ORGANISM: Aspergillus niger

<400> SEQUENCE: 3

```
gcgcggggtt cctgcatgtc tttcatggtt gggaggtata tgtacatgta atgccgttgg     60
gttctggata cccacaataa agtgtttcta ctattacttt tgcattgtta gactttgaag    120
gctgctctgt aagggtccat tccgttggag tcaaacaacc gtctgtccgc gggcatatgt    180
ctcagtctga ggtgagaact gcaatataca ctccaagctt tctcaatctg atgcacagat    240
```

```
tgcaaacatc tcccttgctg tgtggtaaag tctcccttc tcggtgaacc ttcttcgggg      300
tcgcaactga ttccattgac cctcaccatc tgtcgaattg ttcccgaaag ctcgcgtcca      360
aataggcttt acggacgcca cagctgctcg aggccatctc caaggggaa tgaacaatgg       420
aatggtaagc cgctaagaaa ggggaactgt cggttctggt cgattggcag ggtcagggca      480
gtgcttgggc tgttcctctg gccctcctt gcttcaagct ggccccgatt tggcagctcg       540
tgaagctcac cagacattca gccagccaga tgactggcac ctttccgctg gcataaatt       600
ggccctggca gccatgtcat gccaatcttg gctccaggac cagtcattcc ttttcttgtt      660
cctgtcaaac agatcaagtc ctcgaggatg ggagctcttc agtggctgtc catcacggct      720
gctgcggcct ccgcagtgtc agccttgacc ccggagtaag tatctccaat catttggaac      780
tggcccatat tgtgcatagc taaccagctt acctgcatag gcagatgatc ggtgccccac      840
ggagaaccga agttatacca aaccctccg gtgtatgccc attgccaggt ccagccttac       900
aaagaagcgt cgtctgctga cacgagaagg acaccggtct attctcgacc tcccaatggt     960
cgtttgacac tcattctgag agcacctggt ggagcttgat cgacctccaa tcggcaaga     1020
ccaccactct caccgatgat agcgatatcg aggagatcat ctggcttggc tctgacaatt    1080
ctacgctcct ctacatcaac agcaccaacg cgcaggttcc cggtggcgtg agctgtgga    1140
ttgcggactc ttctgactt gcaaatgcgt tggttcaggc ctttaacgat gcctctgcag     1200
actagtgcta atcctacttg gtgcagttac aaggcagcct ctctctccgc cggttttctc    1260
ggcatcaaat caaccgtgac agattccggc gacgtgcatt tcatccttcg tggaaagtcc    1320
tatcccaacg gaacggcata caatgatcag ctcgccgaga cctatcccag tacagcccgc    1380
atctacgaca gcatctttgt gcggcactgg gacacttacc tgaccaccgc ctcccacgct    1440
gtattctccg gtaccctgca aagctcgacc agcgacgacg gcaatgttca atatacctct   1500
tcagggggat tgaccaacct ggttaaccca gtcaagggtg ccgaaagccc attccctcct    1560
tttggaggca acgacgacta tgacctctcg cctgacggca aatgggttac cttcaagagc    1620
aaagcgccag agctgcctct tgctaacaac acggctgcct atgtctatct cgtcccacac    1680
gacggctctg cgactgcctt tgccgtcaac ggccctgata gtcctgcaac cccggaggga    1740
gttgaaggag aatccaacaa tcccgtgttc tcccctgata gcgacaaaat agcgtacttc    1800
caaatggcta ctaatacata cgagtcggac cgcaacgtgc tatacgtata ctccatcgcc    1860
gatgacacca tcactcccct tgcaaaggac tgggaccgat cgcctagctc cgtgacatgg    1920
gtcgatggag acaacctcgt cgtggcaagc caagatctag gacgaaccag acttttcgcc    1980
atcccaggcg atgcagggga cgacttcaag cccacgaact tcaccgacgg cggctccgtg    2040
tcggctcaat acgtcctatc caactctacc ctcctcgtca cgtccagcgc cttctggaca    2100
agctggagcg tctacaccgc cagccctgac gagggcgtga tcaacacact ggcctcagcc    2160
aacgagatcg accccgagct tagcggcctt agttcctccg actttgaaga gttctacttt    2220
gacggcaact ggactaccgt aagtctatcc ctccttgccc ccaccaccac atcacaaaca    2280
tactaaactc accgcagctc caaggatgga tcacctaccc ccaagacttc gactcatcca    2340
agaaataccc cctcgccttc ctcatccacg gcggccccga agacgcctgg gcggatgaat    2400
ggaacctgaa atggcactcc aaggtcttcg ccgaccaggg atacgtcgtc gtccagccaa    2460
accccacagg aagcaccggg ttcggccagc agctcacaga cgctatccaa cttaactgga    2520
gtacgccatt ccctatcccc aaactcccct cttaaacata cagctaacaa atgaaataac    2580
```

```
agccggcgcc gcctacgacg acctaaccaa agcctggcaa tacgtgcacg ataccacga    2640 cttcatcgac acggacaacg gcgtcgccgc gggtcccagc ttcggcgcgt tcatgatcac    2700
ctggatccag ggcgatgact ttggacgcaa gttcaaggcg ctggttagcc atgatggtcc    2760
gttcattggc gatgcgtggg tcgagacgga tgagttatgg tttgttgagc atgaggtgag    2820
tggaccaagc caaacccccc ttttctcccc ttacaccatt accctatac aaatatgatg    2880 attctgaccg tgtatagttc aacggcacct tctggcaagc gcgcgacgca ttccacaaca    2940
cggatccatc cggccccagc cgcgtcctcg catacagcac ccccagctc gtcatccaca    3000 gtgacaagga ttatcgcata cctgtggcaa atgggattgg actgtttaat acgctgcagg    3060 agagggcgt gcccagtcgg ttttgaatt cccggatga ggatcattgg tatgttcata    3120
cccttttctt ccccttttt tctcccatga ttatgggtgt tgtggatgct gatgtagcta    3180
tgtgtgtgtt tagggtcacc gggcaagaaa acagcctcgt ctggtatcag caggtgctgg    3240
gatggattaa tcgtattct ggggtgggag ggtcgaatcc tgatgcgatt gctttggagg    3300
atacggtgaa tccggtggtg gatttgaatc cttgatcatt ccctgttgct cgttactact    3360
agtcagttat gatcatgttc tggctgggtc ccaggataga tggacggtta ttactggtcg    3420
ttatatcctg tttgcagtgg ttactagttg gtagatcagt tacgagatga tgtatgagac    3480
gacagaaaga cttatgctta tgttgggagc tgcttcattt gtatatcaat ttattcttgt    3540
agtgattgat aactaactac tgtctgactg tctgtcaacc gctatactaa cattataca    3600 accaaccaac caatcaaatc aatttctggt tctttcttct cttctgtttc ttcacctcgc    3660
aactagacca attcatcaag gacagggcag gacaggatct ggtatctgaa cggaacaacc    3720
gaaggaaaaa caaatcatac acaagctttt gtacaatcaa accataagaa tcagtacagc    3780
tttctctttc agcctttcca aatgagagga aggacagaga aaatacaaag atgataccct    3840
agaaacgaaa                                                            3850

<210> SEQ ID NO 4
<211> LENGTH: 3139
<212> TYPE: DNA
<213> ORGANISM: Aspergillus niger

<400> SEQUENCE: 4
attgagtagg ctgcgctctt tgattctttg cgaggtacta aacccaaaca ggcaattgag     60
atgttcggga gagaatatgc ggggatgcta tgcctgttgc agggatgatt atctccacac    120
tagcgcgtta aaggtttagt agcctgagat ggattgccga tctccgaccg ggccctgcct    180
cagccccagt acttgtggaa cgcgtcgaag atttacaaca ccatgccaga cctaactagg    240
taataaagtt gcgatgatgg ggactgccgc aaggctgtca atttggggc cgaactcagc    300 ctcaacctgg aaaaattaac tccgattgtt ttgatttgat catgggagat tacagtctac    360
gtgaaatgag cttataaaga acgttggagt accggctctc aacctgtctt gtacctgcaa    420
gctttcctca attcccttct atctttctta aaatcctctc attagacatc atgacgaggc    480
agacttctct cgttcccagg ctactaacgc tagcctcact agctgcactt tcacaagcag    540
agctaggcaa gatccaatgg aaaggatctt gcaacttgac cacttatccg gcattgatct    600
gtggaacact agacgtgcca tacgactaca cggagtcaaa ttccagcaag acactgactc    660
tcgacatcgc caagtggcca gcgaccaaga aaccagtctc ggagcccatc atatttaact    720
ttggaggacc tggtgtcaat tcgttcgagg gccttgggct ttatgagag gaatttcagg    780 cgtaggttgc agttctgctt tgataccgca tcttatgctg actgacattg ttctctagta    840
```

-continued

```
ttcttggagg tcacaatgat ttgatagctt ttaacaaccg gtttgtcgct cttctttctt       900
gagctagaaa catctactaa cgttgtacct ttatatagag gcgttggaaa caccatcccg       960
ttctcctgct acagcgatga cgccacccgt gaactcgtcg cccttcaagc tcctaacgac      1020
ggcagagcgt ccagcacggc tttgggagaa atctgggccc agaacgcaaa catcgcacag      1080
gcatgctatg ctacgaacaa tcaaactggt agtcttattg gaactagctt tgctgcaagg      1140
gacatcatgc aggtcgctga tgcgctcagt ggaaaggata gtttggtcaa ctactggggt      1200
aaatatcacg gctgaaccga gtttatactt ttgctgacaa tctacacttt aggattctca      1260
tacggcacta caatcggtgc tgttctcgca gccatgttcc cggatcgaat ggggaatgtc      1320
gcgcttgacg gagtggacaa ccccagagag gctctttatg gatagtgagt ggcccttgaa      1380
gtttgcccga tctggtatga ttcagacagc taattccttc cgaaaagcaa cgcacaagcg      1440
gttgtggacg tcgacaaagt tttcgaagga ttctgcacgg gctgcatggc cgcaccggac      1500
ctctgcccta tcgccaagga gtacaccagc gccgccaact tggaagccgc aatttacctg      1560
atgctgaaaa acctcaagta caacccgatt gccattcccg aaaccggtgg aatcgtaact      1620
tggagcgacg tcaagtcgac cattttttgag gccatgtacc tgccaagctc ttggcccttg      1680
acctctgagc ttctttacta cgtgcaaacc cgcaacacaa cgatccttgg caactctgaa      1740
gtatacgaca ccatcaaatc ctacggtcaa tcggcttctt tgacttcggc ttccgatgag      1800
gtcggcacgg ccattacatg ctccgacaag catcgatctg ccaccattaa agaggtcctc      1860
ccgtacgtca aagccagaca ggctctgacc aagatcggaa gtgatggctc ggacggcgac      1920
atgagatgcg cgcagtggaa tccgaagatg ttcgccaagg agcgctactc cggtgacttt      1980
gaagtcaaga cagccaaccc ggtgttgatt ctgagcaaca cttacgatcc agcgactcct      2040
cttcccgcag cgaagaacct gacagagacc tttgagggaa gtgtcttgct cgagcagaac      2100
ggatacggtg tatgtttata cttccccttc tcatcatatc aaaagtgagc aagcagctaa      2160
cctactgatg atagcatact accctgtcta tgccatctct ttgcactgcc aaggccgtcc      2220
gggcttactt caccaatggc acattgcccg ctgacgaaac gatctgccag gtggacgtgc      2280
ctctgttcac gaacttgacc tacaaggatg tgtggccgaa gagtttccaa cggagcgttg      2340
agtcgaggga tgatgcgact atcctcaagg ctttgatgtc ggtccgtgat aagatgtcgc      2400
gacgcaggat gtggtaagcg catgctatag atggggatgt tgaaaaccca aagcgatgac      2460
tggataatgt tcttcatata atttattctg tgccgattcc ggcatacgct cgtcatgtaa      2520
tagagtttag ttaatgttgc aagggattgt atagtattta tttgtacacc aacagcgctt      2580
catggagacc ggaacttccc tgagtacaga atttcccatc taggctttta tttaactttg      2640
acaatactca gtagtttgga tgtcgatagc attgaggcaa gtaccggttg ttgttttggt      2700
agtggagtga atcaggactg tcccacaaca atccgctgat ctgaatgttt gatgtttcga      2760
tctgaggtat ctgagctgcg agcctccaaa tcggcaaccc catacttcag ggatattcca      2820
gaacattact agccttggag gctttgaggt ttagctgcag ggcggtcaaa ctaattgatt      2880
tctctcaatt gtcctaccgc tattgagtga tctttagtgg atgagtggaa cggagaattc      2940
ccggtcggat aatgcctgca ttagtattgg ccaacagagt attccatcaa cgactcccgc      3000
gctgacattt aatccatgca caccctgaat tacctcgagc ttattctcgg tcctacattt      3060
gatcctctca tactttccct tatgtccttg cccacttgct ttacagattg aatccggatc      3120
cttcagcact cggcagaca                                                   3139
```

-continued

<210> SEQ ID NO 5
<211> LENGTH: 2940
<212> TYPE: DNA
<213> ORGANISM: Aspergillus niger

<400> SEQUENCE: 5

| | | | | | |
|---|---|---|---|---|---|
| atagcagaac | agaacatgta | tcttgtcaac | gaattgattg | atttcagcac | ggaaatgttc | 60 |
| aaggcatgga | acaattgctt | ctgacccgga | accgcggatt | gcaaggatgg | atatgtggat | 120 |
| cagatggtgt | gaagaagatc | tgtctgttag | catacttcat | aagttccaag | gaggagtaaa | 180 |
| tgtggagtca | taagagtaat | atcgaatatc | atagaatggg | gttgtcttgc | taacggtgaa | 240 |
| tcggactccg | tcggctctgc | cagcgatcgg | caggtcacgc | gtctgcgtaa | cttggtactt | 300 |
| atcttcccag | tcacctaagc | actgttactc | cactcttctc | tctttgacga | taagaagata | 360 |
| gcagagactc | ttgataaaaa | gggttgggag | catgctttga | atttcttcac | tccgagagct | 420 |
| ttctgtcccc | atctggtctc | ttgttgtccc | cgatgtacta | ctctctctgg | ttgctgcct | 480 |
| tggtggccgc | gctgcccgtc | tcccgggccc | agtttgtggc | tccgcccacg | gatctcattc | 540 |
| ccaccaaggg | atatctcgac | atccccgtcc | gctacaaaca | ggtccccacc | ggcatttgtg | 600 |
| agactgatcc | cagtgtcaag | agcttctccg | gttacgtcga | tgtcgctgag | catgagcaca | 660 |
| tcttcttctg | gttcttcgag | gcgcgcaacc | aagatcccac | cgaggctccc | ttgaccgtct | 720 |
| ggatcaatgg | aggcatgtct | gaccccggtc | attatttcct | tccaattgct | aaccgttcgt | 780 |
| aggtcctggt | tcctcctcca | tgatcggctt | gttccaagag | cacggcccat | gcggcattga | 840 |
| cgccaatggc | tccgtctaca | caaccccta | ctcctggaac | aacgccagca | acatgctcta | 900 |
| catcgaccag | cccgtgcaga | ccggcttctc | ctacagcatt | ccggttcccg | gctatgtgga | 960 |
| ttcttccaca | gacaatgtta | ttgctctgcc | ctcccccgcc | tgccccgact | atgcagcgga | 1020 |
| tatgttctgt | ggcacttact | cctacccaa | cgtgagcctt | acggctaatt | ccaccgacaa | 1080 |
| cgccgccccc | aacttctacc | gcgccctaca | gggttttatg | ggcgcatttc | ctcagtactc | 1140 |
| gcgcgaaacc | ttccacttca | ccacggagag | ttatggcggc | cactacgggc | ccgtcttcaa | 1200 |
| cgagtacatc | gaggagcaga | acgcccatct | ccagccggga | gccaagaaga | tccaactggg | 1260 |
| cagtgtgatg | atcggcaatg | gctggtatga | cccgattatt | caataccagg | cctactacaa | 1320 |
| ctttacggta | cactacctgg | tttctgatcc | ttatccttac | agcctggaca | ctaatctatc | 1380 |
| tacaggtata | tccgggcaac | acatacgact | acctgccatt | caacaagtcc | atcagctcgc | 1440 |
| tgatgtacaa | caacctctat | ggccccggaa | actgcctcga | ccagctctac | gactgcgccg | 1500 |
| cccgaggcat | cgacgagatc | tgcagcactg | ccgacgattt | tgcgccaac | gaggtcgaaa | 1560 |
| acgtctacga | catttactcc | ggtcgggatg | agtatgactt | tcgtgaactc | actccggacc | 1620 |
| cgttccctta | cgagttctac | gttgactacc | tgaacaaagc | gtccgtgcag | gccgccatcg | 1680 |
| gcgcatacat | caattacacg | gagagcaaca | acgctgttgg | actcgccttt | tcgtccaccg | 1740 |
| gtgacgacgg | gcgactcatg | aacaccatcc | aggatgtggg | caagctgctc | aaacagggtg | 1800 |
| tcacggtggt | catgtacgcc | ggggatgccg | actataactg | caactggctg | ggtgggaag | 1860 |
| ccgtgtcgtt | gcaggtcaag | gccgccaact | tcagtagtgc | gggttacacc | aacattgtca | 1920 |
| cctcggatga | agtgacacac | ggccaggtgc | gccaggcggg | gcaatttgcc | tttgtgcgag | 1980 |
| tgtatgagag | tggacatgag | gttcccttct | atcaacccct | tgcttgcgctg | gagatgtttg | 2040 |
| agcgcgtcat | tggcggcaag | gatgtggcga | cgggaaagat | tcccatctcg | tcgagtttac | 2100 |
| agacggtggg | cacgcccaag | agttactacc | gggagggcaa | cagcacgatt | cagtgggagg | 2160 |

```
tgttggattc tctggcgacg tacaacacaa ccacgaatgc tccgaacccg gtgagccgga   2220
ggctgaagcg gatgggacca gctttgcggt ttcagatgta gatctgaagt acctgcgatt   2280
gtgcattgaa gtacattgtt cagtgcaatt accgatcatg gctagctgtg ccgcccaaag   2340
ggggaagcta caatctaaac gccatatctt tcgatgcaga caccttacga gccatgaaat   2400 gccatttat gatcaggcta tctactgccg gtgattttat gtagtgttgg aaattttctg    2460
ttcaatcgca acccaaagga accaactggc tgtaaaagac acaacataac tcgccagagc   2520
caaactgtgc gaagatatga gaagcaaagt ttaaacgctc ccaagccatg gtttccctgt   2580
caagcctcat tcactctatt ggcttcagct gaaagaagag gataaacatt cagggggtaga  2640 accagacaaa atctggtctg gcggggatct ggtggggacc cgaatccaag ttgcgttagt   2700
ttgaggcatg gatcgacacg cgacgaacat gcagtggagg gccgctatcg ctgttttgac   2760
tcgacatcgg accaaaacca aggaaattcg tattcatcga tcgatagttc ttctcatctg   2820
gcaaggcatg gatccgtctc cccacttcag ccggtacctc ccggcacaac aaaaggagca   2880
tggcagcctg atttcctgcg ttccaactgt tcgtcggttg atctccctga tcaagtccag   2940

<210> SEQ ID NO 6
<211> LENGTH: 4550
<212> TYPE: DNA
<213> ORGANISM: Aspergillus niger

<400> SEQUENCE: 6
tgaaccatca ggtgggacca cagagcccac cgtccagctc aaggcagctc tctattcgaa     60
gaaagaggta ctggatatat cgggtacttc tagctccagg tcgtgaagcg ttgcgagata   120
cacaaatact gttggcgatc gaatgggacg aacatgtgaa tgttagcacc agaagtggat   180
ggtagctacg aacgatggga ggcggaggtc cgagtgtacg atagagctgt ggagatagat   240
tcgtatataa tagagatata tattcattgc attgcattgc tgtggtagaa aacttgtttt   300
ggatcgcatg aattgctggc ctgaatgatc aggtcagaag acgccgcagc tccgccggac   360
aagagccaat cagagggcgc caatcggggt gtccgcccgg ttcccttttc agtgtctgtc   420
actgcagctc gcctgacttc agttcctttt ctccttcctc acggtcctcg tcattcgccc   480
ctctctgttg cagtctctct tgttggggg tcttgtgaat gtcttgcgtc tggctccaca   540
tccacaaaag gagcctactg tctgtcgcta cgaacaattc tgttgcgagg ccgctgcct    600 ctacctccgc cgcgccgccg ccgccgtcat cgccgccgcc tggttctaat acttattcgc   660
ctctttatcg ccccatcacc aatcccatcg gatttacttt gtcgcctgcg aggtcactag   720
tttctcgcaa tcctaaattt cctgcctatc ggcgctctag tcgacacttt tctttgtgcc   780
cggccgctgc aacgcccggt gtcaccacga gcatctgccc tggtcaggcg cccgtccgct   840
ctctcagctc gctcattata cactctacga gaccccgtgc tatacgtatc cgtaccgacc   900
agatggattt gaatggagac gcaggcgcca agcgcaagcg cagctccatc accacacccg   960
ccgaacggcc cgtaaagcac cttcgccccg aatcgagcgc attgacaccc ggggattcga  1020
cgcctgccaa tgggactgta tacgatgtgg aggatgatga agatgcgagt cgtctgctgc  1080
ctgtagggcc tgctcaggcc gactcaccgg aatggcaagc taccatagag gaggttgtga  1140
aaagcgtagt gtctatccac ttctgtcaga cctgctcctt cgacacggag ctgtccatga  1200
gtagtcaggc tactgggttt gtggtagatg cagagaatgg gtacatattg acaaaccgac  1260
acgtggtttg cccgggacct ttctggggat actgcatctt tgataaccat gaggaagtat  1320
```

-continued

```
gttgtacatt ccacatgtgg atcgccttat gacagtgatg ctgatttgaa ttggttacta    1380
gtgcgacgtt cgtcctgtgt atcgggaccc tgttcacgac tttggaattt tgaaattcga    1440
cccgaaggct attcgatata tgaaattgag ggaactgaaa ctgcagccgg atgcagctaa    1500
agtgggatca gaaattcgcg ttgtgggtaa tgatgcagga gaaaaactga gtattctgtc    1560
tggtgtcatt agtcggctgg atagaaacgc gcccgaatac ggcgatggct acagtgactt    1620
caatacgaat tacatccagg ccgccgcagc agctagcggt ggaagttccg gcagtcctgt    1680
agttaacatt gatggccatg cgattgctct gcaggccggt ggtcgtgcag acggtgcagc    1740
gacggattac ttcctccctc tggaccgacc gctacgcgca ctggaatgca tccgtcgcgg    1800
agagcctgtc acgcgtggaa cgattcagac gcagtggatc ttgaagccgt cgacgagtg    1860 tcgtcggttg ggcttgacgc ctgagtggga ggcgaccgtg cgtaaagcag cgcccacgga    1920
aaccagcatg ctggtggccg agatcatcct gcctgaaggc ccggcggacg aaagctcga    1980 ggaaggagac gtgctcctgc aggtcaacgg ggtgcttctc acccaattca tccgttgga    2040 tgacatcctg gattcgagtg ttgggcagac agtgcgtctg cttgtccaaa gaggcggtca    2100
gaatgtggag attgagtgcc aggttggcga cctgcatgcc atcacgcccg accggttcgt    2160
gacggtggct ggaggcacgt tccataacct gtcttaccag cagtcgcggc tgtatgccat    2220
cgctactcgc ggtgtctacg tctgcgaggc tgccggctcc ttcaaactgg aaaacacact    2280
gtcaggatgg atcatcgact cggtggacaa gcggcccact cgcaatctgg atgagttcgt    2340
ggaggtgatg cgaacgattc ccgatcgttc gcgcgtggtc atctcgtatc ggcatattcg    2400
cgatctccac acccgaggca ccagcatcgt ctatatcgat cgacactggc accccaagat    2460
gcgactggct gtgcgcaacg acgacaccgg tctgtgggac ttttcggacc tcgcggaccc    2520
tatcccagct cttcctccgg ttccgaggaa agccgatttc attcaactcg atggtgttag    2580
ccagcctgct gcggccgaca ttgtgcgcag cttcgtacga gtatcctgta cgatgccct    2640 gaagctggac ggctacccc aggccaagaa gactgggttc ggattggtcg tcgatgcaga    2700
gaagggtttg gtggttgtgt cgcgagcgat cgtgccgtac gacctctgcg acatcaacgt    2760
cacggtggcc gactccatca tcgtgaacgc taaagtagtt ttcctgcatc cgctccaaaa    2820
ctacagcatc atccagtacg acccaagcct ggtgcaggcg ccggttcaga gtgccaaact    2880
cgccaccgac tacatcaagc agggacagga cacgatcttt gtgggattca accagaactt    2940
ccggattgtc gtggccaaga ccgccgtaac cgacatcacc actgtttcta ttccagccaa    3000
cgcgtccgca ccgcgctacc gcgcgatcaa cctggacgcc atcactgtgg acaccggact    3060
cagcgggcag tgttctaacg gtgtcctgat tggcgaggac ggagtggtgc aggcattgtg    3120
gttgaactat cttggagaac gcacatctaa ttcgcataag gatgtggaat accatctagg    3180
atttgcgact ccatctcttc ttcctgtcct gtcgaaggtg cagcagggag agatgccgga    3240
attgcggatt ctgaacatgg agagctacgt ggtccagatg agtcaagctc gtatcatggg    3300
cgtgtcggag gaatggatcg agaaggtgac gcaagctaac ccatcgcggc atcagctctt    3360
catggtgcgc aaggtcgatt gcccaccgcc tgggttcaac tcagcggccg acacgttcga    3420
ggagggtgat atcatcctga ccttggacgg acagctgatc acccgcgtct cggagttgga    3480
tatcatgtac gagaaggata cgctggaagc cctgattgtt cgaaatggac aagaaatgcg    3540
gatccaggtg ccgactgttc aacagagga cctagagact gaccgtgcgg tcgtgttctg    3600
tggtgctgtg ttgcagaaac cacaccatgc ggtccgtcag cagatttcta agctacacag    3660
cgaagtctac gtcagcgcaa gagtatgctc ctcaccccctt aaccactgcc atcaagtaac    3720
```

-continued

| | | |
|---|---|---|
| taaccaccct atcccttcaa cagagtcgcg gatcccctc ctaccaatac ggcttggccc | 3780 |
| caaccaattt catcaccgcc gtaaacggcg ttccaaccc gaacctggac cgcttctccg | 3840 |
| aagaagtgag caaatccccc gacaacacat atttccgcct acgggcggtg acattcgaca | 3900 |
| atgtgccgtg ggtagtgacc gtgaagaaga acgatcatta cgtatgccac aaccccctccc | 3960 |
| tctttacctc caccaaattc agagaatgtg gagactaaca caataatctc cagttcccca | 4020 |
| tgtccgagta tatcaaagac cagtcccagc cttccggttg gcggaccgtg tctcacgaca | 4080 |
| aggataaata taaagacggc attgcaccgg atgctgcgaa cttgaacccg gatgctatgg | 4140 |
| acgaagggtt tgatggagtc agtgatattg agccggattt ggagtgattg aaggcggact | 4200 |
| gtatagtatt ctgtgatgag catggctgtg ttagatgtgt atagcagaca tggcttggaa | 4260 |
| tagtagaaaa agtgaaaaat gggaaaatga tagagattaa atcggttcgc atatacgaag | 4320 |
| ttgtagatgg atgtattgtt tcggatgttt acgtagtacg tagtggctac tctatcgagg | 4380 |
| tgtgatgata gcattagtct ttgatttgtt ttcgtcccat ctgcacatgt actccgtata | 4440 |
| tgagaagtat gttgctcgac aacccaagtc tgaaagtatg aatgaacgaa tcgacaacac | 4500 |
| acatgaagat aattttatcc aagcaaaaga agccccattt catcttattt | 4550 |

<210> SEQ ID NO 7
<211> LENGTH: 2660
<212> TYPE: DNA
<213> ORGANISM: Aspergillus niger

<400> SEQUENCE: 7

| | | |
|---|---|---|
| gaatgcgctg aaaaaaatgc tgttgatagc ctaaggtagt cacccgacgg gcttgtgatt | 60 |
| ggaggaaacc gcaatgacgc tggtcccgtg ccatgagctg actcagctgg ctgactcaac | 120 |
| gcgtgacttt ctgcaaaggg aaggcaccgg catgtgattg gtcgccttcc gttcctgcta | 180 |
| tcgaggcgtc atcgcctaca gcccatcgag tacacctcct cttctctcct ctctccttcc | 240 |
| ttccttcctc tccatcctct tctgggtttc cattgatcac ccagtagctg gtattttctg | 300 |
| agctacttgc ttttttctatt ttgatacttt tgtgtccgta agttcacttt atgccctctg | 360 |
| accccccccct tgataacccg tgctgataag ctccctgccc aggtaccgta ccttccagac | 420 |
| cgcaaggtac ccatcctctg cctactcatc ccatcaccat ctcaattcat accgcccccg | 480 |
| tagggtttca gcaacaatga gagtccttcc agctgctatg ctggttggag cggccacggc | 540 |
| ggccgttcct cccttccagc aggtccttgg aggtaacggt gccaagcacg gtgccgacca | 600 |
| tgcggccgag gtccctgcgg atcacagtgc cgacgggttc tccaagccgc tgcacgcatt | 660 |
| ccaggaggaa ctgaagtctc tctctgacga ggctcgtaag cttttgggatg aggtggccag | 720 |
| cttcttcccg gagagcatgg atcagaaccc tctcttttcc ctccccaaga agcacaaccg | 780 |
| ccgtcccgac tcgcactggg accacatcgt ccgcggctcc gacgttcaga gcgtctgggt | 840 |
| cactggtgag aacggtgaga aggagcgcga ggtcgatggc aagctggaag cctatgatct | 900 |
| cagggtcaag aagaccgatc ctggctctct tggcatcgac cccggcgtga agcagtacac | 960 |
| cggttatctc gatgacaacg agaatgataa gcatttgttc tactgtaagc acaccttggt | 1020 |
| tcaagatcac gcttttttata tgctctggat atctaacgca acttagggtt cttcgagtct | 1080 |
| cgcaatgacc ccgagaatga tcccgttgtt ctgtggctga acggtggccc tgggtgctct | 1140 |
| tccctcaccg gtctcttcat ggagcttggc cctagcagca tcaacaagaa gatccagccg | 1200 |
| gtctacaatg actacgcttg gaactccaac gcgtccgtga tcttccttga ccagcctgtc | 1260 |

```
aatgtcggtt actcctacag taactctgct gtcagcgaca cggtcgctgc tggcaaggac    1320
gtctatgcct tgcttaccct cttcttcaaa caattccccg agtatgctaa gcaggacttc    1380
cacattgccg gtgaatctta tgctggtcac tatatccccg tcttcgcttc ggagatcctg    1440
tctcacaaga agcgcaacat caacctgcag tccgttctca ttggcaacgg tctcaccgac    1500
ggatacaccc agtacgagta ctaccgtccc atggcctgcg gtgacggcgg ttacccagct    1560
gtcttggacg agagctcctg ccagtccatg gacaacgctc ttcctcgctg ccagtctatg    1620
attgagtctt gctacagttc cgagagcgct tgggtttgtg tcccggcctc catctactgt    1680
aacaacgccc tccttgcccc ttaccagcgc actgggcaga acgtctatga tgtccgtggt    1740
aagtgcgagg atagctctaa cctttgctac tcggctatgg gctacgtcag cgactacctg    1800
aacaagcccg aagtcatcga ggctgttggc gctgaggtca acggctacga ctcgtgcaac    1860
tttgacatca accgcaactt cctcttccac ggtgactgga tgaagcccta ccaccgcctc    1920
gttccgggac tcctggagca gatccctgtc ttgatctatg ccggtgatgc tgatttcatt    1980
tgcaactggc tgggcaacaa ggcctggact gaagccctgg agtggcccgg acaggctgaa    2040
tatgcctccg ctgagctgga ggatctggtc attgtcgaca atgagcacac gggcaagaag    2100
attggccagg ttaagtccca tgcaacttc accttcatgc gtctctatgg tggtggccac    2160
atggtcccga tggaccagcc cgagtcgagt ctcgagttct tcaaccgctg gttgggaggt    2220
gaatggttct aaagacgtgc taccaccgca tatagacttt ctggtcattt cggtgacact    2280
gcagatatgt tcttaacga tagtttgagc atgcttgtca atgcccacta gtcccgatcc    2340
ttatatgttg catggtatct atgagttttg tcactatagt gcattataca tttgtacttc    2400
gtatgagaat gaatcgatcg catttacacg catataaata gtacccaaac cgtctggaca    2460
tgaataaggc ccggccagta gtttacatac agtgtagaaa actaggcgta cagacgtctc    2520
agtacgtaat caatggttaa aaaaaccact cccatagaag ccaagccata agagcctact    2580
catgtagttc gccactgaac gcacccgtat atcgtaaacc agcagaaaga gaaaaggaaa    2640
attgaggaaa ggacgatttg                                              2660

<210> SEQ ID NO 8
<211> LENGTH: 1680
<212> TYPE: DNA
<213> ORGANISM: Aspergillus niger

<400> SEQUENCE: 8
aaaacgtgcg cactgcaccc actcgttccg gctggggtct agaaatctgg acggtcccag     60
gcagatcggt gcctgggcaa accttgata aaaatagctt gttcgatctt gagttagaca    120
gccaattgta tactcactag agacacttga tgattcagtc tgtgacgtac gtgcacctcc    180
acactccgtc gatggattat gtgtccccgt gggcacgcgg agatcgggga catcagtcga    240
gaaacttgcc taatctagtg acaagcagaa aagtcaaagt catccgcatg cgacttgcag    300
atcatctaga gggatataat aaagtcgtgc gtttatgacc ttgcaggaaa cgacccgcct    360
cctcctgcct ctttattatc gataccctct gccactagcg tcgtacatca cacttccaca    420
tccattctcc tctcattcat catgaagttc acaaattatc tcttgacgac tgcaacgctc    480
gcaagcagtg tcctagcggc tcctgctccc cgcaccggtt tggaggacag actccgtgcc    540
cggtcattgc agcgtcaatc acatcctctg gcacctattc cacttgacac atccaccaaa    600
gagaattcca gactcctcga agccgacgag aataccaccc atgttacata cagcagtaac    660
tgggcgggcg cagtgcgcga gcaaccacct ccgcaaggca cgtattctgc cgtgtcggca    720
```

-continued

```
accttTcgtg taccagaacc cacggcgcaa ggggggagcg gaacgcaggc tgggtcggcc        780
tgggtcggga tagatggcga cacatacagc aacgccattc tacagacagg agtcgacttc        840
tacgtggaaa acgggcagac gtacaacgat gcctggtatg agtggtaccc agactatgca        900
tatgacttcg acctagatgt aagcacaggg gacacgatcg tcgccaaggt ggaagccatc        960
tcgccaagtc aaggtgtagc cactattgag aacatatcga cggggaagaa ggccacgcag       1020
acgatcagag ccccagctgc gacagctacc cttgccggcc agaatgccga ctggatcgtg       1080
gaggatttcc agtctggcga ctcaatggtc gatctggctg gctttggcga gatcagcttc       1140
tggggcgtgc aagcacaagg aggagggtct acatggggtg tagatgatgc gactattgtc       1200
gaactgaagc agggcaacga agtgttgaca gacgtggagg tgcaaagtga ttcggccttt       1260
acggtgaaat atacgagctg atgtgatggt atatggtcgc atattctcat ccttcgacta       1320
atctttctcc ttttgacggg tgacataatt tttctggttg attttgaaaa tgccttgatg       1380
tatttcggta gtagttttaa ggttgatact tccagcatgc gggctcggct attgggagga       1440
accaagaagg ctatatggcc ctcgggtatt cgccgcattc taaggtcgca tgccttctcg       1500
gctttcctta tatatatcta ctttccattt ccccaacctc attcttgatg cgagaatcta       1560
cccacacata cagttaatca tgtcccgtat ataccaacta agccgagcat ttcagcgcag       1620
ccaagttggc gcgctccggc cgcgctctct actacccgct cggtcatccc gctgcggctt       1680
```

<210> SEQ ID NO 9
<211> LENGTH: 2590
<212> TYPE: DNA
<213> ORGANISM: Aspergillus niger

<400> SEQUENCE: 9

```
ttacatgctc tgtgtgttgg taaacacgct gtcacattct tcatgtcctc tggattgcac         60
gataacttta ccgcgtctct ccaaccggat tgatgaaact atcaacaggg ccccgcatta        120
ttggcataac cgacattttg aaaaagtatc gcgggcgaga agagagcctt tttcgacaac        180
aaacgtcggt ctctttggtt tgcatcgaga gacatagata cagttgaccg cggcgcgaca        240 cttttttagga gcgcagagga cggtttctgc ggcgatttga tccgcaggcg agcaaaggtc        300
taagacacct ctgtttggaa ctgcgcaggt accagaactc gaaactaatg cgacattcga        360
gcgacgatga tatatgtcaa ctatatcctg ggacttctgt ccctcttaca caccgctgta        420
gccacagctc ctgattatgt cgtggtagac caactgaaca gcatccccga cggatggaca        480
aaaggcgcag ctcccccgcc atttactccg atgaagttct ggttgtcgat gcatcacgag        540
tacaaggcgg acttcgagca gaaagtcatc gatatctcga cacccggtca ccggattat         600 ggacggcata tgaaacgcaa cgatgtcatg gcctttatgc gcccatccga tcaggtctca        660
aagatcatct tctcttggct tgagtcggag catgttccac caaatgccat cgaagatcgc        720
ggggattggg tcgccttcac agtcccgttg gcccaagcac aatcaatgat gaagaccgat        780
ttttacaact tccaccacct ggaaacaaac acaaccccaaa ttaggaccct caagtactcc        840
gttcccgagc aagtcgatgc tcatctgcaa atgatccagc caacgactcg cttcggccga        900
cctaagacac aaaccagcct accgagcctc atgccagtgt cggttaacat tgatgaaata        960
agcgaagact gcttgacagg cgtgacgccc atttgccttc gccagctcta tggtttacct       1020
agcaccaagg caagccccga ctcgagaaac gtcctcggaa tttccggcta tctggaccag       1080
tacgcgcgct acagtgaccct cgacgagttt ctagccgtat actctccaaa cagcgtagac       1140
```

```
gccgacttct ccgtagtatc gatcaacgga ggccaaaacc cacaaaactc acaagaggga    1200
agcacagagg ccagtctcga catccaatac gccctctcca tggcatttga cgctaacgcg    1260
actttctaca ctaccgccgg acgtgcgcca tccgtctcag actcgggtac ggtgagcacc    1320
gacggctcga ccaacgagcc gtatctcgaa cagctccagt atctggtggg tcttccggac    1380
gaggatcttc ctgcagtgct tagcacgtct tacggcgagg atgagcaaag tctgccggag    1440
gaatacacag aagccacgtg caatttattt gcccaattag gtgcacgcgg ggtctcggtg    1500
atcttcagca gcggagactc gggcgtcgga ggatcgtgtg tatctaacga cggaagccag    1560
aggacccgct ttcagcctat cttcccggcg tcgtgcccgt ttgttacatc cgtgggtggg    1620
actgagggcg tcgggccgga aaaggctgtg gacttttcga gtggagggtt ctccgagcgc    1680
tttgctcgcc cgtcgtacca gaatgcgagt gtggaagcat accttgcccg cttaggagat    1740
aaatgggatg gattgtataa tccagacgga cggggtattc ctgatgtgtc ggcccaggct    1800
agcaactatg taatcaggga ccatgggcaa tggctacaaa ctgcgggaac aaggttagtg    1860
gccctaccaa gtcaacaatt gaaaatcaaa cgagctgata atattacagt gctgccgccc    1920
ctgtctttgc agcagtcatc tctcgactga acgctgcacg tctcgagcag ggtaaaccta    1980
cactagggtt tctgaatcct tggctgtact cactcgacca gcaaggattt acggatattg    2040
tagacggcgg atcagtgggt tgtgacgggt caaatggagg agctcttgtc ccgtatgcca    2100
gttggaatgc caccaaggga tgggatccgg ttactgggct ggggacacct ctgtatcaga    2160
ctctggagca gttggcgcag tctgcttagt actgcggcgg gatggcctat tttgtgtcgt    2220
tgatgttttt gtcccctaaa tgtcaacgcc attaattctt ctcaagtgcg attagatttc    2280
gtaaaacaga agctggacaa tatgcagaaa ttagagtaca aagctggaga cagaaggtcg    2340
atctccagaa tttgctaatg gttgtggtac tcacgtcagg gtgctcgagc acaccagcta    2400
actaccaact ttacccgtta attctaccgc agtagtaatc tagaaaatac tagataagct    2460
gatcaagctt gaaacaaata agcttaccga ccgagaccca tacagcctcg cagtacaaca    2520
acttactacg ggtgagacat cctcacccgt ccgtaagatc gaaaggatta ctatacacgg    2580
agtaagcact                                                           2590

<210> SEQ ID NO 10
<211> LENGTH: 3080
<212> TYPE: DNA
<213> ORGANISM: Aspergillus niger

<400> SEQUENCE: 10
ggtacagtag tgggttttag tttggatgta tctggagaca tcgatgcttg ttcgccggcg      60
ctaatttggg gccatcgctt agggaagaaa aagaaaggaa ggatttcatc tgccgcggca     120
tttttggtca ggcattggca atactccaag cagcttgcca agtgagaaa tgtgcttatg      180 aataatattg agtaatagtt aatcaattgt cttacaggat aaatatggaa tagcattggc     240
attgcgtggt tggcaggcag catgttgcaa attgcaacaa cgcgatcccg gcgatcgccg     300
tcggactccg gtgggaatc agggttggag acccattgct tatcaacaac agccgacgcc     360
agtcgttctg gggtgcattt gcagaatctt tggacgaatc agccttttgt cagtatcggc     420
cggtccgaat tgacccagct tgctagccgt tggagacatg caatgatgcc attgtctcgt     480
ccgataagca agtgcggcca atccctcgtt ccttctggct gtctcagaaa agttataatg     540
tccgtctcgc ctgcctagcg aacaattcga actctgtgtg tgttgtccct ctcaaggtct     600
ccagcatgcg ttcttccggt ctctacacag cactcctgtg ctccctggcc gcctcgacca     660
```

```
acgcgattgt ccatgaaaag ctcgccgcgg tccccctccgg ctggcatcat gtcgaagatg      720
ctggctccga ccaccagata agcttgtcga tcgcgctggc acgcaagaac ctcgatcagc      780
ttgaatccaa gctgaaagac ttgtcaacac ctggcgaatc gcaatacggc cagtggctgg      840
accaggagga tgtcgacacg ctgttcccgg tggccagcga caaggctgtg attaactggc      900
tgcgcagcgc caacatcacc catatttccc gccaggcag cttggtgaac tttgcgacca       960
cggtcgataa ggtgaacaag cttctcaacg ccacctttgc ctactaccaa agcggctctt     1020
cccagagatt gcgcacaaca gagtactcca tcccggatga tctggtcgac tcaatcgacc     1080
tcatctcccc aacgaccttc ttcggcaagg aaaagaccac tgctggtctg aaccagcggg     1140
cgcaaaagat tgacacccat gtggccaaac gctccaacag ctcgtcctgt gccgatgtca     1200
tcacgctgtc ctgcctgaag agatgtaca attttggcaa ctacactccc agcgcctcgt      1260
cgggcagcaa gctgggcttc ggcagcttcc tgaacgaatc cgcctcgtat tctgaccttg     1320
ccaagttcga gaagctgttt aacctgccct cccagagctt ttccgtggag ttggtcaacg     1380
gcggtgtcaa tgatcagaat caatcgacgg cttccttgac cgaggcggac ctcgatgtgg     1440
aattgctcgt cggagttgct catcccctcc cggtgactga gttcatcact tctggcgaac     1500
cgtgagtatt gaattcctag acagagcttg aatcgaagct aattgtgtag tcctttcatt     1560
cccgaccccg atgagccgag tgccgccgac aacgagaacg agccttacct ccagtactat     1620
gagtaccttc tctccaagcc caactcggct ctgccccaag tgatttccaa ctcctatggt     1680
gacgacgaac aggtacgacc ccacattccc ccttccctgt atgtagatac taaccggacc     1740
agaccgttcc agagtactac gccaagcgag tctgcaacct gatcggactt gttggcctgc     1800
gcggcatcag tgtcctcgag tcgtccggtg acgaaggtac acttacttcc cctgtcctat     1860
tccttgcatc gaaaataccc taacagcagc acaggtatcg gatctggctg ccgaaccacc     1920
gacggcacca accgaaccca attcaacccc atcttcccgg ccacctgtcc ctacgtgact     1980
gccgtgggag gaacaatgtc ctatgccccc gaaatcgcct gggaagccag ttccggcgga     2040
ttcagcaact acttcgagcg ggcgtggttc cagaaggaag ctgtgcagaa ctacctggcg     2100
caccacatca ccaacgagac caagcagtac tactcgcaat tcgccaactt tagcggtcgc     2160
ggatttcctg acgttgctgc ccatagcttt gagccttcgt gagtccattc ccagcatcat     2220
gataatacga aataggggtct aatgacatct gcagatatga ggttatcttc tacggcgccc     2280
gctacggctc cggcggtacc tcagccgcgt gtccccttttt ctctgcgcta gtgggcatgc     2340
tgaacgatgc tcgtctgcgg gcgggcaagt ccacgctggg tttcttgaac ccctgctct     2400 atagcaaggg gtacagagcg ttgactgatg tgacgggggg ccagtcgatc ggatgcaatg     2460
gcattgatcc gcagaatgat gagactgttg ccggcgcggg cattatcccg tgggcgcact     2520
ggaatgccac ggtcggatgg gatccggtga ctggattggg acttcctgac tttgagaagt     2580
tgaggcagtt ggtgctgtcg ttgtagatgt atactatata tatggtatga gattatgtat     2640
gtgatatgtg atattatgtg agagagaatg gtttagactg tgcgtcatat acatggacag     2700 ttcatttct cattaaacga gcaccttcat acggtaagga cctcagaggt tcctcccatt      2760
gttatgaccg cttcccttct ttctagagat acatgcttcc ccaccccgcc tcaacgcgac     2820
cgtctacgga caccagtcag aagaccccaa caacccacta ttagtggcta gtaaggacga     2880
catgcataat tactccgtga aacccccgaa attaagcccg acaggggcat agagaaaccg     2940
atccaatcac ttaacttacc ccgcttctag cacggcatag ggctgagcga tgcgatggtg     3000
```

```
caatggccac gccgttgccg attagccgta gggccagttg tgaatttccg ggatcaccct    3060
acaacacatg cttcatgcgt                                                3080

<210> SEQ ID NO 11
<211> LENGTH: 1890
<212> TYPE: DNA
<213> ORGANISM: Aspergillus niger

<400> SEQUENCE: 11
gaggatgata gtctgatggc cattccgctt gaggcaaagt gtgccccaat gtcacgcggt      60
cagctagtct tctgcaggtc tgcagttgga caggggaact tgagtgctat tatcgccaag     120
gtgaatgttc tctaccgctt tgataccaga gtgatcgtcc cttttgccgt cactcttggt     180
gttgcgaagc agatgtcgtt cgtttgcata tgggagccga agatccacgc agggtgcttg     240
aaaagacata ctgcgatcct cccgtttcca agaatgcttg tacacttgaa gttttttgtca    300 agatccccc gcctggccag tcccgagcta agcgaaatga gctttccctc aatgctgcag     360
acaggagaca ccatcgcttt ggcgccttgg caccatcagc caccgtcggt cctatcatca     420
tcgccctggt caatagggaa cgcgtcaatt gcgtatctgg gtagtgttat ctgctcgata     480
ttgcaccggc agagcaggaa tcgggattgg cggatgtaga gaaaattcag cttcaaggag     540
gggggaaggg agacgctgaa atggtataaa accacgtcca attccctacc agatagccct     600
catccagcag catcaaaagc atcttccact cagactccaa gcagctccca gtccctcttc     660
aattcattac cttccaaaca tcatcccatc aagatgaaga ctactgctct cttgaccgcc     720
ggcctgctgg ccaccactgc tatggccgct cctctgacgg ccaagcgcca ggctgctcgg     780
gccaagcgct ccacgaaccg ccagagcaac cctcccttca agcctggcac caacgaggtc     840 ctcgcccta acggcaccaa gaatgtggag tacagctcca actgggccgg tgccgtcctc     900
attggcactg gttacactgc cgtgaccgcc gagttcgtcg tgcccacccc ctccgtgccc     960
tccggtggct cgagccgcga ggagtactgt gcctccgcct gggtgggcat tgacggtgac    1020
acctgtgaca ctgctatcct ccagaccggt gtggactttt gtgtccaggg cagcgaggtg    1080
agcttcgatg cctggtacga gtggtacccc gactacgcct acgacttcag cggcatctcc    1140
atctcggccg gtgataccat caaggtcacc gtcgatgcca gcagcgacac caccggtact    1200
gccacgattg agaacgtgag cactggtacc acggtcaccc cagcttcac gggcggtgtt    1260 gatggtgatc tgtgtgagta caacgctgag tggatcgtcg aggacttcga ggaggatgac    1320
tccctcgttc cctttgccga ctttggcacc gtgactttca ccagctgctc cgctaccaag    1380
gatggttcct ctgttggccc tgaggatgct accatcatcg acatcgagca gaatgaggtg    1440
ctgacctccg tttccgtctc cagtagcgag gtcgttgtca agtacgtcta agacgttgga    1500 tgtatgggt tcgggattgt tgatgccccg atgggtgtgc tttcgacggc aatggtgaga    1560
tgagtgatgg aaatgagagg ttggtctttt ggcccggggc tagttttctc ttggtactcc    1620
tgaaaagcca atagttcaaa tgtctttatc ttgttagttt gatgttatag tttgccttga    1680
gttgatttaa ttgaaccaac gttggatcat cgtatcccct agcgcaaata aaatattacg    1740 tacgccttt aaaatattat gtatgtctgt taaggttctg actgttcaga tttatgtcaa     1800
acaacagcaa atcattggta atccaggact cggggatatg agcttcagac attcacccca    1860
ttactgcatg actatgaccg tgtctttagc                                     1890

<210> SEQ ID NO 12
<211> LENGTH: 3080
```

<212> TYPE: DNA
<213> ORGANISM: Aspergillus niger

<400> SEQUENCE: 12

| | | | | | |
|---|---|---|---|---|---|
| ttgttgtgat | tgctaagaga | catcacattg | ctcatatgag | tttgattgcg | actgttaata | 60 |
| ttaatgtccg | actgggagga | aatgagtggc | gttatccagg | cagctgcatg | caatactaca | 120 |
| ttcccctcac | gagggaaatc | tggccatctc | ggaaatcaat | ggtgtcatcc | gagttgattc | 180 |
| ccctcaataa | tggtcctgat | aagccactat | tgctgcagaa | cgcctatctg | tgccgttagt | 240 |
| gcatgcatag | tgtccccagt | tcttttctg | ccgattaatc | tattgccaga | cggactccgt | 300 |
| cgcgcttccg | aatgccggga | accgcggcta | agctttgctg | tagctttgct | gcaggaacat | 360 |
| ctgcatcttt | caaatatct | tcagaggagc | cgatcgctga | gtttctcaag | agattagatg | 420 |
| aatgttcgta | cttggccgca | atataagctt | catggcggct | tcaaccttcc | atgagaaata | 480 |
| agaataaggc | tgccggggat | ggcctcaccg | tgtccctgca | tgcaagggat | gcataatgca | 540 |
| ccgtgacctg | ttccaccacg | ccggagcccg | cccgccctcc | gacggcccaa | acccactgca | 600 |
| gaatggcttg | attaagttcc | ccttctataa | ctaaccggtt | gttcctcgtc | gttgtctgct | 660 |
| ctgctctcca | cccagggtcg | ttttgcttt | tgcctcctta | accatggtcg | ccttttcccg | 720 |
| catctcggca | ggcttcgccc | ttgccgcccc | tgccctggcc | agcgtcgtcc | tggagaccgt | 780 |
| caagtctgtt | cccagcgact | ggaagctcgt | ggaggctgct | gataccagct | ccacaatttc | 840 |
| tttgtccgtt | gctctggcgc | gtcagaacct | ggaccagttg | gaggagaagc | tcctggccgt | 900 |
| gtccacccct | ggcaaggaca | cctacggcca | gttcttggat | ctggacgaca | tcaatgagca | 960 |
| gtttcctctc | gcagatgacg | ctgctgttgt | ggcttggctg | aagaaggcag | gcgtcaccca | 1020 |
| gatccataag | gagggtggtc | tgctgaactt | tgcgaccact | gtgggcacag | ccaaccagct | 1080 |
| tctcaacacc | accttctcgg | tgtacaagag | cggatctacc | cagaagctgc | gcacaacgca | 1140 |
| atactctgtt | ccggatgagc | tgaccgggtc | cattgatctc | atctcgccga | ctgttttctt | 1200 |
| tggaaagtcc | aacgctgcgc | gctcggcggc | cgtgcgtgct | tcgcagacta | ccaaggagac | 1260 |
| cagcagaaag | aagagcagta | atgtgtgcga | gtacatcact | ccggattgcc | tcaaagagca | 1320 |
| gtatagcatt | gactatacgc | ccgaggcatc | gtcgggaagt | cgtgttgggt | ttggcagttt | 1380 |
| cttgaacgag | tcggccttgt | actcggattt | ggatctgttc | acccagtact | ttgacattcc | 1440 |
| ccagcagagt | ttcactgttg | agactatcaa | cgggggaatc | aacaaccagg | agaatgatcc | 1500 |
| ggatggtgaa | gccgatctcg | atgtccagaa | catcgtgggc | atctcgcatc | ccttgccggt | 1560 |
| gacggagtac | attaccggag | gatctccgtg | agtgttccca | agatgcaatg | aattaaag | 1620 |
| ctaatggttc | agtccattca | ttcccgacgt | cgagactact | accgacgaga | acgagcctta | 1680 |
| cctgcagtac | tacgagtatc | tgctggccaa | gaccaacgac | gagctgccac | tggttatcag | 1740 |
| caactcgtac | ggcgatgacg | aagatgtaag | catccctgcc | tcccacacaa | atcgcctgct | 1800 |
| gacagaatag | accgttccca | ttgcctacgc | cacccgcgta | tgcaacctca | tcggcctgat | 1860 |
| gggcacacgt | ggtatctcca | tcctcgagtc | ttccggcgac | tctggtacgt | tgtaccccat | 1920 |
| atatattgca | tcaagtcccg | actgacaaat | acaggtgtgg | gcggcgcatg | catgtccaac | 1980 |
| gacggcaccg | acaagaccga | attcaccccc | atgttcccag | gaacatgccc | gtacatcacc | 2040 |
| gcggtcggcg | gcacccaaga | cgtgcccgaa | gtcgcctggg | tggacagctc | cggcggcttc | 2100 |
| agcaactact | tctcgcagcc | gtcgtaccag | tcggatcagg | tggagaccta | cctggacaag | 2160 |
| tacatctctg | cctcgacgaa | gaagtactac | gagcagtaca | ccaacttcag | cggtcgcgcg | 2220 |

-continued

| | |
|---|---|
| ttccctgacg tgtctgcgtt tgcaggttct ccttagtatg tatccatccc agatgattgt | 2280 |
| atggacatct gctaatgtcc gacagctacg aaacttatat tgatggtcag ctcggccttg | 2340 |
| tggcgggtac ttctggcgct agccctgtgt tgcggggat cgtcgcgctg ctgaacgatg | 2400 |
| cccgtctgcg ggccaacaag acatccttgg gcttcctgaa cccttggctg tactcgagcg | 2460 |
| gctacaagag cctgaatgac attaccagtg gcgaggcagt gggctgccaa ggcgatgtgg | 2520 |
| agggcgctgg agtcattcct tgggcgagct ggaatgccac gacgggatgg gatccggcga | 2580 |
| cagggctggg aacgcctaat tttgccaagc tgaaggaggc ggttcttgcg ttgtaagcag | 2640 |
| gaggatactg agtggacgtg cggagtgaag gatatgtgca aggcgttaac ttataatagc | 2700 |
| ctgtgtgtgg actatagaat catctacagc ccacaaccaa ttagcttctg catagtcacc | 2760 |
| acccttaaac taaggataat caattgttta ccgctgtcag tctcaaatcc gtcatgtcat | 2820 |
| ggaccctgtt cgatcaactt gaaacaagct taatctacca gcggcggtga tgaaaccgcc | 2880 |
| agcggacact tgtttcagtt acccgcaagc ctgtatccag tatgcaagcc ctacttaaac | 2940 |
| ccttccaccac cctgattatt ctactctctc tctctctcca accacaccat tcttttcttc | 3000 |
| attgtgccgg tcacatccat tctttacttt cattctcctc ccttctcttc tcttctctac | 3060 |
| ttccccaagt cactcattat | 3080 |

```
<210> SEQ ID NO 13
<211> LENGTH: 3598
<212> TYPE: DNA
<213> ORGANISM: Aspergillus niger

<400> SEQUENCE: 13
```

| | |
|---|---|
| accggagcag aggaacaagc ggagaagctg aaacgtatga atgctgagta cgagcaaaag | 60 |
| ttccctggct gcggtttgt gtatgttctc tcagtatacc caacgacttg tgttggtctg | 120 |
| acatatctcc ctggcatagt acttttgtaa acggtcgcaa ccgggatgtc atcatggagg | 180 |
| agatgcgtga gaggattgac cggggcaatg ccgatcgtga ggtggaggag attatacagg | 240 |
| tgagatggct gtctacccaa acacggagca gtgctgacag ttcgctcctt taaaggcaat | 300 |
| gtgcgatatt gcaaaggatc gggcgcggaa actggagcag tccgctaaga tatagttcac | 360 |
| atactgcaag catatatttta aacaatgaat acccttcgat ttcagcaggc gctgcgacat | 420 |
| ctccttgctg aatcgctgct ttacaagcca tatttcggtc catgcgattc atctatggag | 480 |
| cactctgcct ctgtccggaa acaatggctg gtaatctgca tggaacttgg tgattccgtt | 540 |
| agtataaagt gaccaactag tgccggcgaa ttatgggaag cctgccttgt cttacgacgg | 600 |
| gacgatcttc cgtcgaacgc gtgctaccag catttcata gtatgacggg tccgtatttg | 660 |
| atttactatc gatggtaaaa cgcctcctct atggggtccc ctagcactcg gcaggccagc | 720 |
| ttgtgagaca acccgggagg tcagccatta ttaggccaat gagagctggc aggttggaga | 780 |
| ggttgtactt cgacaatgtt ggacagccat gcaacgtcgg acaatagctt tgatagggaa | 840 |
| tatcctaagg gcgaaccagg agggataggg gtaggtatgg ctgtatcgat tagtagtccc | 900 |
| tctttcaccc agaacaaact ctagtatata tagtagtaaa tgttccgcgg atggccaatg | 960 |
| acccaaatc atctttcatc ccatccacgc atgagcaaac atgcatggtc tgcgcctagt | 1020 |
| atgcagcata gggacattgc ctttggttat cctggcatat ccggcggctt cattgcatac | 1080 |
| aacttcagca gccgtggact tggactccct tcgtctgacc tctaactccg aatacgtcaa | 1140 |
| ttctgtccat gtagacacga atcgatcagt cgcagtgtcc gctgaagaac attataccga | 1200 |
| tacagcagct cgactggttc agaacattgt tcctggagcg agctttcgtc tcatcgatga | 1260 |

-continued

| | |
|---|---|
| ccactttgtc ggcgacaatg gagttgcaca tgtatacttc cgccaaacgc tccatggtat | 1320 |
| tgacattgac aatgcggatt tcaatgttaa tgtctgctcc ccaattactc tgttcggaag | 1380 |
| gaagcttact gttacagatt ggaaaagatg gactggtctt gtctttcgga cattcgttct | 1440 |
| tcacaggcgc gttgccgagc agccatctgg acaataccaa cgttttgagt ccggaggctg | 1500 |
| cacttagagg agcaagggac gctatacagc ttccactgac tattgacaat gtttctactg | 1560 |
| aagctgcaga ggggcggaac gagtacatat tcagagaggc agtgggagcg gtatctgacc | 1620 |
| ccaaagctaa gctagtctac cttgtcaagc cagaagggac tctggcgctc acctggagga | 1680 |
| tagaaacaga catgtatgag cactggctac tgacatacat tgatgcagag actaccactg | 1740 |
| tccacggcgt ggttgactat gtcgcagacg cgacatatca agtttagtga gtggctctcc | 1800 |
| ccatcgaata acgaagctaa gacaacagtc cctggggcac aaacgatcca gcagaaggac | 1860 |
| atcgcaccat tgtcaccgac ccctgggacc tatccgcatc cgcatacacc tggataagcg | 1920 |
| atggacggga caactacacc acaaccagag gcaacaatgc catcgcacac tggaatccga | 1980 |
| ccggcgtgg ctcctatctc tacaacctac gtccatccga ccccaacttg aatttccaat | 2040 |
| ggccatactc cccaaacatg tccccacccc gatcatacat caacgcctcc atcgtccaac | 2100 |
| tcttctacac agcaaacgcc taccacgacc tcctctatac actcggcttc accgaatccg | 2160 |
| ctggcaactt ccaatggaat aacagcgccc acggcggccg agacaaagac tacgtgatcc | 2220 |
| tcaacgcaca agacggctcc gggttcagca cgcaaacttt gcaaccccca cccgatggta | 2280 |
| tccccggccg tatgcgcatg tacatctgga tcgagtctac tccgtcgcgt gatggaagtt | 2340 |
| ttgacgcggg cattgtaatt cacgaataca ctcacggtgg taagcatctc cccagaagat | 2400 |
| ggaagtccta atctaacaaa ccagtatcca atcgtctcac cggcggctcc cacaacgccg | 2460 |
| gatgcctcag cgccctcgaa tcgggtggca tgggcgaagg ctggggcgac tttatggcga | 2520 |
| cggccatccg aatcaagccc aacgatacac gcacaacgtc ttacactatg ggtgcatggg | 2580 |
| cagataatga taaatgtggt gtccgggact atccttattc tacctccttt actgagaacc | 2640 |
| cttttgaacta tacgagcgtg aataccatga acggcgtgca cgccatcgga actgtctggg | 2700 |
| caaccatgct atacgaggtc ttgtggaacc tcatcgacaa gtacgggaag aatgatgggt | 2760 |
| cgaggccggt gtttagaaac ggggtgccta cagatggaaa gtacttgatg atgaagttgg | 2820 |
| tggtggatgg gatggcactg taagtgatgc acagaatagc ttctttcacc tttgtaatgt | 2880 |
| ccgtggtatc ctgactaatg gactgaaggc aaccatgtaa tccgaacttc gtgcaagcca | 2940 |
| gggacgcgat ccttgacgca gacattgtgt tgactggcgg gaagaatcgc tgtgagatct | 3000 |
| ggaggggggtt tgcgaagaga ggattggggc aaggagcggc tcatagtagt ttaaattgga | 3060 |
| tgcggagggg gagtacactt cttcctacgg gatgttagtc ttgcacaggt cgttcttggt | 3120 |
| gagagatgag tggagatgcc tggtttatta gaataggact aattatctag cactaataca | 3180 |
| atatcgacag atctaaacag taagtataaa tctataagtt atcacacgca taaacccat | 3240 |
| cacccctag tctacttcga acaaacacc acaccaccaa catcctcatc ctcaccaaac | 3300 |
| accccctccc cgcataagaa cctaaacaac agccctcaac tccatactct gcgcccccct | 3360 |
| cgccacacac aacaacaacc cacccacgag cagactcacc cccgcgtata tcgacagcgc | 3420 |
| cagaaaccca tacttctgca ccagcgcccc ggaaataggt atcccagcca tagcactaca | 3480 |
| ctcccagata agatatgatt agcaaaatcc acccttactc cccaagaaga tcaattcaaa | 3540 |
| ataaatctaa tgtgcatacc tcaaagccgt agcccccata acaaccccca ccgccaac | 3598 |

-continued

<210> SEQ ID NO 14
<211> LENGTH: 2847
<212> TYPE: DNA
<213> ORGANISM: Aspergillus niger

<400> SEQUENCE: 14

| | | | | | |
|---|---|---|---|---|---|
| cttttggctt | gtgatcttga | ttgctagaga | tgtatatcct | cacgatacc | gccggagtgc | 60 |
| gccatttctg | gttaccttct | ctttcccttt | ttgtctcgat | cgtgaggcgg | aacgcaggat | 120 |
| gaagacacgg | cttctccatc | gcggcccacc | aaccaacaat | gtccttggac | gcccaactct | 180 |
| ccatctactg | gtcattggtc | caatgcagag | actccgtcga | gctcaaatgg | gccggccaac | 240 |
| cccgagtcgt | cagggcagc | ggcagcgacg | agctaaatta | gaccactgat | aagacgcgat | 300 |
| agtccaaagt | ctgaccgtca | cattgtgcca | ggcagataag | ttgaatcgtg | tgactggatg | 360 |
| ttggctaacg | tatggcgtct | ccggaggccc | gacggaccct | gcgcgatcgg | cggtggagcg | 420 |
| caatctaagg | acatccgcgc | ctaagatatc | tacccttcag | cagttcagcc | tagccctgca | 480 |
| gacttgtcgg | accagtgcta | tcgtgatcgg | ccccacggt | cgaatgagct | cttgtctctt | 540 |
| tccgtcagac | cctgccagtt | aatctgctat | ctactccgcg | gtaacatcgt | gcctgtctcc | 600 |
| actaaggcag | ggtccagggc | tgtatgtctt | actttgcacc | gagtcggccg | ccggttggct | 660 |
| ctgtcttggc | aattgcgaat | atcctcacgg | gcgacggacg | acacggattt | ggacggacat | 720 |
| gcggagatct | tcgtcggttt | attcctggaa | gggacatcat | ctccttccat | catgacggct | 780 |
| gccatagcgg | ggactctgag | acatttttgc | tctgaagagc | atggtcgact | tggatgatgg | 840 |
| aggagttgat | cgaggtcaat | gaggagaggc | ttgcaagtat | aagaagagac | tgctcgacca | 900 |
| gcagaatgga | tcttcttgtt | catcaaccaa | gagtccaagg | cttctttgtc | tggttctatc | 960 |
| tcttctccga | actctcttgc | ttgacattct | cgtggtcaaa | atggtcgtct | tcagcaaaac | 1020 |
| cgctgccctc | gttctgggtc | tgtcctccgc | cgtctctgcg | gcgccggctc | ctactcgcaa | 1080 |
| gggcttcacc | atcaaccaga | ttgcccggcc | tgccaacaag | acccgcacca | tcaacctgcc | 1140 |
| aggcatgtac | gcccgttccc | tggccaagtt | tggcggtacg | gtgccccaga | gcgtgaagga | 1200 |
| ggctgccagc | aagggtagtg | ccgtgaccac | gccccagaac | aatgacgagg | agtacctgac | 1260 |
| tcccgtcact | gtcggaaagt | ccacccctcca | tctggacttt | gacaccggat | ctgcagatct | 1320 |
| gtaagcttcc | ctgctcgggt | gttcgggcaa | atcgtgacta | acctggacta | gctgggtctt | 1380 |
| ctcggacgag | ctcccttcct | cggagcagac | cggtcacgat | ctgtacacgc | ctagctccag | 1440 |
| cgcgaccaag | ctgagcggct | acacttggga | catctcctac | ggtgacggca | gctcggccag | 1500 |
| cggagacgtg | taccgggata | ctgtcactgt | cggcggtgtc | accaccaaca | agcaggctgt | 1560 |
| tgaagcagcc | agcaagatca | gctccgagtt | cgttcagaac | acggcaatg | acggcctttt | 1620 |
| gggactggcc | tttagctcca | tcaacactgg | tgagtcaatc | ctacatcagc | cgggttgacc | 1680 |
| tacctgctga | ccgatacaca | gtccagccca | aggcgcagac | caccttcttc | gacaccgtca | 1740 |
| agtcccagct | ggactctccc | cttttcgccg | tgcagctgaa | gcacgacgcc | cccggtgttt | 1800 |
| acgactttgg | ctacatcgat | gactccaagt | acaccggttc | tatcacctac | acggatgccg | 1860 |
| atagctccca | gggttactgg | ggcttcagca | ccgacggcta | cagtatcggt | gacggcagct | 1920 |
| ccagctccag | cggcttcagc | gccattgctg | gtaagaaccg | ccttcattta | acacacaact | 1980 |
| tgtccacctc | tttactaact | agtgtataga | caccggtacc | accctcatcc | tcctcgatga | 2040 |
| cgaaatcgtc | tccgcctact | acgagcaggt | ttctggcgct | caggagagcg | aggaagccgg | 2100 |
| tggctacgtt | ttctcttgct | cgaccaaccc | ccctgacttc | actgtcgtga | ttggcgacta | 2160 |

```
caaggccgtt gttccgggca agtacatcaa ctacgctccc atctcgactg gcagctccac   2220
ctgctttggc ggtatccaga gcaacagcgg tctgggactg tccatcctgg gtgatgtttt   2280
cttgaagagc cagtacgtgg tcttcaactc tgagggccct aagctgggat cgccgctca    2340 ggcttagatt atccactgaa gtggagtcta tgatctgctg attgatccct cgacgatgaa   2400
ctacatgtgg aaatgcatag cagacgaggg tgatggtgat gatgttgatt tgatgatgac   2460
ccgtacatac ttgatgaagc tcggtacata tgcaaatgtg actgtatcta tgtgatgaat   2520
atatgtatcc atctcatggc ttttggctat gagtgcagga taaacacctg aaccagtagt   2580
agtactttcc cacctatatc tactgcggtg cctcgtccgg cccaacatca ccccagaggt   2640
ggccgcagag gagtcttata agatagctac tatcagttac aacacctctc tgacagatgt   2700
gaaggagtac aataaatcac cgaaacacaa attcaactaa agtcggtaag taataataat   2760
ttaagaccca atccacgcaa tgttaaacta tctctggtgt tgaaagatct ctcccctggc   2820
aacacctagt tgtgggagaa ctgtgtt                                        2847
```

<210> SEQ ID NO 15
<211> LENGTH: 2899
<212> TYPE: DNA
<213> ORGANISM: Aspergillus niger

<400> SEQUENCE: 15

```
gcccaggtga agaccggaca ggaagcggat aggtacggga cattttctaa tctacccgcg    60
atcgggacat ggctaaccaa gcatatagac tcgaattcta ccggtaaatc aagtatggga   120
cgtgcatcag gctggatatc ggattacgca aggcgaacag ggggaccgtt agctgtatta   180
tcaacatcta ggctatttca tattaggaca acgactgacg cattgggtat tccgctgggg   240
tagtcttatc ggttggggcc aagtaccttg tagaactgta acccacgtta ataccgccac   300
ttggctgggg cggtgattta gcatatgtaa gctccagttg gacggctacc cgagcttccc   360
atgatctaca ggagtacgtg tctggctgtc tgctgcctac ttggtagaca ggtcagcgat   420
aggtagatag gacctgtccg cagctgttgg ctagtttggt aaggcggttg cgctagtttg   480
aagtaggcag gcaccgggaa cctaaggcgg tcttacatca tcacccgcgc tcggattcgc   540
gtgatccgac catcacgata aggcctcagg tagcaaggag accttccaga cagctctgaa   600
tgagactcaa aggtagatat aatgatggaa agataggata gctagatcag gcttattgta   660
cctgatcgtt aagagcctag agaagatgta cctggaagac ctggcagcta caatcacctg   720
gagcgataac ccgtgacgat ccccttgcca aatgacgcag ccgggctggc caaccattgg   780
ctgcgacctg gcaggtcgct ccgcaaccag cgccgcccgg ctccaagtca cccgcatcac   840
tcttccctac ccccagacct cctctttttcc cttgctatcc tccatctctt cttcatcgtt   900
ctttgtctct atcatcattt tctattcata cgtgcatcat tcagtcgttt ggcccagtcc   960
atcatatccc gctgggtagc cgtttccgcc gtcgcccatc atgaagtcag cctccttgct  1020
cacagcatcc gtgctgttgg gctgtgcctc cgccgaggtt cacaagctca agcttaacaa  1080
ggtgcctctg gaagagcagc ttgtgagtgt ggtctttcac tgctttgttt tttttagcta  1140
gttagcttca aagaagctcc agaaccattc aaagctgatt tcgtggtcta tagtacacgc  1200
ataacatcga cgcccatgtc cgcgctctgg gccagaagta catgggtatc cgcccgtcca  1260
tccacaaaga gctggtcgag gagaacccta tcaatgacat gagccgtcat gatgttctgg  1320
tggacaactt cctgaacgca cagtgtatgg agataccgtc ttcttatggc tgcaactgct  1380
```

-continued

```
gacccttcct gccatagact tctctgagat cgagctgggt actccccccc agaagttcaa   1440
ggttgtcctg gacactggca gctcgaacct ttgggttcct tcgagcgaat gcagctctat   1500
cgcctgctac ctccacaaca agtatgattc gtctgcctcc agtacgtatc acaagaatgg   1560
cagtgaattc gccatcaagt acggctctgg cagccttagc ggattcattt ctcaggacac   1620
cctgaagatt ggcgacctga aggtcaaggg acaggacttc gctgaggcga ccaatgagcc   1680
tggccttgcc tttgccttcg gccggttcga tggcattctc ggcttgggtt atgacaccat   1740
ctccgtgaac aagattgttc ctcccttcta caacatgctt gaccagggac tcctcgacga   1800
gccggtcttt gccttctacc ttggagatac caacaaggag ggtgacgagt ccgtggcgac   1860
cttcggtggt gtcgacaagg accactacac cggcgagctg atcaagattc cctccgtcg   1920 caaggcttac tgggaggttg agcttgacgc cattgctctt ggcgatgatg ttgctgagat   1980
ggagaacacc ggtgtcattc tggacactgg tacctccctg attgctctgc ctgctgacct   2040
ggctgagatc atgtaagtcg aattcttcgg attcctgggt tgaaaagaaa tgctgctaac   2100
aaccttctag caatgctcag atcggtgcta agaagggctg gaccggccag tacaccgttg   2160
actgcgacaa cgctcgtcc ctgcccgatg ttactttcac ccttgccggc acaacttca   2220 ccatctcctc gtatgactac accttggagg tgcagggctc ttgcgtcagt gccttcatgg   2280
gcatggactt ccctgagccg gttggtccct tggccatttt gggcgatgcg ttcctgcgca   2340
agtggtacag cgtgtatgac ctgggcaaca gcgctgttgg tctggccaag gccaagtaaa   2400
ttagttctgc ggggttgatgt ggtatctatg atgcagctgk tgctgtcatt attgcttctt   2460
gtagcttgat ctatgatttt tgcagacgaa cacacgtgat gttgtgaatg gttttcctca   2520
tgtttgcagc ggttgccgga tagattctag ggatcttcaa tggaaagccg gtgatattat   2580 ttgacctta tttgggcact gagaatcttg actgtatgaa atatgatagt aacaccttaa   2640
acatgaatgc aaatggcgta accgtgtga tgcagtcaca ataaccagca accgcggtac   2700
cagccgaagt ctgggccggc gagtctcgcc ccgcacaggc caggcgccaa acccaagcag   2760
cgctcttggc agccaagcct tcttcatcac gctctcacca cctcctccat ccaggctttc   2820
tctctgctcg gtctttgttt catcatcctc ccacgcctgc ccttctattc aaccgctctt   2880
cgatcttcat atccgatcg                                                2899
```

<210> SEQ ID NO 16
<211> LENGTH: 2738
<212> TYPE: DNA
<213> ORGANISM: Aspergillus niger

<400> SEQUENCE: 16

```
gaggcatgag gcatttctga ggcccgctac tccgcattct gcagcatatc gtctctgcgt     60 agggaggtc gaaaccagct gtaggactcg gcttcggtgt atctgtaccg actgactaga    120
aatcgctcaa tcgtgtagta tagctgtctc tttgttcctc acaacatgtc tacgatatgc    180
tattaaaaaa agcagaagat ggagtcagag ccacccggtt agggccgggc cgcccgggag    240
gagaacaaaa tacgggacag aatctcagtg atgggggaga agagagagtg gcgacctgac    300
aattcacaca cgacacgaat aatagccgaa actaacaaga taaatcacat cacatcatga    360
agaagacctg cgtaatgatg ataagcaatc ccaccaataa tacaatgcca ttgatagtgg    420
ctgacctgaa gcaattcggg gaggagacgc caagctcgac gatcaccgga gcttgaaaga    480
ccaacgagac aagatgacag gcccgtcgca ccacgccact aactgcccta acagaaatcg    540
gcctgaatag tgcgacgagt gtcccggttc tgggcctcca cgataagata agtcatgggc    600
```

-continued

```
ttatcgcgtc atcggcgccg atctcgcgat cagctgaaac caatcattca atcaatttgc    660
atcacccgac tggggcgag atttcagggc cagctgaaac ggtcggctgc cgagattgtc     720
agtggatgat gaatgttatg ctggaagaga ggggagaat gacgtctcaa ttctgggtca     780
cttactagtt gactagccac ctagtattta gctgctagct agggattcgg tttaaaagcc    840
tggtggtttc tctcttcttc tcgtcatttt ctcttcatct catacccatt cttcaaaact    900
cctccacttt gatcaattat cctccatcat ggctaccaaa atcaagctca tccccaatct    960
caactacaag cgctcaggca ccaagtccta cgtgcacttg atgcgcaagt accgcttcca   1020
tcccaccaag cctggtccct acactctcag cagctccatc aacagaccg tcgtccgta     1080 cactgaaaag cccatcgggg gtcgggccca tatccggcag ctggtgcgga agaagagcac   1140
caccagcgat gaggttggcg aggttccggc cgaagatgtg cagaacgact ccatgtatct   1200
ggcgaccgtg gggatcggaa ccccggcgca gaacctgaag ttggactttg acactggttc   1260
agctgatctt tgggtacacc cccattatga aagacctaat atggaaacga gcgtcactga   1320
cagatgtagg tctggtccaa caaactcccc tcaaccct tc tatccgagaa caagacccat   1380
gcgatcttcg actcgtccaa atcgagcacc ttcaagacct tggaaggtga atcctggcaa   1440
atctcctacg gagatggatc ctccgcatca gggagtgtgg gcaccgacga cgtcaacatt   1500
ggcggcgtag tcgtcaagaa ccaagccgtt gagctggcag agaagatgtc cagcacattc   1560
gcccaaggcg aagggacgg attgctcggt ctagcattca gcaacatcaa cacggtacag    1620
ccaaagtccg tgaaaacgcc cgtcgagaac atgatcctgc aggatgacat tcccaagtcg   1680
gctgagctgt tcacggccaa gctggatacc tggcgggaca ctgatgacga gtcgttttac   1740
acctttggct tcattgacca ggatctggtg aagacgcag gtgaagaggt ctactacacc    1800
cctgtcgata acagtcaagg cttctggcta ttcaactcga cctccgcgac ggtaaatgga   1860
aagaccatta accggtcggg taacaccgcc attgctgata ccggtacgac gctggccttg   1920
gtggacgatg acacgtgtga ggccattta t agtgcaattg acggcgccta ttatgatcag   1980
gaagtacagg gctggatcta tccgaccgat acggcgcagg ataagctacc cactgtgtcg   2040
tttgccgtgg gtgaaaagca gttcgtggtg cagaaggagg acctggcgtt tcggaggcg    2100 aagacgggct atgtctatgg aggaatccaa agtcgtggtg atatgaccat ggacatcttg   2160
ggagacacat ttttgaagag tatttatgct gtaagtgcat tgctgttggc gttaaggggt   2220
gatatcgaag ctcactaact ggattgcaga tctttgatgt cgggaacctg cgctttggag   2280
ccgtccagcg cgaggagttg cgccagagcc tgaagtcgga gtagacgagt ggctgaatct   2340
atcatggttt gatgatgtta tgtatttgca tgtcccgttt ttttggttaa atcctagtgg   2400
cttttgagcc ccgaagtatg tacgcagtaa atagcagtgc aatatagtac tccgtaccttt  2460 gttatcgat gctctggttt gaagcacaaa ggaagccatc agtctcccaa tcagagcttc    2520
cagcccgccc cgtccttcca tttccacaac ctcagcgcca tgaaacatgc catccctgct   2580
cctaccataa ccgccgcaaa aagctgcccc ttccagaaaa cagcatgttc cagatccaac   2640
aacgccccgg caataggatt tccaatgaga atgccaagcc ccgcgaacac gaaagacatg   2700
cccatccacg tccccacaac agccatgtct ggacacaa                          2738
```

<210> SEQ ID NO 17
<211> LENGTH: 2349
<212> TYPE: DNA
<213> ORGANISM: Aspergillus niger -continued

```
<400> SEQUENCE: 17
cgcgcactaa ccctccacgt attccaatat accaaatctg cccaaagcgc cagccagctt      60
cctcaagcct tgcggtcaga taaggccctg tacctagcta gttgccgctg ctcccggcgc     120
tgggccaagc cgtcggacgt ccgtccccc tctttccccc tcctctcccc tctccactgg     180
tggaacgatg tctggctgtt gccatcgttc tcagaagcaa cgccccctgg atcgggtggc     240
tgtcgtacta ttgcatgttc gtccgcgcta ctaggaaagt ttttttccca cccggagtat     300
ccgtgtttag tccgcgggct ggctgaccgg ctagctggcc gtgccagttg ggtaaggttc     360
caagggagga ccttactagg tagaaacggg atccaacaat gaggggaaaa gggcggatat     420
ggcttgccgg gggttcattg cggcctggac gaagaaaggg agatgatcac taatgcaaca     480
caatcttggc ttgcaaggaa ttgcgctcca accagaatgt ctctgcgtag ggatgccaat     540
tcgtgcgggc catgctggat ggatagtacg ctgctccact ctcgctcgac cttttgcagt     600
ccacaatcgt ttccccgtat cgttgggcgg gggcgttttt ctgcagctat ggttgctgct     660
gccccgacgg tgaacctttc tgcatccccg gttttagtcg attttagttg cgggcctgg      720 agattaaact ccgtcggacg aagaggagca gtggtgtcat cgtcggcgga ttgcatgcta     780
tcggaagagc atggaagagg gaaaacatca acttcatttg caaaacgctc gagcataaat     840
agaggcctgg attccgccgt tctggtgtct tttcttcttc atccagcatc gcaagtctct     900
caagcatcgc ctggttcgtt cttctcactc ttccaccacc agccttgtca ataagttagc     960
tcttcatctt ttcgaagaaa ccaattctcc aaacgtcaaa atgaagttct ctaccatcct    1020
taccggctcc ctcttcgcca ctgccgctct ggctgctcct ctcactgaga agcgccgtgc    1080
tcgcaaggag gcccgcgccg ctggcaagcg ccacagcaac cctccctaca tccctggttc    1140
cgacaaggag atcctcaagc tgaacggcac ctccaacgag gattacagct ccaactgggc    1200
tggtgccgtc ctgatcggcg acggctacac caaggtcact ggcgagttca ctgtccccag    1260
tgtctctgct ggatctagca gctccagtgg ctacggcggt ggctacggct actacaagaa    1320
caagagacaa tccgaggagt actgcgcctc cgcttgggtt ggtatcgacg gtgacacctg    1380
cgagaccgct attctccaga ctggtgtcga cttctgctac gaggatggcc agacttccta    1440
cgatgcctgg tacgagtggt accccgacta cgcctacgac ttcaacgaca tcaccatctc    1500
cgagggtgac accatcaagg tcactgtcga ggccaccagc aagagcagcg gtagcgccac    1560
cgttgagaac ctgaccactg gccagtccgt cacccacacc ttcagcggca acgtcgaggg    1620
tgacctttgc gagaccaacg ccgagtggat cgtcgaggac ttcgagtctg gtgactctct    1680
tgtggctttc gctgacttcg gctccgttac cttcaccaat gctgaggcta ccagcgacgg    1740
ttccactgtc ggcccctctg acgctaccgt tatggacatt gagcaggatg gcaccgtcct    1800
caccgagacc tccgtctctg gcgacagcgt cactgtcacc tacgttttaaa tgcatctcta    1860 tgcatgagat atcggtcgct tcaatgtctt cgagacgaag acaaaccctg gggatgaatg    1920
aaaaaatgag tgatgagcta tccggattga tctgatcttg ttgagttgtt aattccgttt    1980
ctgttgatgt ttttgaatga ttatacctac ttttaagtag aagaaatgga tgagcgcgtg    2040
catgctgaaa atgactgtcc ctgcttatat tgtagaagat cttccagaaa gctgtgctgc    2100
cgatctgaag atctgaagat cactagtgag atctcgcagc tcggctgtgt aagtgcattt    2160
gctctgtcga tcataacttt gtaaaagctt gtatgcatag cagacatctg tcgattattt    2220
agatgcttcg atttgatcat ctttactaga atccccattc gagtagagct tcagagcgtc    2280
gggtggaaat atcgggtcgt ggatggtatc ggagaagtct cacaacatga acgaaagatc    2340
```

-continued

| | |
|---|---:|
| cgcggtata | 2349 |

<210> SEQ ID NO 18
<211> LENGTH: 1495
<212> TYPE: DNA
<213> ORGANISM: Aspergillus niger

<400> SEQUENCE: 18

| | |
|---|---:|
| tgattgtgca gacttcctca tcatcgaagg agacaacaat gaaacccag ggagacacgg | 60 |
| aagcaggaaa acagactgcg gccggcgaga agacacgt gtgacgaagg cttatctcgt | 120 |
| gacgccaaga caatgcgggg aaagctgccc ttccaagacc caactggcct gcctctttct | 180 |
| cattacaacc tcatcgcctt gattgacttt ctggaccttg gtggcttgga ggccggtcgc | 240 |
| atcgagcttg ctactcgcta cttgctttgt ttcgatgact ggctttcgtt gatcgcaaca | 300 |
| ttctttcttg gtatttttgt agggatagct agttgcttat catgggagat tacggccccg | 360 |
| gagtgtcgtc actcacggca cagctacctg gaaatccgcc tgtctctgaa acagatcagg | 420 |
| atgagatctc agtacttgta acgggctttg gggtaagctt ccagtgtcca taccattctc | 480 |
| ccaatatcgc aactcacatg ttctacagcc attcaagtct aatctagtga acgcctcata | 540 |
| tctgatagcc tcgtccctac caccctcttt cacattctca cctgcatctt cagacggctc | 600 |
| tgatgctgtt ccccgtcgag tttcgataaa tgtccatcct tcacccatac ccgttgcata | 660 |
| ttcatcggtg cggacgaccc tccccgtcat tctcgatgac tatgccaaga cgcacggagg | 720 |
| ccgacgccca gacatcgtca tacacattgg catagcagca atgaggaact actattccgt | 780 |
| ggagacgcag gctcaccgtg atgggtatct gatgtccgac atcaaaggca gatccgggta | 840 |
| cgaggatggc gagaagctgt ggagggagct cgacttgcca ctggtgctta gggctggccc | 900 |
| ttcagaggga cacgcctcgg agaagaaaca tctcagcccc cgtccaccgg acgaagattt | 960 |
| cctagcagca tggaagacat tttgccctcc agaaaccgat gcgcggatct ccactgatgc | 1020 |
| cggacgttat ctctgcgagt tcatcctgta caccagcttg gcactggcat accaggcggg | 1080 |
| tgaggatcgc aatgtcacct tcttccatgt tcccgcgtca tgcttggatg aggatataga | 1140 |
| gacgggcaag gaggttgccg tcgcgctaat caaggctctt gtgactagct ggagtgagca | 1200 |
| gcagcacagc gttccctagt tctgaatgac ttttttcaatc ttctcggagt tgtgacattg | 1260 |
| catgtcccag cagttttggt ttatcggtgg tcctatctga gtactatatt ttttttggcaa | 1320 |
| tattttgcat tagtgaatac atatgggcgc ctgatgggtt atgatcgcat cacacctggc | 1380 |
| gccgcataga ttttgggcat aaggagtgtt ggtgtaagat caccatcaat ttattactgg | 1440 |
| tgttggattt gtgtagggat agaaccaata tagattaaat tctcacgcca tacat | 1495 |

<210> SEQ ID NO 19
<211> LENGTH: 2501
<212> TYPE: DNA
<213> ORGANISM: Aspergillus niger

<400> SEQUENCE: 19

| | |
|---|---:|
| gcgtcttcgg caagcggaag ggaccccgca aaagctacgc attgccattg ttcaggaacc | 60 |
| cactaaataa acacacggac atgtggtttt ggctgcccgt gcgccccgaa gccgcagccc | 120 |
| gaacggaggc attaaccctg atgcgtccgt tgattgttat ggtcttgtcc aacataacgg | 180 |
| ggaattctg accgcacacg atgccaggca acccatttta tcacggctga gcatgttgat | 240 |
| aggtgttgaa ttcatttttcc gtaggcagac gtctcctaga gcaatttctg ctgtatggca | 300 |

-continued

```
gacattcgtg accgaaaccg tctcactcac ggtctaccat ggtagttatg cttcgtacat    360
aagacaagaa aggaatgcct tcaatcatgg caagaaggga atttggtaat ttgggtgcta    420
ctgccgtctt cctttgttgt gaaccttctc cattacacac agtgtccctt gaaggccccg    480
tatgccttca tactccgcca caatagccgc catcggggct ttcctgcttt cgcagcccgt    540
catgggctca aggcagggaa aggccccctt tggctggggt actcagtcac ttgctcactt    600
tggtatcaac ccagaccttg ggttgcacaa ccagcagaac ctcaactccc tcatttcaca    660
ttcagcgatg gccactgcgt tggagacgga atatgccacc gtatgaaaag caccagccct    720
ggctcttagt cctgatcact gattgtagac tcagatccct attgaccata caacgcatc    780
ggctggcact tatcaaaatc ggttctgggt cagcgatgaa ttctatcagc ctggcaaccc    840
gatatttgtg tacgataccg gggagtcgga tggcggatcg atagcccagt cctacctaac    900
ctccactctc tccttcttca gagaattcct gatcgaattc aacgccatgg gaatcgcctg    960
ggagcacaga tactatggaa actcgacccc ggctcccgta tcctatgaaa ctccacccga   1020
ggcatggcaa tacctcacca ccaagcaggc gctcgcggac cttccgtact ttgctagtaa   1080
cttagccgc gagaagtatc ctgacatgga cctgacgccg cagggcacgc cgtggatcat   1140
ggtgggcggc tcgtacgcag ggattcgtgc tgcattaact cgcaaggagt acccagagac   1200
gatattcgca gccttttcct catcgtctcc ggtggaagca caggtcaata tgagcgcgta   1260
ttacgaccaa gtctatcgtg gcatggttgc cagcggatgg accaactgct cggcagatat   1320
ccacgctgct ctggaatata ttgacgatca actttcggat gaagatacag ctacctcggt   1380
caaacaactt ttcttcggat ctggcgccga gaccaactcc aacggtgatt tcactgcagc   1440
gctaactgcc atctacggct acttccaaag ttatggtatg gcgggaggta ttggaggtct   1500
aggcgcattc tgcgagtatc tcgaaattga tcccaagacg aacgggacta caggaccgga   1560
tggccttgcc cctacgtatg gcggccagta tgtcgccgaa cgatgggccg catggccaac   1620
ctttctcgag ctggtcaatc tgaatatggg gaccaactgc gggcctcagg acgcgtctca   1680
gccaattgac tgtgactttt ccaagccata cggcgatccc tcggccatca cttggacttg   1740
gcaatactgc agcgaatggg ggttcttcca ggcgaacaac gatgggccgc actcgctggc   1800
ctcgcgatat cagtcggtgg aataccagca agaagtatgt aaccggcagt tccccgatgc   1860
agtggacaag ggactgctgc ctccgtcgcc gcgggcggat gatgtcaacc aagagtttgg   1920
gggatggacg atccgcccgt ccaatgttta cttcagcgga ggagaattcg atccgtggcg   1980
atcattgtcc attctgtcga cagaagattt cgcacctcaa ggggtggagt ttacgagcgc   2040
gatcccagcc tgtggggtgc agaccaatga ggacaccgtc tttggatacg tcatgcagaa   2100
ctcggaacat tgctttgact ttcaagcgac gccgaccgtg gggaagttat cacgcggcat   2160
cttcacatcc gccttgttgc aatggctcga atgttttgga cagaactcaa gccaatccag   2220
gtgatctggg gggccagggg gtgtgtgggt gtgtaggtgt gggtgtgttt ggttgtgctg   2280
gagcctggag ccaggataaa gaagatagga caaggatgac tgagtggatc ctgggatgct   2340
cctacttact tagaaaggta cagggcgcgt cacggcgaag gtagactcgt accccagatt   2400
agatgatcaa cgagaagcct cggaggtttt ggatcaacgt tgggttttag cgtcacgtcc   2460
aaagtcctgc atgcaggtgc cgcttttccc ttttgggaga t                      2501
```

<210> SEQ ID NO 20
<211> LENGTH: 2660
<212> TYPE: DNA
<213> ORGANISM: Aspergillus niger

<400> SEQUENCE: 20

```
agagtccgcc ttgacaatgt ctaagaaagc atgctgagcc ccctccccca gtgtttatag      60
gtgagtagga atggagtata gtgcttgagt gctttcacgc tggtaaacgg acccgctggg     120
cggctagact gccttgtttt cggtctagga accattcaag attcaacggc tacaagtcaa     180
gtcagaccat ctatcaatag tgcgagatag cagagagtcg gaccggagtc tcacaggcat     240
ccttggcggt cgaggagtga tgagttgtgc gaccagcgcg tgttccttat ttaagccgcg     300
cgcgcacctc tgacgcaacg gtctcaaagg ggggtctcac ctcttgcatg ttcggctgca     360
ttcaattcga cctctccgtg tctgtctagc atcaccccaa atcctatcgg aatagtcctc     420
cggttaagtc aacattgcaa atcagtcctt tcattttgc ccagctcagc gctcggcctt      480
ctgtgaccct tggagcctga tcaattgccg aaaggtgttc gggcgggtca gccttggaca     540
gctcatttgc agtgcagagg ttcatcagca tcagctgtac tacttgactt cctatcatca     600
ttattgatta ttatattata tcctatcttc tccgccaatc ttccatcgcc ggtagttttt     660
cgtagacaac atgaagctct caatagctct tgcactcggc gcaacggctt cgacgggggt     720
gttggctgct gttgtaccgc agcaagaacc gctgataacc ccccaagatc ccccaactca     780
tcatcatcag gagaagttct tgatcgagtt ggctccttat cagacgagat gggttaccga     840
ggaagaaaag tgggacttaa aactggtata gcaacattcc ccatttatt actgtcacaa      900
tagcacatct cactgatcgc tctgcgaatg ttccattagg atggcgtgaa cttcatcgat     960
attactgaag aacgaaacac tgggttctac ccaacgttgc atgctggtag ctatgttcac    1020
tatccgccga cgatgaagca tgcggagaag gtggttcccc ttctgcgggg tctctccaag    1080
gacaacatgg agcaaaacct caacaaattt acctcatttc acactcgcta ctataggtcg    1140
tccactggta ttgagtccgc aaagtggcta tacagtaggg tttcggatgt cattgagcag    1200
tcgggtgcag cagagtacgg cgccactgtg gagcagttcg ctcactcatg gggccaattc    1260
agtatcattg ctcggatccc aggccagact aacaaaactg ttgtcctggg cgcacatcag    1320
gacagcatca atcttttcct cccctccatc ctagctgcac ctggtgccga tgatgacgga    1380
agtggaaccg tgactatact cgaagctttg cgtggtctgc tgcagtcaga cgccattgtc    1440
cggggcaacg cttccaacac aatcgaattc cactggtact cggcagagga aggtggtatg    1500
cttggttcgc aagccatatt ctctcaatat aagagagata agcgagacat caaggcgatg    1560
cttcaacagg atatgactgg ttatacccag ggagctctgg acgccggtcg tcaagaagcc    1620
attgggatta tggttgacta cgttgatgag ggactgacac aattcctcaa agatgtcact    1680
actgaggtaa ggtcactccc gctttccttc tttgtgagac atataactaa cgattgcggt    1740
caaagtattg tggtattggc tacatcgaaa ccagatgtgg ctacgcctgt tcggaccaca    1800
cgtccgcaag caaatatggc tatcccgcag ctatggcgac ggaatccgaa atggaaaaca    1860
gcaacaagag gatccacacg actgatgaca gcatccggta tctaagcttc gatcatatgc    1920
tggagcatgc gaggttgaca cttggcttcg cttacgagct ggccttttgct caattctagt    1980
gtccttcatg attttacgtt gtaaccgggt ctagcagata attctggcta actagtgagg    2040
cttatatgtg ttcaggtttc ctatgtcggt ttattgtggc attagacaag attacagagt    2100
aaccaatact ccatttgta atggaataga tgtctgaggc ccaagtgttg gcaaggaacc     2160
ttgcctatat accacagatt aatactattg gctttggtga ttcaagaata ggcctatggc    2220
tggactttat atatgttgac attctatttt gtaccggcaa cagactctaa cactagcacc    2280
```

-continued

| | |
|---|---|
| taacaaataa aacacgtgtg actcttatgg gtggcatgat gatagtctgc agaatggccc | 2340 |
| gataagataa acgaaggaga tcctactata cccgattgag tcacactagc ctgaaacaga | 2400 |
| aagacggtca ctccgccggg gcgatcactt ccactggctt caatcttcga gtcattcctg | 2460 |
| cggtctgttt tctccttgtt accactccct ttgcccttca gatcagatcc tgaacggaga | 2520 |
| aagctcaccc ttcatactac ataatattct acataacttg cttggactga attggcgata | 2580 |
| ttccgtcggt cgctcctatc tatcgcctac gtcaccagcg gtgcccctcc aaggaagacc | 2640 |
| ccaccatcag accttggatc | 2660 |

<210> SEQ ID NO 21
<211> LENGTH: 2047
<212> TYPE: DNA
<213> ORGANISM: Aspergillus niger

<400> SEQUENCE: 21

| | |
|---|---|
| ccgagctata caaatgcgca tacaaaaatg gacagagtta catttcaacg ataaacatga | 60 |
| atgataagct tccagcaatg gcggccaagc gatatgcaaa ccgattttag tacgcattcg | 120 |
| gtttatctgt tatctctctc ggagtaaact gtatgctctt cgccgaaacc acaaaagtaa | 180 |
| gcggggaaac gtatactacc aatcaaacac cccgagatgg tgactccgaa cgcagcagac | 240 |
| ctatttagat atatttaggc atgacaagta tcaatggatg acagaaacac cgagacctgg | 300 |
| tacaatctaa gttgaggaga gatttgaatc agaaagcagc tcgcacattt catcatgaga | 360 |
| actactacgt cttttgctag gcttgcattg gcagtggcct cagttggtat tgtctttgct | 420 |
| agtccaacaa aaaataacga tgggaaactg gtatatggct caccagaatc cgtcggcatg | 480 |
| atatccgccc ctttgcacca aatggtccaa aatgttagcg catatacaca tgctgccaac | 540 |
| tatagcaagt tctcgtacga caaagtccat cccatcgagc cagggtctgt taccctggtg | 600 |
| gctctcgacg gtgtcatcgt cagcgaattt gccttgggca agagaaatct ctacgccgat | 660 |
| gtcaacggca ccaatttacc tcgatacctg caggaagaca ccaccctgga tacagtctac | 720 |
| gatatggcaa gcctcacgaa gctgttcacc acggtagctg cttacgggaa acttgacgct | 780 |
| ggtcgaattg cgcttaatgt aactgttgca acttatatac cggactttgc gacgaatggg | 840 |
| aaggagaata ttactatctt ggagctgttc acgcatacaa gcggtttcgc ttctgatcca | 900 |
| tcgccaccac ttttctctgc ttattatacg acgtatgatg aacgcattaa agcaattttg | 960 |
| acgcaaaaaa ttatcaatac ccccggcagc acatacctct acttagatct caactttatg | 1020 |
| tcgctgggcc tcgttatcga gaccgtaacg ggacgtgccc tggatgatct tatttatgac | 1080 |
| ttcaccagac cgcttgaaat gacatctacc ttcttcaacc gcgggaatat cgaaggctct | 1140 |
| acaccccagt cacccaacta cgaccgcaca gccgtacaag aatttcagat cgcagccctc | 1200 |
| ggaccctcag aaccacagcg tccacaacca gtgcgcggca cagttcacga cgagaacgca | 1260 |
| tggtccctag acgcgtatc aggtcatgca ggtctattct ccactgtgcg cgatacagcg | 1320 |
| acattctgcc agatgatcct caacaacggc acatatgcag ccaacggat ctttctcga | 1380 |
| acagcggtag acatgatttt cacaaacttc aatgccaggt ttccggggga tgctcgtagt | 1440 |
| ttagggtttg agttggatca gtattctact gcgggaccga tggcgagttt gcaaactgcg | 1500 |
| agtcacactg gatttactgg gactacgttg gtgatggata ggacgtataa cgccttttgg | 1560 |
| ttgcattttta gtaaccgggt gcatccgtct agggcatggt ctagcaatac tattgtgaga | 1620 |
| gaggctattg ggtattgggt tgggaagagc ttggggttgg atgttgcgtt tgctctgttg | 1680 |
| taatggttga gcggaggacg taccagatgg gatcctggat tcattccttc gatacacttg | 1740 |

| | |
|---|---|
| tatgtacacg aggaatgtat tcgaatgcaa atacctcata tattacagaa tccgcagtat | 1800 |
| gaatccggat aattttgtta aggcaaatcc agaaatttct aaaggttcac taccataaac | 1860 |
| acaaatattc accattcaat atggcatgtt atcatccatt ctcataaaag accctcgatc | 1920 |
| cggaagaccg atcctgtcag ggaattagtc aaccctctcc aataaatgca gcatgaaaga | 1980 |
| aatctaccat gaatcaaccc cgagccctaa ataatccgaa agatccagt ctggtgacag | 2040 |
| tgcaggg | 2047 |

<210> SEQ ID NO 22
<211> LENGTH: 2730
<212> TYPE: DNA
<213> ORGANISM: Aspergillus niger

<400> SEQUENCE: 22

| | |
|---|---|
| tggccacgcc atcctcttat gctctctcta tccactctct ccctcagctt ctctcaacca | 60 |
| cttccttacc catctttcac cctctcttcc cctttccccc tttcaaatct cttgaccttc | 120 |
| aagtctggcg cgcgtctgga cagcggctct tgtgctagag gtcttaactc ctaccccgcc | 180 |
| ttcctctggc cttgaccttc tctgttcctg aaccaggttc cctcccggtc ctctccgccg | 240 |
| acgttatccc cgacattgtg ctgctcatta cctccgcccc caaggtaacg ggtaagcgaa | 300 |
| aagtgcaagg cccagttggc taaatttcga tgactccttg agcgcgactc caagtccgct | 360 |
| tgggaccgtt tcctccgctc cgtcttcggc aatatctact actactacta ttactattac | 420 |
| taccccggtc agccgccgcc gccgtattac aagtacccat cgcctactga tggtctcctt | 480 |
| atcattccgc ggggagacca cttccattcc ctccatggcg tcctggttgc tctcgacgct | 540 |
| cctttttctg agcccgtcct tggtgtcagc caaatcggcc gcagactatt atgttcactc | 600 |
| cttgcccggt gccccgagg ggcccttgct gaagatgcat gccgggtaag cttcgctgtc | 660 |
| ccggaacggt ccgcttagca cctatatact gacttattgc ctccacgcgc agccatattg | 720 |
| aggtggatcc acagaacaat ggaaatcttt tcttctggca ctaccagaat cgccatattg | 780 |
| ccaaccgcca gcgactgtg atctggttga acggtggtcc cggatgtagt tccatggacg | 840 |
| gcgcgttgat ggaggtcggt ccgtatcgcc tgaaggacaa tgaaaccttg acctataatg | 900 |
| agggttcctg ggacgaattc gccaatttgt tgttcgtcga tcagccagtc ggaaccgggt | 960 |
| tcagttatgt caacacggac agctatcttc atgagctcga tgagatgtcg gctcagttca | 1020 |
| ttgtcttttct ggaagagtgg ttcagattat tccggagta tgaacgcgat gatgtatgct | 1080 |
| gcaatcacct atgctgccct agtcctgcac cttcacggat tctgttctaa catctgcgac | 1140 |
| agatctacat tgccggcgag tcttacgccg tcagcatat tccatacatc gccaaagcca | 1200 |
| tccaggaacg gaacaagaac gttcaaggga agaccatcgc ttcgtggaat ctaaaaggcc | 1260 |
| tattgattgg caatgttgg atttctccta atgaacagta catgtcctac ttgccctacg | 1320 |
| catatgaaga aggccttatc aaggaaggca gccggaccgc gaaggaactc gaagttttac | 1380 |
| agtcagtctg taagtccagg ctggaaactg gcaagaacaa ggtccacctc aacgactgcg | 1440 |
| agaaggtcat gaatgctctg ttggataaga cggtcgaaga caacaaatgt ctcaacatgt | 1500 |
| atgcatccg ccttcgtgac accaccgatg catgcggtat gaactggccc accgacctgg | 1560 |
| aggacgtgaa gccctatctg cagcgggaag atgtggttaa agcgcttaac atcaatccgg | 1620 |
| agaagaagtc tggctgggtg gagtgttcag gtgcagtgag cagcgctttc aatccgcaaa | 1680 |
| agtccccgcc ctcggttcaa ctacttcccg gcttgctgga atcgggactt caaatcctcc | 1740 |

-continued

```
ttttcagcgg agacaaggac ctgatttgca accatgttgg aacggaacag ctcatcaata   1800
acatgaagtg gaacggaggc acgggtttcg agacctcacc tggcgtctgg gctcctcgac   1860
acgactggag tttcgaaggc gagccggcgg gtatctatca atatgccaga aacctgactt   1920
acgtgctcat ctacaacgca agccatatgg ttccctacga ccttcctcgt cagagccggg   1980
acatgctaga tcgcttcatg aatgtcgata tcgcgagcat cggaggcagc cccgccgact   2040
cgcgcattga cggcgagaag ctgccccaga cgtcggtggg cggccatccc aacagcaccg   2100
cggcggagga gcaggagaag gagaggatca aggagacgga atggaaagcc tacgccaagt   2160
caggcgaagc cgttctcctc gtcgtcatta tcggtgtatt agtttgggc ttcttcatct    2220 ggcgcagccg ccggcgtcac cagggatacc ggggcgtctg gcataaggac atgagcggaa   2280
gctctgttct cgagcggttc cacaacaagc gcacggagg cgcagacgtc gaagcggggg    2340
atttcgacga ggcggagctc gatgaccttc attctccaga cctcgaaaga gaacactacg   2400
ccgtgggcga ggacagcgac gaggatgata tttcacgaca gcattctcaa caggcctccc   2460
gagccggggg cagtcataat ctatcctagt tcatctttgg ttgggtaaac ttgtgatggt   2520
gtaggtgtat ggcttgcttg gggtctttgc cttttgtttt tgtttcttg gccacgaaag    2580 gacgtgcctc cttatatgtg catttatcat tttatctagc tggctgcctg gcatcattta   2640
acatttagac atgaacaaag tttatgaccg cttcctgata catagccagg cggaaattcc   2700
tcccgtctat aagccaacag tctcatccac                                    2730
```

<210> SEQ ID NO 23
<211> LENGTH: 2660
<212> TYPE: DNA
<213> ORGANISM: Aspergillus niger

<400> SEQUENCE: 23

```
actttattgc caagcgaatg acttcgactt tcttatttct gcaacgcgtt tggccagtta    60
ataatttgct agactcaact gattgctcgg tgccatctta ccaggatcg gcaagccgaa    120 aagtacgcta ttgcacccaa tctgtaaaga agacttctcc aaaactccaaa gtagaacaga   180 cccatcttta gctttaataa ctccaatcat gacgattgga actatcggaa aatataatct   240
aagttcaatg gatctggtcc gtcgctagaa tatcggagta aatgagccca accccctggcc   300 atcaggttcg acggaggaat tcttctggtt gggtacaaga ttgacacgat ccccttggcc   360
gctgaacgtc actcttccgc tgtcaaagct tgttggctga cttcgatccc ggatgatgtt   420
tctgatttca cctgcagtga cagttgcggc tgcacttctg ctgatcaacg cgcaggagc     480 aactcaatct gaacgaagtc gggctgccgc tcatttttcc aaacgtcatc cgacgtaccg   540
tgctgcgacc agagcccagt cgagcaacac ttccgactac cgattcttca ataataggac   600
caagcgtatg tattacaccg gccatgaact ctattcgtcg ctgacatgtg gtcatccctg   660
gatagcccac ttggtggaaa gcttacccga tgtgcacttc gatgttgggg agatgtactc   720
ggggtcgatc cctatcgatg acagcaacaa tggatctcga tccctgtttt atatcttcca   780
acctaagata ggcgaacctt cagacgacct taccatttac ctcaatggag gccaggctg    840 ttcctccgaa cagggattct ttcaggaaaa tggcaggttc acatggcagc ctggtaccta   900
tgcacccgtc atcaacgaat attcttgggt caatttgacg aacatgctat ggtacgcttc   960
ttcctgagga ttaaattgga ggtatgcact ctgtacattt tatgagacta atgtgaataa   1020
attcagggtt gaccaaccag tcggaaccgg attttccgtt ggaatgttca gccaccaa     1080 cgaagaagag attgccgccg attttctcga cttctttgaa aagtttgaag atctatacgg   1140
```

```
                                    -continued
gataaagaac tttcgcattt tcatgaccgg tgagagctac gccggtcgct atgttcccta      1200
tatctcgtcg gcaatgctag acaagaacga caccacgcgt ttcaatctga gcggtacgag      1260
ccctgtctac tcataactac taccccctata agcttagttg actgaaactg acttttttaac    1320 gtccctctag gagcccttct ttatgacgcc tgcatcggcc aatgggacta catccaggcc      1380
gaactccctg cctaccccctt cgtcaagcag cacgcttcac tattcaactt caatcagtcc     1440
tacatgaacg agcttgaaac cacctacgaa gaatgcggct acaaggccta cttcgatgag      1500
tactttgcct ttccaccaag cggcatccaa cccccaaaat acatgaacta ctccgagtgc      1560
gacatctata acatgatcta ctacgaagcc tataacccga acccatgctt caatccctac      1620
cgcgtcattg atgagtgtcc acttctctgg gacgtcctgg gctggccgac agacttggca      1680
tacgagcctg cgcccaccac atacttcaac cgtatcgatg tcaagaaggc cctgcacgcc      1740
cccatggatg tggaatggga gctctgcagc tacgacctcg tcttcgctgg aggcgacgct      1800
gacccgggtc cggagcagca aggggatgac tcacccaacc ccaccgaggg tgtcctcccg      1860
cgtgttattg aggcgaccaa ccgcgtgctc attgccaacg gtgactggga ctacctgatt      1920
atcaccaacg gcaccctcct cgccatccag aatatgacct ggaacggcca gctgggcttc      1980
cagtccgcac ctgccacacc gatcgatatt cagatgcccg atctccagtg ggttgagatt      2040
tttgaggccc aggagggata tggagggctg gatggccctc aggggttat gggtgtacaa       2100 cattatgagc gcggtttgat gtgggcggag acatatcagt cggggcataa gcaggctcag      2160
gatcagggcc gtgtctcgta tcgccatctg cagtggctgt tggggcaagt tgagattctt      2220
tagtctcccg ccttagatat aattgatatc acactgtaat gttccctcca aaaagcttca     2280
tttattgata gtttcagtga attttgttac ttccagtaac aactctatta tggcattccc      2340 tggttttttaa tgctgcctcc ttttaccgta gctacggcta tgactacata taacggactg    2400
atttttctat ctcaacttaa ctttgtattg ccccctggat cctgactaca gaaaataaat     2460
aattcaaatt gatatttatt ggccttttat tggcagcata atatctttct catataagca     2520
cgcgagaaac ttgttcctca tcatactata tttatcccca cagctgatgc cgtgattcgg     2580
taatgaagat ggagattatg cggattgcgc acttcataat caaacatcgt ataagtgtgt     2640
cagtaatata tatctataat                                                  2660

<210> SEQ ID NO 24
<211> LENGTH: 2800
<212> TYPE: DNA
<213> ORGANISM: Aspergillus niger

<400> SEQUENCE: 24
aatgccgaag cttgacctga tacgacttca aggtatcgtc accgacaatc gttatcatca       60
cgctacaggc ccgcagtttc cgcttgaatt cccgcattag gaaatgagca tcgcattcct      120
cttcccacga ggtctctttc cgagggcagc cgctgcaaca tcattgggat catgcttggt      180
tctcctctcc catagctgtc cgcgagcttc tcattggtac ctcttcgcta cctcgttgca      240
tcctattcgc gcatggcccc gccagagatg tttctgcaag gtcccatcac cttgccgcgt      300
tgctattccc cgccctcgag ttcccgacaa gttactttgt gtcagtggct gagaagcctg      360
gttctgagag tgtactcaga caatcatatg gttccctcca tgtgctacgt cgtcctagcg      420
tcgctgcact acatcatcgt taggcagcat ggaactggca cccgcacata aagccccga      480 caccccccatc gataggctcg gtgttcgtgc acgcctgtcc actggcccct ccccaaagg      540
```

-continued

```
cccttcatca gtatgctgtt tcgcagtctg ttgtcgacgg ctgtcctagc cgtctcgctg      600
tgcacggata atgcttcagc tgctaaacat ggtcgatttg gccaaaaagc tcgcgacgcc      660
atgaacatcg cgaagcgttc cgctaacgcc gtgaaacact cgttgaagat ccctgtcgag      720
gactatcagt tcttgaacaa caagactaag cgtatgtatc tcagttcgat attgaacgat      780
ggctgatttg cttccgtcgg acagcttacc gcgtggaaag cctgcctgat gttcacttcg      840
atctgggcga gatgtattcc ggcttggtcc ctattgagaa gggcaacgtg tcacggtccc      900
ttttctttgt cttccagccc actattggcg agcctgtgga tgagatcacc atctggctga      960
atggtggccc tggttgcagt tcccttgagg cctttctcca ggagaatggt agattcgtgt     1020
ggcagcctgg aacctaccag cctgttgaga acccatactc gtgggtgaat ctcaccaatg     1080
ttctgtggta agtgtgatat tactggatcg ctagttgagt ttacatgggc ggtatcgacc     1140
taacctattt tttgtagggt tgaccaacct gtgggaacgg gattctctct gggtgtccca     1200
accgctacgt ccgaggagga gattgctgaa gactttgtga agttcttcaa gaactggcag     1260
cagatctttg ggatcaaaaa cttcaagatc tatgttactg gagaaagtta tgcgggccgt     1320
tatgttcctt acatatccgc tgcttttccta gatcagaatg atacagaaca cttcaaccta     1380
aaaggtgagt tatacttcac caaagtaatc tttaactagg gcttgtactg attgtactat     1440
ctaggtgcac tggcatatga tccctgtatt ggtcagtttg actacgtgca ggaggaagca     1500
cctgttgttc cctttgtcca agaacaat gccctcttca atttcaatgc aagctttttg      1560
gcggaactag agagcatcca tgagcaatgt ggatacaagg atttcatcga ccagtatcta     1620
gtcttcccag catccggtgt ccagccgcca aaggctatga actggagcga tcccacctgt     1680
gatgtttatg acatcgttaa taacgccgtc ctggatccca acccgtgctt caaccccatc     1740
gaaatcaacg agatgtgccc cattctctgg gacgttcttg gattccccac cgaagtcgac     1800
tatctccctg cgggcgccag catctacttt gaccgcgctg atgttaagcg tgccatgcac     1860
gctcctaaca tcacctggtc cgagtgctcg gtggagagcg tctttgtcgg gggcgacggc     1920
ggtcccgagc aggagggcga ctactcggcc aaccccatcg agcatgtctt gccccaggtc     1980
atcgaaggca ccaaccgagt tctgatcggt aacggtgatt atgacatggt catccttacc     2040
aacggcaccc ttctctcgat ccagaacatg acatggaatg gaaagcttgg attcgacacg     2100
gcccccagca cccccatcaa catcgacatc cctgacctga tgtacaatga agtgttcatt     2160
gagaacggct atgacccaca aggtggtcag ggtgtcatgg gcatccagca ctatgagcgt     2220
ggtcttatgt gggctgagac cttccagagc ggacacatgc agccccaatt ccaacccaga     2280
gtgtcatacc gtcaccttga gtggctgctt ggccggcggg ataccctgta aggcgggtag     2340
gctaccacgg gggacgatgt cacgatgata gtcataagtt atgatctgta gatacgttgt     2400
atgcgaatgt acatgaattg ctttactgg cagtctctaa gcaaaattc atagtagagt      2460
actggcctac ttaccctcac ttcccctatc ttttcaacct gaagaccgga agaattgtaa     2520
ctaacaagca taacgtagct gatttgaagc agagcataac acactctacc cctcggcact     2580
tctacttatg acgctatttg actgctaact cgggtttaat cctgaagctg cagtccaatc     2640
gtacattaaa ctcaatgtgc cttgcccagg aaacgatatt tgacttatat gatctgaaaa     2700
tgaacaattg tccccgagag agagagagag agcgagcggt aaatacttag caagtcagtc     2760
acgcagtatc ctccactaat gccgtaacac aggaaatgga                           2800
```

```
<210> SEQ ID NO 25
<211> LENGTH: 2165
```

<212> TYPE: DNA
<213> ORGANISM: Aspergillus niger

<400> SEQUENCE: 25

```
gaatcaggat ggaggcccga cggccatcaa ccgccgaaca tccggctgct cgaccgaatt      60
cggagacatg gtcggagcta ggcgggaata gccgtccaaa gtcacgatag gtcgcttgta     120
ctgtgtagaa gtcagaccct ttggatccag cgttcgttgt gaatggctcc acgcagcctt     180
tgctttgacc aatttggggc tgagtcactt ggtcgatgat gactggctat accagtgcaa     240
agtgtgagca ccatgcttac actattgcct tagcctggcc gttgaagctg acatgagagg     300
aacaggcaga agagaaatgc tgccttgcct cttgggggcc aatttaacct ccccagactg     360
cggcacatcc gtcttggact tgtgcttctt tgcaacttac gttataacga gtctgtgaac     420
aggaaaacag acgcccggtc agtcaagatg aaaggtgcgg cgctaattcc tcttgcggcg     480
ggcattcctt ttgcccatgg cctgtctctc cataaacgcg acgggcctgc cgtcgttcgt     540
atgcccattg agcgcaggag cgcccagtcc ttgcagaaac gagattctac ggtcggtgtg     600
actttgcaga actgggtatg ttaagctata cggccgtgaa gtatagatca tgctgacaat     660
cgctaggatg cgacctatta cgcagtcaac ctgacgttag gaacacctgc gcaaaaggta     720
tcattagctt tggacactgg cagcagcgac ctctgggtga acaccggcaa ctcaacttac     780
tgctcaatcg acaatctatg caccccttat ggcttgtaca atgccagcga atcgtctact     840
gtaaagaccg tgggcacaca cctcaacgat acatatgcgg acggcacaaa cctttacggt     900
ccttatgtga ccgataagct cacgatcggc aacacaacaa tcgataatat gcagtttggg     960
atcgccgagt caacgactag taaacgtggg tgaaccgttt gtccatgaat gatcgtcgct    1020
gactaggtct actataggcg ggatcgccgg cgtcggttac aagatttcga cctaccaagc    1080
cgagcatgac gacaaagtct acgccaacct ccctcaggcc ctcgtcgaca gcggtgccat    1140
taagtctgct gcgtacagca tatggctaga tagtttggag gcgtcgactg gctccctcct    1200
tttcggaggt gtcaatacag ccaagtacaa gggcgatctg cagactcttc cgatcattcc    1260
tgtgtatggc aaatactact ccctcgccat cgcccttacg gagctcagcg ttgcgaccga    1320
ctccaactcc agtagcttca ccgacagtct ccccctctct gtgtcactcg atactggcac    1380
caccatgacg gcactgccca gcgacctggt caacaaggtc tacgatgcgc tcaacgcaac    1440
ctacgacaag acatacgaca tggcctacat cgactgcgac actagagagg cggattacaa    1500
tgtaacatac agtttctccg gggcaacgat caccgtgagc atgagtgagc tgattatccc    1560
cgcaacggag ccggggtggc ccgacaacac gtgtgtcttg ggcctcgtgc ctagccagcc    1620
gggcgtgaac ctgctcggtg atacattcct gcgcagtgcg tacgtcgtgt atgatctcga    1680
gaacaacgaa atctctctcg ccaataccaa tttcaatcca ggcgacgatg atatcctcga    1740
aatcggaacg ggaacgtctg ctgtgccagg agccacaccg gttccctctg ctgtctcttc    1800
tgcaactgga aatggactga tctcgtctgg caccgcagtg cccacgctgt cgggtgtcac    1860
aataactgct acagccacag caaccggctc aaccggcact ggctctagcg gtggttcgtc    1920
ggctgaagcc acgagtactt cctcggaggg cgctgcggcg caagctacga gcaacccgat    1980
gaacctgctc ccaggacttg cgggtatcgg cctacttctc gctctgtaac gcgattgtac    2040
ctactcaaat agatatcacg acgagactct aatgtaataa tgtggtatac aataacccca    2100
atatctacat ttccttaacc gtaaactgca tactctacac caaatccacc accaaaatac    2160
atacc                                                                2165
```

<210> SEQ ID NO 26
<211> LENGTH: 2800
<212> TYPE: DNA
<213> ORGANISM: Aspergillus niger

<400> SEQUENCE: 26

| | | | | | |
|---|---|---|---|---|---|
| gcccagccaa | tcataagaaa | cccggtcctg | gcaaggtctt | ggcggggatg | gtgcaagcca | 60 |
| gccaaacaac | cggtttgttg | gacgccctgc | ggtacactga | aatcttgggc | tgttcgacaa | 120 |
| aaacaaagca | ggtaacacaa | agatataata | cggcggaatg | ataggatatc | cctgtcgatc | 180 |
| agccggacag | gatggcgcta | gtgtcacctc | cagcttcggc | taccctcgca | gcggacccaa | 240 |
| tcagcgtccc | tcccagcccc | cgatacagta | atggtatgca | catcgcagtc | ttaatcgcct | 300 |
| gcagcggcag | taatgatagt | cctgccggtg | aataatccc | cataacaaac | aaataaataa | 360 |
| tactacttat | ctctcctcgt | cccctttcact | ttcctttgc | cgtcttcaat | ccctcatct | 420 |
| tggtctcttc | ggcagccttt | caccatgctg | tcgtctctcc | ttagccaggg | agcagccgta | 480 |
| tccctcgcgg | tgttgtcgct | gctcccttcg | cctgtagccg | cggagatctt | cgaaaagcta | 540 |
| tccggcgtcc | ccaatggtga | gttatagacc | ccaattcttc | attttgagcc | acatactgac | 600 |
| gtgattcctt | cgaatactac | caggctggag | atacgccaac | aatcctcaag | gcaacgaggt | 660 |
| cattcgcttg | caaatcgccc | ttcagcagca | tgatgtcgct | ggtttcgaac | aagccgtgat | 720 |
| ggatatgtcc | accccccggac | acgccgacta | tggaaagcat | ttccgcaccc | acgatgagat | 780 |
| gaagcgcatg | ttgctcccca | gcgagactgc | cgtcgactca | gtccgcgact | ggctggaatc | 840 |
| cgccggtgtc | cacaatatcc | aggtcgacgc | cgactgggtc | aagttccata | ccaccgtaaa | 900 |
| caaggccaat | gccctgctgg | atgccgactt | caagtggtat | gtcagcgacg | ccaagcatat | 960 |
| tcgtcgtctg | cgcaccctgc | aatactccat | ccccgacgcc | ctggtctcgc | acatcaacat | 1020 |
| gatccagccc | accaccgct | ttggccagat | ccagcccaac | cgtgccacca | tgcgcagcaa | 1080 |
| gcccaagcac | gccgatgaga | cattcctcac | cgcagccacc | ctggcccaga | cacctccca | 1140 |
| ctgcgactcc | atcatcacac | cgcactgtct | gaagcagctg | tacaacatcg | gtgactacca | 1200 |
| ggccgatccc | aagtccggca | gcaagatcgg | cttgtccagc | taccttgagg | aatacgcccg | 1260 |
| gtatgccgat | ctcgagaggt | tcgagcagca | cctggctccc | aatgccatcg | ccagaacttt | 1320 |
| cagcgtcgtc | caattcaacg | gcggcctcaa | cgatcagctt | tcatcgagtg | acagcggcga | 1380 |
| agccaacctc | gacctgcagt | acatcctggg | cgtcagcgct | cccgtccca | tcaccgagta | 1440 |
| cagcaccggc | ggacgcggcg | aactagtccc | cgacctgagc | tcccccgacc | ccaacgacaa | 1500 |
| cagcaacgag | ccctaccttg | acttccttca | gggaatcctc | aagcttaaca | actccgacct | 1560 |
| cccacaagtc | atctctacct | cctacggtga | agacgaacag | gtatgcacct | cacctgaccc | 1620 |
| attccatttt | acatccctca | cctctctcaa | ccaaactaac | aacaccaaca | gactatcccc | 1680 |
| gtcccctacg | cccgcaccgt | ctgcaacctc | tacgcccaac | tcggcagccg | cggcgtctct | 1740 |
| gtaatcttct | ccagcggcga | ctccggcgtc | ggcgccgcct | gcctcaccaa | cgacggcacc | 1800 |
| aaccgcacgc | acttccctcc | tcaattcccc | gcctcctgcc | cctgggtaac | ctccgtcggc | 1860 |
| gcaacctcca | agacctcccc | cgagcaagcc | gtctccttct | cctccggcgg | cttctccgac | 1920 |
| ctctggcccc | gccctccta | ccaacacgcc | gccgtgcaaa | cctacctcac | caagcacctg | 1980 |
| ggcaacaagt | tctcgggggct | tttcaacgcc | tccggccgcg | ccttccccga | cgtctccgcg | 2040 |
| cagggcgtca | actacgctgt | ttacgacaag | ggcatgcttg | ccagttcga | cgggacgagt | 2100 |
| tgctccgcgc | cgacgttcag | tggcgtcatc | gcgttgttga | acgatgcgag | actgagggcc | 2160 |

-continued

```
gggttgcctg tgatggggtt cttgaatccg ttcctgtatg gtgtcggaag tgagaagggt    2220
gcgttgaatg atattgtgaa cggcgggagt gtgggttgtg atgggaggaa tcggttcggg    2280
ggcacgccta atggtagtcc tgttgtgccg tttgctagtt ggaatgccac gaccgggtgg    2340
gatcctgtgt cggggttggg aacgccggat tttgcgaagt tgaaaggggt ggcgttgggt    2400
gaggagggtg gtaattaagt gtgagatggg gggaaaggga ttttcttttc gatgtgaata    2460
ttaggtgaat tgtgtggata attttcatac ataattaagt ctgcattggc agtgataacc    2520
tggaagaaat gtctaatgag tgtgatttgt ttacttatgt atattgagta atggaatgta    2580
gatgacttgt ctttgtactg tataacgaaa tgattatttg agtggagggt attaaagaac    2640
tataaaatat atacaaaggt taacccatgc agtcgtaacc cataatgcaa agctctactc    2700
tatctgtatc ggtagcagat aagtgtatgc aatctatctt tgttgatgat gcaatcaagc    2760
gggcacacca ccagtgccaa acagctccat cttgatgcgg                         2800

<210> SEQ ID NO 27
<211> LENGTH: 2660
<212> TYPE: DNA
<213> ORGANISM: Aspergillus niger

<400> SEQUENCE: 27
ggagacagaa tacatggaat tgatgctcaa caacgacaag gagctcgcgt tccgtaatgc      60
caagttcatc gcttagattg ggaggatcgg ccaggtctgt atataggccg cgatagaaca     120
cgaaataaat gatttatgac tatttgcggg catgagccct cacgtagtgt gctatagacc     180
gtagacttgg taaacattgc tatcgatccc ccccttcgta tattagtcat aattcttcct     240
gatgtcaact ctcaaaacac agcattccac agcgttcata tgatgtcaat gtctcaatcc     300
ctaacgtttt gctgaaacag gtacctcttg gttattttc atatagtagg aaggtcgccc      360
ttgcatgtgg tatgagacca ttggcggcat ctagcttgaa tggtactcaa atgaccagt      420 agtctccact tcagcagtgt gtttgtgata gccaagacat cggcagtagt tcctgcagag     480
cttctacacc tcttcatctt cacttccacc atccactctc tcactgctca cttctagttt     540
cgcaacacta gagaatcatg tggctctttc tcgtgtgcag tatcctgctg ccacttggag     600
tagtcaacgc acagtctcaa tacttcaaca acaaaaccaa aggtatacca catcgcgtca     660
gtttgaatcc cactaacagc gctagaattc gtcgtcaatg gctctgctat tccttttgtc     720
gatttcgaca ttggcgagtc ctatgcgggc tacctaccca acacgccttc tggaatctcg     780
agtctatact tctggttctt tccatcttct gatcctgatg cgtctgatga ggtatgctta     840
tcgccgtctc atatgcttcg cacggctaat aaacagatca ccgtctggct gaatggcggc     900
ccaggatgca gctctctggc aggcatcatg ctcgagaacg gcccctttct atggcaacct     960
ggtacctacc gacccgtgcg caacccttat gcctggaaca acctcacaaa tatggtgtac    1020
attgatcagc ctgctggaac gggattctcg cttggcccgt ctacggtggt ctcagaattt    1080
gatgtagcca gacagtttat ggacttctgg aggcggttca tgaaaacatt cgatctgcag    1140
aatcgaaaga tatatctcac tggcgagagc tatgcgggcc agtacatccc atacatcgcg    1200
tcgcagatgc ttgaccagga tgatgatgag tatttccggg ttgccggcat ccagatcaat    1260
gatccctaca tcaatgagct gccagttttg caagatggta tgcctctgac acaggttatt    1320
gcttactcct ctgacattga tgcttccag tgcctgcagt tgcgaccgtc aatcagcacc     1380
gctccctctt tcccttttaat gacaccttca tgagtcaaat caccaagctt tccgacgatt    1440
```

-continued

| | |
|---|---|
| gtggctacac ttcgtttctt gacgatgccc ttacctttcc accccgttct caattcccat | 1500 |
| cagtgcccta taatgctagc tgcaacatct gggatatcat aaacaacgct tctctagctc | 1560 |
| tcaacccatg cttcaaccgc taccatatcc ccgacgcctg ccccacccc tggaacccag | 1620 |
| tcggcggccc catcgttgga cttggtccga ccaactactt caaccgcagt gacgtccaga | 1680 |
| aagccatcaa cgcgtaccca acggactatt tcgtctgcaa ggatggaatc ttcccgacgg | 1740 |
| ccaacggact ggacacatcc cctccaagct ccctgggacc gctgccgcgc gtcatcgaac | 1800 |
| agaccaacaa taccatcatt gcgcacggcc tgatggattt cgagctgctg gcgcagggaa | 1860 |
| ccctgatcag tatccagaat atgacctgga atgggaagca ggggttcgag cgggagccgg | 1920 |
| tggagccgtt gttcgtgccg tatggtggat catcgggagg aggcgtgctg gaacggcac | 1980 |
| atacagagcg tggattgaca ttttcgacag tatttagttc aggacatggt aggtccatat | 2040 |
| ctcagtatgc gatgcagcgg gttgctaaca ggaatagaaa tcccggaata tgcaccgggg | 2100 |
| gcggcatatc gccagctgga gttttttgctg ggagggttg cgaatctgtc ggtgggttga | 2160 |
| ccggagacag caaagagaat gaagaaaaga aaaaaaaaa aaaaaaacaa tatgaataat | 2220 |
| tgcagacaat tattgagcag gtgcagataa cagagcagaa tggttgagct gtcagatcgg | 2280 |
| ttgactttc ggcaatgaga tttggggaag ctagctctga gattggtcct ccgccaaagc | 2340 |
| tatcgcaatc atgatccaat caacactgca tactaccttg atcccctcgc tgtagacccg | 2400 |
| tattgccgga caaacaattg actagatatg aactcttgat tataaaccaa tcaagacccc | 2460 |
| cagtagcgca tattatcacc cccatacgtt catgatcggc agcctaatcc gaggtcggat | 2520 |
| cgggaattcc ttcaaactct gaaaccgcgc tgggtccacc ccgcatcttc acagtaaaaa | 2580 |
| tctaagattc ccctcaatcc ctgctccatc tactttcctc cctctcatac cacttttgct | 2640 |
| ttttgtatag taaatatcca | 2660 |

<210> SEQ ID NO 28
<211> LENGTH: 1540
<212> TYPE: DNA
<213> ORGANISM: Aspergillus niger

<400> SEQUENCE: 28

| | |
|---|---|
| taaacagaac taagcaaaag tccagatctt gtgtcccctt cgactaccaa tcggaacaat | 60 |
| aggaattaac tattagcctg caactgtctg caccatcatg caacccctct cgttgtgatt | 120 |
| gctcctgttt tacattcccc gagacatgct catctagttg caagccatct ctaacccacc | 180 |
| tgcatgaagg gtgcagaaac acgaacagtg gcgtggtagc acacactctc tgcagtactc | 240 |
| gatgccaata tttccaccag ctgaactaca atctccgcgt cagaattaat atataaccat | 300 |
| caccaatacc ccttacatcc caactcagca actacagcaa tacttacacc tatcctccac | 360 |
| aaccccacaa ctccacccca tcatgtccaa actctccgct gctatctcca aggtacttcc | 420 |
| ccatatccac aacacccccc acaccatccc tcaaatctaa caacaataac aataacctct | 480 |
| caccacccca gctctccctc tccaccatag ccaccactct gctcctcctt accccccaa | 540 |
| ccaccgccta cttctacaaa tatcccgccc tcttcgtcta caaagacacc aactgcaccg | 600 |
| atatctcctt ctcacttgtc tacccctccc tgggtaactg caacggcgga tactacgact | 660 |
| acgcgggctc attccagatg ttcaatatcg atgctgcgta tacctgtaat ggcagtgact | 720 |
| cgacactgat gtttgagatg tataatagct ccggctcgga ttgtggagat gagagtgatt | 780 |
| tgttgtttag acagccggtg acggaggagt gtactgttgc ggatgtggag agtccggggc | 840 |
| cgttggagat gccggtttgg tttgagttgg ggtgtatgta attgattcgt tgagtcggta | 900 |

-continued

```
aggagggatg gacgggggggt tatataggta gcttggtggg taagcactat tggggaattg    960
tggtgggatg gctggtacta tgttgttcgg tgtggggatt cttgagggtg ggttagagac   1020
taaagtgagt tgtctgaggc agtagtggat gacttctgct tctgtgatgc tggtatgtga   1080
taaagttaat tacatatgca aatgtgcaat catagactga taggtggaaa cttgtctact   1140
cgttgagata tatagttata ctggaaatgt tattcatcaa ggctgaatac aagtgtaacc   1200
gtgcacagat tatctttgat actgtctatg ggctgtacga gcgtctctga ctcctacaat   1260
gagttagcgg ctgcacatta ctatgaggac ctgtgaattc gacaccaaaa ataaccagcc   1320
ctgcagccga ttacatctgc ctttccatct attttctgga gtcaagcagg tattccaaca   1380
tactcttact tgcttaatac accaactttc atatatctac ccagaattac tcaatcgtga   1440
tgtaggcact ggcaatcata gtaactatat ttcgtttcat tttatttgtt tgtacaattt   1500
ttttttttccg gtagtttaat cattccaatc aaagaattgt                         1540
```

<210> SEQ ID NO 29
<211> LENGTH: 2800
<212> TYPE: DNA
<213> ORGANISM: Aspergillus niger

<400> SEQUENCE: 29

```
acactttctt cgatgctatg tcccagccat ataaggttca attctccgac tcaagtgaca     60
gaatcagcta tacacggttc actgcttctt atatagtaca tgaggattca ataaagccaa    120
gttcagcaga gtcttggttc cagagcttga atactcggta gcattccagg gattgtgggg    180
agacaatcca ggagcagcag ccatcatttg gtgcctgagg cacacagcac tgcctcgtct    240
ccactcccaa tacttaccaa gtcacccacc attccttccc tctttcggcc tttctctttc    300
tctctctcac ttctgctctc gtgcaccact ttcttcccca ctcacgccat ccttctccat    360
ccatttcctg ccaaactttt gtctgtcatt ttaggttttt tgaaggagat gactcggtga    420
ctactcttca atcccggcgt actcaacatc cataatgcgt cacctcttat cactgctggt    480
gcttctgatc gcatcggccg ccctggtctc cgccgtcccc gccggctcca ttatcactcc    540
acaaccaccc gtcgagcccg ttcaccttct ctcttcccag ccctctgatc cccgaaggcc    600
atggatccgc ctccgtgact ggatcatcga gtccatatgg ggcatcgaaa acccgcatc    660
tcgtcgattc ccactcaacg attccccgcg caatcgctct cctccctccc ggattctggc    720
gcgctacggt agtgacgtcg tacttcgttt cagcctgcgc aatcacgatg aggccgaggc    780
attggcccag gctgcagaca ttctattcct ggacgtatgg gcgtctactc cagcattcgt    840
agatatccga ctggccgagg aagtcgtaag tggttcatcc ttccgtccat atctgcccgg    900
ttgactgatg cctgatccac tgtgaccctc gcaacagatt ccctcattat tgggcttgct    960
accaaattcc ctccagaccg catatactcc cctaatagac aacctggcag agagaatcta   1020
tacgacctat ccatctaaaa agccgatagg acttgaagga caatctggat ttgcgtcctc   1080
gagtcgacct gcgccaaagt tcggtgacct ttttttccac gagtatcagc ctttgtccgt   1140
cattatcccc tggatgcggc tgctggcttc catgtttcca tcccatgtgc gcatgattag   1200
cgttggagta tcttacgagg gtcgcgaaat tccgccctc cgactgagcg caggcagctc   1260
caccgcggcg tcaggccctc gtaaaacaat catcgttacg ggtggtagcc atgcccgcga   1320
atggattggc acctcaaccg tgaaccatgt aatgtacacg ctcattacca agtatggcaa   1380
atccaaggcc gttacccgcc ttctacagga cttcgactgg atcatgatcc ccacgatcaa   1440
```

-continued

```
tcccgacggc tatgtttata cctgggagac ggaccgacta tggcgcaaga atcgacagcg   1500
gaccagccta cgcttctgtc ccggaatcga tcttgaccgc gcctgggct tcgaatggga    1560
cggcggtcgg acccgcgcta acccttgttc agaaaactat gctggagacg agcccttcga   1620
gggaatggaa gcacaacaat tagcacagtg ggcgctcaac gagacacaaa acaacaatgc   1680
cgacatcgtg agcttccttg accttcactc ttactctcaa acaattctct accccttctc   1740
ctactcctgc tcctcgatcc ctccaacgct cgagagcctg aagagctag gccttggcct    1800
agccaaggcc attcggtacg cgactcacga atctacgat gtcacttctg cctgcgaagg    1860
catcgtcacg gccagtgcgg cagataacaa ccccgggcgg ttcttcccca ttggtggcaa   1920
ctccggtggc agtgcgttgg actggtttta ccaccaagtg cacgcgactt attcatacca   1980
gatcaagctt cgtgatcgcg gaagctacg gttcctcctt ccgtctgaac acatcatccc    2040
caccggcaag gagatctaca atgttgttct gaaattggga tccttcctca tcggaggcga   2100
ctcatttgac gtcgattggg aatcagaact cttcgatctg tcaaaggacg aatccgatct   2160
ggatagccgc tattcaaaat ccaatgaccg ctccccggcg tatctacaca cgccaacgg    2220
cccccctgccc aacattgacg aagacgaaga taaggaatgg gtaatggtgg aggaagaaga  2280
ctacacagac gatgacgacg acgatgatga tgatgatgaa gaagaggaag aggaagagga   2340
agatacatat tgggccaccg aacacacata cgaatttcgg cgacgacgct gatgatggac   2400
aaactaatca accctatttta tatgacaccc tcgcccatat actctccttc tgatgacgat   2460
caataatgac taatgacggg tttgcgggag tgattgacgt gtttatcatg ctctgcttct   2520
cgattctttt tattatttta gatactgttc ccttcaggtg cctatagcct atagagctta   2580
ggggtattct ctacataatt aaatacagag taattcaatg aatcgtccta tcaaataatg   2640
gacccgagta actaactggt gtttcattcc ttccgtactg tacttaatct gtaaggaatt   2700
gaaagctaag cctcataagc tacttcaccc cactctttac ccaggtgcag tgtatcatga   2760
tcatcgtcat acattcattc gttaggtatc tttccgatgc                         2800
```

<210> SEQ ID NO 30
<211> LENGTH: 2380
<212> TYPE: DNA
<213> ORGANISM: Aspergillus niger

<400> SEQUENCE: 30

```
cccgcctgta caaggctcat tgagcgacct ttatttctat gaaggcttct tgcagtgtag    60
agccgctgtt tagaactcgg aaataggcgt gcatagtatg gacccaatca acagagttaa   120
tctatttact ctaacgccta gcaagcaatc agtgcccaga ggaagctaac ggatggctgg   180
ccaagctgcg ccagaaacga aatgagtccg taataccatc cctgcatgct tatctgtatt   240
ctgtgcatgc atgatgcttt cctcatgggg cattacccag tagtccgaag acgcaatgtg   300
accatctgac tgagttttaa atatactgtc caagtgcctt ctgacccggt cccgccttga   360
tggcaatcaa caaaaggtga atgtgactga aaggcgcggt ccagacaaca ggacttagac   420
tttgttgtga gactataaaa ggatctaact attgcactac tgaaatcaag tattctagtc   480
taccattgac atttctcccc tttcggtggc tactcgctca acatggcttt cctcaaacgc   540
attctcccgc tgctggccct catcttacct gcagttttca gtgccacaga acaggtccct   600
catccgacca tccagaccat cccggggaag tacattgtta ctttcaagtc cggcattgac   660
aatgcgaaga ttgagtctca tgccgcatgg gtaacggagc tccacaggcg cagcttagaa   720
ggccgcagta caaccgaaga tgaccttccc gccgggatcg aaagaacgta cagaattgcc   780
```

```
aattttgctg ggtacgcggg gtctttcgat gagaaaacta tcgaggagat ccgcaaacat    840
gaccatgttt gtgtccacgt atcctagacc gtatggtttc gactaattgc tgtacaggta    900
gcttatgtgg aacaagatca ggtctggtat ctcgatacgc tagttaccga aaggcgagct    960
ccttggggac tggggagcat ttctcaccgt ggtgggtcta gcaccgacta catctatgat    1020
gacagcgctg ggagggtac atacgcttat gtagtggaca ccggcatctt ggctacgcat    1080
aatgagtttg gtggtcgtgc tagcctggca tataatgctg caggggggtga gcacgttgat    1140 gatgttggac atggtacaca tgtagcaggg accatcgggg gcaaaacata cggggtttcg    1200
aaaaacgctc acctactgtc cgtgaaggtg tttgtaggtg aatccagctc gacatcggtc    1260
attctggatg gcttcaattg ggccgccaat gatattgtga gcaagaaccg gaccagtaag    1320
gcggcgataa atatgagtct tggtatgtgc gccctctctg gggatctaat cccgctaacc    1380
gtgatgcagg tggaggctac tcctatgcgt ttaacaatgc agttgagaat gcttttgacg    1440
agggtgtgct ctcttgtgtt gccgctggaa atgagaatgt aagctctgct gaactgtcca    1500
ccattgagct aaatttagac taatgttttg cagagagatg cagcacggac tagcccggct    1560
tctgcacccg acgccattac tgttgccgct atcaacagaa gcaatgcccg tgcgtcattc    1620
tcaaactacg gctctgtggt tgacattttt gccccgggag agcaagtact ttctgcatgg    1680
accggctcga actcggccac caacacgatc tccggcacgt ccatggctac accccatgtg    1740
acaggtttga tcctctattt gatgggcttg cgggaccttg ctaccccagc ggctgcaacg    1800
accgagctca agaggttggc tacgcggaat gctgtcacca atgtggcggg tagccccaat    1860
cttctggcct acaatggaaa cagcggcgtg tcaaagggg gtagcgatga tggagatgag    1920
gactaggtgc gtaacatgag tgaatatggc ttagaatagt ggggatcgga gagtagacta    1980
gtttatatgc gaaataaagt gtgtatcagc accctggcct gttcatgtaa gtcggcattt    2040 tcactttgc cgacaccgca aatatgctgt gcttgaggct gttgcctccc cagccagcct    2100
tcccgagact gaaactcaca catccattgg atgtataaag ttctgcacat gcgaaatgcc    2160
gctgccgttt acctcccgac gtggtaccgg accgaaggca gacacagatc atggaccgct    2220
ataccgcaca gacaacttgt gctccttact gaaagtacca ttccacaggt cattgcagca    2280
tgatgagtga tgatgtactt ctccccatca agaaccactg gcggtggttg aatgaatct    2340 agatcaaaga gatcaaccgc ttccccggac agatcaggcc                        2380
```

<210> SEQ ID NO 31
<211> LENGTH: 2441
<212> TYPE: DNA
<213> ORGANISM: Aspergillus niger

<400> SEQUENCE: 31

```
aaacgacgtt ttaggtcaat actgaagtcg ttgaaaacgc ttgattcttc gctatctagg    60
cgcgctcgga ggagcagttg aagttacgga gttcgggtca cgtgacctcg actactagta    120
atctactgag attacgttcc aacataattt catcaggaag aatgcaaagg ccccagagaa    180
ggagaatttc acgatcggtg aaaacgacca agcagcatca catttgaatg aaactacatt    240
gctccgtgtt tattccgttt ctctctcttc tctctatcta ttgcttctct ttggctagac    300
ttcaccaact aattaatgct tacacgatga tagctgcatc cattgaatca aactgacccc    360
gcaaagctga ctgaaccaac ccctccggtc ctgttgctac tgccagtttg aattcaatat    420
cctataaccc accctgctca atgatcaccc ttttgtcggc cctgttcggc agcgtagtat    480
```

-continued

```
atgccgctac gcagaccgtg ttagggccag aggggggctga tccctttacg gtgtttcgca    540
gcccacactc accggcattt tcaattcgca tccaggagca gaatgactcg atctgtgatg    600
ctcgttcacc ccaattcact ggttggctcg acattggccc gaagcatctt ttcttttggt    660
attttgaaag ccagaatgac cccttccatg atcccctaac gctatggatg actggggggcc    720
caggagactc gagtatgatt ggacttttcg aagaagttgg cccttgccgg attaatgagt    780
ttgggaatgg aacagatcac aaccctgggg cctggaccaa gaattcatca cttcttttg    840
ttgaccagcc agtcgatgtc gggttttcct atatcgatga gggctatgag ctgcctcatg    900
actcacgtga agccgcggtg gacatgcatc ggttcttgcg attattcata tccgagattt    960
ttcctcacaa acagttcctt cccgttcacc tttccggtga atcttacgca gtaagataga   1020
agccgccccc agaaaagct tgctcagtgt tctaacaatt accttgtgat acactgtgta   1080
gggccggtac attccttatc tggcgaccca atcttggaa caaaatgaac tgtataaaga   1140
tagccccagg ataccgctga aatcgtgctt ggtgggtaac ggattcatgt cacccaagga   1200
tgcaacgttc gggtattggg aaacactgtg tactactaac tcaggagtcc catctcctat   1260
cttcaatgaa actaggtgcg atattatggc ggcgaatatg ccgcactgta tggatctata   1320
tgacatatgc attcaacact cagaccccgc gatatgtcat gcggcccagt ccgtctgtta   1380
cgatagtgtt gtagggtagt atgataacga ggccggcgct gatggccgta acagatttga   1440
tagtgagttg ttatcatcag aggctcatgg ccaaattatt gctaaggatg acgacagtca   1500
ctgcaccttg tgagatcgac gaaatgtgct atatcgaagc ggctctaatt gagagatatt   1560
tgaattcgcc atctgtttgg gaggccctgt cgccaccgca acaggttacc gaatacaaat   1620
tcgtcgctac ttctgttatt gatgcatttg ctcaatcagc ggacggcatg gtgtcgagct   1680
cgaagcagat cgcttttctta ctcgcaaata atgttgactt cttagcgtat caaggcaacc   1740
ttgatctcgc ctgtaatacg gctggcaacc tacgttgggc gaactcgctt tcttggaaag   1800
gccagacaga atttaccgca aagcccttac ttccgtgggt ctcgatcaac tctgggagcc   1860
aggaacctgt ggggagtgcg aaggaaattc aggtttcggt cggtgaaggg acggacgaaa   1920
cgtcacgctt tgcctttgtg actgtggaca acgctggaca cctggtaagt caaagtaaaa   1980
ttaggagaga ggggtttaat gatccagttg gctaacgagt agtgttggta ctatggtagt   2040
tgccccaaga tcggccggat gtagcgcttg acatgatgat tcgctggatt actggggcat   2100
cctttgttta acaaggaaca gttgcgggac tcaaagattt caaactgacc tactccttac   2160
cttttatgaa atgggcccgc tgcctaggtc aaacaagggt gctcgggcaa acaataccag   2220
ttttggacta ggggtccgtc tgctttcatc agcccttcgt agcttggact tttgtccatg   2280
tccctgctgc ctcggtccat cacacgcccg ctccccccat ttcctttcct tcccttctct   2340
tttcgttcta ttatgcttga gtgcccgatc ttccctgcat gctatgccta tttcagtgta   2400
cgcagtttgg gttttttgtcc gaggaagaca atcatccatg c               2441
```

<210> SEQ ID NO 32
<211> LENGTH: 3500
<212> TYPE: DNA
<213> ORGANISM: Aspergillus niger

<400> SEQUENCE: 32

```
gtttgttgtg gttgttgttt ggggtcccat ttgcaatccc tgaaccggac cctgtcaatc     60
cctcccaagt ccctcgttat cttccgcctt ttccacccccc tccacacttt attttttccat   120
ccatcatctt ccagtgcctc aatccaaatc actgtcgttg aatatagatt cgcatctgtt   180
```

-continued

```
ttccgtacgt gtatttgttt actttcggga gggagattct cgccgttcat tccagatttc    240
cgcccgtccg ccaaggcggc tgcgcctcca gccaagccaa aacctccttg gatcgccagg    300
tggaaagaat ccctttcact cccccgtcga gtgagtctgt ctcactgctc cctccggtcg    360
ttgcgcgcgc tctctctttc ctctccacac ctccagtata cttcctctgc gggtgtgtga    420
gagactgcga cgatccggag aagaataaaa ccctccagtg cagcttaatc tccggagtga    480
tccgtcatac atgaccggct cccgagccaa gatctcgact gggtccatcc agtgaaaggg    540
aactcaatcg tttgcacttt tcgtcgctgc ctgatgctgt ggaccgaagg gctctgttga    600
accctgactc tccggatctc tcggtgttgt tttgatgcca gcacgctcgt tccacactca    660
cctttaacct ctcccatcgg ctgtcttcac tcgctgacag caatgcggtt tctcacttat    720
tccctgccct tcattgcaag tgctatctcg ctctttgggg tcaatgtaca aggttagctc    780
ggcgacatcc ggcgcataga tttgttctaa ctggatcaaa tacagctcga tcacaagctc    840
caagtgccat ccgtcatgtg tcgacgcttg accagcccac catcaagaca ccctcacagc    900
gggtcgatca ccttgaccac tttgacatca ccttcaatat tcatgacaag caccagcgga    960
taaagctgga gctggagccc aaccatgaca tcctggcgga agacgcatcc gtacagtatc   1020
tcgacgcgga cgggaacgtg cgacggcacg agcccattgc tccacatgag cataaggtct   1080
tcaaggggag gagtctactc gggcgaggaa aaggcatgtg ggatccggtc ggatgggcgc   1140
ggatctactt gaagcaggat ggctcagagc cactatttga gggagtcttc agtatcgacg   1200
gcgacaacca tcacgttcag ctgaaatcgg catacatgga aagaaacgc cccgtggatg   1260
tcgaccttcc cgactcagcg actgactata tgatcttcta ccgggattcg gatatggtgc   1320
gtctacatac ggaactcaag cggtcgtcgc tcggatcgac ctcgtgtcaa gccgatcagc   1380
tcggcttcaa cactaaccc aaccaccctg tgctacaacc gtatggccag gcagagaccg   1440
atacgtgggg agcaatttca ttgaactcct tgtttggact caacaagcgc caatccgata   1500
tcggaagtgt gtctggcaat gcgggcggag tcaatctggc gtcgaccatt ggtgatactt   1560
cgggctgtcc gagtacgaag caagtagctt tgattggtgt tgcaacggac tgcgccttta   1620
ccggctcatt caacaacgag actgccgcca aggaatgggt catcagtact gtcaacagcg   1680
cgtccaatgt ctacgaaaag tccttcaaca ttacgattgg gctgcggaat ctgactatca   1740
ccgacagctc atgccccgac aacccgcccg cggccacggc atggaacatg ccctgctcca   1800
gcggcaatct cacctcccga ctggatctgt tttccaagtg gcgcggtgag caatcggatg   1860
acaatgctta ttggaccctg atgagcgatt gcgcgacggg caacgaggtc ggactgtcat   1920
ggcttggcca actctgcaat agcgatgctt cttcggatgg ctcgagcacg gtcagtggaa   1980
ctaacgtcgt cgttcggtct tccggctcgg attggcagat cttttgctcat gaatctggcc   2040
acacctttgg cgctgtccac gactgtgact cccagacctg cgcggaggat ctcgaagcct   2100
cgtcccagtg ctgtccgttg acctcgagca cctgcaacgc caacgggaaa tacatcatga   2160
atcctacaac tggaacagac atcactgcgt tctcgcaatg cactatcgga aatatatgcg   2220
cagccctggg ccgcaacagc gttaagtcca gttgtctctc cgccaaccgc gacgtcacca   2280
cctacactgg cagccagtgc ggcaacggaa ttgtcgagtc cggcgaagac tgcgattgtg   2340
gcggggaaga tggttgcggc gacaacaact gctgcgacgc gaagacatgc aagttcaagt   2400
cgggagctgt gtgtgatgac tccaacgaca gctgctgttc aagctgccaa ttctcctcag   2460
ctgggacggt atgtcgtgcc agtcgcgcg actgcgacgt ggcagagacc tgcagcggca   2520
```

| | |
|---|---:|
| actccagtac ttgtcctacc gactcgttca agaaggacgg cacgagctgc ggcagcagtg | 2580 |
| gctcgggact tgcctgcgct agtggccaat gcaccagccg cgactaccag tgccgcagtg | 2640 |
| tgatgggcag tctcctccac agcaacgaca cctacgcctg ttcctccttc agttcctcct | 2700 |
| gcgaactggt ctgcacctcc ccgaagatcg gcacgtgcta cagcgtcaac caaaacttcc | 2760 |
| tcgacggcac tccctgcggt agtggcggct actgcagcaa cggcgactgc aagggccaaa | 2820 |
| acgtcgaatc ctggatcaag aaccacaaag gtatcgtcat tggtgtcgcc tgcgccgtag | 2880 |
| gcgccctgat ccttttggcc ctgatgacct gcatcgtaaa ccgctgtcgc cgggctcgcg | 2940 |
| cgccaaaacc cgtcccgcgt ccagtgcctt acgggccgtg gccgcgcgct aggcctcccc | 3000 |
| cgccgccgcc catgaaccag tggccggcgc gaggctatca aggcttaggg aatgagccgc | 3060 |
| cgcccccgta tccaggtgta cctggtcagc cagtaccgca acatatgcct ccccaggggc | 3120 |
| ggtacgcttg attgacgaga cttcttctgt gcttctttcc atgcgatata gtatgcatta | 3180 |
| cgattcttgc agcactagca ttacaaatgt gacgattact tcattgatcc tttattgacc | 3240 |
| ttacattctt gtcttggagt ggaggcgtgt tctagagttt tggtttgatg ctgaattgtt | 3300 |
| cttttctata cggggggtctg ggcgtttcgt gaattgcagt acttacaatc caggggtgca | 3360 |
| atccccaggg ggttggttcg cgtcttcttt ccctttcttt gcccatatta dacggggccg | 3420 |
| tgggatgtat ggtcggggtc tgatgtatgt attcctgccg tgtataatga acttttccgt | 3480 |
| cataatatat tgcttcttgt | 3500 |

<210> SEQ ID NO 33
<211> LENGTH: 2520
<212> TYPE: DNA
<213> ORGANISM: Aspergillus niger

<400> SEQUENCE: 33

| | |
|---|---:|
| ttgatgcata atgctttcct tcagaggtaa tacttcgagg acggctatga agcgtatgcc | 60 |
| acatacgatt ggtatttgac gatatttgtc atgctataca tgaaatttac atattgtata | 120 |
| tagtgtcatg ggtttgaata aagacatatc gatgtatctt aatagcaggt caattgatga | 180 |
| cgctcttgtt gctccgacga aaagcgactg catcgggccg atgcgggtcc agggtcgtcc | 240 |
| ttatcaacgc cccgtcagca ctaacagttg acatgtttct ccaggtcggc tagaaccgcc | 300 |
| ttttcgcgag aaacgcgtgc tatcgcgagt gcagggcaat tgttgcctag cagtagctaa | 360 |
| agcctgagtt ccgtgatctt cacttctact tcttcttctt ccctgctccc aacccattac | 420 |
| tctgcacccc acgcccaaat gcgtttccta agcagtgcag ccctattcgg cctggcgtat | 480 |
| gcctccaccc aggcggtcct ccagccagag gaaccatccg acttccgtac attccacagc | 540 |
| ccatattccc cgcaccactc gatccgcatc cgccagcaga atgaatcaat ctgcgctgcc | 600 |
| cattccgccc aatacaccgg ctggctcgac atcggccgta acatctctct tctgtggtac | 660 |
| tttgagagcc agaatgaccc tgccaatgat cccctcactc tctggatgac aggagggcca | 720 |
| gggggggtcca gcatgatcgg tctgtttgaa gaagtcgggc catgtctgat caatgagtac | 780 |
| ggcaatggca cttactacaa tccgtggggc tggtcccgga actcctccct actatttgtc | 840 |
| gatcagccag tcgatgtggg atttttcgtac gtcgatgaag agaggacct gccgggcgat | 900 |
| tcgcatcaag ctgcaattga catgcatcgg ttccttgcagt tgtttgtctc ggaggttttc | 960 |
| ccgcaattgc agactcttcc cgttcatctt tctggtgaat cgtatgctgt atgtatcttc | 1020 |
| tctaggtcac ctgagctaag actaacttcc acagggtcac tatgtccctt acctcggcag | 1080 |
| tcagatcgtc caacagaaca agctctatcc cactgagccc caggtccttc tgcactcatg | 1140 |

```
tctcgtaggc aacggctact attctcctcg cgacactacc tacggctact gggaaaccct    1200
ctgcaccact aaccctggag tccccgagcc cgtcttcaac cgaaccagat gcgacatcat    1260
ggcggccaat atgccgcgat gcatggaagt atccgacgta tgtgttcgga accccgatcc    1320
agctatctgc catgctgcgt cggaggtatg ctacgagggc gtgatcggat ggtatgatga    1380
cgagtctggt gaaggtggtc ggaataggtt tgatagtgag cttgccccca tccagttgtc    1440
ccctgtcagc aaatctctgc aatttactga tatgaaacag taaccgctcc ctgcgccctt    1500
gacggcatat gctacatcga ggccgctcgc atcgagcagt acctgaacac acccgcagtt    1560
tgggctgctc tatcaccacc caagaaatc aaagaataca aggttacttc cgacaatgtg    1620
tcgcgcgcat tcgatctcac ttcagacacg atgacgccag cgtctgagca agtcgcgttc    1680
ctgcttgcga atcaggtaca tttcctggcg tatcagggca atctcgatct ggcgtgtaat    1740
acggcgggta atctgcgctg ggcgcattct ctgccatgga gagtcaggt cgagttcgcg    1800 tcgaaggcgc tgcggccatg gagttgggta gatgtggtat ctggaaaagg tggagtggct    1860
ggaacgacga aggaggtgag agtgaaggtt agtgagagta cggataagga gtcgaggttt    1920
gcgctagtta cggttgatgg ggcgggacat tttgtgagta tcccttttcgc cttgtgggat    1980 ccaagtatgc ggattactaa tggtctatta caacttttac agcttcctca agatagacct    2040
gatatcgcgt tggatatgat ggtgcgctgg atatccgggg catcgtttac tgagtgaagc    2100
atgaatgtcg cagacgatgg gataccggca tatttcacag gtttggtgta atatatgtct    2160
tgtagctgtc ttcagcagta tttacaatat gctgctgcct tctctgattt gggtataatt    2220
atagtttaac acaatcaact gcatcggcag agatggatgg gcttgatttc gcacccgcag    2280
cagcgatgaa tttccgtcta accgagcgaa cggtagcgga cactaacact gattgtattt    2340
acaaccctgt ttctttcctc ttgatttgag acagaagtat gtaagctagg cgtagtagaa    2400
tacatttgtc atctacttct actgagttgc ataacgtaag cgactattgg ccgctacctt    2460
gccccagtta gttagttagt agtagtgggt gccgaagtca gcacacattt ttcagccctc    2520
```

<210> SEQ ID NO 34
<211> LENGTH: 1721
<212> TYPE: DNA
<213> ORGANISM: Aspergillus niger

<400> SEQUENCE: 34

```
attgatacga ggcgtttgta ggtggcgttc ctgaagagga tctgataccc actggttttc      60
ccagtgggcc tatgttttcg tgatagtttc ggcatttcta tccatctagg aaaattttga     120
tggcacctgc tagtcgatgt gcccttcctg atggagcgat ctcaaagtgt caaatttctc     180
ggcgaaacgc gtctacccct tctttgggat aattccctgg tatgcagcat tcctgacacg     240
agggattgtt tgggattccc cagattccac gtagcggttg gcaatgatgc ttatgatttt     300
ataattctca tcttgtcctt tgtcctcggt gcagtagaga atcttcactg cccgatacca     360
atatgacatt gttactcaac ttccacgcgc tctttacagt cattcttgtt gccaatcttt     420
caaccagatg cagcgcactg ctctctggac gtgactttg ctccacgcca gcgcccggtg     480
agtcactccg agcggagcat aggaggctgt atgatgtaca ggcccaacgt gacagcaccg     540
ccgaggagag ccgggaggtg gtgccttgga ttgaaatcga gacatggttt catattgtaa     600
gcagcaatga agcagcaaac acagtatcag acgacatgat caccagccag gtccgtcacc     660
attcaacttt tgacccatgc ctgcgcaatg tcgtgttttg gactaacaag tcctagcttt     720
```

```
cctatcttca gaaggcatat gaaagtgcga ctatcaccta tcggttggag ggcataactc    780
gtcacataaa tgactcgtgg gcgcgaaatg atgatgaact ggggatgaag aatgccctac    840
gaagggcaa ttatggcaca ttaaatgtct atttccaaac agatctccag gcgtcatccg     900
acgagaattc tcggactat ccaaatgacg gtaaccgacg aacagatgtg tcagatcaat     960
catcatcaac tgtcctaggc ttctgtacgt tgcctgaccc gagtgtgaat tccagcagcc   1020
ctcgttccag ctacatcaag gatggttgta acgtgttagc ggatatcatg ccgggtggta   1080
gtttagcgca gtacaacaaa ggcggcacag cggttcatga ggttggccat tggaatgggc   1140
tgctgcatac gttcgaaggt gaatcgtgct cccctgataa tgaaggagat tacattgatg   1200
acacccggga gcaatctgag cctacgagcg gatgtcccgc cgagaaagat tcatgccccg   1260
atcttcctgg ccttgatgct attcataatt ttatggacta ttcatctgat gactgttatg   1320
agagttttac tccagatcaa gcggagagaa tgaggagtat gtggtccgct atgcgggaag   1380
ggaagtgacg gacggactcc aagggtatat aatttgcaca tataccagct atagatagac   1440
aactatggta gcacgaatat tgatgtcaac atcttggtct ttcaattccg tgggaattga   1500
ctatcacaat tcatgaacct tttgtagaat ttgtgtattg gagagcgatt gatgcaaact   1560
agacactcgt tcgaaattca cagctagctg tcatgtggaa tgcgaaatca gatcatcgct   1620
tgcgcttttt tccacgatct tcatcgtcca ggccactttc cctgtccttt ttctttgcct   1680
ttgattcgag ttcgtcccag tcttcaccac tctcttcgtc g                       1721
```

<210> SEQ ID NO 35
<211> LENGTH: 3550
<212> TYPE: DNA
<213> ORGANISM: Aspergillus niger

<400> SEQUENCE: 35

```
cctatcctct gctccgcccg gtggagagga tctattgacg ctatggttct tgagcaatgg     60
cgacaagacc caccagtgga gataagagga ccgaaactat ggcttgttca aggtctgctt    120
cgataaaccc ctcatcacga taaaccaagt tgggcttact aacaaggcca atccttcaac    180
aatctcatcg cacaacgacc caaaatccag caaggcacga tccaacatac cctgtaatga    240
caggaaacaa attatcactc ctctgggtgc tgatgcagac caactcagta ttccgcgtgg    300
attgtccgac tccgaagaca agctttggtg tctggtgctg atcgtccgtc gtggagccac    360
cactagtgga ttgaattacc cacacaccca ctacttatac tctttacgct gtctatcatc    420
ttcgtgctga tcagggggtt attttcttgc gctatttggt ttcccactat gcttctgttt    480
tgcagggctg gtcataacaa tttggtagtt tgggttgggt ggcttgttat ggtcgatgtc    540
gggagggggt tcaccgttga acaatatgct tgtcgttagg taggttgaac tgatgcttgt    600
gttttgtttc caggcgccct ggacagcctt tggctatcag caatagctca atagctggtg    660
ttttgctcga acgcgggtct tggtcgggtt gacccagtgt gatctacgct agacgctttc    720
ctgattggcg atggatgtca cgcctcttat cagggtttgg tgatcatatt tagcctacat    780
aggcaggttc ccttccgctg gtatggaagt gcaaacgcc agcgtatgga gagtgaagtg    840
atgctagtca atgggatcag cagcgttctt gtcaactagc atatattccg acgtttccca    900
ccgttcctga tgatgcttg catgccacgc ttgctctgtc gctgcgatca acatgcatgt    960
ctcactttc ctactcagtg ttacggcagc gtttgccagc ccaacacccc ataactatgt   1020
tgttcatgag cggcgcgatg cattgcccag tgtctgggta gaagaaagcc ggctggacaa   1080
aggtgcccta ctgcctatgc ggatagggct tactcagtcc aacctggatc gtggccatga   1140
```

-continued

```
tttattgatg gaggtgtatg tgttccgact cctcaccaga accaagctga ttgtccaggt    1200
ctcatccaca atcgtctcgc tacggaaagc atctctccag cgaggaggtg cacgacctat    1260
ttgccccgtc gaatgaggcc gtcgagaccg tccgaacctg gattgaatcc gccggaattg    1320
ctccaagccg catctcgcaa tcatacaaca agcagtggct acagttcgat gcccatgcaa    1380
gcgaggttga gcagcttctg cagacggaat actacatcta cacccatgcc gacacgggaa    1440
gttcccatgt gacatgccac gagtgagtcc attttctaca tgccatgaca ccgctaacca    1500
gttaggtacc atgtgcccga aaccatccaa tcgcacatcg actacataac accaggagta    1560
aagatgctgg aagtgcgcgg cacgccctcc aaaaagagag atgcagagaa gcgctctctt    1620
ggcagtctgc ccccaatctt agcaccacta ccaatcaata tcacgaagat tttcgacgac    1680
ccgctagcac actgcgatct ggcggtaacc ccagactgca ttcgaggtac gttcatccat    1740
cccaattcaa gatttcacgc taaccgtcta gccatgtaca acatcaccaa aggaacaaca    1800
gccacaaagg gcaacgagct cggcatcttc gaggacctag gagacatcta cagccaagat    1860
gacctcaacc ttttcttcgc caactttgcc aggttcgatt actctccacc ctcccttaga    1920
cacaactaac accaccaagc gacatcccac agggaaccca tccaaccctc gactccatcg    1980
acggcgccac cgccccaaca gacgtcacca acgccggccc cgaatccgac ctggacttcc    2040
aaatcgccta cccaatcatc tggccccaga acaccatcct ctaccaaacc gacgacccca    2100
actacgaaga caactacaac ttcaaaggac tcctcaacaa cttcctctac gccatcgacg    2160
gctcctattg caacgaaacc tcctctctag accctcaata cccagatccc tccccaggcg    2220
gctactcctc ccccaagcaa tgcggcgtct acaccccccac aaacgtaatc tccatctcct    2280
acggcagccc cgaagccgac ctcccccatcg cctaccaacg ccgccaatgc cacgagttca    2340
tgaaactcgg ccttcagggc atcagcgtgg tcgtcgcatc gggcgactcc ggcgtcgcct    2400
ccagcacggg cacctgcttt ggcgatgcag acaacgtctt cgtcccagat ttcccagcca    2460
catgtcccta tctcaccgca gtaggaggca catacctccc cctaggcgca gacgcagcca    2520
aggaccagga aatagcagtc acccgcttcc cctccggcgg cggcttcagc aatatctacg    2580
cccgaccatc ctaccagaac cactccgtgg agacctattt ctccactacc agcgacgacc    2640
tcacctaccc ttactactcc ggagtaaact acacagactt ctccaacaca gatgggtat    2700
acaaccgcat cggacgagga taccccgatg tttcagctat cgcagacaat atcatcatct    2760
acaaccaggg cgaagcgaca ctggtggtg gtacgtctgc cgcggcgccg gcgttcgcgg    2820
ccatgttgac gcgcattaac gaggagaggc tggcgaaggg gaagtccacg gtggggtttg    2880
tgaacccggt gctgtatgaa catcctgagg cgtttaggga tgtgactgtt gggtcgaatc    2940
ccgggtgtgg gactgatggg ttcccggttg ctggggggtg ggatccggtg acggggttgg    3000
ggacgccgcg gtttgaggat ttgatggata tatttgtggg tgatgattga tggctgagac    3060
aagatgtggg aaggtgtaat gaagatgatc ctatttaatc cggtaatcta ccacacattc    3120
atattactag tttatagcct agtcagatat ataacattgt actactacta tagaggcgtg    3180
tgatgcaaat gctaaaatat tgatatacta ttaagcaact acattatgat ctaaacttta    3240
cagttcatag tacagaaagg ctttgatcag tcctagttca ataaaaggta tagactactc    3300
actacatatt aaacaccaca actcgggatg cttggggtat agtgatctga gagtcgcggg    3360
aatgcccaaa tgctctgttc gatcatatct tggttgatgt catgttggac gcattatatc    3420
aaaagtcatc tagcgctttt ctgaaagttc tattatgaga attttgcttg tttatagcta    3480
```

```
                                    -continued
gcgggtggat gattaatttt gtatgagtga ttctatagac gttgatcatt tccatgattt    3540
agaaactgag                                                          3550

<210> SEQ ID NO 36
<211> LENGTH: 2280
<212> TYPE: DNA
<213> ORGANISM: Aspergillus niger

<400> SEQUENCE: 36
ctgcctctca gcgaaaaccc caaaaccaaa catttctaga tcagacaatc aattgcggac      60
tgagttccct gaatggtgga agatgccata ctgttagcgg ggactatttt tagcatgtca    120
tgacttggtc ggcgtccgta catagaaggt tagcggatgt cttgatgatc acacaaaaaa    180
gggataggat gaaactggat gtctcactgg ctatctcatt tgcccaacag catcagtcgt    240
tccggcccgc tagttccacc acatgtcact tgtctcggat tattctcgaa ggtctggtat    300
ttcaatgttc cacctggtcg ctctacataa atagacctt acgccgtttt gttttcttct     360
tcgttctacg tcgtttattt atccaaaatg gcttccaaga ccctcctact cattccggca    420
ctggccacag ccgctctggg aagtgtattg gacctagata tcaaggttca aaatggctat    480
gtatgtcaat gagaagctca gctccctgag aaatatctac taactcggcg aagaggacta    540
tcgaggtaga ccttggaacc ccaggtggcc cgtttgattt gatgtacgac accggatcat    600
caacactctg ggtgcttgat agcaattgta cagatgattg tccaaatgtt agcgggttag    660
ttgattcatc ccaccattcc ttaagcctac actaatcacg agcgccaggt actcccgaca    720
cggctacaac ctcacctcta ctggtgtcaa cttaggtgtc aacgacagca ttgcttacag    780
cggaggcact gtcagcggct tcactgccac ggatattctc acggttcccg acaccaacgt    840
ctcatatcgc cagagctttg ccgtcattac cgacagtacc tgggcggcct tagcagccga    900
tgggttcatc ggcctggcat cgtctaccat cgcattcaag aatactacga cagccgtcga    960
acagatgatg caggatggac ttttggatga acctcgattc gccatatatg caggttcagg   1020
ggaatcgacc gtgaccaacc ctaatccgga gaataatggc gtgttcacct ttggtggcag   1080
ccatgaggaa acctatgcgg acggggaact gcaatggatg aagatgctct ccccctttga   1140
aatatacaaa acaaatctcc ttggaattca gggacacaac aactccgatg ccaggccct    1200 gtcaagcgac gtcctgaact ggtacggcca ggttattttc gataccggta ggcattttct   1260
accacactgt tttctttagc ttgctagact aatctattca acgtcgcagg tgcttcatcg   1320
ataagcattc ccaacgacca gattgaggcg atgtatgccc taacgccttt ctcatacgct   1380
gacatctcat ctggataccg acctctgtgc tccgatttca atgatacatg gtcgatctct   1440
tttacaatgg gcttctatgg cgagggtgtc accttcaatt tgaccggtga tcagctggcc   1500
gtgcctggct atcaggacga cgaccactgc ttccctccct tcaatccatg ggacagctac   1560
aacacgatta ttggtcagca ttggttgagc aatttctatg ctgtattcga cttcggatca   1620
ttcgacccgg agacatacga tatacgtgtt gggctggctc ctttgaagaa ggaatacctg   1680
ccgagcgctt gacctaagaa cttctattcg tgtctttgag catttagttc aaacctcttg   1740
ctcggacgtc aatgtttaag catgcgtaaa actatctact agaagttaat gttcatcgag   1800
agttcatcgt ttaaataagc agcttatctt cattctttac agccactata cgcgacatga   1860
caattgtttt atgggtcggt gcgataaagt ggccatctaa aggcaatagc aattaaaata   1920
agccaggaga tggaacatga agaatcttac tctctttgtca tggcctcatg caactttggt   1980
gcgggctgtc ggtgaccctg tggggcacat ctccggggag tggaggccgt taagcttcgg   2040
```

```
acaacattat tcttcagct caaccatgaa aaggttcggg gacctgcatg catcccccaa    2100
gcccgcaagt ccgcgtcatc aacaaatatt gcgaagaaat ggtacgcttt agagccatgc    2160
gggctatatt ttcggttcta tagattgtta gatataatta ttgcttgtcg aacccagatg    2220
cagcattgat ctgttataat cctcatattc cgcgagtcac ttgattccgt gatcaagatt    2280
```

<210> SEQ ID NO 37
<211> LENGTH: 2287
<212> TYPE: DNA
<213> ORGANISM: Aspergillus niger

<400> SEQUENCE: 37

```
tagttgaagg aggcttttgg ctttcttcct ctttatcttt cttctgttgt cagtgattct      60
gatcgcagaa gatgtgcaca agatgaagac cgccccgagt catctatgga tactgaagag     120
atggaagaga tctgacaacc aaggagtttg tattatccag ttccagtttc atgttttgcc     180
tccgtctgat agttccacca aagatactgc cattttgtat ccgtagttag acggagacaa     240
attgacaacg acagccttgg gggccaagtt cagacatact tccagccgca cgcatggatg     300
tataccttgt tgctacgtga gcgtacgcca gcttatcgac ctattttagg acctgctccc     360
acgtggagat tctgcagcaa acgcaggaaa caaggaccag aaattcgtca tcatcgtttc     420
tccttagcaa tcggctagga tgtttccctg ctctcgtatt tggtctctgc tcgttgcagc     480
cgccaccgct agtgctgtac ccaccagtct ggccaccacg cacctgcaat cggttgactt     540
gcttctgact cgcagttctt acgggtttct tactgacata gcccttggaa ctccgggtca     600
gagcctgccg tatctggttg actggacctg gaccggccac tatgtggtga ccaccttgtg     660
ctacaacgat cccaccgcca cctacgattg tctcaacgtc gatcagaaaa ttttcaacca     720
gactttgtca tccactttta tcaaccaaac tgaccagtat ggctatcttt actgggatcc     780
caaccacttc tactttacgg agcccgcagc agccgatgtg gcgacggaca tgctgcgcat     840
cggtcccacc gcggtgaaca ccaccatcca agcagccaat ttcgtcttca acgagactat     900
tagcgcattc cctttctcgg gagtatatgg actctcacct gttttcagg gtgacaatcg     960 tgagttgttt ccccaccgtc ataaaactaa ttcatgttaa cacgaatcat aggatccgtg    1020
caagcgtcct tctaccaagg atggaggagc ggcgcctggc actctccaat tgtctctttt    1080
atctactgcc acgacaatgc caccaaagcg gtatgcagtg gttacgacgg ccttcagaca    1140
ctaggcggat acaacacctc tcacgtccag ggagatatca cctggtacga catcattgtc    1200
acggaggcga tcaacacgct ggactttgtc tatgcgccag ccgtgattaa ttattgggcg    1260
ttgaacctca cgcgcttctc tatcggagac gaagagcaag agctcaacaa gaccactact    1320
ctggatggaa agcaagccgc cgttgccgcg ttcgaccacg cttcgtatgg tcgcggtgcc    1380
ccagtgtctg tgtacggtta ccagcgtcta gtcgagctgg tcggggcaaa agccgtcacg    1440
ctttccgatc ctccaaataa cggtgagcag ggattctatc agttcgattg ccggaactcg    1500
agtttactgc caccgctgcg gtatgagttt gccgggtcag agcgggcgtg ggagattgtg    1560
cccgagaact atgtggaggt gctggcgaac ggaaccaata agtgcacctt taatgtacgc    1620
accctgggag atggagcgat ggtaatggga aattttggcg agacatttgc cattgataag    1680
tatgtcatgt ttgactttga gaagttgcag gtggggatta cagacttcgc gtggtaatgg    1740
tataaggatg tgtgtttgaa catgtgcatt atctcgagtt tgactgaata gacggagaat    1800
ccaagaccgt agatcatgat gctatctgct tgattatttt caatgtctct agtatgggga    1860
```

```
aagtaataca tgtgataata tctccaaagt agtaattaaa agagaaaact aatcaccact   1920
agtaattaat actgcaaata gcgctgttcc acattgagac aaccatataa taataagtta   1980
gtggatatac ggaatattag aggtcatctt aataccatac tagtggatac aaccatccgt   2040
acatacggaa taggaaggag gagcgagatg gtcatcattt gacactgagc atactgtgtt   2100
ggcccagtca agctgttgta tgggggagct cctagtgtgc ccaaggctcc agcatcttca   2160
ccttccgcaa cgactttact tagtttacat taggtgagcc tttctgttac atagttgatt   2220
gaaagcctct ccccaattgt cttagcatga tagaggttac tcggagaacg tactaatcag   2280
gaggcca                                                             2287

<210> SEQ ID NO 38
<211> LENGTH: 1950
<212> TYPE: DNA
<213> ORGANISM: Aspergillus niger

<400> SEQUENCE: 38
gatctttcta gagcattgtc ttgattgtgt cattctgtca ttgactccgg ctatgaaata     60
ttattctcaa tctgcctaaa accaaattct actctatcac tacacatttg tatcacctga   120
tctggctgag ataggagagt ccggcatctc atcgtctgca tcagacaatt gcgataaatt   180
cattgcttgc acctgttatt gattcttcca agttatgcat ctcccacagc gtctcgttac   240
agcagcgtgt ctttgcgcca gtgccacggc tttcatccca tacaccatca aactcgatac   300
gtcggacgac atctcagccc gtgattcatt agctcgtcgt ttcctgccag taccaaaacc   360
aagcgatgct ctagcagacg attccacctc atctgccagc gatgagtccc tgtcactgaa   420
catcaaaagg attcccgttc gtcgtgacaa tgatttcaag attgtggtag cggaaactcc   480
ctcttggtct aacaccgccg ctctcgatca agatggtagc gacatttcat acatctctgt   540
cgtcaacatt gggtctgatg agaaatctat gtacatgttg ctcgacacag gcggctctga   600
tacctgggtt ttcggttcca actgcacgtc cacaccctgc acgatgcaca ataccttcgg   660
ttcggacgat tcttcgaccc ttgaaatgac atcggaagag tggagtgtgg gctatggaac   720
tgggtctgtc agcggcttgc taggaaaaga caagctcacg attgcaaatg tcactgtacg   780
catgactttc ggacttgctt ccaacgcatc ggataacttc gagtcgtacc caatggacgg   840
cattctcggt ctcggtcgaa ccaacgatag ttcctacgac aacccaacat tcatggatgc   900
cgttgcagaa agtaacgttt tcaagtcgaa tatcgttggc ttcgcccttt cacgtagccc   960
cgccaaggat ggcacggtca gctttggcac tactgacaag gacaagtaca ccggcgatat  1020
cacctacacc gataccgtcg gatcggacag ctattggcgc attcccgtgg acgatgtcta  1080
tgttggcggc acttcatgcg atttctccaa caaatcagcc atcatcgata ccggaacttc  1140
ttatgctatg ctgccttcaa gcgactcgaa gacgctgcac agtctcattc ccggcgccaa  1200
atcttcgggg agctaccaca ttattccgtg caacacaact actaagctac aagtggcatt  1260
ctctggtgtg aattacacca tctcgccgaa ggactacgtg ggagcaactt caggttctgg  1320
atgcgtttcg aacattatca gctacgactt atttggtgat gacatctggc tcctgggtga  1380 cacgttctc aaaaatgtgt atgctgtgtt tgactacgat gagttacggg tcggatttgc  1440
agagcgttcc tcgaacacca cctctgcgtc gaactctacg agctctggaa caagcagcac  1500
ctcgggatcc actacaacgg gcagctcaac gactacgacg agctctgcta gctctagtag  1560
ttcatctgat gctgaatcag gaagtagcat gaccattccc gctcctcagt atttcttctc  1620
tgctctggcg attgcttcct tcatgctttg gctctagtta accgcatctt actcgacgcc  1680
```

-continued

```
tgaacctcgg gaaacatatg cattatttac acatgctgct gatttgtatt tgcatatatt      1740
cttcgagcct ggacggcgtg cgggtcatat taccttacat tcgaagtcct tctctaatca      1800
atcaacattt attcttactc caccagttct ggctcgcaat taaccctgtc taagaaaaag      1860
ttggtataga acatggcatc cactacctgg aacattcaaa gaaccttgtc cgggatcagt      1920
gtgtatgact cgggtacga ttctgacatg                                         1950
```

<210> SEQ ID NO 39
<211> LENGTH: 2660
<212> TYPE: DNA
<213> ORGANISM: Aspergillus niger

<400> SEQUENCE: 39

```
accttctggg gtggattatc tgaagagatg aactgccccg cccaagtgca agaagatgat        60
gcctgacagt tgatgcctga gggatgcttg tatcaggtga tcccggctat ggtggtctaa      120
cccagttggg ctgaattgac cacatttagt tagtgtcagc cttaaacaga tgaggctttt      180
cgcatgattc atttccaagg aacccaagga aatggtcaaa cagcaaagga ataatgaccc      240
aacagttata cctagctatg cagcataaaa gagaaaaaaa acttgaactg atacgagcca      300
tcatgtaacc tccgtctctg gctcaattct ccatccaatc acaattcttc caagcaaact      360
tgggattcgc cgggttctcg gcaaccctaa cctctaccag taaaggttga tccttccccc      420
acccgatttc gcatggcttg gaccccctgaa atatagttcc tctacgtgcc tgaatatgga      480
gcacgttatt cgtcttttcag ggtcttgggg ccttggcctt ggggctgcca agcgggcggc      540
ggagtgtgcc ccgtggtgcc ctgttttgag cttggatgcg attactatca tcacttaata      600
agagcaagac cctgcgtcga tattgacggt caatacactg acctcagaga accgtcgatg      660
tgcctgattt cgctccatca aaatgacgtc ttctaccttg cgccttgccg tcgcgttggc      720
tttgtcaact tgcagcagtg ccctatcgag ccagcgagat gattcacttg tggttccatt      780
tccttttggc aatcttgagg atgtccatat tgccaagcgg gatagctcca agacagtaga      840
agctcctcta gtgatatatg tcagtcagct ctcccactct ccatctatgt catcaactcg      900
acaaccctaa caatcaacag ggcgacagct actggatgaa cgcctcaatt ggaaccccctg      960 cgcagtcact aagtttccta ctagatctta cgcgctcaag ggtcgagccc gcatacaccc     1020
tcgatgagaa ttacgaatgt tctgacgatg aactctgctc cgaattcggc ttctacaaac     1080 ccaccgatctc atccacttat cagcatctca cctacacaca gagacacgat gcaggtgtcg     1140
actactccta ccttgatacc ataactcttg gagatcacgc aaccgacaat gtcccactgg     1200
acatgtatct tttgtcctac atttcctgtc agttccccct ctctcccta ccacccctatt     1260 tatccatcat ctgaccattg tctaaccacc acatagacag ctccctcggt ctctcctccg     1320
tcaacaccag cttcccctac atcctggtcg atcgcggcct caccacctcc ccatccttca     1380
gcctaatcgg cgacaacgga aacaccacca ccccccagcat catctttgga ggcatcaaca     1440
cctccaaatt caacgggccc ctgcaagcct tctccttcgc agaccacagc atcaccaaca     1500
atccattcgt caccgtcgaa gctgactccc tccaactaac caccaacacc aacgataatt     1560
ccacctaccc tattccctcc tccacccccca tgatgctcag aaccgaagaa ctaatcacct     1620
acctccccaa ctcgaccgtc caatccctct acaccgacct taacataacc atggacggcg     1680
tgatctccac ttcaagattc tacgggtccc ttccctgcgc ccgccaggaa accgaatctc     1740
acacaatctc tctagccatc ggcaacatga ccttctctgt gtcctgggat gagctcttcg     1800
```

-continued

```
tcccgtggac gcgtgacgga ctatgcaagt tcggcattca ggcccaggat tcagattaca     1860
aaactcgtgc ggagctgggt gttccctttc tgagacggga gtatgtcgct gtggattata     1920
ataatcagtt tgtgggcgtt gcgacgctga aggatgatga tgatcagaat ggaggtgaag     1980
atgagattgt ggagattggc actgggacgg cgttgcctag tgctgtcggg gattggccgg     2040
ctagtgttac ggcgtatacg cctgctgctt ctacagggac ggcggctgcg acgttgacat     2100
tcacgacggc gacgtctagc gggggaggtg tggtgccgac gggtctatca gagttgggta     2160
gggcgttttt ggtgccgggg gtgctgggga tggctgtttt gcaggctgtt taggttagag     2220
attgtggtac gattattctg taggttaaag atgtatattg tctgttattg tacttgatag     2280
cttgatatgt ataatgaaag tagtatagtt tgaattttg ttatacacca cgtgaaccca     2340
ctggaccgtt gtctactgct cgcagtgagt gatatagtgt agacccgtat tactagtcat     2400
gtaggaccct accttgatac cataacactc ggagaccacg caaccgacaa cgtcccactg     2460
gacatgtacc ttttgtccta catttcctgt cagccccttt ttgaatgtac ctacatccct     2520
ctaaactcta gtactatcac gaacagcaaa tgacattcaa tctattctat gcatattacc     2580
cttctaacaa tacccagatt ctatcaaatc acgtgaacat acagccctcc caagtcacct     2640
gacaaagcgg acaacaatgc                                                  2660

<210> SEQ ID NO 40
<211> LENGTH: 2501
<212> TYPE: DNA
<213> ORGANISM: Aspergillus niger

<400> SEQUENCE: 40
tgattcccaa atcgcaccag atgaagttga atcagtggta cagtttagcg ggtggctgtc       60
atgacagaca gaccctcaaa ttgaagcaat ggcagataga tatggtctcc agtccaccga      120
ttgaatgcag ttggagaagt caatcccccc ttggaaagcc cccaacgttg cgctttctga      180
ccacctgaaa tctgacaatc agcaatcctt cagctcttct cagcgtctct tggggccgat      240
ccccatcgga tgaacacgcc tcatccctca ttaggcatgg ctgagctgca tgtcagcgga      300
gtcccaacac ccaaaccaat cctttagcgc gcaccgggcc tgcgaagcca tcaccatcgc      360
ccgccttgca gcaatgtgct ccccggtcgc attcctttcg tttcataatc tcacctccgg      420
ccagcccata tccttcatct cgcagctttt ccctactcct tcttttcttt tgctttcttc      480
ccccatcgca ggctgtttga atgcctgctg aagtatccat ggtatgatgc gaccgatact      540
tctcccccta ctgggggtat ttctgcagac ctcctcggca tccaatccct atgtaatgag      600
ctggtcttcc caagcctacg gtccagatgg cccgtggcag gccgtatcca tcgacgtggg      660
cagcaaccag cagacggtcg atctttaccc cggagccaac tatgctagca cgatcctgat      720
gagcactctc tgcacgaaca aaaccctgtc atccacctgc tacgctgccg aagcaggcac      780
gttcaaccaa aacacctcca ccactgccta caccaccgcc agctcgtggg aaacaactta      840
ctgggccgtc gagggtggaa gccaagaggc tgtgctcggc gatgaggtca ccttagggtc      900
gtttgtcgtc cccaatgtga gcttcgaagc catctaccag acctaccaga cctatcccaa      960
tggcatcgcc tatcctgtct cggtcggcag tctggccctg ggggtccgt acttgtcgga     1020 taccgtctcc aattcgacgg tcctgaacat gatcgcagga tggctttact cgtccaacga     1080
cattccgtcc tactcgtacg gcatgcatat cgggtcggta gaccccaaaa tcccaggctc     1140
cctgatcttg gggggctacg ataagagccg agtgatcgga gacgtgagtg cgcagggagt     1200
agtgtcttcg agtggtcttt tggaacttga attaaaggat attgggctgg gtgttgcggc     1260
```

-continued

```
gggttcctct cccttcagct tcaacaacga aagtggcttg tttctccaaa gcagtggttc    1320
ggttcaggcc aagaccgtcc agattgatcc aaccaagccc tacatgtacc ttccccaggc    1380
gacatgcgat gccatcacct ccaccatgcc gatctccttc aattccagct tggggctata    1440
cttctgggac accacgagcg atgattatct gaatatcacg tcttccgccg catacctctc    1500
ctttgtgttc aacatgaatg gggtcaacaa caagaacatt accatcaaga ttcccttttc    1560
ccagctcaat cttacgctgc aagaaccgct ggtcgatcaa aacgtcacct acttcccgtg    1620
cttcctcact acctccaccc cggtgctcgg tcgagccttt ctccagtccg cattcgttgg    1680
ggtgaactgg ttcaacggga caactcggg cacatggttt ctggcacagg cccccggccc    1740
gggttacgcc agtgaagaca tcacccggat cgcagtgagt gacacgtcgc tttctgcctc    1800
taacggtacc tgggaagaga cctgggctac gtactgggc atcaaaacat ccgacaactc    1860
gagcagctcc aagagtggcc tgtcttccgg tgccaaaatt ggaattggcg tcggggtggg    1920
tgtcggtgga gcagtgttga tcgcagcagg tatagccatt gcattctgtc ttcgccgtcg    1980
ccgcggggcg agtcaagagg cggctggaga gcaacggagg tcgatgttta ggggctttgc    2040
ggagctaccg ggaggtgctc acagtgaacc ggcgaaggag ttggatacga agatgcataa    2100
gccgccgcag gaaatgatgg cttcgcagga ggtagagcga tacgagctgg ggtgatggct    2160
aattctaaat tttaatatgc gaagggatcc ctacaggata ctacaggata ccatatacgt    2220
gcgaatataa tagctagttg ttccaatatt atgtatcaag cttatactgt ggattaacca    2280
acgacttgtc tccgatacat agggtagtac gtagtcatgg atccggggtg tattgtcatt    2340
cagcatgacg cattgctcaa gccaaaagta agctgggcca gtgtatcacc catgaaagca    2400
accctctctc acctctgtac tgatgacttg gtggaaattt ggatcctcgg aaattgtgat    2460
taacacgtgg atctagaccc gaccaggcgg gagcttggca t                        2501
```

<210> SEQ ID NO 41
<211> LENGTH: 3570
<212> TYPE: DNA
<213> ORGANISM: Aspergillus niger

<400> SEQUENCE: 41

```
gaaaaggatt gtccccatgc ataataggcg ttccaccacc tgcatatcca tacatgcagc      60
ccgagttatg cgatgtgatc gggcctggaa taacatgatc tccgatctaa cgggggccca     120 aaagggcag ccaagatctg ctaggcccaa ccaggctagc ggcgggccat ctgaggcggt      180
gatccatttt gggcgaggaa aaggcaaaaa gtggatcggc gaaaggcaag ttggagtgtc     240
gggagtttgg tctcccgccc cagggccgcg tattagtcta gctctctttc tattcactcg     300
ggccaactcg tcaactctct ccctcgcttt cattcagatt tcattatttc tcttacggtc     360
ttgccattct tgccactttc ggtccttatt attgcttttg atccccagtt cccttttccc     420
aactgggtgg cgctcctaca gaccgacaca tacctggcgg actttccttg cttctggctg     480
tacaccggga cccgcctcat acccagtacg tgttggtcca tggcaagcct cctacttggc     540
ctgattacat cgtcctgaga gagagagttc accaaaactc tcccccaaac gatgcgtctt     600
acaggtggtg tcgctgcggc tctgggcctc tgcgctgctg cctccgcttc tctccatccc     660
catcgttcct acgagaccca tgattacttc gctctacacc ttgatgaatc cacctcgccg     720
gccgacgtcg cccaacgact aggtgctcgc cacgaaggcc ccgtcggaga attaccctca     780
catcatacct tctcgatacc ccgtgaaaac agtgacgatg tccatgcgct gctggatcaa     840
```

-continued

| | |
|---|---|
| ttgcgcgatc gtcggaggtt acgccgccgc tccggagatg acgccgctgt ccttccctcc | 900 |
| ttggtcgggc gagacgaagg tctaggtggc attctttggt ccgagaagct ggctccccag | 960 |
| agaaagctcc ataaaagagt gccgccgaca ggatatgctg ccagatcgcc cgtcaacact | 1020 |
| cagaatgacc cccaagcgct tgcggcgcag aaacgcattg cctcggaatt gggcatcgcg | 1080 |
| gaccccatct tcggcgaaca atggcatttg tataatactg ttcagttggg ccatgatctt | 1140 |
| aacgtgacgg gtatctggct ggagggcgtt acagggcagg gtgtcacgac ggctattgtc | 1200 |
| gatgacggtt tggacatgta cagcaacgat cttaggccga actattttgc ggcgggttct | 1260 |
| tatgactata acgacaaagt accagagccg aggccgcgct tgagcgatga ccgccacggt | 1320 |
| actagatgcg cgggtgaaat cggtgcggcg aagaacgacg tgtgcggggt tggtgttgcg | 1380 |
| tatgatagtc gcatcgctgg tattcggatt ctctccgcac ccattgatga cactgatgag | 1440 |
| gctgcggcta ttaactacgc ctatcaggag aacgatatct actcgtgttc ctggggtccc | 1500 |
| tatgacgatg gcgccacaat ggaagccccg ggcaccctga tcaagcgggc catggtcaat | 1560 |
| ggtatccaaa atggtcgtgg tggaaaaggc tcggtttttg tgtttgcggc tggtaacggt | 1620 |
| gccattcatg acgataactg taactttgac ggttacacca acagtatcta cagcatcacg | 1680 |
| gtgggtgcca ttgatcggga gggtaaccat cctccgtatt cggaatcctg ctcggcgcaa | 1740 |
| ctggtggttg cctacagcag cggcgccagt gatgcaattc ataccacgga cgtcggcaca | 1800 |
| gacaagtgct cgactaccca tggtggaact tcggcggccg gcccgctcgc tgcgggaacc | 1860 |
| gtggcgctgg ccctcagtgt gcggccggaa ctcacctggc gtgacgttca gtatttgatg | 1920 |
| attgaggcgg cagtgcctgt tcatgaagat gatggaagct ggcaggacac taagaacggg | 1980 |
| aagaagttca gccatgactg gggatatggt aaggtcgaca catatacgct ggtgaaacgg | 2040 |
| gcagagacct gggatctggt gaagcctcaa gcctggctcc attcccctg gcagcgggtt | 2100 |
| gagcatgaga tcccacaggg cgagcagggc ttggctagtt cgtacgaggt gacggaggat | 2160 |
| atgttgaagg gagccaacct ggaacggctg gagcatgtca cggtcaccat gaatgttaac | 2220 |
| cacacccgcc gaggcgatct cagcgtggag ttacggagcc ctgacggtcg ggtcagtcac | 2280 |
| ctcagtacgc cccggcggcc agataatcaa gaggtgggct atgttgactg gaccttcatg | 2340 |
| agcgttgctc actggtaagt aaactttttc tcggttgtcg gttcttctgc taatacatat | 2400 |
| ctagggcga gtccgggatt ggcaaatgga ctgtgattgt caaggacacc aatgtcaacg | 2460 |
| agcatactgg gcaattcatc gattggcgac tcaacttgtg gggcgaggcg attgacggag | 2520 |
| ccgagcagcc tctccacccc atgcctactg aacacgatga cgaccacagc tatgaggaag | 2580 |
| gaaacgtggc taccacgagc atcagcgccg ttcccacgaa aaccgagctg cctgacaagc | 2640 |
| ccactggtgg cgttgatcgc ccggtgaacg ttaagcctac aacatccgcg atgccgaccg | 2700 |
| gtagtcttac agagcccatc gatgatgaag aactccagaa gaccccctagt acagaggcaa | 2760 |
| gctcaacacc aagtccttct ccgaccaccg cgtcagatag tatcctgcct tccttcttcc | 2820 |
| ccacgttcgg tgcgtcgaag cggacgcaag tttggatcta cgctgcgatc ggctccatca | 2880 |
| ttgtgttctg cattggcctg gcgtctact tccatgtgca cgccgcaaa cgtattcgcg | 2940 |
| acgacagccg ggatgactac gatttcgaga tgatcgagga cgaggatgag ctacaggcaa | 3000 |
| tgaacggacg gtcgaaccgt tcacgtcgcc ggggtggcga gctgtacaat gcttttgcgg | 3060 |
| gcgagagcga tgaggaaccg ttattcagtg atgaggatga tgaaccgtat cgggatcggg | 3120 |
| ggatcagcgc cgaacaagaa cgggagggcg cagatggaga gcattctcgg agatgaagtg | 3180 |
| cagtagatga gggttgattt tatttcggac agtgtttctt acttgttgga tgacctgcgt | 3240 |

-continued

| | |
|---|---|
| tgaacaatat tcctgctgtg tatgctgcat agagaaagcg tgtatatacc atgtatgtgt | 3300 |
| gcatcatctt tgatcgggtt attattcttc atctgccatg gtttgtgatc tccggaatag | 3360 |
| taccaaagga acactaaatt aagggtcttg gcgatgacgc ttcccgtcgc tgcttttgac | 3420 |
| ttcctccgca tctcgtctct cctgctgttg accgcccgcc aaccaacctc catctcctca | 3480 |
| ctcctcccac cttaatcttg ctgtcctgct tctagagccc cccagtttaa tttaaaaacc | 3540 |
| ggcttttcct agctccacgt attgtacctc | 3570 |

<210> SEQ ID NO 42
<211> LENGTH: 1236
<212> TYPE: DNA
<213> ORGANISM: Aspergillus niger

<400> SEQUENCE: 42

| | |
|---|---|
| aggtcccgga cagatgacaa ggctctaaga ctgtatgtct cattcaggggt ctagccgtgc | 60 |
| ccgctcttat tggcccggac gcttcacgcc gcgattactg cgccccgca tgtctctctc | 120 |
| tccgctcgct atcgatgcgg tgtttgcccg ccattgatgg gaggaatgtc tcacttcggg | 180 |
| cttgtgcttc gcagatccat acccctcaat gacctagtat agcaaacagg cgtgatgtca | 240 |
| atgattgtgt ttctattcag agcatcaggc ctcccatgtc tatacctcag ttatggagcc | 300 |
| ttggccgcct tgggtaggca aggcctcccg ggtattctca ttgccatttc accgctactg | 360 |
| cagcttcaag tgaagagaaa gaggggaaag aaagaatata agtagcttga caatctcctg | 420 |
| cacgtcctcc tcttcagctc acatcaaaca tctattcttc actcctcaag agtaaaccac | 480 |
| tactaccaaa cacaatctca tctatagctc acgagtacca gcatcactca tctaccacaa | 540 |
| tgaagaccctt ctctaccgtc acctctctcc tcgctctctt ctcctcggct ctggccgcac | 600 |
| ccgttgacag cgctgaagcc gccggcacca ccgtctctgt ctcatacgac actgcctacg | 660 |
| atgtctctgg agcttccttg accaccgtct cctgctcgga cggtgccaac ggcctgatca | 720 |
| ataagggcta ctccaacttc ggctcccttc cgggcttccc caagattgga ggcgccccta | 780 |
| ccattgcagg ctggaactct cccaactgcg gcaagtgcta cgccctgacg tacaacggcc | 840 |
| agacagtcaa cattctggcc attgattccg cacctggtgg cttcaacatc gctctggagg | 900 |
| ccatgaacac cctcaccaac aaccaggccc agcagctggg tcgtatcgaa gctacctata | 960 |
| ctgaggtgga tgtcagtctt tgcgcataaa cgccaaacat tcagcaaatg cttgggggat | 1020 |
| gaattcggcc atggcaggga atggttatag ttggatatga tttcgggatt tacgattgat | 1080 |
| acgcttattt gggatacttt cctttatctt acctattgtt aatagcataa tacggagcat | 1140 |
| cacatacgta catacacata catcaatata gtgatatatg aacttgaata cagagctttt | 1200 |
| tgaaaatgaa atgagagatt ctaaggtcgt atctac | 1236 |

<210> SEQ ID NO 43
<211> LENGTH: 1750
<212> TYPE: DNA
<213> ORGANISM: Aspergillus niger

<400> SEQUENCE: 43

| | |
|---|---|
| gtgaaagata tcggatagcc gtagaccctg aaagattatt tgagcctaag ggctcttgca | 60 |
| gtgacgctag caacagcgaa cccactggga tccaaaacac tagatgaagc tattgtaagc | 120 |
| cggaacccctt ccggcgcccc acccagctcc tgcaggggcg aaaacatgac tctctaactt | 180 |
| aggagaaatc acagccaagg cccaagttca ctgagagacc gaaatggcgt gaatttaaat | 240 |

-continued

| | |
|---|---|
| gttgcctttc gcgcacttta ctattcccctt gttcctatca gcagtcactg cttggcctcc | 300 |
| tttctagtga gcagttccat tcactttagg ccccacggct tcgttacaag agcagtatgg | 360 |
| ctcaaatatt ctggctttca ctcttcctgc ttgtctcttg ggtcagagcc gagtccaacc | 420 |
| gcaccgaggt ggacctgatt ttcccaagaa atgataccct tgcgccaatg cctttgatgc | 480 |
| cggttgtatt cgccgttcaa gccccttccg tcgcccataa agttaataca tacatcgagt | 540 |
| acggctatta cccagtaggc cgtccaaatg aaacagttat tggccagacc gaccatgtgt | 600 |
| ccgactcaac aaacgaaacc acttatttca gtgtctctgg tatcggcaga acgttcaata | 660 |
| ccactggcag ctgggagctg ttttggaggc tgagatggac caattgttca atctcagaag | 720 |
| actcgagata ctacaaccaa tcctacccct ggatatcctc cccatacatc gacggtagcc | 780 |
| tcaacatcga caaggtctat gagggctttc actacacagc atacaatgtc attgtcgaca | 840 |
| gggttacctt cagcactcgc gaagatgcta gccaacccaa cctcacgacc ctcaccaata | 900 |
| gcgagaactc cgataaagtc tcgtctcttg ctctattgtc gattgtggac tccctaagga | 960 |
| ttccacccca gttaccccaa gaagatattg ataccgtgtc aatgtgccca caactcgccg | 1020 |
| atgccaggct aaattcaact tcaacttcaa gcccctgcag cgttagcatt agtcccgagg | 1080 |
| ttgagtctaa tatcctggcc aagatcgcag acaatgaatg caataacgca cttcaccccg | 1140 |
| ctgtgagttg caccactgaa gaaaccaagg aaggcagcgc gagcagccat gaccacggcc | 1200 |
| atgctgtatg gcttgtcatt acgctagctt ttgccttcct tttctaaagg atccaatgct | 1260 |
| agatgtgctc gactcaggct ttgagacagg tagacaggaa acaggctttt attgtcacgt | 1320 |
| cgccagtagg ggaccatcaa ccacacatat gtccctacga gaccatagct atcaggaaca | 1380 |
| atgtacgggc tggaactcca ctcactctta ggttgtaaat cccatttctc aatacatagt | 1440 |
| ttgtgagcaa accacgcttt tcttgaatca ttgcatcctc tttagcttca attccttacc | 1500 |
| cacaaacacg agaggagcgg acccgccatt ccacatagtg tcttggcagg gtcgcctctc | 1560 |
| caactacaat gcccaacttc agaggcccag actatctctg ccaagtgcca aggctggact | 1620 |
| caaattacgg aactctcgga tgcttgtgcc atggcttatt gcttgaaggg tttggaggtt | 1680 |
| tcggtggtta gcgcccggat aggcagtaga acacctccaa atgaggaatg cggccgaagg | 1740 |
| taggtggggc | 1750 |

<210> SEQ ID NO 44
<211> LENGTH: 2030
<212> TYPE: DNA
<213> ORGANISM: Aspergillus niger

<400> SEQUENCE: 44

| | |
|---|---|
| tggatgccga gcaaattaat taactgcgct tacatggctg tcctaacaaa tcccttggca | 60 |
| ctcttagcag tggtgcctgg atgggacgaa gccctgggca tagcttgttc atcggtaggc | 120 |
| cgaaactctc ttttacgtac cgtacggcca atatcagtgt gaacccgcaa tttagatact | 180 |
| attaacttac aagtaccctc acgttatgta gccgaatgtt taaaagcgat ggaccggttt | 240 |
| aaagtctccg ttgtgcgatg gctgttatta acttggatta acttgcaatt tgcatcaagt | 300 |
| aagacgtgct tctttttgga tcttttttaca cacattactt acggcggatg ctctcgacac | 360 |
| tccggatttc accagggtgg tgttagtcca ccatcggact ccgatgcatc ttaacatggg | 420 |
| tggtcgagat gtcgccattc tcagcaggca ctttgctgtg acatcctcac aaagtgttaa | 480 |
| tggcgttgtc tctgggatgg tatgaggaag aatgatgcca tccgtgaaga gtgtcgactt | 540 |
| gatagatact caacaaaaag tcatcctata agtattgggt tggatctgct gttcttatca | 600 |

```
tttcgtctcc atcccactgc aatcttcttc aagacttcaa agtccatagt tccaacacac      660
agtcacctct tcacccagct tcactaccaa ccaattcttc aagaagaagt tcactgctgc      720
aattgctact gccattttcg caagcgttgc cgtcgcagct ccccagcgtg gcctcgaggc      780
ccgcctcaag gcccgcggca gcagcaaggg atcccgaccc ctccaggcag ttgctagacc      840
tgcatcaacc aagaaccaga ccaacgttga gtacagctcc aactggtccg gtgccgtgct      900
ggtggagcct ccctctgctg cagcgaccta cactgcggtg accggcacct tcactgtccc      960
tgagcccacc ggcaactctg gaggcagtca ggctgcatct gcctgggttg gtatcgacgg     1020
tgatacctat ggaaacgcca ttcttcagac cggtgttgac ttcaccgtga ccgacggaga     1080
ggcctcgttc gatgcctggt atgagtggta cccggattac gcctacgact tcagcggcat     1140
cgacatctcg gcaggcgatg agattgttgc cattgtggag tcctacacct cgactaccgg     1200
tattgccatt attgagaaca gagcaccgg ccagaaggtg tccaaggagc tgtcgtccag     1260
ctccagcctc ggtggacaga acgctgagtg gattgtggaa ggtaatatga acatacatt      1320
cctcattcaa cattaccaaa cgctaacgcg atcttagact tcgaggaaaa tggttcgctc     1380
gtcaacctgg tggactttgg caccgtcacc ttcactggtg ctgttgccaa ggcggcgggt     1440
ggtgagagtg ttggacttac cgatgcgacc atcatcgaga ttgaggagaa tggccaggtt     1500
gtcactgacg ttaccatcga cagcgactct gaggtgacca tcacctacga gtaaatttgc     1560
acacgaggcc tgtcactgtg actgacggtg ttgagtgtct caatacaaag cgggttgatt     1620
ggtatgcagg gatgtgatga tgtgatcagg tcagcgcttg atttcaatcg acgaggcagt     1680
ggagaacgaa gatgtagata gttttgattt ctagtactac tttgcggggc ccctgttgaa     1740
tttgagtcat tcttttgatt gatcctccgg aatcatatat caagtaatgg tgcagcgtag     1800
ggagtactcc ataaggcaga tgaagtacag gtcttaaaac ggtatgatcc agtaagacaa     1860
agcggatctt gtattccaaa caatcacgtc ggtaacatgg actactactt tcatctataa     1920
tgtttgtatg ccagttgtgc tgcagattat taatttgtat aggcattgta caggtgcgct     1980
acattgttca gcaagtaaac gtgattttga agtccccaag aacacaaagc               2030
```

<210> SEQ ID NO 45
<211> LENGTH: 3080
<212> TYPE: DNA
<213> ORGANISM: Aspergillus niger

<400> SEQUENCE: 45

```
cttcggctgc gtcatgattc atgcgtcaaa tcagtggact cttagtaggt ggatgtacag       60
cacttatttg atacttcgag tgtccgccaa catccggccg tctatattct ataccaatcc      120
acattatgcc caacgaaact gtatgctgtg atttaagcag aagtgagcaa agcactgtgt      180
cagctgatct aatatactat atgctccgat taaacccaag cagtctgcta ccagggagac      240
taccaggcag aaagtatctg ctgcatttg tcccagtctg cacaggactc gctatgttat       300
ggagcagaag tattgtgcat ggattccatc tgtcccacta gcatgactat ctcaatatcc      360
accgggtaca tgatttagcc ggtatcactc ccccgtccct gtagcaaagg cccgcgcaag      420
aggtgtttcc agaaagggct ccacgcttag caccgttcag caaattctgc atcagccgcg      480
gggaaactgc ggtttgttgc caggtcgagg tgcttaaata ccaccgtctt ctcgctcgtc      540
agtgctctgc tcaggcgtcg ctcagtcaag ttcagttcaa gactcaggat atccgggcag      600
tcctccgcaa ctatgcgctg ctccctcatc tcccttctag gcctggcggc catcccggcc      660
```

-continued

| | |
|---|---|
| cttggaggct gtcccttcgc acacactgcg aacatgggca ttgataacat ggtgaaagca | 720 |
| cacgctcaca tgtcccgacc gttgattgcc tccaagagca gcccctcaac tgttcctacc | 780 |
| tcctctagca ccccttctgt cgggcagaaa ggcgtgttca tgatgaaccg cattgctcct | 840 |
| ggcacatccg agctctacat tgccaacaca gatggcagta atgaacgccc actcctctcc | 900 |
| aaccccgtct acgagtacca tgcctccttc tccccggatg tagaatggat caccttcacc | 960 |
| agcgagcgca atggtgacgg taactctgac atctaccgcg tacggaccaa cggctccgat | 1020 |
| ctccaggaat tggttgccac gcctgcagtg gaagactccg ttgttatctc tcccaacggc | 1080 |
| cgcctggcag cctacgtctc caccgccaac aacatgaagg caaacatctg gatccttgat | 1140 |
| cttcagaccg gcgcgcagtg gaacctcaca aatacaccca ccactgccgc caactcctcc | 1200 |
| ctcatggaga gctatctccg tcctgcctgg tctcctgatg gcgaatggat cgccttctct | 1260 |
| tcggaccgca acacccaatg ggacggacac ggcgtaccga ccttcctcgg ccgcacgggc | 1320 |
| tgggagacga cgcaagaact ctctctctac gccatccgtc ccaatggctc tgacttccgt | 1380 |
| cagatcatct ccaagccata ctactctctt ggatctccga aatggtcagc agacggtaaa | 1440 |
| cgcatcgtct actacgaaat gacccgggaa gacacctaca cgcccatcg tccagaaacc | 1500 |
| attaccacag ccaactcgac gatcatgtcc gtagacttcg agacaggcac cgatgtgcgc | 1560 |
| gtggaagtcg ccggctccgg tgtcaagcaa ttccctcagt acctggacaa gaacggcacc | 1620 |
| atcgcctaca ccctcaaagg cggcaccagc gagggcttct acacgaccgc gggactctac | 1680 |
| gtcaacacga cctcggcgac cctcaggtcc cggcgtggt ctcccgacgg caagcaagta | 1740 |
| gtctacgaaa agagcacctg gagcatccgc tcggggtaca agcagctcta cagctgggac | 1800 |
| agtgactggg actaccgctt cacggacgtc ttccctcagg tctcgcacca ggagcgcgtc | 1860 |
| gccatcacac agaagcagct gggcaattcg tccatcgtga cgttgaacac aaccggaggc | 1920 |
| gacttgcaac tcgtctacga ccccagcacg gcggactttg tcagcgatga cgaaaccaca | 1980 |
| ggactgagcg cttaccagcc cagctggtca ccctgcggcg agtggctcgt cttcggcgtc | 2040 |
| ggattctggt tcgagacgag agaagcctca ggcggatgga tcgtgcgggc caccgccaac | 2100 |
| gggagctact cggaggttct cgtgaacagc agctactcca tcaccgagga tggagccctg | 2160 |
| aacagcgggt tcccgagttt ctcgccggat ggcaagaaag tggtgtatcg ggtttgggga | 2220 |
| gccgacactg caacctacgg caacgccagc gagatcgggc tgcgggtgct ggacctcgag | 2280 |
| acgcgaaaga caaccgtcct aaccacagaa tgggacaatc tgccccagtt ctctcccgat | 2340 |
| ggagagctca tcctattcac acgcaaaacc agcacgtaca attacgatgt gtgcacgatc | 2400 |
| cggccggatg ggacagatct ccgcgtgttg acgagcagcg gtgctaatga tgcgcatgcg | 2460 |
| gtctggtcgc aggatggacg gattatgtgg tctaccggca tgtatgggtt ccggtttgag | 2520 |
| tgtgcgctgt atggtgatac gttccagccg tatgggcagg ttatgattat ggatgcggat | 2580 |
| gggggaaata agaagttgat gaccaactcg atgtgggaag attcgatgcc gttgttcttg | 2640 |
| ccgagggagg tactttagtt ggtggcggga ggatgctctg attttagag gatatgtgac | 2700 |
| gtttgatgta tgataagaat tacacaagta gttttgatca taacgcgttg aagaggatga | 2760 |
| aaaaaaaccc ccgttgttcg acttgatctt ggcgatccgg tgtagggttg ttggacgagc | 2820 |
| aggatgtact gcttaattca agcaagtttg ctactccgat tcagtatgga ggggcaatta | 2880 |
| atgatgacga tattctgcac tttctactct acctactact tatctgtata tgaatgagaa | 2940 |
| aaaaatagta tgcaacgaat atagatcgta ttgacagaac ctgtcagaga gaatgacctc | 3000 |
| gatagtcgac tccatagcat ttgatctttt actaacagcg aaagattccg gactaactat | 3060 |

-continued

| | |
|---|---:|
| ccatatatag tactcctaca | 3080 |

<210> SEQ ID NO 46
<211> LENGTH: 3290
<212> TYPE: DNA
<213> ORGANISM: Aspergillus niger

<400> SEQUENCE: 46

| | |
|---|---:|
| ttccaacttc ccatgaagtg atgtagtagt ctgctaataa tacctcaaga tagaatatag | 60 |
| tatttactac ttatcgtcag ctttgtcgaa aattcaaagg tttgtggaag gccacctcat | 120 |
| ccgcacctgt tgcctacagg gatagcatcc tgcgaggtgc ttatccgctt atcagcaaag | 180 |
| gtggcagggg gggtaaggct atcccgggtt aggaaggccc gcggcacgat gcgatccttc | 240 |
| cagactagga agctacctaa tagggacagt aaggaccaa tctcaggact aaaccgtgca | 300 |
| gcctactgaa tctcaccact cggacctgat atttgccttc ggcttgcagg gtatatcat | 360 |
| ctcaatatcc tctagtggac ggaaactagc aactagtact ttgagctgac tcggccacta | 420 |
| taaatatgcg gtcttatgct cctcaacgac aggcaactgc tctgactacc aaaatctgag | 480 |
| taggactagc accgttgcga gctcctcttc acgataccga atcttttata agcaagtggt | 540 |
| ccaatatcca ggtctaacgt atccatacaa tgcctccgga tgcaaaatcg cctggctacc | 600 |
| agcctggtat ggcagtatta ccatctaggc cacatcctgc caagggaaaa gccattcgat | 660 |
| tcctcctttc ccttgcattg gtcgcgtttg ctattgttca attatgtggt aatttccaca | 720 |
| aaaataggag cgttgaacaa cagcttcaga gtcaaacact tgatgatgag tccttttaaat | 780 |
| gggaagatgt gtgtaaatct atcacgttgg gatgtaacgt tctaacgcac tctattaggt | 840 |
| tactcctacc aagcaactcg tataccatcc atgctttggt gatcacgaat gcgctcgctt | 900 |
| gtcgcttcca atgaattgga accgaactga tggtgaaggg tcaaaaattg ccttggcgt | 960 |
| tatcaaactt cctgccaagg tacctgtcac agatgcgcga tatggtggtg ccattcttct | 1020 |
| gaatccaggt atgtagagcc atattgctac tcttcagcgg ctgtgctgag tttcaaatag | 1080 |
| gtggtcctgg tggatccgga gtgagcatgg tcttagata cgggaaagct atccagacca | 1140 |
| tcgtcgactc cccagaatca ccaagtgcag attcagcgag cggaaagtat ttcgatgttg | 1200 |
| ttagctttga tccaagaggg gtcaacaaca caacacctaa ttttcctgc ttccctgacc | 1260 |
| ccgcgacgag gaaagcgtgg ttactgcagt cagaggcaga gggtctactt gggagttctg | 1320 |
| aaggagtctt cgatactcga tgggcaaggt acgaagcttt tggtatgagc tgcaatcaac | 1380 |
| aaggagtcac agcgtcaaag gatggagaat ggataggaaa attcatgaat acggcccccg | 1440 |
| tggtggcgga tatggttgaa ctcgtagagc gccatggaga gtggcgtgaa cgggaaacag | 1500 |
| agcggctact ttcgacagct ccgaacactt tcccagttgg aacaaacgtt gacgccgaga | 1560 |
| ggataaggct gcacaaccgt tggaaaaaag gggaggagaa gctgctatac tgggcttttt | 1620 |
| cctatgggac aatcctgggt tccacgtttg cggctatgca gcctcatcgc ataaaccgtg | 1680 |
| ctgtcataga cggagtctgc aacgctgatg attattacgc cggcaactgg cttaccaatt | 1740 |
| tacaagattc ggatgcagca ttcaataaat ttttcgagta ctgctacaca gctggcccat | 1800 |
| cagcgtgtcc gtttgcgctc ggcggagatc ccgaagatct caagtctcgt tatgagcaga | 1860 |
| ttttgaccaa tcttacatcg agccctattg ctgtgtctcc ttctggaaat aggggcccag | 1920 |
| agataataac ctatagtgat gtgaagtcat tggtcgtgca agctctctat gtgcctttga | 1980 |
| aattattcga tttggtggct aggctattag ctgagctcga gcaaggtaac ggctcttcat | 2040 |

-continued

```
tcgctgactt gaagtatgaa gccaaacaat ggccagtacc gcctccatgc gattcctcgt    2100
ccacacaata caaagtacct ggcgagagtg atcaggaggc cgggaggaat atcctatgta    2160
cagatggtcc aggcctcgac ggaactgcca aggaggattt ccggagctac tggaatatgc    2220
tccggggaca aagtaaggcg gttggagatt tctgggccga ggttcgcatg tcgtgtgtca    2280
aactggagac gcgacctgag tggcgctatg atggtaggtc cgaccaacac catattatac    2340
acacaatata agctgacagg tatgcgtatc caagggccct tcgcaggcaa tacatcgcac    2400
ccattgctgt ttatcgggaa tacttatgat ccagtaacgc cgctacggaa gtaagctttg    2460
ttcacctgat cgtagcagac tttgaagtac agactgacga ataggcagtg ctcatacgat    2520
ggcgcgtgga tttcctgagt caatcgttct agagcagaac tctgtcggag tgagtacctt    2580
atctgttccc caacccatat gcaagatgac taactgttca atgtcgcagc attgcacact    2640
gagtggccca tccttgtgta cagcgaaagc gatacgccag tatttccaga ccggagagtt    2700
acctgacccc ggaactgttt gccaggtaga ggagcttccc tttcgtcttg ccggatatga    2760
gagaagtcag gtcatgtcgc caggtgacac agaattgatg tccgccttgc attcgctgag    2820
cgagttccgc catctgctag gcgcgtgaaa aaggttaaat aagtgtcgcc agcgagcgct    2880
gcagttatta atcctttaca tcataggagc tggctagaat gttaacgatg cagtttgccc    2940
ctgtatctcg accaagagca tgaataacac attatatcag caaatgttat tgagcaaatc    3000
aattattcac ctgcactcaa ttcaatttaa gatctgttgc ctagactacc agaattatta    3060
aggcgacctt atcgaagcat ttgcagacca acccctgtcc atcgtcaggg gcaagacaga    3120
catttcttct agaacccgga tgatgtataa tcgcggtggg gaagatcatc ctaaaccatt    3180
gccccagact cgcctacctt aggtaatcca tacaaatgcc ggggaaatca ctgaggtgtt    3240
gttcatcacg gcgttgaatc ggcttctgcg gtattaccac cataactgta              3290
```

<210> SEQ ID NO 47
<211> LENGTH: 3080
<212> TYPE: DNA
<213> ORGANISM: Aspergillus niger

<400> SEQUENCE: 47

```
gaaaatcccg accgttaggc tacctaatct gctgtcttta cccccgttag cccacttacc      60
cagctttagt ctctcgaagg aaaagaaaac aaagtaatcg ggagcctata atattcggcc     120
agaagtgggg caatcacttc aaccgttcat ctgttattga gttatcaagt ctgtcaagtt     180
cgtcggagct ggataaggta gtcgccatcc ccatttccgc tgtgcaatgc cgcagcgccg     240
aagtgtctgc agctagctct attttgttca gctacgtatc tgtctcttaa ccaaatggat     300
gtcgccattc gcccactaac aacgccattc cccacgcccg acggactccg cgcaagggc     360 ctgataagcg ttagctccga ctccgagtta gtcatgcggc ttattacgcg cccttctccc     420
ctcacgatgt tgatgctttt tctggtatct ctggcataac tggcaaagat caggctgtgg     480
tcataagagt atcattgcct tcagcttctt cgccatgttg agtagtctgc tgcttggggg     540
tcttctgggt ctagcgaccg ctcaatttcc tcccgagccg gaaggcatca ctgtgctcaa     600
gtccaagttg catgagaatg tgactatttc tttcaaagag gtgtgtgcag agtatctaga     660
aatagctttt atgctcgatg ccgtgctgat tgtcagcctg gaatttgcga aactacgccg     720
ggtgtccgat cttattcggg ctatgtacac cttcccccg gtttcctttc gacgggaca     780 ggagaagtgc aggattatcc tatcaacacg taagccaatc tcgaaacatt ggaggatgag     840
caattactga gcctcaacca gcttcttttg gttttttcgaa gcccgcaaag atcccagcaa     900
```

-continued

```
tgcgcctctg gccatctggc tcaatggcgg tccgggtggc tcgtcgctca tggggctcct      960
tgaagaatta ggtccttgtt ccattgcatc agactccaag accacagtcc tcaatccttg     1020
gagttggaac aatgaagtca atcttctatt ccttgaccag ccaactcaag tcggcttctc     1080
atacgatgtc caacaaatg gcactttggt tcggactgcg gacggcgaag aagagatagt      1140
ttccggtgat ttctccattg atgttcccca gtccaacttc acccatcatg ttggtaccttt    1200
tgcaagccag aagcttgcac agacagctaa tgggactgca ttcgcggctc acgctctatg     1260
gcatttcgcg caaacctggt ttttcgagtt cccacactac aagccaaacg atgatcgtgt     1320
cagtctctgg gctgaaagtt acggaggcca ttatggtcca ggcatctttc ggttcttcca     1380
acagcagaat gacaaaatcg cagaggggac tgcagaagac ggtgcacagt atttgcatct     1440
cgacacgctt ggcattgtga acggcttgat ggatatggtg atccaagaag aggcttacat     1500
tacttggcca tacaataacg taaggctcgc cccttcttca ttcaactcgc gtaatgccta     1560
attcagttca gacctacggc ctcgaaatct tcgataaacc cctctacgaa gaactgatgt     1620
ataactggac gcatccagga ggctttcgcg atcaggccct cgcctgcgaa gcggctttga     1680
agaacgcga ttccggcttg cctcactcag ggaagaatat ctctgaaatt tgcggaggcc      1740
ttgcactaga atggggagat ggccccatca cctactacca caccttcaat cgcgggtggt     1800
acgacatcgc ccatcctaag aacgacccat tccctgccaa gcacatgctc ggatatttga     1860
cgcaggagtc cgtccttgcc gctcttgggg taccagtcaa tttcacatcg tcttcgagtg     1920
ccgtggctac acagttcata aaacctttg atatcgtcca cggcggcttc ctggatgcaa      1980
ttggctacct cctcgacagt ggtgtaaaag tacacatgat gtacggagat cgtgattacg     2040
cctgcaattg ggtcggggc gaaaaagcca gccttgcagt tccgtattcc cgtatcaccg      2100
aatttgccga cacgggatac tccccactcc ttacgcccga cgggatcagc ggcatgaccc     2160
gccagctggg caactacagc ttcactcgcg tcttccaagc cgggcatgag gtcccctcct     2220
accagcctgt cgcggcgtat gagatcttca tgcgggcgac attcaacaaa gatatcccta     2280
ctggcctctt ggctgttgat gacgaattcc agtcggttgg acctaaggat acgtggcata     2340
tcaagaatat ccctcctatt atgccaaagc cgcagtgcta tgttctaagt cccggcacgt     2400
gtaccccgga ggtttgggag accgttttga acggatccgc gacggtaaag gattggtatg     2460
tcgtggatga tagcgcgggt gttgaggacc acgagggtt cagcattctt ggaggggatg      2520
agttgtagta gctagaagt ctaccggaaa gccttgctag ctcttaaaat acgacacaaa      2580
tagttgagcg acatagtcta ctctctcact tacgaacacg tgatgaatct ctccagcaat     2640
aaagtggacc aatcaattgg aggaaaatat atccacgatg gtcggacggg ccaacgaaaa    2700
gggccaacta gcgcccctct gaggatgatg gtctagtctg caggatatga gattgttcac    2760
atcttatggg tcttcaactg cacaaattag gcggaggtcg cctcaccgaa agagacgtaa    2820
gctgcttttt ggtggattca ttattagccg ttatgccatt tactaaaaca ccgcagttcc   2880
agatcgcgta gatggcctca aagtgttcgc cagatttgat tgagggctac ttcgcccaag    2940
cctatggcct gtagatgcca atttcttcaa tacaaagata ggcgaaacat gttgaaaatc    3000
catcatattc aattaaattt caaaacatag cgagacatta agtattacat atatttcaat    3060
gaatagagac ttcttgcaca                                                3080
```

<210> SEQ ID NO 48
<211> LENGTH: 2520
<212> TYPE: DNA

<213> ORGANISM: Aspergillus niger

<400> SEQUENCE: 48

```
tctcgcctgc ctcgaccttc ctgctatggc aattctttcc ccaagctgag cggttccatc      60
cgcttcccga ccgccaaact tatcaacccg agcgatacgg agaggggaaa ggctatcacg     120
gcaatgattg cgcaactctg cgataagata accccatgtt ttgacgtagc ctcggccctg     180
tcttctcctc attattatcc tccgattccc ccagggttcc tgtcttctgc agaaagtgct     240
ctcggaatcg aagatgacca ggtttcaatt gcttcccctt gtcgcagggc tgcttgcccc     300
ttcaattgca gcccttagca tcccttcccc gcagcagatc ctcgattctc tcactttcgg     360
agagcacacc gacggctttt gtccgctggc acccaaggtt gaggttcctg acgatggttt     420
cttccagct ctcaagttcg tagaagatgc ctcgttcaag tcgcgccaag tcaatcgtct     480
ctccagggcg gttcaagttc cgaccgcaat cgacgactac atgaaggatc cctacgacga     540
aaagttcgcc ccattcctcg acttccagaa gctcctgcag accctctttc ccctcacgta     600
cgtccccagt cccgtcttc atggctccat ctaacgcaat ccagccactc ctacgcccgc     660
gtagatcaca tcaaccgatt tggtctcgtc ttcacccctca atggcacaga tgactcgctc     720
aagcccctgc tattcaccgc gcaccaggac gtcgtgccca tcaacgaccc tgccgactgg     780
acctatcccc ccttcgatgg ccactacgac ggcgaatggc tctggggccg cggtgccagc     840
gactgcaaga acgtcctgat cggtctcatg tccgttgttg aagacctact ctcccaaaag     900
tgggagccaa cccgcacagt cgtcctggcc ttcggattcg acgaagaatc ccacggcttc     960
ctcggcgccg gatccatcgc caaattcctt gagaagaaat acggaccgga cagcttcgaa    1020
tttatcctcg acgaaggcgg catgggcctc gaagttctag acgacaacaa caacggcgtc    1080
gtctacgctc tccccggcgt tggcgaaaag ggcagcatcg acgttgtgct cactctggcc    1140
gtaccaggcg gccacagctc cgtgcccct ccacacacgg gaatcggcat catcgccgag    1200
atcatctatg agctagaacg ccaggacctc ttcgtccccg tcctagacac tcaccacccg    1260
acccgcaaga tgctcgaatg ccaagtccgc cactcccct cgcaagtcga accgtggctc    1320
gcctccgccc tccaatcaag cgactacatc tccctagcag agaaactggc ctcctcgcgc    1380
ggcgacaagt tccgcttcat cctccaaacc tcccaagcag cggacatcat caacggcggc    1440
gtcaaatcca acgctctccc cgagaaaatc aacgccctcg tcaactaccg catcgctctg    1500
caccaaaccc cagacgatat caagaaccgc gctgtggaga tcatctctcc catcgtcaag    1560
aaatataacc tctccctcac ggccttcccg gaaagcgaca ccgttgaccc ctccctcaac    1620
aaccacctca cccttactac cctcagcggc gccctcagtc ccgccccggt cagcccaacg    1680
gacatcgaca ccgacgccgt ctgggcccgt ttctcgggcg tcactcgctc ggtcttcgaa    1740
tctgtcccta gtctcgaggg cagaaaggtc gtcgtgagcg gcgacatcat gaccgggaat    1800
acggatacga gattctactg ggctttgtcg aggaatattt acaggtggag tccgtcgagg    1860
gcgggtaaag cgctgaatat tcatactgtt gatgagagga tcgatattga tattcatctt    1920
gaggcgatga tgctgtatta cggtatgcat ctctcctttt atggatactc ctatcagact    1980
aacttgtatc tctagatctt attcgctctt tcgatggacg gaccgattca tctgtcattt    2040
ctgctgcgtc ggcagctgct gatgatgaac ttgctcacga cgtgctgtga gtctgtagga    2100
actctcctac tctttagggt ggctcaggat gaatgatggt tatgaatcat gtggtctact    2160
gcgccaaaag ttcatgtctt tcctggagtt caacgagaac cagatctata tttccacgaa    2220
tagctccagt atatagccaa atgcaaccac gtatttgtct atcgatctga cagtctaatt    2280
```

```
cttaccttta tactaggggt aagaaagggt aagaaaataa aataatatttt gcagcggcct    2340 atgaagataa ttatgtactc gacgttgccc aatgcactgt agccctctc cctgtaacag     2400 gagtagccat aaaagcaaaa cgaaagtggt aagaagacgg gggcaatatc cctgctttag    2460
caatatacaa caatagtaac aatcgagagc tcaatatgaa tgtataacga gtgacctgca    2520

<210> SEQ ID NO 49
<211> LENGTH: 2730
<212> TYPE: DNA
<213> ORGANISM: Aspergillus niger

<400> SEQUENCE: 49
tttagttgtg atctcaatcg caaatggaca ggagatgata ttcatgtcat aatcagagtg      60
ccatgtcagc gaccatgtct tgccaagagt catcatttcc ggtaaaaccg acggaggtaa     120
aaccccggtc attcactagt tcgagggagg aatagtctc gcaggtctct tcttctttct     180
tcctcggggt ggcggatgga tcacttcttc atttgatggt tgcctgccaa cgacccactt     240
gactaggttt cccccttgat gggattcgtt ggttttacca gacagagcct cttcacagcc     300
cagcgcgtgt tccgcaaaag caacagccca agggtctgaa ggctgacatt ggagcgggtc     360
tgacgcagga tggcttgctg ttaaaaaaac tcaggaacag gccaagacga agcgaccgcg     420
caaggctgag cagttctccg atttccccgt gccctcctg cgcctccat gggcgacttt      480 tgatcccaga tccatcgttt ctgcaccgac catataagaa gctccgcacc cccaaactcc     540
cctggcaagt tcctgccccc aaattacgtg agacagggaa ccatcacagc aacaccatga     600
agagcaccac tcttcttttcc ttggcctggg ctgcccagtc cgcctattcc ctctctatcc     660
acgagcgcga tgaacccgct actcttcagt tcaactttga acgtcgtcag atcgccgacc     720
ggtcccgtcg gaagcgatcg acggcctcgg ccgacctcgt taacctggta tgttcccatc     780
ccgagtctca aatcagggga attatgacgg tcgctaatgc aggtttctag gctacgaatc     840
ttggctacac gatgaaccctc acactcggca ctcccggcca ggaagtcagt gtgacgttgg     900
acaccggcag cagcgatctc tgggtcaatg gggccaactc gtccgtctgc ccctgtaccg     960
attacggctc ttacaactca agcgcttctt ccacctacac cttcgtgaac gatgagtttt    1020
atatccagta tgtcgacggc agtgaagcca caggcgacta tgtcaacgat actctaaagt    1080
tctccaatgt gactttgacg aactttcaat ttgccgtcgc atatgacggc gactccgagg    1140
gtaagtcttc gctattccct cactttcatt ttacactttg ctaacggtttt taccatgcag    1200 aggggtcct cggtatcgga tacgccagca atgaagccag ccaggccacc gtcggtggtg    1260
gtgaatacac caacttcccc gaagccctcg tcgatcaagg cgcgatcaac tggccggcct    1320
acagtctatg gctcgatgac ctcgacgaag gaaaaggcac cattctgttc ggcggagtca    1380
acaccgccaa gtactacggc agcctgcaga ccctgcctat cgtctccatc gaagacatgt    1440
acgtcgagtt cgcggtcaac ctgacggccg tgcaccttga agaacggc aactccgtct      1500 cggtcaacaa cagcgccacg caattcccca tccccgccgt gctggacagc ggcacggccc    1560
tgacctacat cccgacctcc gccgcagcca gcatctacga ggccgtcggt gcccaatacc    1620
tgagcgagta cgggtacgga gtgatcgagt gcgacgtcaa ggacgaagac ttcaccttcc    1680
tgttcgactt tggatccttc aacatgagcg ttgacatcag cgagatgatc ctcgaggcca    1740
gttccgacat gaccgacatg aacgttttgta cgtttggcct cgcagtgatc gaaaatgagg    1800
ccctgctggg cgataccttc ctgcgcagcg catacgtcgt ctacgatctc ggaaacaacg    1860
```

-continued

```
agatctccct ggccaaggcc aacttcaacc ccggcgagga ccacgtcctg gagatcggca    1920
ccggatcgga tgccgtgccc aaggcgacgg gggcgacggc gaccggcgcg gcagccacat    1980
ccacggcctc gagcgacaag tcggacaagg agagttcggc tacagtgccg cgcagccaga    2040
ttgtctcgct ggtggcggga gtcttggtcg gtgttttctt ggttctgtaa atatagagat    2100
ttcacgttgc atgttgatga tacataccat agatttgctt ctaattgccc cttacatctc    2160
gaaatgtttt ctgtttttag cttgatatcc catcgcttca ggtttcagat atggaaatga    2220
aatgaaaatc ggaatgcaag atctgatcga atagttgttt cactgccgcg tggctggtcc    2280
gatcggcacg aagccagtaa tcgacaacca atcatacatt gtgatttcct gtcaacctcc    2340
ttgcgactac tactaatttt atcatatcat gccgttgtga cctatcctac tcggtgtccc    2400
cacaccgatg atagccaccc cgaccggat aatcggtaac ctgccaagag tcgaacggct    2460
ttcctgtgga aagggtggct gcaacctgtt tgtttcagtt tttgtgttgc agaattgact    2520
atccttctga cctgtgaatg atactgggat ggtgacgtag tgaaaatgtt ggtggagcga    2580
ttaaggtttg tgcctgtcag cctcgtcaag tccatcatca tgtcttttcc ggactatcac    2640
ttcctctact ctgaagtacc gggactcccc gccagtattc gtttcgccaa tcagagcatt    2700
cgatgtgaac cggattgaag agtgcccggt                                     2730
```

```
<210> SEQ ID NO 50
<211> LENGTH: 3231
<212> TYPE: DNA
<213> ORGANISM: Aspergillus niger

<400> SEQUENCE: 50
```

```
ccgacgcgac ggcattagtt cctcgatagc gtgggaagac catggagaga ccggccgata     60
agctgcagag gagctttctg tgggctgacc agtgcctatc agcaaatgga cacgcggtga    120 caccccccgca atcgcaagac cgcctcgaca ccgtccatcc aggcaccatc gcaacggcaa    180
accagcctct cctccaatca aaccatcgat gtgatattgc tagcggcggt gagaacagca    240
ggtcgaatgt cgcaattaat tctcgcatcg tccctcactg caaggggccc actaccagag    300
ctctgcggcg ttgttattta aatccgttgt tgggacccttt cggtcatcag ccactgtgtc    360
tggtcactat cgcgctggtt caacctcaac atgttggtcc gtcagcttgc cctggctctg    420
gccattgcgg ccttgtccga tgccattccg acatccatca agcatgtcct gcacgagaaa    480
cgtcacaagc ccgcatccga ctgggtgaag ggtgcgcgcg ttgagagcga tgcggtcctg    540
cctatgcgca ttggccttgc ccagaacaac ttggacaagg ctatgactt cctgatggaa    600 gtgtgagtca aaatctacct ttttatgct atatgcctag ttttaggatc gcaatggatg    660
acctcgaaac atgctgacat gagattggcg cagatcggac cccaagtctt ccaaatacgg    720
ccagtactgg tcggcagacg aggtgcacga catcttttcg ccatccgagg aggctgttga    780
ggcagtgaga gaatggcttg tcgcctctgg tatccatccg tcgcgggtgg tgcactccga    840
caacaagggc tggctcgcgt tcgacgccta cgcccatgaa gccgagaggc tgttcatgac    900
ggaattccac gagcacgaga gcgaccgaag tgctaagatc agggttggat gcgaccagta    960
agaagattct tctatcacct tccatgagta gctattaatc ggaatctaga taccacgtcc   1020
ccgaacacat ccgaagcac atcgactaca ttacccctgg agtgaagctc acccaggtcg   1080
tgaagaggac caacaaagtc aagcgtgctt cccaactagc tcactcttcc aaggccaagt   1140
ctgctgccca aggtccgcag ccactcccca acaaggccaa gttcctgcct gaagacctcc   1200
gcggctgcgg ttacaacatc acccccctcgt gtatcaaggc cttgtatcag atcccagacg   1260
```

-continued

```
ctaagacggc gaccccgaac aacagcctgg gtctgtacga gcagggtgac tactttgcca    1320
agtccgacct cgacctcttc tataaggagt atgcgccgtg ggttccccag ggtacctatc    1380
ccatcccagc cctgattgat ggcgccaatt actcggttcc ttcctacagc tccctgaaca    1440
cgggtgaatc cgacattgac attgacatgg cgtgagtcat ttctgcacct tgtcatcaga    1500
cccctactga cgttttgaag ctactccctg ctctaccctc agcaggtgac cctctaccag    1560
gttgacgacc agctctacga accagtcgag gtcgacacaa ccaatctgtt caacaccttc    1620
ctcgacgctc tcgatggcgt gagtacagac ctcgttctca gtcttaccca gctaacaccc    1680
ctagtcctac tgcacctaca gcgcctacgg cgagaccggc gatgacccgt cgatcgaccc    1740 cgtataccccc gacacccgcc ccggcggcta caaaggtacc tacctacacc acctcttccc    1800
catacaatcc aacctaacac accaacagga aagctccagt gcggcgtcta taagcccact    1860
aacgtaatca gcgcctccta cggccaatcc gaagccgacc tccccgtcag ctacaccaag    1920
cgccaatgca atgagttcat gaagctcggt ctacagggac actccatcct cttcgcgtct    1980
ggcgactacg gcgtcgcgtc tttcgccggc gacggtgacg agaacggctg tctcggccca    2040
gagggcaaga tcttcaaccc ccagtacccc tccaactgcc cctacgtcac ctccgttgga    2100
ggtaccatgc tgtacggcta ccagaccgtc aacgacagcg agagcgtcat gcacgttaac    2160
cttggcggaa ccgcaagtaa cttcagcact tctggtggct tctcgaatta cttcccccaa    2220
ccggcatatc agtttgctgc tgtggagcaa tacttccagt ctgcgaacct gtcgtatccg    2280
tattactcgg agtttgaggt cgatgttaac acgaccaagg gtctctacaa taggcttggt    2340
cgtgcttatc cggatgtctc ggcgaatgga gcgcatttcc gcgcttatat ggatggatac    2400
gattatcatt ggtatggatc gagtttggcg tcgcctttgt tcgcgtcggt tcttactttg    2460
gtgagctttg tcaccccca ttactaatta ttgacacatg gctgaccgac ttagctcaac    2520
gaggaacgct tcgctatcgg caagggcccc gtgggattcg tgaatcccgt gctttatgct    2580
tatccgcaag tgctgaacga tatcactaat ggtactaatg ctgggtgtgg aacttatggg    2640
tttagtgcta ttgagggggta agtgctcagt acttggttct gtcaggaggg gtgtgctaat    2700
tgatgactat agatgggatc cgctagtggg tttgggtacg cctaactacc cattgatgaa    2760
ggagctgttc ctctctttgc cttaggattg aacggtgctg tgtcagaggg tgataggtgg    2820
tcaagctgtg tatatatgtc tgatggggaa atatttacga tcataggata atgtgtcgac    2880
gagcatgaat ggccaattat ctcgcctgtc accgtgaata aggtcaaatg tagatcggtt    2940
taatagttca actacagaga attcttggat attgtcaaat gttgactatt cgctgtctct    3000
ttatcgtcta atgtataata tcatcaaata acctaaccca agggatatca aaaacataag    3060
aaaataataa accggtacta tgtgtcgaaa aaggaatgt ttgtgaattt tttaaaaccg    3120
ttcatacctc ccgtccatgt ccaccaaatg cacagcgctg gtcgaatccc tctccgaccg    3180
tgtcgtatag tcaacggaga tattcactga cttggaaatc ttgctgttgg t            3231
```

<210> SEQ ID NO 51
<211> LENGTH: 2660
<212> TYPE: DNA
<213> ORGANISM: Aspergillus niger

<400> SEQUENCE: 51

```
tcctgagcaa gcagctaccg gtaatctgag acctaatcct ggtaagtgga tcgagttcat      60
ttacctcatc atctaacctc gcttcatgat tcgcaggcgc tttccgcgac tagtcgatgc     120
```

-continued

```
cagtatccat tgcctgcag atccgatgct tccaccgacc accgttactt ctctccagac      180
ccccatccgg ctttccgacg gcctcctctg catcccctca caaagcaagc ggagacctgc      240
ctgaataggg agagttttt caatgagccc acacgcagtt acctcgcttc cgcatgagat       300
gggtccattc ttgacaatgc tgcctaatgc gcagaagggc cgtcatgcgc ctggagaact      360
acataaatag gaccacgca tgccccgacg atgtatgaat tgttcaaact ctccgccca        420 agtgagttct cttttcattc cattccgaag ggagaatcac cagtatgcgg gttaccacgg      480
caattgcttc attactactg gtcggctcgg ccaccagtct ccaaaatcct catcgtcggg      540
ctgttccgcc ccctctctcg catcgcagcg tagcgtctcg ctccgtgccc gttgagcgcc      600
gaaccaccga ctttgagtat ttgactaaca agactgcaag tgcgtgattc cgttttttaa      660
ctaccgcatt tatcgttcta agatcaattg caggattcct ggtcaatggc acaagcatcc      720
ccgaagtcga tttcgacgtc ggcgagtcct acgccggcct ctccccaat acgcccactg       780 gcaattctag cctattcttc tggttcttcc cctcgcaaaa tccagaggcc agcgatgagg      840
ttagtggtcg ctctgttttt tccggtcatg cgtcagccag ctaacaatta acaaagatca     900
ccatctggct caacggcggc cccggatgta gctccctaga cggcctgctt caagagaacg     960
gcccattcct ctggcagcct ggcacttaca agcccgttcc taatccatac tcatggacca   1020
acctcaccaa tgtggtttac atcgaccaac ccgccggcac aggcttctcc ccgggccccct  1080 cgaccgtaaa taacgaggaa gacgtggctg cccagttcaa cagctggttc aagcacttcg    1140
tcgacacctt cgacctgcac ggccgcaagg tctacatcac cggtgaaagc tacgcgggca    1200
tgtacgtccc ctacattgcc gatgccatgc tgaacgagga ggatacaacc tacttcaact    1260
tgaagggtat ccagatcaac gacccgtcca tcaacgcga ctcggtcatg atgtactgta     1320
tgtttccctt catataccte cacctccacc accaccacca ctaacaacat cacccaccag    1380
cccccgccgt ccgccatctg aaccactaca acaacatctt ccagctaaac tccacttttcc   1440 tctcctacat caacgccaaa gccgacaagt gcggctacaa cgccttcctc gacaaagcca   1500
tcacctaccc accccccagt cccttcccca ccgcccctga atcaccgaa gactgccaag     1560 tctgggacga agtcgtcatg gccgcctacg acatcaaccc ctgcttcaat tactaccacc    1620
tgatcgactt ctgcccctac ctctgggacg tgctcggctt ccctcccctc gcctccggcc    1680
caaacaacta cttcaaccgc tccgacgtcc agaagatcct gcacgtccct ccaacggact    1740
actccgtgtg ctcggagacc gtcatcttcg cgaacggcga cggcagcgac cccagctcct    1800 ggggtccct acccagcgtc atcgaacgca ctaacaacac tatcatcggc cacggctggc    1860
tcgattacct cctcttcttg aacggctcgc tcgccacaat ccagaacatg acctggaacg    1920
gtaagcaagg gttccagcgt cctcccgtgg aaccgctctt cgtcccttac cattatggtc    1980
tggctgagct gtactgggg gatgagcctg acccgtataa ccttgatgct ggcgctggat    2040
acctgggtac agcgcatacc gagcgcgggt tgactttcag ctcggtgtat ttgtctggtc    2100
atggtaagtt tattatatcc ccttggaagc ggtatgatga acgttagaga gtgctgactg   2160
ttgcttcctc ctcgtgatag aaatcccgca gtatgttcct ggtgcggctt accgccagtt   2220
ggagttcctg ctcggtagga ttagtagtct ttcggcgaag gggaactata cctcttgatt   2280
tcagcggatg acgacaaaaa gatgatgagg aagatgattg gatgctttca gatgggaatg    2340
cgtgcatagg agatgagatg agatgatgta tcattgaggt gtgatgactt gtacatatgt   2400
agatcggtag taaaagggat actataggat atggtatttg atgtatcatt tatgtacacc    2460
acgtggattc aattgagggg agcttcaatt cctggttatt acttatcata tttccaacat    2520
```

```
gtccgcgtat aaccggtaac aactaacggc ttcatgtttg tcaagtgact gtcttggtac    2580
aatactactg tttctatatt ctactgttgg taacttaatc tggacatatt ctatatccac    2640
gtacagattc tcgctagatt                                                2660

<210> SEQ ID NO 52
<211> LENGTH: 3150
<212> TYPE: DNA
<213> ORGANISM: Aspergillus niger

<400> SEQUENCE: 52
ccaatcaacc acggatgatt gggttcaggt cctggaggca cggagtcgga ccaagacact      60
aaggtacagc actagcgaga caatgtgtta tcgctattat tggcaaaatg gccgcgggat     120
ctcttatgca gggttcggct ccatcctccc ccctcttcct atccagtcaa tccgcctcgg     180
ttattgaagg agatcctgag ctgtttaact gacgcctcac cgatcaggcc ggaaatggtg     240
gcgggataca acatcgtttc cacacaatag tgcttgtctc ctgcgatctg catggcatgc     300
taatctccgc cagcatgtat cttctatcca ctggatatga attttcctcc cctcacacca     360
tgtgggcctg ggggttttcc ctcaaacttt gtcgctcatg taacgatgta tataaagccc     420
tgaggatggc atcccccacc catcggtctt ttgctgaccg ttctccttga agaaattctc     480
gagtggcttg tggtgcatgt atagatttaa tcttcgaggg ttattaacta ggtatagctg     540
tgactaagtc tgtccttgca ttgaacaaca caccatgcgt ggctctcggt tggtgctctt     600
gttgcccctg gctgcactta gttgtgctat gcccgagaat gaatggtcat ctacgataag     660
aaggcagtta ccaaaagcgt ccactggcgt caaatcgata aaaccccaa acaatgtcac      720 tatcaggtat aaagaaccag gaaccgaagg aatttgtgag acaacacctg gggtcaaatc     780
atactccgga tatgtcgatc tttcgccaga gtcgcatact ttcttttggt ttttcgagtc     840
acgccgtgac cccgaaaatg atccagtgac tctgtggctg aatggtggcc ctggaagcga     900
ttccttgatt gggctttttg aaggttggcc aaatatcctg acggaaaaga taaaattcag     960
cttgcatgtt ctgacgcctt cacaacagag ttgggtccgt gtcacatcac accagagtac    1020
gaatcaatca tcaatcagta ctcctggaac gaggtcacca atcttctttt cttgtctcag    1080
cccctcggtg tgggtatgga atattgctgc cttcatacat cctgagtaca ttgcttacgg    1140
tcttatctgc gaagggttct cttacagtga aaccgaggcc gggtccttga atccatttac    1200
tggagccgtc gagaacgcct cctttgctgg agttcagggt cgatacccag ttattgatgc    1260
cactatcatc ggtaagttgt ccggtttgac tctcacctag cattctcctc aatgtcctac    1320
tttacagaca cgaccgatat cgctgcacgc gcaacctggg aggtgcttca gggcttcctc    1380
agtggcctgt cgcagctaga ttccgaagtc aagtccaagg agttcaacct gtggacagag    1440
agttacggag ggtgagtgca actttcatac cagaccgacg taagctgact tgatcaagac    1500
actatggacc agcggtaggt tgtctttctct ggttgcacac atattgatct aatgaccgaa    1560
gttcttcaat catttctacg agcaaaaattc gaagatcgct agcggggaag tcaatggcgt    1620
ccaactgaat tttaactccc tcgggattat caacggcatc attgatgccg cgattcaggt    1680
acttagaaat gcagctcgcg cagaggctgc ggcctagaag gacatcgcta agtaattaa     1740 taggcagact actacgcaga ctttgccgtt aataatacat atggaatcaa agctgtaagt    1800
ttaaatacac gtacatcgtg gatttaagat caaccgtgct catgcttgct aggtcaatga    1860
cacagtgtac aactatatga agttcgccaa cacgatgcca aatggatgcc aggatcaggt    1920
```

```
tgcttcgtgt aaattgacca ataggacctc gctttctgat tatgctatat gtacagaagc   1980
agccaatatg tgcagggaca atgtcggtga gtggttctac tgtttctctg cagggqtgca   2040 atgatgaagg actttgctaa gctgtcatgt acagaagggc cttactacca gtttggcggc   2100
cgtggcgtgt atgatattcg gcacccctac aatgtaagtg gcaaggataa ggattgtact   2160
ttccgaacag ggacactgct catatgtcaa cgtaggaccc gaccccgccg tcctactttg   2220
ttgactacct caagaaagac tcagtcatgg atgctatcgg cgtggacatt aactacaccg   2280
agtccagcgg cgaagtatat tatgcattcc agcagaccgg cgactttgta tggccgaatt   2340
tcattgagga ccctcgaagag atcctccaac tccccgtacg cgtgtcgttg atctacggcg   2400
atgccgacta tatctgtaac tggttcggcg gtcaggccat ctcactcgca gttaactacc   2460
cccatgcagc tcagttccgt gcagcgggat acacacccat gacagtagat ggggtcgaat   2520
acggtgagac tcgcgagtat ggcaactttt cgttcacccg cgtatatcag gctgggcacg   2580
aggttccata ctatcaaccg atcgcagcgt tgcagctgtt caaccgtact ttatttggat   2640
gggatattgc agcgggtaca actcagattt ggcccgaata tagcaccaac gggacatcgc   2700
aggctacaca cacggagtcg ttcgtgccac tgtccacggc gtcgagtacc accgtcaatt   2760
aggattgggg gaaattttc cctctttggt atggctaatg ctgtgttatc cattccgata   2820
cttgtccata acctaaaaga gtggcacgga agctttccta gacatgcttg ctctagtcaa   2880
cttttatcct accactgtgt ggtcctacca taatgtcatc ctaaacttat caggtgtctt   2940
acatcatttt gcagtgacca taaaagtcat gtcatattaa gtccattacg gtagttcgta   3000
acttgctgat ggcttacgta attgtgcctc agcaggatgt cgtgatacgc tccaaaaccc   3060
aatctgatca tggatatcca gcggaataac acaaaagaaa aaataaacat aaccaaccac   3120
caaaatgaca gaggctaatg cctggacaac                                    3150
```

<210> SEQ ID NO 53
<211> LENGTH: 3221
<212> TYPE: DNA
<213> ORGANISM: Aspergillus niger

<400> SEQUENCE: 53

```
ccatcagctc ttgttgttat gttttatgtc atagtgtaat gctagcctta gcgtgcgtgg    60
tgtttgaatt tcagattggg catggatacc tgggcgtctc gggatggata ctgggacgtg   120
gtaagatgct tggaagcgtt gattttgagt ttgacaatat atccctatgt ttctcttctc   180
cacacccttt taccgtaatg cgacagcatt gtgtagagtg cattgcctta attagaaacct   240 acgaatcctt gatttgtata tgacacccga tcaccatcga gccacctaca tcatggcgcg   300
ctctcagatc ctccgaacca aaacagtaat gtcgatcgtc gcgcctgaac caaggctgat   360
tttccctgct gaagcgtgtc ataaagtgaa acatactttg tagataaact cggcaattaa   420
ctgccactta ccccatacat cgctaccgga gagtggagca agtgcacggc catcaagtga   480
aactgataac cggcgatccg ccggcttatc ggcgatggcg ttatcagagg gaccttagta   540
ggttgcacag ttcactagta tttattacta agtacttcct tcgccttgct tattgcccat   600
gattcgtcct tctcttttc tttggttaat tgaactactc tccatgagag ttctgtacag   660
gttgagatag accaaccacc accaccatgc ctttcccctt tcgtccgct cttctcggct   720 atatcttaac tacgagcact actctcacct ccctagtcgc aggacagtat taccctccga   780
cgcctgagga tctcaccgtt attcattcgg agatattccc tggtgcgagg atctcctata   840
agcaagtgag aaatacacca cccttctcct caatcccaat ctaacacccc atactaatac   900
```

-continued

```
tatgtgacca gccccctcggc atctgcacca ccaccccctc cacccccagc tactccggct    960
acatccacct cccccccacac acccttacca atctctccat tccaggaatc agcatctcgc   1020
aaccataccc tatcaatacc tttttctggt actttccttc ccgccatcac cacaacaatg   1080
atacatcccc actcaccatc tggatgaacg gcgggcccgg cggatcctcc atgattgggc   1140
tatttcaaga gaacgggcca tgtactgtga atacggactc gaattccacg gcctataatc   1200
cctggtcgtg gaatgagtac gtcgatatgt tgtatattga gcagccggtg cagacgggat   1260
ttagttatga tgtgttgagg aatgggacgt tagatttggt tagtgggggag atagatgtta   1320
gtattagtga tggtgagagg gatggagtag gacagaatga gacgttttttg gtggggacgt   1380
tgccgagtca ggatgtgcat gggacggtga atgggacggt taatggggga agggcgcttt   1440
gggttgcgtt gcaggtttgg ttgggtgaat tctctgaata tgtttcttct gttgacggga   1500
atggtggtgg tgatgacagg gtgagtatat ggacggagtc atatggggga cggtatggac   1560
cggcatacac ggcgctcttt caggagatga atgagaggat tgagagtggg gaggtaagca   1620
ccgggaagaa gatccatttg gatacgctgg gcattatcaa tgggtgtgtg gatttactcg   1680
tgcaggtccc ttcgttccct gagcaggcgt ataacaatac gtatgggatc gagggaatca   1740
atcgcacgct ctacgaccgg gctatggata gttggagcaa gcctggcggg tgcagggata   1800
tgatcatcga gtgtcgcgat gctggcgagc tcggagatcc cctcatgtat ggcgacaatg   1860
agacggtaaa tagcatctgc gaggaggcgt cggactactg ttcgcgggag atcaagagcc   1920
tgtatacgaa tacctccggg cgaggatact acgacatagc gcatttcacg ccggatgcag   1980
ctctcgtgcc ttacttcgtc gggttcttga atcgcccatg ggtgcaaaag gcacttgggg   2040
tcccggtgaa ctataccatg tcgtcagagg cagtggggaa cagtttcgcc tcgacgggcg   2100
attatccgcg aaatgatccc cgcggaatga tcggggatat tggatacttg cttgactccg   2160
gtgtcaaggt ggctatggta tatggggacc gggactatgc ttgtccgtgg cgcggcgggg   2220
aagatgtcag cctgctggtg gagtacgagg atgcggagaa gttccgtgct gctgggtatg   2280
ccgaagtgca gacgaagtca tcctacgttg ggggtctagt aaggcagtat gggaacttct   2340
cgttcacgcg tgtctttcag gcgggccatg aggtgccatt ttatcagccc gaaacggcgt   2400
atgagatttt taatcgcgct cagtttaatt gggatattgc gacgggaggc atttctctgg   2460
agcagaatca gagctatggg acggagggac cgtcgtcaac gtggcatatc aaaaacgaag   2520
tgccggagag ccctgagccg acgtgctatt tgttggcgat ggattcgact tgtacggatg   2580
agcagaggga acgggtgctg agtggggatg cggtggtgag ggattgggtt gttgttgatg   2640
atattgaggc tgaaagctcg ttcagcggtg ttggtgatca gctggcacag gtccctttgg   2700
gacattgacg ttggttgcca tatgttgaca gtgttggtgg atgaaagtga tatagatgga   2760
taaagttagt gcataagtgc atagctgact aagaatgagc atcattcata tatggataag   2820
tctggctagc tcgatccggc aagtggccgg ctgactgcct aaagtggaag actggaagcc   2880
ttcagatttc catcagtcca tctcaatatc tccatctggc ttgtcaaact cctatatcca   2940
ccggccggac ccttctatta ttaacagcgc cgctatcacc cggacaatcc gtatggcatc   3000
acgggttgac ccctccattg cggccatcga accttctcga accttctatt ggtcgaccgc   3060
tgcggtcaac gtcacacgtc accgcaggct cacctgaaag ccgccggcgt tgcactatac   3120
atcagccctc gtcctcacac ctggctttct ccgctaatcc tccaagtaca cccttcactg   3180
tgccttgatg tcttgaatca acatctataa aaactgcatt a                       3221
```

<210> SEQ ID NO 54
<211> LENGTH: 2590
<212> TYPE: DNA
<213> ORGANISM: Aspergillus niger

<400> SEQUENCE: 54

| | | | | | |
|---|---|---|---|---|---|
| gagtgagtaa | attgatctaa | cggcgtcgcg | ctgacaaaca | tcatagctat | caatcagaaa | 60 |
| aagcgaagca | tatttcacat | acgatcggat | agcctaccaa | ggaactgagg | atatacgtac | 120 |
| agctttcgct | tggctgacac | gtaaagtcat | ttggtgattt | tggagcgact | ttggatctcc | 180 |
| ttccatgtaa | gttataacct | accgcaattc | caaagtatag | ctagtagctg | tcagtcactc | 240 |
| aagaacttgc | agcaaggcga | tggcaagaca | aaacaatcga | tggtacggag | tagatagaag | 300 |
| acactaaagc | actttcacat | gacactgttg | acatagtgct | tatgctcttt | acactcaaca | 360 |
| tgagtcactt | tgataaggtg | atttcgccag | atggtggcat | tattgactcc | tgattggatc | 420 |
| caccgataag | gaaccacttt | ttggctggca | atgtactatg | ttattgacag | gcatcgaact | 480 |
| tccccaaatc | tcaggctggg | ccgccagcaa | atggcgcggt | tccggactcc | ggcggggct | 540 |
| gacagggcca | accgttggct | gcttgtccct | tgccgccgga | gagcttattt | aactcttgtc | 600 |
| tctcctcttc | ccccacaaag | ctcactcagc | actcaaggcc | tcaccgcgcc | atagtcccgc | 660 |
| tcttgatcat | cctagcaaa | acggctgtaa | atcatgagaa | catctactct | tttgctcctc | 720 |
| tggagcactg | caggagcagc | tttggcttct | ccgtacccgc | ttcccgactc | gcaagtagtc | 780 |
| ttcgccgcgg | atcacgaggt | cccgaataca | caggcaaaac | acgtcgtgga | cgaggccata | 840 |
| ctctcggcgc | tgaacgctca | ttctgaccca | gtcgctgcaa | tggtgtctct | acgtcccgaa | 900 |
| actgcagctt | ttctagctga | acctcgtctc | ttgcacattc | ggggcgaaga | gaaggcggaa | 960 |
| tggatgaccg | aaggcgacaa | gctgcgcctc | cgccaacgcg | gaaagaagtt | catggacatt | 1020 |
| accgagcatc | aggacttcta | cgcagagcag | gcgatggctt | cgtttgctgg | ggatcctagt | 1080 |
| taatctccct | tttgtcgagg | taattaatac | tgtgttaacg | cccctttagat | cttcccaagc | 1140 |
| tgtcccataa | aggtctcgtc | aagccgctgt | tctctcaaat | cgagacggaa | cgaatgcacg | 1200 |
| atatcctgca | gcacatgacc | tcctactaca | atcgatacta | cggtgattat | cacggcgaga | 1260 |
| tgagctccga | atggctgcac | gactacattg | ctgcggtatc | tccacccct | acagccacaa | 1320 |
| tttttgaaca | tgaacttact | caaccaagat | catctccaaa | tcgcctttcc | gcacccacat | 1380 |
| ctctctcgaa | tacttcaccc | atcctttccg | ccaatcttca | attattgcac | gcttcgagcc | 1440 |
| taaagttcgc | agcttctccc | aacctttgac | catcattggt | gcgcaccaag | attcggccaa | 1500 |
| ttatcttttt | ccctgctgc | ccgcccctgg | cgctgacgat | gactgttccg | gcactgtcag | 1560 |
| tatcctcgag | gccttccgcg | ttctggcgga | gaatggctac | acgcccaagg | acgggcctgt | 1620 |
| tgaattccat | tggtatgcgg | ctgaagaggc | cgggctactg | ggcagccaag | ccatcgcgcg | 1680 |
| gtacaagaag | gagcagggcg | ctaaaattga | tgccatgatg | gagtttgtag | gttcccatca | 1740 |
| tccaacggac | ttggaatcac | ttttgacttt | cggttattaa | catctgcata | ggatatgacg | 1800 |
| gcttttattg | cccgtaacgc | caccgagacc | atcgggtttg | ttgcaaccca | agccgatgca | 1860 |
| gcgctcacaa | actgggccct | caacctcagt | cgagaataca | tctccattcc | ggcggaagtc | 1920 |
| tatgaacttg | gccgtaagaa | ccccagaata | tccccagagg | catgtcaagt | gctgaatgat | 1980 |
| ttcttagcaa | cgctggatcc | gactacatgt | catacactaa | gctcaactac | cccgctgcct | 2040 |
| ttgcatccga | aggcaacccg | ctcgctgggg | gctctttccc | gggtgaaatg | gacccctacg | 2100 |
| tacacggcat | caaggatagg | atggacgttg | acgatgaaac | gggcgtcttc | tctatcgaag | 2160 |

-continued

```
taagttgacc gcactcaacc tgtccatctt cttgctaacg atttgccagc acatggctcg    2220
gttctccgag ttggctatcg catttgttgt cgagcaggct gggtgggata atacatggcg    2280
gtagagtata tacagggatg tttccagctt catagcatat agagctggta tatagtcatt    2340
gtgcttacaa tatataccat tctattgagt tcttgacaga gttattatgt cagaatggta    2400
atcagtctaa atcaatgcgc ccttaaatca agaagtacac tagtgcccat gaccaaaaca    2460
atttccactt acacatacca cctatctgcc tcactacgaa acccttacca tacaatgttt    2520
acgttgtgct cctttcaata ctccatttcc atagttcatg ctatcgtggg ataaacatgc    2580
acatatcctc                                                          2590

<210> SEQ ID NO 55
<211> LENGTH: 3290
<212> TYPE: DNA
<213> ORGANISM: Aspergillus niger

<400> SEQUENCE: 55
gagaggcaga aggagtcatt tatcacttgt attccaatgt attttccatt tatagatact     60
gcattcaaat gcaccgttta gcatagcatc ccacattcta tttcattcca atctcatgcc    120
attgccatcc ccgtattaa tttacttctc cgccttatct tgcaatcttg caatctcttt    180
ctcctcgtta tcacgcgttc ctgcaggcgc acctccgatg gcactgcagc cggagtcccc    240
gcggcgccgg cactactaaa gactaaagtg tctagtctag cctccaatgt gctcacctcc    300
atcagcatct catccattta tcttctgacg atgtcatctg caggctccac cccctccggc    360
cgccccgacg ctctccgacg gtgcacaaca atcaattctg cagtcacgct caagattcgt    420
ccctgccgga ctcctcatgc cgtgcctggt ttaatctatg caatggagta aggtagtatc    480
gcctagcagg agcggagttc ctgctgcgct cacgccatgg tgccggcgca gacataaatc    540
gctcgtttcc tccggcgctg gccgttctct cgagccagtt tgtctgttgt ggttgtagga    600
tcctctgttc ccctcgacag ctcacaatgc gttccttctc cgttgtcgct gccgcgtcac    660
tggcgctctc ttgggcgtct ctggcccagg ctgctcgccc ccgtcttgtg cccaagccta    720
tctctcggcc agcttcgagt aagtcggctg cgactacggg tgaggcttat tttgagcagc    780
tgctggacca tcacaacccg gagaagggaa cgttttccca gcggtactgg tggagtactg    840
aatactgggg tggacctggg tcaccggtgc gtctctgaca tttggtctta tgaccggcca    900
tattgaaact tagccggtgg caaggtccgc aatcatgagg aacattgctg attaaactag    960
gtggtcctct ttaaccctgg agaggtctct gccgatggct atgagggta tctcaccaac    1020 gatactctca ctggtgtcta tgcgcaggag atccagggtg ccgtcattct cattgaacgt    1080
gagtgtcact gctaccatgg aaaaaagaca ttcgctgatc gaccccaatc tagaccgcta    1140
ctggggcgac tcttcgcctt atgaggtgct caatgccgaa acacttcagt atctcacact    1200
ggatcagtcc attctggaca tgacctactt cgccgagacg gtaaagctgc agttcgataa    1260
tagcagccgc agcaatgcgc agaatgctgt atgttacctt caccgctcta tgtttctgat    1320
aggtactgac aacgtagccc tgggtcatgg tcggtggctc atacagcggt gccttgacgg    1380
cttggaccga gtctatcgcg cctggaacgt tctgggctta ccatgccacc agtgcgcctg    1440
tggaggctat ctatgacttt gtaggtgtag cctgctcttg ttatctatac ttgcagctaa    1500
ccaagccagt ggcaatactt ctaccccatt cagcaaggta tggcacagaa ctgcagcaag    1560
gatgtgtctc tggtagccga gtatgtcgac aaaattggga agaatggaac tgccaaggaa    1620
```

| cagcaggagc tcaaagaatt gtttggtctg ggagctgttg agcattacga tgactttgcc | 1680 |
| gcgtgagtac ttcaaagtct atagacgagc ttttctgaca ggaacagtgt cctgcccaac | 1740 |
| ggaccgtacc tctggcaaga caacgacttt gtcacaggat actcttcctt cttccagttc | 1800 |
| tgtgatgctg tcgaggtgag ttaccaccag attcctcttg attgaagcaa tatactaacg | 1860 |
| gacacagggt gtcgaagccg cgcggcagt gaccccggc cccgagggcg tcggacttga | 1920 |
| aaaggccctg gccaactacg caaactggtt caattcaacc atactcccta actgtatttc | 1980 |
| accatctctt gtctcgttcc tctcccttat cctcccagac taacctagtg acagactgcg | 2040 |
| caagctacgg ctactggacc gacgaatgga gcgtcgcctg tttcgacagc tataatgcct | 2100 |
| cgagccccat cttcaccgac acctccgtgg gtaaccctgt cgaccgccaa tgggaatggt | 2160 |
| tcctctgcaa cgagccttc ttctggtggc aggagtgcgt accccttacc tcattcatga | 2220 |
| taacacacga acaattccac taacaaagat ccagcggtgc ccccgaggga acctccacta | 2280 |
| ttgtgccccg gctcgtcagc gcctcctact ggcaacgcca atgcccgctc tacttccccg | 2340 |
| aagttaacgg ctacacgtac ggcagcgcga agggtaaaaa ctccgctacg gtgaacagct | 2400 |
| ggacgggtgg atgggatatg acccgcaaca cgacgcggtt gatctggacg aacgggtagg | 2460 |
| tctcccccta atttccgttg aatgtgatgt gaagataaac tcaatgctaa taaattgaga | 2520 |
| aggcaatatg accctggcg cgactccggt gtgtcgagca ctttccggcc cggtggtccg | 2580 |
| ctggttagca cggcgaacga acccgtgcag attattccgg gcgggttcca ttgctcggac | 2640 |
| ttgtatatgg aggattacta tgcgaatgag ggtgtgagga aggtggttga taatgaggtg | 2700 |
| aagcagatta aggagtgggt ggaggagtat tatgcttgat gaagatactg gtggacatat | 2760 |
| ggagtgtaca taagatgaat ggtcataaaa tgatgatggt agatacggct atggctgttg | 2820 |
| attagatggt cctttcgcat ttcctaatta ctgagcacgt gctccatggt atgggaagtg | 2880 |
| gagacgttgc tatatatatt gactgtcggg ctattgttca cggcgtagaa gctagacgct | 2940 |
| ttgtctatgt ggccttcact aaagaccgtg actctgccca gtcttccccc cttcgaggac | 3000 |
| ctggtattag ccaaacccac ccacaaacct aacaaagatc atcgtgacat tgaagtcact | 3060 |
| ctaggtactg ctggcgctga ttacagtggc tcaattcgaa catttcaaca gcacataagg | 3120 |
| gaagggtcgc ttcacttgct accttgatac gaaagcagcc acgcccaaca cttatagggg | 3180 |
| tgacaaccat cggcatgctg ggttatctac tatatctcct gattctgtgg atcctggaga | 3240 |
| tcgatctggt acactaatct actacaatgc atgtgaagta gggataggca | 3290 |

<210> SEQ ID NO 56
<211> LENGTH: 2044
<212> TYPE: DNA
<213> ORGANISM: Aspergillus niger

<400> SEQUENCE: 56

| ggctttgttg ggctgagcgc tacttctttc tctctcttgg tctgttcgtt gctccgccag | 60 |
| ttggttcact cagcctcgta acatcagtat accaggctaa gtcaggactt tggcccccat | 120 |
| actgcttccc cttttttat aaaactcaat ccttctggaa aggattctat ttctcaattc | 180 |
| tcagactact taatacgttc tttgttttca aattgttttg tttctgaaac ttgccgggcc | 240 |
| ctatccccctc ttttttatag tccgcctgtc gacatcatat ccagagtgag ccaccatgca | 300 |
| gctcctccag tccctcattg ttgccgtttg cttcagctac ggcgtcctct ccttacccca | 360 |
| tggcccgtca aaccagcaca aagcacgttc cttcaaggtt gaacgggtcc gtcgtggaac | 420 |
| cggtgctctg catgggcccg ctgctctccg caaagcatac cggaagtacg gaatagctcc | 480 |

| | |
|---|---|
| cagcagtttc aacatcgatc tggcagactt taaacccatt acgacaaccc atgctgctgc | 540 |
| tgggagcgag attgcagagc ctgatcagac tggcgctgtc agtgctactt ccgtcgagaa | 600 |
| cgatgccgag ttcgtttcgc ctgttcttat tggcggccag aagatcgtca tgacatttga | 660 |
| cactggttct tctgacttgt aagtcttgga tgcagctgtt tactctttgg tacagtgatt | 720 |
| aacgtcgatc tacagttggg tgttcgatac gaatctcaat gaaaccttga cgggacacac | 780 |
| ggagtacaac ccttcgaact cctcgacctt caagaagatg gacggataca ccttcgatgt | 840 |
| ctcgtatggt gacgactcgt acgcctctgg ccccgtcgga acggataccg tcaacattgg | 900 |
| cggcgccatt gtcaaggagc aagccttcgg tgtccccgac caggtatccc agtcgttcat | 960 |
| cgaggacacg aactccaacg gcctggtcgg gttgggcttt tcctccatca acaccatcaa | 1020 |
| accggaggcg caagacacgt tcttcgccaa tgtcgcacca agtctggacg agcccgtcat | 1080 |
| gaccgcctcg ctcaaggctg acggagtggg cgagtacgag ttcggcacga tcgacaaaga | 1140 |
| caagtaccag ggcaacattg ccaacatcag cgtggactca tcgaacggat actggcagtt | 1200 |
| ctccactccc aagtactccg tggcagacga gagctgaag gacattggaa gcttgaacac | 1260 |
| ctcgatcgcg gacaccggta cctcccttat gctgctggat gaagacgtgg ttactgccta | 1320 |
| ctatgcgcaa gttcccaact cggtctacgt gagcagtgcc ggtggttaca tctacccctg | 1380 |
| caacaccact cttcccagct tctcgcttgt cctcggcgag tcgagcctgg ccacgatccc | 1440 |
| cggtaacctg atcaatttct ccaaggttgg caccaacacc accaccggac aggcctgtaa | 1500 |
| gttgctcccc ttcttttgca tgattgaaca tgattgactg attgtgctgg ttagtgtgct | 1560 |
| ttggcggcat tcaatccaac ggaaacacct cgctgcagat tctgggcgat attttcctga | 1620 |
| aggcttttt cgttgtcttc gacatgcgcg gcccctcgct tggtgttgcc tctcccaaga | 1680 |
| actagttttcc ttttcctgta cttttccccc gcgtgtaata atatcgtctg attttttgga | 1740 |
| ctgtctccta cgtgggcaag atggatggat agtttgctca cgtgcattgc tttaccttgg | 1800 |
| gtctgtgagt caaggcagga gtgcgtggct gtatctacaa ttcaagttac agtgccgacc | 1860 |
| gttattgcct tccacatcga aaacataga cactctttct aaccctaatc catgatacaa | 1920 |
| gtatatactt cgagtccata ttatggtggt gtatcaaggc gccatgttta tatctaatga | 1980 |
| aaccaacgta ggtctcatct tcatacgttg tttaaaggt gccgaagaat atacgaagat | 2040 |
| agat | 2044 |

<210> SEQ ID NO 57
<211> LENGTH: 3916
<212> TYPE: DNA
<213> ORGANISM: Aspergillus niger

<400> SEQUENCE: 57

| | |
|---|---|
| ttcgcagata ttcgagtcaa taccttgtat attaacggaa aagggtttgg gaagcgttgc | 60 |
| cttcaaggat gaaattcaaa acgtagagta tcttgacctc aatgacctca tgatccccctt | 120 |
| gaccgtacag ctagtgatct cacggtggta attgctcgat tcgattccaa actacagcaa | 180 |
| gaagcatgcc cgacaggaaa gtcaagttac aagagatcta gaacgggct gctacggctc | 240 |
| tgaccaacct ttgtctgttc tagatgaggc tgcagtgacg taactccggc caagaaaat | 300 |
| gggtggtaac cgaccgttgg aaatcccatg gaactggcgg ggttcaaatt cccgataact | 360 |
| gtaccgaatc cttgtatccg gataggcg accgatagta gtagctatag tcagacgtag | 420 |
| cacagcatta ctgtgtcccc ctggtcataa gagtatttgt tacaataaga agggaccgtc | 480 |

-continued

```
tagttgtgta tcacaacaac tgacacttgc ggaacaggta tcagatcctt gcgctggcat      540
cgactccagc aatggcttgc tctgtttcgg acgaatatca tcgggctaga ctgtgacctg      600
aaggatcgat ccaggagttt gacggcttgg gtttctaatc cgatctggaa gattattgtt      660
tagtcaagac cgggaacagc aagaaccgga agattatctg tttaactact tgccaaaac      720 agttattcaa tgtcatgctg agtgcgatgg ggacccaagc tcacgagtga tgctgatcaa      780
agggtccgtt cggtttggga aaggaagggc gccctgtgct tgccgttgga atccacggaa      840
cgattccgat tgactgcacg ggatttgcaa actgactccc agtgggacga agaaagaaac      900
ccatcttact ttgcggaggc aggatggcac tttgtgtcgg aagggtggtg actcctggtg      960
ttgccgagaa gatggaatgg tggagaattg ccttgaaaat gaggctgtag gggcactaac     1020
ccagtcgggc cgagcgtgac gccttttccg atgaggcagg tcaggtgggt gtcacgggtc     1080
tatcttatcg cttatcatct gaccggttcc tggcagaagc tccccttccc agctcctcgt     1140
atttattcct ccccaggttg ttgtttgctc ttctccctgt ctcgccttct ctccagcctc     1200
cattcaacgg gctccatccc cttctctccg gatccctcta tcccttattc ttccttagat     1260
atcattattc atatagtgcc ttgtttcgct caccatgcgc attgactccg cggcgctaca     1320
tctggtccca gtcctcctgg gccaggtcgg tgctttacaa ttacccttgg tccaagactc     1380
caattcacag tggcagaaac caaatgcagg tgataaaccc ctaattagct ctccgttgct     1440
tcaagagcag gtcaaggcgg agaatctgtt ggacagggcc cggcagcttt acaagattgc     1500
ggagctggga gaagacgagt ataaccaccc cactcgcgtc attggcagta aaggtacgat     1560 atatttttc atcatgtccc tggaatacga taattagctg acaacctttg ctccccaggt     1620
caccttggca cgctcgacta catatactcc acccttaccg acctcggtga ttattatact     1680
gtcgtcaatc agtccttccc tgccgtgagc ggtaatgtct tcgagtctcg ccttgtcctt     1740
ggtcacgatg ttcccaagtc agctacacca atgggtctca ctcccccaac gaggaataag     1800
gagccggtat atggctccct ggttgctgta tccaacctcg ggtgtgaggc ctcggactac     1860
tcgtccaact tgaaaggcgc cgttgcattt atcagtcggg gaagctgtcc gttcgggacc     1920
aagtctcaat tagctggtaa agcgggagct gttgctgccg tcatctacaa caacgagcgg     1980
ggtgacctaa gcggaactct aggaaaccca accccccgatc atgttgctac ctttggtatc     2040
tcagacgagg atgctgcccc agtcctggag aagttgaata aaggcgagaa ggtggacgct     2100
atcgcctacg ttgatgcgat agtagagacc atccacacca ccaatatcat cgcgcagacc     2160
acggatggtg acccgaacaa ttgtgtaatg ctgggtggcc acagtgacag cgtggccgag     2220
ggcccgggta tcaatgacga cgggtccggt actctgaccc ttttggagct tgccacattg     2280
ctcacccagt tccgtgtcaa caactgcgtg cgatttgctt ggtgggccgc cgaggaggaa     2340
ggccttctcg gatctgacta ttacgtgtcc gttctcacac cggaagagaa ccgcaagatc     2400
cgcttgttca tggactacga catgctcggc tcgccgaact ttgcgtacca agtttacaat     2460
gccactaatg ctgtgaaccc cgagggatct gaggagcttc gtgatctgta caccgacttt     2520
tacgaagatc atgggttcaa ctacacgtac attccgtttg acggacgcag cgactatgat     2580
gccttcattc ggcatggtat cccgggtggt ggcattgcca cgggagcaga gggtatcaag     2640
actgtcgagg aagcggacat gtttggtggg gttgctggcc aatggtatga cccgtgttac     2700
catcagatct gcgatacggt ggccaatgtg aacttgactg cgtgggagtg gaacaccaag     2760
gtaggaccgc atccagcatt agttactgtt atgccgatca ttcttttgct aactgggatg     2820
atttacctta gctcgttgcc cactccattg cgacttacgc caagtccttt gacggattcc     2880
```

-continued

| | |
|---|---|
| cggaacggtc cgatgaaccc atcagccctg ctgcttttga ggaaccgaag taccatggcc | 2940 |
| acgcgttgca attgtaagat ccgtgtgccc caaagcttgg tagtggggca aatatctgta | 3000 |
| gcagagacca agtcctttct cgaacctgag tcccacttgg tctttccatc ttttgagttg | 3060 |
| aacaagtaga ccgttactcg tcatgtagac gaagacctgg cagaaccgtt gtactatgta | 3120 |
| gacatttatc ggggattgtc tgttatgaat tcatgtgctt gtgggatatg gttaggtatt | 3180 |
| tctcgcaaat gaccacggct tcctctatca tttcccgcct cgcaccctca taccgatttc | 3240 |
| cgttaactta atatcatctg tagacttcgc ggtaatacta cagggaccca gagcgtcctg | 3300 |
| tggggagccc aaatccagaa tggaacagct gcatcggtgc ttaatctatt gtccatacga | 3360 |
| cgcagaggca ctttcagtct aagctaaaag caagcattat tcagagatac agtgagtgtc | 3420 |
| aatatgccgt tggttcatgc gcgattcgtg caaaaacagc ccaccgccct atataacaga | 3480 |
| gtatattgct ctctgcctct ccgggtagag atcgacattt ccgggaccgc catgaaacgt | 3540 |
| tggtgggcct cggagcgtcg aggattgaca ctagggccgc gctagaatcc cccagggtct | 3600 |
| gcaaaatacc ctatggggtg acctcgaaca gggcgtgaaa cggcaattcc tccgaaagcg | 3660 |
| ttgcgaaagt gtctacaaag tggtgatcca gaccatcacg cggttccgga acaattgccc | 3720 |
| ttcttatttg gcactttacg gcgtggagtg gagtcatccc cctttgttga acaacacgg | 3780 |
| gcatgtttcc tttgccgtcc ggttcgttac ctataaagac agggtaggtc tgttcgggaa | 3840 |
| aaagacacaa tcagcgccta tcccgtccgt cgaagtctat tgccataccc tatcacggat | 3900 |
| catcagactc ataaca | 3916 |

<210> SEQ ID NO 58
<211> LENGTH: 1443
<212> TYPE: DNA
<213> ORGANISM: Aspergillus niger

<400> SEQUENCE: 58

| | |
|---|---|
| atgcatctcc cacagcgtct cgttacagca gcgtgtcttt gcgccagtgc cacggctttc | 60 |
| atcccataca ccatcaaact cgatacgtcg gacgacatct cagcccgtga ttcattagct | 120 |
| cgtcgttttcc tgccagtacc aaaaccaagc gatgctctag cagacgattc cacctcatct | 180 |
| gccagcgatg agtccctgtc actgaacatc aaaaggattc ccgttcgtcg tgacaatgat | 240 |
| ttcaagattg tggtagcgga aactccctct tggtctaaca ccgccgctct cgatcaagat | 300 |
| ggtagcgaca tttcatacat ctctgtcgtc aacattgggt ctgatgagaa atctatgtac | 360 |
| atgttgctcg acacaggcgg ctctgatacc tgggttttcg gttccaactg cacgtccaca | 420 |
| ccctgcacga tgcacaatac cttcggttcg gacgattctt cgacccttga atgacatcg | 480 |
| gaagagtgga gtgtgggcta tggaactggg tctgtcagcg gcttgctagg aaaagacaag | 540 |
| ctcacgattg caaatgtcac tgtacgcatg actttcggac ttgcttccaa cgcatcggat | 600 |
| aacttcgagt cgtacccaat ggacggcatt ctcggtctcg gtcgaaccaa cgatagttcc | 660 |
| tacgacaacc caacattcat ggatgccgtt gcagaaagta acgttttcaa gtcgaatatc | 720 |
| gttggcttcg cccttttcacg tagccccgcc aaggatggca cggtcagctt tggcactact | 780 |
| gacaaggaca agtacaccgg cgatataccc tacaccgata ccgtcggatc ggacagctat | 840 |
| tggcgcattc ccgtggacga tgtctatgtt ggcggcactt catgcgattt ctccaacaaa | 900 |
| tcagccatca tcgataccgg aacttcttat gctatgctgc cttcaagcga ctcgaagacg | 960 |
| ctgcacagtc tcattcccgg cgccaaatct tcggggagct accacattat tccgtgcaac | 1020 |

-continued

| | |
|---|---:|
| acaactacta agctacaagt ggcattctct ggtgtgaatt acaccatctc gccgaaggac | 1080 |
| tacgtgggag caacttcagg ttctggatgc gtttcgaaca ttatcagcta cgacttattt | 1140 |
| ggtgatgaca tctggctcct gggtgacacg tttctcaaaa atgtgtatgc tgtgtttgac | 1200 |
| tacgatgagt tacgggtcgg atttgcagag cgttcctcga acaccacctc tgcgtcgaac | 1260 |
| tctacgagct ctggaacaag cagcacctcg ggatccacta caacgggcag ctcaacgact | 1320 |
| acgacgagct ctgctagctc tagtagttca tctgatgctg aatcaggaag tagcatgacc | 1380 |
| attcccgctc ctcagtattt cttctctgct ctggcgattg cttccttcat gctttggctc | 1440 |
| tag | 1443 |

<210> SEQ ID NO 59
<211> LENGTH: 3300
<212> TYPE: DNA
<213> ORGANISM: Aspergillus niger

<400> SEQUENCE: 59

| | |
|---|---:|
| atgcttcgtg gtcttcgtga tgtcgtatta ttacaatttg caatcccctt gttcttgcta | 60 |
| ttgcattttta gattatcgct acggggtgtg atcacaggat ttggttctaa atcacatttc | 120 |
| cagagaccat tgagcaaaat gtcatctact caaaagagcc atttcaagct actccagaag | 180 |
| ttcaaaccgg agtactcgcc tagcgagttt gctcagtatg agtcggagag aacaggcatg | 240 |
| agggtagtgg tcattgacca aaaggaccc aaagtcacag gttattttgt tctagccaca | 300 |
| gagattctcg atgattcagg tgctcctcac acgttggagc acttgtgctt tatgggctcg | 360 |
| cggaactata gatataaggg cttccttgac aagctagcaa cacgtgttta ttcgagcacc | 420 |
| aatgcctgga cggccacaga ccacacggcc tacaccttgg acacagcagg ctgggaaggg | 480 |
| ttcgctcaaa tcttgcccgt gtacctagag catgttatag ctccaacact gacagatgaa | 540 |
| gggtgctata ccgaagtgca tcatattgat ggcgctggag acgacgctgg agtcgtctac | 600 |
| tcggagatgc agggtgtgca gaataactct gcagagttaa tcgatctaac cgctcgtcga | 660 |
| ttgacttacc cgcatggtgt aggttttcgc tacgagacag gcggtatgat ggagcagctc | 720 |
| cgcgtcctca ccgcggaccg tatccgagcg ttccatcgtg agatgtacca gcccaagaac | 780 |
| ttatgcctaa tcatcacagg cgaagtagat caccagaaca tgctggagac cttgacaag | 840 |
| ttcgaagata ctattctaga tgtcattccc agtcctgatt caccttcaa gaggccgtgg | 900 |
| gtagattcca agcaggcgcc gccattggag aagtccattg tccagactgt ggaatttccg | 960 |
| gaagaagatg aatctttcgg ggagatagaa attagattcc tcggtccgga ctgtaccgac | 1020 |
| cctgttcaaa ccggggctgt caatgttgca ttgctgtatc tggccggttc atctgcttct | 1080 |
| ctattggata acatcctggt tgagaaggag cagctcgcca gtgctgtcta ttatgctacc | 1140 |
| gaagatcatc ccagcattga gatccgcttc acattaacca gtgtggagac agagaaactc | 1200 |
| gcgaaggtag agcaacggtt tttcgaagtg ctcaaggacg ctatgagaa agatttagac | 1260 |
| atgaggtata tcaaggagtg cattgaccgg caaagacgga cctggaagtt ctctaccgaa | 1320 |
| agctccgcct cttcctttgc ggagtacgtg atctcggatt ttcttttcgg aaagagagac | 1380 |
| ggatcgacta tgcttgatgt tgcgaccttg caagagtacg acgtgctgga gaagtggagt | 1440 |
| gaagaacagt ggcgcagttt tatcaaaaca tggatttctg atgccaacca tgtcactatc | 1500 |
| cttggtgttc cgtccgttaa gatgtctgac acattaaaga aggaggagga agctagagtc | 1560 |
| gcagagcaaa agaagcgctt gggtgatgag gggctgaaga agttggccga caagctggaa | 1620 |
| aaagctaaag ctgaaaatga caaggagatc cccaaggaga tgctggagag gttccaaatc | 1680 |

-continued

| | |
|---|---|
| cctggaatag agtctatcca tttcgtggac actactacag ccaggtctgg tgcagccctc | 1740 |
| gatgccgggc gcccatccca caaggcgcaa aaactggtgg atgctgatgg ctctgatctg | 1800 |
| cccttgttca tccatttcga gcatatcccc agtagcttcg tgcagctctc cctcctcatc | 1860 |
| tcggcacagg ccgtacctgt gcagcttcgt ccactgctgt ctgtgtatac tgaggcattc | 1920 |
| ttcaacctgc ctgtcaaccg gaacggggaa accatcaact ttgagcaggt ggttgtcgag | 1980 |
| ttggaaaggg atactgttgg ctactccatg gaaggagcta gaagcctagg aaactcggag | 2040 |
| atgttgcgga tctcattcca ggtggagctt gagaagtatc acacggcgat cgcatggatc | 2100 |
| caggaacttt cctggaactc gattttcgat gtcgagcgac tccgagcgat taccagtcga | 2160 |
| ctgctctccg atgtgcccga ttccaagcgt agtggcgacg acatgctcgc ggctgttcat | 2220 |
| gtgatggtcc actatgcagc agagtctatt gttccggctc ggagcacctt ggtgaaggcg | 2280 |
| cgttatttga aacggatcaa gaagcaatta gcagaagagc cgaagtctgt cgttgcgcgg | 2340 |
| atggaagaaa tcagagatgc gcttttccgt ttcgagaaca tgcgagtctt agttatcgct | 2400 |
| gacctggaga aacttcaaaa ccctgtgtca gcatggaaac catttgctga gcgtttgggt | 2460 |
| gcaggtgccc ctctacagcc tatcacgact agaagaccgt tgctcagtga ggcaggccag | 2520 |
| aagttgggcg gtaagtcgta tgtggttcct atgccgacga ttgattcatc gttcgcatat | 2580 |
| gctaccgcac gtggtttgga ttcttatgat gatccaagac ttcctgcctt aatggttgca | 2640 |
| attgcataca tgaacgcggt tgagggtccc ctctggggttg cagttcgagg caagggtttg | 2700 |
| gcatatggca cgaactttgc ctataacatt gataccggat tcgtcaactt cgacgtttac | 2760 |
| cgctccccca acgcccataa agccttcgac tccagcaagc agattgttga ggatcacctc | 2820 |
| tctggtgcga tgcccttcga tcccttgatg ctggagggtt ccattagcag cattgtggta | 2880 |
| agctttgcga atgaacagtc gacaattggt agcgcagcct caggcagttt catccgacag | 2940 |
| gtgattcggc gcctgcctag cgactacaag gagcgggtgc tcaagcaggt gcgggctact | 3000 |
| agcgttgatg acgtgaaagg cgctctgaag gacatcattc tgcctttgtt taacccgtcc | 3060 |
| acggccaata tcgtgttac ctgcgctaca gtgcttgagg agactatcaa ggaaggtctc | 3120 |
| caggcatcgg gattcacgcc tgcggtgcag ccactcaaag aattcgaaga tgactatggg | 3180 |
| ctgaaggtcg gcgatgacga ggacgaggag tccgacgatg acgacgatga gtatgaaacc | 3240 |
| ggatctgaag atgaagatga cagtgatgaa gacatggagg atgacgaaga tgatgagtga | 3300 |

<210> SEQ ID NO 60
<211> LENGTH: 2181
<212> TYPE: DNA
<213> ORGANISM: Aspergillus niger

<400> SEQUENCE: 60

| | |
|---|---|
| atgggagctc ttcagtggct gtccatcacg gctgctgcgg cctccgcagt gtcagccttg | 60 |
| accccggagc agatgatcgg tgccccacgg agaaccgaag ttataccaaa ccccctccggt | 120 |
| gacaccggtc tattctcgac ctcccaatgg tcgtttgaca ctcattctga gagcaccctgg | 180 |
| tggagcttga tcgacctcca atcgggcaag accaccactc tcaccgatga tagcgatatc | 240 |
| gaggagatca tctggcttgg ctctgacaat tctacgctcc tctacatcaa cagcaccaac | 300 |
| gcgcaggttc ccggtggcgt ggagctgtgg attgcggact cttctgactt tgcaaatgct | 360 |
| tacaaggcag cctctctctc cgccggtttt ctcggcatca aatcaaccgt gacagattcc | 420 |
| ggcgacgtgc atttcatcct tcgtggaaag tcctatccca acggaacggc atacaatgat | 480 |

-continued

| | |
|---|---|
| cagctcgccg agacctatcc cagtacagcc cgcatctacg acagcatctt tgtgcggcac | 540 |
| tgggacactt acctgaccac cgcctcccac gctgtattct ccggtaccct gcaaagctcg | 600 |
| accagcgacg acggcaatgt tcaatatacc tcttcagggg gattgaccaa cctggttaac | 660 |
| ccagtcaagg gtgccgaaag cccattccct ccttttggag gcaacgacga ctatgacctc | 720 |
| tcgcctgacg gcaaatgggt taccttcaag agcaaagcgc cagagctgcc tcttgctaac | 780 |
| aacacggctg cctatgtcta tctcgtccca cacgacggct ctgcgactgc ctttgccgtc | 840 |
| aacggccctg atagtcctgc aaccccggag ggagttgaag gagaatccaa caatcccgtg | 900 |
| ttctcccctg atagcgacaa aatagcgtac ttccaaatgg ctactaatac atacgagtcg | 960 |
| gaccgcaacg tgctatacgt atactccatc gccgatgaca ccatcactcc ccttgcaaag | 1020 |
| gactgggacc gatcgcctag ctccgtgaca tgggtcgatg agacaacct cgtcgtggca | 1080 |
| agccaagatc taggacgaac cagactttc gccatcccag gcgatgcagg ggacgacttc | 1140 |
| aagcccacga acttcaccga cggcggctcc gtgtcggctc aatacgtcct atccaactct | 1200 |
| accctcctcg tcacgtccag cgccttctgg acaagctgga gcgtctacac cgccagccct | 1260 |
| gacgagggcg tgatcaacac actggcctca gccaacgaga tcgaccccga gcttagcggc | 1320 |
| cttagttcct ccgactttga agagttctac tttgacggca actggactac cctccaagga | 1380 |
| tggatcacct accccaaga cttcgactca tccaagaaat accccctcgc cttcctcatc | 1440 |
| cacggcggcc ccgaagacgc ctgggcggat gaatggaacc tgaaatggca ctccaaggtc | 1500 |
| ttcgccgacc agggatacgt cgtcgtccag ccaaaccca caggaagcac cgggttcggc | 1560 |
| cagcagctca cagacgctat ccaacttaac tggaccggcg ccgcctacga cgacctaacc | 1620 |
| aaagcctggc aatacgtgca cgatacctac gacttcatcg acacggacaa cggcgtcgcc | 1680 |
| gcgggtccca gcttcggcgc gttcatgatc acctggatcc agggcgatga ctttggacgc | 1740 |
| aagttcaagg cgctggttag ccatgatggt ccgttcattg gcgatgcgtg ggtcgagacg | 1800 |
| gatgagttat ggtttgttga gcatgagttc aacggcacct tctggcaagc gcgcgacgca | 1860 |
| ttccacaaca cggatccatc cggccccagc cgcgtcctcg catacagcac cccccagctc | 1920 |
| gtcatccaca gtgacaagga ttatcgcata cctgtggcaa atgggattgg actgtttaat | 1980 |
| acgctgcagg agaggggcgt gcccagtcgg ttttgaatt cccggatga ggatcattgg | 2040 |
| gtcaccgggc aagaaaacag cctcgtctgg tatcagcagg tgctgggatg gattaatcgg | 2100 |
| tattctgggg tgggagggtc gaatcctgat gcgattgctt tggaggatac ggtgaatccg | 2160 |
| gtggtggatt tgaatccttg a | 2181 |

<210> SEQ ID NO 61
<211> LENGTH: 1695
<212> TYPE: DNA
<213> ORGANISM: Aspergillus niger

<400> SEQUENCE: 61

| | |
|---|---|
| atgacgaggc agacttctct cgttcccagg ctactaacgc tagcctcact agctgcactt | 60 |
| tcacaagcag agctaggcaa gatccaatgg aaaggatctt gcaacttgac cacttatccg | 120 |
| gcattgatct gtggaacact agacgtgcca tacgactaca cggagtcaaa ttccagcaag | 180 |
| acactgactc tcgacatcgc caagtggcca gcgaccaaga aaccagtctc ggagcccatc | 240 |
| atatttaact ttggaggacc tggtgtcaat tcgttcgagg gccttgggct tatggagag | 300 |
| gaatttcagg ctattcttgg aggtcacaat gatttgatag cttttaacaa ccgaggcgtt | 360 |
| ggaaacacca tcccgttctc ctgctacagc gatgacgcca cccgtgaact cgtcgccctt | 420 |

-continued

```
caagctccta acgacggcag agcgtccagc acggctttgg gagaaatctg ggcccagaac      480
gcaaacatcg cacaggcatg ctatgctacg aacaatcaaa ctggtagtct tattggaact      540
agctttgctg caaggacat catgcaggtc gctgatgcgc tcagtggaaa ggatagtttg        600
gtcaactact ggggattctc atacggcact acaatcggtg ctgttctcgc agccatgttc      660
ccggatcgaa tggggaatgt cgcgcttgac ggagtggaca accccagaga ggctctttat      720
ggatacaacg cacaagcggt tgtggacgtc gacaaagttt tcgaaggatt ctgcacgggc      780
tgcatggccg caccgaccct ctgccctatc gccaaggagt acaccagcgc cgccaacttg      840
gaagccgcaa tttacctgat gctggaaaac ctcaagtaca acccgattgc cattcccgaa      900
accggtggaa tcgtaacttg gagcgacgtc aagtcgacca tttttgaggc catgtacctg      960
ccaagctctt ggcccttgac ctctgagctt ctttactacg tgcaaacccg caacacaacg     1020
atccttggca actctgaagt atacgacacc atcaaatcct acggtcaatc ggcttctttg     1080
acttcggctt ccgatgaggt cggcacggcc attacatgct ccgacaagca tcgatctgcc     1140
accattaaag aggtcctccc gtacgtcaaa gccagacagg ctctgaccaa gatcggaagt     1200
gatggctcgg acggcgacat gagatgcgcg cagtggaatc cgaagatgtt cgccaaggag     1260
cgctactccg gtgactttga agtcaagaca gccaacccgg tgttgattct gagcaacact     1320
tacgatccag cgactcctct tcccgcagcg aagaacctga cagagacctt tgagggaagt     1380
gtcttgctcg agcagaacgg atacggtcat actaccctgt ctatgccatc tctttgcact     1440
gccaaggccg tccgggctta cttcaccaat ggcacattgc ccgctgacgg aacgatctgc     1500
caggtggacg tgcctctgtt cacgaacttg acctacaagg atgtgtggcc gaagagtttc     1560
caacggagcg ttgagtcgag ggatgatgcg actatcctca aggctttgat gtcggtccgt     1620
gataagatgt cgcgacgcag gatgtgtatt tatttgtaca ccaacagcgc ttcatggaga     1680
ccggaacttc cctga                                                      1695
```

<210> SEQ ID NO 62
<211> LENGTH: 1581
<212> TYPE: DNA
<213> ORGANISM: Aspergillus niger

<400> SEQUENCE: 62

```
atgtactact ctctctgggt tgctgccttg gtggccgcgc tgcccgtctc ccgggcccag       60
tttgtggctc cgcccacgga tctcattccc accaagggat atctcgacat ccccgtccgc      120
tacaaacagg tccccaccgg catttgtgag actgatccca gtgtcaagag cttctccggt      180
tacgtcgatg tcgctgagca tgagcacatc ttcttctggt tcttcgaggc gcgcaaccaa      240
gatcccaccg aggctcccctt gaccgtctgg atcaatggag gcatgtctga ccccggtcct      300
ggttcctcct ccatgatcgg cttgttccaa gagcacggcc catgcggcat tgacgccaat      360
ggctccgtct acaacaaccc ctactcctgg aacaacgcca gcaacatgct ctacatcgac      420
cagcccgtgc agaccggctt ctcctacagc attccggttc ccggctatgt ggattcttcc      480
acagacaatg gttttatggg cgcatttcct cagtactcgc gcgaaacctt ccacttcacc      540
acggagagtt atggcggcca ctacgggccc gtcttcaacg agtacatcga ggagcagaac      600
gcccatctcc agcgggagc caagaagatc caactgggca gtgtgatgat cggcaatggc      660
tggtatgacc cgattattca ataccaggcc tactacaact ttacggtata tccgggcaac      720
acatacgact acctgccatt caacaagtcc atcagctcgc tgatgtacaa caacctctat      780
```

| | |
|---|---:|
| ggccccggaa actgcctcga ccagctctac gactgcgccg cccgaggcat cgacgagatc | 840 |
| tgcagcactg ccgacgattt tgcgccaac gaggtcgaaa acgtctacga catttactcc | 900 |
| ggtcgggatg agtatgactt tcgtgaactc actccggacc cgttcccttta cgagttctac | 960 |
| gttgactacc tgaacaaagc gtccgtgcag gccgccatcg cgcatacat caattacacg | 1020 |
| gagagcaaca acgctgttgg actcgccttt tcgtccaccg gtgacgacgg gcgactcatg | 1080 |
| aacaccatcc aggatgtggg caagctgctc aaacagggtg tcacggtggt catgtacgcc | 1140 |
| ggggatgccg actataactg caactggctg gtgggaag ccgtgtcgtt gcaggtcaag | 1200 |
| gccgccaact tcagtagtgc gggttacacc aacattgtca cctcggatgg agtgacacac | 1260 |
| ggccaggtgc gccaggcggg gcaatttgcc tttgtgcgag tgtatgagag tggacatgag | 1320 |
| gttcccttct atcaaccctt gcttgcgctg agatgtttg agcgcgtcat ggcggcaag | 1380 |
| gatgtggcga cgggaaagat tcccatctcg tcgagtttac agacggtggg cacgcccaag | 1440 |
| agttactacc gggagggcaa cagcacgatt cagtgggagg tgttggattc tctggcgacg | 1500 |
| tacaacacaa ccacgaatgc tccgaacccg gtgagccgga ggctgaagcg gatgggacca | 1560 |
| gctttgcggt tcagatgta g | 1581 |

<210> SEQ ID NO 63
<211> LENGTH: 3471
<212> TYPE: DNA
<213> ORGANISM: Aspergillus niger

<400> SEQUENCE: 63

| | |
|---|---:|
| atgtcttgcg tctggctcca catccacaaa aggagcctac tgtctgtcgc tacgaacaat | 60 |
| tctgttgcga gggccgctgc ctctacctcc gccgcgccgc cgccgccgtc atcgccgccg | 120 |
| cctggttcta atacttattc gcctctttat cgccccatca ccaatcccat cggatttact | 180 |
| ttgtcgcctg cgaggtcact agtttctcgc aatcctaaat ttcctgccta tcggcgctct | 240 |
| agtcgacact tttcttttgtg cccggccgct gcaacgcccg gtgtcaccac gagcatctgc | 300 |
| cctggtcagg cgcccgtccg ctctctcagc tcgctcatta tacactctac gagacccgt | 360 |
| gctatacgta tccgtaccga ccagatggat ttgaatggag acgcaggcgc caagcgcaag | 420 |
| cgcagctcca tcaccacacc cgccgaacgg cccgtaaagc accttcgccc gaatcgagc | 480 |
| gcattgacac ccgggattc gacgcctgcc aatgggactg tatacgatgt ggaggatgat | 540 |
| gaagatgcga gtcgtctgct gcctgtaggc cctgctcagg ccgactcacc ggaatggcaa | 600 |
| gctaccatag aggaggttgt gaaaagcgta gtgtctatcc acttctgtca gacctgctcc | 660 |
| ttcgacacgg agctgtccat gagtagtcag gctactgggt ttgtggtaga tgcagagaat | 720 |
| gggtacatat tgacaaaccg acacgtggtt tgcccggac ctttctgggg atactgcatc | 780 |
| tttgataacc atgaggaatg cgacgttcgt cctgtgtatc gggaccctgt tcacgacttt | 840 |
| ggaattttga aattcgaccc gaaggctatt cgatatatga aattgaggga actgaaactg | 900 |
| cagccggatg cagctaaagt gggatcagaa attcgcgttg tgggtaatga tgcaggagaa | 960 |
| aaactgagta ttctgtctgg tgtcattagt cggctggata gaaacgcgcc cgaatacggc | 1020 |
| gatggctaca gtgacttcaa tacgaattac atccaggccg ccgcagcagc tagcggtgga | 1080 |
| agttccggca gtcctgtagt taacattgat ggccatgcga ttgctctgca ggccggtggt | 1140 |
| cgtgcagacg gtgcagcgac ggattacttc ctccctctgg accgaccgct acgcgcactg | 1200 |
| gaatgcatcc gtcgcggaga gcctgtcacg cgtggaacga ttcagacgca gtggatcttg | 1260 |
| aagccgttcg acgagtgtcg tcggttgggc ttgacgcctg agtgggaggc gaccgtgcgt | 1320 |

```
aaagcagcgc ccacggaaac cagcatgctg gtggccgaga tcatcctgcc tgaaggcccg    1380
gcggacggaa agctcgagga aggagacgtg ctcctgcagg tcaacggggt gcttctcacc    1440
caattcatcc ggttggatga catcctggat tcgagtgttg ggcagacagt gcgtctgctt    1500
gtccaaagag gcggtcagaa tgtggagatt gagtgccagg ttggcgacct gcatgccatc    1560
acgcccgacc ggttcgtgac ggtggctgga ggcacgttcc ataacctgtc ttaccagcag    1620
tcgcggctgt atgccatcgc tactcgcggt gtctacgtct gcgaggctgc cggctccttc    1680
aaactggaaa acacactgtc aggatggatc atcgactcgg tggacaagcg gcccactcgc    1740
aatctggatg agttcgtgga ggtgatgcga acgattccg atcgttcgcg cgtggtcatc    1800
tcgtatcggc atattcgcga tctccacacc cgaggcacca gcatcgtcta tatcgatcga    1860
cactggcacc ccaagatgcg actggctgtg cgcaacgacg acaccggtct gtgggacttt    1920
tcggacctcg cggaccctat cccagctctt cctccggttc cgaggaaagc cgatttcatt    1980
caactcgatg gtgttagcca gcctgctgcg gccgacattg tgcgcagctt cgtacgagta    2040
tcctgtacga tgcccctgaa gctggacggc taccccagg ccaagaagac tgggttcgga    2100
ttggtcgtcg atgcagagaa gggtttggtg gttgtgtcgc gagcgatcgt gccgtacgac    2160
ctctgcgaca tcaacgtcac ggtggccgac tccatcatcg tgaacgctaa agtagttttc    2220
ctgcatccgc tccaaaacta cagcatcatc cagtacgacc aagcctggt gcaggcgccg    2280 gttcagagtg ccaaactcgc caccgactac atcaagcagg acaggacac gatctttgtg    2340 ggattcaacc agaacttccg gattgtcgtg gccaagaccc cgtaaccga catcaccact    2400 gtttctattc cagccaacgc gtccgcaccg cgctaccgcg cgatcaacct ggacgccatc    2460
actgtgacca ccgactcag cgggcagtgt tctaacggtg tcctgattgg cgaggacgga    2520
gtggtgcagg cattgtggtt gaactatctt ggagaacgca catctaattc gcataaggat    2580
gtggaatacc atctaggatt tgcgactcca tctcttcttc ctgtcctgtc gaaggtgcag    2640
cagggagaga tgccggaatt gcggattctg aacatggaga gctacgtggt ccagatgagt    2700
caagctcgta tcatgggcgt gtcggaggaa tggatcgaga aggtgacgca agctaaccca    2760
tcgcggcatc agctcttcat ggtgcgcaag gtcgattgcc caccgcctgg gttcaactca    2820
gcggccgaca cgttcgagga gggtgatatc atcctgacct tggacggaca gctgatcacc    2880
cgcgtctcgg agttggatat catgtacgag aaggatacgc tggaagccct gattgttcga    2940
aatggacaag aaatgcggat ccaggtgccg actgttccaa cagaggacct agagactgac    3000
cgtgcggtcg tgttctgtgg tgctgtgttg cagaaaccac accatgcggt ccgtcagcag    3060
atttctaagc tacacagcga agtctacgtc agcgcaagaa gtcgcggatc ccctcctac     3120 caatacggct tggccccaac caatttcatc accgccgtaa acggcgttcc aaccccgaac    3180
ctggaccgct tctccgaaga agtgagcaaa atccccgaca cacatatttt ccgcctacgg    3240
gcggtgacat tcgacaatgt gccgtgggta gtgaccgtga agaagaacga tcattacttc    3300
cccatgtccg agtatatcaa agaccagtcc cagccttccg gttggcggac cgtgtctcac    3360
gacaaggata aatataaaga cggcattgca ccggatgctg cgaacttgaa cccggatgct    3420
atggacgaag ggtttgatgg agtcagtgat attgagccgg atttggagtg a            3471
```

<210> SEQ ID NO 64
<211> LENGTH: 1611
<212> TYPE: DNA
<213> ORGANISM: Aspergillus niger

```
<400> SEQUENCE: 64
atgagagtcc ttccagctgc tatgctggtt ggagcggcca cggcggccgt tcctcccttc      60
cagcaggtcc ttggaggtaa cggtgccaag cacggtgccg accatgcggc cgaggtccct     120
gcggatcaca gtgccgacgg gttctccaag ccgctgcacg cattccagga ggaactgaag     180
tctctctctg acgaggctcg taagctttgg gatgaggtgg ccagcttctt cccggagagc     240
atggatcaga accctctctt ttccctcccc aagaagcaca accgccgtcc cgactcgcac     300
tgggaccaca tcgtcgatgg caagctggaa gcctatgatc tcagggtcaa gaagaccgat     360
cctggctctc ttggcatcga ccccggcgtg aagcagtaca ccggttatct cgatgacaac     420
gagaatgata agcatttgtt ctactggttc ttcgagtctc gcaatgaccc cgagaatgat     480
cccgttgttc tgtggctgaa cggtggccct gggtgctctt ccctcaccgg tctcttcatg     540
gagcttggcc ctagcagcat caacaagaag atccagccgg tctacaatga ctacgcttgg     600
aactccaacg cgtccgtgat cttccttgac cagcctgtca atgtcggtta ctcctacagt     660
aactctgctg tcagcgacac ggtcgctgct ggcaaggacg tctatgcctt gcttaccctc     720
ttcttcaaac aattccccga gtatgctaag caggacttcc acattgccgg tgaatcttat     780
gctggtcact atatccccgt cttcgcttcg gagatcctgt ctcacaagaa gcgcaacatc     840
aacctgcagt ccgttctcat ggcaacggt ctcaccgacg gatacaccca gtacgagtac      900
taccgtccca tggcctgcgg tgacggcggt tacccagctg tcttggacga gagctcctgc     960
cagtccatgg acaacgctct tcctcgctgc cagtctatga ttgagtcttg ctacagttcc    1020
gagagcgctt gggtttgtgt cccggcctcc atctactgta caacgccct ccttgcccct     1080 taccagcgca ctgggcagaa cgtctatgat gtccgtggta agtgcgagga tagctctaac    1140
ctttgctact cggctatggg ctacgtcagc gactacctga acaagcccga agtcatcgag    1200
gctgttggcg ctgaggtcaa cggctacgac tcgtgcaact ttgacatcaa ccgcaacttc    1260
ctcttccacg gtgactggat gaagccctac caccgcctcg ttccgggact cctggagcag    1320
atccctgtct tgatctatgc cggtgatgct gatttcattt gcaactggct gggcaacaag    1380
gcctggactg aagccctgga gtggcccgga caggctgaat atgcctccgc tgagctggag    1440
gatctggtca ttgtcgacaa tgagcacacg ggcaagaaga ttggccaggt taagtcccat    1500
ggcaacttca ccttcatgcg tctctatggt ggtggccaca tggtcccgat ggaccagccc    1560
gagtcgagtc tcgagttctt caaccgctgg ttgggaggtg aatggttcta a             1611

<210> SEQ ID NO 65
<211> LENGTH: 840
<212> TYPE: DNA
<213> ORGANISM: Aspergillus niger

<400> SEQUENCE: 65
atgaagttca caaattatct cttgacgact gcaacgctcg caagcagtgt cctagcggct      60
cctgctcccc gcaccggttt ggaggacaga ctccgtgccc ggtcattgca gcgtcaatca     120
catcctctgg cacctattcc acttgacaca tccaccaaag agaattccag actcctcgaa     180
gccgacgaga ataccaccca tgttacatac agcagtaact gggcgggcgc agtgcgcgag     240
caaccacctc gcaaggcac gtattctgcc gtgtcggcaa cctttcgtgt accagaaccc     300
acggcgcaag gggggagcgg aacgcaggct gggtcggcct gggtcgggat agatggcgac     360
acatacagca acgccattct acagacagga gtcgacttct acgtggaaaa cgggcagacg     420
tacaacgatg cctggtatga gtggtaccca gactatgcat atgacttcga cctagatgta     480
```

```
agcacagggg acacgatcgt cgccaaggtg aagccatct cgccaagtca aggtgtagcc      540
actattgaga acatatcgac ggggaagaag gccacgcaga cgatcagagc cccagctgcg      600
acagctaccc ttgccggcca gaatgccgac tggatcgtgg aggatttcca gtctggcgac      660
tcaatggtcg atctggctgg ctttggcgag atcagcttct ggggcgtgca agcacaagga      720
ggagggtcta catggggtgt agatgatgcg actattgtcg aactgaagca gggcaacgaa      780
gtgttgacag acgtggaggt gcaaagtgat tcggccttta cggtgaaata tacgagctga      840
```

<210> SEQ ID NO 66
<211> LENGTH: 1722
<212> TYPE: DNA
<213> ORGANISM: Aspergillus niger

<400> SEQUENCE: 66

```
atgatatatg tcaactatat cctgggactt ctgtccctct tacacaccgc tgtagccaca       60
gctcctgatt atgtcgtggt agaccaactg aacagcatcc ccgacggatg gacaaaaggc      120
gcagctcccc cgccatttac tccgatgaag ttctggttgt cgatgcatca cgagtacaag      180
gcggacttcg agcagaaagt catcgatatc tcgacacccg gtcaccggga ttatggacgg      240
catatgaaac gcaacgatgt catggccttt atgcgcccat ccgatcaggt ctcaaagatc      300
atcttctctt ggcttgagtc ggagcatgtt ccaccaaatg ccatcgaaga tcgcggggat      360
tgggtcgcct tcacagtccc gttggcccaa gcacaatcaa tgatgaagac cgattttac       420 aacttccacc acctggaaac aaacacaacc caaattagga ccctcaagta ctccgttccc      480
gagcaagtcg atgctcatct gcaaatgatc cagccaacga ctcgcttcgg ccgacctaag      540
acacaaacca gcctaccgag cctcatgcca gtgtcggtta acattgatga ataagcgaa       600 gactgcttga caggcgtgac gcccatttgc cttcgccagc tctatggttt acctagcacc      660
aaggcaagcc ccgactcgag aaacgtcctc ggaatttccg gctatctgga ccagtacgcg      720
cgctacagtg acctcgacga gtttctagcc gtatactctc caaacagcgt agacgccgac      780
ttctccgtag tatcgatcaa cggaggccaa aacccacaaa actcacaaga gggaagcaca      840
gaggccagtc tcgacatcca atacgccctc tccatggcat ttgacgctaa cgcgactttc      900
tacactaccg ccgacgtgc gccatccccg tatctcgaac agctccagta tctggtgggt       960
cttccggacg aggatcttcc tgcagtgctt agcacgtctt acggcgagga tgagcaaagt     1020
ctgccggaga atacacaga gccacgtgc aatttatttg cccaattagg tgcacgcggg       1080
gtctcggtga tcttcagcag cggagactcg ggcgtcggag gatcgtgtgt atctaacgac     1140
ggaagccaga ggaccgcttt tcagcctatc ttcccggcgt cgtgcccgtt tgttacatcc     1200
gtgggtggga ctgagggcgt cgggccggaa aaggctgtgg acttttcgag tggagggttc     1260
tccgagcgct ttgctcgccc gtcgtaccag aatgcgagtg tggaagcata ccttgcccgc     1320
ttaggagata aatgggatgg attgtataat ccagacggac ggggtattcc tgatgtgtcg     1380
gcccaggcta gcaactatgt aatcagggac catgggcaat ggctacaaac tgcgggaaca     1440
agtgctgccg cccctgtctt tgcagcagtc atctctcgac tgaacgctgc acgtctcgag     1500
cagggtaaac ctacactagg gtttctgaat ccttggctgt actcactcga ccagcaagga     1560
tttacggata ttgtagacgg cggatcagtg ggttgtgacg ggtcaaatgg aggagctctt     1620
gtcccgtatg ccagttggaa tgccaccaag ggatgggatc cggttactgg gctggggaca     1680
cctctgtatc agactctgga gcagttggcg cagtctgctt ag                        1722
```

-continued

<210> SEQ ID NO 67
<211> LENGTH: 1758
<212> TYPE: DNA
<213> ORGANISM: Aspergillus niger

<400> SEQUENCE: 67

| | |
|---|---|
| atgcgttctt ccggtctcta cacagcactc ctgtgctccc tggccgcctc gaccaacgcg | 60 |
| attgtccatg aaaagctcgc cgcggtcccc tccggctggc atcatgtcga agatgctggc | 120 |
| tccgaccacc agataagctt gtcgatcgcg ctggcacgca agaacctcga tcagcttgaa | 180 |
| tccaagctga aagacttgtc aacacctggc gaatcgcaat acggccagtg gctgaccag | 240 |
| gaggatgtcg acacgctgtt cccggtggcc agcgacaagg ctgtgattaa ctggctgcgc | 300 |
| agcgccaaca tcacccatat tcccgccag ggcagcttgg tgaactttgc gaccacggtc | 360 |
| gataaggtga acaagcttct caacgccacc tttgcctact accaaagcgg ctcttcccag | 420 |
| agattgcgca acagagta ctccatcccg gatgatctgg tcgactcaat cgacctcatc | 480 |
| tccccaacga ccttcttcgg caaggaaaag accactgctg gtctgaacca gcgggcgcaa | 540 |
| aagattgaca cccatgtggc caaacgctcc aacagctcgt cctgtgccga tgtcatcacg | 600 |
| ctgtcctgcc tgaaggagat gtacaatttt ggcaactaca ctcccagcgc ctcgtcgggc | 660 |
| agcaagctgg gcttcggcag cttcctgaac gaatccgcct cgtattctga ccttgccaag | 720 |
| ttcgagaagc tgtttaacct gccctcccag agcttttccg tggagttggt caacggcggt | 780 |
| gtcaatgatc agaatcaatc gacggcttcc ttgaccgagg cggacctcga tgtggaattg | 840 |
| ctcgtcggag ttgctcatcc cctcccggtg actgagttca tcacttctgg cgaacctgcc | 900 |
| gccgacaacg agaacgagcc ttacctccag tactatgagt accttctctc caagcccaac | 960 |
| tcggctctgc cccaagtgat tccaactcc tatggtgacg acgaacagac cgttccagag | 1020 |
| tactacgcca agcgagtctg caacctgatc ggacttgttg gcctgcgcgg catcagtgtc | 1080 |
| ctcgagtcgt ccggtgacga aggtatcgga tctggctgcc gaaccaccga cggcaccaac | 1140 |
| cgaacccaat tcaaccccat cttcccggcc acctgtccct acgtgactgc cgtgggagga | 1200 |
| acaatgtcct atgcccccga aatcgcctgg gaagccagtt ccggcggatt cagcaactac | 1260 |
| ttcgagcggg cgtggttcca gaaggaagct gtgcagaact acctggcgca ccacatcacc | 1320 |
| aacgagacca agcagtacta ctcgcaattc gccaactta gcggtcgcgg atttcctgac | 1380 |
| gttgctgccc atagctttga gccttcatat gaggttatct tctacggcgc ccgctacggc | 1440 |
| tccggcggta cctcagccgc gtgtcccctt ttctctgcgc tagtgggcat gctgaacgat | 1500 |
| gctcgtctgc gggcgggcaa gtccacgctg ggtttcttga accccctgct ctatagcaag | 1560 |
| gggtacagag cgttgactga tgtgacgggg gccagtcga tcggatgcaa tggcattgat | 1620 |
| ccgcagaatg atgagactgt tgccggcgcg ggcattatcc cgtgggcgca ctggaatgcc | 1680 |
| acggtcggat gggatccggt gactggattg ggacttcctg actttgagaa gttgaggcag | 1740 |
| ttggtgctgt cgttgtag | 1758 |

<210> SEQ ID NO 68
<211> LENGTH: 798
<212> TYPE: DNA
<213> ORGANISM: Aspergillus niger

<400> SEQUENCE: 68

| | |
|---|---|
| atgaagacta ctgctctctt gaccgccggc ctgctggcca ccactgctat ggccgctcct | 60 |
| ctgacggcca agcgccaggc tgctcgggcc aagcgctcca cgaaccgcca gagcaaccct | 120 |

```
cccttcaagc ctggcaccaa cgaggtcctc gcccttaacg gcaccaagaa tgtggagtac      180
agctccaact gggccggtgc cgtcctcatt ggcactggtt acactgccgt gaccgccgag      240
ttcgtcgtgc ccaccccctc cgtgccctcc ggtggctcga gccgcgagga gtactgtgcc      300
tccgcctggg tgggcattga cggtgacacc tgtgacactg ctatcctcca gaccggtgtg      360
gacttttgtg tccagggcag cgaggtgagc ttcgatgcct ggtacgagtg gtaccccgac      420
tacgcctacg acttcagcgg catctccatc tcggccggtg ataccatcaa ggtcaccgtc      480
gatgccagca gcgacaccac cggtactgcc acgattgaga cgtgagcac tggtaccacg       540 gtcacccaca gcttcacggg cggtgttgat ggtgatctgt gtgagtacaa cgctgagtgg      600
atcgtcgagg acttcgagga ggatgactcc ctcgttccct tgccgactt tggcaccgtg       660 actttcacca gctgctccgc taccaaggat ggttcctctg ttggccctga ggatgctacc      720
atcatcgaca tcgagcagaa tgaggtgctg acctccgttt ccgtctccag tagcgaggtc      780
gttgtcaagt acgtctaa                                                    798

<210> SEQ ID NO 69
<211> LENGTH: 1743
<212> TYPE: DNA
<213> ORGANISM: Aspergillus niger

<400> SEQUENCE: 69
atggtcgcct tttcccgcat ctcggcaggc ttcgcccttg ccgccctgc cctggccagc        60 gtcgtcctgg agaccgtcaa gtctgttccc agcgactgga agctcgtgga ggctgctgat      120
accagctcca caatttcttt gtccgttgct ctggcgcgtc agaacctgga ccagttggag      180
gagaagctcc tggccgtgtc caccctggc aaggacacct acggcagtt cttggatctg        240 gacgacatca atgagcagtt tcctctcgca gatgacgctg ctgttgtggc ttggctgaag      300
aaggcaggcg tcacccagat ccataaggag ggtggtctgc tgaactttgc gaccactgtg      360
ggcacagcca accagcttct caacaccacc ttctcggtgt acaagagcgg atctacccag      420
aagctgcgca caacgcaata ctctgttccg gatgagctga ccgggtccat tgatctcatc      480
tcgccgactg ttttctttgg aaagtccaac gctgcgcgct cggcggccgt gcgtgcttcg      540
cagactacca aggagaccag cagaaagaag agcagtaatg tgtgcgagta catcactccg      600
gattgcctca agagcagta tagcattgac tatacgcccg aggcatcgtc gggaagtcgt       660
gttgggtttg gcagtttctt gaacgagtcg gccttgtact cggatttgga tctgttcacc      720
cagtactttg acattcccca gcagagtttc actgttgaga ctatcaacgg gggaatcaac      780
aaccaggaga atgatccgga tggtgaagcc gatctcgatg tccagaacat cgtgggcatc      840
tcgcatccct tgccggtgac ggagtacatt accggaggat ctcctccatt cattcccgac      900
gtcgagacta ctaccgacga gaacgagcct tacctgcagt actacgagta tctgctggcc      960
aagaccaacg acgagctgcc actggttatc agcaactcgt acggcgatga cgaagatacc     1020
gttcccattg cctacgccac ccgcgtatgc aacctcatcg gcctgatggg cacacgtggt     1080
atctccatcc tcgagtcttc cggcgactct ggtgtgggcg cgcatgcat gtccaacgac      1140 ggcaccgaca gaccgaatt caccccatg ttcccaggaa catgcccgta catcaccgcg       1200
gtcggcggca cccaagacgt gcccgaagtc gcctgggtgg acagctccgg cggcttcagc    1260
aactacttct cgcagccgtc gtaccagtcg gatcaggtgg agacctacct ggacaagtac    1320
atctctgcct cgacgaagaa gtactacgag cagtacacca cttcagcgg tcgcgcgttc     1380
```

| | |
|---|---|
| cctgacgtgt ctgcgtttgc aggttctcct tactacgaaa cttatattga tggtcagctc | 1440 |
| ggccttgtgg cgggtacttc tggcgctagc cctgtgtttg cggggatcgt cgcgctgctg | 1500 |
| aacgatgccc gtctgcgggc caacaagaca tccttgggct tcctgaaccc ttggctgtac | 1560 |
| tcgagcggct acaagagcct gaatgacatt accagtggcg aggcagtggg ctgccaaggc | 1620 |
| gatgtggagg cgctggagt cattccttgg gcgagctgga atgccacgac gggatgggat | 1680 |
| ccggcgacag ggctgggaac gcctaatttt gccaagctga aggaggcggt tcttgcgttg | 1740 |
| taa | 1743 |

<210> SEQ ID NO 70
<211> LENGTH: 1896
<212> TYPE: DNA
<213> ORGANISM: Aspergillus niger

<400> SEQUENCE: 70

| | |
|---|---|
| atgcatggtc tgcgcctagt atgcagcata gggacattgc ctttggttat cctggcatat | 60 |
| ccggcggctt cattgcatac aacttcagca gccgtggact tggactccct tcgtctgacc | 120 |
| tctaactccg aatacgtcaa ttctgtccat gtagacacga tcgatcagt cgcagtgtcc | 180 |
| gctgaagaac attataccga tacagcagct cgactggttc agaacattgt tcctggagcg | 240 |
| agctttcgtc tcatcgatga ccactttgtc ggcgacaatg gagttgcaca tgtatacttc | 300 |
| cgccaaacgc tccatggtat tgacattgac aatgcggatt tcaatgttaa tattggaaaa | 360 |
| gatggactgg tcttgtcttt cggacattcg ttcttcacag gcgcgttgcc gagcagccat | 420 |
| ctggacaata ccaacgtttt gagtccggag gctgcactta gaggagcaag ggacgctata | 480 |
| cagcttccac tgactattga caatgtttct actgaagctg cagaggggcg gaacgagtac | 540 |
| atattcagag aggcagtggg agcggtatct gaccccaaag ctaagctagt ctaccttgtc | 600 |
| aagccagaag ggactctggc gctcacctgg aggatagaaa cagacatgta tgagcactgg | 660 |
| ctactgacat acattgatgc agagactacc actgtccacg gcgtggttga ctatgtcgca | 720 |
| gacgcgacat atcaagttta tccctggggc acaaacgatc cagcagaagg acatcgcacc | 780 |
| attgtcaccg accctgga cctatccgca tccgcataca cctggataag cgatggacgg | 840 |
| gacaactaca ccacaaccag aggcaacaat gccatcgcac actggaatcc gaccggcggt | 900 |
| ggctcctatc tctacaacct acgtccatcc gaccccaact tgaatttcca atggccatac | 960 |
| tccccaaaca tgtccccacc ccgatcatac atcaacgcct ccatcgtcca actcttctac | 1020 |
| acagcaaacg cctaccacga cctcctctat acactcggct tcaccgaatc cgctggcaac | 1080 |
| ttccaatgga ataacagcgc ccacggcggc cgagacaaag actacgtgat cctcaacgca | 1140 |
| caagacggct ccgggttcag caacgcaaac tttgcaaccc cacccgatgg tatccccggc | 1200 |
| cgtatgcgca tgtacatctg gatcgagtct actccgtcgc gtgatggaag ttttgacgcg | 1260 |
| ggcattgtaa ttcacgaata cactcacggt gtatccaatc gtctcaccgg cggctcccac | 1320 |
| aacgccggat gcctcagcgc cctcgaatcg gtggcatgg gcgaaggctg gggcgacttt | 1380 |
| atggcgacgg ccatccgaat caagcccaac gatacacgca caacgtctta cactatgggt | 1440 |
| gcatgggcag ataatgataa atgtggtgtc cgggactatc cttattctac ctcctttact | 1500 |
| gagaacccctt tgaactatac gagcgtgaat accatgaacg gcgtgcacgc catcggaact | 1560 |
| gtctgggcaa ccatgctata cgaggtcttg tggaacctca tcgacaagta cgggaagaat | 1620 |
| gatgggtcga ggccggtgtt tagaaacggg gtgcctacag atggaaagta cttgatgatg | 1680 |
| aagttggtgg tggatgggat ggcactgcaa ccatgtaatc cgaacttcgt gcaagccagg | 1740 |

```
gacgcgatcc ttgacgcaga cattgtgttg actggcggga agaatcgctg tgagatctgg    1800 aggggtttg  cgaagagagg attggggcaa ggagcggctc atagtagttt aaattggatg    1860
cggaggggga gtacacttct tcctacggga tgttag                              1896

<210> SEQ ID NO 71
<211> LENGTH: 1185
<212> TYPE: DNA
<213> ORGANISM: Aspergillus niger

<400> SEQUENCE: 71
atggtcgtct tcagcaaaac cgctgccctc gttctgggtc tgtcctccgc cgtctctgcg      60
gcgccggctc ctactcgcaa gggcttcacc atcaaccaga ttgcccggcc tgccaacaag    120
acccgcacca tcaacctgcc aggcatgtac gcccgttccc tggccaagtt tggcggtacg    180
gtgcccagag cgtgaagga ggctgccagc aagggtagtg ccgtgaccac gccccagaac     240
aatgacgagg agtacctgac tcccgtcact gtcggaaagt ccaccctcca tctggacttt    300
gacaccggat ctgcagatct ctgggtcttc tcggacgagc tcccttcctc ggagcagacc    360
ggtcacgatc tgtacacgcc tagctccagc gcgaccaagc tgagcggcta cacttgggac    420
atctcctacg gtgacggcag ctcggccagc ggagacgtgt accgggatac tgtcactgtc    480
ggcggtgtca ccaccaacaa gcaggctgtt gaagcagcca gcaagatcag ctccgagttc    540
gttcagaaca cggccaatga cggcttttg ggactggcct ttagctccat caacactgtc     600
cagcccaagg cgcagaccac cttcttcgac accgtcaagt cccagctgga ctctccccctt   660 ttcgccgtgc agctgaagca cgacgccccc ggtgtttacg actttggcta catcgatgac    720
tccaagtaca ccggttctat cacctacacg gatgccgata gctcccaggg ttactggggc    780
ttcagcaccg acggctacag tatcggtgac ggcagctcca gctccagcgg cttcagcgcc    840
attgctgaca ccgtgtaccac cctcatcctc ctcgatgacg aaatcgtctc cgcctactac    900
gagcaggttt ctggcgctca ggagagcgag gaagccggtg gctacgtttt ctcttgctcg    960
accaaccccc ctgacttcac tgtcgtgatt ggcgactaca aggccgttgt tccgggcaag    1020
tacatcaact acgctcccat ctcgactggc agctccacct gctttggcgg tatccagagc    1080
aacagcggtc tgggactgtc catcctgggt gatgttttct tgaagagcca gtacgtggtc    1140
ttcaactctg agggccctaa gctgggattc gccgctcagg cttag                    1185

<210> SEQ ID NO 72
<211> LENGTH: 1197
<212> TYPE: DNA
<213> ORGANISM: Aspergillus niger

<400> SEQUENCE: 72
atgaagtcag cctccttgct cacagcatcc gtgctgttgg gctgtgcctc cgccgaggtt      60
cacaagctca agcttaacaa ggtgcctctg aagagcagc tttacacgca taacatcgac     120
gcccatgtcc gcgctctggg ccagaagtac atgggtatcc gcccgtccat ccacaaagag    180
ctggtcgagg agaaccctat caatgacatg agccgtcatg atgttctggt ggacaacttc    240
ctgaacgcac agtacttctc tgagatcgag ctggtactc ccccccagaa gttcaaggtt     300
gtcctggaca ctggcagctc gaacctttgg gttccttcga gcgaatgcag ctctatcgcc    360
tgctacctcc acaacaagta tgattcgtct gcctccagta cgtatcacaa gaatggcagt    420
gaattcgcca tcaagtacgg ctctggcagc cttagcggat tcatttctca ggacacccctg   480
```

| | | |
|---|---|---|
| aagattggcg acctgaaggt caagggacag gacttcgctg aggcgaccaa tgagcctggc | 540 | |
| cttgcctttg ccttcggccg gttcgatggc attctcggct tgggttatga caccatctcc | 600 | |
| gtgaacaaga ttgttcctcc cttctacaac atgcttgacc agggactcct cgacgagccg | 660 | |
| gtctttgcct tctaccttgg agataccaac aaggagggtg acgagtccgt ggcgaccttc | 720 | |
| ggtggtgtcg acaaggacca ctacaccggc gagctgatca agattcccct ccgtcgcaag | 780 | |
| gcttactggg aggttgagct tgacgccatt gctcttggcg atgatgttgc tgagatggag | 840 | |
| aacaccggtg tcattctgga cactggtacc tccctgattg ctctgcctgc tgacctggct | 900 | |
| gagatgatca atgctcagat cggtgctaag aagggctgga ccggccagta caccgttgac | 960 | |
| tgcgacaagc gctcgtccct gcccgatgtt actttcaccc ttgccggcca caacttcacc | 1020 | |
| atctcctcgt atgactacac cttggaggtg cagggctctt gcgtcagtgc cttcatgggc | 1080 | |
| atggacttcc ctgagccggt tggtcccttg gccattttgg gcgatgcgtt cctgcgcaag | 1140 | |
| tggtacagcg tgtatgacct gggcaacagc gctgttggtc tggccaaggc caagtaa | 1197 | |

<210> SEQ ID NO 73
<211> LENGTH: 1182
<212> TYPE: DNA
<213> ORGANISM: Aspergillus niger

<400> SEQUENCE: 73

| | | |
|---|---|---|
| atgcgcaagt accgcttcca tcccaccaag cctggtccct cactctcag cagctccatc | 60 | |
| caacagaccg tcgtccgta cactgaaaag cccatcgggg gtcgggccca tatccggcag | 120 | |
| ctggtgcgga agaagagcac caccagcgat gaggttggcg aggttccggc cgaagatgtg | 180 | |
| cagaacgact ccatgtatct ggcgaccgtg gggatcggaa ccccggcgca gaacctgaag | 240 | |
| ttggactttg acactggttc agctgatctt tgggtctggt ccaacaaact ccctcaacc | 300 | |
| cttctatccg agaacaagac ccatgcgatc ttcgactcgt ccaaatcgag cacccttcaag | 360 | |
| accttggaag gtgaatcctg gcaaatctcc tacggagatg gatcctccgc atcagggagt | 420 | |
| gtgggcaccg acgacgtcaa cattggcggc gtagtcgtca agaaccaagc cgttgagctg | 480 | |
| gcagagaaga tgtccagcac attcgcccaa ggcgaagggg acggattgct cggtctagca | 540 | |
| ttcagcaaca tcaacacggt acagccaaag tccgtgaaaa cgcccgtcga gaacatgatc | 600 | |
| ctgcaggatg acattcccaa gtcggctgag ctgttcacgg ccaagctgga tacctggcgg | 660 | |
| gacactgatg acgagtcgtt ttacaccttt ggcttcattg accaggatct ggtgaagacg | 720 | |
| gcaggtgaag aggtctacta caccctgtc gataacagtc aaggcttctg gctattcaac | 780 | |
| tcgacctccg cgacggtaaa tggaaagacc attaaccggt cgggtaacac cgccattgct | 840 | |
| gataccggta cgacgctggc cttggtggac gatgacacgt gtgaggccat ttatagtgca | 900 | |
| attgacggcg cctattatga tcaggaagta cagggctgga tctatccgac cgatacggcg | 960 | |
| caggataagc tacccactgt gtcgtttgcc gtgggtgaaa agcagttcgt ggtgcagaag | 1020 | |
| gaggacctgg cgttttcgga ggcgaagacg ggctatgtct atggaggaat ccaaagtcgt | 1080 | |
| ggtgatatga ccatggacat cttgggagac acattttga agagtattta tgctgtaagt | 1140 | |
| gcattgctgt tggcgttaag gggtgatatc gaagctcact aa | 1182 | |

<210> SEQ ID NO 74
<211> LENGTH: 849
<212> TYPE: DNA
<213> ORGANISM: Aspergillus niger

<400> SEQUENCE: 74

-continued

```
atgaagttct ctaccatcct taccggctcc ctcttcgcca ctgccgctct ggctgctcct      60
ctcactgaga agcgccgtgc tcgcaaggag cccgcgccg ctggcaagcg ccacagcaac      120
cctccctaca tccctggttc cgacaaggag atcctcaagc tgaacggcac ctccaacgag    180
gattacagct ccaactgggc tggtgccgtc ctgatcggcg acggctacac caaggtcact    240
ggcgagttca ctgtccccag tgtctctgct ggatctagca gctccagtgg ctacggcggt    300
ggctacggct actacaagaa caagagacaa tccgaggagt actgcgcctc cgcttgggtt    360
ggtatcgacg tgacacctg cgagaccgct attctccaga ctggtgtcga cttctgctac    420
gaggatggcc agacttccta cgatgcctgg tacgagtggt accccgacta cgcctacgac    480
ttcaacgaca tcaccatctc cgagggtgac accatcaagg tcactgtcga ggccaccagc    540
aagagcagcg gtagcgccac cgttgagaac ctgaccactg gccagtccgt cacccacacc    600
ttcagcggca acgtcgaggg tgaccttttgc gagaccaacg ccgagtggat cgtcgaggac    660
ttcgagtctg gtgactctct tgtggctttc gctgacttcg gctccgttac cttcaccaat    720
gctgaggcta ccagcgacgg ttccactgtc ggcccctctg acgctaccgt tatggacatt    780
gagcaggatg gcaccgtcct caccgagacc tccgtctctg gcgacagcgt cactgtcacc    840
tacgtttaa                                                              849
```

<210> SEQ ID NO 75
<211> LENGTH: 822
<212> TYPE: DNA
<213> ORGANISM: Aspergillus niger

<400> SEQUENCE: 75

```
atgggagatt acggccccgg agtgtcgtca ctcacggcac agctacctgg aaatccgcct      60
gtctctgaaa cagatcagga tgagatctca gtacttgtaa cgggctttgg gccattcaag    120
tctaatctag tgaacgcctc atatctgata gcctcgtccc taccaccctc tttcacattc    180
tcacctgcat cttcagacgg ctctgatgct gttccccgtc gagtttcgat aaatgtccat    240
ccttcaccca tacccgttgc atattcatcg gtgcggacga ccctcccgt cattctcgat    300 gactatgcca agacgcacgg aggccgacgc ccagacatcg tcatacacat tggcatagca    360
gcaatgagga actactattc cgtggagacg caggctcacc gtgatgggta tctgatgtcc    420
gacatcaaag gcagatccgg gtacgaggat ggcgagaagc tgtggaggga gctcgacttg    480
ccactggtgc ttagggctgg cccttcagag ggacacgcct cggagaagaa acatctcagc    540
ccccgtccac cggacgaaga tttcctagca gcatggaaga cattttgccc tccagaaacc    600
gatgcgcgga tctccactga tgccggacgt tatctctgcg agttcatcct gtacaccagc    660
ttggcactgg cataccaggc gggtgaggat cgcaatgtca ccttcttcca tgttcccgcg    720
tcatgcttgg atgaggatat agagacgggc aaggaggttg ccgtcgcgct aatcaaggct    780
cttgtgacta gctggagtga gcagcagcac agcgttccct ag                         822
```

<210> SEQ ID NO 76
<211> LENGTH: 1629
<212> TYPE: DNA
<213> ORGANISM: Aspergillus niger

<400> SEQUENCE: 76

```
atgggctcaa ggcagggaaa ggccccctt ggctggggta tcagtcact tgctcacttt      60 ggtatcaacc cagaccttgg gttgcacaac cagcagaacc tcaactccct catttcacat    120
```

```
tcagcgatgg ccactgcgtt ggagacggaa tatgccacca tccctattga ccataacaac      180
gcatcggctg gcacttatca aaatcggttc tgggtcagcg atgaattcta tcagcctggc      240
aacccgatat ttgtgtacga taccggggag tcggatggcg gatcgatagc ccagtcctac      300
ctaacctcca ctctctcctt cttcagagaa ttcctgatcg aattcaacgc catgggaatc      360
gcctgggagc acagatacta tggaaactcg accccggctc ccgtatccta tgaaactcca      420
cccgaggcat ggcaatacct caccaccaag caggcgctcg cggaccttcc gtactttgct      480
agtaacttta gccgcgagaa gtatcctgac atggacctga cgccgcaggg cacgccgtgg      540
atcatggtgg gcgctcgta cgcagggatt cgtgctgcat taactcgcaa ggagtaccca      600
gagacgatat tcgcagcctt ttcctcatcg tctccggtgg aagcacaggt caatatgagc      660
gcgtattacg accaagtcta tcgtggcatg gttgccagcg gatggaccaa ctgctcggca      720
gatatccacg ctgctctgga atatattgac gatcaacttt cggatgaaga tacagctacc      780
tcggtcaaac aacttttctt cggatctggc gccgagacca actccaacgg tgatttcact      840
gcagcgctaa ctgccatcta cggctacttc caaagttatg gtatggcggg aggtattgga      900
ggtctaggcg cattctgcga gtatctcgaa attgatccca agacgaacgg gactacagga      960
ccggatggcc ttgcccctac gtatggcggc cagtatgtcg ccgaacgatg ggccgcatgg     1020
ccaaccttc tcgagctggt caatctgaat atggggacca actgcgggcc tcaggacgcg     1080
tctcagccaa ttgactgtga cttttccaag ccatacggcg atccctcggc catcacttgg     1140
acttggcaat actgcagcga atgggggttc ttccaggcga caacgatgg gccgcactcg     1200
ctggcctcgc gatatcagtc ggtggaatac cagcaagaag tatgtaaccg gcagttcccc     1260
gatgcagtgg acaagggact gctgcctccg tcgccgcggg cggatgatgt caaccaagag     1320
tttgggggat ggacgatccg cccgtccaat gtttacttca gcggaggaga attcgatccg     1380
tggcgatcat tgtccattct gtcgacagaa gatttcgcac ctcaagggggt ggagtttacg     1440
agcgcgatcc cagcctgtgg ggtgcagacc aatgaggaca ccgtctttgg atacgtcatg     1500
cagaactcgg aacattgctt tgactttcaa gcgacgccga ccgtggggaa gttatcacgc     1560
ggcatcttca catccgcctt gttgcaatgg ctcgaatgtt ttggacagaa ctcaagccaa     1620
tccaggtga                                                             1629
```

<210> SEQ ID NO 77
<211> LENGTH: 1176
<212> TYPE: DNA
<213> ORGANISM: Aspergillus niger

<400> SEQUENCE: 77

```
atgaagctct caatagctct tgcactcggc gcaacggctt cgacgggggt gttggctgct       60
gttgtaccgc agcaagaacc gctgataacc ccccaagatc ccccaactca tcatcatcag      120
gagaagttct tgatcgagtt ggctccttat cagacgagat gggttaccga ggaagaaaag      180
tgggacttaa aactggatgg cgtgaacttc atcgatatta ctgaagaacg aaacactggg      240
ttctacccaa cgttgcatgc tggtagctat gttcactatc cgccgacgat gaagcatgcg      300
gagaaggtgg ttccccttct gcggggtctc tccaaggaca acatggagca aaacctcaac      360
aaatttacct catttcacac tcgctactat aggtcgtcca ctggtattga gtccgcaaag      420
tggctataca gtagggtttc ggatgtcatt gagcagtcgg gtgcagcaga gtacggcgcc      480
actgtggagc agttcgctca ctcatggggc caattcagta tcattgctcg gatcccaggc      540
cagactaaca aaactgttgt cctgggcgca catcaggaca gcatcaatct tttcctcccc      600
```

-continued

```
tccatcctag ctgcacctgg tgccgatgat gacggaagtg gaaccgtgac tatactcgaa    660
gctttgcgtg gtctgctgca gtcagacgcc attgtccggg gcaacgcttc caacacaatc    720
gaattccact ggtactcggc agaggaaggt ggtatgcttg gttcgcaagc catattctct    780
caatataaga gagataagcg agacatcaag gcgatgcttc aacaggatat gactggttat    840
acccagggag ctctggacgc cggtcgtcaa gaagccattg ggattatggt tgactacgtt    900
gatgagggac tgacacaatt cctcaaagat gtcactactg agtattgtgg tattggctac    960
atcgaaacca gatgtggcta cgcctgttcg gaccacacgt ccgcaagcaa atatggctat   1020
cccgcagcta tggcgacgga atccgaaatg gaaaacagca acaagaggat ccacacgact   1080
gatgacagca tccggtatct aagcttcgat catatgctgg agcatgcgag gttgacacgt   1140
ggcttcgctt acgagctggc ctttgctcaa ttctag                              1176
```

<210> SEQ ID NO 78
<211> LENGTH: 1329
<212> TYPE: DNA
<213> ORGANISM: Aspergillus niger

<400> SEQUENCE: 78

```
atgagaacta ctacgtcttt tgctaggctt gcattggcag tggcctcagt tggtattgtc     60
tttgctagtc aacaaaaaaa taacgatggg aaactggtat atggctcacc agaatccgtc    120
ggcatgatat ccgccccttt gcaccaaatg gtccaaaatg ttagcgcata tacacatgct    180
gccaactata gcaagttctc gtacgacaaa gtccatccca tcgagccagg gtctgttacc    240
ctggtggctc tcgacggtgt catcgtcagc gaatttgcct tgggcaagag aaatctctac    300
gccgatgtca acggcaccaa tttacctcga tacctgcagg aagacaccac cctggataca    360
gtctacgata tggcaagcct cacgaagctg ttccaccacg gtagctgcttt acgggaactt    420 gacgctggtc gaattgcgct taatgtaact gttgcaactt atataccgga ctttgcgacg    480
aatgggaagg agaatattac tatcttggag ctgttcacgc atacaagcgg tttcgcttct    540
gatccatcgc caccactttt ctctgcttat tatacgacgt atgatgaacg cattaaagca    600
attttgacgc aaaaaattat caataccccc ggcagcacat acctctactt agatctcaac    660
tttatgtcgc tgggcctcgt tatcgagacc gtaacgggac gtgccctgga tgatcttatt    720
tatgacttca ccagaccgct tgaaatgaca tctaccttct tcaaccgcgg gaatatcgaa    780
ggctctacac cccagtcacc caactacgac cgcacagccg tacaagaatt tcagatcgca    840
gccctcggac cctcagaacc acagcgtcca caaccagtgc gcggcacagt tcacgacgag    900
aacgcatggt ccctagacgg cgtatcaggt catgcaggtc tattctccac tgtgcgcgat    960
acagcgacat tctgccagat gatcctcaac aacggcacat atgcaggcca acggatcctt   1020
tctcgaacag cggtagacat gattttcaca aacttcaatg ccaggtttcc gggggatgct   1080
cgtagtttag ggtttgagtt ggatcagtat tctactgcgg gaccgatggc gagtttgcaa   1140
actgcgagtc acactggatt tactgggact acgttggtga tggataggac gtataacgcc   1200
ttttggttgc attttagtaa ccgggtgcat ccgtctaggg catggtctag caatactatt   1260
gtgagagagg ctattgggta ttgggttggg aagagcttgg ggttggatgt tgcgtttgct   1320
ctgttgtaa                                                          1329
```

<210> SEQ ID NO 79
<211> LENGTH: 1839
<212> TYPE: DNA

<213> ORGANISM: Aspergillus niger

<400> SEQUENCE: 79

| | | | | | |
|---|---|---|---|---|---|
| atggcgtcct | ggttgctctc | gacgctcctt | tttctgagcc | cgtccttggt | gtcagccaaa | 60 |
| tcggccgcag | actattatgt | tcactccttg | cccggtgccc | ccgagggggcc | cttgctgaag | 120 |
| atgcatgccg | gccatattga | ggtggatcca | cagaacaatg | gaaatctttt | cttctggcac | 180 |
| taccagaatc | gccatattgc | caaccgccag | cggactgtga | tctggttgaa | cggtggtccc | 240 |
| ggatgtagtt | ccatggacgg | cgcgttgatg | gaggtcggtc | cgtatcgcct | gaaggacaat | 300 |
| gaaaccttga | cctataatga | gggttcctgg | acgaattcg | ccatttgtt | gttcgtcgat | 360 |
| cagccagtcg | gaaccgggtt | cagttatgtc | aacacggaca | gctatcttca | tgagctcgat | 420 |
| gagatgtcgg | ctcagttcat | tgtctttctg | gaagagtggt | tcagattatt | ccggagtat | 480 |
| gaacgcgatg | atatctacat | tgccggcgag | tcttacgccg | gtcagcatat | tccatacatc | 540 |
| gccaaagcca | tccaggaacg | gaacaagaac | gttcaaggga | gaccatcgc | ttcgtggaat | 600 |
| ctaaaaggcc | tattgattgg | caatggttgg | atttctccta | atgaacagta | catgtcctac | 660 |
| ttgccctacg | catatgaaga | aggccttatc | aaggaaggca | gccggaccgc | gaaggaactc | 720 |
| gaagttttac | agtcagtctg | taagtccagg | ctggaaactg | gcaagaacaa | ggtccacctc | 780 |
| aacgactgcg | agaaggtcat | gaatgctctg | ttggataaga | cggtcgaaga | caacaaatgt | 840 |
| ctcaacatgt | atgacatccg | ccttcgtgac | accaccgatg | catgcggtat | gaactggccc | 900 |
| accgacctgg | aggacgtgaa | gcccctatctg | cagcgggaag | atgtggttaa | agcgcttaac | 960 |
| atcaatccgg | agaagaagtc | tggctgggtg | gagtgttcag | gtgcagtgag | cagcgctttc | 1020 |
| aatccgcaaa | agtccccgcc | ctcggttcaa | ctacttcccg | gcttgctgga | atcgggactt | 1080 |
| caaatcctcc | ttttcagcgg | agacaaggac | ctgatttgca | accatgttgg | aacggaacag | 1140 |
| ctcatcaata | acatgaagtg | gaacggaggc | acgggtttcg | agacctcacc | tggcgtctgg | 1200 |
| gctcctcgac | acgactggag | tttcgaaggc | gagccggcgg | gtatctatca | atatgccaga | 1260 |
| aacctgactt | acgtgctcat | ctacaacgca | agccatatgg | ttccctacga | ccttcctcgt | 1320 |
| cagagccggg | acatgctaga | tcgcttcatg | aatgtcgata | tcgcgagcat | cggaggcagc | 1380 |
| cccgccgact | cgcgcattga | cggcgagaag | ctgccccaga | cgtcggtggg | cggccatccc | 1440 |
| aacagcaccg | cggcggagga | gcaggagaag | gagaggatca | aggagacgga | atggaaagcc | 1500 |
| tacgccaagt | caggcgaagc | cgttctcctc | gtcgtcatta | tcggtgtatt | agtttggggc | 1560 |
| ttcttcatct | ggcgcagccg | ccggcgtcac | caggatacc | ggggcgtctg | gcataaggac | 1620 |
| atgagcggaa | gctctgttct | cgagcggttc | cacaacaagc | gcacgggagg | cgcagacgtc | 1680 |
| gaagcggggg | atttcgacga | ggcggagctc | gatgaccttc | attctccaga | cctcgaaaga | 1740 |
| gaacactacg | ccgtgggcga | ggacagcgac | gaggatgata | tttcacgaca | gcattctcaa | 1800 |
| caggcctccc | gagccggggg | cagtcataat | ctatcctag | | | 1839 |

<210> SEQ ID NO 80
<211> LENGTH: 1596
<212> TYPE: DNA
<213> ORGANISM: Aspergillus niger

<400> SEQUENCE: 80

| | | | | | |
|---|---|---|---|---|---|
| atgtttctga | tttcacctgc | agtgacagtt | gcggctgcac | ttctgctgat | caacggcgca | 60 |
| ggagcaactc | aatctgaacg | aagtcgggct | gccgctcatt | tttccaaacg | tcatccgacg | 120 |
| taccgtgctg | cgaccagagc | ccagtcgagc | aacacttccg | actaccgatt | cttcaataat | 180 |

-continued

```
aggaccaagc cccacttggt ggaaagctta cccgatgtgc acttcgatgt tggggagatg      240
tactcggggt cgatccctat cgatgacagc aacaatggat ctcgatccct gttttatatc      300
ttccaaccta agataggcga accttcagac gaccttacca tttacctcaa tggagggcca      360
ggctgttcct ccgaacaggg attctttcag gaaaatggca ggttcacatg gcagcctggt      420
acctatgcac ccgtcatcaa cgaatattct tgggtcaatt tgacgaacat gctatgggtt      480
gaccaaccag tcggaaccgg attttccgtt ggaaatgtta cagccaccaa cgaagaagag      540
attgccgccg attttctcga cttctttgaa aagtttgaag atctatacgg gataaagaac      600
tttcgcattt tcatgaccgg tgagagctac gccggtcgct atgttcccta tatctcgtcg      660
gcaatgctag acaagaacga caccacgcgt ttcaatctga gcggagccct tctttatgac      720
gcctgcatcg gccaatggga ctacatccag gccgaactcc ctgcctaccc cttcgtcaag      780
cagcacgctt cactattcaa cttcaatcag tcctacatga acgagcttga aaccaccctac      840 gaagaatgcg gctacaaggc ctacttcgat gagtactttg cctttccacc aagcggcatc      900 caaccccaa aatacatgaa ctactccgag tgcgacatct ataacatgat ctactacgaa      960
gcctataacc cgaacccatg cttcaatccc taccgcgtca ttgatgagtg tccacttctc     1020
tgggacgtcc tgggctggcc gacagacttg gcatacgagc ctgcgcccac cacatacttc     1080
aaccgtatcg atgtcaagaa ggccctgcac gcccccatgg atgtggaatg ggagctctgc     1140
agctacgacc tcgtcttcgc tggaggcgac gctgacccgg gtccggagca gcaaggggat     1200
gactcaccca accccaccga gggtgtcctc ccgcgtgtta ttgaggcgac caaccgcgtg     1260
ctcattgcca acggtgactg ggactacctg attatcacca acggcaccct cctcgccatc     1320
cagaatatga cctggaacgg ccagctgggc ttccagtccg cacctgccac accgatcgat     1380
attcagatgc ccgatctcca gtgggttgag atttttgagg cccaggaggg atatggaggg     1440
ctggatggcc ctcagggggt tatgggtgta caacattatg agcgcggttt gatgtgggcg     1500
gagacatatc agtcggggca taagcaggct caggatcagg ccgtgtctc gtatcgccat     1560 ctgcagtggc tgttggggca agttgagatt ctttag                                1596
```

<210> SEQ ID NO 81
<211> LENGTH: 1596
<212> TYPE: DNA
<213> ORGANISM: Aspergillus niger

<400> SEQUENCE: 81

```
atgctgtttc gcagtctgtt gtcgacggct gtcctagccg tctcgctgtg cacggataat       60
gcttcagctg ctaaacatgg tcgatttggc caaaaagctc gcgacgccat gaacatcgcg      120
aagcgttccg ctaacgccgt gaaacactcg ttgaagatcc ctgtcgagga ctatcagttc      180
ttgaacaaca agactaagcc ttaccgcgtg gaaagcctgc ctgatgttca cttcgatctg      240
ggcgagatgt attccggctt ggtccctatt gagaagggca acgtgtcacg gtccctttc      300 tttgtcttcc agcccactat tggcgagcct gtggatgaga tcaccatctg gctgaatggt      360
ggccctggtt gcagttccct tgaggccttt ctccaggaga atggtagatt cgtgtggcag      420
cctggaacct accagcctgt tgagaaccca tactcgtggg tgaatctcac caatgttctg      480
tgggttgacc aacctgtggg aacgggattc tctctggggtg tcccaaccgc tacgtccgag      540
gaggagattg ctgaagactt tgtgaagttc ttcaagaact ggcagcagat ctttgggatc      600
aaaaacttca agatctatgt tactggagaa agttatgcgg gccgttatgt tccttacata      660
```

-continued

```
tccgctgctt tcctagatca gaatgataca gaacacttca acctaaaagg tgcactggca      720
tatgatccct gtattggtca gtttgactac gtgcaggagg aagcacctgt tgttcccttt      780
gtccagaaga acaatgccct cttcaatttc aatgcaagct ttttggcgga actagagagc      840
atccatgagc aatgtggata caaggatttc atcgaccagt atctagtctt cccagcatcc      900
ggtgtccagc cgccaaaggc tatgaactgg agcgatccca cctgtgatgt ttatgacatc      960
gttaataacg ccgtcctgga tcccaacccg tgcttcaacc cctacgaaat caacgagatg     1020
tgccccattc tctgggacgt tcttggattc cccaccgaag tcgactatct ccctgcgggc     1080
gccagcatct actttgaccg cgctgatgtt aagcgtgcca tgcacgctcc taacatcacc     1140
tggtccgagt gctcggtgga gagcgtcttt gtcggggggcg acggcggtcc cgagcaggag     1200
ggcgactact cggccaaccc catcgagcat gtccttgcccc aggtcatcga aggcaccaac     1260
cgagttctga tcggtaacgg tgattatgac atggtcatcc ttaccaacgg caccttctc     1320
tcgatccaga acatgacatg gaatggaaag cttggattcg cacggccccc cagcacccc     1380
atcaacatcg acatccctga cctgatgtac aatgaagtgt tcattgagaa cggctatgac     1440
ccacaaggtg gtcagggtgt catgggcatc cagcactatg agcgtggtct tatgtgggct     1500
gagaccttcc agagcggaca catgcagccc caattccaac ccagagtgtc ataccgtcac     1560
cttgagtggc tgcttggccg gcgggatacc ctgtaa                              1596
```

<210> SEQ ID NO 82
<211> LENGTH: 1479
<212> TYPE: DNA
<213> ORGANISM: Aspergillus niger

<400> SEQUENCE: 82

```
atgaaaggtg cggcgctaat tcctcttgcg gcgggcattc cttttgccca tggcctgtct       60
ctccataaac gcgacgggcc tgccgtcgtt cgtatgccca ttgagcgcag gagcgcccag      120
tccttgcaga aacgagattc tacggtcggt gtgactttgc agaactggga tgcgacctat      180
tacgcagtca acctgacgtt aggaacacct gcgcaaaagg tatcattagc tttggacact      240
ggcagcagcg acctctgggt gaacaccggc aactcaactt actgctcaat cgacaatcta      300
tgcacccctt atggcttgta caatgccagc gaatcgtcta ctgtaaagac cgtgggcaca      360
cacctcaacg atacatatgc ggacggcaca aaccttacg gtcccttatgt gaccgataag      420
ctcacgatcg gcaacacaac aatcgataat atgcagtttg ggatcgccga gtcaacgact      480
agtaaacgcg ggatcgccgg cgtcggttac aagatttcga cctaccaagc cgagcatgac      540
gacaaagtct acgccaacct ccctcaggcc ctcgtcgaca gcggtgccat taagtctgct      600
gcgtacagca tatggctaga tagtttggag gcgtcgactg gctccctcct tttcggaggt      660
gtcaatacag ccaagtacaa gggcgatctg cagactcttc cgatcattcc tgtgtatggc      720
aaatactact ccctcgccat cgcccttacg gagctcagcg ttgcgaccga ctccaactcc      780
agtagcttca ccgacagtct cccccctctct gtgtcactcg atactggcac caccatgacg      840
gcactgccca gcgacctggt caacaaggtc tacgatgcgc tcaacgcaac ctacgacaag      900
acatacgaca tggcctacat cgactgcgac actagagagg cggattacaa tgtaacatac      960
agtttctccg gggcaacgat caccgtgagc atgagtgagc tgattatccc cgcaacggag     1020
ccggggtggc ccgacaacac gtgtgtcttg ggcctcgtgc ctagccagcc gggcgtgaac     1080
ctgctcggtg atacattcct gcgcagtgcg tacgtcgtgt atgatctcga gaacaacgaa     1140
atctctctcg ccaataccaa tttcaatcca ggcgacgatg atatcctcga aatcggaacg     1200
```

|  |  |
|---|---|
| ggaacgtctg ctgtgccagg agccacaccg gttccctctg ctgtctcttc tgcaactgga | 1260 |
| aatggactga tctcgtctgg caccgcagtg cccacgctgt cgggtgtcac aataactgct | 1320 |
| acagccacag caaccggctc aaccggcact ggctctagcg gtggttcgtc ggctgaagcc | 1380 |
| acgagtactt cctcggaggg cgctgcggcg caagctacga gcaacccgat gaacctgctc | 1440 |
| ccaggacttg cgggtatcgg cctacttctc gctctgtaa | 1479 |

<210> SEQ ID NO 83
<211> LENGTH: 1836
<212> TYPE: DNA
<213> ORGANISM: Aspergillus niger

<400> SEQUENCE: 83

|  |  |
|---|---|
| atgctgtcgt ctctccttag ccagggagca gccgtatccc tcgcggtgtt gtcgctgctc | 60 |
| ccttcgcctg tagccgcgga gatcttcgaa aagctatccg cgtccccaa tggctggaga | 120 |
| tacgccaaca atcctcaagg caacgaggtc attcgcttgc aaatcgccct tcagcagcat | 180 |
| gatgtcgctg gtttcgaaca agccgtgatg gatatgtcca ccccgggaca cgccgactat | 240 |
| ggaaagcatt tccgcaccca cgatgagatg aagcgcatgt tgctcccag cgagactgcc | 300 |
| gtcgactcag tccgcgactg gctggaatcc gccggtgtcc acaatatcca ggtcgacgcc | 360 |
| gactgggtca agttccatac caccgtaaac aaggccaatg ccctgctgga tgccgacttc | 420 |
| aagtggtatg tcagcgacgc caagcatatt cgtcgtctgc gcaccctgca atactccatc | 480 |
| cccgacgccc tggtctcgca catcaacatg atccagccca ccaccgcctt tggccagatc | 540 |
| cagcccaacc gtgccaccat gcgcagcaag cccaagcacg ccgatgagac attcctcacc | 600 |
| gcagccaccc tggcccagaa cacctcccac tgcgactcca tcatcacacc gcactgtctg | 660 |
| aagcagctgt acaacatcgg tgactaccag gccgatccca gtccggcag caagatcggc | 720 |
| tttgccagct accttgagga atacgcccgg tatgccgatc tcgagaggtt cgagcagcac | 780 |
| ctggctccca atgccatcgg ccagaacttc agcgtcgtcc aattcaacgg cggcctcaac | 840 |
| gatcagcttt catcgagtga cagcggcgaa gccaacctcg acctgcagta catcctgggc | 900 |
| gtcagcgctc ccgtccccat caccgagtac agcaccggcg gacgcggcga actagtcccc | 960 |
| gacctgagct cccccgaccc caacgacaac agcaacgagc cctaccttga cttccttcag | 1020 |
| ggaatcctca gcttaacaa ctccgacctc ccacaagtca tctctacctc ctacggtgaa | 1080 |
| gacgaacaga ctatcccccgt cccctacgcc cgcaccgtct gcaacctcta cgcccaactc | 1140 |
| ggcagccgcg gcgtctctgt aatcttctcc agcggcgact ccggcgtcgg cgccgcctgc | 1200 |
| ctcaccaacg acggcaccaa ccgcacgcac ttccctcctc aattccccgc ctcctgcccc | 1260 |
| tgggtaacct ccgtcggcgc aacctccaag acctccccg agcaagccgt ctccttctcc | 1320 |
| tccggcggct tctccgacct ctggccccgc cctcctacc aacacgccgc cgtgcaaacc | 1380 |
| tacctcacca agcacctggg caacaagttc tcggggcttt tcaacgcctc cggccgcgcc | 1440 |
| ttccccgacg tctccgcgca gggcgtcaac tacgctgttt acgacaaggg catgcttggc | 1500 |
| cagttcgacg ggacgagttg ctccgcgccg acgttcagtg gcgtcatcgc gttgttgaac | 1560 |
| gatgcgagac tgagggccgg gttgcctgtg atggggttct tgaatccgtt cctgtatggt | 1620 |
| gtcggaagtg agaagggtgc gttgaatgat attgtgaacg gcgggagtgt gggttgtgat | 1680 |
| gggaggaatc ggttcggggg cacgcctaat ggtagtcctg ttgtgccgtt tgctagttgg | 1740 |
| aatgccacga ccgggtggga tcctgtgtcg gggttgggaa cgccggattt tgcgaagttg | 1800 |

-continued

| | |
|---|---|
| aaagggtgg cgttgggtga ggagggtggt aattaa | 1836 |

<210> SEQ ID NO 84
<211> LENGTH: 1437
<212> TYPE: DNA
<213> ORGANISM: Aspergillus niger

<400> SEQUENCE: 84

| | |
|---|---|
| atgtggctct ttctcgtgtg cagtatcctg ctgccacttg gagtagtcaa cgcacagtct | 60 |
| caatacttca acaacaaaac caaagaattc gtcgtcaatg gctctgctat tccttttgtc | 120 |
| gatttcgaca ttggcgagtc ctatgcgggc tacctaccca cacgccttc tggaatctcg | 180 |
| agtctatact tctggttctt tccatcttct gatcctgatg cgtctgatga gatcaccgtc | 240 |
| tggctgaatg gcgccccagg atgcagctct ctggcaggca tcatgctcga gaacggcccc | 300 |
| tttctatggc aacctggtac ctaccgaccc gtgcgcaacc cttatgcctg aacaaacctc | 360 |
| acaaatatgg tgtacattga tcagcctgct ggaacgggat tctcgcttgg cccgtctacg | 420 |
| gtggtctcag aatttgatgt agccagacag tttatggact tctggaggcg gttcatgaaa | 480 |
| acattcgatc tgcagaatcg aaagatatat ctcactggcg agagctatgc gggccagtac | 540 |
| atcccataca tcgcgtcgca gatgcttgac caggatgatg atgagtattt ccggttgcc | 600 |
| ggcatccaga tcaatgatcc ctacatcaat gagctgccag ttttgcaaga tgttgcgacc | 660 |
| gtcaatcagc accgctccct ctttcccttt aatgacacct tcatgagtca aatcaccaag | 720 |
| cttccgacg attgtggcta cacttcgttt cttgacgatg cccttacctt tccacccgt | 780 |
| tctcaattcc catcagtgcc ctataatgct agctgcaaca tctgggatat cataaacaac | 840 |
| gcttctctag ctctcaaccc atgcttcaac cgctaccata tccccgacgc ctgccccacc | 900 |
| ccctggaacc cagtcggcgg ccccatcgtt ggacttggtc cgaccaacta cttcaaccgc | 960 |
| agtgacgtcc agaaagccat caacgcgtac ccaacggact atttcgtctg caaggatgga | 1020 |
| atcttcccga cggccaacgg actggacaca tcccctccaa gctccctggg accgctgccg | 1080 |
| cgcgtcatcg aacagaccaa caataccatc attgcgcacg gcctgatgga tttcgagctg | 1140 |
| ctggcgcagg gaaccctgat cagtatccag aatatgacct ggaatgggaa gcaggggttc | 1200 |
| gagcgggagc cggtggagcc gttgttcgtg ccgtatggtg gatcatcggg aggaggcgtg | 1260 |
| ctgggaacgg cacatacaga gcgtggattg acattttcga cagtatttag ttcaggacat | 1320 |
| gaaatcccgg aatatgcacc gggggcggca tatcgccagc tggagttttt gctggggagg | 1380 |
| gttgcgaatc tgtcgacaat tattgagcag gtgcagataa cagagcagaa tggttga | 1437 |

<210> SEQ ID NO 85
<211> LENGTH: 633
<212> TYPE: DNA
<213> ORGANISM: Aspergillus niger

<400> SEQUENCE: 85

| | |
|---|---|
| atgtccaaac tctccgctgc tatctccaag ctctccctct ccaccatagc caccactctg | 60 |
| ctcctcctta cccccccaac caccgcctac ttctacaaat atcccgccct cttcgtctac | 120 |
| aaagacacca actgcaccga tatctccttc tcacttgtct accctcct gggtaactgc | 180 |
| aacggcggat actacgacta cgcgggctca ttccagatgt tcaatatcga tgctgcgtat | 240 |
| acctgtaatg gcagtgactc gacactgatg tttgagatgt ataatagctc cggctcggat | 300 |
| tgtgagatg agagtgattt gttgtttaga cagccggtga cggaggagtg tactgttgcg | 360 |
| gatgtggaga gtccggggcc gttggagatg ccggtttggt ttgagttggg gtcactattg | 420 |

```
gggaattgtg gtgggatggc tggtactatg ttgttcggtg tggggattct tgagggtggg    480
ttagagacta aattatactg gaaatgttat tcatcaaggc tgaatacaag tgtaaccgtg    540
cacagattat ctttgatact gtctatgggc tgtacgagcg tctctgactc ctacaatgag    600
ttagcggctg cacattacta tgaggacctg tga                                  633
```

<210> SEQ ID NO 86
<211> LENGTH: 1827
<212> TYPE: DNA
<213> ORGANISM: Aspergillus niger

<400> SEQUENCE: 86

```
atgcgtcacc tcttatcact gctggtgctt ctgatcgcat cggccgccct ggtctccgcc     60
gtccccgccg gctccattat cactccacaa ccacccgtcg agcccgttca ccttctctct    120
tcccagccct ctgatccccg aaggccatgg atccgcctcc gtgactggat catcgagtcc    180
atatggggca tcgaaaaacc cgcatctcgt cgattcccac tcaacgattc cccgcgcaat    240
cgctctcctc cctcccggat tctggcgcgc tacggtagtg acgtcgtact tcgtttcagc    300
ctgcgcaatc acgatgaggc cgaggcattg gcccaggctg cagacattct attcctggac    360
gtatgggcgt ctactccagc attcgtagat atccgactgg ccgaggaagt caccgcatat    420
actcccctaa tagacaacct ggcagagaga atctatacga cctatccatc taaaaagccg    480
ataggacttg aaggacaatc tggatttgcg tcctcgagtc gacctgcgcc aaagttcggt    540 gaccttttt tccacgagta tcagcctttg tccgtcatta tccctggat gcggctgctg    600 gcttccatgt ttccatccca tgtgcgcatg attagcgttg gagtatctta cgagggtcgc    660
gaaattcccg ccctccgact gagcgcaggc agctccaccg cggcgtcagg ccctcgtaaa    720
acaatcatcg ttacgggtgg tagccatgcc cgcgaatgga ttggcacctc aaccgtgaac    780
catgtaatgt acacgctcat taccaagtat ggcaaatcca aggccgttac ccgccttcta    840
caggacttcg actggatcat gatccccacg atcaatcccg acggctatgt ttatacctgg    900
gagacggacc gactatggcg caagaatcga cagcggacca gcctacgctt ctgtcccgga    960
atcgatcttg accgcgcctg gggcttcgaa tgggacggcg tcggacccg cgctaaccct   1020 tgttcagaaa actatgctgg agacgagccc ttcgaggaa tggaagcaca acaattagca   1080
cagtgggcgc tcaacgagac acaaaacaac aatgccgaca tcgtgagctt ccttgacctt   1140
cactcttact ctcaaacaat tctctacccc ttctcctact cctgctcctc gatccctcca   1200
acgctcgaga gcctggaaga gctaggcctt ggcctagcca aggccattcg gtacgcgact   1260
cacgaaatct acgatgtcac ttctgcctgc gaaggcatcg tcacggccag tgcggcagat   1320
aacaaccccg gcggttctt ccccattggt ggcaactccg gtggcagtgc gttggactgg   1380
ttttaccacc aagtgcacgc gacttattca taccagatca agcttcgtga tcgcggaagc   1440
tacgggttcc tccttccgtc tgaacacatc atccccaccg gcaaggagat ctacaatgtt   1500
gttctgaaat tggatccttt cctcatcgga ggcgactcat ttgacgtcga ttgggaatca   1560
gaactcttcg atctgtcaaa ggacgaatcc gatctggata ccgctattc aaaatccaat   1620 gaccgctccc cggcgtatct acacaacgcc aacggccccc tgcccaacat tgacgaagac   1680
gaagataagg aatgggtaat ggtggaggaa gaagactaca cagacgatga cgacgacgat   1740
gatgatgatg atgaagaaga ggaagaggaa gaggaagata catattgggc caccgaacac   1800
acatacgaat ttcggcgacg acgctga                                       1827
```

<210> SEQ ID NO 87
<211> LENGTH: 1251
<212> TYPE: DNA
<213> ORGANISM: Aspergillus niger

<400> SEQUENCE: 87

| | | | | | |
|---|---|---|---|---|---|
| atggctttcc | tcaaacgcat | tctcccgctg | ctggccctca | tcttacctgc | agttttcagt | 60 |
| gccacagaac | aggtccctca | tccgaccatc | cagaccatcc | cggggaagta | cattgttact | 120 |
| ttcaagtccg | gcattgacaa | tgcgaagatt | gagtctcatg | ccgcatgggt | aacggagctc | 180 |
| cacaggcgca | gcttagaagg | ccgcagtaca | accgaagatg | accttcccgc | cgggatcgaa | 240 |
| agaacgtaca | gaattgccaa | ttttgctggg | tacgcggggt | ctttcgatga | gaaaactatc | 300 |
| gaggagatcc | gcaaacatga | ccatgtagct | tatgtgaaac | aagatcaggt | ctggtatctc | 360 |
| gatacgctag | ttaccgaaag | gcgagctcct | tggggactgg | ggagcatttc | tcaccgtggt | 420 |
| gggtctagca | ccgactacat | ctatgatgac | agcgctgggg | aggtacata | cgcttatgta | 480 |
| gtggacaccg | gcatcttggc | tacgcataat | gagtttggtg | tcgtgctag | cctggcatat | 540 |
| aatgctgcag | gggtgagca | cgttgatgat | gttggacatg | gtacacatgt | agcagggacc | 600 |
| atcgggggca | aaacatacgg | ggtttcgaaa | aacgctcacc | tactgtccgt | gaaggtgttt | 660 |
| gtaggtgaat | ccagctcgac | atcggtcatt | ctggatggct | tcaattgggc | cgccaatgat | 720 |
| attgtgagca | agaaccggac | cagtaaggcg | gcgataaata | tgagtcttgg | tggaggctac | 780 |
| tcctatgcgt | ttaacaatgc | agttgagaat | gcttttgacg | agggtgtgct | ctcttgtgtt | 840 |
| gccgctggaa | atgagaatag | agatgcagca | cggactagcc | cggcttctgc | acccgacgcc | 900 |
| attactgttg | ccgctatcaa | cagaagcaat | gcccgtgcgt | cattctcaaa | ctacggctct | 960 |
| gtggttgaca | ttttttgcccc | gggagagcaa | gtactttctg | catggaccgg | ctcgaactcg | 1020 |
| gccaccaaca | cgatctccgg | cacgtccatg | gctacacccc | atgtgacagg | tttgatcctc | 1080 |
| tatttgatgg | gcttgcggga | ccttgctacc | ccagcggctg | caacgaccga | gctcaagagg | 1140 |
| ttggctacgc | ggaatgctgt | caccaatgtg | gcgggtagcc | ccaatcttct | ggcctacaat | 1200 |
| ggaaacagcg | gcgtgtcaaa | agggggtagc | gatgatggag | atgaggacta | g | 1251 |

<210> SEQ ID NO 88
<211> LENGTH: 1368
<212> TYPE: DNA
<213> ORGANISM: Aspergillus niger

<400> SEQUENCE: 88

| | | | | | |
|---|---|---|---|---|---|
| atgatcaccc | ttttgtcggc | cctgttcggc | agcgtagtat | atgccgctac | gcagaccgtg | 60 |
| ttagggccag | aggggctga | tcccttacg | gtgtttcgca | gcccacactc | accggcattt | 120 |
| tcaattcgca | tccaggagca | gaatgactcg | atctgtgatg | ctcgttcacc | ccaattcact | 180 |
| ggttggctcg | acattggccc | gaagcatctt | ttctttttggt | attttgaaag | ccagaatgac | 240 |
| cccttccatg | atcccctaac | gctatggatg | actggggcc | aggagactc | gagtatgatt | 300 |
| ggacttttcg | aagaagttgg | cccttgccgg | attaatgagt | ttgggaatgg | aacagatcac | 360 |
| aaccccctggg | cctggaccaa | gaattcatca | cttctttttg | ttgaccagcc | agtcgatgtc | 420 |
| gggttttcct | atatcgatga | gggctatgag | ctgcctcatg | actcacgtga | agccgcggtg | 480 |
| gacatgcatc | ggttcttgcg | attattcata | tccgagattt | tccctcacaa | acagttcctt | 540 |
| cccgttcacc | tttccggtga | atcttacgca | ggccggtaca | ttccttatct | ggcgacccaa | 600 |
| atcttggaac | aaaatgaact | gtataaagat | agccccagga | taccgctgaa | atcgtgcttg | 660 |

-continued

```
gtgggtaacg gattcatgtc acccaaggat gcaacgttcg ggtattggga aacactgtgt      720
actactaact caggagtccc atctcctatc ttcaatgaaa ctaggtgcga tattatggcg      780
gcgaatatgc cgcactgtat ggatctatat gacatatgca ttcaacactc agaccccgcg      840
atatgtcatg cggcccagtc cgtctgttac gatagtgttg tagggctcat ggccaaatta      900
ttgctaagga tgacgacagt cactgcacct tgtgagatcg acgaaatgtg ctatatcgaa      960
gcggctctaa ttgagagata tttgaattcg ccatctgttt gggaggccct gtcgccaccg     1020
caacaggtta ccgaatacaa attcgtcgct acttctgtta ttgatgcatt tgctcaatca     1080
gcggacggca tggtgtcgag ctcgaagcag atcgctttct tactcgcaaa taatgttgac     1140
ttcttagcgt atcaaggcaa ccttgatctc gcctgtaata cggctggcaa cctacgttgg     1200
gcgaactcgc tttcttggaa aggccagaca gaatttaccg caaagccctt acttccgtgg     1260
gaaattcagg tttcggtcgg tgaagggacg acgaaacgt cacgctttgc ctttgtgact      1320
gtggacaacg ctggacacct gttgcgggac tcaaagattt caaactga                  1368
```

<210> SEQ ID NO 89
<211> LENGTH: 2376
<212> TYPE: DNA
<213> ORGANISM: Aspergillus niger

<400> SEQUENCE: 89

```
atgcggtttc tcacttattc cctgcccttc attgcaagtg ctatctcgct ctttggggtc       60
aatgtacaag ctcgatcaca agctccaagt gccatccgtc atgtgtcgac gcttgaccag      120
cccaccatca agacccctc acagcgggtc gatcaccttg accactttga catcaccttc       180
aatattcatg acaagcacca gcggataaag ctggagctgg agcccaacca tgacatcctg      240
gcggaagacg catccgtaca gtatctcgac gcggacggga acgtgcgacg cacgagccc      300 attgctccac atgagcataa ggtcttcaag ggaggagtc tactcgggcg aggaaaaggc       360
atgtgggatc cggtcggatg ggcgcggatc tacttgaagc aggatggctc agagccacta      420
tttgagggag tcttcagtat cgacggcgac aaccatcacg ttcagctgaa atcggcatac      480
atggagaaga aacgccccgt ggatgtcgac cttcccgact cagcgactga ctatatgatc      540
ttctaccggg attcggatat ggtgcgtcta catacggaac tcaagcggtc gtcgctcgga      600
tcgacctcgt gtcaagccga tcagctcggc ttcaacacta accccaacca ccctgtgcta      660
caaccgtatg gccaggcaga gaccgatacg tgggagcaa tttcattgaa ctccttgttt      720
ggactcaaca agcgccaatc cgatatcgga agtgtgtctg gcaatgcggg cggagtcaat      780
ctggcgtcga ccattggtga tacttcgggc tgtccgagta cgaagcaagt agctttgatt      840
ggtgttgcaa cggactgcgc ctttaccggc tcattcaaca acgagactgc cgccaaggaa      900
tgggtcatca gtactgtcaa cagcgcgtcc aatgtctacg aaaagtcctt caacattacg      960
attgggctgc ggaatctgac tatcaccgac agctcatgcc ccgacaaccc gcccgcggcc     1020
acggcatgga acatgccctg ctccagcggc aatctcacct cccgactgga tctgtttttcc    1080 aagtggcgcg gtgagcaatc ggatgacaat gcttattgga ccctgatgag cgattgcgcg    1140
acgggcaacg aggtcggact gtcatggctt ggccaactct gcaatagcga tgcttcttcg    1200
gatggctcga gcacggtcag tggaactaac gtcgtcgttc ggtcttccgg ctcggattgg   1260
cagatctttg ctcatgaatc tggccacacc tttggcgctg tccacgactg tgactcccag   1320
acctgcgcgg aggatctcga agcctcgtcc cagtgctgtc cgttgacctc gagcacctgc   1380
```

```
aacgccaacg ggaaatacat catgaatcct acaactggaa cagacatcac tgcgttctcg    1440
caatgcacta tcggaaatat atgcgcagcc ctgggccgca acagcgttaa gtccagttgt    1500
ctctccgcca accgcgacgt caccacctac actggcagcc agtgcggcaa cggaattgtc    1560
gagtccggcg aagactgcga ttgtggcggg gaagatggtt gcggcgacaa caactgctgc    1620
gacgcgaaga catgcaagtt caagtcggga gctgtgtgtg atgactccaa cgacagctgc    1680
tgttcaagct gccaattctc ctcagctggg acggtatgtc gtgccagtcg cggcgactgc    1740
gacgtggcag agacctgcag cggcaactcc agtacttgtc ctaccgactc gttcaagaag    1800
gacggcacga gctgcggcag cagtggctcg ggacttgcct cgctagtggc caatgcacc     1860 agccgcgact accagtgccg cagtgtgatg ggcagtctcc tccacagcaa cgacacctac    1920
gcctgttcct ccttcagttc ctcctgcgaa ctggtctgca cctccccgaa gatcggcacg    1980
tgctacagcg tcaaccaaaa cttcctcgac ggcactccct gcggtagtgg cggctactgc    2040
agcaacggcg actgcaaggg ccaaaacgtc gaatcctgga tcaagaacca caaggtatc    2100 gtcattggtg tcgcctgcgc cgtaggcgcc ctgatccttt tggccctgat gacctgcatc    2160
gtaaaccgct gtcgcgggc tcgcgcgcca aaacccgtcc cgcgtccagt gccttacggg     2220
ccgtggcccg gcgctaggcc tccccgccg ccgcccatga accagtggcc ggcgcgaggc     2280
tatcaaggct tagggaatga gccgccgccc ccgtatccag gtgtacctgg tcagccagta    2340
ccgcaacata tgcctcccca ggggcggtac gcttga                              2376

<210> SEQ ID NO 90
<211> LENGTH: 1446
<212> TYPE: DNA
<213> ORGANISM: Aspergillus niger

<400> SEQUENCE: 90
atgcgtttcc taagcagtgc agccctattc ggcctggcgt atgcctccac ccaggcggtc      60
ctccagccag aggaaccatc cgacttccgt acattccaca gcccatattc cccgcaccac     120
tcgatccgca tccgccagca gaatgaatca atctcgcgctg cccattccgc ccaatacacc    180
ggctggctcg acatcggccg taaacatctc ttcttctggt actttgagag ccagaatgac     240
cctgccaatg atcccctcac tctctggatg acaggagggc caggggggtc cagcatgatc     300
ggtctgtttg aagaagtcgg gccatgtctg atcaatgagt acggcaatgg cacttactac     360
aatccgtggg gctggtcccg gaactcctcc ctactatttg tcgatcagcc agtcgatgtg     420
ggattttcgt acgtcgatga aggagaggac ctgccgggcg attcgcatca agctgcaatt     480
gacatgcatc ggttcttgca gttgtttgtc tcggaggttt tccgcaatt gcagactctt     540 cccgttcatc tttctggtga atcgtatgct ggtcactatg tcccttacct cggcagtcag    600
atcgtccaac agaacaagct ctatcccact gagccccagg tccttctgca ctcatgtctc    660
gtaggcaacg gctactattc tcctcgcgac actacctacg ctactgggga aaccctctgc    720
accactaacc ctggagtccc cgagcccgtc ttcaaccgaa ccagatgcga catcatggcg    780
gccaatatgc cgcgatgcat ggaagtatcc gacgtatgtt tcggaacccc gatccagct     840 atctgccatg ctgcgtcgga ggtatgctac gagggcgtga tcggatggta tgatgacgag    900
tctggtgaag gtggtcggaa tagggtttgat ataaccgctc cctgcgccct tgacggcata    960
tgctacatcg aggccgctcg catcgagcag tacctgaaca cacccgcagt ttgggctgct   1020
ctatcaccac ccaaagaaat caaagaatac aaggttactt ccgacaatgt gtcgcgcgca    1080
ttcgatctca cttcagacac gatgacgcca gcgtctgagc aagtcgcgtt cctgcttgcg   1140
```

```
aatcaggtac atttcctggc gtatcagggc aatctcgatc tggcgtgtaa tacggcgggt    1200
aatctgcgct gggcgcattc tctgccatgg agaggtcagg tcgagttcgc gtcgaaggcg    1260
ctgcggccat ggagttgggt agatgtggta tctggaaaag gtggagtggc tggaacgacg    1320
aaggaggagt cgaggtttgc gctagttacg gttgatgggg cgggacattt tcttcctcaa    1380
gatagacctg atatcgcgtt ggatatgatg gtgcgctgga tatccggggc atcgtttact    1440
gagtga                                                               1446

<210> SEQ ID NO 91
<211> LENGTH: 960
<212> TYPE: DNA
<213> ORGANISM: Aspergillus niger

<400> SEQUENCE: 91
atgacattgt tactcaactt ccacgcgctc tttacagtca ttcttgttgc caatctttca     60
accagatgca gcgcactgct ctctggacgt gacttttgct ccacgccagc gcccggtgag    120
tcactccgag cggagcatag gaggctgtat gatgtacagg cccaacgtga cagcaccgcc    180
gaggagagcc gggaggtggt gccttggatt gaaatcgaga catggtttca tattgtaagc    240
agcaatgaag cagcaaacac agtatcagac gacatgatca ccagccagct ttcctatctt    300
cagaaggcat atgaaagtgc gactatcacc tatcggttgg agggcataac tcgtcacata    360
aatgactcgt gggcgcgaaa tgatgatgaa ctggggatga agaatgccct acgaagggggc    420 aattatggca cattaaatgt ctatttccaa acagatctcc aggcgtcatc cgacgagaat    480
tctcgggact atccaaatga cggtaaccga cgaacagatg tgtcagatca atcatcatca    540
actgtcctag gcttctgtac gttgcctgac ccgagtgtga attccagcag ccctcgttcc    600
agctacatca aggatggttg taacgtgtta gcggatatca tgccgggtgg tagtttagcg    660
cagtacaaca aaggcggcac agcggttcat gaggttggcc attggaatgg gctgctgcat    720
acgttcgaag gtgaatcgtg ctcccctgat aatgaaggag attacattga tgacaccccg    780
gagcaatctg agcctacgag cggatgtccc gccgagaaag attcatgccc cgatcttcct    840
ggccttgatg ctattcataa tttttatggac tattcatctg atgactgtta tgagagtttt    900
actccagatc aagcggagag aatgaggagt atgtggtccg ctatgcggga agggaagtga    960

<210> SEQ ID NO 92
<211> LENGTH: 1920
<212> TYPE: DNA
<213> ORGANISM: Aspergillus niger

<400> SEQUENCE: 92
atgcatgtct cactttttcct actcagtgtt acggcagcgt ttgccagccc aacacccccat     60 aactatgttg ttcatgagcg gcgcgatgca ttgcccagtg tctgggtaga agaaaagccgg    120 ctggacaaag gtgccctact gcctatgcgg atagggctta ctcagtccaa cctggatcgt    180
ggccatgatt tattgatgga ggtgtctcat ccacaatcgt ctcgctacgg aaagcatctc    240
tccagcgagg aggtgcacga cctatttgcc ccgtcgaatg aggccgtcga gaccgtccga    300
acctggattg aatccgccgg aattgctcca agccgcatct cgcaatcata caacaagcag    360
tggctacagt tcgatgccca tgcaagcgag gttgagcagc ttctgcagac ggaatactac    420
atctacaccc atgccgacac gggaagttcc catgtgacat gccacgagta ccatgtgccc    480
gaaaccatcc aatcgcacat cgactacata acaccaggag taaagatgct ggaagtgcgc    540
```

-continued

| | |
|---|---|
| ggcacgccct ccaaaaagag agatgcagag aagcgctctc ttggcagtct gcccccaatc | 600 |
| ttagcaccac taccaatcaa tatcacgaag attttcgacg acccgctagc acactgcgat | 660 |
| ctggcgtaa ccccagactg cattcgagcc atgtacaaca tcaccaaagg aacaacagcc | 720 |
| acaaagggca acgagctcgg catcttcgag gacctaggag acatctacag ccaagatgac | 780 |
| ctcaacctt tcttcgccaa cttttgccagc gacatcccac agggaaccca tccaaccctc | 840 |
| gactccatcg acggcgccac cgccccaaca gacgtcacca acgccggccc cgaatccgac | 900 |
| ctggacttcc aaatcgccta cccaatcatc tggccccaga acaccatcct ctaccaaaacc | 960 |
| gacgacccca actacgaaga caactacaac ttcaaaggac tcctcaacaa cttcctctac | 1020 |
| gccatcgacg gctcctattg caacgaaacc tcctctctag accctcaata cccagatccc | 1080 |
| tccccaggcg gctactcctc ccccaagcaa tgcggcgtct acaccccac aaacgtaatc | 1140 |
| tccatctcct acggcagccc cgaagccgac ctccccatcg cctaccaacg ccgccaatgc | 1200 |
| cacgagttca tgaaactcgg ccttcagggc atcagcgtgg tcgtcgcatc gggcgactcc | 1260 |
| ggcgtcgcct ccagcacggg cacctgcttt ggcgatgcag acaacgtctt cgtcccagat | 1320 |
| ttcccagcca catgtcccta tctcaccgca gtaggaggca catacctccc cctaggcgca | 1380 |
| gacgcagcca aggaccagga aatagcagtc acccgcttcc cctccggcgg cggcttcagc | 1440 |
| aatatctacg cccgaccatc ctaccagaac cactccgtgg agacctattt ctccactacc | 1500 |
| agcgacgacc tcacctaccc ttactactcc ggagtaaact acacagactt ctccaacaca | 1560 |
| gatgggtat acaaccgcat cggacgagga taccccgatg tttcagctat cgcagacaat | 1620 |
| atcatcatct acaaccaggg cgaagcgaca ctggtgggtg gtacgtctgc cgcggcgccg | 1680 |
| gcgttcgcgg ccatgttgac gcgcattaac gaggagaggc tggcgaaggg gaagtccacg | 1740 |
| gtggggtttg tgaacccggt gctgtatgaa catcctgagg cgtttaggga tgtgactgtt | 1800 |
| gggtcgaatc ccggggtgtg gactgatggg ttccccggttg ctgggggggtg ggatccggtg | 1860 |
| acgggggttgg ggacgccgcg gtttgaggat ttgatggata tatttgtggg tgatgattga | 1920 |

<210> SEQ ID NO 93
<211> LENGTH: 1116
<212> TYPE: DNA
<213> ORGANISM: Aspergillus niger

<400> SEQUENCE: 93

| | |
|---|---|
| atggcttcca agaccctcct actcattccg gcactggcca cagccgctct gggaagtgta | 60 |
| ttggacctag atatcaaggt agaccttgga accccaggtg gcccgtttga tttgatgtac | 120 |
| gacaccggat catcaacact ctgggtgctt gatagcaatt gtacagatga ttgtccaaat | 180 |
| gttagcgggt actcccgaca cggctacaac ctcacctcta ctggtgtcaa cttaggtgtc | 240 |
| aacgacagca ttgcttacag cggaggcact gtcagcggct tcactgccac ggatattctc | 300 |
| acggttcccg acaccaacgt ctcatatcgc cagagctttg ccgtcattac cgacagtacc | 360 |
| tgggcggcct tagcagccga tgggttcatc ggcctggcat cgtctaccat cgcattcaag | 420 |
| aatactacga cagccgtcga acagatgatg caggatggac ttttggatga acctcgattc | 480 |
| gccatatatg caggttcagg ggaatcgacc gtgaccaacc ctaatccgga gaataatggc | 540 |
| gtgttcacct ttggtggcag ccatgaggaa acctatgcgg acggggaact gcaatggatg | 600 |
| aagatgctct ccccctttga aatatacaaa acaaatctcc ttggaattca gggacacaac | 660 |
| aactccgatg ccaggccct gtcaagcgac gtcctgaact ggtacggcca gactaatcta | 720 |
| ttcaacgtcg caggtgcttc atcgataagc attcccaacg accagattga ggcgatgtat | 780 |

-continued

```
gccctaacgc ctttctcata cgctgacatc tcatctggat accgacctct gtgctccgat      840
ttcaatgata catggtcgat ctcttttaca atgggcttct atggcgaggg tgtcaccttc      900
aatttgaccg gtgatcagct ggccgtgcct ggctatcagg acgacgacca ctgcttccct      960
cccttcaatc catgggacag ctacaacacg attattggtc agcattggtt gagcaatttc     1020
tatgctgtat cgacttcgg atcattcgac ccggagacat acgatatacg tgttgggctg     1080
gctcctttga agaaggaata cctgccgagc gcttga                               1116
```

<210> SEQ ID NO 94
<211> LENGTH: 1245
<212> TYPE: DNA
<213> ORGANISM: Aspergillus niger

<400> SEQUENCE: 94

```
atgtttccct gctctcgtat ttggtctctg ctcgttgcag ccgccaccgc tagtgctgta       60
cccaccagtc tggccaccac gcacctgcaa tcggttgact tgcttctgac tcgcagttct      120
tacgggtttc ttactgacat agcccttgga actccgggtc agagcctgcc gtatctggtt      180
gactggacct ggaccggcca ctatgtggtg accaccttgt gctacaacga tcccaccgcc      240
acctacgatt gtctcaacgt cgatcagaaa attttcaacc agactttgtc atccactttt      300
atcaaccaaa ctgaccagta tggctatctt tactgggatc caaccactt ctactttacg      360 gagcccgcag cagccgatgt ggcgacggac atgctgcgca tcggtcccac cgcggtgaac      420
accaccatcc aagcagccaa tttcgtcttc aacgagacta ttagcgcatt ccctttctcg      480
ggagtatatg gactctcacc tgtttttcag ggtgacaatc gatccgtgca agcgtccttc      540
taccaaggat ggaggagcgg cgcctggcac tctccaattg tctcttttat ctactgccac      600
gacaatgcca ccaaagcggt atgcagtggt tacgacggcc ttcagacact aggcggatac      660
aacacctctc acgtccaggg agatatcacc tggtacgaca tcattgtcac ggaggcgatc      720
aacacgctgg actttgtcta tgcgccagcc gtgattaatt attgggcgtt gaacctcacg      780
cgcttctcta tcggagacga agagcaagag ctcaacaaga ccactactct ggatggaaag      840
caagccgccg ttgccgcgtt cgaccacgct tcgtatggtc gcggtgcccc agtgtctgtg      900
tacggttacc agcgtctagt cgagctggtc ggggcaaaag ccgtcacgct ttccgatcct      960
ccaaataacg gtgagcaggg attctatcag ttcgattgcc ggaactcgag tttactgcca     1020
ccgctgcggt atgagtttgc cgggtcagag cgggcgtggg agattgtgcc cgagaactat     1080
gtggaggtgc tggcgaacgg aaccaataag tgcacccta atgtacgcac cctgggagat     1140
ggagcgatgg taatgggaaa ttttggcgag acatttgcca ttgataagta tgtcatgttt     1200
gactttgaga agttgcaggt ggggattgca gacttcgcgt ggtaa                    1245
```

<210> SEQ ID NO 95
<211> LENGTH: 1443
<212> TYPE: DNA
<213> ORGANISM: Aspergillus niger

<400> SEQUENCE: 95

```
atgcatctcc cacagcgtct cgttacagca gcgtgtcttt gcgccagtgc cacggctttc       60
atcccataca ccatcaaact cgatacgtcg gacgacatct cagcccgtga ttcattagct      120
cgtcgtttcc tgccagtacc aaaaccaagc gatgctctag cagacgattc cacctcatct      180
gccagcgatg agtccctgtc actgaacatc aaaaggattc ccgttcgtcg tgacaatgat      240
```

-continued

| | |
|---|---|
| ttcaagattg tggtagcgga aactccctct tggtctaaca ccgccgctct cgatcaagat | 300 |
| ggtagcgaca tttcatacat ctctgtcgtc aacattgggt ctgatgagaa atctatgtac | 360 |
| atgttgctcg acacaggcgg ctctgatacc tgggttttcg gttccaactg cacgtccaca | 420 |
| ccctgcacga tgcacaatac cttcggttcg gacgattctt cgacccttga aatgacatcg | 480 |
| gaagagtgga gtgtgggcta tggaactggg tctgtcagcg gcttgctagg aaaagacaag | 540 |
| ctcacgattg caaatgtcac tgtacgcatg actttcggac ttgcttccaa cgcatcggat | 600 |
| aacttcgagt cgtacccaat ggacggcatt ctcggtctcg gtcgaaccaa cgatagttcc | 660 |
| tacgacaacc caacattcat ggatgccgtt gcagaaagta acgttttcaa gtcgaatatc | 720 |
| gttggcttcg ccctttcacg tagccccgcc aaggatggca cggtcagctt tggcactact | 780 |
| gacaaggaca agtacaccgg cgatatcacc tacaccgata ccgtcggatc ggacagctat | 840 |
| tggcgcattc ccgtggacga tgtctatgtt ggcggcactt catgcgattt ctccaacaaa | 900 |
| tcagccatca tcgataccgg aacttcttat gctatgctgc cttcaagcga ctcgaagacg | 960 |
| ctgcacagtc tcattcccgg cgccaaatct tcggggagct accacattat tccgtgcaac | 1020 |
| acaactacta agctacaagt ggcattctct ggtgtgaatt acaccatctc gccgaaggac | 1080 |
| tacgtgggag caacttcagg ttctggatgc gtttcgaaca ttatcagcta cgacttattt | 1140 |
| ggtgatgaca tctggctcct gggtgacacg tttctcaaaa atgtgtatgc tgtgtttgac | 1200 |
| tacgatgagt tacgggtcgg atttgcagag cgttcctcga acaccacctc tgcgtcgaac | 1260 |
| tctacgagct ctggaacaag cagcaccteg ggatccacta caacgggcag ctcaacgact | 1320 |
| acgacgagct ctgctagctc tagtagttca tctgatgctg aatcaggaag tagcatgacc | 1380 |
| attcccgctc ctcagtattt cttctctgct ctggcgattg cttccttcat gctttggctc | 1440 |
| tag | 1443 |

<210> SEQ ID NO 96
<211> LENGTH: 1401
<212> TYPE: DNA
<213> ORGANISM: Aspergillus niger

<400> SEQUENCE: 96

| | |
|---|---|
| atgacgtctt ctaccttgcg ccttgccgtc gcgttggctt tgtcaacttg cagcagtgcc | 60 |
| ctatcgagcc agcgagatga ttcacttgtg gttccatttc cttttggcaa tcttgaggat | 120 |
| gtccatattg ccaagcggga tagctccaag acagtagaag ctcctctagt gatatatggc | 180 |
| gacagctact ggatgaacgc ctcaattgga acccctgcgc agtcactaag tttcctacta | 240 |
| gatcttacgc gctcaagggt cgagcccgca tacaccctcg atgagaatta cgaatgttct | 300 |
| gacgatgaac tctgctccga attcggcttc tacaaaccca ccgattcatc cacttatcag | 360 |
| catctcacct acacagagag acacgatgca ggtgtcgact actcctacct tgataccata | 420 |
| actcttggag atcacgcaac cgacaatgtc ccactggaca tgtatctttt gtcctacatt | 480 |
| tcctacagct ccctcggtct ctcctccgtc aacaccagct cccctacat cctggtcgat | 540 |
| cgcggcctca ccacctcccc atccttcagc ctaatcggcg acaacggaaa caccaccacc | 600 |
| cccagcatca tctttggagg catcaacacc tccaaattca cgggcccct gcaagccttc | 660 |
| tccttcgcag accacagcat caccaacaat ccattcgtca ccgtcgaagc tgactccctc | 720 |
| caactaaccca ccaacaccaa cgataattcc acctacccta ttccctcctc caccccatg | 780 |
| atgctcagaa ccgaagaact aatcacctac ctccccaact cgaccgtcca atccctctac | 840 |
| accgacctta acataaccat ggacggcgtg atctccactt caagattcta cggggtccttt | 900 |

-continued

```
ccctgcgccc gccaggaaac cgaatctcac acaatctctc tagccatcgg caacatgacc      960
ttctctgtgt cctgggatga gctcttcgtc ccgtggacgc gtgacggact atgcaagttc     1020
ggcattcagg cccaggattc agattacaaa actcgtgcgg agctgggtgt tcccttctg     1080 agacggatgt atgtcgctgt ggattataat aatcagtttg tgggcgttgc gacgctgaag     1140
gatgatgatg atcagaatgg aggtgaagat gagattgtgg agattggcac tgggacggcg     1200
ttgcctagtg ctgtcgggga ttggccggct agtgttacgg cgtatacgcc tgctgcttct     1260
acagggacgg cggctgcgac gttgacattc acgacggcga cgtctagcgg gggaggtgtg     1320
gtgccgacgg gtctatcaga gttgggtagg gcgttttttgg tgccgggggt gctggggatg     1380
gctgttttgc aggctgttta g                                                1401
```

<210> SEQ ID NO 97
<211> LENGTH: 1632
<212> TYPE: DNA
<213> ORGANISM: Aspergillus niger

<400> SEQUENCE: 97

```
atgatgcgac cgatacttct cccctactg ggggtatttc tgcagacctc ctcggcatcc        60
aatccctatg taatgagctg gtcttcccaa gcctacggtc cagatggccc gtggcaggcc      120
gtatccatcg acgtgggcag caaccagcag acggtcgatc tttaccccgg agccaactat      180
gctagcacga tcctgatgag cactctctgc acgaacaaaa ccctgtcatc cacctgctac      240
gctgccgaag caggcacgtt caaccaaaac acctccacca ctgcctacac caccgccagc      300
tcgtgggaaa caacttactg ggccgtcgag ggtggaagcc aagaggctgt gctcggcgat      360
gaggtcacct taggggtcgtt tgtcgtcccc aatgtgagct cgaagccat ctaccagacc      420 taccagaccct atcccaatgg catcgcctat cctgtctcgg tcggcagtct ggccctgggg      480
ggtccgtact tgtcggatac cgtctccaat tcgacggtcc tgaacatgat cgcaggatgg      540
ctttactcgt ccaacgacat tccgtcctac tcgtacggca tgcatatcgg gtcggtagac      600
cccaaaatcc caggctccct gatcttgggg ggctacgata agagccgagt gatcggagac      660
gtgagtgcgc agggagtagt gtcttcgagt ggtctttttgg aacttgaatt aaaggatatt      720
gggctgggtg ttgcggcggg ttcctctccc ttcagcttca acaacgaaag tggcttgttt      780
ctccaaagca gtggttcggt tcaggccaag accgtccaga ttgatccaac caagccctac      840
atgtaccttc cccaggcgac atgcgatgcc atcacctcca ccatgccgat ctccttcaat      900
tccagcttgg ggctatactt ctgggacacc acgagcgatg attatctgaa tatcacgtct      960
tccgccgcat acctctcctt tgtgttcaac atgaatgggg tcaacaacaa gaacattacc     1020
atcaagattc ccttttccca gctcaatctt acgctgcaag aaccgctggt cgatcaaaac     1080
gtcacctact tcccgtgctt cctcactacc tccaccccgg tgctcggtcg agcctttctc     1140
cagtccgcat tcgttggggt gaactggttc aacgggaaca actcgggcac atggtttctg     1200
gcacaggccc ccgcccgggg ttacgccagt gaagacatca cccggatcgc agtgagtgac     1260
acgtcgcttt ctgcctctaa cggtacctgg gaagagacct gggctacgta ctgggcatc     1320 aaaacatccg acaactcgag cagctccaag agtggcctgt cttccggtgc caaaattgga     1380
attggcgtcg gggtgggtgt cggtggagca gtgttgatcg cagcaggtat agccattgca     1440
ttctgtcttc gccgtcgccg cggggcgagt caagaggcgg ctggagagca acggaggtcg     1500
atgtttaggg gcttttgcgga gctaccggga ggtgctcaca gtgaaccggc gaaggagttg     1560
```
gatacgaaga tgcataagcc gccgcaggaa atgatggctt cgcaggaggt agagcgatac   1620
gagctggggt ga                                                      1632

<210> SEQ ID NO 98
<211> LENGTH: 2535
<212> TYPE: DNA
<213> ORGANISM: Aspergillus niger

<400> SEQUENCE: 98
atgcgtctta caggtggtgt cgctgcggct ctgggcctct cgctgctgc ctccgcttct     60 ctccatcccc atcgttccta cgagacccat gattacttcg ctctacacct tgatgaatcc   120
acctcgccgg ccgacgtcgc ccaacgacta ggtgctcgcc acgaaggccc cgtcggagaa   180
ttaccctcac atcataccct ctcgataccc cgtgaaaaca gtgacgatgt ccatgcgctg   240
ctggatcaat tgcgcgatcg tcggaggtta cgccgccgct ccggagatga cgccgctgtc   300 cttcctcct tggtcgggcg agacgaaggt ctaggtggca ttctttggtc cgagaagctg   360
gctccccaga gaaagctcca taaaagagtg ccgccgacag gatatgctgc cagatcgccc   420
gtcaacactc agaatgaccc ccaagcgctt gcggcgcaga aacgcattgc ctcggaattg   480
ggcatcgcgg accccatctt cggcgaacaa tggcatttgt ataatactgt tcagttgggc   540
catgatctta acgtgacggg tatctggctg agggcgttta cagggcaggg tgtcacgacg   600
gctattgtcg atgacggttt ggacatgtac agcaacgatc ttaggccgaa ctattttgcg   660
gcgggttctt atgactataa cgacaaagta ccagagccga ggccgcgctt gagcgatgac   720
cgccacggta ctagatgcgc gggtgaaatc ggtgcggcga agaacgacgt gtgcggggtt   780
ggtgttgcgt atgatagtcg catcgctggt attcggattc tctccgcacc cattgatgac   840
actgatgagg ctgcggctat taactacgcc tatcaggaga acgatatcta ctcgtgttcc   900
tggggtccct atgacgatgg cgccacaatg gaagccccgg gcaccctgat caagcgggcc   960
atggtcaatg gtatccaaaa tggtcgtggt ggaaaaggct cggttttgt gtttgcggct  1020 ggtaacggtg ccattcatga cgataactgt aactttgacg gttacaccaa cagtatctac  1080
agcatcacgg tgggtgccat tgatcgggag ggtaaccatc ctccgtattc ggaatcctgc  1140
tcggcgcaac tggtggttgc ctacagcagc ggcgccagtg atgcaattca taccacggac  1200
gtcggcacag acaagtgctc gactacccat ggtggaactt cggcggccgg cccgctcgct  1260
gcgggaaccg tggcgctggc cctcagtgtg cggccggaac tcacctggcg tgacgttcag  1320
tatttgatga ttgaggcggc agtgcctgtt catgaagatg atggaagctg gcaggacact  1380
aagaacggga gaagttcag ccatgactgg ggatatggta aggtcgacac atatacgctg  1440
gtgaaacggg cagagacctg ggatctggtg aagcctcaag cctggctcca ttccccctgg  1500
cagcgggttg agcatgagat cccacagggc gagcagggct tggctagttc gtacgaggtg  1560
acggaggata tgttgaaggg agccaacctg aacggctgg agcatgtcac ggtcaccatg  1620
aatgttaacc acacccgccg aggcgatctc agcgtggagt tacggagccc tgacggtcgg  1680
gtcagtcacc tcagtacgcc ccggcggcca gataatcaag aggtgggcta tgttgactgg  1740
accttcatga gcgttgctca ctggggcgag tccgggattg gcaaatggac tgtgattgtc  1800
aaggacacca atgtcaacga gcatactggg caattcatcg attggcgact caacttgtgg  1860
ggcgaggcga ttgacggagc cgagcagcct ctccacccca tgcctactga acacgatgac  1920
gaccacagct atgaggaagg aaacgtggct accacgagca tcagcgccgt tcccacgaaa  1980
accgagctgc ctgacaagcc cactggtggc gttgatcgcc cggtgaacgt taagcctaca  2040

```
acatccgcga tgccgaccgg tagtcttaca gagcccatcg atgatgaaga actccagaag    2100 accctagta cagaggcaag ctcaacacca agtccttctc cgaccaccgc gtcagatagt    2160
atcctgcctt ccttcttccc cacgttcggt gcgtcgaagc ggacgcaagt ttggatctac    2220
gctgcgatcg gctccatcat tgtgttctgc attggcctgg gcgtctactt ccatgtgcag    2280
cgccgcaaac gtattcgcga cgacagccgg gatgactacg atttcgagat gatcgaggac    2340
gaggatgagc tacaggcaat aacggacgg tcgaaccgtt cacgtcgccg gggtggcgag    2400
ctgtacaatg cttttgcggg cgagagcgat gaggaaccgt tattcagtga tgaggatgat    2460
gaaccgtatc gggatcgggg gatcagcggc gaacaagaac gggagggcgc agatggagag    2520
cattctcgga gatga                                                    2535
```

<210> SEQ ID NO 99
<211> LENGTH: 450
<212> TYPE: DNA
<213> ORGANISM: Aspergillus niger

<400> SEQUENCE: 99

```
atgaagacct tctctaccgt cacctctctc ctcgctctct tctcctcggc tctggccgca     60
cccgttgaca cgcgtgaagc cgccggcacc accgtctctg tctcatacga cactgcctac    120
gatgtctctg gagcttcctt gaccaccgtc tcctgctcgg acggtgccaa cggcctgatc    180
aataagggct actccaactt cggctcccct ccgggcttcc ccaagattgg aggcgcccct    240
accattgcag gctggaactc tcccaactgc ggcaagtgct acgccctgac gtacaacggc    300
cagacagtca acattctggc cattgattcc gcacctggtg gcttcaacat cgctctggag    360
gccatgaaca ccctcaccaa caaccaggcc cagcagctgg gtcgtatcga agctacctat    420
actgaggtgg atgtcagtct ttgcgcataa                                    450
```

<210> SEQ ID NO 100
<211> LENGTH: 891
<212> TYPE: DNA
<213> ORGANISM: Aspergillus niger

<400> SEQUENCE: 100

```
atggctcaaa tattctggct ttcactcttc ctgcttgtct cttgggtcag agccgagtcc     60
aaccgcaccg aggtggacct gattttccca agaaatgata cctttgcgcc aatgcctttg    120
atgccggttg tattcgccgt tcaagcccct tccgtcgccc ataaagttaa tacatacatc    180
gagtacggct attacccagt aggccgtcca atgaaacag ttattggcca gaccgaccat    240
gtgtccgact caacaaacga aaccacttat ttcagtgtct ctggtatcgg cagaacgttc    300
aataccactg gcagctggga gctgttttgg aggctgagat ggaccaattg ttcaatctca    360
gaagactcga gatactacaa ccaatcctac ccctggatat cctccccata catcgacggt    420
agcctcaaca tcgacaaggt ctatgagggc tttcactaca cagcatacaa tgtcattgtc    480
gacagggtta ccttcagcac tcgcgaagat gctagccaac ccaacctcac gaccctcacc    540
aatagcgaga actgcgataa agtctcgtct cttgctctat tgtcgattgt ggactcccta    600
aggattccac cccagttacc ccaagaagat attgataccg tgtcaatgtg cccacaactc    660
gccgatgcca ggctaaattc aacttcaact tcaagcccct gcagcgttag cattagtccc    720
gaggttgagt ctaatatcct ggccaagatc gcagacaatg aatgcaataa cgcacttcac    780
cccgctgtga gttgcaccac tgaagaaacc aaggaaggca gcgcgagcag ccatgaccac    840
```

```
ggccatgctg tatggcttgt cattacgcta gcttttgcct tccttttcta a          891
```

<210> SEQ ID NO 101
<211> LENGTH: 933
<212> TYPE: DNA
<213> ORGANISM: Aspergillus niger

<400> SEQUENCE: 101

```
atgggtggtc gagatgtcgc cattctcagc aggcactttg ctgtgacatc ctcacaaagt   60
gttaatggcg ttgtctctgg gatgttccaa cacacagtca cctcttcacc cagcttcact  120
accaaccaat tcttcaagaa gaagttcact gctgcaattg ctactgccat tttcgcaagc  180
gttgccgtcg cagctcccca gcgtggcctc gaggcccgcc tcaaggcccg cggcagcagc  240
aagggatccc gacccctcca ggcagttgct agacctgcat caaccaagaa ccagaccaac  300
gttgagtaca gctccaactg gtccggtgcc gtgctggtgg agcctccctc tgctgcagcg  360
acctacactg cggtgaccgg caccttcact gtccctgagc ccaccggcaa ctctggaggc  420
agtcaggctg catctgcctg ggttggtatc gacggtgata cctatggaaa cgccattctt  480
cagaccggtg ttgacttcac cgtgaccgac ggagaggcct cgttcgatgc ctggtatgag  540
tggtacccgg attacgccta cgacttcagc ggcatcgaca tctcggcagg cgatgagatt  600
gttgccattg tggagtccta cacctcgact accggtattg ccattattga gaacaagagc  660
accggccaga aggtgtccaa ggagctgtcg tccagctcca gcctcggtgg acagaacgct  720
gagtggattg tggaagactt cgaggaaaat ggttcgctcg tcaacctggt ggactttggc  780
accgtcacct tcactggtgc tgttgccaag gcggcgggtg gtgagagtgt tggacttacc  840
gatgcgacca tcatcgagat tgaggagaat ggccaggttg tcactgacgt taccatcgac  900
agcgactctg aggtgaccat cacctacgag taa                               933
```

<210> SEQ ID NO 102
<211> LENGTH: 2046
<212> TYPE: DNA
<213> ORGANISM: Aspergillus niger

<400> SEQUENCE: 102

```
atgcgctgct ccctcatctc ccttctaggc ctggcggcca tcccggcccc tggaggctgt   60
cccttcgcac acactgcgaa catgggcatt gataacatgg tgaaagcaca cgctcacatg  120
tcccgaccgt tgattgcctc caagagcagc cctcaactgt tcctacctc ctctagcacc  180
ccttctgtcg ggcagaaagg cgtgttcatg atgaaccgca ttgctcctgg cacatccgag  240
ctctacattg ccaacacaga tggcagtaat gaacgcccac tcctctccaa ccccgtctac  300
gagtaccatg cctccttctc cccggatgta gaatggatcg ccttcaccag cgagcgcaat  360
ggtgacggta actctgacat ctaccgcgta cggaccaacg gctccgatct ccaggaattg  420
gttgccacgc ctgcagtgga agactccgtt gttatctctc caacggccg cctggcagcc  480
tacgtctcca ccgccaacaa catgaaggca acatctggaa tccttgatct tcagaccggc  540
gcgcagtgga acctcacaaa tacacccacc actgccgcca actcctccct catggagagc  600
tatctccgtc ctgcctggtc tcctgatggc gaatggatcg ccttctcttc ggaccgcaac  660
acccaatggg acgacacggc gtaccgacc ttcctcggcc gcacgggctg ggagacgacg  720
caagaactct ctctctacgc catccgtccc aatggctctg acttccgtca gatcatctcc  780
aagccatact actctcttgg atctccgaaa tggtcagcag acggtaaacg catcgtctac  840
tacgaaatga cccgggaaga cacctacaac gcccatcgtc cagaaaccat taccacagcc  900
```

-continued

| | |
|---|---|
| aactcgacga tcatgtccgt agacttcgag acaggcaccg atgtgcgcgt ggaagtcgcc | 960 |
| ggctccggtg tcaagcaatt ccctcagtac ctggacaaga acggcaccat cgcctacacc | 1020 |
| ctcaaaggcg gcaccagcga gggcttctac acgaccgcgg gactctacgt caacacgacc | 1080 |
| tcggcgaccc tcaggtcccc ggcgtggtct cccgacggca agcaagtagt ctacgaaaag | 1140 |
| agcacctgga gcatccgctc ggggtacaag cagctctaca gctgggacag tgactgggac | 1200 |
| taccgcttca cggacgtctt ccctcaggtc tcgcaccagg agcgcgtcgc catcacacag | 1260 |
| aagcagctgg gcaattcgtc catcgtgacg ttgaacacaa ccggaggcga cttgcaactc | 1320 |
| gtctacgacc ccagcacggc ggactttgtc agcgatgacg aaaccacagg actgagcgct | 1380 |
| taccagccca gctggtcacc ctgcggcgag tggctcgtct tcggcgtcgg attctggttc | 1440 |
| gagacgagag aagcctcagg cggatggatc gtgcgggcca ccgccaacgg gagctactcg | 1500 |
| gaggttctcg tgaacagcag ctactccatc accgaggatg gagccctgaa cagcgggttc | 1560 |
| ccgagtttct cgccggatgg caagaaagtg gtgtatcggg tttggggagc cgacactgca | 1620 |
| acctacggca acgccagcga gatcgggctg cgggtgctgg acctcgagac gcgaaagaca | 1680 |
| accgtcctaa ccacagaatg ggacaatctg ccccagttct ctcccgatgg agagctcatc | 1740 |
| ctattcacac gcaaaaccag cacgtacaat tacgatgtgt gcacgatccg gccggatggg | 1800 |
| acagatctcc gcgtgttgac gagcagcggt gctaatgatg cgcatgcggt ctggtcgcag | 1860 |
| gatggacgga ttatgtggtc taccggcatg tatgggttcc ggtttgagtg tgcgctgtat | 1920 |
| ggtgatacgt tccagccgta tgggcaggtt atgattatgg atgcggatgg gggaaataag | 1980 |
| aagttgatga ccaactcgat gtgggaagat tcgatgccgt tgttcttgcc gagggaggta | 2040 |
| ctttag | 2046 |

<210> SEQ ID NO 103
<211> LENGTH: 1875
<212> TYPE: DNA
<213> ORGANISM: Aspergillus niger

<400> SEQUENCE: 103

| | |
|---|---|
| atgcctccgg atgcaaaatc gcctggctac cagcctggta tggcagtatt accatctagg | 60 |
| ccacatcctg ccaagggaaa agccattcga ttcctccttt cccttgcatt ggtcgcgttt | 120 |
| gctattgttc aattatgtgg taatttccac aaaaatagga gcgttgaaca acagcttcag | 180 |
| agtcaaacac ttgatgatga gtcctttaaa tgggaagatg ttactcctac caagcaactc | 240 |
| gtataccatc catgctttgg tgatcacgaa tgcgctcgct tgtcgcttcc aatgaattgg | 300 |
| aaccgaactg atggtgaagg gtcaaaaatt gccttggcgg ttatcaaact tcctgccaag | 360 |
| gtacctgtca cagatgcgcg atatggtggt gccattcttc tgaatccagg tggtcctggt | 420 |
| ggatccggag tgagcatggt ctttagatac gggaaagcta tccagaccat cgtcgactcc | 480 |
| ccagaatcac caagtgcaga ttcagcgagc ggaaagtatt tcgatgttgt tagctttgat | 540 |
| ccaagagggg tcaacaacac aacacctaat ttttcctgct ccctgacccc gcgacgagg | 600 |
| aaagcgtggt tactgcagtc agaggcagag ggtctacttg ggagttctga aggagtcttc | 660 |
| gatactcgat gggcaaggta cgaagctttt gagcggctac tttcgacagc tccgaacact | 720 |
| ttcccagttg gaacaaacgt tgacgccgag aggataaggc tgcacaaccg ttggaaaaaa | 780 |
| ggggaggaga agctgctata ctgggctttt tcctatggga caatcctggg ttccacgttt | 840 |
| gcggctatgc agcctcatcg cataaaccgt gctgtcatag acggagtctg caacgctgat | 900 |

-continued

```
gattattacg ccggcaactg gcttaccaat ttacaagatt cggatgcagc attcaataaa      960
tttttcgagt actgctacac agctggccca tcagcgtgtc cgtttgcgct cggcggagat     1020
cccgaagatc tcaagtctcg ttatgagcag attttgacca atcttacatc gagccctatt     1080
gctgtgtctc cttctggaaa taggggccca gagataataa cctatagtga tgtgaagtca     1140
ttggtcgtgc aagctctcta tgtgcctttg aaattattcg atttggtggc taggctatta     1200
gctgagctcg agcaaggtaa cggctcttca ttcgctgact gaagtatga agccaaacaa      1260
tggccagtac cgcctccatg cgattcctcg tccacacaat acaaagtacc tggcgagagt     1320
gatcaggagg ccgggaggaa tatcctatgt acagatggtc caggcctcga cggaactgcc     1380
aaggaggatt ccggagcta ctggaatatg ctccggggac aaagtaaggc ggttggagat      1440
ttctggcccg aggttcgcat gtcgtgtgtc aaactggaga cgcgacctga gtggcgctat     1500
gatggtatgc gtatccaagg gcccttcgca ggcaatacat cgcacccatt gctgtttatc     1560
gggaatactt atgatccagt aacgccgcta cggaatgctc atacgatggc gcgtggattt     1620
cctgagtcaa tcgttctaga gcagaactct gtcggacatt gcacactgag tggcccatcc     1680
ttgtgtacag cgaaagcgat acgccagtat tccagaccg gagagttacc tgaccccgga     1740
actgtttgcc aggtagagga gcttcccttt cgtcttgccg gatatgagag aagtcaggtc     1800
atgtcgccag gtgacacaga attgatgtcc gccttgcatt cgctgagcga gttccgccat     1860
ctgctaggcg cgtga                                                     1875
```

<210> SEQ ID NO 104
<211> LENGTH: 1665
<212> TYPE: DNA
<213> ORGANISM: Aspergillus niger

<400> SEQUENCE: 104

```
atgttgagta gtctgctgct tgggggtctt ctgggtctag cgaccgctca atttcctccc      60
gagccggaag gcatcactgt gctcaagtcc aagttgcatg agaatgtgac tatttctttc     120
aaagagcctg gaatttgcga aactacgccg ggtgtccgat cttattcggg ctatgtacac     180
cttcccccg cctcaaccag cttcttttgg tttttcgaag cccgcaaaga tcccagcaat     240
gcgcctctgg ccatctggct caatggcggt ccgggtggct cgtcgctcat ggggctcctt     300
gaagaattag gtccttgttc cattgcatca gactccaaga ccacagtcct caatccttgg     360
agttggaaca atgaagtcaa tcttctattc cttgaccagc caactcaagt cggcttctca     420
tacgatgtcc caacaaatgg cactttgaca gctaatggga ctgcattcgc ggctcacgct     480
ctatggcatt tcgcgcaaac ctggtttttc gagttccac actacaagcc aaacgatgat      540
cgtgtcagtc tctgggctga agttacgga ggccattatg gtccaggcat ctttcggttc      600
ttccaacagc agaatgacaa aatcgcagag gggactgcag agacggtgc acagtatttg      660
catctcgaca cgcttggcat tgtgaacggc ttgatggata tggtgatcca agaagaggct     720
tacattactt ggccatacaa taacgtaagg ctcgcccctt cttcattcaa ctcgcgaggc     780
tttcgcgatc aggccctcgc ctgcgaagcg gctttgaaag aacgcgattc cggcttgcct      840
cactcaggga agaatatctc tgaaatttgc ggaggccttg cactagaatg gggagatggc     900
cccatcacct actaccacac cttcaatcgc gggtggtacg acatcgccca tcctaagaac     960
gacccattcc ctgccaagca catgctcgga tatttgacgc aggagtccgt ccttgccgct    1020
cttgggtac cagtcaattt cacatcgtct tcgagtgccg tggctacaca gttcataaaa     1080
acctttgata tcgtccacgg cggcttcctg gatgcaattg gctacctcct cgacagtggt     1140
```

-continued

```
gtaaaagtac acatgatgta cggagatcgt gattacgcct gcaattgggt cgggggcgaa    1200
aaagccagcc ttgcagttcc gtattccgt atcaccgaat ttgccgacac gggatactcc     1260
ccactcctta cgcccgacgg gatcagcgg atgacccgcc agctgggcaa ctacagcttc     1320
actcgcgtct ccaagccgg gcatgaggtc ccctcctacc agcctgtcgc ggcgtatgag     1380
atcttcatgc gggcgacatt caacaaagat atccctactg gcctcttggc tgttgatgac    1440
gaattccagt cggttggacc taaggatacg tggcatatca agaatatccc tcctattatg    1500
ccaaagccgc agtgctatgt tctaagtccc ggcacgtgta ccccggaggt ttgggagacc    1560
gttttgaacg gatccgcgac ggtaaaggat tggtatgtcg tggatgatag cgcgggtgtt    1620
gaggaccacg aggggttcag cattcttgga ggggatgagt tgtag                    1665
```

<210> SEQ ID NO 105
<211> LENGTH: 1737
<212> TYPE: DNA
<213> ORGANISM: Aspergillus niger

<400> SEQUENCE: 105

```
atgaccaggt ttcaattgct tcccttgtc gcagggctgc ttgcccctc aattgcagcc       60 cttagcatcc cttccccgca gcagatcctc gattctctca ctttcggaga gcacaccgac    120
ggcttttgtc cgctggcacc caaggttgag gttcctgacg atggtttctt ccagctctc     180 aagttcgtag aagatgcctc gttcaagtcg cgccaagtca atcgtctctc cagggcggtt    240
caagttccga ccgcaatcga cgactacatg aaggatccct acgacgaaaa gttcgcccca    300
ttcctcgact tccagaagct cctgcagacc ctctttcccc tcaccactc ctacgcccgc     360 gtagatcaca tcaaccgatt tggtctcgtc ttcacccctca atggcacaga tgactcgctc    420
aagcccctgc tattcaccgc gcaccaggac gtcgtgccca tcaacgaccc tgccgactgg    480
acctatcccc ccttcgatgg ccactacgac ggcgaatggc tctggggccg cggtgccagc    540
gactgcaaga acgtcctgat cggtctcatg tccgttgttg aagacctact ctcccaaaag    600
tgggagccaa cccgcacagt cgtcctggcc ttcggattcg acgaagaatc ccacggcttc    660
ctcggcgccg gatccatcgc caaattcctt gagaagaaat acggaccgga cagcttcgaa    720
tttatcctcg acgaaggcgg catgggcctc gaagttctag acgacaacaa caacggcgtc    780
gtctacgctc tccccggcgt tggcgaaaag ggcagcatcg acgttgtgct cactctggcc    840
gtaccaggcg gccacagctc cgtgcccct ccacacacgg gaatcggcat catcgccgag     900
atcatctatg agctagaacg ccaggacctc ttcgtccccg tcctagacac tcaccacccg    960
acccgcaaga tgctcgaatg ccaagtccgc cactcccct cgcaagtcga accgtggctc     1020
gcctccgccc tccaatcaag cgactacatc tccctagcag agaaactggc ctcctcgcgc    1080
ggcgacaagt tccgcttcat cctccaaacc tcccaagcag cggacatcat caacggcggc    1140
gtcaaatcca acgtctcccc cgagaaaatc aacgccctcg tcaactaccg catcgctctg    1200
caccaaaccc cagacgatat caagaaccgc gctgtggaga tcatctctcc catcgtcaag    1260
aaatataacc tctccctcac ggccttcccg gaaagcgaca ccgttgaccc ctccctcaac    1320
aaccacctca cccttactac cctcagcggc gccctcagtc ccgccccggt cagcccaacg    1380
gacatcgaca ccgacgccgt ctgggcccgt ttctcgggcg tcactcgctc ggtcttcgaa    1440
tctgtcccta gtctcgaggg cagaaaggtc gtcgtgagcg cgacatcat gaccgggaat     1500 acggatacga gattctactg ggctttgtcg aggaatattt acaggtggag tccgtcgagg    1560
```

-continued

| | |
|---|---|
| gcgggtaaag cgctgaatat tcatactgtt gatgagagga tcgatattga tattcatctt | 1620 |
| gaggcgatga tgctgtatta cgatcttatt cgctctttcg atggacggac cgattcatct | 1680 |
| gtcatttctg ctgcgtcggc agctgctgat gatgaacttg ctcacgacgt gctgtga | 1737 |

<210> SEQ ID NO 106
<211> LENGTH: 1371
<212> TYPE: DNA
<213> ORGANISM: Aspergillus niger

<400> SEQUENCE: 106

| | |
|---|---|
| atgaagagca ccactcttct ttccttggcc tgggctgccc agtccgccta ttccctctct | 60 |
| atccacgagc gcgatgaacc cgctactctt cagttcaact ttgaacgtcg tcagatcgcc | 120 |
| gaccggtccc gtcggaagcg atcgacggcc tcggccgacc tcgttaacct ggctacgaat | 180 |
| cttggctaca cgatgaacct cacactcggc actcccggcc aggaagtcag tgtgacgttg | 240 |
| gacaccggca gcagcgatct ctgggtcaat ggggccaact cgtccgtctg ccctgtacc | 300 |
| gattacggct cttacaactc aagcgcttct tccacctaca ccttcgtgaa cgatgagttt | 360 |
| tatatccagt atgtcgacgg cagtgaagcc acaggcgact atgtcaacga tactctaaag | 420 |
| ttctccaatg tgactttgac gaactttcaa tttgccgtcg catatgacgg cgactccgag | 480 |
| gaggggggtcc tcggtatcgg atacgccagc aatgaagcca gccaggccac cgtcggtggt | 540 |
| ggtgaataca ccaacttccc cgaagccctc gtcgatcaag gcgcgatcaa ctggccggcc | 600 |
| tacagtctat ggctcgatga cctcgacgaa ggaaaaggca ccattctgtt cggcggagtc | 660 |
| aacaccgcca agtactacgg cagcctgcag accctgccta tcgtctccat cgaagacatg | 720 |
| tacgtcgagt tcgcggtcaa cctgacggcc gtgcaccttg agaagaacgg caactccgtc | 780 |
| tcggtcaaca acagcgccac gcaattcccc atccccgccg tgctggacag cggcacggcc | 840 |
| ctgacctaca tcccgacctc cgccgcagcc agcatctacg aggccgtcgg tgcccaatac | 900 |
| ctgagcgagt acgggtacgg agtgatcgag tgcgacgtca aggacgaaga cttcaccttc | 960 |
| ctgttcgact ttggatcctt caacatgagc gttgacatca gcgagatgat cctcgaggcc | 1020 |
| agttccgaca tgaccgacat gaacgtttgt acgtttggcc tcgcagtgat cgaaaatgag | 1080 |
| gccctgctgg gcgatacctt cctgcgcagc gcatacgtcg tctacgatct cggaaacaac | 1140 |
| gagatctccc tggccaaggc caacttcaac cccggcgagg accacgtcct ggagatcggc | 1200 |
| accggatcgg atgccgtgcc caaggcgacg ggggcgacgg cgaccggcgc ggcagccaca | 1260 |
| tccacggcct cgagcgacaa gtcggacaag gagagttcgg ctacagtgcc gcgcagccag | 1320 |
| attgtctcgc tggtggcggg agtcttggtc ggtgttttct tggttctgta a | 1371 |

<210> SEQ ID NO 107
<211> LENGTH: 1995
<212> TYPE: DNA
<213> ORGANISM: Aspergillus niger

<400> SEQUENCE: 107

| | |
|---|---|
| atgttggtcc gtcagcttgc cctggctctg gccattgcgg ccttgtccga tgccattccg | 60 |
| acatccatca gcatgtcct gcacgagaaa cgtcacaagc ccgcatccga ctgggtgaag | 120 |
| ggtgcgcgcg ttgagagcga tgcggtcctg cctatgcgca ttggccttgc ccagaacaac | 180 |
| ttggacaagg gctatgactt cctgatggaa gtatcggacc ccaagtcttc caaatacggc | 240 |
| cagtactggt cggcagacga ggtgcacgac atcttttcgc catccgagga ggctgttgag | 300 |
| gcagtgagag aatggcttgt cgcctctggt atccatccgt cgcgggtggt gcactccgac | 360 |

```
aacaagggct ggctcgcgtt cgacgcctac gcccatgaag ccgagaggct gttcatgacg      420
gaattccacg agcacgagag cgaccgaagt gctaagatca gggttggatg cgaccaatac      480
cacgtccccg aacacatcca gaagcacatc gactacatta cccctggagt gaagctcacc      540
caggtcgtga agaggaccaa caaagtcaag cgtgcttccc aactagctca ctcttccaag      600
gccaagtctg ctgcccaagg tccgcagcca ctccccaaca aggccaagtt cctgcctgaa      660
gacctccgcg gctgcggtta acatcacc ccctcgtgta tcaaggcctt gtatcagatc       720
ccagacgcta agacggcgac cccgaacaac agcctgggtc tgtacgagca gggtgactac      780
tttgccaagt ccgacctcga cctcttctat aaggagtatg cgccgtgggt tccccagggt      840
acctatccca tcccagccct gattgatggc gccaattact cggttccttc ctacagctcc      900
ctgaacacgg gtgaatccga cattgacatt gacatggcct actccctgct ctaccctcag      960
caggtgaccc tctaccaggt tgacgaccag ctctacgaac cagtcgaggt cgacacaacc     1020
aatctgttca acaccttcct cgacgctctc gatggctcct actgcaccta cagcgcctac     1080
ggcgagaccg cgcgatgaccc gtcgatcgac cccgtatacc ccgacacccg cccggcggc     1140 tacaaaggaa agctccagtg cggcgtctat aagcccacta acgtaatcag cgcctcctac     1200
ggccaatccg aagccgacct ccccgtcagc tacaccaagc gccaatgcaa tgagttcatg     1260
aagctcggtc tacagggaca ctccatcctc ttcgcgtctg cgactacgg cgtcgcgtct      1320 ttcgccggcg acgtgacga gaacggctgt ctcggcccag agggcaagat cttcaacccc      1380
cagtacccct ccaactgccc ctacgtcacc tccgttggag gtaccatgct gtacggctac     1440
cagaccgtca acgacagcga gagcgtcatg cacgttaacc ttggcggaac cgcaagtaac     1500
ttcagcactt ctggtggctt ctcgaattac ttcccccaac cggcatatca gtttgctgct     1560
gtggagcaat acttccagtc tgcgaacctg tcgtatccgt attactcgga gtttgaggtc     1620
gatgttaaca cgaccaaggg tctctacaat aggcttggtc gtgcttatcc ggatgtctcg     1680
gcgaatggag cgcatttccg cgcttatatg gatggatacg attatcattg gtatggatcg     1740
agtttggcgt cgcctttgtt cgcgtcggtt cttactttgc tcaacgagga acgcttcgct     1800
atcggcaagg gccccgtggg attcgtgaat cccgtgcttt atgcttatcc gcaagtgctg     1860
aacgatatca ctaatggtac taatgctggg tgtggaactt atgggtttag tgctattgag     1920
ggatgggatc ccgctagtgg tttgggtacg cctaactacc cattgatgaa ggagctgttc     1980
ctctctttgc cttag                                                      1995
```

<210> SEQ ID NO 108
<211> LENGTH: 1563
<212> TYPE: DNA
<213> ORGANISM: Aspergillus niger

<400> SEQUENCE: 108

```
atgcgggtta ccacggcaat tgcttcatta ctactggtcg gctcggccac cagtctccaa       60
aatcctcatc gtcgggctgt tccgcccct ctctcgcatc gcagcgtagc gtctcgctcc       120
gtgcccgttg agcgccgaac caccgacttt gagtatttga ctaacaagac tgcaagattc      180
ctggtcaatg gcacaagcat ccccgaagtc gatttcgacg tcggcgagtc ctacgccggc      240
cttctcccca atacgcccac tggcaattct agcctattct tctggttctt cccctcgcaa      300
aatccagagg ccagcgatga gatcaccatc tggctcaacg gcggccccgg atgtagctcc      360
ctagacggcc tgcttcaaga gaacggccca ttcctctggc agcctggcac ttacaagccc      420
```

| | |
|---|---|
| gttcctaatc catactcatg gaccaacctc accaatgtgg tttacatcga ccaacccgcc | 480 |
| ggcacaggct tctccccggg cccctcgacc gtaaataacg aggaagacgt ggctgcccag | 540 |
| ttcaacagct ggttcaagca cttcgtcgac accttcgacc tgcacggccg caaggtctac | 600 |
| atcaccggtg aaagctacgc gggcatgtac gtcccctaca ttgccgatgc catgctgaac | 660 |
| gaggaggata caacctactt caacttgaag ggtatccaga tcaacgaccc gtccatcaac | 720 |
| agcgactcgg tcatgatgta ctcccccgcc gtccgccatc tgaaccacta caacaacatc | 780 |
| ttccagctaa actccacttt cctctcctac atcaacgcca agccgacaa gtgcggctac | 840 |
| aacgccttcc tcgacaaagc catcacctac ccacccccca gtcccttccc caccgccct | 900 |
| gaaatcaccg aagactgcca agtctgggac gaagtcgtca tggccgccta cgacatcaac | 960 |
| ccctgcttca attactacca cctgatcgac ttctgcccct acctctggga cgtgctcggc | 1020 |
| ttcccctccc tcgcctccgg cccaaacaac tacttcaacc gctccgacgt ccagaagatc | 1080 |
| ctgcacgtcc ctccaacgga ctactccgtg tgctcggaga ccgtcatctt cgcgaacggc | 1140 |
| gacggcagcg accccagctc ctggggtccc ctacccagcg tcatcgaacg cactaacaac | 1200 |
| actatcatcg ccacggctg gctcgattac ctcctcttct tgaacggctc gctcgccaca | 1260 |
| atccagaaca tgacctggaa cggtaagcaa gggttccagc gtcctcccgt ggaaccgctc | 1320 |
| ttcgtcccctt accattatgg tctggctgag ctgtactggg gcgatgagcc tgacccgtat | 1380 |
| aaccttgatg ctggcgctgg atacctgggt acagcgcata ccgagcgcgg gttgactttc | 1440 |
| agctcggtgt atttgtctgg tcatgaaatc ccgcagtatg ttcctggtgc ggcttaccgc | 1500 |
| cagttggagt tcctgctcgg taggattagt agtctttcgg cgaagggaa ctatacctct | 1560 |
| tga | 1563 |

<210> SEQ ID NO 109
<211> LENGTH: 1656
<212> TYPE: DNA
<213> ORGANISM: Aspergillus niger

<400> SEQUENCE: 109

| | |
|---|---|
| atgcgtggct ctcggttggt gctcttgttg cccctggctg cacttagttg tgctatgccc | 60 |
| gagaatgaat ggtcatctac gataagaagg cagttaccaa aagcgtccac tggcgtcaaa | 120 |
| tcgataaaaa ccccaaacaa tgtcactatc aggtataaag aaccaggaac cgaaggaatt | 180 |
| tgtgagacaa cacctggggt caaatcatac tccggatatg tcgatctttc gccagagtcg | 240 |
| catactttct tttggttttt cgagtcacgc cgtgaccccg aaaatgatcc agtgactctg | 300 |
| tggctgaatg gtggccctgg aagcgattcc ttgattgggc tttttgaaga gttgggtccg | 360 |
| tgtcacatca caccagagta cgaatcaatc atcaatcagt actcctggaa cgaggtcacc | 420 |
| aatcttcttt tcttgtctca gcccctcggt gtggggttct cttacagtga aaccgaggcc | 480 |
| gggtccttga atccatttac tggagccgtc gagaacgcct cctttgctgg agttcagggt | 540 |
| cgatacccag ttattgatgc cactatcatc gacacgaccg atatcgctgc acgcgcaacc | 600 |
| tgggaggtgc ttcagggctt cctcagtggc ctgtcgcagc tagattccga agtcaagtcc | 660 |
| aaggagttca acctgtggac agagagttac ggaggacact atggaccagc gttcttcaat | 720 |
| catttctacg agcaaaattc gaagatcgct agcggggaag tcaatggcgt ccaactgaat | 780 |
| tttaactccc tcgggattat caacggcatc attgatgccg cgattcaggc agactactac | 840 |
| gcagactttg ccgttaataa tacatatgga atcaaagctg tcaatgacac agtgtacaac | 900 |
| tatatgaagt tcgccaacac gatgccaaat ggatgccagg atcaggttgc ttcgtgtaaa | 960 |

```
ttgaccaata ggacctcgct ttctgattat gctatatgta cagaagcagc caatatgtgc   1020
agggacaatg tcgaagggcc ttactaccag tttggcggcc gtggcgtgta tgatattcgg   1080 caccccctaca atgacccgac cccgccgtcc tactttgttg actacctcaa gaaagactca   1140
gtcatggatg ctatcggcgt ggacattaac tacaccgagt ccagcggcga agtatattat   1200
gcattccagc agaccggcga ctttgtatgg ccgaatttca ttgaggacct cgaagagatc   1260
ctccaactcc ccgtacgcgt gtcgttgatc tacggcgatg ccgactatat ctgtaactgg   1320
ttcggcggtc aggccatctc actcgcagtt aactacccc atgcagctca gttccgtgca    1380
gcgggataca cacccatgac agtagatggg gtcgaatacg gtgagactcg cgagtatggc   1440 aactttttcgt tcacccgcgt atatcaggct gggcacgagg ttccatacta tcaaccgatc   1500
gcagcgttgc agctgttcaa ccgtacttta tttggatggg atattgcagc gggtacaact   1560
cagatttggc ccgaatatag caccaacggg acatcgcagg ctacacacac ggagtcgttc   1620
gtgccactgt ccacggcgtc gagtaccgtc aattag                             1656

<210> SEQ ID NO 110
<211> LENGTH: 1872
<212> TYPE: DNA
<213> ORGANISM: Aspergillus niger

<400> SEQUENCE: 110
atgccttttc ccttttcgtc cgctcttctc ggctatatct taactacgag cactactctc     60
acctccctag tcgcaggaca gtattaccct ccgacgcctg aggatctcac cgttattcat    120
tcggagatat tccctggtgc gaggatctcc tataagcaac ccctcggcat ctgcaccacc    180
accccctcca cccccagcta ctccggctac atccacctcc ccccacacac ccttaccaat    240
ctctccattc caggaatcag catctcgcaa ccatacccta tcaataccct tttctggtac    300
tttccttccc gccatcacca caacaatgat acatccccac tcaccatctg gatgaacggc    360
gggcccggcg gatcctccat gattgggcta tttcaagaga cgggccatg  tactgtgaat    420 acggactcga attccacggc ctataatccc tggtcgtgga atgagtacgt cgatatgttg    480
tatattgagc agccggtgca gacgggattt agttatgatg tgttgaggaa tgggacgtta    540
gatttgaatg agacgttttt ggtggggacg ttgccgagtc aggatgtgca tgggacggtg    600
aatgggacgg ttaatggggg aagggcgctt tgggttgcgt tgcaggtttg gttgggtgaa    660
ttctctgaat atgtttcttc tgttgacggg aatggtggtg gtgatgacag ggtgagtata    720
tggacggagt catatggggg acggtatgga ccggcataca cggcgctctt tcaggagatg    780
aatgagagga ttgagagtgg ggaggtaagc accgggaaga agatccattt ggatacgctg    840
ggcattatca atgggtgtgt ggatttactc gtgcaggtcc cttcgttccc tgagcaggcg    900
tataacaata cgtatgggat cgagggaatc aatcgcacgc tctacgaccg ggctatggat    960
agttggagca agcctggcgg gtgcagggat atgatcatcg agtgtcgcga tgctggcgag   1020
ctcggagatc ccctcatcat ctgcgaggag gcgtcggact actgttcgcg ggagatcaag   1080
agcctgtata cgaataccct cgggcgagga tactacgaca tagcgcattt cacgccggat   1140
gcagctctcg tgccttactt cgtcgggttc ttgaatcgcc catgggtgca aaaggcactt   1200
ggggtcccgg tgaactatac catgtcgtca gaggcagtgg ggaacagttt cgcctcgacg   1260
ggcgattatc cgcgaaatga tccccgcgga atgatcgggg atattggata cttgcttgac   1320
tccggtgtca aggtggctat ggtatatggg gaccgggact atgcttgtcc gtggcgcggc   1380
```

-continued

| | |
|---|---|
| gggggaagatg tcagcctgct ggtggagtac gaggatgcgg agaagttccg tgctgctggg | 1440 |
| tatgccgaag tgcagacgaa gtcatcctac gttggggtc tagtaaggca gtatgggaac | 1500 |
| ttctcgttca cgcgtgtctt tcaggcgggc catgaggtgc cattttatca gcccgaaacg | 1560 |
| gcgtatgaga tttttaatcg cgctcagttt aattgggata ttgcgacggg aggcatttct | 1620 |
| ctggagcaga atcagagcta tgggacggag ggaccgtcgt caacgtggca tatcaaaaac | 1680 |
| gaagtgccgg agagccctga ccgacgtgc tatttgttgg cgatggattc gacttgtacg | 1740 |
| gatgagcaga gggaacgggt gctgagtggg gatgcggtgg tgagggattg ggttgttgtt | 1800 |
| gatgatattg aggctgaaag ctcgttcagc ggtgttggtg atcagctggc acaggtccct | 1860 |
| ttgggacatt ga | 1872 |

<210> SEQ ID NO 111
<211> LENGTH: 1320
<212> TYPE: DNA
<213> ORGANISM: Aspergillus niger

<400> SEQUENCE: 111

| | |
|---|---|
| atgagaacat ctactctttt gctcctctgg agcactgcag agcagctttt ggcttctccg | 60 |
| tacccgcttc ccgactcgca agtagtcttc gccgcggatc acgaggtccc gaatacacag | 120 |
| ggcaaacacg tcgtggacga ggccatactc tcggcgctga acgctcattc tgacccagtc | 180 |
| gctgcaatgg tgtctctacg tcccgaaact gcagcttttc tagctgaacc tcgtctcttg | 240 |
| cacattcggg gcgaagagaa ggcggaatgg atgaccgaag cgacaagct gcgcctccgc | 300 |
| caacgcggaa agaagttcat ggacattacc gagcatcagg acttctacgc agagcaggcg | 360 |
| atggcttcgt ttgctgggga tcctaatctt cccaagctgt cccataaagg tctcgtcaag | 420 |
| ccgctgttct ctcaaatcga gacggaacga atgcacgata tcctgcagca catgacctcc | 480 |
| tactacaatc gatactacgg tgattatcac ggcgagatga gctccgaatg gctgcacgac | 540 |
| tacattgctg cgatcatctc caaatcgcct ttccgcaccc acatctctct cgaatacttc | 600 |
| acccatcctt tccgccaatc ttcaattatt gcacgcttcg agcctaaagt tcgcagcttc | 660 |
| tcccaacctt tgaccatcat tggtgcgcac caagattcgg ccaattatct ttttcccctg | 720 |
| ctgcccgccc ctggcgctga cgatgactgt ccggcactg tcagtatcct cgaggccttc | 780 |
| cgcgttctgg cggagaatgg ctacacgccc aaggacgggc ctgttgaatt ccattggtat | 840 |
| gcggctgaag aggccgggct actgggcagc caagccatcg cgcggtacaa gaaggagcag | 900 |
| ggcgctaaaa ttgatgccat gatggagttt gatatgacgg ctttattgc ccgtaacgcc | 960 |
| accgagacca tcgggttgt tgcaacccaa gccgatgcag cgctcacaaa ctgggccctc | 1020 |
| aacctcagtc gagaatacat ctccattccg gcggaagtct atgaacttgg ccccaacgct | 1080 |
| ggatccgact acatgtcata cactaagctc aactaccccg ctgcctttgc atccgaaggc | 1140 |
| aacccgctcg ctgggggctc tttcccgggt gaaatggacc cctacgtaca cggcatcaag | 1200 |
| gataggatgg acgttgacga tgaaacgggc gtcttctcta tcgaacacat ggctcggttc | 1260 |
| tccgagttgg ctatcgcatt tgttgtcgag caggctgggt gggataatac atggcggtag | 1320 |

<210> SEQ ID NO 112
<211> LENGTH: 1581
<212> TYPE: DNA
<213> ORGANISM: Aspergillus niger

<400> SEQUENCE: 112

| | |
|---|---|
| atgcgttcct tctccgttgt cgctgccgcg tcactggcgc tctcttgggc gtctctggcc | 60 |

```
caggctgctc gccccgtct tgtgcccaag cctatctctc ggccagcttc gagtaagtcg      120
gctgcgacta cgggtgaggc ttattttgag cagctgctgg accatcacaa cccggagaag      180
ggaacgtttt cccagcggta ctggtggagt actgaatact ggggtggacc tgggtcaccg      240
gtggtcctct ttaaccctgg agaggtctct gccgatggct atgagggta tctcaccaac       300 gatactctca ctggtgtcta tgcgcaggag atccagggtg ccgtcattct cattgaacac      360
cgctactggg gcgactcttc gccttatgag gtgctcaatg ccgaaacact tcagtatctc      420
acactggatc agtccattct ggacatgacc tacttcgccg agacggtaaa gctgcagttc      480
gataatagca gccgcagcaa tgcgcagaat gctccctggg tcatggtcgg tggctcatac      540
agcggtgcct tgacggcttg gaccgagtct atcgcgcctg aacgttctg ggcttaccat       600 gccaccagtg cgcctgtgga ggctatctat gacttttggc aatacttcta ccccattcag      660
caaggtatgg cacagaactg cagcaaggat gtgtctctgg tagccgagta tgtcgacaaa      720
attgggaaga atggaactgc caaggaacag caggagctca agaattgtt tggtctggga      780 gctgttgagc attacgatga ctttgccgct gtcctgccca acggaccgta cctctggcaa      840
gacaacgact ttgtcacagg atactcttcc ttcttccagt tctgtgatgc tgtcgagggt      900
gtcgaagccg gcgcggcagt gaccccggc cccgagggcg tcggacttga aaaggccctg       960
gccaactacg caaactggtt caattcaacc atactcccta actactgcgc aagctacggc     1020
tactggaccg acgaatggag cgtcgcctgt ttcgacagct ataatgcctc gagccccatc     1080
ttcaccgaca cctccgtggg taaccctgtc gaccgccaat gggaatggtt cctctgcaac     1140
gagcctttct tctggtggca ggacggtgcc cccgagggaa cctccactat tgtgccccgg     1200
ctcgtcagcg cctcctactg gcaacgccaa tgcccgctct acttccccga gttaacggc      1260 tacacgtacg gcagcgcgaa gggtaaaaac tccgctacgg tgaacagctg acgggtgga     1320 tgggatatga cccgcaacac gacgcggttg atctggacga acgggcaata tgaccctgg     1380 cgcgactccg gtgtgtcgag cactttccgg cccggtggtc cgctggttag cacggcgaac     1440
gaacccgtgc agattattcc gggcgggttc cattgctcgg acttgtatat ggaggattac     1500
tatgcgaatg agggtgtgag gaaggtggtt gataatgagg tgaagcagat taaggagtgg     1560
gtggaggagt attatgcttg a                                               1581
```

<210> SEQ ID NO 113
<211> LENGTH: 1275
<212> TYPE: DNA
<213> ORGANISM: Aspergillus niger

<400> SEQUENCE: 113

```
atgcagctcc tccagtccct cattgttgcc gtttgcttca gctacggcgt cctctcctta       60
ccccatggcc cgtcaaacca gcacaaagca cgttccttca aggttgaacg ggtccgtcgt      120
ggaaccggtg ctctgcatgg gcccgctgct ctccgcaaag cataccggaa gtacggaata      180
gctcccagca gtttcaacat cgatctggca gactttaaac ccattacgac aacccatgct      240
gctgctggga gcgagattgc agagcctgat cagactggcg ctgtcagtgc acttccgtc       300 gagaacgatg ccgagttcgt ttcgcctgtt cttattggcg ccagaagat cgtcatgaca       360 tttgacactg gttcttctga cttttgggtg ttcgatacga atctcaatga aaccttgacg      420
ggacacacgg agtacaaccc ttcgaactcc tcgaccttca agaagatgga cggatacacc      480
ttcgatgtct cgtatggtga cgactcgtac gcctctggcc ccgtcggaac ggataccgtc      540
```

-continued

```
aacattggcg gcgccattgt caaggagcaa gccttcggtg tccccgacca ggtatcccag    600
tcgttcatcg aggacacgaa ctccaacggc ctggtcgggt tgggcttttc ctccatcaac    660
accatcaaac cggaggcgca agacacgttc ttcgccaatg tcgcaccaag tctggacgag    720
cccgtcatga ccgcctcgct caaggctgac ggagtgggcg agtacgagtt cggcacgatc    780
gacaaagaca agtaccaggg caacattgcc aacatcagcg tggactcatc gaacggatac    840
tggcagttct ccactcccaa gtactccgtg gcagacggag agctgaagga cattggaagc    900
ttgaacacct cgatcgcgga caccggtacc tcccttatgc tgctggatga agacgtggtt    960
actgcctact atgcgcaagt tcccaactcg gtctacgtga gcagtgccgg tggttacatc   1020 taccctgca acaccactct tcccagcttc tcgcttgtcc tcggcgagtc gagcctggcc   1080
acgatccccg gtaacctgat caatttctcc aaggttggca ccaacaccac caccggacag   1140
gccttgtgct ttggcggcat tcaatccaac ggaaacacct cgctgcagat tctgggcgat   1200
attttcctga aggccttttt cgttgtcttc gacatgcgcg ccccctcgct tggtgttgcc   1260
tctcccaaga actag                                                    1275
```

<210> SEQ ID NO 114
<211> LENGTH: 1647
<212> TYPE: DNA
<213> ORGANISM: Aspergillus niger

<400> SEQUENCE: 114

```
atgcgcattg actccgcggc gctacatctg gtcccagtcc tcctgggcca ggtcggtgct     60
ttacaattac ccttggtcca agactccaat tcacagtggc agaaaccaaa tgcaggtgat    120
aaacccctaa ttagctctcc gttgcttcaa gagcaggtca aggcggagaa tctgttggac    180
agggcccggc agctttacaa gattgcggag ctgggagaag acgagtataa ccacccccact   240 cgcgtcattg gcagtaaagg tcaccttggc acgctcgact acatatactc caccctacc    300 gacctcggtg attattatac tgtcgtcaat cagtccttcc ctgccgtgag cggtaatgtc    360
ttcgagtctc gccttgtcct tggtcacgat gttcccaagt cagctacacc aatgggtctc    420
actcccccaa cgaggaataa ggagccggta tatggctccc tggttgctgt atccaacctc    480
gggtgtgagg cctcggacta ctcgtccaac ttgaaaggcg ccgttgcatt tatcagtcgg    540
ggaagctgtc cgttcgggac caagtctcaa ttagctggta agcgggagc tgttgctgcc     600 gtcatctaca caacgagcg gggtgaccta agcggaactc taggaaaccc aaccccccgat   660 catgttgcta cctttggtat ctcagacgag gatgctgccc cagtcctgga agttgaat     720 aaaggcgaga aggtggacgc tatcgcctac gttgatgcga tagtagagac catccacacc    780
accaatatca tcgcgcagac cacggatggt gacccgaaca attgtgtaat gctgggtggc    840
cacagtgaca gcgtggccga gggcccgggt atcaatgacg acgggtccgg tactctgacc    900
cttttggagc ttgccacatt gctcacccag ttccgtgtca caactgcgt gcgatttgct    960 tggtgggccg ccgaggagga aggccttctc ggatctgact attacgtgtc cgttctcaca   1020
ccggaagaga accgcaagat ccgcttgttc atggactacg acatgctcgg ctcgccgaac   1080
tttgcgtacc aagtttacaa tgccactaat gctgtgaacc ccgagggatc tgaggagctt   1140
cgtgatctgt acaccgactt ttacgaagat catgggttca actacacgta cattccgttt   1200
gacggacgca gcgactatga tgccttcatt cggcatggta tcccgggtgg tggcattgcc   1260
acgggagcag agggtatcaa gactgtcgag gaagcggaca tgtttggtgg ggttgctggc   1320
caatggtatg acccgtgtta ccatcagatc tgcgatacgg tggccaatgt gaacttgact   1380
```

-continued

```
gcgtgggagt ggaacaccaa gctcgttgcc cactccattg cgacttacgc caagtccttt    1440
gacggattcc cggaacggtc cgatgaaccc atcagccctg ctgcttttga ggaaccgaag    1500
taccatggcc acgcgttgca attacttcgc ggtaatacta cagggaccca gagcgtcctg    1560
tggggagccc aaatccagaa tggaacagct gcatcggtgc ttaatctatt gtccatacga    1620
cgcagaggca ctttcagtct aagctaa                                       1647
```

<210> SEQ ID NO 115
<211> LENGTH: 480
<212> TYPE: PRT
<213> ORGANISM: Aspergillus niger

<400> SEQUENCE: 115

```
Met His Leu Pro Gln Arg Leu Val Thr Ala Ala Cys Leu Cys Ala Ser
1               5                   10                  15

Ala Thr Ala Phe Ile Pro Tyr Thr Ile Lys Leu Asp Thr Ser Asp Asp
            20                  25                  30

Ile Ser Ala Arg Asp Ser Leu Ala Arg Arg Phe Leu Pro Val Pro Lys
        35                  40                  45

Pro Ser Asp Ala Leu Ala Asp Asp Ser Thr Ser Ala Ser Asp Glu
    50                  55                  60

Ser Leu Ser Leu Asn Ile Lys Arg Ile Pro Val Arg Arg Asp Asn Asp
65                  70                  75                  80

Phe Lys Ile Val Val Ala Glu Thr Pro Ser Trp Ser Asn Thr Ala Ala
                85                  90                  95

Leu Asp Gln Asp Gly Ser Asp Ile Ser Tyr Ile Ser Val Val Asn Ile
            100                 105                 110

Gly Ser Asp Glu Lys Ser Met Tyr Met Leu Leu Asp Thr Gly Gly Ser
        115                 120                 125

Asp Thr Trp Val Phe Gly Ser Asn Cys Thr Ser Thr Pro Cys Thr Met
    130                 135                 140

His Asn Thr Phe Gly Ser Asp Ser Ser Thr Leu Glu Met Thr Ser
145                 150                 155                 160

Glu Glu Trp Ser Val Gly Tyr Gly Thr Gly Ser Val Ser Gly Leu Leu
                165                 170                 175

Gly Lys Asp Lys Leu Thr Ile Ala Asn Val Thr Val Arg Met Thr Phe
            180                 185                 190

Gly Leu Ala Ser Asn Ala Ser Asp Asn Phe Glu Ser Tyr Pro Met Asp
        195                 200                 205

Gly Ile Leu Gly Leu Gly Arg Thr Asn Asp Ser Ser Tyr Asp Asn Pro
    210                 215                 220

Thr Phe Met Asp Ala Val Ala Glu Ser Asn Val Phe Lys Ser Asn Ile
225                 230                 235                 240

Val Gly Phe Ala Leu Ser Arg Ser Pro Ala Lys Asp Gly Thr Val Ser
                245                 250                 255

Phe Gly Thr Thr Asp Lys Asp Lys Tyr Thr Gly Asp Ile Thr Tyr Thr
            260                 265                 270

Asp Thr Val Gly Ser Asp Ser Tyr Trp Arg Ile Pro Val Asp Asp Val
        275                 280                 285

Tyr Val Gly Gly Thr Ser Cys Asp Phe Ser Asn Lys Ser Ala Ile Ile
    290                 295                 300

Asp Thr Gly Thr Ser Tyr Ala Met Leu Pro Ser Ser Asp Ser Lys Thr
305                 310                 315                 320
```

```
Leu His Ser Leu Ile Pro Gly Ala Lys Ser Gly Ser Tyr His Ile
            325                 330                 335

Ile Pro Cys Asn Thr Thr Lys Leu Gln Val Ala Phe Ser Gly Val
            340                 345                 350

Asn Tyr Thr Ile Ser Pro Lys Asp Tyr Val Gly Ala Thr Ser Gly Ser
            355                 360                 365

Gly Cys Val Ser Asn Ile Ile Ser Tyr Asp Leu Phe Gly Asp Asp Ile
    370                 375                 380

Trp Leu Leu Gly Asp Thr Phe Leu Lys Asn Val Tyr Ala Val Phe Asp
385                 390                 395                 400

Tyr Asp Glu Leu Arg Val Gly Phe Ala Glu Arg Ser Ser Asn Thr Thr
                405                 410                 415

Ser Ala Ser Asn Ser Thr Ser Ser Gly Thr Ser Ser Thr Ser Gly Ser
            420                 425                 430

Thr Thr Thr Gly Ser Ser Thr Thr Thr Ser Ser Ala Ser Ser Ser
            435                 440                 445

Ser Ser Ser Asp Ala Glu Ser Gly Ser Ser Met Thr Ile Pro Ala Pro
    450                 455                 460

Gln Tyr Phe Phe Ser Ala Leu Ala Ile Ala Ser Phe Met Leu Trp Leu
465                 470                 475                 480

<210> SEQ ID NO 116
<211> LENGTH: 1099
<212> TYPE: PRT
<213> ORGANISM: Aspergillus niger

<400> SEQUENCE: 116

Met Leu Arg Gly Leu Arg Asp Val Val Leu Gln Phe Ala Ile Pro
1               5                   10                  15

Leu Phe Leu Leu Leu His Phe Arg Leu Ser Leu Arg Gly Val Ile Thr
                20                  25                  30

Gly Phe Gly Ser Lys Ser His Phe Gln Arg Pro Leu Ser Lys Met Ser
            35                  40                  45

Ser Thr Gln Lys Ser His Phe Lys Leu Leu Gln Lys Phe Lys Pro Glu
    50                  55                  60

Tyr Ser Pro Ser Glu Phe Ala Gln Tyr Glu Ser Glu Arg Thr Gly Met
65                  70                  75                  80

Arg Val Val Val Ile Asp Gln Lys Gly Pro Lys Val Thr Gly Tyr Phe
                85                  90                  95

Val Leu Ala Thr Glu Ile Leu Asp Asp Ser Gly Ala Pro His Thr Leu
            100                 105                 110

Glu His Leu Cys Phe Met Gly Ser Arg Asn Tyr Arg Tyr Lys Gly Phe
        115                 120                 125

Leu Asp Lys Leu Ala Thr Arg Val Tyr Ser Ser Thr Asn Ala Trp Thr
    130                 135                 140

Ala Thr Asp His Thr Ala Tyr Thr Leu Asp Thr Ala Gly Trp Glu Gly
145                 150                 155                 160

Phe Ala Gln Ile Leu Pro Val Tyr Leu Glu His Val Ile Ala Pro Thr
                165                 170                 175

Leu Thr Asp Glu Gly Cys Tyr Thr Glu Val His His Ile Asp Gly Ala
            180                 185                 190

Gly Asp Asp Ala Gly Val Val Tyr Ser Glu Met Gln Gly Val Gln Asn
        195                 200                 205

Asn Ser Ala Glu Leu Ile Asp Leu Thr Ala Arg Arg Leu Thr Tyr Pro
    210                 215                 220
```

```
His Gly Val Gly Phe Arg Tyr Glu Thr Gly Met Met Glu Gln Leu
225                 230                 235                 240

Arg Val Leu Thr Ala Asp Arg Ile Arg Ala Phe His Arg Glu Met Tyr
            245                 250                 255

Gln Pro Lys Asn Leu Cys Leu Ile Ile Thr Gly Glu Val Asp His Gln
            260                 265                 270

Asn Met Leu Glu Thr Leu Asp Lys Phe Glu Asp Thr Ile Leu Asp Val
            275                 280                 285

Ile Pro Ser Pro Asp Ser Pro Phe Lys Arg Pro Trp Val Asp Ser Lys
290                 295                 300

Gln Ala Pro Pro Leu Glu Lys Ser Ile Val Gln Thr Val Glu Phe Pro
305                 310                 315                 320

Glu Glu Asp Glu Ser Phe Gly Glu Ile Glu Ile Arg Phe Leu Gly Pro
                325                 330                 335

Asp Cys Thr Asp Pro Val Gln Thr Gly Ala Val Asn Val Ala Leu Leu
                340                 345                 350

Tyr Leu Ala Gly Ser Ser Ala Ser Leu Leu Asp Asn Ile Leu Val Glu
            355                 360                 365

Lys Glu Gln Leu Ala Ser Ala Val Tyr Tyr Ala Thr Glu Asp His Pro
370                 375                 380

Ser Ile Glu Ile Arg Phe Thr Leu Thr Ser Val Glu Thr Glu Lys Leu
385                 390                 395                 400

Ala Lys Val Glu Gln Arg Phe Phe Glu Val Leu Lys Asp Ala Met Glu
                405                 410                 415

Lys Asp Leu Asp Met Arg Tyr Ile Lys Glu Cys Ile Asp Arg Gln Arg
            420                 425                 430

Arg Thr Trp Lys Phe Ser Thr Glu Ser Ser Ala Ser Ser Phe Ala Glu
            435                 440                 445

Tyr Val Ile Ser Asp Phe Leu Phe Gly Lys Arg Asp Gly Ser Thr Met
450                 455                 460

Leu Asp Val Ala Thr Leu Gln Glu Tyr Asp Val Leu Glu Lys Trp Ser
465                 470                 475                 480

Glu Glu Gln Trp Arg Ser Phe Ile Lys Thr Trp Ile Ser Asp Ala Asn
                485                 490                 495

His Val Thr Ile Leu Gly Val Pro Ser Val Lys Met Ser Asp Thr Leu
            500                 505                 510

Lys Lys Glu Glu Glu Ala Arg Val Ala Glu Gln Lys Lys Arg Leu Gly
            515                 520                 525

Asp Glu Gly Leu Lys Lys Leu Ala Asp Lys Leu Glu Lys Ala Lys Ala
530                 535                 540

Glu Asn Asp Lys Glu Ile Pro Lys Glu Met Leu Glu Arg Phe Gln Ile
545                 550                 555                 560

Pro Gly Ile Glu Ser Ile His Phe Val Asp Thr Thr Ala Arg Ser
                565                 570                 575

Gly Ala Ala Leu Asp Ala Gly Arg Pro Ser His Lys Ala Gln Lys Leu
            580                 585                 590

Val Asp Ala Asp Gly Ser Asp Leu Pro Leu Phe Ile His Phe Glu His
            595                 600                 605

Ile Pro Ser Ser Phe Val Gln Leu Ser Leu Leu Ile Ser Ala Gln Ala
            610                 615                 620

Val Pro Val Gln Leu Arg Pro Leu Leu Ser Val Tyr Thr Glu Ala Phe
625                 630                 635                 640
```

-continued

```
Phe Asn Leu Pro Val Asn Arg Asn Gly Glu Thr Ile Asn Phe Glu Gln
                645                 650                 655

Val Val Val Glu Leu Arg Asp Thr Val Gly Tyr Ser Met Glu Gly
            660                 665                 670

Ala Arg Ser Leu Gly Asn Ser Glu Met Leu Arg Ile Ser Phe Gln Val
            675                 680                 685

Glu Leu Glu Lys Tyr His Thr Ala Ile Ala Trp Ile Gln Glu Leu Ser
            690                 695                 700

Trp Asn Ser Ile Phe Asp Val Glu Arg Leu Arg Ala Ile Thr Ser Arg
705                 710                 715                 720

Leu Leu Ser Asp Val Pro Asp Ser Lys Arg Ser Gly Asp Met Leu
                725                 730                 735

Ala Ala Val His Val Met Val His Tyr Ala Ala Glu Ser Ile Val Arg
                740                 745                 750

Ala Arg Ser Thr Leu Val Lys Ala Arg Tyr Leu Lys Arg Ile Lys Lys
            755                 760                 765

Gln Leu Ala Glu Glu Pro Lys Ser Val Val Ala Arg Met Glu Glu Ile
770                 775                 780

Arg Asp Ala Leu Phe Arg Phe Glu Asn Met Arg Val Leu Val Ile Ala
785                 790                 795                 800

Asp Leu Glu Lys Leu Gln Asn Pro Val Ser Ala Trp Lys Pro Phe Ala
                805                 810                 815

Glu Arg Leu Gly Ala Gly Ala Pro Leu Gln Pro Ile Thr Thr Arg Arg
            820                 825                 830

Pro Leu Leu Ser Glu Ala Gly Gln Lys Leu Gly Gly Lys Ser Tyr Val
            835                 840                 845

Val Pro Met Pro Thr Ile Asp Ser Ser Phe Ala Tyr Ala Thr Ala Arg
    850                 855                 860

Gly Leu Asp Ser Tyr Asp Asp Pro Arg Leu Pro Ala Leu Met Val Ala
865                 870                 875                 880

Ile Ala Tyr Met Asn Ala Val Glu Gly Pro Leu Trp Val Ala Val Arg
                885                 890                 895

Gly Lys Gly Leu Ala Tyr Gly Thr Asn Phe Ala Tyr Asn Ile Asp Thr
            900                 905                 910

Gly Phe Val Asn Phe Asp Val Tyr Arg Ser Pro Asn Ala His Lys Ala
            915                 920                 925

Phe Asp Ser Ser Lys Gln Ile Val Glu Asp His Leu Ser Gly Ala Met
    930                 935                 940

Pro Phe Asp Pro Leu Met Leu Glu Gly Ser Ile Ser Ser Ile Val Val
945                 950                 955                 960

Ser Phe Ala Asn Glu Gln Ser Thr Ile Gly Ser Ala Ala Ser Gly Ser
                965                 970                 975

Phe Ile Arg Gln Val Ile Arg Arg Leu Pro Ser Asp Tyr Lys Glu Arg
            980                 985                 990

Val Leu Lys Gln Val Arg Ala Thr Ser Val Asp Asp Val Lys Gly Ala
            995                1000                1005

Leu Lys Asp Ile Ile Leu Pro Leu Phe Asn Pro Ser Thr Ala Asn
    1010                1015                1020

Ile Val Val Thr Cys Ala Thr Val Leu Glu Glu Thr Ile Lys Glu
    1025                1030                1035

Gly Leu Gln Ala Ser Gly Phe Thr Pro Ala Val Gln Pro Leu Lys
    1040                1045                1050

Glu Phe Glu Asp Asp Tyr Gly Leu Lys Val Gly Asp Asp Glu Asp
```

-continued

```
            1055                1060                1065

Glu  Glu   Ser  Asp  Asp  Asp   Asp  Glu  Tyr  Glu   Thr  Gly  Ser  Glu
           1070                1075                1080

Asp  Glu   Asp  Asp  Ser  Asp   Glu  Asp  Met  Glu   Asp  Asp  Glu  Asp  Asp
           1085                1090                1095

Glu
```

```
<210> SEQ ID NO 117
<211> LENGTH: 726
<212> TYPE: PRT
<213> ORGANISM: Aspergillus niger

<400> SEQUENCE: 117

Met Gly Ala Leu Gln Trp Leu Ser Ile Thr Ala Ala Ala Ser Ala
 1               5                  10                  15

Val Ser Ala Leu Thr Pro Glu Gln Met Ile Gly Ala Pro Arg Arg Thr
                20                  25                  30

Glu Val Ile Pro Asn Pro Ser Gly Asp Thr Gly Leu Phe Ser Thr Ser
             35                  40                  45

Gln Trp Ser Phe Asp Thr His Ser Glu Ser Thr Trp Trp Ser Leu Ile
     50                  55                  60

Asp Leu Gln Ser Gly Lys Thr Thr Thr Leu Thr Asp Ser Asp Ile
 65                  70                  75                  80

Glu Glu Ile Ile Trp Leu Gly Ser Asp Asn Ser Thr Leu Leu Tyr Ile
                 85                  90                  95

Asn Ser Thr Asn Ala Gln Val Pro Gly Gly Val Glu Leu Trp Ile Ala
                100                 105                 110

Asp Ser Ser Asp Phe Ala Asn Ala Tyr Lys Ala Ala Ser Leu Ser Ala
            115                 120                 125

Gly Phe Leu Gly Ile Lys Ser Thr Val Thr Asp Ser Gly Asp Val His
        130                 135                 140

Phe Ile Leu Arg Gly Lys Ser Tyr Pro Asn Gly Thr Ala Tyr Asn Asp
145                 150                 155                 160

Gln Leu Ala Glu Thr Tyr Pro Ser Thr Ala Arg Ile Tyr Asp Ser Ile
                165                 170                 175

Phe Val Arg His Trp Asp Thr Tyr Leu Thr Thr Ala Ser His Ala Val
            180                 185                 190

Phe Ser Gly Thr Leu Gln Ser Ser Thr Ser Asp Asp Gly Asn Val Gln
        195                 200                 205

Tyr Thr Ser Ser Gly Gly Leu Thr Asn Leu Val Asn Pro Val Lys Gly
    210                 215                 220

Ala Glu Ser Pro Phe Pro Pro Phe Gly Gly Asn Asp Asp Tyr Asp Leu
225                 230                 235                 240

Ser Pro Asp Gly Lys Trp Val Thr Phe Lys Ser Lys Ala Pro Glu Leu
                245                 250                 255

Pro Leu Ala Asn Asn Thr Ala Ala Tyr Val Tyr Leu Val Pro His Asp
            260                 265                 270

Gly Ser Ala Thr Ala Phe Ala Val Asn Gly Pro Asp Ser Pro Ala Thr
        275                 280                 285

Pro Glu Gly Val Glu Gly Glu Ser Asn Asn Pro Val Phe Ser Pro Asp
    290                 295                 300

Ser Asp Lys Ile Ala Tyr Phe Gln Met Ala Thr Asn Thr Tyr Glu Ser
305                 310                 315                 320

Asp Arg Asn Val Leu Tyr Val Tyr Ser Ile Ala Asp Asp Thr Ile Thr
```

-continued

```
                325                 330                 335
Pro Leu Ala Lys Asp Trp Asp Arg Ser Pro Ser Ser Val Thr Trp Val
            340                 345                 350
Asp Gly Asp Asn Leu Val Val Ala Ser Gln Asp Leu Gly Arg Thr Arg
            355                 360                 365
Leu Phe Ala Ile Pro Gly Asp Ala Gly Asp Phe Lys Pro Thr Asn
            370                 375                 380
Phe Thr Asp Gly Gly Ser Val Ser Ala Gln Tyr Val Leu Ser Asn Ser
385                 390                 395                 400
Thr Leu Leu Val Thr Ser Ser Ala Phe Trp Thr Ser Trp Ser Val Tyr
                405                 410                 415
Thr Ala Ser Pro Asp Glu Gly Val Ile Asn Thr Leu Ala Ser Ala Asn
            420                 425                 430
Glu Ile Asp Pro Glu Leu Ser Gly Leu Ser Ser Ser Asp Phe Glu Glu
            435                 440                 445
Phe Tyr Phe Asp Gly Asn Trp Thr Thr Leu Gln Gly Trp Ile Thr Tyr
            450                 455                 460
Pro Gln Asp Phe Asp Ser Ser Lys Lys Tyr Pro Leu Ala Phe Leu Ile
465                 470                 475                 480
His Gly Gly Pro Glu Asp Ala Trp Ala Asp Glu Trp Asn Leu Lys Trp
                485                 490                 495
His Ser Lys Val Phe Ala Asp Gln Gly Tyr Val Val Gln Pro Asn
            500                 505                 510
Pro Thr Gly Ser Thr Gly Phe Gly Gln Gln Leu Thr Asp Ala Ile Gln
            515                 520                 525
Leu Asn Trp Thr Gly Ala Ala Tyr Asp Asp Leu Thr Lys Ala Trp Gln
            530                 535                 540
Tyr Val His Asp Thr Tyr Asp Phe Ile Asp Thr Asp Asn Gly Val Ala
545                 550                 555                 560
Ala Gly Pro Ser Phe Gly Ala Phe Met Ile Thr Trp Ile Gln Gly Asp
                565                 570                 575
Asp Phe Gly Arg Lys Phe Lys Ala Leu Val Ser His Asp Gly Pro Phe
            580                 585                 590
Ile Gly Asp Ala Trp Val Glu Thr Asp Glu Leu Trp Phe Val Glu His
            595                 600                 605
Glu Phe Asn Gly Thr Phe Trp Gln Ala Arg Asp Ala Phe His Asn Thr
            610                 615                 620
Asp Pro Ser Gly Pro Ser Arg Val Leu Ala Tyr Ser Thr Pro Gln Leu
625                 630                 635                 640
Val Ile His Ser Asp Lys Asp Tyr Arg Ile Pro Val Ala Asn Gly Ile
                645                 650                 655
Gly Leu Phe Asn Thr Leu Gln Glu Arg Gly Val Pro Ser Arg Phe Leu
            660                 665                 670
Asn Phe Pro Asp Glu Asp His Trp Val Thr Gly Gln Glu Asn Ser Leu
            675                 680                 685
Val Trp Tyr Gln Gln Val Leu Gly Trp Ile Asn Arg Tyr Ser Gly Val
            690                 695                 700
Gly Gly Ser Asn Pro Asp Ala Ile Ala Leu Glu Asp Thr Val Asn Pro
705                 710                 715                 720
Val Val Asp Leu Asn Pro
                725
```

<210> SEQ ID NO 118

```
<211> LENGTH: 564
<212> TYPE: PRT
<213> ORGANISM: Aspergillus niger

<400> SEQUENCE: 118

Met Thr Arg Gln Thr Ser Leu Val Pro Arg Leu Leu Thr Leu Ala Ser
1               5                   10                  15

Leu Ala Ala Leu Ser Gln Ala Glu Leu Gly Lys Ile Gln Trp Lys Gly
            20                  25                  30

Ser Cys Asn Leu Thr Thr Tyr Pro Ala Leu Ile Cys Gly Thr Leu Asp
        35                  40                  45

Val Pro Tyr Asp Tyr Thr Glu Ser Asn Ser Ser Lys Thr Leu Thr Leu
    50                  55                  60

Asp Ile Ala Lys Trp Pro Ala Thr Lys Lys Pro Val Ser Glu Pro Ile
65                  70                  75                  80

Ile Phe Asn Phe Gly Gly Pro Gly Val Asn Ser Phe Glu Gly Leu Gly
                85                  90                  95

Leu Tyr Gly Glu Glu Phe Gln Ala Ile Leu Gly Gly His Asn Asp Leu
            100                 105                 110

Ile Ala Phe Asn Asn Arg Gly Val Gly Asn Thr Ile Pro Phe Ser Cys
        115                 120                 125

Tyr Ser Asp Asp Ala Thr Arg Glu Leu Val Ala Leu Gln Ala Pro Asn
    130                 135                 140

Asp Gly Arg Ala Ser Ser Thr Ala Leu Gly Glu Ile Trp Ala Gln Asn
145                 150                 155                 160

Ala Asn Ile Ala Gln Ala Cys Tyr Ala Thr Asn Asn Gln Thr Gly Ser
                165                 170                 175

Leu Ile Gly Thr Ser Phe Ala Ala Arg Asp Ile Met Gln Val Ala Asp
            180                 185                 190

Ala Leu Ser Gly Lys Asp Ser Leu Val Asn Tyr Trp Gly Phe Ser Tyr
        195                 200                 205

Gly Thr Thr Ile Gly Ala Val Leu Ala Ala Met Phe Pro Asp Arg Met
    210                 215                 220

Gly Asn Val Ala Leu Asp Gly Val Asp Asn Pro Arg Glu Ala Leu Tyr
225                 230                 235                 240

Gly Tyr Asn Ala Gln Ala Val Val Asp Val Asp Lys Val Phe Glu Gly
                245                 250                 255

Phe Cys Thr Gly Cys Met Ala Ala Pro Asp Leu Cys Pro Ile Ala Lys
            260                 265                 270

Glu Tyr Thr Ser Ala Ala Asn Leu Glu Ala Ala Ile Tyr Leu Met Leu
        275                 280                 285

Glu Asn Leu Lys Tyr Asn Pro Ile Ala Ile Pro Glu Thr Gly Gly Ile
    290                 295                 300

Val Thr Trp Ser Asp Val Lys Ser Thr Ile Phe Glu Ala Met Tyr Leu
305                 310                 315                 320

Pro Ser Ser Trp Pro Leu Thr Ser Glu Leu Leu Tyr Tyr Val Gln Thr
                325                 330                 335

Arg Asn Thr Thr Ile Leu Gly Asn Ser Glu Val Tyr Asp Thr Ile Lys
            340                 345                 350

Ser Tyr Gly Gln Ser Ala Ser Leu Thr Ser Ala Ser Asp Glu Val Gly
        355                 360                 365

Thr Ala Ile Thr Cys Ser Asp Lys His Arg Ser Ala Thr Ile Lys Glu
    370                 375                 380

Val Leu Pro Tyr Val Lys Ala Arg Gln Ala Leu Thr Lys Ile Gly Ser
```

-continued

```
            385                 390                 395                 400
Asp Gly Ser Asp Gly Asp Met Arg Cys Ala Gln Trp Asn Pro Lys Met
                405                 410                 415
Phe Ala Lys Glu Arg Tyr Ser Gly Asp Phe Glu Val Lys Thr Ala Asn
            420                 425                 430
Pro Val Leu Ile Leu Ser Asn Thr Tyr Asp Pro Ala Thr Pro Leu Pro
            435                 440                 445
Ala Ala Lys Asn Leu Thr Glu Thr Phe Glu Gly Ser Val Leu Leu Glu
            450                 455                 460
Gln Asn Gly Tyr Gly His Thr Thr Leu Ser Met Pro Ser Leu Cys Thr
465                 470                 475                 480
Ala Lys Ala Val Arg Ala Tyr Phe Thr Asn Gly Thr Leu Pro Ala Asp
                485                 490                 495
Gly Thr Ile Cys Gln Val Asp Val Pro Leu Phe Thr Asn Leu Thr Tyr
                500                 505                 510
Lys Asp Val Trp Pro Lys Ser Phe Gln Arg Ser Val Glu Ser Arg Asp
                515                 520                 525
Asp Ala Thr Ile Leu Lys Ala Leu Met Ser Val Arg Asp Lys Met Ser
            530                 535                 540
Arg Arg Arg Met Cys Ile Tyr Leu Tyr Thr Asn Ser Ala Ser Trp Arg
545                 550                 555                 560
Pro Glu Leu Pro

<210> SEQ ID NO 119
<211> LENGTH: 526
<212> TYPE: PRT
<213> ORGANISM: Aspergillus niger

<400> SEQUENCE: 119

Met Tyr Tyr Ser Leu Trp Val Ala Ala Leu Val Ala Ala Leu Pro Val
1               5                   10                  15
Ser Arg Ala Gln Phe Val Ala Pro Pro Thr Asp Leu Ile Pro Thr Lys
            20                  25                  30
Gly Tyr Leu Asp Ile Pro Val Arg Tyr Lys Gln Val Pro Thr Gly Ile
        35                  40                  45
Cys Glu Thr Asp Pro Ser Val Lys Ser Phe Ser Gly Tyr Val Asp Val
    50                  55                  60
Ala Glu His Glu His Ile Phe Phe Trp Phe Phe Glu Ala Arg Asn Gln
65                  70                  75                  80
Asp Pro Thr Glu Ala Pro Leu Thr Val Trp Ile Asn Gly Gly Met Ser
                85                  90                  95
Asp Pro Gly Pro Gly Ser Ser Ser Met Ile Gly Leu Phe Gln Glu His
            100                 105                 110
Gly Pro Cys Gly Ile Asp Ala Asn Gly Ser Val Tyr Asn Asn Pro Tyr
        115                 120                 125
Ser Trp Asn Asn Ala Ser Asn Met Leu Tyr Ile Asp Gln Pro Val Gln
    130                 135                 140
Thr Gly Phe Ser Tyr Ser Ile Pro Val Pro Gly Tyr Val Asp Ser Ser
145                 150                 155                 160
Thr Asp Asn Gly Phe Met Gly Ala Phe Pro Gln Tyr Ser Arg Glu Thr
                165                 170                 175
Phe His Phe Thr Thr Glu Ser Tyr Gly Gly His Tyr Gly Pro Val Phe
            180                 185                 190
Asn Glu Tyr Ile Glu Glu Gln Asn Ala His Leu Gln Pro Gly Ala Lys
```

```
            195                 200                 205
Lys Ile Gln Leu Gly Ser Val Met Ile Gly Asn Gly Trp Tyr Asp Pro
            210                 215                 220

Ile Ile Gln Tyr Gln Ala Tyr Tyr Asn Phe Thr Val Tyr Pro Gly Asn
225                 230                 235                 240

Thr Tyr Asp Tyr Leu Pro Phe Asn Lys Ser Ile Ser Ser Leu Met Tyr
                245                 250                 255

Asn Asn Leu Tyr Gly Pro Gly Asn Cys Leu Asp Gln Leu Tyr Asp Cys
            260                 265                 270

Ala Ala Arg Gly Ile Asp Glu Ile Cys Ser Thr Ala Asp Asp Phe Cys
            275                 280                 285

Ala Asn Glu Val Glu Asn Val Tyr Asp Ile Tyr Ser Gly Arg Asp Glu
            290                 295                 300

Tyr Asp Phe Arg Glu Leu Thr Pro Asp Pro Phe Pro Tyr Glu Phe Tyr
305                 310                 315                 320

Val Asp Tyr Leu Asn Lys Ala Ser Val Gln Ala Ala Ile Gly Ala Tyr
                325                 330                 335

Ile Asn Tyr Thr Glu Ser Asn Asn Ala Val Gly Leu Ala Phe Ser Ser
            340                 345                 350

Thr Gly Asp Asp Gly Arg Leu Met Asn Thr Ile Gln Asp Val Gly Lys
            355                 360                 365

Leu Leu Lys Gln Gly Val Thr Val Met Tyr Ala Gly Asp Ala Asp
            370                 375                 380

Tyr Asn Cys Asn Trp Leu Gly Gly Glu Ala Val Ser Leu Gln Val Lys
385                 390                 395                 400

Ala Ala Asn Phe Ser Ser Ala Gly Tyr Thr Asn Ile Val Thr Ser Asp
                405                 410                 415

Gly Val Thr His Gly Gln Val Arg Gln Ala Gly Gln Phe Ala Phe Val
            420                 425                 430

Arg Val Tyr Glu Ser Gly His Glu Val Pro Phe Tyr Gln Pro Leu Leu
            435                 440                 445

Ala Leu Glu Met Phe Glu Arg Val Ile Gly Gly Lys Asp Val Ala Thr
            450                 455                 460

Gly Lys Ile Pro Ile Ser Ser Leu Gln Thr Val Gly Thr Pro Lys
465                 470                 475                 480

Ser Tyr Tyr Arg Glu Gly Asn Ser Thr Ile Gln Trp Glu Val Leu Asp
                485                 490                 495

Ser Leu Ala Thr Tyr Asn Thr Thr Asn Ala Pro Asn Pro Val Ser
            500                 505                 510

Arg Arg Leu Lys Arg Met Gly Pro Ala Leu Arg Phe Gln Met
            515                 520                 525

<210> SEQ ID NO 120
<211> LENGTH: 1156
<212> TYPE: PRT
<213> ORGANISM: Aspergillus niger

<400> SEQUENCE: 120

Met Ser Cys Val Trp Leu His Ile His Lys Arg Ser Leu Leu Ser Val
1               5                   10                  15

Ala Thr Asn Asn Ser Val Ala Arg Ala Ala Ser Thr Ser Ala Ala
            20                  25                  30

Pro Pro Pro Ser Ser Pro Pro Gly Ser Asn Thr Tyr Ser Pro
            35                  40                  45
```

```
Leu Tyr Arg Pro Ile Thr Asn Pro Ile Gly Phe Thr Leu Ser Pro Ala
     50                  55                  60

Arg Ser Leu Val Ser Arg Asn Pro Lys Phe Pro Ala Tyr Arg Arg Ser
 65                  70                  75                  80

Ser Arg His Phe Ser Leu Cys Pro Ala Ala Thr Pro Gly Val Thr
                 85                  90                  95

Thr Ser Ile Cys Pro Gly Gln Ala Pro Val Arg Ser Leu Ser Ser Leu
                100                 105                 110

Ile Ile His Ser Thr Arg Pro Arg Ala Ile Arg Ile Arg Thr Asp Gln
            115                 120                 125

Met Asp Leu Asn Gly Asp Ala Gly Lys Arg Lys Arg Ser Ser Ile
    130                 135                 140

Thr Thr Pro Ala Glu Arg Pro Val Lys His Leu Arg Pro Glu Ser Ser
145                 150                 155                 160

Ala Leu Thr Pro Gly Asp Ser Thr Pro Ala Asn Gly Thr Val Tyr Asp
                165                 170                 175

Val Glu Asp Asp Glu Asp Ala Ser Arg Leu Leu Pro Val Gly Pro Ala
            180                 185                 190

Gln Ala Asp Ser Pro Glu Trp Gln Ala Thr Ile Glu Glu Val Val Lys
            195                 200                 205

Ser Val Val Ser Ile His Phe Cys Gln Thr Cys Ser Phe Asp Thr Glu
210                 215                 220

Leu Ser Met Ser Ser Gln Ala Thr Gly Phe Val Val Asp Ala Glu Asn
225                 230                 235                 240

Gly Tyr Ile Leu Thr Asn Arg His Val Val Cys Pro Gly Pro Phe Trp
                245                 250                 255

Gly Tyr Cys Ile Phe Asp Asn His Glu Glu Cys Asp Val Arg Pro Val
            260                 265                 270

Tyr Arg Asp Pro Val His Asp Phe Gly Ile Leu Lys Phe Asp Pro Lys
            275                 280                 285

Ala Ile Arg Tyr Met Lys Leu Arg Glu Leu Lys Leu Gln Pro Asp Ala
            290                 295                 300

Ala Lys Val Gly Ser Glu Ile Arg Val Val Gly Asn Asp Ala Gly Glu
305                 310                 315                 320

Lys Leu Ser Ile Leu Ser Gly Val Ile Ser Arg Leu Asp Arg Asn Ala
                325                 330                 335

Pro Glu Tyr Gly Asp Gly Tyr Ser Asp Phe Asn Thr Asn Tyr Ile Gln
            340                 345                 350

Ala Ala Ala Ala Ser Gly Gly Ser Ser Gly Ser Pro Val Val Asn
            355                 360                 365

Ile Asp Gly His Ala Ile Ala Leu Gln Ala Gly Gly Arg Ala Asp Gly
    370                 375                 380

Ala Ala Thr Asp Tyr Phe Leu Pro Leu Asp Arg Pro Leu Arg Ala Leu
385                 390                 395                 400

Glu Cys Ile Arg Arg Gly Glu Pro Val Thr Arg Gly Thr Ile Gln Thr
                405                 410                 415

Gln Trp Ile Leu Lys Pro Phe Asp Glu Cys Arg Arg Leu Gly Leu Thr
            420                 425                 430

Pro Glu Trp Glu Ala Thr Val Arg Lys Ala Ala Pro Thr Glu Thr Ser
            435                 440                 445

Met Leu Val Ala Glu Ile Ile Leu Pro Glu Gly Pro Ala Asp Gly Lys
450                 455                 460

Leu Glu Glu Gly Asp Val Leu Leu Gln Val Asn Gly Val Leu Leu Thr
```

-continued

```
                465                 470                 475                 480
            Gln Phe Ile Arg Leu Asp Asp Ile Leu Asp Ser Ser Val Gly Gln Thr
                                485                 490                 495
            Val Arg Leu Leu Val Gln Arg Gly Gln Asn Val Glu Ile Glu Cys
                        500                 505                 510
            Gln Val Gly Asp Leu His Ala Ile Thr Pro Asp Arg Phe Val Thr Val
                        515                 520                 525
            Ala Gly Gly Thr Phe His Asn Leu Ser Tyr Gln Gln Ser Arg Leu Tyr
                        530                 535                 540
            Ala Ile Ala Thr Arg Gly Val Tyr Val Cys Glu Ala Ala Gly Ser Phe
            545                 550                 555                 560
            Lys Leu Glu Asn Thr Leu Ser Gly Trp Ile Ile Asp Ser Val Asp Lys
                                565                 570                 575
            Arg Pro Thr Arg Asn Leu Asp Glu Phe Val Glu Val Met Arg Thr Ile
                        580                 585                 590
            Pro Asp Arg Ser Arg Val Val Ile Ser Tyr Arg His Ile Arg Asp Leu
                        595                 600                 605
            His Thr Arg Gly Thr Ser Ile Val Tyr Ile Asp Arg His Trp His Pro
                610                 615                 620
            Lys Met Arg Leu Ala Val Arg Asn Asp Asp Thr Gly Leu Trp Asp Phe
            625                 630                 635                 640
            Ser Asp Leu Ala Asp Pro Ile Pro Ala Leu Pro Val Pro Arg Lys
                                645                 650                 655
            Ala Asp Phe Ile Gln Leu Asp Gly Val Ser Gln Pro Ala Ala Ala Asp
                        660                 665                 670
            Ile Val Arg Ser Phe Val Arg Val Ser Cys Thr Met Pro Leu Lys Leu
                        675                 680                 685
            Asp Gly Tyr Pro Gln Ala Lys Lys Thr Gly Phe Gly Leu Val Val Asp
                690                 695                 700
            Ala Glu Lys Gly Leu Val Val Ser Arg Ala Ile Val Pro Tyr Asp
            705                 710                 715                 720
            Leu Cys Asp Ile Asn Val Thr Val Ala Asp Ser Ile Ile Val Asn Ala
                                725                 730                 735
            Lys Val Val Phe Leu His Pro Leu Gln Asn Tyr Ser Ile Ile Gln Tyr
                        740                 745                 750
            Asp Pro Ser Leu Val Gln Ala Pro Val Gln Ser Ala Lys Leu Ala Thr
                        755                 760                 765
            Asp Tyr Ile Lys Gln Gly Gln Asp Thr Ile Phe Val Gly Phe Asn Gln
                        770                 775                 780
            Asn Phe Arg Ile Val Val Ala Lys Thr Ala Val Thr Asp Ile Thr Thr
            785                 790                 795                 800
            Val Ser Ile Pro Ala Asn Ala Ser Ala Pro Arg Tyr Arg Ala Ile Asn
                                805                 810                 815
            Leu Asp Ala Ile Thr Val Asp Thr Gly Leu Ser Gly Gln Cys Ser Asn
                        820                 825                 830
            Gly Val Leu Ile Gly Glu Asp Gly Val Val Gln Ala Leu Trp Leu Asn
                        835                 840                 845
            Tyr Leu Gly Glu Arg Thr Ser Asn Ser His Lys Asp Val Glu Tyr His
                        850                 855                 860
            Leu Gly Phe Ala Thr Pro Ser Leu Leu Pro Val Leu Ser Lys Val Gln
            865                 870                 875                 880
            Gln Gly Glu Met Pro Glu Leu Arg Ile Leu Asn Met Glu Ser Tyr Val
                                885                 890                 895
```

```
Val Gln Met Ser Gln Ala Arg Ile Met Gly Val Ser Glu Trp Ile
            900                 905                 910

Glu Lys Val Thr Gln Ala Asn Pro Ser Arg His Gln Leu Phe Met Val
        915                 920                 925

Arg Lys Val Asp Cys Pro Pro Gly Phe Asn Ser Ala Ala Asp Thr
        930                 935                 940

Phe Glu Glu Gly Asp Ile Ile Leu Thr Leu Asp Gly Gln Leu Ile Thr
945                 950                 955                 960

Arg Val Ser Glu Leu Asp Ile Met Tyr Glu Lys Asp Thr Leu Glu Ala
            965                 970                 975

Leu Ile Val Arg Asn Gly Gln Glu Met Arg Ile Gln Val Pro Thr Val
        980                 985                 990

Pro Thr Glu Asp Leu Glu Thr Asp Arg Ala Val Val Phe Cys Gly Ala
            995                 1000                1005

Val Leu Gln Lys Pro His His Ala Val Arg Gln Gln Ile Ser Lys
        1010                1015                1020

Leu His Ser Glu Val Tyr Val Ser Ala Arg Ser Arg Gly Ser Pro
        1025                1030                1035

Ser Tyr Gln Tyr Gly Leu Ala Pro Thr Asn Phe Ile Thr Ala Val
        1040                1045                1050

Asn Gly Val Pro Thr Pro Asn Leu Asp Arg Phe Ser Glu Glu Val
        1055                1060                1065

Ser Lys Ile Pro Asp Asn Thr Tyr Phe Arg Leu Arg Ala Val Thr
        1070                1075                1080

Phe Asp Asn Val Pro Trp Val Val Thr Val Lys Lys Asn Asp His
        1085                1090                1095

Tyr Phe Pro Met Ser Glu Tyr Ile Lys Asp Gln Ser Gln Pro Ser
        1100                1105                1110

Gly Trp Arg Thr Val Ser His Asp Lys Asp Lys Tyr Lys Asp Gly
        1115                1120                1125

Ile Ala Pro Asp Ala Ala Asn Leu Asn Pro Asp Ala Met Asp Glu
        1130                1135                1140

Gly Phe Asp Gly Val Ser Asp Ile Glu Pro Asp Leu Glu
        1145                1150                1155

<210> SEQ ID NO 121
<211> LENGTH: 536
<212> TYPE: PRT
<213> ORGANISM: Aspergillus niger

<400> SEQUENCE: 121

Met Arg Val Leu Pro Ala Met Leu Val Gly Ala Ala Thr Ala Ala
1               5                   10                  15

Val Pro Pro Phe Gln Gln Val Leu Gly Gly Asn Gly Ala Lys His Gly
            20                  25                  30

Ala Asp His Ala Ala Glu Val Pro Ala Asp His Ser Ala Asp Gly Phe
        35                  40                  45

Ser Lys Pro Leu His Ala Phe Gln Glu Glu Leu Lys Ser Leu Ser Asp
        50                  55                  60

Glu Ala Arg Lys Leu Trp Asp Glu Val Ala Ser Phe Phe Pro Glu Ser
65                  70                  75                  80

Met Asp Gln Asn Pro Leu Phe Ser Leu Pro Lys Lys His Asn Arg Arg
                85                  90                  95

Pro Asp Ser His Trp Asp His Ile Val Asp Gly Lys Leu Glu Ala Tyr
```

-continued

```
                 100                 105                 110
Asp Leu Arg Val Lys Lys Thr Asp Pro Gly Ser Leu Gly Ile Asp Pro
                115                 120                 125
Gly Val Lys Gln Tyr Thr Gly Tyr Leu Asp Asp Asn Glu Asn Asp Lys
            130                 135                 140
His Leu Phe Tyr Trp Phe Glu Ser Arg Asn Asp Pro Glu Asn Asp
145                 150                 155                 160
Pro Val Val Leu Trp Leu Asn Gly Gly Pro Gly Cys Ser Ser Leu Thr
                165                 170                 175
Gly Leu Phe Met Glu Leu Gly Pro Ser Ser Ile Asn Lys Lys Ile Gln
                180                 185                 190
Pro Val Tyr Asn Asp Tyr Ala Trp Asn Ser Asn Ala Ser Val Ile Phe
                195                 200                 205
Leu Asp Gln Pro Val Asn Val Gly Tyr Ser Tyr Ser Asn Ser Ala Val
            210                 215                 220
Ser Asp Thr Val Ala Ala Gly Lys Asp Val Tyr Ala Leu Leu Thr Leu
225                 230                 235                 240
Phe Phe Lys Gln Phe Pro Glu Tyr Ala Lys Gln Asp Phe His Ile Ala
                245                 250                 255
Gly Glu Ser Tyr Ala Gly His Tyr Ile Pro Val Phe Ala Ser Glu Ile
                260                 265                 270
Leu Ser His Lys Lys Arg Asn Ile Asn Leu Gln Ser Val Leu Ile Gly
            275                 280                 285
Asn Gly Leu Thr Asp Gly Tyr Thr Gln Tyr Glu Tyr Tyr Arg Pro Met
290                 295                 300
Ala Cys Gly Asp Gly Tyr Pro Ala Val Leu Asp Glu Ser Ser Cys
305                 310                 315                 320
Gln Ser Met Asp Asn Ala Leu Pro Arg Cys Gln Ser Met Ile Glu Ser
                325                 330                 335
Cys Tyr Ser Ser Glu Ser Ala Trp Val Cys Val Pro Ala Ser Ile Tyr
            340                 345                 350
Cys Asn Asn Ala Leu Leu Ala Pro Tyr Gln Arg Thr Gly Gln Asn Val
            355                 360                 365
Tyr Asp Val Arg Gly Lys Cys Glu Asp Ser Ser Asn Leu Cys Tyr Ser
        370                 375                 380
Ala Met Gly Tyr Val Ser Asp Tyr Leu Asn Lys Pro Glu Val Ile Glu
385                 390                 395                 400
Ala Val Gly Ala Glu Val Asn Gly Tyr Asp Ser Cys Asn Phe Asp Ile
                405                 410                 415
Asn Arg Asn Phe Leu Phe His Gly Asp Trp Met Lys Pro Tyr His Arg
            420                 425                 430
Leu Val Pro Gly Leu Leu Glu Gln Ile Pro Val Leu Ile Tyr Ala Gly
            435                 440                 445
Asp Ala Asp Phe Ile Cys Asn Trp Leu Gly Asn Lys Ala Trp Thr Glu
            450                 455                 460
Ala Leu Glu Trp Pro Gly Gln Ala Glu Tyr Ala Ser Ala Glu Leu Glu
465                 470                 475                 480
Asp Leu Val Ile Val Asp Asn Glu His Thr Gly Lys Lys Ile Gly Gln
                485                 490                 495
Val Lys Ser His Gly Asn Phe Thr Phe Met Arg Leu Tyr Gly Gly Gly
            500                 505                 510
His Met Val Pro Met Asp Gln Pro Glu Ser Ser Leu Glu Phe Phe Asn
            515                 520                 525
```

```
Arg Trp Leu Gly Gly Glu Trp Phe
    530                 535

<210> SEQ ID NO 122
<211> LENGTH: 279
<212> TYPE: PRT
<213> ORGANISM: Aspergillus niger

<400> SEQUENCE: 122

Met Lys Phe Thr Asn Tyr Leu Thr Thr Ala Thr Leu Ala Ser Ser
1               5                   10                  15

Val Leu Ala Ala Pro Ala Pro Arg Thr Gly Leu Glu Asp Arg Leu Arg
            20                  25                  30

Ala Arg Ser Leu Gln Arg Gln Ser His Pro Leu Ala Pro Ile Pro Leu
        35                  40                  45

Asp Thr Ser Thr Lys Glu Asn Ser Arg Leu Leu Glu Ala Asp Glu Asn
    50                  55                  60

Thr Thr His Val Thr Tyr Ser Ser Asn Trp Ala Gly Ala Val Arg Glu
65                  70                  75                  80

Gln Pro Pro Gln Gly Thr Tyr Ser Ala Val Ser Ala Thr Phe Arg
                85                  90                  95

Val Pro Glu Pro Thr Ala Gln Gly Gly Ser Gly Thr Gln Ala Gly Ser
            100                 105                 110

Ala Trp Val Gly Ile Asp Gly Asp Thr Tyr Ser Asn Ala Ile Leu Gln
        115                 120                 125

Thr Gly Val Asp Phe Tyr Val Glu Asn Gly Gln Thr Tyr Asn Asp Ala
    130                 135                 140

Trp Tyr Glu Trp Tyr Pro Asp Tyr Ala Tyr Asp Phe Asp Leu Asp Val
145                 150                 155                 160

Ser Thr Gly Asp Thr Ile Val Ala Lys Val Glu Ala Ile Ser Pro Ser
                165                 170                 175

Gln Gly Val Ala Thr Ile Glu Asn Ile Ser Thr Gly Lys Lys Ala Thr
            180                 185                 190

Gln Thr Ile Arg Ala Pro Ala Ala Thr Ala Thr Leu Ala Gly Gln Asn
        195                 200                 205

Ala Asp Trp Ile Val Glu Asp Phe Gln Ser Gly Asp Ser Met Val Asp
    210                 215                 220

Leu Ala Gly Phe Gly Glu Ile Ser Phe Trp Gly Val Gln Ala Gln Gly
225                 230                 235                 240

Gly Gly Ser Thr Trp Gly Val Asp Asp Ala Thr Ile Val Glu Leu Lys
                245                 250                 255

Gln Gly Asn Glu Val Leu Thr Asp Val Glu Val Gln Ser Asp Ser Ala
            260                 265                 270

Phe Thr Val Lys Tyr Thr Ser
        275

<210> SEQ ID NO 123
<211> LENGTH: 573
<212> TYPE: PRT
<213> ORGANISM: Aspergillus niger

<400> SEQUENCE: 123

Met Ile Tyr Val Asn Tyr Ile Leu Gly Leu Leu Ser Leu Leu His Thr
1               5                   10                  15

Ala Val Ala Thr Ala Pro Asp Tyr Val Val Asp Gln Leu Asn Ser
            20                  25                  30
```

-continued

```
Ile Pro Asp Gly Trp Thr Lys Gly Ala Ala Pro Pro Phe Thr Pro
         35                  40                  45
Met Lys Phe Trp Leu Ser Met His His Glu Tyr Lys Ala Asp Phe Glu
 50                  55                  60
Gln Lys Val Ile Asp Ile Ser Thr Pro Gly His Arg Asp Tyr Gly Arg
 65                  70                  75                  80
His Met Lys Arg Asn Asp Val Met Ala Phe Met Arg Pro Ser Asp Gln
                 85                  90                  95
Val Ser Lys Ile Ile Phe Ser Trp Leu Glu Ser Glu His Val Pro Pro
            100                 105                 110
Asn Ala Ile Glu Asp Arg Gly Asp Trp Val Ala Phe Thr Val Pro Leu
        115                 120                 125
Ala Gln Ala Gln Ser Met Met Lys Thr Asp Phe Tyr Asn Phe His His
    130                 135                 140
Leu Glu Thr Asn Thr Thr Gln Ile Arg Thr Leu Lys Tyr Ser Val Pro
145                 150                 155                 160
Glu Gln Val Asp Ala His Leu Gln Met Ile Gln Pro Thr Thr Arg Phe
                165                 170                 175
Gly Arg Pro Lys Thr Gln Thr Ser Leu Pro Ser Leu Met Pro Val Ser
            180                 185                 190
Val Asn Ile Asp Glu Ile Ser Glu Asp Cys Leu Thr Gly Val Thr Pro
        195                 200                 205
Ile Cys Leu Arg Gln Leu Tyr Gly Leu Pro Ser Thr Lys Ala Ser Pro
    210                 215                 220
Asp Ser Arg Asn Val Leu Gly Ile Ser Gly Tyr Leu Asp Gln Tyr Ala
225                 230                 235                 240
Arg Tyr Ser Asp Leu Asp Glu Phe Leu Ala Val Tyr Ser Pro Asn Ser
                245                 250                 255
Val Asp Ala Asp Phe Ser Val Val Ser Ile Asn Gly Gly Gln Asn Pro
            260                 265                 270
Gln Asn Ser Gln Glu Gly Ser Thr Glu Ala Ser Leu Asp Ile Gln Tyr
        275                 280                 285
Ala Leu Ser Met Ala Phe Asp Ala Asn Ala Thr Phe Tyr Thr Thr Ala
    290                 295                 300
Gly Arg Ala Pro Ser Pro Tyr Leu Glu Gln Leu Gln Tyr Leu Val Gly
305                 310                 315                 320
Leu Pro Asp Glu Asp Leu Pro Ala Val Leu Ser Thr Ser Tyr Gly Glu
                325                 330                 335
Asp Glu Gln Ser Leu Pro Glu Glu Tyr Thr Glu Ala Thr Cys Asn Leu
            340                 345                 350
Phe Ala Gln Leu Gly Ala Arg Gly Val Ser Val Ile Phe Ser Ser Gly
        355                 360                 365
Asp Ser Gly Val Gly Ser Cys Val Ser Asn Asp Gly Ser Gln Arg
    370                 375                 380
Thr Arg Phe Gln Pro Ile Phe Pro Ala Ser Cys Pro Phe Val Thr Ser
385                 390                 395                 400
Val Gly Gly Thr Glu Gly Val Gly Pro Glu Lys Ala Val Asp Phe Ser
                405                 410                 415
Ser Gly Gly Phe Ser Glu Arg Phe Ala Arg Pro Ser Tyr Gln Asn Ala
            420                 425                 430
Ser Val Glu Ala Tyr Leu Ala Arg Leu Gly Asp Lys Trp Asp Gly Leu
        435                 440                 445
```

```
Tyr Asn Pro Asp Gly Arg Gly Ile Pro Asp Val Ser Ala Gln Ala Ser
    450                 455                 460

Asn Tyr Val Ile Arg Asp His Gly Gln Trp Leu Gln Thr Ala Gly Thr
465                 470                 475                 480

Ser Ala Ala Pro Val Phe Ala Val Ile Ser Arg Leu Asn Ala
            485                 490                 495

Ala Arg Leu Glu Gln Gly Lys Pro Thr Leu Gly Phe Leu Asn Pro Trp
        500                 505                 510

Leu Tyr Ser Leu Asp Gln Gln Gly Phe Thr Asp Ile Val Asp Gly Gly
            515                 520                 525

Ser Val Gly Cys Asp Gly Ser Asn Gly Gly Ala Leu Val Pro Tyr Ala
    530                 535                 540

Ser Trp Asn Ala Thr Lys Gly Trp Asp Pro Val Thr Gly Leu Gly Thr
545                 550                 555                 560

Pro Leu Tyr Gln Thr Leu Glu Gln Leu Ala Gln Ser Ala
                565                 570

<210> SEQ ID NO 124
<211> LENGTH: 585
<212> TYPE: PRT
<213> ORGANISM: Aspergillus niger

<400> SEQUENCE: 124

Met Arg Ser Ser Gly Leu Tyr Thr Ala Leu Leu Cys Ser Leu Ala Ala
1               5                   10                  15

Ser Thr Asn Ala Ile Val His Glu Lys Leu Ala Ala Val Pro Ser Gly
            20                  25                  30

Trp His His Val Glu Asp Ala Gly Ser Asp His Gln Ile Ser Leu Ser
        35                  40                  45

Ile Ala Leu Ala Arg Lys Asn Leu Asp Gln Leu Glu Ser Lys Leu Lys
    50                  55                  60

Asp Leu Ser Thr Pro Gly Glu Ser Gln Tyr Gly Gln Trp Leu Asp Gln
65                  70                  75                  80

Glu Asp Val Asp Thr Leu Phe Pro Val Ala Ser Asp Lys Ala Val Ile
                85                  90                  95

Asn Trp Leu Arg Ser Ala Asn Ile Thr His Ile Ser Arg Gln Gly Ser
            100                 105                 110

Leu Val Asn Phe Ala Thr Thr Val Asp Lys Val Asn Lys Leu Leu Asn
        115                 120                 125

Ala Thr Phe Ala Tyr Tyr Gln Ser Gly Ser Ser Gln Arg Leu Arg Thr
    130                 135                 140

Thr Glu Tyr Ser Ile Pro Asp Asp Leu Val Asp Ser Ile Asp Leu Ile
145                 150                 155                 160

Ser Pro Thr Thr Phe Phe Gly Lys Glu Lys Thr Thr Ala Gly Leu Asn
                165                 170                 175

Gln Arg Ala Gln Lys Ile Asp Thr His Val Ala Lys Arg Ser Asn Ser
            180                 185                 190

Ser Ser Cys Ala Asp Val Ile Thr Leu Ser Cys Leu Lys Glu Met Tyr
        195                 200                 205

Asn Phe Gly Asn Tyr Thr Pro Ser Ala Ser Gly Ser Lys Leu Gly
    210                 215                 220

Phe Gly Ser Phe Leu Asn Glu Ser Ala Ser Tyr Ser Asp Leu Ala Lys
225                 230                 235                 240

Phe Glu Lys Leu Phe Asn Leu Pro Ser Gln Ser Phe Ser Val Glu Leu
                245                 250                 255
```

```
Val Asn Gly Gly Val Asn Asp Gln Asn Gln Ser Thr Ala Ser Leu Thr
            260                 265                 270

Glu Ala Asp Leu Asp Val Glu Leu Leu Val Gly Val Ala His Pro Leu
            275                 280                 285

Pro Val Thr Glu Phe Ile Thr Ser Gly Glu Pro Ala Ala Asp Asn Glu
            290                 295                 300

Asn Glu Pro Tyr Leu Gln Tyr Tyr Glu Tyr Leu Leu Ser Lys Pro Asn
305                 310                 315                 320

Ser Ala Leu Pro Gln Val Ile Ser Asn Ser Tyr Gly Asp Asp Glu Gln
            325                 330                 335

Thr Val Pro Glu Tyr Tyr Ala Lys Arg Val Cys Asn Leu Ile Gly Leu
            340                 345                 350

Val Gly Leu Arg Gly Ile Ser Val Leu Glu Ser Ser Gly Asp Glu Gly
            355                 360                 365

Ile Gly Ser Gly Cys Arg Thr Thr Asp Gly Thr Asn Arg Thr Gln Phe
370                 375                 380

Asn Pro Ile Phe Pro Ala Thr Cys Pro Tyr Val Thr Ala Val Gly Gly
385                 390                 395                 400

Thr Met Ser Tyr Ala Pro Glu Ile Ala Trp Glu Ala Ser Ser Gly Gly
                    405                 410                 415

Phe Ser Asn Tyr Phe Glu Arg Ala Trp Phe Gln Lys Glu Ala Val Gln
            420                 425                 430

Asn Tyr Leu Ala His His Ile Thr Asn Glu Thr Lys Gln Tyr Tyr Ser
            435                 440                 445

Gln Phe Ala Asn Phe Ser Gly Arg Gly Phe Pro Asp Val Ala Ala His
    450                 455                 460

Ser Phe Glu Pro Ser Tyr Glu Val Ile Phe Tyr Gly Ala Arg Tyr Gly
465                 470                 475                 480

Ser Gly Gly Thr Ser Ala Ala Cys Pro Leu Phe Ser Ala Leu Val Gly
                485                 490                 495

Met Leu Asn Asp Ala Arg Leu Arg Ala Gly Lys Ser Thr Leu Gly Phe
            500                 505                 510

Leu Asn Pro Leu Leu Tyr Ser Lys Gly Tyr Arg Ala Leu Thr Asp Val
            515                 520                 525

Thr Gly Gly Gln Ser Ile Gly Cys Asn Gly Ile Asp Pro Gln Asn Asp
            530                 535                 540

Glu Thr Val Ala Gly Ala Gly Ile Ile Pro Trp Ala His Trp Asn Ala
545                 550                 555                 560

Thr Val Gly Trp Asp Pro Val Thr Gly Leu Gly Leu Pro Asp Phe Glu
                565                 570                 575

Lys Leu Arg Gln Leu Val Leu Ser Leu
            580                 585

<210> SEQ ID NO 125
<211> LENGTH: 265
<212> TYPE: PRT
<213> ORGANISM: Aspergillus niger

<400> SEQUENCE: 125

Met Lys Thr Thr Ala Leu Leu Thr Ala Gly Leu Leu Ala Thr Thr Ala
1               5                   10                  15

Met Ala Ala Pro Leu Thr Ala Lys Arg Gln Ala Ala Arg Ala Lys Arg
            20                  25                  30

Ser Thr Asn Arg Gln Ser Asn Pro Pro Phe Lys Pro Gly Thr Asn Glu
```

```
                35                  40                  45
Val Leu Ala Leu Asn Gly Thr Lys Asn Val Glu Tyr Ser Ser Asn Trp
 50                  55                  60

Ala Gly Ala Val Leu Ile Gly Thr Gly Tyr Thr Ala Val Thr Ala Glu
 65                  70                  75                  80

Phe Val Val Pro Thr Pro Ser Val Pro Ser Gly Gly Ser Ser Arg Glu
                 85                  90                  95

Glu Tyr Cys Ala Ser Ala Trp Val Gly Ile Asp Gly Asp Thr Cys Asp
            100                 105                 110

Thr Ala Ile Leu Gln Thr Gly Val Asp Phe Cys Val Gln Gly Ser Glu
        115                 120                 125

Val Ser Phe Asp Ala Trp Tyr Glu Trp Tyr Pro Asp Tyr Ala Tyr Asp
130                 135                 140

Phe Ser Gly Ile Ser Ile Ser Ala Gly Asp Thr Ile Lys Val Thr Val
145                 150                 155                 160

Asp Ala Ser Ser Asp Thr Thr Gly Thr Ala Thr Ile Glu Asn Val Ser
                165                 170                 175

Thr Gly Thr Thr Val Thr His Ser Phe Thr Gly Gly Val Asp Gly Asp
            180                 185                 190

Leu Cys Glu Tyr Asn Ala Glu Trp Ile Val Glu Asp Phe Glu Glu Asp
        195                 200                 205

Asp Ser Leu Val Pro Phe Ala Asp Phe Gly Thr Val Thr Phe Thr Ser
    210                 215                 220

Cys Ser Ala Thr Lys Asp Gly Ser Ser Val Gly Pro Glu Asp Ala Thr
225                 230                 235                 240

Ile Ile Asp Ile Glu Gln Asn Glu Val Leu Thr Ser Val Ser Val Ser
                245                 250                 255

Ser Ser Glu Val Val Val Lys Tyr Val
            260                 265

<210> SEQ ID NO 126
<211> LENGTH: 580
<212> TYPE: PRT
<213> ORGANISM: Aspergillus niger

<400> SEQUENCE: 126

Met Val Ala Phe Ser Arg Ile Ser Ala Gly Phe Ala Leu Ala Ala Pro
  1               5                  10                  15

Ala Leu Ala Ser Val Val Leu Glu Thr Val Lys Ser Val Pro Ser Asp
             20                  25                  30

Trp Lys Leu Val Glu Ala Ala Asp Thr Ser Ser Thr Ile Ser Leu Ser
         35                  40                  45

Val Ala Leu Ala Arg Gln Asn Leu Asp Gln Leu Glu Glu Lys Leu Leu
 50                  55                  60

Ala Val Ser Thr Pro Gly Lys Asp Thr Tyr Gly Gln Phe Leu Asp Leu
 65                  70                  75                  80

Asp Asp Ile Asn Glu Gln Phe Pro Leu Ala Asp Ala Ala Val Val
                 85                  90                  95

Ala Trp Leu Lys Lys Ala Gly Val Thr Gln Ile His Lys Glu Gly Gly
            100                 105                 110

Leu Leu Asn Phe Ala Thr Thr Val Gly Thr Ala Asn Gln Leu Leu Asn
        115                 120                 125

Thr Thr Phe Ser Val Tyr Lys Ser Gly Ser Thr Gln Lys Leu Arg Thr
    130                 135                 140
```

-continued

```
Thr Gln Tyr Ser Val Pro Asp Glu Leu Thr Gly Ser Ile Asp Leu Ile
145                 150                 155                 160

Ser Pro Thr Val Phe Phe Gly Lys Ser Asn Ala Ala Arg Ser Ala Ala
                165                 170                 175

Val Arg Ala Ser Gln Thr Thr Lys Glu Thr Ser Arg Lys Lys Ser Ser
            180                 185                 190

Asn Val Cys Glu Tyr Ile Thr Pro Asp Cys Leu Lys Glu Gln Tyr Ser
        195                 200                 205

Ile Asp Tyr Thr Pro Glu Ala Ser Ser Gly Ser Arg Val Gly Phe Gly
    210                 215                 220

Ser Phe Leu Asn Glu Ser Ala Leu Tyr Ser Asp Leu Asp Leu Phe Thr
225                 230                 235                 240

Gln Tyr Phe Asp Ile Pro Gln Gln Ser Phe Thr Val Glu Thr Ile Asn
                245                 250                 255

Gly Gly Ile Asn Asn Gln Glu Asn Asp Pro Asp Gly Glu Ala Asp Leu
            260                 265                 270

Asp Val Gln Asn Ile Val Gly Ile Ser His Pro Leu Pro Val Thr Glu
        275                 280                 285

Tyr Ile Thr Gly Gly Ser Pro Pro Phe Ile Pro Asp Val Glu Thr Thr
    290                 295                 300

Thr Asp Glu Asn Glu Pro Tyr Leu Gln Tyr Tyr Glu Tyr Leu Leu Ala
305                 310                 315                 320

Lys Thr Asn Asp Glu Leu Pro Leu Val Ile Ser Asn Ser Tyr Gly Asp
                325                 330                 335

Asp Glu Asp Thr Val Pro Ile Ala Tyr Ala Thr Arg Val Cys Asn Leu
            340                 345                 350

Ile Gly Leu Met Gly Thr Arg Gly Ile Ser Ile Leu Glu Ser Ser Gly
        355                 360                 365

Asp Ser Gly Val Gly Gly Ala Cys Met Ser Asn Asp Gly Thr Asp Lys
    370                 375                 380

Thr Glu Phe Thr Pro Met Phe Pro Gly Thr Cys Pro Tyr Ile Thr Ala
385                 390                 395                 400

Val Gly Gly Thr Gln Asp Val Pro Glu Val Ala Trp Val Asp Ser Ser
                405                 410                 415

Gly Gly Phe Ser Asn Tyr Phe Ser Gln Pro Ser Tyr Gln Ser Asp Gln
            420                 425                 430

Val Glu Thr Tyr Leu Asp Lys Tyr Ile Ser Ala Ser Thr Lys Lys Tyr
        435                 440                 445

Tyr Glu Gln Tyr Thr Asn Phe Ser Gly Arg Ala Phe Pro Asp Val Ser
    450                 455                 460

Ala Phe Ala Gly Ser Pro Tyr Tyr Glu Thr Tyr Ile Asp Gly Gln Leu
465                 470                 475                 480

Gly Leu Val Ala Gly Thr Ser Gly Ala Ser Pro Val Phe Ala Gly Ile
                485                 490                 495

Val Ala Leu Leu Asn Asp Ala Arg Leu Arg Ala Asn Lys Thr Ser Leu
            500                 505                 510

Gly Phe Leu Asn Pro Trp Leu Tyr Ser Ser Gly Tyr Lys Ser Leu Asn
        515                 520                 525

Asp Ile Thr Ser Gly Glu Ala Val Gly Cys Gln Gly Asp Val Glu Gly
    530                 535                 540

Ala Gly Val Ile Pro Trp Ala Ser Trp Asn Ala Thr Thr Gly Trp Asp
545                 550                 555                 560

Pro Ala Thr Gly Leu Gly Thr Pro Asn Phe Ala Lys Leu Lys Glu Ala
```

-continued

```
                565                 570                 575
Val Leu Ala Leu
        580

<210> SEQ ID NO 127
<211> LENGTH: 631
<212> TYPE: PRT
<213> ORGANISM: Aspergillus niger

<400> SEQUENCE: 127

Met His Gly Leu Arg Leu Val Cys Ser Ile Gly Thr Leu Pro Leu Val
1               5                   10                  15

Ile Leu Ala Tyr Pro Ala Ala Ser Leu His Thr Thr Ser Ala Ala Val
            20                  25                  30

Asp Leu Asp Ser Leu Arg Leu Thr Ser Asn Ser Glu Tyr Val Asn Ser
        35                  40                  45

Val His Val Asp Thr Asn Arg Ser Val Ala Val Ser Ala Glu Glu His
    50                  55                  60

Tyr Thr Asp Thr Ala Ala Arg Leu Val Gln Asn Ile Val Pro Gly Ala
65                  70                  75                  80

Ser Phe Arg Leu Ile Asp Asp His Phe Val Gly Asp Asn Gly Val Ala
                85                  90                  95

His Val Tyr Phe Arg Gln Thr Leu His Gly Ile Asp Ile Asp Asn Ala
            100                 105                 110

Asp Phe Asn Val Asn Ile Gly Lys Asp Gly Leu Val Leu Ser Phe Gly
        115                 120                 125

His Ser Phe Phe Thr Gly Ala Leu Pro Ser Ser His Leu Asp Asn Thr
    130                 135                 140

Asn Val Leu Ser Pro Glu Ala Ala Leu Arg Gly Ala Arg Asp Ala Ile
145                 150                 155                 160

Gln Leu Pro Leu Thr Ile Asp Asn Val Ser Thr Glu Ala Ala Glu Gly
                165                 170                 175

Arg Asn Glu Tyr Ile Phe Arg Glu Ala Val Gly Ala Val Ser Asp Pro
            180                 185                 190

Lys Ala Lys Leu Val Tyr Leu Val Lys Pro Glu Gly Thr Leu Ala Leu
        195                 200                 205

Thr Trp Arg Ile Glu Thr Asp Met Tyr Glu His Trp Leu Leu Thr Tyr
    210                 215                 220

Ile Asp Ala Glu Thr Thr Val His Gly Val Val Asp Tyr Val Ala
225                 230                 235                 240

Asp Ala Thr Tyr Gln Val Tyr Pro Trp Gly Thr Asn Asp Pro Ala Glu
                245                 250                 255

Gly His Arg Thr Ile Val Thr Asp Pro Trp Asp Leu Ser Ala Ser Ala
            260                 265                 270

Tyr Thr Trp Ile Ser Asp Gly Arg Asp Asn Tyr Thr Thr Thr Arg Gly
        275                 280                 285

Asn Asn Ala Ile Ala His Trp Asn Pro Thr Gly Gly Gly Ser Tyr Leu
    290                 295                 300

Tyr Asn Leu Arg Pro Ser Asp Pro Asn Leu Asn Phe Gln Trp Pro Tyr
305                 310                 315                 320

Ser Pro Asn Met Ser Pro Pro Arg Ser Tyr Ile Asn Ala Ser Ile Val
                325                 330                 335

Gln Leu Phe Tyr Thr Ala Asn Ala Tyr His Asp Leu Leu Tyr Thr Leu
            340                 345                 350
```

```
Gly Phe Thr Glu Ser Ala Gly Asn Phe Gln Trp Asn Asn Ser Ala His
            355                 360                 365

Gly Gly Arg Asp Lys Asp Tyr Val Ile Leu Asn Ala Gln Asp Gly Ser
    370                 375                 380

Gly Phe Ser Asn Ala Asn Phe Ala Thr Pro Pro Asp Gly Ile Pro Gly
385                 390                 395                 400

Arg Met Arg Met Tyr Ile Trp Ile Glu Ser Thr Pro Ser Arg Asp Gly
                405                 410                 415

Ser Phe Asp Ala Gly Ile Val Ile His Glu Tyr Thr His Gly Val Ser
            420                 425                 430

Asn Arg Leu Thr Gly Gly Ser His Asn Ala Gly Cys Leu Ser Ala Leu
            435                 440                 445

Glu Ser Gly Gly Met Gly Glu Gly Trp Gly Asp Phe Met Ala Thr Ala
    450                 455                 460

Ile Arg Ile Lys Pro Asn Asp Thr Arg Thr Thr Ser Tyr Thr Met Gly
465                 470                 475                 480

Ala Trp Ala Asp Asn Asp Lys Cys Gly Val Arg Asp Tyr Pro Tyr Ser
                485                 490                 495

Thr Ser Phe Thr Glu Asn Pro Leu Asn Tyr Thr Ser Val Asn Thr Met
            500                 505                 510

Asn Gly Val His Ala Ile Gly Thr Val Trp Ala Thr Met Leu Tyr Glu
            515                 520                 525

Val Leu Trp Asn Leu Ile Asp Lys Tyr Gly Lys Asn Asp Gly Ser Arg
530                 535                 540

Pro Val Phe Arg Asn Gly Val Pro Thr Asp Gly Lys Tyr Leu Met Met
545                 550                 555                 560

Lys Leu Val Val Asp Gly Met Ala Leu Gln Pro Cys Asn Pro Asn Phe
                565                 570                 575

Val Gln Ala Arg Asp Ala Ile Leu Asp Ala Asp Ile Val Leu Thr Gly
            580                 585                 590

Gly Lys Asn Arg Cys Glu Ile Trp Arg Gly Phe Ala Lys Arg Gly Leu
        595                 600                 605

Gly Gln Gly Ala Ala His Ser Ser Leu Asn Trp Met Arg Arg Gly Ser
    610                 615                 620

Thr Leu Leu Pro Thr Gly Cys
625                 630

<210> SEQ ID NO 128
<211> LENGTH: 394
<212> TYPE: PRT
<213> ORGANISM: Aspergillus niger

<400> SEQUENCE: 128

Met Val Val Phe Ser Lys Thr Ala Ala Leu Val Leu Gly Leu Ser Ser
1               5                   10                  15

Ala Val Ser Ala Ala Pro Ala Pro Thr Arg Lys Gly Phe Thr Ile Asn
            20                  25                  30

Gln Ile Ala Arg Pro Ala Asn Lys Thr Arg Thr Ile Asn Leu Pro Gly
        35                  40                  45

Met Tyr Ala Arg Ser Leu Ala Lys Phe Gly Gly Thr Val Pro Gln Ser
    50                  55                  60

Val Lys Glu Ala Ala Ser Lys Gly Ser Ala Val Thr Pro Gln Asn
65                  70                  75                  80

Asn Asp Glu Glu Tyr Leu Thr Pro Val Thr Val Gly Lys Ser Thr Leu
                85                  90                  95
```

-continued

```
His Leu Asp Phe Asp Thr Gly Ser Ala Asp Leu Trp Val Phe Ser Asp
            100                 105                 110

Glu Leu Pro Ser Ser Glu Gln Thr Gly His Asp Leu Tyr Thr Pro Ser
        115                 120                 125

Ser Ser Ala Thr Lys Leu Ser Gly Tyr Thr Trp Asp Ile Ser Tyr Gly
    130                 135                 140

Asp Gly Ser Ser Ala Ser Gly Asp Val Tyr Arg Asp Thr Val Thr Val
145                 150                 155                 160

Gly Gly Val Thr Asn Lys Gln Ala Val Glu Ala Ser Lys Ile
                165                 170                 175

Ser Ser Glu Phe Val Gln Asn Thr Ala Asn Asp Gly Leu Leu Gly Leu
            180                 185                 190

Ala Phe Ser Ser Ile Asn Thr Val Gln Pro Lys Ala Gln Thr Thr Phe
            195                 200                 205

Phe Asp Thr Val Lys Ser Gln Leu Asp Ser Pro Leu Phe Ala Val Gln
        210                 215                 220

Leu Lys His Asp Ala Pro Gly Val Tyr Asp Phe Gly Tyr Ile Asp Asp
225                 230                 235                 240

Ser Lys Tyr Thr Gly Ser Ile Thr Tyr Thr Asp Ala Asp Ser Ser Gln
                245                 250                 255

Gly Tyr Trp Gly Phe Ser Thr Asp Gly Tyr Ser Ile Gly Asp Gly Ser
            260                 265                 270

Ser Ser Ser Ser Gly Phe Ser Ala Ile Ala Asp Thr Gly Thr Thr Leu
        275                 280                 285

Ile Leu Leu Asp Asp Glu Ile Val Ser Ala Tyr Tyr Glu Gln Val Ser
        290                 295                 300

Gly Ala Gln Glu Ser Glu Glu Ala Gly Gly Tyr Val Phe Ser Cys Ser
305                 310                 315                 320

Thr Asn Pro Pro Asp Phe Thr Val Val Ile Gly Asp Tyr Lys Ala Val
                325                 330                 335

Val Pro Gly Lys Tyr Ile Asn Tyr Ala Pro Ile Ser Thr Gly Ser Ser
            340                 345                 350

Thr Cys Phe Gly Gly Ile Gln Ser Asn Ser Gly Leu Gly Leu Ser Ile
        355                 360                 365

Leu Gly Asp Val Phe Leu Lys Ser Gln Tyr Val Val Phe Asn Ser Glu
    370                 375                 380

Gly Pro Lys Leu Gly Phe Ala Ala Gln Ala
385                 390

<210> SEQ ID NO 129
<211> LENGTH: 398
<212> TYPE: PRT
<213> ORGANISM: Aspergillus niger

<400> SEQUENCE: 129

Met Lys Ser Ala Ser Leu Leu Thr Ala Ser Val Leu Leu Gly Cys Ala
1               5                   10                  15

Ser Ala Glu Val His Lys Leu Lys Leu Asn Lys Val Pro Leu Glu Glu
            20                  25                  30

Gln Leu Tyr Thr His Asn Ile Asp Ala His Val Arg Ala Leu Gly Gln
        35                  40                  45

Lys Tyr Met Gly Ile Arg Pro Ser Ile His Lys Glu Leu Val Glu Glu
    50                  55                  60

Asn Pro Ile Asn Asp Met Ser Arg His Asp Val Leu Val Asp Asn Phe
```

-continued

```
                65                  70                  75                  80
Leu Asn Ala Gln Tyr Phe Ser Glu Ile Glu Leu Gly Thr Pro Pro Gln
                    85                  90                  95
Lys Phe Lys Val Val Leu Asp Thr Gly Ser Ser Asn Leu Trp Val Pro
                100                 105                 110
Ser Ser Glu Cys Ser Ser Ile Ala Cys Tyr Leu His Asn Lys Tyr Asp
                115                 120                 125
Ser Ser Ala Ser Ser Thr Tyr His Lys Asn Gly Ser Glu Phe Ala Ile
            130                 135                 140
Lys Tyr Gly Ser Gly Ser Leu Ser Gly Phe Ile Ser Gln Asp Thr Leu
145                 150                 155                 160
Lys Ile Gly Asp Leu Lys Val Lys Gly Gln Asp Phe Ala Glu Ala Thr
                165                 170                 175
Asn Glu Pro Gly Leu Ala Phe Ala Phe Gly Arg Phe Asp Gly Ile Leu
                180                 185                 190
Gly Leu Gly Tyr Asp Thr Ile Ser Val Asn Lys Ile Val Pro Pro Phe
            195                 200                 205
Tyr Asn Met Leu Asp Gln Gly Leu Leu Asp Glu Pro Val Phe Ala Phe
210                 215                 220
Tyr Leu Gly Asp Thr Asn Lys Glu Gly Asp Glu Ser Val Ala Thr Phe
225                 230                 235                 240
Gly Gly Val Asp Lys Asp His Tyr Thr Gly Glu Leu Ile Lys Ile Pro
                245                 250                 255
Leu Arg Arg Lys Ala Tyr Trp Glu Val Glu Leu Asp Ala Ile Ala Leu
                260                 265                 270
Gly Asp Asp Val Ala Glu Met Glu Asn Thr Gly Val Ile Leu Asp Thr
                275                 280                 285
Gly Thr Ser Leu Ile Ala Leu Pro Ala Asp Leu Ala Glu Met Ile Asn
            290                 295                 300
Ala Gln Ile Gly Ala Lys Lys Gly Trp Thr Gly Gln Tyr Thr Val Asp
305                 310                 315                 320
Cys Asp Lys Arg Ser Ser Leu Pro Asp Val Thr Phe Thr Leu Ala Gly
                325                 330                 335
His Asn Phe Thr Ile Ser Ser Tyr Asp Tyr Thr Leu Glu Val Gln Gly
                340                 345                 350
Ser Cys Val Ser Ala Phe Met Gly Met Asp Phe Pro Glu Pro Val Gly
            355                 360                 365
Pro Leu Ala Ile Leu Gly Asp Ala Phe Leu Arg Lys Trp Tyr Ser Val
            370                 375                 380
Tyr Asp Leu Gly Asn Ser Ala Val Gly Leu Ala Lys Ala Lys
385                 390                 395

<210> SEQ ID NO 130
<211> LENGTH: 393
<212> TYPE: PRT
<213> ORGANISM: Aspergillus niger

<400> SEQUENCE: 130

Met Arg Lys Tyr Arg Phe His Pro Thr Lys Pro Gly Pro Tyr Thr Leu
1               5                   10                  15
Ser Ser Ser Ile Gln Gln Thr Gly Arg Pro Tyr Thr Glu Lys Pro Ile
                20                  25                  30
Gly Gly Arg Ala His Ile Arg Gln Leu Val Arg Lys Lys Ser Thr Thr
            35                  40                  45
```

```
Ser Asp Glu Val Gly Glu Val Pro Ala Glu Asp Val Gln Asn Asp Ser
 50                  55                  60

Met Tyr Leu Ala Thr Val Gly Ile Gly Thr Pro Ala Gln Asn Leu Lys
 65                      70                  75                  80

Leu Asp Phe Asp Thr Gly Ser Ala Asp Leu Trp Val Trp Ser Asn Lys
                 85                  90                  95

Leu Pro Ser Thr Leu Ser Glu Asn Lys Thr His Ala Ile Phe Asp
            100                 105                 110

Ser Ser Lys Ser Ser Thr Phe Lys Thr Leu Glu Gly Glu Ser Trp Gln
            115                 120                 125

Ile Ser Tyr Gly Asp Gly Ser Ala Ser Gly Ser Val Gly Thr Asp
    130                 135                 140

Asp Val Asn Ile Gly Gly Val Val Lys Asn Gln Ala Val Glu Leu
145                 150                 155                 160

Ala Glu Lys Met Ser Ser Thr Phe Ala Gln Gly Glu Gly Asp Gly Leu
                165                 170                 175

Leu Gly Leu Ala Phe Ser Asn Ile Asn Thr Val Gln Pro Lys Ser Val
            180                 185                 190

Lys Thr Pro Val Glu Asn Met Ile Leu Gln Asp Ile Pro Lys Ser
            195                 200                 205

Ala Glu Leu Phe Thr Ala Lys Leu Asp Thr Trp Arg Asp Thr Asp
210                 215                 220

Glu Ser Phe Tyr Thr Phe Gly Phe Ile Asp Gln Asp Leu Val Lys Thr
225                 230                 235                 240

Ala Gly Glu Glu Val Tyr Tyr Thr Pro Val Asp Asn Ser Gln Gly Phe
                245                 250                 255

Trp Leu Phe Asn Ser Thr Ser Ala Thr Val Asn Gly Lys Thr Ile Asn
            260                 265                 270

Arg Ser Gly Asn Thr Ala Ile Ala Asp Thr Gly Thr Thr Leu Ala Leu
            275                 280                 285

Val Asp Asp Asp Thr Cys Glu Ala Ile Tyr Ser Ala Ile Asp Gly Ala
290                 295                 300

Tyr Tyr Asp Gln Glu Val Gln Gly Trp Ile Tyr Pro Thr Asp Thr Ala
305                 310                 315                 320

Gln Asp Lys Leu Pro Thr Val Ser Phe Ala Val Gly Glu Lys Gln Phe
                325                 330                 335

Val Val Gln Lys Glu Asp Leu Ala Phe Ser Glu Ala Lys Thr Gly Tyr
            340                 345                 350

Val Tyr Gly Gly Ile Gln Ser Arg Gly Asp Met Thr Met Asp Ile Leu
            355                 360                 365

Gly Asp Thr Phe Leu Lys Ser Ile Tyr Ala Val Ser Ala Leu Leu Leu
370                 375                 380

Ala Leu Arg Gly Asp Ile Glu Ala His
385                 390

<210> SEQ ID NO 131
<211> LENGTH: 282
<212> TYPE: PRT
<213> ORGANISM: Aspergillus niger

<400> SEQUENCE: 131

Met Lys Phe Ser Thr Ile Leu Thr Gly Ser Leu Phe Ala Thr Ala Ala
 1               5                  10                  15

Leu Ala Ala Pro Leu Thr Glu Lys Arg Arg Ala Arg Lys Glu Ala Arg
                20                  25                  30
```

```
Ala Ala Gly Lys Arg His Ser Asn Pro Pro Tyr Ile Pro Gly Ser Asp
        35                  40                  45

Lys Glu Ile Leu Lys Leu Asn Gly Thr Ser Asn Glu Asp Tyr Ser Ser
 50                  55                  60

Asn Trp Ala Gly Ala Val Leu Ile Gly Asp Gly Tyr Thr Lys Val Thr
 65                  70                  75                  80

Gly Glu Phe Thr Val Pro Ser Val Ser Ala Gly Ser Ser Ser Ser Ser
                 85                  90                  95

Gly Tyr Gly Gly Gly Tyr Gly Tyr Tyr Lys Asn Lys Arg Gln Ser Glu
            100                 105                 110

Glu Tyr Cys Ala Ser Ala Trp Val Gly Ile Asp Gly Asp Thr Cys Glu
            115                 120                 125

Thr Ala Ile Leu Gln Thr Gly Val Asp Phe Cys Tyr Glu Asp Gly Gln
        130                 135                 140

Thr Ser Tyr Asp Ala Trp Tyr Glu Trp Tyr Pro Asp Tyr Ala Tyr Asp
145                 150                 155                 160

Phe Asn Asp Ile Thr Ile Ser Glu Gly Asp Thr Ile Lys Val Thr Val
                165                 170                 175

Glu Ala Thr Ser Lys Ser Ser Gly Ser Ala Thr Val Glu Asn Leu Thr
            180                 185                 190

Thr Gly Gln Ser Val Thr His Thr Phe Ser Gly Asn Val Glu Gly Asp
        195                 200                 205

Leu Cys Glu Thr Asn Ala Glu Trp Ile Val Glu Asp Phe Glu Ser Gly
    210                 215                 220

Asp Ser Leu Val Ala Phe Ala Asp Phe Gly Ser Val Thr Phe Thr Asn
225                 230                 235                 240

Ala Glu Ala Thr Ser Asp Gly Ser Thr Val Gly Pro Ser Asp Ala Thr
                245                 250                 255

Val Met Asp Ile Glu Gln Asp Gly Thr Val Leu Thr Glu Thr Ser Val
            260                 265                 270

Ser Gly Asp Ser Val Thr Val Thr Tyr Val
        275                 280

<210> SEQ ID NO 132
<211> LENGTH: 273
<212> TYPE: PRT
<213> ORGANISM: Aspergillus niger

<400> SEQUENCE: 132

Met Gly Asp Tyr Gly Pro Gly Val Ser Ser Leu Thr Ala Gln Leu Pro
1               5                   10                  15

Gly Asn Pro Pro Val Ser Glu Thr Asp Gln Asp Glu Ile Ser Val Leu
            20                  25                  30

Val Thr Gly Phe Gly Pro Phe Lys Ser Asn Leu Val Asn Ala Ser Tyr
        35                  40                  45

Leu Ile Ala Ser Ser Leu Pro Pro Ser Phe Thr Phe Ser Pro Ala Ser
    50                  55                  60

Ser Asp Gly Ser Asp Ala Val Pro Arg Arg Val Ser Ile Asn Val His
65                  70                  75                  80

Pro Ser Pro Ile Pro Val Ala Tyr Ser Ser Val Arg Thr Thr Leu Pro
                85                  90                  95

Val Ile Leu Asp Asp Tyr Ala Lys Thr His Gly Gly Arg Arg Pro Asp
            100                 105                 110

Ile Val Ile His Ile Gly Ile Ala Ala Met Arg Asn Tyr Tyr Ser Val
```

```
                    115                 120                     125
Glu Thr Gln Ala His Arg Asp Gly Tyr Leu Met Ser Asp Ile Lys Gly
    130                 135                 140

Arg Ser Gly Tyr Glu Asp Gly Glu Lys Leu Trp Arg Glu Leu Asp Leu
145                 150                 155                 160

Pro Leu Val Leu Arg Ala Gly Pro Ser Glu Gly His Ala Ser Glu Lys
                165                 170                 175

Lys His Leu Ser Pro Arg Pro Pro Asp Glu Asp Phe Leu Ala Ala Trp
            180                 185                 190

Lys Thr Phe Cys Pro Pro Glu Thr Asp Ala Arg Ile Ser Thr Asp Ala
        195                 200                 205

Gly Arg Tyr Leu Cys Glu Phe Ile Leu Tyr Thr Ser Leu Ala Leu Ala
    210                 215                 220

Tyr Gln Ala Gly Glu Asp Arg Asn Val Thr Phe Phe His Val Pro Ala
225                 230                 235                 240

Ser Cys Leu Asp Glu Asp Ile Glu Thr Gly Lys Glu Val Ala Val Ala
                245                 250                 255

Leu Ile Lys Ala Leu Val Thr Ser Trp Ser Glu Gln Gln His Ser Val
            260                 265                 270

Pro

<210> SEQ ID NO 133
<211> LENGTH: 542
<212> TYPE: PRT
<213> ORGANISM: Aspergillus niger

<400> SEQUENCE: 133

Met Gly Ser Arg Gln Gly Lys Ala Pro Phe Gly Trp Gly Thr Gln Ser
1               5                   10                  15

Leu Ala His Phe Gly Ile Asn Pro Asp Leu Gly Leu His Asn Gln Gln
            20                  25                  30

Asn Leu Asn Ser Leu Ile Ser His Ser Ala Met Ala Thr Ala Leu Glu
        35                  40                  45

Thr Glu Tyr Ala Thr Ile Pro Ile Asp His Asn Asn Ala Ser Ala Gly
    50                  55                  60

Thr Tyr Gln Asn Arg Phe Trp Val Ser Asp Glu Phe Tyr Gln Pro Gly
65                  70                  75                  80

Asn Pro Ile Phe Val Tyr Asp Thr Gly Glu Ser Asp Gly Gly Ser Ile
                85                  90                  95

Ala Gln Ser Tyr Leu Thr Ser Thr Leu Ser Phe Phe Arg Glu Phe Leu
            100                 105                 110

Ile Glu Phe Asn Ala Met Gly Ile Ala Trp Glu His Arg Tyr Tyr Gly
        115                 120                 125

Asn Ser Thr Pro Ala Pro Val Ser Tyr Glu Thr Pro Pro Glu Ala Trp
    130                 135                 140

Gln Tyr Leu Thr Thr Lys Gln Ala Leu Ala Asp Leu Pro Tyr Phe Ala
145                 150                 155                 160

Ser Asn Phe Ser Arg Glu Lys Tyr Pro Asp Met Asp Leu Thr Pro Gln
                165                 170                 175

Gly Thr Pro Trp Ile Met Val Gly Gly Ser Tyr Ala Gly Ile Arg Ala
            180                 185                 190

Ala Leu Thr Arg Lys Glu Tyr Pro Glu Thr Ile Phe Ala Ala Phe Ser
        195                 200                 205

Ser Ser Ser Pro Val Glu Ala Gln Val Asn Met Ser Ala Tyr Tyr Asp
```

```
            210                 215                 220
Gln Val Tyr Arg Gly Met Val Ala Ser Gly Trp Thr Asn Cys Ser Ala
225                 230                 235                 240

Asp Ile His Ala Ala Leu Glu Tyr Ile Asp Asp Gln Leu Ser Asp Glu
                245                 250                 255

Asp Thr Ala Thr Ser Val Lys Gln Leu Phe Gly Ser Gly Ala Glu
                260                 265                 270

Thr Asn Ser Asn Gly Asp Phe Thr Ala Leu Thr Ala Ile Tyr Gly
                275                 280                 285

Tyr Phe Gln Ser Tyr Gly Met Ala Gly Gly Ile Gly Gly Leu Gly Ala
290                 295                 300

Phe Cys Glu Tyr Leu Glu Ile Asp Pro Lys Thr Asn Gly Thr Thr Gly
305                 310                 315                 320

Pro Asp Gly Leu Ala Pro Thr Tyr Gly Gly Gln Tyr Val Ala Glu Arg
                325                 330                 335

Trp Ala Ala Trp Pro Thr Phe Leu Glu Leu Val Asn Leu Asn Met Gly
                340                 345                 350

Thr Asn Cys Gly Pro Gln Asp Ala Ser Gln Pro Ile Asp Cys Asp Phe
                355                 360                 365

Ser Lys Pro Tyr Gly Asp Pro Ser Ala Ile Thr Trp Thr Trp Gln Tyr
370                 375                 380

Cys Ser Glu Trp Gly Phe Phe Gln Ala Asn Asn Asp Gly Pro His Ser
385                 390                 395                 400

Leu Ala Ser Arg Tyr Gln Ser Val Glu Tyr Gln Gln Glu Val Cys Asn
                405                 410                 415

Arg Gln Phe Pro Asp Ala Val Asp Lys Gly Leu Leu Pro Pro Ser Pro
                420                 425                 430

Arg Ala Asp Asp Val Asn Gln Glu Phe Gly Gly Trp Thr Ile Arg Pro
                435                 440                 445

Ser Asn Val Tyr Phe Ser Gly Gly Glu Phe Asp Pro Trp Arg Ser Leu
450                 455                 460

Ser Ile Leu Ser Thr Glu Asp Phe Ala Pro Gln Gly Val Glu Phe Thr
465                 470                 475                 480

Ser Ala Ile Pro Ala Cys Gly Val Gln Thr Asn Glu Asp Thr Val Phe
                485                 490                 495

Gly Tyr Val Met Gln Asn Ser Glu His Cys Phe Asp Phe Gln Ala Thr
                500                 505                 510

Pro Thr Val Gly Lys Leu Ser Arg Gly Ile Phe Thr Ser Ala Leu Leu
                515                 520                 525

Gln Trp Leu Glu Cys Phe Gly Gln Asn Ser Ser Gln Ser Arg
530                 535                 540

<210> SEQ ID NO 134
<211> LENGTH: 391
<212> TYPE: PRT
<213> ORGANISM: Aspergillus niger

<400> SEQUENCE: 134

Met Lys Leu Ser Ile Ala Leu Ala Leu Gly Ala Thr Ala Ser Thr Gly
1               5                   10                  15

Val Leu Ala Ala Val Val Pro Gln Gln Glu Pro Leu Ile Thr Pro Gln
                20                  25                  30

Asp Pro Pro Thr His His Gln Glu Lys Phe Leu Ile Glu Leu Ala
                35                  40                  45
```

```
Pro Tyr Gln Thr Arg Trp Val Thr Glu Glu Lys Trp Asp Leu Lys
    50                  55                  60

Leu Asp Gly Val Asn Phe Ile Asp Ile Thr Glu Arg Asn Thr Gly
65                  70                  75                  80

Phe Tyr Pro Thr Leu His Ala Gly Ser Tyr Val His Tyr Pro Pro Thr
                85                  90                  95

Met Lys His Ala Glu Lys Val Val Pro Leu Leu Arg Gly Leu Ser Lys
            100                 105                 110

Asp Asn Met Glu Gln Asn Leu Asn Lys Phe Thr Ser Phe His Thr Arg
            115                 120                 125

Tyr Tyr Arg Ser Ser Thr Gly Ile Glu Ser Ala Lys Trp Leu Tyr Ser
    130                 135                 140

Arg Val Ser Asp Val Ile Glu Gln Ser Gly Ala Ala Glu Tyr Gly Ala
145                 150                 155                 160

Thr Val Glu Gln Phe Ala His Ser Trp Gly Gln Phe Ser Ile Ile Ala
                165                 170                 175

Arg Ile Pro Gly Gln Thr Asn Lys Thr Val Val Leu Gly Ala His Gln
                180                 185                 190

Asp Ser Ile Asn Leu Phe Leu Pro Ser Ile Leu Ala Ala Pro Gly Ala
    195                 200                 205

Asp Asp Asp Gly Ser Gly Thr Val Thr Ile Leu Glu Ala Leu Arg Gly
210                 215                 220

Leu Leu Gln Ser Asp Ala Ile Val Arg Gly Asn Ala Ser Asn Thr Ile
225                 230                 235                 240

Glu Phe His Trp Tyr Ser Ala Glu Glu Gly Gly Met Leu Gly Ser Gln
                245                 250                 255

Ala Ile Phe Ser Gln Tyr Lys Arg Asp Lys Arg Asp Ile Lys Ala Met
                260                 265                 270

Leu Gln Gln Asp Met Thr Gly Tyr Thr Gln Gly Ala Leu Asp Ala Gly
        275                 280                 285

Arg Gln Glu Ala Ile Gly Ile Met Val Asp Tyr Val Asp Glu Gly Leu
    290                 295                 300

Thr Gln Phe Leu Lys Asp Val Thr Thr Glu Tyr Cys Gly Ile Gly Tyr
305                 310                 315                 320

Ile Glu Thr Arg Cys Gly Tyr Ala Cys Ser Asp His Thr Ser Ala Ser
                325                 330                 335

Lys Tyr Gly Tyr Pro Ala Ala Met Ala Thr Glu Ser Glu Met Glu Asn
            340                 345                 350

Ser Asn Lys Arg Ile His Thr Thr Asp Asp Ser Ile Arg Tyr Leu Ser
        355                 360                 365

Phe Asp His Met Leu Glu His Ala Arg Leu Thr Leu Gly Phe Ala Tyr
    370                 375                 380

Glu Leu Ala Phe Ala Gln Phe
385                 390

<210> SEQ ID NO 135
<211> LENGTH: 442
<212> TYPE: PRT
<213> ORGANISM: Aspergillus niger

<400> SEQUENCE: 135

Met Arg Thr Thr Thr Ser Phe Ala Arg Leu Ala Leu Ala Val Ala Ser
1               5                   10                  15

Val Gly Ile Val Phe Ala Ser Pro Thr Lys Asn Asn Asp Gly Lys Leu
            20                  25                  30
```

-continued

```
Val Tyr Gly Ser Pro Glu Ser Val Gly Met Ile Ser Ala Pro Leu His
         35                  40                  45

Gln Met Val Gln Asn Val Ser Ala Tyr Thr His Ala Ala Asn Tyr Ser
 50                  55                  60

Lys Phe Ser Tyr Asp Lys Val His Pro Ile Glu Pro Gly Ser Val Thr
 65                  70                  75                  80

Leu Val Ala Leu Asp Gly Val Ile Val Ser Glu Phe Ala Leu Gly Lys
                 85                  90                  95

Arg Asn Leu Tyr Ala Asp Val Asn Gly Thr Asn Leu Pro Arg Tyr Leu
            100                 105                 110

Gln Glu Asp Thr Thr Leu Asp Thr Val Tyr Asp Met Ala Ser Leu Thr
        115                 120                 125

Lys Leu Phe Thr Thr Val Ala Ala Leu Arg Glu Leu Asp Ala Gly Arg
    130                 135                 140

Ile Ala Leu Asn Val Thr Val Ala Thr Tyr Ile Pro Asp Phe Ala Thr
145                 150                 155                 160

Asn Gly Lys Glu Asn Ile Thr Ile Leu Glu Leu Phe Thr His Thr Ser
                165                 170                 175

Gly Phe Ala Ser Asp Pro Ser Pro Pro Leu Phe Ser Ala Tyr Tyr Thr
            180                 185                 190

Thr Tyr Asp Glu Arg Ile Lys Ala Ile Leu Thr Gln Lys Ile Ile Asn
        195                 200                 205

Thr Pro Gly Ser Thr Tyr Leu Tyr Leu Asp Leu Asn Phe Met Ser Leu
    210                 215                 220

Gly Leu Val Ile Glu Thr Val Thr Gly Arg Ala Leu Asp Asp Leu Ile
225                 230                 235                 240

Tyr Asp Phe Thr Arg Pro Leu Glu Met Thr Ser Thr Phe Phe Asn Arg
                245                 250                 255

Gly Asn Ile Glu Gly Ser Thr Pro Gln Ser Pro Asn Tyr Asp Arg Thr
            260                 265                 270

Ala Val Gln Glu Phe Gln Ile Ala Ala Leu Gly Pro Ser Glu Pro Gln
        275                 280                 285

Arg Pro Gln Pro Val Arg Gly Thr Val His Asp Glu Asn Ala Trp Ser
    290                 295                 300

Leu Asp Gly Val Ser Gly His Ala Gly Leu Phe Ser Thr Val Arg Asp
305                 310                 315                 320

Thr Ala Thr Phe Cys Gln Met Ile Leu Asn Asn Gly Thr Tyr Ala Gly
                325                 330                 335

Gln Arg Ile Leu Ser Arg Thr Ala Val Asp Met Ile Phe Thr Asn Phe
            340                 345                 350

Asn Ala Arg Phe Pro Gly Asp Ala Arg Ser Leu Gly Phe Glu Leu Asp
        355                 360                 365

Gln Tyr Ser Thr Ala Gly Pro Met Ala Ser Leu Gln Thr Ala Ser His
    370                 375                 380

Thr Gly Phe Thr Gly Thr Thr Leu Val Met Asp Arg Thr Tyr Asn Ala
385                 390                 395                 400

Phe Trp Leu His Phe Ser Asn Arg Val His Pro Ser Arg Ala Trp Ser
                405                 410                 415

Ser Asn Thr Ile Val Arg Glu Ala Ile Gly Tyr Trp Val Gly Lys Ser
            420                 425                 430

Leu Gly Leu Asp Val Ala Phe Ala Leu Leu
        435                 440
```

<210> SEQ ID NO 136
<211> LENGTH: 612
<212> TYPE: PRT
<213> ORGANISM: Aspergillus niger

<400> SEQUENCE: 136

```
Met Ala Ser Trp Leu Leu Ser Thr Leu Leu Phe Leu Ser Pro Ser Leu
 1               5                  10                  15

Val Ser Ala Lys Ser Ala Ala Asp Tyr Tyr Val His Ser Leu Pro Gly
            20                  25                  30

Ala Pro Glu Gly Pro Leu Leu Lys Met His Ala Gly His Ile Glu Val
        35                  40                  45

Asp Pro Gln Asn Asn Gly Asn Leu Phe Phe Trp His Tyr Gln Asn Arg
    50                  55                  60

His Ile Ala Asn Arg Gln Arg Thr Val Ile Trp Leu Asn Gly Gly Pro
65                  70                  75                  80

Gly Cys Ser Ser Met Asp Gly Ala Leu Met Glu Val Gly Pro Tyr Arg
                85                  90                  95

Leu Lys Asp Asn Glu Thr Leu Thr Tyr Asn Glu Gly Ser Trp Asp Glu
            100                 105                 110

Phe Ala Asn Leu Leu Phe Val Asp Gln Pro Val Gly Thr Gly Phe Ser
        115                 120                 125

Tyr Val Asn Thr Asp Ser Tyr Leu His Glu Leu Asp Glu Met Ser Ala
    130                 135                 140

Gln Phe Ile Val Phe Leu Glu Glu Trp Phe Arg Leu Phe Pro Glu Tyr
145                 150                 155                 160

Glu Arg Asp Asp Ile Tyr Ile Ala Gly Glu Ser Tyr Ala Gly Gln His
                165                 170                 175

Ile Pro Tyr Ile Ala Lys Ala Ile Gln Glu Arg Asn Lys Asn Val Gln
            180                 185                 190

Gly Lys Thr Ile Ala Ser Trp Asn Leu Lys Gly Leu Leu Ile Gly Asn
        195                 200                 205

Gly Trp Ile Ser Pro Asn Glu Gln Tyr Met Ser Tyr Leu Pro Tyr Ala
    210                 215                 220

Tyr Glu Glu Gly Leu Ile Lys Glu Gly Ser Arg Thr Ala Lys Glu Leu
225                 230                 235                 240

Glu Val Leu Gln Ser Val Cys Lys Ser Arg Leu Glu Thr Gly Lys Asn
                245                 250                 255

Lys Val His Leu Asn Asp Cys Glu Lys Val Met Asn Ala Leu Leu Asp
            260                 265                 270

Lys Thr Val Glu Asp Asn Lys Cys Leu Asn Met Tyr Asp Ile Arg Leu
        275                 280                 285

Arg Asp Thr Thr Asp Ala Cys Gly Met Asn Trp Pro Thr Asp Leu Glu
    290                 295                 300

Asp Val Lys Pro Tyr Leu Gln Arg Glu Asp Val Lys Ala Leu Asn
305                 310                 315                 320

Ile Asn Pro Glu Lys Lys Ser Gly Trp Val Glu Cys Ser Gly Ala Val
                325                 330                 335

Ser Ser Ala Phe Asn Pro Gln Lys Ser Pro Ser Val Gln Leu Leu
            340                 345                 350

Pro Gly Leu Leu Glu Ser Gly Leu Gln Ile Leu Phe Ser Gly Asp
        355                 360                 365

Lys Asp Leu Ile Cys Asn His Val Gly Thr Glu Gln Leu Ile Asn Asn
    370                 375                 380
```

-continued

```
Met Lys Trp Asn Gly Gly Thr Gly Phe Glu Thr Ser Pro Gly Val Trp
385                 390                 395                 400

Ala Pro Arg His Asp Trp Ser Phe Glu Gly Glu Pro Ala Gly Ile Tyr
            405                 410                 415

Gln Tyr Ala Arg Asn Leu Thr Tyr Val Leu Ile Tyr Asn Ala Ser His
            420                 425                 430

Met Val Pro Tyr Asp Leu Pro Arg Gln Ser Arg Asp Met Leu Asp Arg
            435                 440                 445

Phe Met Asn Val Asp Ile Ala Ser Ile Gly Ser Pro Ala Asp Ser
450                 455                 460

Arg Ile Asp Gly Glu Lys Leu Pro Gln Thr Ser Val Gly His Pro
465                 470                 475                 480

Asn Ser Thr Ala Ala Glu Glu Gln Glu Lys Glu Arg Ile Lys Glu Thr
            485                 490                 495

Glu Trp Lys Ala Tyr Ala Lys Ser Gly Glu Ala Val Leu Leu Val Val
            500                 505                 510

Ile Ile Gly Val Leu Val Trp Gly Phe Phe Ile Trp Arg Ser Arg Arg
            515                 520                 525

Arg His Gln Gly Tyr Arg Gly Val Trp His Lys Asp Met Ser Gly Ser
530                 535                 540

Ser Val Leu Glu Arg Phe His Asn Lys Arg Thr Gly Gly Ala Asp Val
545                 550                 555                 560

Glu Ala Gly Asp Phe Asp Glu Ala Glu Leu Asp Asp Leu His Ser Pro
            565                 570                 575

Asp Leu Glu Arg Glu His Tyr Ala Val Gly Glu Asp Ser Asp Glu Asp
            580                 585                 590

Asp Ile Ser Arg Gln His Ser Gln Gln Ala Ser Arg Ala Gly Gly Ser
            595                 600                 605

His Asn Leu Ser
    610

<210> SEQ ID NO 137
<211> LENGTH: 531
<212> TYPE: PRT
<213> ORGANISM: Aspergillus niger

<400> SEQUENCE: 137

Met Phe Leu Ile Ser Pro Ala Val Thr Val Ala Ala Leu Leu Leu
1               5                   10                  15

Ile Asn Gly Ala Gly Ala Thr Gln Ser Glu Arg Ser Arg Ala Ala Ala
            20                  25                  30

His Phe Ser Lys Arg His Pro Thr Tyr Arg Ala Ala Thr Arg Ala Gln
        35                  40                  45

Ser Ser Asn Thr Ser Asp Tyr Arg Phe Phe Asn Asn Arg Thr Lys Pro
    50                  55                  60

His Leu Val Glu Ser Leu Pro Asp Val His Phe Asp Val Gly Glu Met
65                  70                  75                  80

Tyr Ser Gly Ser Ile Pro Ile Asp Asp Ser Asn Asn Gly Ser Arg Ser
                85                  90                  95

Leu Phe Tyr Ile Phe Gln Pro Lys Ile Gly Glu Pro Ser Asp Asp Leu
            100                 105                 110

Thr Ile Tyr Leu Asn Gly Gly Pro Gly Cys Ser Ser Glu Gln Gly Phe
        115                 120                 125

Phe Gln Glu Asn Gly Arg Phe Thr Trp Gln Pro Gly Thr Tyr Ala Pro
```

```
            130                 135                 140
Val Ile Asn Glu Tyr Ser Trp Val Asn Leu Thr Asn Met Leu Trp Val
145                 150                 155                 160

Asp Gln Pro Val Gly Thr Gly Phe Ser Val Gly Asn Val Thr Ala Thr
                165                 170                 175

Asn Glu Glu Glu Ile Ala Ala Asp Phe Leu Asp Phe Glu Lys Phe
                180                 185                 190

Glu Asp Leu Tyr Gly Ile Lys Asn Phe Arg Ile Phe Met Thr Gly Glu
                195                 200                 205

Ser Tyr Ala Gly Arg Tyr Val Pro Tyr Ile Ser Ser Ala Met Leu Asp
                210                 215                 220

Lys Asn Asp Thr Thr Arg Phe Asn Leu Ser Gly Ala Leu Leu Tyr Asp
225                 230                 235                 240

Ala Cys Ile Gly Gln Trp Asp Tyr Ile Gln Ala Glu Leu Pro Ala Tyr
                245                 250                 255

Pro Phe Val Lys Gln His Ala Ser Leu Phe Asn Phe Asn Gln Ser Tyr
                260                 265                 270

Met Asn Glu Leu Glu Thr Thr Tyr Glu Glu Cys Gly Tyr Lys Ala Tyr
                275                 280                 285

Phe Asp Glu Tyr Phe Ala Phe Pro Pro Ser Gly Ile Gln Pro Pro Lys
                290                 295                 300

Tyr Met Asn Tyr Ser Glu Cys Asp Ile Tyr Asn Met Ile Tyr Tyr Glu
305                 310                 315                 320

Ala Tyr Asn Pro Asn Pro Cys Phe Asn Pro Tyr Arg Val Ile Asp Glu
                325                 330                 335

Cys Pro Leu Leu Trp Asp Val Leu Gly Trp Pro Thr Asp Leu Ala Tyr
                340                 345                 350

Glu Pro Ala Pro Thr Thr Tyr Phe Asn Arg Ile Asp Val Lys Lys Ala
                355                 360                 365

Leu His Ala Pro Met Asp Val Glu Trp Glu Leu Cys Ser Tyr Asp Leu
                370                 375                 380

Val Phe Ala Gly Gly Asp Ala Asp Pro Gly Pro Glu Gln Gln Gly Asp
385                 390                 395                 400

Asp Ser Pro Asn Pro Thr Glu Gly Val Leu Pro Arg Val Ile Glu Ala
                405                 410                 415

Thr Asn Arg Val Leu Ile Ala Asn Gly Asp Trp Asp Tyr Leu Ile Ile
                420                 425                 430

Thr Asn Gly Thr Leu Leu Ala Ile Gln Asn Met Thr Trp Asn Gly Gln
                435                 440                 445

Leu Gly Phe Gln Ser Ala Pro Ala Thr Pro Ile Asp Ile Gln Met Pro
450                 455                 460

Asp Leu Gln Trp Val Glu Ile Phe Glu Ala Gln Glu Gly Tyr Gly Gly
465                 470                 475                 480

Leu Asp Gly Pro Gln Gly Val Met Gly Val Gln His Tyr Glu Arg Gly
                485                 490                 495

Leu Met Trp Ala Glu Thr Tyr Gln Ser Gly His Lys Gln Ala Gln Asp
                500                 505                 510

Gln Gly Arg Val Ser Tyr Arg His Leu Gln Trp Leu Leu Gly Gln Val
                515                 520                 525

Glu Ile Leu
    530

<210> SEQ ID NO 138
```

<211> LENGTH: 531
<212> TYPE: PRT
<213> ORGANISM: Aspergillus niger

<400> SEQUENCE: 138

```
Met Leu Phe Arg Ser Leu Leu Ser Thr Ala Val Leu Ala Val Ser Leu
 1               5                  10                  15

Cys Thr Asp Asn Ala Ser Ala Ala Lys His Gly Arg Phe Gly Gln Lys
             20                  25                  30

Ala Arg Asp Ala Met Asn Ile Ala Lys Arg Ser Ala Asn Ala Val Lys
         35                  40                  45

His Ser Leu Lys Ile Pro Val Glu Asp Tyr Gln Phe Leu Asn Asn Lys
     50                  55                  60

Thr Lys Pro Tyr Arg Val Glu Ser Leu Pro Asp Val His Phe Asp Leu
 65                  70                  75                  80

Gly Glu Met Tyr Ser Gly Leu Val Pro Ile Glu Lys Gly Asn Val Ser
                 85                  90                  95

Arg Ser Leu Phe Phe Val Phe Gln Pro Thr Ile Gly Glu Pro Val Asp
            100                 105                 110

Glu Ile Thr Ile Trp Leu Asn Gly Gly Pro Gly Cys Ser Ser Leu Glu
        115                 120                 125

Ala Phe Leu Gln Glu Asn Gly Arg Phe Val Trp Gln Pro Gly Thr Tyr
    130                 135                 140

Gln Pro Val Glu Asn Pro Tyr Ser Trp Val Asn Leu Thr Asn Val Leu
145                 150                 155                 160

Trp Val Asp Gln Pro Val Gly Thr Gly Phe Ser Leu Gly Val Pro Thr
                165                 170                 175

Ala Thr Ser Glu Glu Glu Ile Ala Glu Asp Phe Val Lys Phe Phe Lys
            180                 185                 190

Asn Trp Gln Gln Ile Phe Gly Ile Lys Asn Phe Lys Ile Tyr Val Thr
        195                 200                 205

Gly Glu Ser Tyr Ala Gly Arg Tyr Val Pro Tyr Ile Ser Ala Ala Phe
    210                 215                 220

Leu Asp Gln Asn Asp Thr Glu His Phe Asn Leu Lys Gly Ala Leu Ala
225                 230                 235                 240

Tyr Asp Pro Cys Ile Gly Gln Phe Asp Tyr Val Gln Glu Glu Ala Pro
                245                 250                 255

Val Val Pro Phe Val Gln Lys Asn Asn Ala Leu Phe Asn Phe Asn Ala
            260                 265                 270

Ser Phe Leu Ala Glu Leu Glu Ser Ile His Glu Gln Cys Gly Tyr Lys
        275                 280                 285

Asp Phe Ile Asp Gln Tyr Leu Val Phe Pro Ala Ser Gly Val Gln Pro
    290                 295                 300

Pro Lys Ala Met Asn Trp Ser Asp Pro Thr Cys Asp Val Tyr Asp Ile
305                 310                 315                 320

Val Asn Asn Ala Val Leu Asp Pro Asn Pro Cys Phe Asn Pro Tyr Glu
                325                 330                 335

Ile Asn Glu Met Cys Pro Ile Leu Trp Asp Val Leu Gly Phe Pro Thr
            340                 345                 350

Glu Val Asp Tyr Leu Pro Ala Gly Ala Ser Ile Tyr Phe Asp Arg Ala
        355                 360                 365

Asp Val Lys Arg Ala Met His Ala Pro Asn Ile Thr Trp Ser Glu Cys
    370                 375                 380

Ser Val Glu Ser Val Phe Val Gly Gly Asp Gly Gly Pro Glu Gln Glu
```

-continued

```
                385                 390                 395                 400
Gly Asp Tyr Ser Ala Asn Pro Ile Glu His Val Leu Pro Gln Val Ile
                405                 410                 415

Glu Gly Thr Asn Arg Val Leu Ile Gly Asn Gly Asp Tyr Asp Met Val
            420                 425                 430

Ile Leu Thr Asn Gly Thr Leu Leu Ser Ile Gln Asn Met Thr Trp Asn
        435                 440                 445

Gly Lys Leu Gly Phe Asp Thr Ala Pro Ser Thr Pro Ile Asn Ile Asp
    450                 455                 460

Ile Pro Asp Leu Met Tyr Asn Glu Val Phe Ile Glu Asn Gly Tyr Asp
465                 470                 475                 480

Pro Gln Gly Gly Gln Gly Val Met Gly Ile Gln His Tyr Glu Arg Gly
                485                 490                 495

Leu Met Trp Ala Glu Thr Phe Gln Ser Gly His Met Gln Pro Gln Phe
            500                 505                 510

Gln Pro Arg Val Ser Tyr Arg His Leu Glu Trp Leu Leu Gly Arg Arg
        515                 520                 525

Asp Thr Leu
    530

<210> SEQ ID NO 139
<211> LENGTH: 492
<212> TYPE: PRT
<213> ORGANISM: Aspergillus niger

<400> SEQUENCE: 139

Met Lys Gly Ala Ala Leu Ile Pro Leu Ala Ala Gly Ile Pro Phe Ala
1               5                   10                  15

His Gly Leu Ser Leu His Lys Arg Asp Gly Pro Ala Val Val Arg Met
            20                  25                  30

Pro Ile Glu Arg Arg Ser Ala Gln Ser Leu Gln Lys Arg Asp Ser Thr
        35                  40                  45

Val Gly Val Thr Leu Gln Asn Trp Asp Ala Thr Tyr Tyr Ala Val Asn
    50                  55                  60

Leu Thr Leu Gly Thr Pro Ala Gln Lys Val Ser Leu Ala Leu Asp Thr
65                  70                  75                  80

Gly Ser Ser Asp Leu Trp Val Asn Thr Gly Asn Ser Thr Tyr Cys Ser
                85                  90                  95

Ile Asp Asn Leu Cys Thr Pro Tyr Gly Leu Tyr Asn Ala Ser Glu Ser
            100                 105                 110

Ser Thr Val Lys Thr Val Gly Thr His Leu Asn Asp Thr Tyr Ala Asp
        115                 120                 125

Gly Thr Asn Leu Tyr Gly Pro Tyr Val Thr Asp Lys Leu Thr Ile Gly
    130                 135                 140

Asn Thr Thr Ile Asp Asn Met Gln Phe Gly Ile Ala Glu Ser Thr Thr
145                 150                 155                 160

Ser Lys Arg Gly Ile Ala Gly Val Gly Tyr Lys Ile Ser Thr Tyr Gln
                165                 170                 175

Ala Glu His Asp Asp Lys Val Tyr Ala Asn Leu Pro Gln Ala Leu Val
            180                 185                 190

Asp Ser Gly Ala Ile Lys Ser Ala Tyr Ser Ile Trp Leu Asp Ser
        195                 200                 205

Leu Glu Ala Ser Thr Gly Ser Leu Leu Phe Gly Gly Val Asn Thr Ala
    210                 215                 220
```

-continued

```
Lys Tyr Lys Gly Asp Leu Gln Thr Leu Pro Ile Ile Pro Val Tyr Gly
225                 230                 235                 240

Lys Tyr Tyr Ser Leu Ala Ile Ala Leu Thr Glu Leu Ser Val Ala Thr
            245                 250                 255

Asp Ser Asn Ser Ser Phe Thr Asp Ser Leu Pro Leu Ser Val Ser
        260                 265                 270

Leu Asp Thr Gly Thr Thr Met Thr Ala Leu Pro Ser Asp Leu Val Asn
        275                 280                 285

Lys Val Tyr Asp Ala Leu Asn Ala Thr Tyr Asp Lys Thr Tyr Asp Met
290                 295                 300

Ala Tyr Ile Asp Cys Asp Thr Arg Glu Ala Asp Tyr Asn Val Thr Tyr
305                 310                 315                 320

Ser Phe Ser Gly Ala Thr Ile Thr Val Ser Met Ser Glu Leu Ile Ile
            325                 330                 335

Pro Ala Thr Glu Pro Gly Trp Pro Asp Asn Thr Cys Val Leu Gly Leu
            340                 345                 350

Val Pro Ser Gln Pro Gly Val Asn Leu Leu Gly Asp Thr Phe Leu Arg
            355                 360                 365

Ser Ala Tyr Val Val Tyr Asp Leu Glu Asn Asn Glu Ile Ser Leu Ala
        370                 375                 380

Asn Thr Asn Phe Asn Pro Gly Asp Asp Ile Leu Glu Ile Gly Thr
385                 390                 395                 400

Gly Thr Ser Ala Val Pro Gly Ala Thr Pro Val Pro Ser Ala Val Ser
            405                 410                 415

Ser Ala Thr Gly Asn Gly Leu Ile Ser Ser Gly Thr Ala Val Pro Thr
            420                 425                 430

Leu Ser Gly Val Thr Ile Thr Ala Thr Ala Thr Ala Thr Gly Ser Thr
            435                 440                 445

Gly Thr Gly Ser Ser Gly Gly Ser Ser Ala Glu Ala Thr Ser Thr Ser
450                 455                 460

Ser Glu Gly Ala Ala Ala Gln Ala Thr Ser Asn Pro Met Asn Leu Leu
465                 470                 475                 480

Pro Gly Leu Ala Gly Ile Gly Leu Leu Leu Ala Leu
            485                 490

<210> SEQ ID NO 140
<211> LENGTH: 611
<212> TYPE: PRT
<213> ORGANISM: Aspergillus niger

<400> SEQUENCE: 140

Met Leu Ser Ser Leu Leu Ser Gln Gly Ala Ala Val Ser Leu Ala Val
1               5                   10                  15

Leu Ser Leu Leu Pro Ser Pro Val Ala Ala Glu Ile Phe Glu Lys Leu
            20                  25                  30

Ser Gly Val Pro Asn Gly Trp Arg Tyr Ala Asn Asn Pro Gln Gly Asn
        35                  40                  45

Glu Val Ile Arg Leu Gln Ile Ala Leu Gln Gln His Asp Val Ala Gly
    50                  55                  60

Phe Glu Gln Ala Val Met Asp Met Ser Thr Pro Gly His Ala Asp Tyr
65                  70                  75                  80

Gly Lys His Phe Arg Thr His Asp Glu Met Lys Arg Met Leu Leu Pro
                85                  90                  95

Ser Glu Thr Ala Val Asp Ser Val Arg Asp Trp Leu Glu Ser Ala Gly
            100                 105                 110
```

```
Val His Asn Ile Gln Val Asp Ala Asp Trp Val Lys Phe His Thr Thr
    115                 120                 125
Val Asn Lys Ala Asn Ala Leu Leu Asp Ala Asp Phe Lys Trp Tyr Val
130                 135                 140
Ser Asp Ala Lys His Ile Arg Arg Leu Arg Thr Leu Gln Tyr Ser Ile
145                 150                 155                 160
Pro Asp Ala Leu Val Ser His Ile Asn Met Ile Gln Pro Thr Thr Arg
                    165                 170                 175
Phe Gly Gln Ile Gln Pro Asn Arg Ala Thr Met Arg Ser Lys Pro Lys
                180                 185                 190
His Ala Asp Glu Thr Phe Leu Thr Ala Ala Thr Leu Ala Gln Asn Thr
                195                 200                 205
Ser His Cys Asp Ser Ile Ile Thr Pro His Cys Leu Lys Gln Leu Tyr
    210                 215                 220
Asn Ile Gly Asp Tyr Gln Ala Asp Pro Lys Ser Gly Ser Lys Ile Gly
225                 230                 235                 240
Phe Ala Ser Tyr Leu Glu Glu Tyr Ala Arg Tyr Ala Asp Leu Glu Arg
                245                 250                 255
Phe Glu Gln His Leu Ala Pro Asn Ala Ile Gly Gln Asn Phe Ser Val
                260                 265                 270
Val Gln Phe Asn Gly Gly Leu Asn Asp Gln Leu Ser Ser Ser Asp Ser
            275                 280                 285
Gly Glu Ala Asn Leu Asp Leu Gln Tyr Ile Leu Gly Val Ser Ala Pro
290                 295                 300
Val Pro Ile Thr Glu Tyr Ser Thr Gly Gly Arg Gly Glu Leu Val Pro
305                 310                 315                 320
Asp Leu Ser Ser Pro Asp Pro Asn Asp Asn Ser Asn Glu Pro Tyr Leu
                325                 330                 335
Asp Phe Leu Gln Gly Ile Leu Lys Leu Asn Asn Ser Asp Leu Pro Gln
                340                 345                 350
Val Ile Ser Thr Ser Tyr Gly Glu Asp Glu Gln Thr Ile Pro Val Pro
                355                 360                 365
Tyr Ala Arg Thr Val Cys Asn Leu Tyr Ala Gln Leu Gly Ser Arg Gly
    370                 375                 380
Val Ser Val Ile Phe Ser Ser Gly Asp Ser Gly Val Gly Ala Ala Cys
385                 390                 395                 400
Leu Thr Asn Asp Gly Thr Asn Arg Thr His Phe Pro Pro Gln Phe Pro
                405                 410                 415
Ala Ser Cys Pro Trp Val Thr Ser Val Gly Ala Thr Ser Lys Thr Ser
                420                 425                 430
Pro Glu Gln Ala Val Ser Phe Ser Ser Gly Gly Phe Ser Asp Leu Trp
            435                 440                 445
Pro Arg Pro Ser Tyr Gln His Ala Ala Val Gln Thr Tyr Leu Thr Lys
            450                 455                 460
His Leu Gly Asn Lys Phe Ser Gly Leu Phe Asn Ala Ser Gly Arg Ala
465                 470                 475                 480
Phe Pro Asp Val Ser Ala Gln Gly Val Asn Tyr Ala Val Tyr Asp Lys
                    485                 490                 495
Gly Met Leu Gly Gln Phe Asp Gly Thr Ser Cys Ser Ala Pro Thr Phe
                500                 505                 510
Ser Gly Val Ile Ala Leu Leu Asn Asp Ala Arg Leu Arg Ala Gly Leu
            515                 520                 525
```

-continued

```
Pro Val Met Gly Phe Leu Asn Pro Phe Leu Tyr Gly Val Gly Ser Glu
    530                 535                 540

Lys Gly Ala Leu Asn Asp Ile Val Asn Gly Gly Ser Val Gly Cys Asp
545                 550                 555                 560

Gly Arg Asn Arg Phe Gly Gly Thr Pro Asn Gly Ser Pro Val Val Pro
                565                 570                 575

Phe Ala Ser Trp Asn Ala Thr Thr Gly Trp Asp Pro Val Ser Gly Leu
            580                 585                 590

Gly Thr Pro Asp Phe Ala Lys Leu Lys Gly Val Ala Leu Gly Glu Glu
        595                 600                 605

Gly Gly Asn
    610

<210> SEQ ID NO 141
<211> LENGTH: 478
<212> TYPE: PRT
<213> ORGANISM: Aspergillus niger

<400> SEQUENCE: 141

Met Trp Leu Phe Leu Val Cys Ser Ile Leu Pro Leu Gly Val Val
1               5                   10                  15

Asn Ala Gln Ser Gln Tyr Phe Asn Asn Lys Thr Lys Glu Phe Val Val
                20                  25                  30

Asn Gly Ser Ala Ile Pro Phe Val Asp Phe Asp Ile Gly Glu Ser Tyr
            35                  40                  45

Ala Gly Tyr Leu Pro Asn Thr Pro Ser Gly Ile Ser Ser Leu Tyr Phe
    50                  55                  60

Trp Phe Phe Pro Ser Ser Asp Pro Asp Ala Ser Asp Glu Ile Thr Val
65                  70                  75                  80

Trp Leu Asn Gly Gly Pro Gly Cys Ser Ser Leu Ala Gly Ile Met Leu
                85                  90                  95

Glu Asn Gly Pro Phe Leu Trp Gln Pro Gly Thr Tyr Arg Pro Val Arg
            100                 105                 110

Asn Pro Tyr Ala Trp Asn Asn Leu Thr Asn Met Val Tyr Ile Asp Gln
        115                 120                 125

Pro Ala Gly Thr Gly Phe Ser Leu Gly Pro Ser Thr Val Val Ser Glu
    130                 135                 140

Phe Asp Val Ala Arg Gln Phe Met Asp Phe Trp Arg Arg Phe Met Lys
145                 150                 155                 160

Thr Phe Asp Leu Gln Asn Arg Lys Ile Tyr Leu Thr Gly Glu Ser Tyr
                165                 170                 175

Ala Gly Gln Tyr Ile Pro Tyr Ile Ala Ser Gln Met Leu Asp Gln Asp
            180                 185                 190

Asp Asp Glu Tyr Phe Arg Val Ala Gly Ile Gln Ile Asn Asp Pro Tyr
        195                 200                 205

Ile Asn Glu Leu Pro Val Leu Gln Asp Val Ala Thr Val Asn Gln His
    210                 215                 220

Arg Ser Leu Phe Pro Phe Asn Asp Thr Phe Met Ser Gln Ile Thr Lys
225                 230                 235                 240

Leu Ser Asp Asp Cys Gly Tyr Thr Ser Phe Leu Asp Asp Ala Leu Thr
                245                 250                 255

Phe Pro Pro Arg Ser Gln Phe Pro Ser Val Pro Tyr Asn Ala Ser Cys
            260                 265                 270

Asn Ile Trp Asp Ile Ile Asn Asn Ala Ser Leu Ala Leu Asn Pro Cys
        275                 280                 285
```

-continued

```
Phe Asn Arg Tyr His Ile Pro Asp Ala Cys Pro Thr Pro Trp Asn Pro
    290                 295                 300

Val Gly Gly Pro Ile Val Gly Leu Gly Pro Thr Asn Tyr Phe Asn Arg
305                 310                 315                 320

Ser Asp Val Gln Lys Ala Ile Asn Ala Tyr Pro Thr Asp Tyr Phe Val
                325                 330                 335

Cys Lys Asp Gly Ile Phe Pro Thr Ala Asn Gly Leu Asp Thr Ser Pro
            340                 345                 350

Pro Ser Ser Leu Gly Pro Leu Pro Arg Val Ile Glu Gln Thr Asn Asn
        355                 360                 365

Thr Ile Ile Ala His Gly Leu Met Asp Phe Glu Leu Leu Ala Gln Gly
    370                 375                 380

Thr Leu Ile Ser Ile Gln Asn Met Thr Trp Asn Gly Lys Gln Gly Phe
385                 390                 395                 400

Glu Arg Glu Pro Val Glu Pro Leu Phe Val Pro Tyr Gly Gly Ser Ser
                405                 410                 415

Gly Gly Gly Val Leu Gly Thr Ala His Thr Glu Arg Gly Leu Thr Phe
            420                 425                 430

Ser Thr Val Phe Ser Ser Gly His Glu Ile Pro Glu Tyr Ala Pro Gly
        435                 440                 445

Ala Ala Tyr Arg Gln Leu Glu Phe Leu Leu Gly Arg Val Ala Asn Leu
    450                 455                 460

Ser Thr Ile Ile Glu Gln Val Gln Ile Thr Glu Gln Asn Gly
465                 470                 475

<210> SEQ ID NO 142
<211> LENGTH: 210
<212> TYPE: PRT
<213> ORGANISM: Aspergillus niger

<400> SEQUENCE: 142

Met Ser Lys Leu Ser Ala Ala Ile Ser Lys Leu Ser Leu Ser Thr Ile
1               5                   10                  15

Ala Thr Thr Leu Leu Leu Leu Thr Pro Pro Thr Thr Ala Tyr Phe Tyr
            20                  25                  30

Lys Tyr Pro Ala Leu Phe Val Tyr Lys Asp Thr Asn Cys Thr Asp Ile
        35                  40                  45

Ser Phe Ser Leu Val Tyr Pro Ser Leu Gly Asn Cys Asn Gly Gly Tyr
    50                  55                  60

Tyr Asp Tyr Ala Gly Ser Phe Gln Met Phe Asn Ile Asp Ala Ala Tyr
65                  70                  75                  80

Thr Cys Asn Gly Ser Asp Ser Thr Leu Met Phe Glu Met Tyr Asn Ser
                85                  90                  95

Ser Gly Ser Asp Cys Gly Asp Glu Ser Asp Leu Leu Phe Arg Gln Pro
            100                 105                 110

Val Thr Glu Glu Cys Thr Val Ala Asp Val Glu Ser Pro Gly Pro Leu
        115                 120                 125

Glu Met Pro Val Trp Phe Glu Leu Gly Ser Leu Leu Gly Asn Cys Gly
    130                 135                 140

Gly Met Ala Gly Thr Met Leu Phe Gly Val Gly Ile Leu Glu Gly Gly
145                 150                 155                 160

Leu Glu Thr Lys Leu Tyr Trp Lys Cys Tyr Ser Ser Arg Leu Asn Thr
                165                 170                 175

Ser Val Thr Val His Arg Leu Ser Leu Ile Leu Ser Met Gly Cys Thr
```

-continued

```
                180                 185                 190
Ser Val Ser Asp Ser Tyr Asn Glu Leu Ala Ala Ala His Tyr Tyr Glu
        195                 200                 205

Asp Leu
    210

<210> SEQ ID NO 143
<211> LENGTH: 608
<212> TYPE: PRT
<213> ORGANISM: Aspergillus niger

<400> SEQUENCE: 143

Met Arg His Leu Leu Ser Leu Val Leu Leu Ile Ala Ser Ala Ala
1               5                   10                  15

Leu Val Ser Ala Val Pro Ala Gly Ser Ile Ile Thr Pro Gln Pro
            20                  25                  30

Val Glu Pro Val His Leu Leu Ser Ser Gln Pro Ser Asp Pro Arg Arg
        35                  40                  45

Pro Trp Ile Arg Leu Arg Asp Trp Ile Ile Glu Ser Ile Trp Gly Ile
    50                  55                  60

Glu Lys Pro Ala Ser Arg Arg Phe Pro Leu Asn Asp Ser Pro Arg Asn
65                  70                  75                  80

Arg Ser Pro Pro Ser Arg Ile Leu Ala Arg Tyr Gly Ser Asp Val Val
                85                  90                  95

Leu Arg Phe Ser Leu Arg Asn His Asp Glu Ala Glu Ala Leu Ala Gln
            100                 105                 110

Ala Ala Asp Ile Leu Phe Leu Asp Val Trp Ala Ser Thr Pro Ala Phe
        115                 120                 125

Val Asp Ile Arg Leu Ala Glu Glu Val Thr Ala Tyr Thr Pro Leu Ile
    130                 135                 140

Asp Asn Leu Ala Glu Arg Ile Tyr Thr Thr Tyr Pro Ser Lys Lys Pro
145                 150                 155                 160

Ile Gly Leu Glu Gly Gln Ser Gly Phe Ala Ser Ser Arg Pro Ala
                165                 170                 175

Pro Lys Phe Gly Asp Leu Phe Phe His Glu Tyr Gln Pro Leu Ser Val
            180                 185                 190

Ile Ile Pro Trp Met Arg Leu Leu Ala Ser Met Phe Pro Ser His Val
        195                 200                 205

Arg Met Ile Ser Val Gly Val Ser Tyr Glu Gly Arg Glu Ile Pro Ala
    210                 215                 220

Leu Arg Leu Ser Ala Gly Ser Ser Thr Ala Ala Ser Gly Pro Arg Lys
225                 230                 235                 240

Thr Ile Ile Val Thr Gly Gly Ser His Ala Arg Glu Trp Ile Gly Thr
                245                 250                 255

Ser Thr Val Asn His Val Met Tyr Thr Leu Ile Thr Lys Tyr Gly Lys
            260                 265                 270

Ser Lys Ala Val Thr Arg Leu Leu Gln Asp Phe Asp Trp Ile Met Ile
        275                 280                 285

Pro Thr Ile Asn Pro Asp Gly Tyr Val Tyr Thr Trp Glu Thr Asp Arg
    290                 295                 300

Leu Trp Arg Lys Asn Arg Gln Arg Thr Ser Leu Arg Phe Cys Pro Gly
305                 310                 315                 320

Ile Asp Leu Asp Arg Ala Trp Gly Phe Glu Trp Asp Gly Gly Arg Thr
                325                 330                 335
```

```
Arg Ala Asn Pro Cys Ser Glu Asn Tyr Ala Gly Asp Glu Pro Phe Glu
            340                 345                 350

Gly Met Glu Ala Gln Gln Leu Ala Gln Trp Ala Leu Asn Glu Thr Gln
        355                 360                 365

Asn Asn Asn Ala Asp Ile Val Ser Phe Leu Asp Leu His Ser Tyr Ser
370                 375                 380

Gln Thr Ile Leu Tyr Pro Phe Ser Tyr Ser Cys Ser Ser Ile Pro Pro
385                 390                 395                 400

Thr Leu Glu Ser Leu Glu Glu Leu Gly Leu Gly Leu Ala Lys Ala Ile
                405                 410                 415

Arg Tyr Ala Thr His Glu Ile Tyr Asp Val Thr Ser Ala Cys Glu Gly
            420                 425                 430

Ile Val Thr Ala Ser Ala Ala Asp Asn Asn Pro Gly Arg Phe Phe Pro
            435                 440                 445

Ile Gly Gly Asn Ser Gly Gly Ser Ala Leu Asp Trp Phe Tyr His Gln
        450                 455                 460

Val His Ala Thr Tyr Ser Tyr Gln Ile Lys Leu Arg Asp Arg Gly Ser
465                 470                 475                 480

Tyr Gly Phe Leu Leu Pro Ser Glu His Ile Ile Pro Thr Gly Lys Glu
                485                 490                 495

Ile Tyr Asn Val Val Leu Lys Leu Gly Ser Phe Leu Ile Gly Gly Asp
            500                 505                 510

Ser Phe Asp Val Asp Trp Glu Ser Glu Leu Phe Asp Leu Ser Lys Asp
        515                 520                 525

Glu Ser Asp Leu Asp Ser Arg Tyr Ser Lys Ser Asn Asp Arg Ser Pro
    530                 535                 540

Ala Tyr Leu His Asn Ala Asn Gly Pro Leu Pro Asn Ile Asp Glu Asp
545                 550                 555                 560

Glu Asp Lys Glu Trp Val Met Val Glu Glu Asp Tyr Thr Asp Asp
                565                 570                 575

Asp Asp Asp Asp Asp Asp Asp Glu Glu Glu Glu Glu Glu Glu
            580                 585                 590

Asp Thr Tyr Trp Ala Thr Glu His Thr Tyr Glu Phe Arg Arg Arg Arg
            595                 600                 605

<210> SEQ ID NO 144
<211> LENGTH: 416
<212> TYPE: PRT
<213> ORGANISM: Aspergillus niger

<400> SEQUENCE: 144

Met Ala Phe Leu Lys Arg Ile Leu Pro Leu Leu Ala Leu Ile Leu Pro
1               5                   10                  15

Ala Val Phe Ser Ala Thr Glu Gln Val Pro His Pro Thr Ile Gln Thr
            20                  25                  30

Ile Pro Gly Lys Tyr Ile Val Thr Phe Lys Ser Gly Ile Asp Asn Ala
        35                  40                  45

Lys Ile Glu Ser His Ala Ala Trp Val Thr Glu Leu His Arg Arg Ser
    50                  55                  60

Leu Glu Gly Arg Ser Thr Thr Glu Asp Leu Pro Ala Gly Ile Glu
65                  70                  75                  80

Arg Thr Tyr Arg Ile Ala Asn Phe Ala Gly Tyr Ala Gly Ser Phe Asp
                85                  90                  95

Glu Lys Thr Ile Glu Glu Ile Arg Lys His Asp His Val Ala Tyr Val
            100                 105                 110
```

```
Glu Gln Asp Gln Val Trp Tyr Leu Asp Thr Leu Val Thr Glu Arg Arg
            115                 120                 125

Ala Pro Trp Gly Leu Gly Ser Ile Ser His Arg Gly Ser Ser Thr
130                 135                 140

Asp Tyr Ile Tyr Asp Asp Ser Ala Gly Glu Gly Thr Tyr Ala Tyr Val
145                 150                 155                 160

Val Asp Thr Gly Ile Leu Ala Thr His Asn Glu Phe Gly Gly Arg Ala
                165                 170                 175

Ser Leu Ala Tyr Asn Ala Ala Gly Glu His Val Asp Asp Val Gly
            180                 185                 190

His Gly Thr His Val Ala Gly Thr Ile Gly Gly Lys Thr Tyr Gly Val
            195                 200                 205

Ser Lys Asn Ala His Leu Leu Ser Val Lys Val Phe Val Gly Glu Ser
            210                 215                 220

Ser Ser Thr Ser Val Ile Leu Asp Gly Phe Asn Trp Ala Ala Asn Asp
225                 230                 235                 240

Ile Val Ser Lys Asn Arg Thr Ser Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Cys Val Ala Ala Gly Asn Glu Asn Arg Asp
            275                 280                 285

Ala Ala Arg Thr Ser Pro Ala Ser Ala Pro Asp Ala Ile Thr Val Ala
            290                 295                 300

Ala Ile Asn Arg Ser Asn Ala Arg Ala Ser Phe Ser Asn Tyr Gly Ser
305                 310                 315                 320

Val Val Asp Ile Phe Ala Pro Gly Glu Gln Val Leu Ser Ala Trp Thr
                325                 330                 335

Gly Ser Asn Ser Ala Thr Asn Thr Ile Ser Gly Thr Ser Met Ala Thr
            340                 345                 350

Pro His Val Thr Gly Leu Ile Leu Tyr Leu Met Gly Leu Arg Asp Leu
            355                 360                 365

Ala Thr Pro Ala Ala Ala Thr Thr Glu Leu Lys Arg Leu Ala Thr Arg
370                 375                 380

Asn Ala Val Thr Asn Val Ala Gly Ser Pro Asn Leu Leu Ala Tyr Asn
385                 390                 395                 400

Gly Asn Ser Gly Val Ser Lys Gly Gly Ser Asp Asp Gly Asp Glu Asp
                405                 410                 415

<210> SEQ ID NO 145
<211> LENGTH: 455
<212> TYPE: PRT
<213> ORGANISM: Aspergillus niger

<400> SEQUENCE: 145

Met Ile Thr Leu Leu Ser Ala Leu Phe Gly Ser Val Val Tyr Ala Ala
1               5                   10                  15

Thr Gln Thr Val Leu Gly Pro Glu Gly Ala Asp Pro Phe Thr Val Phe
            20                  25                  30

Arg Ser Pro His Ser Pro Ala Phe Ser Ile Arg Ile Gln Glu Gln Asn
        35                  40                  45

Asp Ser Ile Cys Asp Ala Arg Ser Pro Gln Phe Thr Gly Trp Leu Asp
    50                  55                  60

Ile Gly Pro Lys His Leu Phe Phe Trp Tyr Phe Glu Ser Gln Asn Asp
```

```
                65                  70                  75                  80
Pro Phe His Asp Pro Leu Thr Leu Trp Met Thr Gly Gly Pro Gly Asp
                    85                  90                  95

Ser Ser Met Ile Gly Leu Phe Glu Glu Val Gly Pro Cys Arg Ile Asn
                100                 105                 110

Glu Phe Gly Asn Gly Thr Asp His Asn Pro Trp Ala Trp Thr Lys Asn
                115                 120                 125

Ser Ser Leu Leu Phe Val Asp Gln Pro Val Asp Val Gly Phe Ser Tyr
            130                 135                 140

Ile Asp Glu Gly Tyr Glu Leu Pro His Asp Ser Arg Glu Ala Ala Val
145                 150                 155                 160

Asp Met His Arg Phe Leu Arg Leu Phe Ile Ser Glu Ile Phe Pro His
                165                 170                 175

Lys Gln Phe Leu Pro Val His Leu Ser Gly Glu Ser Tyr Ala Gly Arg
                180                 185                 190

Tyr Ile Pro Tyr Leu Ala Thr Gln Ile Leu Glu Gln Asn Glu Leu Tyr
                195                 200                 205

Lys Asp Ser Pro Arg Ile Pro Leu Lys Ser Cys Leu Val Gly Asn Gly
210                 215                 220

Phe Met Ser Pro Lys Asp Ala Thr Phe Gly Tyr Trp Glu Thr Leu Cys
225                 230                 235                 240

Thr Thr Asn Ser Gly Val Pro Ser Pro Ile Phe Asn Glu Thr Arg Cys
                245                 250                 255

Asp Ile Met Ala Ala Asn Met Pro His Cys Met Asp Leu Tyr Asp Ile
                260                 265                 270

Cys Ile Gln His Ser Asp Pro Ala Ile Cys His Ala Ala Gln Ser Val
                275                 280                 285

Cys Tyr Asp Ser Val Val Gly Leu Met Ala Lys Leu Leu Leu Arg Met
                290                 295                 300

Thr Thr Val Thr Ala Pro Cys Glu Ile Asp Glu Met Cys Tyr Ile Glu
305                 310                 315                 320

Ala Ala Leu Ile Glu Arg Tyr Leu Asn Ser Pro Ser Val Trp Glu Ala
                325                 330                 335

Leu Ser Pro Pro Gln Gln Val Thr Glu Tyr Lys Phe Val Ala Thr Ser
                340                 345                 350

Val Ile Asp Ala Phe Ala Gln Ser Ala Asp Gly Met Val Ser Ser Ser
                355                 360                 365

Lys Gln Ile Ala Phe Leu Leu Ala Asn Asn Val Asp Phe Leu Ala Tyr
                370                 375                 380

Gln Gly Asn Leu Asp Leu Ala Cys Asn Thr Ala Gly Asn Leu Arg Trp
385                 390                 395                 400

Ala Asn Ser Leu Ser Trp Lys Gly Gln Thr Glu Phe Thr Ala Lys Pro
                405                 410                 415

Leu Leu Pro Trp Glu Ile Gln Val Ser Val Gly Glu Gly Thr Asp Glu
                420                 425                 430

Thr Ser Arg Phe Ala Phe Val Thr Val Asp Asn Ala Gly His Leu Leu
                435                 440                 445

Arg Asp Ser Lys Ile Ser Asn
    450                 455

<210> SEQ ID NO 146
<211> LENGTH: 791
<212> TYPE: PRT
<213> ORGANISM: Aspergillus niger
```

```
<400> SEQUENCE: 146

Met Arg Phe Leu Thr Tyr Ser Leu Pro Phe Ile Ala Ser Ala Ile Ser
1               5                   10                  15

Leu Phe Gly Val Asn Val Gln Ala Arg Ser Gln Ala Pro Ser Ala Ile
            20                  25                  30

Arg His Val Ser Thr Leu Asp Gln Pro Thr Ile Lys Thr Pro Ser Gln
        35                  40                  45

Arg Val Asp His Leu Asp His Phe Asp Ile Thr Phe Asn Ile His Asp
    50                  55                  60

Lys His Gln Arg Ile Lys Leu Glu Leu Glu Pro Asn His Asp Ile Leu
65                  70                  75                  80

Ala Glu Asp Ala Ser Val Gln Tyr Leu Asp Ala Asp Gly Asn Val Arg
                85                  90                  95

Arg His Glu Pro Ile Ala Pro His Glu His Lys Val Phe Lys Gly Arg
            100                 105                 110

Ser Leu Leu Gly Arg Gly Lys Gly Met Trp Asp Pro Val Gly Trp Ala
        115                 120                 125

Arg Ile Tyr Leu Lys Gln Asp Gly Ser Glu Pro Leu Phe Glu Gly Val
    130                 135                 140

Phe Ser Ile Asp Gly Asp Asn His His Val Gln Leu Lys Ser Ala Tyr
145                 150                 155                 160

Met Glu Lys Lys Arg Pro Val Asp Val Asp Leu Pro Asp Ser Ala Thr
                165                 170                 175

Asp Tyr Met Ile Phe Tyr Arg Asp Ser Asp Met Val Arg Leu His Thr
            180                 185                 190

Glu Leu Lys Arg Ser Ser Leu Gly Ser Thr Ser Cys Gln Ala Asp Gln
        195                 200                 205

Leu Gly Phe Asn Thr Asn Pro Asn His Pro Val Leu Gln Pro Tyr Gly
    210                 215                 220

Gln Ala Glu Thr Asp Thr Trp Gly Ala Ile Ser Leu Asn Ser Leu Phe
225                 230                 235                 240

Gly Leu Asn Lys Arg Gln Ser Asp Ile Gly Ser Val Ser Gly Asn Ala
                245                 250                 255

Gly Gly Val Asn Leu Ala Ser Thr Ile Gly Asp Thr Ser Gly Cys Pro
            260                 265                 270

Ser Thr Lys Gln Val Ala Leu Ile Gly Val Ala Thr Asp Cys Ala Phe
        275                 280                 285

Thr Gly Ser Phe Asn Asn Glu Thr Ala Ala Lys Glu Trp Val Ile Ser
    290                 295                 300

Thr Val Asn Ser Ala Ser Asn Val Tyr Glu Lys Ser Phe Asn Ile Thr
305                 310                 315                 320

Ile Gly Leu Arg Asn Leu Thr Ile Thr Asp Ser Ser Cys Pro Asp Asn
                325                 330                 335

Pro Pro Ala Ala Thr Ala Trp Asn Met Pro Cys Ser Ser Gly Asn Leu
            340                 345                 350

Thr Ser Arg Leu Asp Leu Phe Ser Lys Trp Arg Gly Glu Gln Ser Asp
        355                 360                 365

Asp Asn Ala Tyr Trp Thr Leu Met Ser Asp Cys Ala Thr Gly Asn Glu
    370                 375                 380

Val Gly Leu Ser Trp Leu Gly Gln Leu Cys Asn Ser Asp Ala Ser Ser
385                 390                 395                 400

Asp Gly Ser Ser Thr Val Ser Gly Thr Asn Val Val Val Arg Ser Ser
```

```
                405               410               415
Gly Ser Asp Trp Gln Ile Phe Ala His Glu Ser His Thr Phe Gly
            420                   425               430
Ala Val His Asp Cys Asp Ser Gln Thr Cys Ala Glu Asp Leu Glu Ala
        435                   440                   445
Ser Ser Gln Cys Cys Pro Leu Thr Ser Ser Thr Cys Asn Ala Asn Gly
    450                   455                   460
Lys Tyr Ile Met Asn Pro Thr Thr Gly Thr Asp Ile Thr Ala Phe Ser
465                   470                   475                   480
Gln Cys Thr Ile Gly Asn Ile Cys Ala Ala Leu Gly Arg Asn Ser Val
                485                   490                   495
Lys Ser Ser Cys Leu Ser Ala Asn Arg Asp Val Thr Thr Tyr Thr Gly
            500                   505                   510
Ser Gln Cys Gly Asn Gly Ile Val Glu Ser Gly Glu Asp Cys Asp Cys
        515                   520                   525
Gly Gly Glu Asp Gly Cys Gly Asp Asn Cys Cys Asp Ala Lys Thr
    530                   535                   540
Cys Lys Phe Lys Ser Gly Ala Val Cys Asp Asp Ser Asn Asp Ser Cys
545                   550                   555                   560
Cys Ser Ser Cys Gln Phe Ser Ser Ala Gly Thr Val Cys Arg Ala Ser
                565                   570                   575
Arg Gly Asp Cys Asp Val Ala Glu Thr Cys Ser Gly Asn Ser Ser Thr
            580                   585                   590
Cys Pro Thr Asp Ser Phe Lys Lys Asp Gly Thr Ser Cys Gly Ser Ser
        595                   600                   605
Gly Ser Gly Leu Ala Cys Ala Ser Gly Gln Cys Thr Ser Arg Asp Tyr
    610                   615                   620
Gln Cys Arg Ser Val Met Gly Ser Leu Leu His Ser Asn Asp Thr Tyr
625                   630                   635                   640
Ala Cys Ser Ser Phe Ser Ser Ser Cys Glu Leu Val Cys Thr Ser Pro
                645                   650                   655
Lys Ile Gly Thr Cys Tyr Ser Val Asn Gln Asn Phe Leu Asp Gly Thr
            660                   665                   670
Pro Cys Gly Ser Gly Gly Tyr Cys Ser Asn Gly Asp Cys Lys Gly Gln
        675                   680                   685
Asn Val Glu Ser Trp Ile Lys Asn His Lys Gly Ile Val Ile Gly Val
    690                   695                   700
Ala Cys Ala Val Gly Ala Leu Ile Leu Leu Ala Leu Met Thr Cys Ile
705                   710                   715                   720
Val Asn Arg Cys Arg Arg Ala Arg Ala Pro Lys Pro Val Pro Arg Pro
                725                   730                   735
Val Pro Tyr Gly Pro Trp Pro Gly Ala Arg Pro Pro Pro Pro Pro
            740                   745                   750
Met Asn Gln Trp Pro Ala Arg Gly Tyr Gln Gly Leu Gly Asn Glu Pro
        755                   760                   765
Pro Pro Pro Tyr Pro Gly Val Pro Gly Gln Pro Val Pro Gln His Met
    770                   775                   780
Pro Pro Gln Gly Arg Tyr Ala
785                   790
```

<210> SEQ ID NO 147
<211> LENGTH: 481
<212> TYPE: PRT
<213> ORGANISM: Aspergillus niger -continued

<400> SEQUENCE: 147

```
Met Arg Phe Leu Ser Ser Ala Ala Leu Phe Gly Leu Ala Tyr Ala Ser
1               5                   10                  15

Thr Gln Ala Val Leu Gln Pro Glu Pro Ser Asp Phe Arg Thr Phe
            20                  25                  30

His Ser Pro Tyr Ser Pro His His Ser Ile Arg Ile Arg Gln Gln Asn
            35                  40                  45

Glu Ser Ile Cys Ala Ala His Ser Ala Gln Tyr Thr Gly Trp Leu Asp
        50                  55                  60

Ile Gly Arg Lys His Leu Phe Phe Trp Tyr Phe Glu Ser Gln Asn Asp
65                  70                  75                  80

Pro Ala Asn Asp Pro Leu Thr Leu Trp Met Thr Gly Pro Gly Gly
                85                  90                  95

Ser Ser Met Ile Gly Leu Phe Glu Glu Val Gly Pro Cys Leu Ile Asn
            100                 105                 110

Glu Tyr Gly Asn Gly Thr Tyr Tyr Asn Pro Trp Gly Trp Ser Arg Asn
            115                 120                 125

Ser Ser Leu Leu Phe Val Asp Gln Pro Val Asp Val Gly Phe Ser Tyr
        130                 135                 140

Val Asp Glu Gly Glu Asp Leu Pro Gly Asp Ser His Gln Ala Ala Ile
145                 150                 155                 160

Asp Met His Arg Phe Leu Gln Leu Phe Val Ser Glu Val Phe Pro Gln
                165                 170                 175

Leu Gln Thr Leu Pro Val His Leu Ser Gly Glu Ser Tyr Ala Gly His
            180                 185                 190

Tyr Val Pro Tyr Leu Gly Ser Gln Ile Val Gln Gln Asn Lys Leu Tyr
            195                 200                 205

Pro Thr Glu Pro Gln Val Leu Leu His Ser Cys Leu Val Gly Asn Gly
        210                 215                 220

Tyr Tyr Ser Pro Arg Asp Thr Thr Tyr Gly Tyr Trp Glu Thr Leu Cys
225                 230                 235                 240

Thr Thr Asn Pro Gly Val Pro Glu Pro Val Phe Asn Arg Thr Arg Cys
                245                 250                 255

Asp Ile Met Ala Ala Asn Met Pro Arg Cys Met Glu Val Ser Asp Val
            260                 265                 270

Cys Val Arg Asn Pro Asp Pro Ala Ile Cys His Ala Ala Ser Glu Val
        275                 280                 285

Cys Tyr Glu Gly Val Ile Gly Trp Tyr Asp Asp Glu Ser Gly Glu Gly
        290                 295                 300

Gly Arg Asn Arg Phe Asp Ile Thr Ala Pro Cys Ala Leu Asp Gly Ile
305                 310                 315                 320

Cys Tyr Ile Glu Ala Ala Arg Ile Glu Gln Tyr Leu Asn Thr Pro Ala
                325                 330                 335

Val Trp Ala Ala Leu Ser Pro Lys Glu Ile Lys Glu Tyr Lys Val
            340                 345                 350

Thr Ser Asp Asn Val Ser Arg Ala Phe Asp Leu Thr Ser Asp Thr Met
        355                 360                 365

Thr Pro Ala Ser Glu Gln Val Ala Phe Leu Leu Ala Asn Gln Val His
        370                 375                 380

Phe Leu Ala Tyr Gln Gly Asn Leu Asp Leu Ala Cys Asn Thr Ala Gly
385                 390                 395                 400

Asn Leu Arg Trp Ala His Ser Leu Pro Trp Arg Gly Gln Val Glu Phe
```

-continued

```
                405                 410                 415
Ala Ser Lys Ala Leu Arg Pro Trp Ser Trp Val Asp Val Ser Gly
        420                 425                 430
Lys Gly Gly Val Ala Gly Thr Thr Lys Glu Glu Ser Arg Phe Ala Leu
        435                 440                 445
Val Thr Val Asp Gly Ala Gly His Phe Leu Pro Gln Asp Arg Pro Asp
        450                 455                 460
Ile Ala Leu Asp Met Met Val Arg Trp Ile Ser Gly Ala Ser Phe Thr
465                 470                 475                 480
Glu

<210> SEQ ID NO 148
<211> LENGTH: 319
<212> TYPE: PRT
<213> ORGANISM: Aspergillus niger

<400> SEQUENCE: 148

Met Thr Leu Leu Leu Asn Phe His Ala Leu Phe Thr Val Ile Leu Val
1               5                   10                  15
Ala Asn Leu Ser Thr Arg Cys Ser Ala Leu Leu Ser Gly Arg Asp Phe
            20                  25                  30
Cys Ser Thr Pro Ala Pro Gly Glu Ser Leu Arg Ala Glu His Arg Arg
        35                  40                  45
Leu Tyr Asp Val Gln Ala Gln Arg Asp Ser Thr Ala Glu Glu Ser Arg
    50                  55                  60
Glu Val Val Pro Trp Ile Glu Ile Glu Thr Trp Phe His Ile Val Ser
65                  70                  75                  80
Ser Asn Glu Ala Ala Asn Thr Val Ser Asp Asp Met Ile Thr Ser Gln
                85                  90                  95
Leu Ser Tyr Leu Gln Lys Ala Tyr Glu Ser Ala Thr Ile Thr Tyr Arg
            100                 105                 110
Leu Glu Gly Ile Thr Arg His Ile Asn Asp Ser Trp Ala Arg Asn Asp
        115                 120                 125
Asp Glu Leu Gly Met Lys Asn Ala Leu Arg Arg Gly Asn Tyr Gly Thr
    130                 135                 140
Leu Asn Val Tyr Phe Gln Thr Asp Leu Gln Ala Ser Ser Asp Glu Asn
145                 150                 155                 160
Ser Arg Asp Tyr Pro Asn Asp Gly Asn Arg Arg Thr Asp Val Ser Asp
                165                 170                 175
Gln Ser Ser Ser Thr Val Leu Gly Phe Cys Thr Leu Pro Asp Pro Ser
            180                 185                 190
Val Asn Ser Ser Pro Arg Ser Ser Tyr Ile Lys Asp Gly Cys Asn
        195                 200                 205
Val Leu Ala Asp Ile Met Pro Gly Gly Ser Leu Ala Gln Tyr Asn Lys
    210                 215                 220
Gly Gly Thr Ala Val His Glu Val Gly His Trp Asn Gly Leu Leu His
225                 230                 235                 240
Thr Phe Glu Gly Glu Ser Cys Ser Pro Asp Asn Glu Gly Asp Tyr Ile
                245                 250                 255
Asp Asp Thr Pro Glu Gln Ser Glu Pro Thr Ser Gly Cys Pro Ala Glu
            260                 265                 270
Lys Asp Ser Cys Pro Asp Leu Pro Gly Leu Asp Ala Ile His Asn Phe
        275                 280                 285
Met Asp Tyr Ser Ser Asp Asp Cys Tyr Glu Ser Phe Thr Pro Asp Gln
```

```
                   290                 295                 300
Ala Glu Arg Met Arg Ser Met Trp Ser Ala Met Arg Glu Gly Lys
305                 310                 315

<210> SEQ ID NO 149
<211> LENGTH: 639
<212> TYPE: PRT
<213> ORGANISM: Aspergillus niger

<400> SEQUENCE: 149

Met His Val Ser Leu Phe Leu Leu Ser Val Thr Ala Ala Phe Ala Ser
1               5                  10                  15

Pro Thr Pro His Asn Tyr Val Val His Glu Arg Arg Asp Ala Leu Pro
            20                  25                  30

Ser Val Trp Val Glu Ser Arg Leu Asp Lys Gly Ala Leu Leu Pro
        35                  40                  45

Met Arg Ile Gly Leu Thr Gln Ser Asn Leu Asp Arg Gly His Asp Leu
50                  55                  60

Leu Met Glu Val Ser His Pro Gln Ser Ser Arg Tyr Gly Lys His Leu
65                  70                  75                  80

Ser Ser Glu Glu Val His Asp Leu Phe Ala Pro Ser Asn Glu Ala Val
                85                  90                  95

Glu Thr Val Arg Thr Trp Ile Glu Ser Ala Gly Ile Ala Pro Ser Arg
            100                 105                 110

Ile Ser Gln Ser Tyr Asn Lys Gln Trp Leu Gln Phe Asp Ala His Ala
        115                 120                 125

Ser Glu Val Glu Gln Leu Leu Gln Thr Glu Tyr Tyr Ile Tyr Thr His
130                 135                 140

Ala Asp Thr Gly Ser Ser His Val Thr Cys His Glu Tyr His Val Pro
145                 150                 155                 160

Glu Thr Ile Gln Ser His Ile Asp Tyr Ile Thr Pro Gly Val Lys Met
                165                 170                 175

Leu Glu Val Arg Gly Thr Pro Ser Lys Lys Arg Asp Ala Glu Lys Arg
            180                 185                 190

Ser Leu Gly Ser Leu Pro Pro Ile Leu Ala Pro Leu Pro Ile Asn Ile
        195                 200                 205

Thr Lys Ile Phe Asp Asp Pro Leu Ala His Cys Asp Leu Ala Val Thr
210                 215                 220

Pro Asp Cys Ile Arg Ala Met Tyr Asn Ile Thr Lys Gly Thr Thr Ala
225                 230                 235                 240

Thr Lys Gly Asn Glu Leu Gly Ile Phe Glu Asp Leu Gly Asp Ile Tyr
                245                 250                 255

Ser Gln Asp Asp Leu Asn Leu Phe Phe Ala Asn Phe Ala Ser Asp Ile
            260                 265                 270

Pro Gln Gly Thr His Pro Thr Leu Asp Ser Ile Asp Gly Ala Thr Ala
        275                 280                 285

Pro Thr Asp Val Thr Asn Ala Gly Pro Glu Ser Asp Leu Asp Phe Gln
290                 295                 300

Ile Ala Tyr Pro Ile Ile Trp Pro Gln Asn Thr Ile Leu Tyr Gln Thr
305                 310                 315                 320

Asp Asp Pro Asn Tyr Glu Asp Asn Tyr Asn Phe Lys Gly Leu Leu Asn
                325                 330                 335

Asn Phe Leu Tyr Ala Ile Asp Gly Ser Tyr Cys Asn Glu Thr Ser Ser
            340                 345                 350
```

-continued

```
Leu Asp Pro Gln Tyr Pro Asp Pro Ser Pro Gly Gly Tyr Ser Ser Pro
        355                 360                 365
Lys Gln Cys Gly Val Tyr Thr Pro Thr Asn Val Ile Ser Ile Ser Tyr
    370                 375                 380
Gly Ser Pro Glu Ala Asp Leu Pro Ile Ala Tyr Gln Arg Arg Gln Cys
385                 390                 395                 400
His Glu Phe Met Lys Leu Gly Leu Gln Gly Ile Ser Val Val Ala
                405                 410                 415
Ser Gly Asp Ser Gly Val Ala Ser Ser Thr Gly Thr Cys Phe Gly Asp
            420                 425                 430
Ala Asp Asn Val Phe Val Pro Asp Phe Pro Ala Thr Cys Pro Tyr Leu
        435                 440                 445
Thr Ala Val Gly Gly Thr Tyr Leu Pro Leu Gly Ala Asp Ala Ala Lys
    450                 455                 460
Asp Gln Glu Ile Ala Val Thr Arg Phe Pro Ser Gly Gly Phe Ser
465                 470                 475                 480
Asn Ile Tyr Ala Arg Pro Ser Tyr Gln Asn His Ser Val Glu Thr Tyr
                485                 490                 495
Phe Ser Thr Thr Ser Asp Asp Leu Thr Tyr Pro Tyr Tyr Ser Gly Val
            500                 505                 510
Asn Tyr Thr Asp Phe Ser Asn Thr Asp Gly Val Tyr Asn Arg Ile Gly
        515                 520                 525
Arg Gly Tyr Pro Asp Val Ser Ala Ile Ala Asp Asn Ile Ile Ile Tyr
    530                 535                 540
Asn Gln Gly Glu Ala Thr Leu Val Gly Gly Thr Ser Ala Ala Ala Pro
545                 550                 555                 560
Ala Phe Ala Ala Met Leu Thr Arg Ile Asn Glu Glu Arg Leu Ala Lys
                565                 570                 575
Gly Lys Ser Thr Val Gly Phe Val Asn Pro Val Leu Tyr Glu His Pro
            580                 585                 590
Glu Ala Phe Arg Asp Val Thr Val Gly Ser Asn Pro Gly Cys Gly Thr
        595                 600                 605
Asp Gly Phe Pro Val Ala Gly Gly Trp Asp Pro Val Thr Gly Leu Gly
    610                 615                 620
Thr Pro Arg Phe Glu Asp Leu Met Asp Ile Phe Val Gly Asp Asp
625                 630                 635
```

<210> SEQ ID NO 150
<211> LENGTH: 371
<212> TYPE: PRT
<213> ORGANISM: Aspergillus niger

<400> SEQUENCE: 150

```
Met Ala Ser Lys Thr Leu Leu Leu Ile Pro Ala Leu Ala Thr Ala Ala
1               5                   10                  15
Leu Gly Ser Val Leu Asp Leu Asp Ile Lys Val Asp Leu Gly Thr Pro
            20                  25                  30
Gly Gly Pro Phe Asp Leu Met Tyr Asp Thr Gly Ser Ser Thr Leu Trp
        35                  40                  45
Val Leu Asp Ser Asn Cys Thr Asp Asp Cys Pro Asn Val Ser Gly Tyr
    50                  55                  60
Ser Arg His Gly Tyr Asn Leu Thr Ser Gly Val Asn Leu Gly Val
65                  70                  75                  80
Asn Asp Ser Ile Ala Tyr Ser Gly Gly Thr Val Ser Gly Phe Thr Ala
                85                  90                  95
```

-continued

```
Thr Asp Ile Leu Thr Val Pro Asp Thr Asn Val Ser Tyr Arg Gln Ser
            100                 105                 110
Phe Ala Val Ile Thr Asp Ser Thr Trp Ala Ala Leu Ala Ala Asp Gly
        115                 120                 125
Phe Ile Gly Leu Ala Ser Ser Thr Ile Ala Phe Lys Asn Thr Thr Thr
    130                 135                 140
Ala Val Glu Gln Met Met Gln Asp Gly Leu Leu Asp Glu Pro Arg Phe
145                 150                 155                 160
Ala Ile Tyr Ala Gly Ser Gly Glu Ser Thr Val Thr Asn Pro Asn Pro
                165                 170                 175
Glu Asn Asn Gly Val Phe Thr Phe Gly Gly Ser His Glu Glu Thr Tyr
            180                 185                 190
Ala Asp Gly Glu Leu Gln Trp Met Lys Met Leu Ser Pro Phe Glu Ile
        195                 200                 205
Tyr Lys Thr Asn Leu Leu Gly Ile Gln Gly His Asn Asn Ser Asp Gly
    210                 215                 220
Gln Ala Leu Ser Ser Asp Val Leu Asn Trp Tyr Gly Gln Thr Asn Leu
225                 230                 235                 240
Phe Asn Val Ala Gly Ala Ser Ser Ile Ser Ile Pro Asn Asp Gln Ile
                245                 250                 255
Glu Ala Met Tyr Ala Leu Thr Pro Phe Ser Tyr Ala Asp Ile Ser Ser
            260                 265                 270
Gly Tyr Arg Pro Leu Cys Ser Asp Phe Asn Asp Thr Trp Ser Ile Ser
        275                 280                 285
Phe Thr Met Gly Phe Tyr Gly Glu Gly Val Thr Phe Asn Leu Thr Gly
    290                 295                 300
Asp Gln Leu Ala Val Pro Gly Tyr Gln Asp Asp His Cys Phe Pro
305                 310                 315                 320
Pro Phe Asn Pro Trp Asp Ser Tyr Asn Thr Ile Ile Gly Gln His Trp
                325                 330                 335
Leu Ser Asn Phe Tyr Ala Val Phe Asp Phe Gly Ser Phe Asp Pro Glu
            340                 345                 350
Thr Tyr Asp Ile Arg Val Gly Leu Ala Pro Leu Lys Lys Glu Tyr Leu
        355                 360                 365
Pro Ser Ala
    370

<210> SEQ ID NO 151
<211> LENGTH: 414
<212> TYPE: PRT
<213> ORGANISM: Aspergillus niger

<400> SEQUENCE: 151

Met Phe Pro Cys Ser Arg Ile Trp Ser Leu Leu Val Ala Ala Ala Thr
1               5                   10                  15
Ala Ser Ala Val Pro Thr Ser Leu Ala Thr Thr His Leu Gln Ser Val
            20                  25                  30
Asp Leu Leu Leu Thr Arg Ser Ser Tyr Gly Phe Leu Thr Asp Ile Ala
        35                  40                  45
Leu Gly Thr Pro Gly Gln Ser Leu Pro Tyr Leu Val Asp Trp Thr Trp
    50                  55                  60
Thr Gly His Tyr Val Val Thr Thr Leu Cys Tyr Asn Asp Pro Thr Ala
65                  70                  75                  80
Thr Tyr Asp Cys Leu Asn Val Asp Gln Lys Ile Phe Asn Gln Thr Leu
```

```
                    85                  90                  95
Ser Ser Thr Phe Ile Asn Gln Thr Asp Gln Tyr Gly Tyr Leu Tyr Trp
                100                 105                 110
Asp Pro Asn His Phe Tyr Phe Thr Glu Pro Ala Ala Ala Asp Val Ala
                115                 120                 125
Thr Asp Met Leu Arg Ile Gly Pro Thr Ala Val Asn Thr Thr Ile Gln
            130                 135                 140
Ala Ala Asn Phe Val Phe Asn Glu Thr Ile Ser Ala Phe Pro Phe Ser
145                 150                 155                 160
Gly Val Tyr Gly Leu Ser Pro Val Phe Gln Gly Asp Asn Arg Ser Val
                165                 170                 175
Gln Ala Ser Phe Tyr Gln Gly Trp Arg Ser Gly Ala Trp His Ser Pro
                180                 185                 190
Ile Val Ser Phe Ile Tyr Cys His Asp Asn Ala Thr Lys Ala Val Cys
                195                 200                 205
Ser Gly Tyr Asp Gly Leu Gln Thr Leu Gly Gly Tyr Asn Thr Ser His
            210                 215                 220
Val Gln Gly Asp Ile Thr Trp Tyr Asp Ile Ile Val Thr Glu Ala Ile
225                 230                 235                 240
Asn Thr Leu Asp Phe Val Tyr Ala Pro Ala Val Ile Asn Tyr Trp Ala
                245                 250                 255
Leu Asn Leu Thr Arg Phe Ser Ile Gly Asp Glu Gln Glu Leu Asn
                260                 265                 270
Lys Thr Thr Thr Leu Asp Gly Lys Gln Ala Ala Val Ala Ala Phe Asp
            275                 280                 285
His Ala Ser Tyr Gly Arg Gly Ala Pro Val Ser Val Tyr Gly Tyr Gln
            290                 295                 300
Arg Leu Val Glu Leu Val Gly Ala Lys Ala Val Thr Leu Ser Asp Pro
305                 310                 315                 320
Pro Asn Asn Gly Glu Gln Gly Phe Tyr Gln Phe Asp Cys Arg Asn Ser
                325                 330                 335
Ser Leu Leu Pro Pro Leu Arg Tyr Glu Phe Ala Gly Ser Glu Arg Ala
                340                 345                 350
Trp Glu Ile Val Pro Glu Asn Tyr Val Glu Val Leu Ala Asn Gly Thr
                355                 360                 365
Asn Lys Cys Thr Phe Asn Val Arg Thr Leu Gly Asp Gly Ala Met Val
            370                 375                 380
Met Gly Asn Phe Gly Glu Thr Phe Ala Ile Asp Lys Tyr Val Met Phe
385                 390                 395                 400
Asp Phe Glu Lys Leu Gln Val Gly Ile Ala Asp Phe Ala Trp
                405                 410

<210> SEQ ID NO 152
<211> LENGTH: 480
<212> TYPE: PRT
<213> ORGANISM: Aspergillus niger

<400> SEQUENCE: 152

Met His Leu Pro Gln Arg Leu Val Thr Ala Ala Cys Leu Cys Ala Ser
1               5                   10                  15
Ala Thr Ala Phe Ile Pro Tyr Thr Ile Lys Leu Asp Thr Ser Asp Asp
                20                  25                  30
Ile Ser Ala Arg Asp Ser Leu Ala Arg Arg Phe Leu Pro Val Pro Lys
            35                  40                  45
```

-continued

```
Pro Ser Asp Ala Leu Ala Asp Asp Ser Thr Ser Ala Ser Asp Glu
50              55                  60
Ser Leu Ser Leu Asn Ile Lys Arg Ile Pro Val Arg Arg Asp Asn Asp
65                  70                  75                  80
Phe Lys Ile Val Val Ala Glu Thr Pro Ser Trp Ser Asn Thr Ala Ala
                85                  90                  95
Leu Asp Gln Asp Gly Ser Asp Ile Ser Tyr Ile Ser Val Val Asn Ile
            100                 105                 110
Gly Ser Asp Glu Lys Ser Met Tyr Met Leu Leu Asp Thr Gly Gly Ser
            115                 120                 125
Asp Thr Trp Val Phe Gly Ser Asn Cys Thr Ser Thr Pro Cys Thr Met
    130                 135                 140
His Asn Thr Phe Gly Ser Asp Asp Ser Ser Thr Leu Glu Met Thr Ser
145                 150                 155                 160
Glu Glu Trp Ser Val Gly Tyr Gly Thr Gly Ser Val Ser Gly Leu Leu
                165                 170                 175
Gly Lys Asp Lys Leu Thr Ile Ala Asn Val Thr Val Arg Met Thr Phe
            180                 185                 190
Gly Leu Ala Ser Asn Ala Ser Asp Asn Phe Glu Ser Tyr Pro Met Asp
            195                 200                 205
Gly Ile Leu Gly Leu Gly Arg Thr Asn Asp Ser Ser Tyr Asp Asn Pro
        210                 215                 220
Thr Phe Met Asp Ala Val Ala Glu Ser Asn Val Phe Lys Ser Asn Ile
225                 230                 235                 240
Val Gly Phe Ala Leu Ser Arg Ser Pro Ala Lys Asp Gly Thr Val Ser
                245                 250                 255
Phe Gly Thr Thr Asp Lys Asp Lys Tyr Thr Gly Asp Ile Thr Tyr Thr
            260                 265                 270
Asp Thr Val Gly Ser Asp Ser Tyr Trp Arg Ile Pro Val Asp Asp Val
        275                 280                 285
Tyr Val Gly Gly Thr Ser Cys Asp Phe Ser Asn Lys Ser Ala Ile Ile
    290                 295                 300
Asp Thr Gly Thr Ser Tyr Ala Met Leu Pro Ser Asp Ser Lys Thr
305                 310                 315                 320
Leu His Ser Leu Ile Pro Gly Ala Lys Ser Ser Gly Ser Tyr His Ile
                325                 330                 335
Ile Pro Cys Asn Thr Thr Lys Leu Gln Val Ala Phe Ser Gly Val
            340                 345                 350
Asn Tyr Thr Ile Ser Pro Lys Asp Tyr Val Gly Ala Thr Ser Gly Ser
            355                 360                 365
Gly Cys Val Ser Asn Ile Ile Ser Tyr Asp Leu Phe Gly Asp Ile
    370                 375                 380
Trp Leu Leu Gly Asp Thr Phe Leu Lys Asn Val Tyr Ala Val Phe Asp
385                 390                 395                 400
Tyr Asp Glu Leu Arg Val Gly Phe Ala Glu Arg Ser Ser Asn Thr Thr
                405                 410                 415
Ser Ala Ser Asn Ser Thr Ser Ser Gly Thr Ser Ser Thr Ser Gly Ser
            420                 425                 430
Thr Thr Thr Gly Ser Ser Thr Thr Thr Ser Ser Ala Ser Ser Ser
        435                 440                 445
Ser Ser Ser Asp Ala Glu Ser Gly Ser Ser Met Thr Ile Pro Ala Pro
450                 455                 460
Gln Tyr Phe Phe Ser Ala Leu Ala Ile Ala Ser Phe Met Leu Trp Leu
```

| | | | |
|---|---|---|---|
| 465 | 470 | 475 | 480 |

<210> SEQ ID NO 153
<211> LENGTH: 466
<212> TYPE: PRT
<213> ORGANISM: Aspergillus niger

<400> SEQUENCE: 153

Met Thr Ser Ser Thr Leu Arg Leu Ala Val Ala Leu Ala Leu Ser Thr
1               5                   10                  15

Cys Ser Ser Ala Leu Ser Ser Gln Arg Asp Asp Ser Leu Val Val Pro
            20                  25                  30

Phe Pro Phe Gly Asn Leu Glu Asp Val His Ile Ala Lys Arg Asp Ser
        35                  40                  45

Ser Lys Thr Val Glu Ala Pro Leu Val Ile Tyr Gly Asp Ser Tyr Trp
    50                  55                  60

Met Asn Ala Ser Ile Gly Thr Pro Ala Gln Ser Leu Ser Phe Leu Leu
65                  70                  75                  80

Asp Leu Thr Arg Ser Arg Val Glu Pro Ala Tyr Thr Leu Asp Glu Asn
                85                  90                  95

Tyr Glu Cys Ser Asp Asp Glu Leu Cys Ser Glu Phe Gly Phe Tyr Lys
            100                 105                 110

Pro Thr Asp Ser Ser Thr Tyr Gln His Leu Thr Tyr Thr Gln Arg His
        115                 120                 125

Asp Ala Gly Val Asp Tyr Ser Tyr Leu Asp Thr Ile Thr Leu Gly Asp
    130                 135                 140

His Ala Thr Asp Asn Val Pro Leu Asp Met Tyr Leu Leu Ser Tyr Ile
145                 150                 155                 160

Ser Tyr Ser Ser Leu Gly Leu Ser Ser Val Asn Thr Ser Phe Pro Tyr
                165                 170                 175

Ile Leu Val Asp Arg Gly Leu Thr Thr Ser Pro Ser Phe Ser Leu Ile
            180                 185                 190

Gly Asp Asn Gly Asn Thr Thr Thr Pro Ser Ile Ile Phe Gly Gly Ile
        195                 200                 205

Asn Thr Ser Lys Phe Asn Gly Pro Leu Gln Ala Phe Ser Phe Ala Asp
    210                 215                 220

His Ser Ile Thr Asn Asn Pro Phe Val Thr Val Glu Ala Asp Ser Leu
225                 230                 235                 240

Gln Leu Thr Thr Asn Thr Asn Asp Asn Ser Thr Tyr Pro Ile Pro Ser
                245                 250                 255

Ser Thr Pro Met Met Leu Arg Thr Glu Glu Leu Ile Thr Tyr Leu Pro
            260                 265                 270

Asn Ser Thr Val Gln Ser Leu Tyr Thr Asp Leu Asn Ile Thr Met Asp
        275                 280                 285

Gly Val Ile Ser Thr Ser Arg Phe Tyr Gly Val Leu Pro Cys Ala Arg
    290                 295                 300

Gln Glu Thr Glu Ser His Thr Ile Ser Leu Ala Ile Gly Asn Met Thr
305                 310                 315                 320

Phe Ser Val Ser Trp Asp Glu Leu Phe Val Pro Trp Thr Arg Asp Gly
                325                 330                 335

Leu Cys Lys Phe Gly Ile Gln Ala Gln Asp Ser Asp Tyr Lys Thr Arg
            340                 345                 350

Ala Glu Leu Gly Val Pro Phe Leu Arg Arg Met Tyr Val Ala Val Asp
        355                 360                 365

-continued

Tyr Asn Asn Gln Phe Val Gly Val Ala Thr Leu Lys Asp Asp Asp
    370                 375                 380

Gln Asn Gly Gly Glu Asp Glu Ile Val Glu Ile Gly Thr Gly Thr Ala
385                 390                 395                 400

Leu Pro Ser Ala Val Gly Asp Trp Pro Ala Ser Val Thr Ala Tyr Thr
                405                 410                 415

Pro Ala Ala Ser Thr Gly Thr Ala Ala Ala Thr Leu Thr Phe Thr Thr
            420                 425                 430

Ala Thr Ser Ser Gly Gly Val Val Pro Thr Gly Leu Ser Glu Leu
        435                 440                 445

Gly Arg Ala Phe Leu Val Pro Gly Val Leu Gly Met Ala Val Leu Gln
450                 455                 460

Ala Val
465

<210> SEQ ID NO 154
<211> LENGTH: 543
<212> TYPE: PRT
<213> ORGANISM: Aspergillus niger

<400> SEQUENCE: 154

Met Met Arg Pro Ile Leu Leu Pro Leu Leu Gly Val Phe Leu Gln Thr
1               5                   10                  15

Ser Ser Ala Ser Asn Pro Tyr Val Met Ser Trp Ser Ser Gln Ala Tyr
                20                  25                  30

Gly Pro Asp Gly Pro Trp Gln Ala Val Ser Ile Asp Val Gly Ser Asn
            35                  40                  45

Gln Gln Thr Val Asp Leu Tyr Pro Gly Ala Asn Tyr Ala Ser Thr Ile
50                  55                  60

Leu Met Ser Thr Leu Cys Thr Asn Lys Thr Leu Ser Ser Thr Cys Tyr
65                  70                  75                  80

Ala Ala Glu Ala Gly Thr Phe Asn Gln Asn Thr Ser Thr Thr Ala Tyr
                85                  90                  95

Thr Thr Ala Ser Ser Trp Glu Thr Thr Tyr Trp Ala Val Glu Gly Gly
            100                 105                 110

Ser Gln Glu Ala Val Leu Gly Asp Glu Val Thr Leu Gly Ser Phe Val
        115                 120                 125

Val Pro Asn Val Ser Phe Glu Ala Ile Tyr Gln Thr Tyr Gln Thr Tyr
130                 135                 140

Pro Asn Gly Ile Ala Tyr Pro Val Ser Val Gly Ser Leu Ala Leu Gly
145                 150                 155                 160

Gly Pro Tyr Leu Ser Asp Thr Val Ser Asn Ser Thr Val Leu Asn Met
                165                 170                 175

Ile Ala Gly Trp Leu Tyr Ser Ser Asn Asp Ile Pro Ser Tyr Ser Tyr
            180                 185                 190

Gly Met His Ile Gly Ser Val Asp Pro Lys Ile Pro Gly Ser Leu Ile
        195                 200                 205

Leu Gly Gly Tyr Asp Lys Ser Arg Val Ile Gly Asp Val Ser Ala Gln
    210                 215                 220

Gly Val Val Ser Ser Gly Leu Leu Glu Leu Glu Leu Lys Asp Ile
225                 230                 235                 240

Gly Leu Gly Val Ala Ala Gly Ser Ser Pro Phe Ser Phe Asn Asn Glu
                245                 250                 255

Ser Gly Leu Phe Leu Gln Ser Ser Gly Ser Val Gln Ala Lys Thr Val
            260                 265                 270

```
Gln Ile Asp Pro Thr Lys Pro Tyr Met Tyr Leu Pro Gln Ala Thr Cys
            275                 280                 285

Asp Ala Ile Thr Ser Thr Met Pro Ile Ser Phe Asn Ser Ser Leu Gly
        290                 295                 300

Leu Tyr Phe Trp Asp Thr Ser Asp Asp Tyr Leu Asn Ile Thr Ser
305                 310                 315                 320

Ser Ala Ala Tyr Leu Ser Phe Val Phe Asn Met Asn Gly Val Asn Asn
                325                 330                 335

Lys Asn Ile Thr Ile Lys Ile Pro Phe Ser Gln Leu Asn Leu Thr Leu
            340                 345                 350

Gln Glu Pro Leu Val Asp Gln Asn Val Thr Tyr Phe Pro Cys Phe Leu
            355                 360                 365

Thr Thr Ser Thr Pro Val Leu Gly Arg Ala Phe Leu Gln Ser Ala Phe
        370                 375                 380

Val Gly Val Asn Trp Phe Asn Gly Asn Asn Ser Gly Thr Trp Phe Leu
385                 390                 395                 400

Ala Gln Ala Pro Gly Pro Gly Tyr Ala Ser Glu Asp Ile Thr Arg Ile
                405                 410                 415

Ala Val Ser Asp Thr Ser Leu Ser Ala Ser Asn Gly Thr Trp Glu Glu
            420                 425                 430

Thr Trp Ala Thr Tyr Trp Gly Ile Lys Thr Ser Asp Asn Ser Ser Ser
        435                 440                 445

Ser Lys Ser Gly Leu Ser Ser Gly Ala Lys Ile Gly Ile Gly Val Gly
450                 455                 460

Val Gly Val Gly Gly Ala Val Leu Ile Ala Ala Gly Ile Ala Ile Ala
465                 470                 475                 480

Phe Cys Leu Arg Arg Arg Gly Ala Ser Gln Glu Ala Ala Gly Glu
                485                 490                 495

Gln Arg Arg Ser Met Phe Arg Gly Phe Ala Glu Leu Pro Gly Gly Ala
            500                 505                 510

His Ser Glu Pro Ala Lys Glu Leu Asp Thr Lys Met His Lys Pro Pro
            515                 520                 525

Gln Glu Met Met Ala Ser Gln Glu Val Glu Arg Tyr Glu Leu Gly
            530                 535                 540

<210> SEQ ID NO 155
<211> LENGTH: 844
<212> TYPE: PRT
<213> ORGANISM: Aspergillus niger

<400> SEQUENCE: 155

Met Arg Leu Thr Gly Gly Val Ala Ala Ala Leu Gly Leu Cys Ala Ala
1               5                   10                  15

Ala Ser Ala Ser Leu His Pro His Arg Ser Tyr Glu Thr His Asp Tyr
            20                  25                  30

Phe Ala Leu His Leu Asp Glu Ser Thr Ser Pro Ala Asp Val Ala Gln
        35                  40                  45

Arg Leu Gly Ala Arg His Glu Gly Pro Val Gly Glu Leu Pro Ser His
    50                  55                  60

His Thr Phe Ser Ile Pro Arg Glu Asn Ser Asp Val His Ala Leu
65                  70                  75                  80

Leu Asp Gln Leu Arg Asp Arg Arg Leu Arg Arg Ser Gly Asp
                85                  90                  95

Asp Ala Ala Val Leu Pro Ser Leu Val Gly Arg Asp Glu Gly Leu Gly
```

-continued

```
                100                 105                 110
Gly Ile Leu Trp Ser Glu Lys Leu Ala Pro Gln Arg Lys Leu His Lys
            115                 120                 125
Arg Val Pro Pro Thr Gly Tyr Ala Ala Arg Ser Pro Val Asn Thr Gln
130                 135                 140
Asn Asp Pro Gln Ala Leu Ala Ala Gln Lys Arg Ile Ala Ser Glu Leu
145                 150                 155                 160
Gly Ile Ala Asp Pro Ile Phe Gly Glu Gln Trp His Leu Tyr Asn Thr
                165                 170                 175
Val Gln Leu Gly His Asp Leu Asn Val Thr Gly Ile Trp Leu Glu Gly
            180                 185                 190
Val Thr Gly Gln Gly Val Thr Thr Ala Ile Val Asp Asp Gly Leu Asp
            195                 200                 205
Met Tyr Ser Asn Asp Leu Arg Pro Asn Tyr Phe Ala Ala Gly Ser Tyr
            210                 215                 220
Asp Tyr Asn Asp Lys Val Pro Glu Pro Arg Pro Arg Leu Ser Asp Asp
225                 230                 235                 240
Arg His Gly Thr Arg Cys Ala Gly Glu Ile Gly Ala Ala Lys Asn Asp
                245                 250                 255
Val Cys Gly Val Gly Val Ala Tyr Asp Ser Arg Ile Ala Gly Ile Arg
            260                 265                 270
Ile Leu Ser Ala Pro Ile Asp Asp Thr Asp Glu Ala Ala Ala Ile Asn
            275                 280                 285
Tyr Ala Tyr Gln Glu Asn Asp Ile Tyr Ser Cys Ser Trp Gly Pro Tyr
            290                 295                 300
Asp Asp Gly Ala Thr Met Glu Ala Pro Gly Thr Leu Ile Lys Arg Ala
305                 310                 315                 320
Met Val Asn Gly Ile Gln Asn Gly Arg Gly Lys Gly Ser Val Phe
                325                 330                 335
Val Phe Ala Ala Gly Asn Gly Ala Ile His Asp Asp Asn Cys Asn Phe
            340                 345                 350
Asp Gly Tyr Thr Asn Ser Ile Tyr Ser Ile Thr Val Gly Ala Ile Asp
            355                 360                 365
Arg Glu Gly Asn His Pro Pro Tyr Ser Glu Ser Cys Ser Ala Gln Leu
            370                 375                 380
Val Val Ala Tyr Ser Ser Gly Ala Ser Asp Ala Ile His Thr Thr Asp
385                 390                 395                 400
Val Gly Thr Asp Lys Cys Ser Thr Thr His Gly Gly Thr Ser Ala Ala
                405                 410                 415
Gly Pro Leu Ala Ala Gly Thr Val Ala Leu Ala Leu Ser Val Arg Pro
            420                 425                 430
Glu Leu Thr Trp Arg Asp Val Gln Tyr Leu Met Ile Glu Ala Ala Val
            435                 440                 445
Pro Val His Glu Asp Asp Gly Ser Trp Gln Asp Thr Lys Asn Gly Lys
            450                 455                 460
Lys Phe Ser His Asp Trp Gly Tyr Gly Lys Val Asp Thr Tyr Thr Leu
465                 470                 475                 480
Val Lys Arg Ala Glu Thr Trp Asp Leu Val Lys Pro Gln Ala Trp Leu
                485                 490                 495
His Ser Pro Trp Gln Arg Val Glu His Glu Ile Pro Gln Gly Glu Gln
            500                 505                 510
Gly Leu Ala Ser Ser Tyr Glu Val Thr Glu Asp Met Leu Lys Gly Ala
            515                 520                 525
```

```
Asn Leu Glu Arg Leu Glu His Val Thr Val Thr Met Asn Val Asn His
    530                 535                 540

Thr Arg Arg Gly Asp Leu Ser Val Glu Leu Arg Ser Pro Asp Gly Arg
545                 550                 555                 560

Val Ser His Leu Ser Thr Pro Arg Arg Pro Asp Asn Gln Glu Val Gly
                565                 570                 575

Tyr Val Asp Trp Thr Phe Met Ser Val Ala His Trp Gly Glu Ser Gly
            580                 585                 590

Ile Gly Lys Trp Thr Val Ile Val Lys Asp Thr Asn Val Asn Glu His
        595                 600                 605

Thr Gly Gln Phe Ile Asp Trp Arg Leu Asn Leu Trp Gly Glu Ala Ile
    610                 615                 620

Asp Gly Ala Glu Gln Pro Leu His Pro Met Pro Thr Glu His Asp Asp
625                 630                 635                 640

Asp His Ser Tyr Glu Glu Gly Asn Val Ala Thr Thr Ser Ile Ser Ala
                645                 650                 655

Val Pro Thr Lys Thr Glu Leu Pro Asp Lys Pro Thr Gly Gly Val Asp
            660                 665                 670

Arg Pro Val Asn Val Lys Pro Thr Thr Ser Ala Met Pro Thr Gly Ser
        675                 680                 685

Leu Thr Glu Pro Ile Asp Asp Glu Glu Leu Gln Lys Thr Pro Ser Thr
    690                 695                 700

Glu Ala Ser Ser Thr Pro Ser Pro Ser Pro Thr Thr Ala Ser Asp Ser
705                 710                 715                 720

Ile Leu Pro Ser Phe Phe Pro Thr Phe Gly Ala Ser Lys Arg Thr Gln
                725                 730                 735

Val Trp Ile Tyr Ala Ala Ile Gly Ser Ile Ile Val Phe Cys Ile Gly
            740                 745                 750

Leu Gly Val Tyr Phe His Val Gln Arg Lys Arg Ile Arg Asp Asp
        755                 760                 765

Ser Arg Asp Asp Tyr Asp Phe Glu Met Ile Glu Asp Glu Asp Glu Leu
    770                 775                 780

Gln Ala Met Asn Gly Arg Ser Asn Arg Ser Arg Arg Gly Gly Glu
785                 790                 795                 800

Leu Tyr Asn Ala Phe Ala Gly Glu Ser Asp Glu Pro Leu Phe Ser
                805                 810                 815

Asp Glu Asp Glu Pro Tyr Arg Asp Arg Gly Ile Ser Gly Glu Gln
            820                 825                 830

Glu Arg Glu Gly Ala Asp Gly Glu His Ser Arg Arg
        835                 840

<210> SEQ ID NO 156
<211> LENGTH: 149
<212> TYPE: PRT
<213> ORGANISM: Aspergillus niger

<400> SEQUENCE: 156

Met Lys Thr Phe Ser Thr Val Thr Ser Leu Leu Ala Leu Phe Ser Ser
1               5                   10                  15

Ala Leu Ala Ala Pro Val Asp Ser Ala Glu Ala Gly Thr Thr Val
            20                  25                  30

Ser Val Ser Tyr Asp Thr Ala Tyr Asp Val Ser Gly Ala Ser Leu Thr
        35                  40                  45

Thr Val Ser Cys Ser Asp Gly Ala Asn Gly Leu Ile Asn Lys Gly Tyr
```

-continued

```
            50                  55                  60
Ser Asn Phe Gly Ser Leu Pro Gly Phe Pro Lys Ile Gly Gly Ala Pro
 65                  70                  75                  80

Thr Ile Ala Gly Trp Asn Ser Pro Asn Cys Gly Lys Cys Tyr Ala Leu
                 85                  90                  95

Thr Tyr Asn Gly Gln Thr Val Asn Ile Leu Ala Ile Asp Ser Ala Pro
                100                 105                 110

Gly Gly Phe Asn Ile Ala Leu Glu Ala Met Asn Thr Leu Thr Asn Asn
            115                 120                 125

Gln Ala Gln Gln Leu Gly Arg Ile Glu Ala Thr Tyr Thr Glu Val Asp
        130                 135                 140

Val Ser Leu Cys Ala
145
```

<210> SEQ ID NO 157
<211> LENGTH: 296
<212> TYPE: PRT
<213> ORGANISM: Aspergillus niger

<400> SEQUENCE: 157

```
Met Ala Gln Ile Phe Trp Leu Ser Leu Phe Leu Val Ser Trp Val
 1               5                  10                  15

Arg Ala Glu Ser Asn Arg Thr Glu Val Asp Leu Ile Phe Pro Arg Asn
                 20                  25                  30

Asp Thr Phe Ala Pro Met Pro Leu Met Pro Val Val Phe Ala Val Gln
             35                  40                  45

Ala Pro Ser Val Ala His Lys Val Asn Thr Tyr Ile Glu Tyr Gly Tyr
 50                  55                  60

Tyr Pro Val Gly Arg Pro Asn Glu Thr Val Ile Gly Gln Thr Asp His
 65                  70                  75                  80

Val Ser Asp Ser Thr Asn Glu Thr Thr Tyr Phe Ser Val Ser Gly Ile
                 85                  90                  95

Gly Arg Thr Phe Asn Thr Thr Gly Ser Trp Glu Leu Phe Trp Arg Leu
            100                 105                 110

Arg Trp Thr Asn Cys Ser Ile Ser Glu Asp Ser Arg Tyr Tyr Asn Gln
        115                 120                 125

Ser Tyr Pro Trp Ile Ser Pro Tyr Ile Asp Gly Ser Leu Asn Ile
    130                 135                 140

Asp Lys Val Tyr Glu Gly Phe His Tyr Thr Ala Tyr Asn Val Ile Val
145                 150                 155                 160

Asp Arg Val Thr Phe Ser Thr Arg Glu Asp Ala Ser Gln Pro Asn Leu
                165                 170                 175

Thr Thr Leu Thr Asn Ser Glu Asn Cys Asp Lys Val Ser Ser Leu Ala
            180                 185                 190

Leu Leu Ser Ile Val Asp Ser Leu Arg Ile Pro Pro Gln Leu Pro Gln
        195                 200                 205

Glu Asp Ile Asp Thr Val Ser Met Cys Pro Gln Leu Ala Asp Ala Arg
    210                 215                 220

Leu Asn Ser Thr Ser Thr Ser Ser Pro Cys Ser Val Ser Ile Ser Pro
225                 230                 235                 240

Glu Val Glu Ser Asn Ile Leu Ala Lys Ile Ala Asp Asn Glu Cys Asn
                245                 250                 255

Asn Ala Leu His Pro Ala Val Ser Cys Thr Thr Glu Glu Thr Lys Glu
            260                 265                 270
```

```
Gly Ser Ala Ser Ser His Asp His Gly His Ala Val Trp Leu Val Ile
        275                 280                 285

Thr Leu Ala Phe Ala Phe Leu Phe
        290                 295

<210> SEQ ID NO 158
<211> LENGTH: 310
<212> TYPE: PRT
<213> ORGANISM: Aspergillus niger

<400> SEQUENCE: 158

Met Gly Gly Arg Asp Val Ala Ile Leu Ser Arg His Phe Ala Val Thr
1               5                   10                  15

Ser Ser Gln Ser Val Asn Gly Val Ser Gly Met Phe Gln His Thr
            20                  25                  30

Val Thr Ser Ser Pro Ser Phe Thr Thr Asn Gln Phe Phe Lys Lys Lys
        35                  40                  45

Phe Thr Ala Ala Ile Ala Thr Ala Ile Phe Ala Ser Val Ala Val Ala
    50                  55                  60

Ala Pro Gln Arg Gly Leu Glu Ala Arg Leu Lys Ala Arg Gly Ser Ser
65                  70                  75                  80

Lys Gly Ser Arg Pro Leu Gln Ala Val Ala Arg Pro Ala Ser Thr Lys
                85                  90                  95

Asn Gln Thr Asn Val Glu Tyr Ser Ser Asn Trp Ser Gly Ala Val Leu
            100                 105                 110

Val Glu Pro Pro Ser Ala Ala Thr Tyr Thr Ala Val Thr Gly Thr
        115                 120                 125

Phe Thr Val Pro Glu Pro Thr Gly Asn Ser Gly Ser Gln Ala Ala
    130                 135                 140

Ser Ala Trp Val Gly Ile Asp Gly Asp Thr Tyr Gly Asn Ala Ile Leu
145                 150                 155                 160

Gln Thr Gly Val Asp Phe Thr Val Thr Asp Gly Glu Ala Ser Phe Asp
                165                 170                 175

Ala Trp Tyr Glu Trp Tyr Pro Asp Tyr Ala Tyr Asp Phe Ser Gly Ile
            180                 185                 190

Asp Ile Ser Ala Gly Asp Glu Ile Val Ala Ile Val Glu Ser Tyr Thr
        195                 200                 205

Ser Thr Thr Gly Ile Ala Ile Ile Glu Asn Lys Ser Thr Gly Gln Lys
    210                 215                 220

Val Ser Lys Glu Leu Ser Ser Ser Ser Leu Gly Gly Gln Asn Ala
225                 230                 235                 240

Glu Trp Ile Val Glu Asp Phe Glu Glu Asn Gly Ser Leu Val Asn Leu
                245                 250                 255

Val Asp Phe Gly Thr Val Thr Phe Thr Gly Ala Val Ala Lys Ala Ala
            260                 265                 270

Gly Gly Glu Ser Val Gly Leu Thr Asp Ala Thr Ile Glu Ile Glu
        275                 280                 285

Glu Asn Gly Gln Val Val Thr Asp Val Thr Ile Asp Ser Asp Ser Glu
    290                 295                 300

Val Thr Ile Thr Tyr Glu
305                 310

<210> SEQ ID NO 159
<211> LENGTH: 681
<212> TYPE: PRT
<213> ORGANISM: Aspergillus niger
```

<400> SEQUENCE: 159

```
Met Arg Cys Ser Leu Ile Ser Leu Leu Gly Leu Ala Ala Ile Pro Ala
1               5                   10                  15

Leu Gly Gly Cys Pro Phe Ala His Thr Ala Asn Met Gly Ile Asp Asn
            20                  25                  30

Met Val Lys Ala His Ala His Met Ser Arg Pro Leu Ile Ala Ser Lys
        35                  40                  45

Ser Ser Pro Ser Thr Val Pro Thr Ser Ser Ser Thr Pro Ser Val Gly
    50                  55                  60

Gln Lys Gly Val Phe Met Met Asn Arg Ile Ala Pro Gly Thr Ser Glu
65                  70                  75                  80

Leu Tyr Ile Ala Asn Thr Asp Gly Ser Asn Glu Arg Pro Leu Leu Ser
                85                  90                  95

Asn Pro Val Tyr Glu Tyr His Ala Ser Phe Ser Pro Asp Val Glu Trp
            100                 105                 110

Ile Thr Phe Thr Ser Glu Arg Asn Gly Asp Gly Asn Ser Asp Ile Tyr
        115                 120                 125

Arg Val Arg Thr Asn Gly Ser Asp Leu Gln Glu Leu Val Ala Thr Pro
130                 135                 140

Ala Val Glu Asp Ser Val Val Ile Ser Pro Asn Gly Arg Leu Ala Ala
145                 150                 155                 160

Tyr Val Ser Thr Ala Asn Asn Met Lys Ala Asn Ile Trp Ile Leu Asp
                165                 170                 175

Leu Gln Thr Gly Ala Gln Trp Asn Leu Thr Asn Thr Pro Thr Thr Ala
            180                 185                 190

Ala Asn Ser Ser Leu Met Glu Ser Tyr Leu Arg Pro Ala Trp Ser Pro
        195                 200                 205

Asp Gly Glu Trp Ile Ala Phe Ser Ser Asp Arg Asn Thr Gln Trp Asp
    210                 215                 220

Gly His Gly Val Pro Thr Phe Leu Gly Arg Thr Gly Trp Glu Thr Thr
225                 230                 235                 240

Gln Glu Leu Ser Leu Tyr Ala Ile Arg Pro Asn Gly Ser Asp Phe Arg
                245                 250                 255

Gln Ile Ile Ser Lys Pro Tyr Tyr Ser Leu Gly Ser Pro Lys Trp Ser
            260                 265                 270

Ala Asp Gly Lys Arg Ile Val Tyr Tyr Glu Met Thr Arg Glu Asp Thr
        275                 280                 285

Tyr Asn Ala His Arg Pro Glu Thr Ile Thr Thr Ala Asn Ser Thr Ile
    290                 295                 300

Met Ser Val Asp Phe Glu Thr Gly Thr Asp Val Arg Val Glu Val Ala
305                 310                 315                 320

Gly Ser Gly Val Lys Gln Phe Pro Gln Tyr Leu Asp Lys Asn Gly Thr
                325                 330                 335

Ile Ala Tyr Thr Leu Lys Gly Gly Thr Ser Glu Gly Phe Tyr Thr Thr
            340                 345                 350

Ala Gly Leu Tyr Val Asn Thr Thr Ser Ala Thr Leu Arg Ser Pro Ala
        355                 360                 365

Trp Ser Pro Asp Gly Lys Gln Val Val Tyr Lys Ser Thr Trp Ser
    370                 375                 380

Ile Arg Ser Gly Tyr Lys Gln Leu Tyr Ser Trp Asp Ser Asp Trp Asp
385                 390                 395                 400

Tyr Arg Phe Thr Asp Val Phe Pro Gln Val Ser His Gln Glu Arg Val
```

-continued

```
                405                 410                 415
Ala Ile Thr Gln Lys Gln Leu Gly Asn Ser Ser Ile Val Thr Leu Asn
            420                 425                 430

Thr Thr Gly Gly Asp Leu Gln Leu Val Tyr Asp Pro Ser Thr Ala Asp
            435                 440                 445

Phe Val Ser Asp Asp Glu Thr Thr Gly Leu Ser Ala Tyr Gln Pro Ser
            450                 455                 460

Trp Ser Pro Cys Gly Glu Trp Leu Val Phe Val Gly Phe Trp Phe
465                 470                 475                 480

Glu Thr Arg Glu Ala Ser Gly Gly Trp Ile Val Arg Ala Thr Ala Asn
            485                 490                 495

Gly Ser Tyr Ser Glu Val Leu Val Asn Ser Ser Tyr Ser Ile Thr Glu
            500                 505                 510

Asp Gly Ala Leu Asn Ser Gly Phe Pro Ser Phe Ser Pro Asp Gly Lys
            515                 520                 525

Lys Val Val Tyr Arg Val Trp Gly Ala Asp Thr Ala Thr Tyr Gly Asn
            530                 535                 540

Ala Ser Glu Ile Gly Leu Arg Val Leu Asp Leu Glu Thr Arg Lys Thr
545                 550                 555                 560

Thr Val Leu Thr Thr Glu Trp Asp Asn Leu Pro Gln Phe Ser Pro Asp
            565                 570                 575

Gly Glu Leu Ile Leu Phe Thr Arg Lys Thr Ser Thr Tyr Asn Tyr Asp
            580                 585                 590

Val Cys Thr Ile Arg Pro Asp Gly Thr Asp Leu Arg Val Leu Thr Ser
            595                 600                 605

Ser Gly Ala Asn Asp Ala His Ala Val Trp Ser Gln Asp Gly Arg Ile
            610                 615                 620

Met Trp Ser Thr Gly Met Tyr Gly Phe Arg Phe Glu Cys Ala Leu Tyr
625                 630                 635                 640

Gly Asp Thr Phe Gln Pro Tyr Gly Gln Val Met Ile Met Asp Ala Asp
            645                 650                 655

Gly Gly Asn Lys Lys Leu Met Thr Asn Ser Met Trp Glu Asp Ser Met
            660                 665                 670

Pro Leu Phe Leu Pro Arg Glu Val Leu
            675                 680

<210> SEQ ID NO 160
<211> LENGTH: 624
<212> TYPE: PRT
<213> ORGANISM: Aspergillus niger

<400> SEQUENCE: 160

Met Pro Pro Asp Ala Lys Ser Pro Gly Tyr Gln Pro Gly Met Ala Val
1               5                   10                  15

Leu Pro Ser Arg Pro His Pro Ala Lys Gly Lys Ala Ile Arg Phe Leu
            20                  25                  30

Leu Ser Leu Ala Leu Val Ala Phe Ala Ile Val Gln Leu Cys Gly Asn
            35                  40                  45

Phe His Lys Asn Arg Ser Val Glu Gln Gln Leu Gln Ser Gln Thr Leu
        50                  55                  60

Asp Asp Glu Ser Phe Lys Trp Glu Asp Val Thr Pro Thr Lys Gln Leu
65                  70                  75                  80

Val Tyr His Pro Cys Phe Gly Asp His Glu Cys Ala Arg Leu Ser Leu
            85                  90                  95
```

-continued

```
Pro Met Asn Trp Asn Arg Thr Asp Gly Glu Gly Ser Lys Ile Ala Leu
            100                 105                 110
Ala Val Ile Lys Leu Pro Ala Lys Val Pro Val Thr Asp Ala Arg Tyr
        115                 120                 125
Gly Gly Ala Ile Leu Leu Asn Pro Gly Gly Pro Gly Gly Ser Gly Val
    130                 135                 140
Ser Met Val Phe Arg Tyr Gly Lys Ala Ile Gln Thr Ile Val Asp Ser
145                 150                 155                 160
Pro Glu Ser Pro Ser Ala Asp Ser Ala Ser Gly Lys Tyr Phe Asp Val
                165                 170                 175
Val Ser Phe Asp Pro Arg Gly Val Asn Asn Thr Pro Asn Phe Ser
            180                 185                 190
Cys Phe Pro Asp Pro Ala Thr Arg Lys Ala Trp Leu Leu Gln Ser Glu
        195                 200                 205
Ala Glu Gly Leu Leu Gly Ser Ser Glu Gly Val Phe Asp Thr Arg Trp
    210                 215                 220
Ala Arg Tyr Glu Ala Phe Glu Arg Leu Leu Ser Thr Ala Pro Asn Thr
225                 230                 235                 240
Phe Pro Val Gly Thr Asn Val Asp Ala Glu Arg Ile Arg Leu His Asn
                245                 250                 255
Arg Trp Lys Lys Gly Glu Glu Lys Leu Leu Tyr Trp Gly Phe Ser Tyr
            260                 265                 270
Gly Thr Ile Leu Gly Ser Thr Phe Ala Ala Met Gln Pro His Arg Ile
        275                 280                 285
Asn Arg Ala Val Ile Asp Gly Val Cys Asn Ala Asp Asp Tyr Tyr Ala
    290                 295                 300
Gly Asn Trp Leu Thr Asn Leu Gln Asp Ser Asp Ala Ala Phe Asn Lys
305                 310                 315                 320
Phe Phe Glu Tyr Cys Tyr Thr Ala Gly Pro Ser Ala Cys Pro Phe Ala
                325                 330                 335
Leu Gly Gly Asp Pro Glu Asp Leu Lys Ser Arg Tyr Glu Gln Ile Leu
            340                 345                 350
Thr Asn Leu Thr Ser Ser Pro Ile Ala Val Ser Pro Ser Gly Asn Arg
        355                 360                 365
Gly Pro Glu Ile Ile Thr Tyr Ser Asp Val Lys Ser Leu Val Val Gln
    370                 375                 380
Ala Leu Tyr Val Pro Leu Lys Leu Phe Asp Leu Val Ala Arg Leu Leu
385                 390                 395                 400
Ala Glu Leu Glu Gln Gly Asn Gly Ser Ser Phe Ala Asp Leu Lys Tyr
                405                 410                 415
Glu Ala Lys Gln Trp Pro Val Pro Pro Cys Asp Ser Ser Ser Thr
            420                 425                 430
Gln Tyr Lys Val Pro Gly Glu Ser Asp Gln Glu Ala Gly Arg Asn Ile
        435                 440                 445
Leu Cys Thr Asp Gly Pro Gly Leu Asp Gly Thr Ala Lys Glu Asp Phe
    450                 455                 460
Arg Ser Tyr Trp Asn Met Leu Arg Gly Gln Ser Lys Ala Val Gly Asp
465                 470                 475                 480
Phe Trp Ala Glu Val Arg Met Ser Cys Val Lys Leu Glu Thr Arg Pro
                485                 490                 495
Glu Trp Arg Tyr Asp Gly Met Arg Ile Gln Gly Pro Phe Ala Gly Asn
            500                 505                 510
Thr Ser His Pro Leu Leu Phe Ile Gly Asn Thr Tyr Asp Pro Val Thr
```

-continued

```
              515                 520                 525
Pro Leu Arg Asn Ala His Thr Met Ala Arg Gly Phe Pro Glu Ser Ile
            530                 535                 540

Val Leu Glu Gln Asn Ser Val Gly His Cys Thr Leu Ser Gly Pro Ser
545                 550                 555                 560

Leu Cys Thr Ala Lys Ala Ile Arg Gln Tyr Phe Gln Thr Gly Glu Leu
                565                 570                 575

Pro Asp Pro Gly Thr Val Cys Gln Val Glu Leu Pro Phe Arg Leu
                580                 585                 590

Ala Gly Tyr Glu Arg Ser Gln Val Met Ser Pro Gly Asp Thr Glu Leu
            595                 600                 605

Met Ser Ala Leu His Ser Leu Ser Glu Phe Arg His Leu Leu Gly Ala
            610                 615                 620

<210> SEQ ID NO 161
<211> LENGTH: 554
<212> TYPE: PRT
<213> ORGANISM: Aspergillus niger

<400> SEQUENCE: 161

Met Leu Ser Ser Leu Leu Gly Gly Leu Gly Leu Ala Thr Ala
1               5                   10                  15

Gln Phe Pro Pro Glu Pro Glu Gly Ile Thr Val Leu Lys Ser Lys Leu
                20                  25                  30

His Glu Asn Val Thr Ile Ser Phe Lys Glu Pro Gly Ile Cys Glu Thr
            35                  40                  45

Thr Pro Gly Val Arg Ser Tyr Ser Gly Tyr Val His Leu Pro Pro Ala
        50                  55                  60

Ser Thr Ser Phe Phe Trp Phe Phe Glu Ala Arg Lys Asp Pro Ser Asn
65                  70                  75                  80

Ala Pro Leu Ala Ile Trp Leu Asn Gly Gly Pro Gly Ser Ser Leu
                85                  90                  95

Met Gly Leu Leu Glu Glu Leu Gly Pro Cys Ser Ile Ala Ser Asp Ser
            100                 105                 110

Lys Thr Thr Val Leu Asn Pro Trp Ser Trp Asn Asn Glu Val Asn Leu
        115                 120                 125

Leu Phe Leu Asp Gln Pro Thr Gln Val Gly Phe Ser Tyr Asp Val Pro
    130                 135                 140

Thr Asn Gly Thr Leu Thr Ala Asn Gly Thr Ala Phe Ala Ala His Ala
145                 150                 155                 160

Leu Trp His Phe Ala Gln Thr Trp Phe Phe Glu Phe Pro His Tyr Lys
                165                 170                 175

Pro Asn Asp Asp Arg Val Ser Leu Trp Ala Glu Ser Tyr Gly Gly His
            180                 185                 190

Tyr Gly Pro Gly Ile Phe Arg Phe Gln Gln Asn Asp Lys Ile
        195                 200                 205

Ala Glu Gly Thr Ala Glu Asp Gly Ala Gln Tyr Leu His Leu Asp Thr
    210                 215                 220

Leu Gly Ile Val Asn Gly Leu Met Asp Met Val Ile Gln Glu Glu Ala
225                 230                 235                 240

Tyr Ile Thr Trp Pro Tyr Asn Asn Val Arg Leu Ala Pro Ser Ser Phe
                245                 250                 255

Asn Ser Arg Gly Phe Arg Asp Gln Ala Leu Ala Cys Glu Ala Ala Leu
            260                 265                 270
```

-continued

```
Lys Glu Arg Asp Ser Gly Leu Pro His Ser Gly Lys Asn Ile Ser Glu
        275                 280                 285

Ile Cys Gly Gly Leu Ala Leu Glu Trp Gly Asp Gly Pro Ile Thr Tyr
        290                 295                 300

Tyr His Thr Phe Asn Arg Gly Trp Tyr Asp Ile Ala His Pro Lys Asn
305                 310                 315                 320

Asp Pro Phe Pro Ala Lys His Met Leu Gly Tyr Leu Thr Gln Glu Ser
                325                 330                 335

Val Leu Ala Ala Leu Gly Val Pro Val Asn Phe Thr Ser Ser Ser Ser
            340                 345                 350

Ala Val Ala Thr Gln Phe Ile Lys Thr Phe Asp Ile Val His Gly Gly
        355                 360                 365

Phe Leu Asp Ala Ile Gly Tyr Leu Leu Asp Ser Gly Val Lys Val His
370                 375                 380

Met Met Tyr Gly Asp Arg Asp Tyr Ala Cys Asn Trp Val Gly Gly Glu
385                 390                 395                 400

Lys Ala Ser Leu Ala Val Pro Tyr Ser Arg Ile Thr Glu Phe Ala Asp
                405                 410                 415

Thr Gly Tyr Ser Pro Leu Leu Thr Pro Asp Gly Ile Ser Gly Met Thr
            420                 425                 430

Arg Gln Leu Gly Asn Tyr Ser Phe Thr Arg Val Phe Gln Ala Gly His
        435                 440                 445

Glu Val Pro Ser Tyr Gln Pro Val Ala Ala Tyr Glu Ile Phe Met Arg
    450                 455                 460

Ala Thr Phe Asn Lys Asp Ile Pro Thr Gly Leu Leu Ala Val Asp Asp
465                 470                 475                 480

Glu Phe Gln Ser Val Gly Pro Lys Asp Thr Trp His Ile Lys Asn Ile
                485                 490                 495

Pro Pro Ile Met Pro Lys Pro Gln Cys Tyr Val Leu Ser Pro Gly Thr
            500                 505                 510

Cys Thr Pro Glu Val Trp Glu Thr Val Leu Asn Gly Ser Ala Thr Val
        515                 520                 525

Lys Asp Trp Tyr Val Val Asp Asp Ser Ala Gly Val Glu Asp His Glu
    530                 535                 540

Gly Phe Ser Ile Leu Gly Gly Asp Glu Leu
545                 550
```

<210> SEQ ID NO 162
<211> LENGTH: 578
<212> TYPE: PRT
<213> ORGANISM: Aspergillus niger

<400> SEQUENCE: 162

```
Met Thr Arg Phe Gln Leu Leu Pro Leu Val Ala Gly Leu Leu Ala Pro
1               5                   10                  15

Ser Ile Ala Ala Leu Ser Ile Pro Ser Pro Gln Ile Leu Asp Ser
            20                  25                  30

Leu Thr Phe Gly Glu His Thr Asp Gly Phe Cys Pro Leu Ala Pro Lys
        35                  40                  45

Val Glu Val Pro Asp Asp Gly Phe Pro Ala Leu Lys Phe Val Glu
    50                  55                  60

Asp Ala Ser Phe Lys Ser Arg Gln Val Asn Arg Leu Ser Arg Ala Val
65                  70                  75                  80

Gln Val Pro Thr Ala Ile Asp Asp Tyr Met Lys Asp Pro Tyr Asp Glu
                85                  90                  95
```

-continued

```
Lys Phe Ala Pro Phe Leu Asp Phe Gln Lys Leu Leu Gln Thr Leu Phe
            100                 105                 110

Pro Leu Thr His Ser Tyr Ala Arg Val Asp His Ile Asn Arg Phe Gly
            115                 120                 125

Leu Val Phe Thr Leu Asn Gly Thr Asp Asp Ser Leu Lys Pro Leu Leu
            130                 135                 140

Phe Thr Ala His Gln Asp Val Val Pro Ile Asn Asp Pro Ala Asp Trp
145                 150                 155                 160

Thr Tyr Pro Pro Phe Asp Gly His Tyr Asp Gly Glu Trp Leu Trp Gly
                    165                 170                 175

Arg Gly Ala Ser Asp Cys Lys Asn Val Leu Ile Gly Leu Met Ser Val
            180                 185                 190

Val Glu Asp Leu Leu Ser Gln Lys Trp Glu Pro Thr Arg Thr Val Val
            195                 200                 205

Leu Ala Phe Gly Phe Asp Glu Glu Ser His Gly Phe Leu Gly Ala Gly
            210                 215                 220

Ser Ile Ala Lys Phe Leu Glu Lys Lys Tyr Gly Pro Asp Ser Phe Glu
225                 230                 235                 240

Phe Ile Leu Asp Glu Gly Gly Met Gly Leu Glu Val Leu Asp Asp Asn
                    245                 250                 255

Asn Asn Gly Val Val Tyr Ala Leu Pro Gly Val Gly Glu Lys Gly Ser
            260                 265                 270

Ile Asp Val Val Leu Thr Leu Ala Val Pro Gly Gly His Ser Ser Val
            275                 280                 285

Pro Pro Pro His Thr Gly Ile Gly Ile Ile Ala Glu Ile Ile Tyr Glu
            290                 295                 300

Leu Glu Arg Gln Asp Leu Phe Val Pro Val Leu Asp Thr His His Pro
305                 310                 315                 320

Thr Arg Lys Met Leu Glu Cys Gln Val Arg His Ser Pro Ser Gln Val
                    325                 330                 335

Glu Pro Trp Leu Ala Ser Ala Leu Gln Ser Ser Asp Tyr Ile Ser Leu
            340                 345                 350

Ala Glu Lys Leu Ala Ser Ser Arg Gly Asp Lys Phe Arg Phe Ile Leu
            355                 360                 365

Gln Thr Ser Gln Ala Ala Asp Ile Ile Asn Gly Gly Val Lys Ser Asn
            370                 375                 380

Ala Leu Pro Glu Lys Ile Asn Ala Leu Val Asn Tyr Arg Ile Ala Leu
385                 390                 395                 400

His Gln Thr Pro Asp Asp Ile Lys Asn Arg Ala Val Glu Ile Ile Ser
                    405                 410                 415

Pro Ile Val Lys Lys Tyr Asn Leu Ser Leu Thr Ala Phe Pro Glu Ser
            420                 425                 430

Asp Thr Val Asp Pro Ser Leu Asn Asn His Leu Thr Leu Thr Thr Leu
            435                 440                 445

Ser Gly Ala Leu Ser Pro Ala Pro Val Ser Pro Thr Asp Ile Asp Thr
450                 455                 460

Asp Ala Val Trp Ala Arg Phe Ser Gly Val Thr Arg Ser Val Phe Glu
465                 470                 475                 480

Ser Val Pro Ser Leu Glu Gly Arg Lys Val Val Ser Gly Asp Ile
            485                 490                 495

Met Thr Gly Asn Thr Asp Thr Arg Phe Tyr Trp Ala Leu Ser Arg Asn
            500                 505                 510
```

```
Ile Tyr Arg Trp Ser Pro Ser Arg Ala Gly Lys Ala Leu Asn Ile His
        515                 520                 525

Thr Val Asp Glu Arg Ile Asp Ile Asp Ile His Leu Glu Ala Met Met
    530                 535                 540

Leu Tyr Tyr Asp Leu Ile Arg Ser Phe Asp Gly Arg Thr Asp Ser Ser
545                 550                 555                 560

Val Ile Ser Ala Ala Ser Ala Ala Ala Asp Asp Glu Leu Ala His Asp
                565                 570                 575

Val Leu

<210> SEQ ID NO 163
<211> LENGTH: 456
<212> TYPE: PRT
<213> ORGANISM: Aspergillus niger

<400> SEQUENCE: 163

Met Lys Ser Thr Thr Leu Leu Ser Leu Ala Trp Ala Ala Gln Ser Ala
1               5                   10                  15

Tyr Ser Leu Ser Ile His Glu Arg Asp Glu Pro Ala Thr Leu Gln Phe
                20                  25                  30

Asn Phe Glu Arg Arg Gln Ile Ala Asp Arg Ser Arg Arg Lys Arg Ser
            35                  40                  45

Thr Ala Ser Ala Asp Leu Val Asn Leu Ala Thr Asn Leu Gly Tyr Thr
    50                  55                  60

Met Asn Leu Thr Leu Gly Thr Pro Gly Gln Glu Val Ser Val Thr Leu
65                  70                  75                  80

Asp Thr Gly Ser Ser Asp Leu Trp Val Asn Gly Ala Asn Ser Ser Val
                85                  90                  95

Cys Pro Cys Thr Asp Tyr Gly Ser Tyr Asn Ser Ser Ala Ser Ser Thr
                100                 105                 110

Tyr Thr Phe Val Asn Asp Glu Phe Tyr Ile Gln Tyr Val Asp Gly Ser
            115                 120                 125

Glu Ala Thr Gly Asp Tyr Val Asn Asp Thr Leu Lys Phe Ser Asn Val
    130                 135                 140

Thr Leu Thr Asn Phe Gln Phe Ala Val Ala Tyr Asp Gly Asp Ser Glu
145                 150                 155                 160

Glu Gly Val Leu Gly Ile Gly Tyr Ala Ser Asn Glu Ala Ser Gln Ala
                165                 170                 175

Thr Val Gly Gly Gly Glu Tyr Thr Asn Phe Pro Glu Ala Leu Val Asp
            180                 185                 190

Gln Gly Ala Ile Asn Trp Pro Ala Tyr Ser Leu Trp Leu Asp Asp Leu
    195                 200                 205

Asp Glu Gly Lys Gly Thr Ile Leu Phe Gly Gly Val Asn Thr Ala Lys
210                 215                 220

Tyr Tyr Gly Ser Leu Gln Thr Leu Pro Ile Val Ser Ile Glu Asp Met
225                 230                 235                 240

Tyr Val Glu Phe Ala Val Asn Leu Thr Ala Val His Leu Glu Lys Asn
                245                 250                 255

Gly Asn Ser Val Ser Val Asn Asn Ser Ala Thr Gln Phe Pro Ile Pro
            260                 265                 270

Ala Val Leu Asp Ser Gly Thr Ala Leu Thr Tyr Ile Pro Thr Ser Ala
    275                 280                 285

Ala Ala Ser Ile Tyr Glu Ala Val Gly Ala Gln Tyr Leu Ser Glu Tyr
290                 295                 300
```

```
Gly Tyr Gly Val Ile Glu Cys Asp Val Lys Asp Glu Asp Phe Thr Phe
305                 310                 315                 320

Leu Phe Asp Phe Gly Ser Phe Asn Met Ser Val Asp Ile Ser Glu Met
            325                 330                 335

Ile Leu Glu Ala Ser Ser Asp Met Thr Asp Met Asn Val Cys Thr Phe
            340                 345                 350

Gly Leu Ala Val Ile Glu Asn Glu Ala Leu Leu Gly Asp Thr Phe Leu
            355                 360                 365

Arg Ser Ala Tyr Val Val Tyr Asp Leu Gly Asn Asn Glu Ile Ser Leu
            370                 375                 380

Ala Lys Ala Asn Phe Asn Pro Gly Glu Asp His Val Leu Glu Ile Gly
385                 390                 395                 400

Thr Gly Ser Asp Ala Val Pro Lys Ala Thr Gly Ala Thr Ala Thr Gly
            405                 410                 415

Ala Ala Ala Thr Ser Thr Ala Ser Ser Asp Lys Ser Asp Lys Glu Ser
            420                 425                 430

Ser Ala Thr Val Pro Arg Ser Gln Ile Val Ser Leu Val Ala Gly Val
            435                 440                 445

Leu Val Gly Val Phe Leu Val Leu
    450                 455

<210> SEQ ID NO 164
<211> LENGTH: 664
<212> TYPE: PRT
<213> ORGANISM: Aspergillus niger

<400> SEQUENCE: 164

Met Leu Val Arg Gln Leu Ala Leu Ala Leu Ala Ile Ala Ala Leu Ser
1               5                   10                  15

Asp Ala Ile Pro Thr Ser Ile Lys His Val Leu His Glu Lys Arg His
            20                  25                  30

Lys Pro Ala Ser Asp Trp Val Lys Gly Ala Arg Val Glu Ser Asp Ala
        35                  40                  45

Val Leu Pro Met Arg Ile Gly Leu Ala Gln Asn Asn Leu Asp Lys Gly
    50                  55                  60

Tyr Asp Phe Leu Met Glu Val Ser Asp Pro Lys Ser Ser Lys Tyr Gly
65                  70                  75                  80

Gln Tyr Trp Ser Ala Asp Glu Val His Asp Ile Phe Ser Pro Ser Glu
                85                  90                  95

Glu Ala Val Glu Ala Val Arg Glu Trp Leu Val Ala Ser Gly Ile His
                100                 105                 110

Pro Ser Arg Val Val His Ser Asp Asn Lys Gly Trp Leu Ala Phe Asp
            115                 120                 125

Ala Tyr Ala His Glu Ala Glu Arg Leu Phe Met Thr Glu Phe His Glu
130                 135                 140

His Glu Ser Asp Arg Ser Ala Lys Ile Arg Val Gly Cys Asp Gln Tyr
145                 150                 155                 160

His Val Pro Glu His Ile Gln Lys His Ile Asp Tyr Ile Thr Pro Gly
                165                 170                 175

Val Lys Leu Thr Gln Val Val Lys Arg Thr Asn Lys Val Lys Arg Ala
            180                 185                 190

Ser Gln Leu Ala His Ser Ser Lys Ala Lys Ser Ala Ala Gln Gly Pro
            195                 200                 205

Gln Pro Leu Pro Asn Lys Ala Lys Phe Leu Pro Glu Asp Leu Arg Gly
210                 215                 220
```

-continued

```
Cys Gly Tyr Asn Ile Thr Pro Ser Cys Ile Lys Ala Leu Tyr Gln Ile
225                 230                 235                 240

Pro Asp Ala Lys Thr Ala Thr Pro Asn Asn Ser Leu Gly Leu Tyr Glu
            245                 250                 255

Gln Gly Asp Tyr Phe Ala Lys Ser Asp Leu Asp Leu Phe Tyr Lys Glu
            260                 265                 270

Tyr Ala Pro Trp Val Pro Gln Gly Thr Tyr Pro Ile Pro Ala Leu Ile
            275                 280                 285

Asp Gly Ala Asn Tyr Ser Val Pro Ser Tyr Ser Ser Leu Asn Thr Gly
290                 295                 300

Glu Ser Asp Ile Asp Ile Asp Met Ala Tyr Ser Leu Leu Tyr Pro Gln
305                 310                 315                 320

Gln Val Thr Leu Tyr Gln Val Asp Asp Gln Leu Tyr Glu Pro Val Glu
            325                 330                 335

Val Asp Thr Thr Asn Leu Phe Asn Thr Phe Leu Asp Ala Leu Asp Gly
            340                 345                 350

Ser Tyr Cys Thr Tyr Ser Ala Tyr Gly Glu Thr Gly Asp Asp Pro Ser
            355                 360                 365

Ile Asp Pro Val Tyr Pro Asp Thr Arg Pro Gly Gly Tyr Lys Gly Lys
370                 375                 380

Leu Gln Cys Gly Val Tyr Lys Pro Thr Asn Val Ile Ser Ala Ser Tyr
385                 390                 395                 400

Gly Gln Ser Glu Ala Asp Leu Pro Val Ser Tyr Thr Lys Arg Gln Cys
            405                 410                 415

Asn Glu Phe Met Lys Leu Gly Leu Gln Gly His Ser Ile Leu Phe Ala
            420                 425                 430

Ser Gly Asp Tyr Gly Val Ala Ser Phe Ala Gly Asp Gly Asp Glu Asn
            435                 440                 445

Gly Cys Leu Gly Pro Glu Gly Lys Ile Phe Asn Pro Gln Tyr Pro Ser
450                 455                 460

Asn Cys Pro Tyr Val Thr Ser Val Gly Gly Thr Met Leu Tyr Gly Tyr
465                 470                 475                 480

Gln Thr Val Asn Asp Ser Glu Ser Val Met His Val Asn Leu Gly Gly
            485                 490                 495

Thr Ala Ser Asn Phe Ser Thr Ser Gly Gly Phe Ser Asn Tyr Phe Pro
            500                 505                 510

Gln Pro Ala Tyr Gln Phe Ala Ala Val Glu Gln Tyr Phe Gln Ser Ala
            515                 520                 525

Asn Leu Ser Tyr Pro Tyr Tyr Ser Glu Phe Glu Val Asp Val Asn Thr
530                 535                 540

Thr Lys Gly Leu Tyr Asn Arg Leu Gly Arg Ala Tyr Pro Asp Val Ser
545                 550                 555                 560

Ala Asn Gly Ala His Phe Arg Ala Tyr Met Asp Gly Tyr Asp Tyr His
            565                 570                 575

Trp Tyr Gly Ser Ser Leu Ala Ser Pro Leu Phe Ala Ser Val Leu Thr
            580                 585                 590

Leu Leu Asn Glu Glu Arg Phe Ala Ile Gly Lys Gly Pro Val Gly Phe
            595                 600                 605

Val Asn Pro Val Leu Tyr Ala Tyr Pro Gln Val Leu Asn Asp Ile Thr
            610                 615                 620

Asn Gly Thr Asn Ala Gly Cys Gly Thr Tyr Gly Phe Ser Ala Ile Glu
625                 630                 635                 640
```

```
Gly Trp Asp Pro Ala Ser Gly Leu Gly Thr Pro Asn Tyr Pro Leu Met
                645                 650                 655

Lys Glu Leu Phe Leu Ser Leu Pro
            660
```

<210> SEQ ID NO 165
<211> LENGTH: 520
<212> TYPE: PRT
<213> ORGANISM: Aspergillus niger

<400> SEQUENCE: 165

```
Met Arg Val Thr Thr Ala Ile Ala Ser Leu Leu Val Gly Ser Ala
1               5                   10                  15

Thr Ser Leu Gln Asn Pro His Arg Arg Ala Val Pro Pro Leu Ser
                20                  25                  30

His Arg Ser Val Ala Ser Arg Ser Val Pro Val Glu Arg Arg Thr Thr
                35                  40                  45

Asp Phe Glu Tyr Leu Thr Asn Lys Thr Ala Arg Phe Leu Val Asn Gly
    50                  55                  60

Thr Ser Ile Pro Glu Val Asp Phe Asp Val Gly Glu Ser Tyr Ala Gly
65                  70                  75                  80

Leu Leu Pro Asn Thr Pro Thr Gly Asn Ser Ser Leu Phe Phe Trp Phe
                85                  90                  95

Phe Pro Ser Gln Asn Pro Glu Ala Ser Asp Glu Ile Thr Ile Trp Leu
                100                 105                 110

Asn Gly Gly Pro Gly Cys Ser Ser Leu Asp Gly Leu Leu Gln Glu Asn
                115                 120                 125

Gly Pro Phe Leu Trp Gln Pro Gly Thr Tyr Lys Pro Val Pro Asn Pro
        130                 135                 140

Tyr Ser Trp Thr Asn Leu Thr Asn Val Val Tyr Ile Asp Gln Pro Ala
145                 150                 155                 160

Gly Thr Gly Phe Ser Pro Gly Pro Ser Thr Val Asn Asn Glu Glu Asp
                165                 170                 175

Val Ala Ala Gln Phe Asn Ser Trp Phe Lys His Phe Val Asp Thr Phe
            180                 185                 190

Asp Leu His Gly Arg Lys Val Tyr Ile Thr Gly Glu Ser Tyr Ala Gly
            195                 200                 205

Met Tyr Val Pro Tyr Ile Ala Asp Ala Met Leu Asn Glu Glu Asp Thr
        210                 215                 220

Thr Tyr Phe Asn Leu Lys Gly Ile Gln Ile Asn Asp Pro Ser Ile Asn
225                 230                 235                 240

Ser Asp Ser Val Met Met Tyr Ser Pro Ala Val Arg His Leu Asn His
                245                 250                 255

Tyr Asn Asn Ile Phe Gln Leu Asn Ser Thr Phe Leu Ser Tyr Ile Asn
            260                 265                 270

Ala Lys Ala Asp Lys Cys Gly Tyr Asn Ala Phe Leu Asp Lys Ala Ile
            275                 280                 285

Thr Tyr Pro Pro Pro Ser Pro Phe Pro Thr Ala Pro Glu Ile Thr Glu
        290                 295                 300

Asp Cys Gln Val Trp Asp Glu Val Met Ala Ala Tyr Asp Ile Asn
305                 310                 315                 320

Pro Cys Phe Asn Tyr Tyr His Leu Ile Asp Phe Cys Pro Tyr Leu Trp
                325                 330                 335

Asp Val Leu Gly Phe Pro Ser Leu Ala Ser Gly Pro Asn Asn Tyr Phe
            340                 345                 350
```

-continued

Asn Arg Ser Asp Val Gln Lys Ile Leu His Val Pro Pro Thr Asp Tyr
        355                 360                 365

Ser Val Cys Ser Glu Thr Val Ile Phe Ala Asn Gly Asp Gly Ser Asp
        370                 375                 380

Pro Ser Ser Trp Gly Pro Leu Pro Ser Val Ile Glu Arg Thr Asn Asn
385                 390                 395                 400

Thr Ile Ile Gly His Gly Trp Leu Asp Tyr Leu Leu Phe Leu Asn Gly
                405                 410                 415

Ser Leu Ala Thr Ile Gln Asn Met Thr Trp Asn Gly Lys Gln Gly Phe
        420                 425                 430

Gln Arg Pro Pro Val Glu Pro Leu Phe Val Pro Tyr His Tyr Gly Leu
        435                 440                 445

Ala Glu Leu Tyr Trp Gly Asp Glu Pro Asp Pro Tyr Asn Leu Asp Ala
        450                 455                 460

Gly Ala Gly Tyr Leu Gly Thr Ala His Thr Glu Arg Gly Leu Thr Phe
465                 470                 475                 480

Ser Ser Val Tyr Leu Ser Gly His Glu Ile Pro Gln Tyr Val Pro Gly
                485                 490                 495

Ala Ala Tyr Arg Gln Leu Glu Phe Leu Leu Gly Arg Ile Ser Ser Leu
        500                 505                 510

Ser Ala Lys Gly Asn Tyr Thr Ser
        515                 520

<210> SEQ ID NO 166
<211> LENGTH: 551
<212> TYPE: PRT
<213> ORGANISM: Aspergillus niger

<400> SEQUENCE: 166

Met Arg Gly Ser Arg Leu Val Leu Leu Pro Leu Ala Ala Leu Ser
1               5                   10                  15

Cys Ala Met Pro Glu Asn Glu Trp Ser Ser Thr Ile Arg Arg Gln Leu
                20                  25                  30

Pro Lys Ala Ser Thr Gly Val Lys Ser Ile Lys Thr Pro Asn Asn Val
        35                  40                  45

Thr Ile Arg Tyr Lys Glu Pro Gly Thr Glu Gly Ile Cys Glu Thr Thr
    50                  55                  60

Pro Gly Val Lys Ser Tyr Ser Gly Tyr Val Asp Leu Ser Pro Glu Ser
65                  70                  75                  80

His Thr Phe Phe Trp Phe Phe Glu Ser Arg Arg Asp Pro Glu Asn Asp
                85                  90                  95

Pro Val Thr Leu Trp Leu Asn Gly Gly Pro Gly Ser Asp Ser Leu Ile
                100                 105                 110

Gly Leu Phe Glu Glu Leu Gly Pro Cys His Ile Thr Pro Glu Tyr Glu
            115                 120                 125

Ser Ile Ile Asn Gln Tyr Ser Trp Asn Glu Val Thr Asn Leu Leu Phe
        130                 135                 140

Leu Ser Gln Pro Leu Gly Val Gly Phe Ser Tyr Ser Glu Thr Glu Ala
145                 150                 155                 160

Gly Ser Leu Asn Pro Phe Thr Gly Ala Val Glu Asn Ala Ser Phe Ala
                165                 170                 175

Gly Val Gln Gly Arg Tyr Pro Val Ile Asp Ala Thr Ile Ile Asp Thr
            180                 185                 190

Thr Asp Ile Ala Ala Arg Ala Thr Trp Glu Val Leu Gln Gly Phe Leu

```
                195                 200                 205
Ser Gly Leu Ser Gln Leu Asp Ser Glu Val Lys Ser Lys Glu Phe Asn
    210                 215                 220
Leu Trp Thr Glu Ser Tyr Gly Gly His Tyr Gly Pro Ala Phe Phe Asn
225                 230                 235                 240
His Phe Tyr Glu Gln Asn Ser Lys Ile Ala Ser Gly Glu Val Asn Gly
                245                 250                 255
Val Gln Leu Asn Phe Asn Ser Leu Gly Ile Ile Asn Gly Ile Ile Asp
            260                 265                 270
Ala Ala Ile Gln Ala Asp Tyr Tyr Ala Asp Phe Ala Val Asn Asn Thr
            275                 280                 285
Tyr Gly Ile Lys Ala Val Asn Asp Thr Val Tyr Asn Tyr Met Lys Phe
            290                 295                 300
Ala Asn Thr Met Pro Asn Gly Cys Gln Asp Gln Val Ala Ser Cys Lys
305                 310                 315                 320
Leu Thr Asn Arg Thr Ser Leu Ser Asp Tyr Ala Ile Cys Thr Glu Ala
                325                 330                 335
Ala Asn Met Cys Arg Asp Asn Val Glu Gly Pro Tyr Tyr Gln Phe Gly
            340                 345                 350
Gly Arg Gly Val Tyr Asp Ile Arg His Pro Tyr Asn Asp Pro Thr Pro
            355                 360                 365
Pro Ser Tyr Phe Val Asp Tyr Leu Lys Lys Asp Ser Val Met Asp Ala
    370                 375                 380
Ile Gly Val Asp Ile Asn Tyr Thr Glu Ser Ser Gly Glu Val Tyr Tyr
385                 390                 395                 400
Ala Phe Gln Gln Thr Gly Asp Phe Val Trp Pro Asn Phe Ile Glu Asp
                405                 410                 415
Leu Glu Glu Ile Leu Gln Leu Pro Val Arg Val Ser Leu Ile Tyr Gly
            420                 425                 430
Asp Ala Asp Tyr Ile Cys Asn Trp Phe Gly Gly Gln Ala Ile Ser Leu
            435                 440                 445
Ala Val Asn Tyr Pro His Ala Ala Gln Phe Arg Ala Ala Gly Tyr Thr
    450                 455                 460
Pro Met Thr Val Asp Gly Val Glu Tyr Gly Glu Thr Arg Glu Tyr Gly
465                 470                 475                 480
Asn Phe Ser Phe Thr Arg Val Tyr Gln Ala Gly His Glu Val Pro Tyr
                485                 490                 495
Tyr Gln Pro Ile Ala Ala Leu Gln Leu Phe Asn Arg Thr Leu Phe Gly
            500                 505                 510
Trp Asp Ile Ala Ala Gly Thr Thr Gln Ile Trp Pro Glu Tyr Ser Thr
            515                 520                 525
Asn Gly Thr Ser Gln Ala Thr His Thr Glu Ser Phe Val Pro Leu Ser
    530                 535                 540
Thr Ala Ser Ser Thr Val Asn
545                 550

<210> SEQ ID NO 167
<211> LENGTH: 623
<212> TYPE: PRT
<213> ORGANISM: Aspergillus niger

<400> SEQUENCE: 167

Met Pro Phe Pro Phe Ser Ser Ala Leu Leu Gly Tyr Ile Leu Thr Thr
1               5                   10                  15
```

```
Ser Thr Thr Leu Thr Ser Leu Val Ala Gly Gln Tyr Tyr Pro Pro Thr
        20              25                  30
Pro Glu Asp Leu Thr Val Ile His Ser Glu Ile Phe Pro Gly Ala Arg
            35              40              45
Ile Ser Tyr Lys Gln Pro Leu Gly Ile Cys Thr Thr Thr Pro Ser Thr
50                      55              60
Pro Ser Tyr Ser Gly Tyr Ile His Leu Pro Pro His Thr Leu Thr Asn
65                  70              75                      80
Leu Ser Ile Pro Gly Ile Ser Ile Ser Gln Pro Tyr Pro Ile Asn Thr
                85              90              95
Phe Phe Trp Tyr Phe Pro Ser Arg His His Asn Asn Asp Thr Ser
            100             105             110
Pro Leu Thr Ile Trp Met Asn Gly Pro Gly Gly Ser Ser Met Ile
        115             120             125
Gly Leu Phe Gln Glu Asn Gly Pro Cys Thr Val Asn Thr Asp Ser Asn
130             135             140
Ser Thr Ala Tyr Asn Pro Trp Ser Trp Asn Glu Tyr Val Asp Met Leu
145                 150             155                 160
Tyr Ile Glu Gln Pro Val Gln Thr Gly Phe Ser Tyr Asp Val Leu Arg
                165             170             175
Asn Gly Thr Leu Asp Leu Asn Glu Thr Phe Leu Val Gly Thr Leu Pro
            180             185             190
Ser Gln Asp Val His Gly Thr Val Asn Gly Thr Val Asn Gly Gly Arg
            195             200             205
Ala Leu Trp Val Ala Leu Gln Val Trp Leu Gly Glu Phe Ser Glu Tyr
            210             215             220
Val Ser Val Asp Gly Asn Gly Gly Asp Asp Arg Val Ser Ile
225             230             235             240
Trp Thr Glu Ser Tyr Gly Gly Arg Tyr Gly Pro Ala Tyr Thr Ala Leu
            245             250             255
Phe Gln Glu Met Asn Glu Arg Ile Glu Ser Gly Glu Val Ser Thr Gly
            260             265             270
Lys Lys Ile His Leu Asp Thr Leu Gly Ile Ile Asn Gly Cys Val Asp
            275             280             285
Leu Leu Val Gln Val Pro Ser Phe Pro Glu Gln Ala Tyr Asn Asn Thr
        290             295             300
Tyr Gly Ile Glu Gly Ile Asn Arg Thr Leu Tyr Asp Arg Ala Met Asp
305             310             315             320
Ser Trp Ser Lys Pro Gly Gly Cys Arg Asp Met Ile Ile Glu Cys Arg
                325             330             335
Asp Ala Gly Glu Leu Gly Asp Pro Leu Ile Ile Cys Glu Glu Ala Ser
            340             345             350
Asp Tyr Cys Ser Arg Glu Ile Lys Ser Leu Tyr Thr Asn Thr Ser Gly
            355             360             365
Arg Gly Tyr Tyr Asp Ile Ala His Phe Thr Pro Asp Ala Ala Leu Val
            370             375             380
Pro Tyr Phe Val Gly Phe Leu Asn Arg Pro Trp Val Gln Lys Ala Leu
385             390             395             400
Gly Val Pro Val Asn Tyr Thr Met Ser Ser Glu Ala Val Gly Asn Ser
                405             410             415
Phe Ala Ser Thr Gly Asp Tyr Pro Arg Asn Asp Pro Arg Gly Met Ile
            420             425             430
Gly Asp Ile Gly Tyr Leu Leu Asp Ser Gly Val Lys Val Ala Met Val
```

```
                435                 440                 445
Tyr Gly Asp Arg Asp Tyr Ala Cys Pro Trp Arg Gly Gly Glu Asp Val
            450                 455                 460

Ser Leu Leu Val Glu Tyr Glu Asp Ala Glu Lys Phe Arg Ala Ala Gly
465                 470                 475                 480

Tyr Ala Glu Val Gln Thr Lys Ser Ser Tyr Val Gly Gly Leu Val Arg
                485                 490                 495

Gln Tyr Gly Asn Phe Ser Phe Thr Arg Val Phe Gln Ala Gly His Glu
            500                 505                 510

Val Pro Phe Tyr Gln Pro Glu Thr Ala Tyr Glu Ile Phe Asn Arg Ala
        515                 520                 525

Gln Phe Asn Trp Asp Ile Ala Thr Gly Ile Ser Leu Glu Gln Asn
        530                 535                 540

Gln Ser Tyr Gly Thr Glu Gly Pro Ser Ser Thr Trp His Ile Lys Asn
545                 550                 555                 560

Glu Val Pro Glu Ser Pro Glu Pro Thr Cys Tyr Leu Leu Ala Met Asp
                565                 570                 575

Ser Thr Cys Thr Asp Glu Gln Arg Glu Arg Val Leu Ser Gly Asp Ala
            580                 585                 590

Val Val Arg Asp Trp Val Val Asp Asp Ile Glu Ala Glu Ser Ser
        595                 600                 605

Phe Ser Gly Val Gly Asp Gln Leu Ala Gln Val Pro Leu Gly His
    610                 615                 620

<210> SEQ ID NO 168
<211> LENGTH: 439
<212> TYPE: PRT
<213> ORGANISM: Aspergillus niger

<400> SEQUENCE: 168

Met Arg Thr Ser Thr Leu Leu Leu Trp Ser Thr Ala Gly Ala Ala
1               5                   10                  15

Leu Ala Ser Pro Tyr Pro Leu Pro Asp Ser Gln Val Val Phe Ala Ala
            20                  25                  30

Asp His Glu Val Pro Asn Thr Gln Gly Lys His Val Val Asp Glu Ala
        35                  40                  45

Ile Leu Ser Ala Leu Asn Ala His Ser Asp Pro Val Ala Ala Met Val
    50                  55                  60

Ser Leu Arg Pro Glu Thr Ala Ala Phe Leu Ala Glu Pro Arg Leu Leu
65                  70                  75                  80

His Ile Arg Gly Glu Glu Lys Ala Glu Trp Met Thr Glu Gly Asp Lys
                85                  90                  95

Leu Arg Leu Arg Gln Arg Gly Lys Lys Phe Met Asp Ile Thr Glu His
            100                 105                 110

Gln Asp Phe Tyr Ala Glu Gln Ala Met Ala Ser Phe Ala Gly Asp Pro
        115                 120                 125

Asn Leu Pro Lys Leu Ser His Lys Gly Leu Val Lys Pro Leu Phe Ser
    130                 135                 140

Gln Ile Glu Thr Glu Arg Met His Asp Ile Leu Gln His Met Thr Ser
145                 150                 155                 160

Tyr Tyr Asn Arg Tyr Tyr Gly Asp Tyr His Gly Glu Met Ser Ser Glu
                165                 170                 175

Trp Leu His Asp Tyr Ile Ala Ala Ile Ile Ser Lys Ser Pro Phe Arg
            180                 185                 190
```

```
Thr His Ile Ser Leu Glu Tyr Phe Thr His Pro Phe Arg Gln Ser Ser
        195                 200                 205

Ile Ile Ala Arg Phe Glu Pro Lys Val Arg Ser Phe Ser Gln Pro Leu
    210                 215                 220

Thr Ile Ile Gly Ala His Gln Asp Ser Ala Asn Tyr Leu Phe Pro Leu
225                 230                 235                 240

Leu Pro Ala Pro Gly Ala Asp Asp Cys Ser Gly Thr Val Ser Ile
                245                 250                 255

Leu Glu Ala Phe Arg Val Leu Ala Glu Asn Gly Tyr Thr Pro Lys Asp
                260                 265                 270

Gly Pro Val Glu Phe His Trp Tyr Ala Ala Glu Ala Gly Leu Leu
            275                 280                 285

Gly Ser Gln Ala Ile Ala Arg Tyr Lys Lys Glu Gln Gly Ala Lys Ile
        290                 295                 300

Asp Ala Met Met Glu Phe Asp Met Thr Ala Phe Ile Ala Arg Asn Ala
305                 310                 315                 320

Thr Glu Thr Ile Gly Phe Val Ala Thr Gln Ala Asp Ala Ala Leu Thr
                325                 330                 335

Asn Trp Ala Leu Asn Leu Ser Arg Glu Tyr Ile Ser Ile Pro Ala Glu
            340                 345                 350

Val Tyr Glu Leu Gly Pro Asn Ala Gly Ser Asp Tyr Met Ser Tyr Thr
        355                 360                 365

Lys Leu Asn Tyr Pro Ala Ala Phe Ala Ser Glu Gly Asn Pro Leu Ala
    370                 375                 380

Gly Gly Ser Phe Pro Gly Glu Met Asp Pro Tyr Val His Gly Ile Lys
385                 390                 395                 400

Asp Arg Met Asp Val Asp Asp Glu Thr Gly Val Phe Ser Ile Glu His
                405                 410                 415

Met Ala Arg Phe Ser Glu Leu Ala Ile Ala Phe Val Val Glu Gln Ala
            420                 425                 430

Gly Trp Asp Asn Thr Trp Arg
        435

<210> SEQ ID NO 169
<211> LENGTH: 526
<212> TYPE: PRT
<213> ORGANISM: Aspergillus niger

<400> SEQUENCE: 169

Met Arg Ser Phe Ser Val Val Ala Ala Ser Leu Ala Leu Ser Trp
1               5                   10                  15

Ala Ser Leu Ala Gln Ala Ala Arg Pro Arg Leu Val Pro Lys Pro Ile
            20                  25                  30

Ser Arg Pro Ala Ser Ser Lys Ser Ala Ala Thr Thr Gly Glu Ala Tyr
        35                  40                  45

Phe Glu Gln Leu Leu Asp His His Asn Pro Glu Lys Gly Thr Phe Ser
    50                  55                  60

Gln Arg Tyr Trp Trp Ser Thr Glu Tyr Trp Gly Gly Pro Gly Ser Pro
65                  70                  75                  80

Val Val Leu Phe Asn Pro Gly Glu Val Ser Ala Asp Gly Tyr Glu Gly
                85                  90                  95

Tyr Leu Thr Asn Asp Thr Leu Thr Gly Val Tyr Ala Gln Glu Ile Gln
            100                 105                 110

Gly Ala Val Ile Leu Ile Glu His Arg Tyr Trp Gly Asp Ser Ser Pro
        115                 120                 125
```

```
Tyr Glu Val Leu Asn Ala Glu Thr Leu Gln Tyr Leu Thr Leu Asp Gln
    130                 135                 140

Ser Ile Leu Asp Met Thr Tyr Phe Ala Glu Thr Val Lys Leu Gln Phe
145                 150                 155                 160

Asp Asn Ser Ser Arg Ser Asn Ala Gln Asn Ala Pro Trp Val Met Val
                165                 170                 175

Gly Gly Ser Tyr Ser Gly Ala Leu Thr Ala Trp Thr Glu Ser Ile Ala
                180                 185                 190

Pro Gly Thr Phe Trp Ala Tyr His Ala Thr Ser Ala Pro Val Glu Ala
            195                 200                 205

Ile Tyr Asp Phe Trp Gln Tyr Phe Tyr Pro Ile Gln Gln Gly Met Ala
210                 215                 220

Gln Asn Cys Ser Lys Asp Val Ser Leu Val Ala Glu Tyr Val Asp Lys
225                 230                 235                 240

Ile Gly Lys Asn Gly Thr Ala Lys Glu Gln Gln Glu Leu Lys Glu Leu
                245                 250                 255

Phe Gly Leu Gly Ala Val Glu His Tyr Asp Asp Phe Ala Ala Val Leu
            260                 265                 270

Pro Asn Gly Pro Tyr Leu Trp Gln Asp Asn Asp Phe Val Thr Gly Tyr
        275                 280                 285

Ser Ser Phe Phe Gln Phe Cys Asp Ala Val Glu Gly Val Glu Ala Gly
    290                 295                 300

Ala Ala Val Thr Pro Gly Pro Glu Gly Val Gly Leu Glu Lys Ala Leu
305                 310                 315                 320

Ala Asn Tyr Ala Asn Trp Phe Asn Ser Thr Ile Leu Pro Asn Tyr Cys
                325                 330                 335

Ala Ser Tyr Gly Tyr Trp Thr Asp Glu Trp Ser Val Ala Cys Phe Asp
            340                 345                 350

Ser Tyr Asn Ala Ser Ser Pro Ile Phe Thr Asp Thr Ser Val Gly Asn
        355                 360                 365

Pro Val Asp Arg Gln Trp Glu Trp Phe Leu Cys Asn Glu Pro Phe Phe
    370                 375                 380

Trp Trp Gln Asp Gly Ala Pro Glu Gly Thr Ser Thr Ile Val Pro Arg
385                 390                 395                 400

Leu Val Ser Ala Ser Tyr Trp Gln Arg Gln Cys Pro Leu Tyr Phe Pro
                405                 410                 415

Glu Val Asn Gly Tyr Thr Tyr Gly Ser Ala Lys Gly Lys Asn Ser Ala
            420                 425                 430

Thr Val Asn Ser Trp Thr Gly Gly Trp Asp Met Thr Arg Asn Thr Thr
        435                 440                 445

Arg Leu Ile Trp Thr Asn Gly Gln Tyr Asp Pro Trp Arg Asp Ser Gly
    450                 455                 460

Val Ser Ser Thr Phe Arg Pro Gly Gly Pro Leu Val Ser Thr Ala Asn
465                 470                 475                 480

Glu Pro Val Gln Ile Ile Pro Gly Gly Phe His Cys Ser Asp Leu Tyr
                485                 490                 495

Met Glu Asp Tyr Tyr Ala Asn Glu Gly Val Arg Lys Val Val Asp Asn
            500                 505                 510

Glu Val Lys Gln Ile Lys Glu Trp Val Glu Glu Tyr Tyr Ala
    515                 520                 525

<210> SEQ ID NO 170
<211> LENGTH: 424
```

```
<212> TYPE: PRT
<213> ORGANISM: Aspergillus niger

<400> SEQUENCE: 170

Met Gln Leu Leu Gln Ser Leu Ile Val Ala Val Cys Phe Ser Tyr Gly
1               5                   10                  15

Val Leu Ser Leu Pro His Gly Pro Ser Asn Gln His Lys Ala Arg Ser
            20                  25                  30

Phe Lys Val Glu Arg Val Arg Arg Gly Thr Gly Ala Leu His Gly Pro
        35                  40                  45

Ala Ala Leu Arg Lys Ala Tyr Arg Lys Tyr Gly Ile Ala Pro Ser Ser
50                  55                  60

Phe Asn Ile Asp Leu Ala Asp Phe Lys Pro Ile Thr Thr Thr His Ala
65                  70                  75                  80

Ala Ala Gly Ser Glu Ile Ala Glu Pro Asp Gln Thr Gly Ala Val Ser
                85                  90                  95

Ala Thr Ser Val Glu Asn Asp Ala Glu Phe Val Ser Pro Val Leu Ile
            100                 105                 110

Gly Gly Gln Lys Ile Val Met Thr Phe Asp Thr Gly Ser Ser Asp Phe
        115                 120                 125

Trp Val Phe Asp Thr Asn Leu Asn Glu Thr Leu Thr Gly His Thr Glu
130                 135                 140

Tyr Asn Pro Ser Asn Ser Ser Thr Phe Lys Lys Met Asp Gly Tyr Thr
145                 150                 155                 160

Phe Asp Val Ser Tyr Gly Asp Ser Tyr Ala Ser Gly Pro Val Gly
                165                 170                 175

Thr Asp Thr Val Asn Ile Gly Gly Ala Ile Val Lys Glu Gln Ala Phe
            180                 185                 190

Gly Val Pro Asp Gln Val Ser Gln Ser Phe Ile Glu Asp Thr Asn Ser
        195                 200                 205

Asn Gly Leu Val Gly Leu Gly Phe Ser Ser Ile Asn Thr Ile Lys Pro
210                 215                 220

Glu Ala Gln Asp Thr Phe Phe Ala Asn Val Ala Pro Ser Leu Asp Glu
225                 230                 235                 240

Pro Val Met Thr Ala Ser Leu Lys Ala Asp Gly Val Gly Glu Tyr Glu
                245                 250                 255

Phe Gly Thr Ile Asp Lys Asp Lys Tyr Gln Gly Asn Ile Ala Asn Ile
            260                 265                 270

Ser Val Asp Ser Ser Asn Gly Tyr Trp Gln Phe Ser Thr Pro Lys Tyr
        275                 280                 285

Ser Val Ala Asp Gly Glu Leu Lys Asp Ile Gly Ser Leu Asn Thr Ser
290                 295                 300

Ile Ala Asp Thr Gly Thr Ser Leu Met Leu Leu Asp Glu Asp Val Val
305                 310                 315                 320

Thr Ala Tyr Tyr Ala Gln Val Pro Asn Ser Val Tyr Val Ser Ser Ala
                325                 330                 335

Gly Gly Tyr Ile Tyr Pro Cys Asn Thr Thr Leu Pro Ser Phe Ser Leu
            340                 345                 350

Val Leu Gly Glu Ser Ser Leu Ala Thr Ile Pro Gly Asn Leu Ile Asn
        355                 360                 365

Phe Ser Lys Val Gly Thr Asn Thr Thr Thr Gly Gln Ala Leu Cys Phe
370                 375                 380

Gly Gly Ile Gln Ser Asn Gly Asn Thr Ser Leu Gln Ile Leu Gly Asp
385                 390                 395                 400
```

```
Ile Phe Leu Lys Ala Phe Phe Val Phe Asp Met Arg Gly Pro Ser
            405                 410                 415
Leu Gly Val Ala Ser Pro Lys Asn
            420

<210> SEQ ID NO 171
<211> LENGTH: 548
<212> TYPE: PRT
<213> ORGANISM: Aspergillus niger

<400> SEQUENCE: 171

Met Arg Ile Asp Ser Ala Ala Leu His Leu Val Pro Val Leu Leu Gly
1               5                   10                  15

Gln Val Gly Ala Leu Gln Leu Pro Leu Val Gln Asp Ser Asn Ser Gln
                20                  25                  30

Trp Gln Lys Pro Asn Ala Gly Asp Lys Pro Leu Ile Ser Ser Pro Leu
            35                  40                  45

Leu Gln Glu Gln Val Lys Ala Glu Asn Leu Leu Asp Arg Ala Arg Gln
    50                  55                  60

Leu Tyr Lys Ile Ala Glu Leu Gly Glu Asp Tyr Asn His Pro Thr
65                  70                  75                  80

Arg Val Ile Gly Ser Lys Gly His Leu Gly Thr Leu Asp Tyr Ile Tyr
                85                  90                  95

Ser Thr Leu Thr Asp Leu Gly Asp Tyr Tyr Thr Val Val Asn Gln Ser
            100                 105                 110

Phe Pro Ala Val Ser Gly Asn Val Phe Glu Ser Arg Leu Val Leu Gly
        115                 120                 125

His Asp Val Pro Lys Ser Ala Thr Pro Met Gly Leu Thr Pro Pro Thr
130                 135                 140

Arg Asn Lys Glu Pro Val Tyr Gly Ser Leu Val Ala Val Ser Asn Leu
145                 150                 155                 160

Gly Cys Glu Ala Ser Asp Tyr Ser Ser Asn Leu Lys Gly Ala Val Ala
                165                 170                 175

Phe Ile Ser Arg Gly Ser Cys Pro Phe Gly Thr Lys Ser Gln Leu Ala
            180                 185                 190

Gly Lys Ala Gly Ala Val Ala Ala Val Ile Tyr Asn Asn Glu Arg Gly
        195                 200                 205

Asp Leu Ser Gly Thr Leu Gly Asn Pro Thr Pro Asp His Val Ala Thr
    210                 215                 220

Phe Gly Ile Ser Asp Glu Asp Ala Ala Pro Val Leu Glu Lys Leu Asn
225                 230                 235                 240

Lys Gly Glu Lys Val Asp Ala Ile Ala Tyr Val Asp Ala Ile Val Glu
                245                 250                 255

Thr Ile His Thr Thr Asn Ile Ile Ala Gln Thr Thr Asp Gly Asp Pro
            260                 265                 270

Asn Asn Cys Val Met Leu Gly Gly His Ser Asp Ser Val Ala Glu Gly
        275                 280                 285

Pro Gly Ile Asn Asp Asp Gly Ser Gly Thr Leu Thr Leu Leu Glu Leu
    290                 295                 300

Ala Thr Leu Leu Thr Gln Phe Arg Val Asn Asn Cys Val Arg Phe Ala
305                 310                 315                 320

Trp Trp Ala Ala Glu Glu Gly Leu Leu Gly Ser Asp Tyr Tyr Val
                325                 330                 335

Ser Val Leu Thr Pro Glu Glu Asn Arg Lys Ile Arg Leu Phe Met Asp
```

-continued

```
                     340                 345                 350
Tyr Asp Met Leu Gly Ser Pro Asn Phe Ala Tyr Gln Val Tyr Asn Ala
            355                 360                 365

Thr Asn Ala Val Asn Pro Glu Gly Ser Glu Glu Leu Arg Asp Leu Tyr
    370                 375                 380

Thr Asp Phe Tyr Glu Asp His Gly Phe Asn Tyr Thr Tyr Ile Pro Phe
385                 390                 395                 400

Asp Gly Arg Ser Asp Tyr Asp Ala Phe Ile Arg His Gly Ile Pro Gly
                405                 410                 415

Gly Gly Ile Ala Thr Gly Ala Glu Gly Ile Lys Thr Val Glu Glu Ala
            420                 425                 430

Asp Met Phe Gly Gly Val Ala Gly Gln Trp Tyr Asp Pro Cys Tyr His
            435                 440                 445

Gln Ile Cys Asp Thr Val Ala Asn Val Asn Leu Thr Ala Trp Glu Trp
        450                 455                 460

Asn Thr Lys Leu Val Ala His Ser Ile Ala Thr Tyr Ala Lys Ser Phe
465                 470                 475                 480

Asp Gly Phe Pro Glu Arg Ser Asp Glu Pro Ile Ser Pro Ala Ala Phe
                485                 490                 495

Glu Glu Pro Lys Tyr His Gly His Ala Leu Gln Leu Leu Arg Gly Asn
                500                 505                 510

Thr Thr Gly Thr Gln Ser Val Leu Trp Gly Ala Gln Ile Gln Asn Gly
            515                 520                 525

Thr Ala Ala Ser Val Leu Asn Leu Leu Ser Ile Arg Arg Arg Gly Thr
            530                 535                 540

Phe Ser Leu Ser
545
```

GENES ENCODING NOVEL PROTEOLYTIC ENZYMES

CROSS-REFERENCE TO RELATED APPLICATION

This application is the national phase of PCT application PCT/EP02/01984 having an international filing date of 22 Feb. 2002, and claims priority from European applications: 01205117.3 filed 21 Dec. 2001; 01204464.0 filed 15 Nov. 2001; 01000552.8, 01000553.6, 01000554.4, 01000556.9, 01000557.7 and 01000558.5 filed 22 Oct. 2001; 01000478.6 and 01000483.6 filed 20 Sep. 2001; 01000374.7 and 01000377.0 filed 16 Aug. 2001; 01000357.2 filed 9 Aug. 2001; 01000341.6, 01000342.4, 01000343.2 and 01000344.0 filed 2 Aug. 2001; 01000320.0, 01000321.8, 01000322.6, 01000323.4 and 01000327.5 filed 30 Jul. 2001; 01000280.6, 01000285.5, 01000286.3 and 01000287.1 filed 12 Jul. 2001; 01000234.3, 01000237.6, 01000238.4, 01000240.0, 01000242.6, 01000244.2 and 01000246.7 filed 21 Jun. 2001; 01000225.1 and 01000229.3 filed 20 Jun. 2001; 01000156.8, 01000159.2, 01000160.0, 01000162.6, 01000165.9, 01000166.7 and 01000168.3 filed 21 May 2001; 01000075.0, 01000078.4, 01000080.0, 01000084.2, 01000085.9, 01000087.5 and 01000088.3 filed 28 Mar. 2001; 01200707.6, 01200708.4, 01200719.1 and 01200706.8 filed 26 Feb. 2001; and 01200660.7, 01200658.1 and 01200657.3 filed 23 Feb. 2001. The contents of these documents are incorporated herein by reference.

FIELD OF THE INVENTION

The invention relates to newly identified polynucleotide sequences comprising genes that encode novel proteases isolated from *Aspergillus niger*. The invention features the full length nucleotide sequence of the novel genes, the cDNA sequences comprising the full length coding sequences of the novel proteases as well as the amino acid sequences of the full-length functional proteins and fragments and variants thereof. The invention also relates to methods of using these enzymes in industrial processes and methods of diagnosing fungal infections. Also included in the invention are cells transformed with a polynucleotide according to the invention and cells wherein a protease according to the invention is genetically modified to enhance or reduce its activity and/or level of expression.

BACKGROUND OF THE INVENTION

Proteolytic Enzymes

Proteins can be regarded hetero-polymers that consist of amino acid building blocks connected by a peptide bond. The repetitive unit in proteins is the central alpha carbon atom with an amino group and a carboxyl group. Except for glycine, a so-called amino acid side chain substitutes one of the two remaining alpha carbon hydrogen atoms. The amino acid side chain renders the central alpha carbon asymmetric. In general, in proteins the L-enantiomer of the amino acid is found. The following terms describe the various types of polymerized amino acids. Peptides are short chains of amino acid residues with defined sequence. Although there is not really a maximum to the number of residues, the term usually indicates a chain which properties are mainly determined by its amino acid composition and which does not have a fixed three-dimensional conformation. The term polypeptide is usually used for the longer chains, usually of defined sequence and length and in principle of the appropriate length to fold into a three-dimensional structure. Protein is reserved for polypeptides that occur naturally and exhibit a defined three-dimensional structure. In case the proteins main function is to catalyze a chemical reaction it usually is called an enzyme. Proteases are the enzymes that catalyze the hydrolysis of the peptide bond in (poly)peptides and proteins.

Under physiological conditions proteases catalyse the hydrolysis of the peptide bond. The International Union of Biochemistry and Molecular Biology (1984) has recommended to use the term peptidase for the subset of peptide bond hydrolases (Subclass E.C 3.4.). The terms protease and peptide hydrolase are synonymous with peptidase and may also be used here. Proteases comprise two classes of enzymes: the endo-peptidases and the exo-peptidases, which cleave peptide bonds at points within the protein and remove amino acids sequentially from either N or C-terminus respectively. Proteinase is used as a synonym for endo-peptidase. The peptide bond may occur in the context of di-, tri-, tetra-peptides, peptides, polypeptides or proteins. In general the amino acid composition of natural peptides and polypeptides comprises 20 different amino acids, which exhibit the L-configuration (except for glycine which does not have a chiral centre). However the proteolytic activity of proteases is not limited to peptides that contain only the 20 natural amino acids. Peptide bonds between so-called non-natural amino acids can be cleaved too, as well as peptide bonds between modified amino acids or amino acid analogues. Some proteases do accept D enantiomers of amino acids at certain positions. In general the remarkable stereo-selectivity of proteases makes them very useful in the process of chemical resolution. Many proteases exhibit interesting side activities such as esterase activity, thiol esterase activity and (de)amidase activity. These side activities are usually not limited to amino acids only and might turn out to be very useful in bioconversions in the area of fine chemicals.

There are a number of reasons why proteases of filamentous fungi, eukaryotic microorganisms, are of particular interest. The basic process of hydrolytic cleavage of peptide bonds in proteins appears costly and potentially detrimental to an organism if not properly controlled. The desired limits to proteolytic action are achieved through the specificity of proteinases, by compartmentalization of proteases and substrates within the cell, through modification of the substrates allowing recognition by the respective proteases, by regulation via zymogen activation, and the presence or absence of specific inhibitors, as well through the regulation of protease gene expression. In fungi, proteases are also involved in other fundamental cellular processes, including intracellular protein turnover, processing, translocation, sporulation, germination and differentiation. In fact, *Aspergillus nidulans* and *Neurospora crassa* have been used as model organisms for analyzing the molecular basis of a range of physiological and developmental processes. Their genetics enable direct access to biochemical and genetical studies, under defined nutrient and cultivation conditions. Furthermore, a large group of fungi pathogenic to humans, live-stock and crop, has been isolated and proteolysis has been suggested to play a role in their pathogenicity (host penetration, countering host defense mechanisms and/or nutrition during infection). Proteases are also frequently used in laboratory, clinical and industrial processes; both microbial and non-microbial proteases are widely used in the food industry (baking, brewing, cheese manufacturing, meat tenderizing), in tanning industry and in the manufacture of biological detergents (Aunstrup, 1980). The commercial interest in exploiting certain filamentous fungi, especially the *Aspergilli*, as hosts for the production of both homologous and heterologous proteins, has also recently renewed interests in fungal proteases (van Brunt, 1986ab). Proteases often cause problems in heterologous expression and homologous overexpression of proteins in fungi. In particular, heterologous expression is hampered by the proteolytic degradation of the expressed products by homologous proteases. These commercial interests have resulted in detailed studies of proteolytic spectra and construction of protease deficient strains and have improved the knowledge about protease expression and regulation in these organisms. Consequently there is a great need to identify and eliminate novel proteases in filamentous fungi.

Micro-organisms such as for example fungi are particularly useful in the large scale production of proteins. In particular when such proteins are secreted into the medium. Proteolytic enzymes play a role in these production processes. On the one hand particular proteolytic enzymes are in general required for proper processing of the target protein and the metabolic well-being of the production host. On the other hand proteolytic degradation may significantly decrease the yield of secreted proteins. Poor folding in the secretion pathway may lead to degradation by intracellular proteases. This might be a particular problem with producing heterologous proteins. The details of the proteolytic processes, which are responsible for the degradation of the proteins that are diverted from the secretory process in fungi are not exactly known. In eukaryotes the degradation of cellular proteins is achieved by a proteasome and usually involves ubiquitin labelling of proteins to be degraded. In fungi, proteasomal and vacuolar proteases are also likely candidates for the proteolytic degradation of poorly folded secretory proteins. The proteolytic degradation is likely cytoplasmic, but endoplamatic reticulum resident proteases cannot be excluded. From the aspect of production host strain improvement the proteolytic system may be an interesting target for genetic engineering and production strain improvement. Additional copies of protease genes, overexpression of certain proteases, modification of transcriptional control, as well as knock out procedures for deletion of protease genes may provide a more detailed insight in the function a given protease. Deletion of protease encoding genes can be a valuable strategy for host strain improvement in order to improve production yield for homologous as well as heterologous proteins.

Eukaryotic microbial proteases have been reviewed by North (1982). More recently, Suarez Rendueles and Wolf (1988) have reviewed the *S. cerevisiae* proteases and their function.

Apart from the hydrolytic cleavage of bonds, proteases may also be applied in the formation of bonds. Bonds in this aspect comprise not only peptide and amide bonds but also ester bonds. Whether a protease catalyses the cleavage or the formation of a particular bond does in the first place depend on the thermodynamics of the reaction. An enzyme such as a protease does not affect the equilibrium of the reaction. The equilibrium is dependent on the particular conditions under which the reaction occurs. Under physiological conditions the thermodynamics of the reactions is in favour of the hydrolysis of the peptide due to the thermodynamically very stable structure of the zwitterionic product. By application of physical-chemical principles to influence the equilibrium, or by manipulating the concentrations or the nature of the reactants and products, or by exploiting the kinetic parameters of the enzyme reaction it is possible to apply proteases for the purpose of synthesis of peptide bonds. The addition of water miscible organic solvents decreases the extent of ionisation of the carboxyl component, thereby increasing the concentration of substrate available for the reaction. Biphasic systems, water mimetics, reverse micelles, anhydrous media, or modified amino and carboxyl groups to invoke precipitation of products are often employed to improve yields. When the proteases with the right properties are available the application of proteases for synthesis offers substantial advantages. As proteases are stereoselective as well as regio-selective, sensitive groups on the reactants do usually not need protection and reactants do not need to be optically pure. As conditions of enzymatic synthesis are mild, racemization and decomposition of labile reactants or products can be prevented. Apart from bonds between amino acids, also other compounds exhibiting a primary amino group, a thiol group or a carboxyl group may be linked by properly selected proteases. In addition esters, thiol esters and amides may be synthesized by certain proteases. Protease have been shown to exhibit regioselectively in the acylation of mono, di- and tri-saccharides, nucleosides, and riboflavin. Problems with stability under the sometimes harsh reaction conditions may be prevented by proper formulation. Encapsulation and immobilisation do not only stabilise enzymes but also allow easy recovery and separation from the reaction medium. Extensive crosslinking, treatment with aldehydes or covering the surface with certain polymers such as dextrans, polyethyleneglycol, polyimines may substantially extend the lifetime of the biocatalyst.

The Natural Roles of Proteases

Traditionally, proteases have been regarded as degrading enzymes, capable of cleaving proteins into small peptides and/or amino acids, and whose role it is to digest nutrient protein or to participate in the turnover of cellular proteins. In addition, it has been shown that proteases also play key roles in a wide range of cellular processes, via mechanisms of selective modification by limited proteolysis, and thus can have essential regulatory functions (Holzer and Tschensche 1979; Holzer and Heinrich, 1980). The specificity of a proteinase is assumed to be closely related to its physiological function and its mode of expression. With respect to the function of a particular protease, its localisation is often very important; for example, a lot of the vacuolar and periplasmic proteases are involved in protein degradation, while many of the membrane-bound proteases are important in protein processing (Suarez Rendueles and Wolf, 1988). The different roles of proteases in many cellular processes can be divided into four main functions of proteases: 1) protein degradation, 2) posttranslational processing and (in)activation of specific proteins, 3) morphogenesis, and 4) pathogenesis.

An obvious role for proteases in organisms which utilise protein as a nutrient source is in the hydrolysis of nutrients. In fungi, this would involve the degradation outside the cells by extracellular broad specificity proteases. Protein degradation is also important for rapid turnover of cellular proteins and allows the cell to remove abnormal proteins and to adapt their complement of protein to changing physiological conditions. Generally, proteases of rather broad specificity should be extremely well-controlled in order to protect the cell from random degradation of other than correct target proteins.

Contrary to the hydrolysis the synthesis of polypeptides occurs in vivo by an ATP driven process on the ribosome.

Ultimately the sequence in which the amino acids are linked is dictated by the information derived from the genome. This process is known as the transcription. Primary translation products are often longer than the final functional products, and after the transcription usually further processing of such precursor proteins by proteases is required. Proteases play a key role in the maturation of such precursor proteins to obtain the final functional protein. In contrast to the very controlled trimming and reshaping of proteins, proteases can also be very destructive and may completely degrade polypeptides into peptides and amino acids. In order to avoid that proteolytic activity is unleashed before it is required, proteases are subject to extensive regulation. Many proteases are synthesized as larger precursors known as zymogens, which become activated when required. Remarkably this activation always occurs by proteolysis. Apart from direct involvement in the processing, selective activation and inactivation of individual proteins are well-known phenomena catalyzed by specific proteases.

The selectivety of limited proteolysis appears to reside more directly in the proteinase-substrate interaction. Specificity may be derived from the proteolytic enzyme which recognizes only specific amino acid target sequences. On the other hand, it may also be the result of selective exposure of the 'processing site' under certain conditions such as pH, ionic strength or secondary modifications, thus allowing an otherwise non-specific protease to catalyze a highly specific event. The activation of vacuolar zymogens by limited proteolysis gives an example of the latter kind.

Morphogenesis or differentiation can be defined as a regulated series of events leading to changes from one state to another in an organism. Although direct relationships between proteases and morphological effects could not be established in many cases, the present evidence suggests a significant involvement of proteases in fungal morphogenesis; apart form the observed extensive protein turnover during differentiation, sporulation and spore germination, proteases are thought to be directly involved in normal processes as hyphal tip branching and septum formation, (Deshpande, 1992).

Species of *Aspergillus*, in particular *A. fumigatus* and *A. flavus*, have been implicated as the causative agents of a number of diseases in humans and animals called *aspergillosis* (Bodey and Vartivarian, 1989). It has been repeatedly suggested that proteases are involved in virulence of *A. fumigatus* and *A. flavus* like there are many studies linking secreted proteases and virulence of bacteria. In fact, most human infections due to *Aspergillus* species are characterised by an extensive degradation of the parenchyma of the lung which is mainly composed of collagen and elastin (Campbell et al., 1994). Research has been focussed on the putative role of the secreted proteases in virulence of *A. fumigatus* and *A. flavus* which are the main human pathogens and are known to possess elastinolytic and collagenic activities (Kolattukudy et al., 1993). These elastinolytic activities were shown to correlate in vitro with infectivity in mice (Kothary et al., 1984). Two secreted proteases are known to be produced by *A. fumigatus* and *A. flavus*, an alkaline serine protease (ALP) and a neutral metallo protease (MEP). In *A. fumigatus* both the genes encoding these proteases were isolated, characterised and disrupted (Reicherd et al., 1990; Tang et al, 1992, 1993; Jaton-Ogay et al., 1994). However, alp mep double mutants showed no differences in pathogenecity when compared with wild type strains. Therefore, it must be concluded that the secreted *A. fumigatus* proteases identified in vitro are not essential factors for the invasion of tissue (Jaton Ogay et al., 1994).

Although *A. fumigatus* accounts for only a small proportion of the airborne mould spores, it is the most frequently isolated fungus from lung and sputum (Schmitt et al., 1991). Other explanations for the virulence of the fungus could be that the conditions in the bronchia (temperature and nutrients) are favourable for the parasitic growth of *A. fumigatus*. As a consequence, invasive apergillosis could be a circumstancial event, when the host pathogenic defences have been weakened by immunosuppressive treatments or diseases like AIDS.

Four major classes of proteases are known and are designated by the principal functional groups in their active site: the 'serine', the 'thiol' or 'cysteine', the 'aspartic' or 'carboxyl' and the 'metallo' proteases. A detailed state of the art review on these major classes of proteases, minor classes and unclassified proteases can be found in Methods in Enzymology part 244 and 248 (A. J. Barrett ed, 1994 and 1995).

Specificity of Proteases

Apart from the catalytic machinery of proteases another important aspect of proteolytic enzymes is the specificity of proteases. The specificity of a protease indicates which substrates the protease is likely to hydrolyze. The twenty natural amino acids offer a large number of possibilities to make up peptides. Eg with twenty amino acids one can make up already 400 dipeptides and 800 different tripeptide, and so on. With longer peptides the number of possibilities will become almost unlimited. Certain proteases hydrolyze only particular sequences at a very specific position. The interaction of the protease with the peptide substrate may encompass one up to ten amino acid residues of the peptide substrate. With large proteinacious substrates there may be even more residues of the substrate that interact with the proteases. However this likely involves less specific interactions with protease residues outside the active site binding cleft. In general the specific recognition is restricted to the linear peptide, which is bound in the active site of the protease.

The nomenclature to describe the interaction of a substrate with a protease has been introduced in 1967 by Schechter and Berger (Biochem. Biophys. Res. Corn., 1967, 27, 157-162) and is now widely used in the literature. In this system, it is considered that the amino acid residues of the polypeptide substrate bind to so-called sub-sites in the active site. By convention, these sub-sites on the protease are called S (for sub-sites) and the corresponding amino acid residues are called P (for peptide). The amino acid residues of the N-terminal side of the scissile bond are numbered P3, P2, P1 and those residues of the C-terminal side are numbered P1', P2', P3'. The P1 or P1' residues are the amino acid residues located near the scissile bond. The substrate residues around the cleavage site can then be numbered up to P8. The corresponding sub-sites on the protease that complement the substrate binding residues are numbered S3, S2, S1, S1', S2', S3', etc, etc. The preferences of the sub-sites in the peptide binding site determine the preference of the protease for cleaving certain specific amino acid sequences at a particular spot. The amino acid sequence of the substrate should conform with the preferences exhibited by the sub-sites. The specificity towards a certain substrate is clearly dependant both on the binding affinity for the substrate and on the velocity at which subsequently the scissile bond is hydrolysed. Therefore the specificity of a protease for a certain substrate is usually indicated by its kcat/Km ratio, better known as the specificity constant. In this specificity constant kcat represents the turn-over rate and Km is the dissociation constant.

Apart from amino acid residues involved in catalysis and binding, proteases contain many other essential amino acid residues. Some residues are critical in folding, some residues maintain the overall three dimensional architecture of the protease, some residues may be involved in regulation of the proteolytic activity and some residue may target the protease for a particular location. Many proteases contain outside the active site one or more binding sites for metal ions. These metal ions often play a role in stabilizing the structure. In addition secreted eukaryotic microbial proteases may be extensively glycosylated. Both N- and O-linked glycosylation occurs. Glycosylation may aid protein folding, may increase solubility, prevent aggregation and as such stabilize the mature protein. In addition the extent of glycosylation may influence secretion as well as water binding by the protein.

Regulation of Proteolytic Activity

A substantial number of proteases are subject to extensive regulation of the proteolytic activity in order to avoid undesired proteolytic damage. To a certain extent this regulation takes place at transcription level. For example in fungi the transcription of secreted protease genes appears to be sensitive to external carbon and nitrogen sources, whereas genes encoding intracellular proteases are insensitive. The extracellular pH is sensed by fungi and some genes are regulated by pH. In this process transcriptional regulator proteins play a crucial role. Proteolytic processing of such regulator proteins is often the switch that turns the regulator proteins either on or off.

Proteases are subject to intra- as well as intermolecular regulation. This implies certain amino acids in the proteolytic enzyme molecule that are essential for such regulation. Proteases are typically synthesized as larger precursors known as zymogens, which are catalytically inactive. Usually the peptide chain extension rendering the precursor protease inactive is located at the amino terminus of the protease. The precursor is better known as pro-protein. As many of the proteases processed in this way are secreted from the cells they contain in addition a signal sequence (pre sequence) so that the complete precursor is synthesized as a pre-pro-protein. Apart from rendering the protease inactive the pro-peptide often is essential for mediating productive folding. Examples of proteases include serine proteases (alpha lytic protease, subtilisin, aqualysin, prohormone convertase), thiol proteases (cathepsin L and cruzian), aspartic proteases (proteinase A and cathepsin D) and metalloproteases. In addition the pro-peptide might play a role in cellular transport either alone or in conjunction with signal peptides. It may facilitate interaction with cellular chaperones or it may facilitate transport over the membrane. The size of the extension in the precursor pre-pro-protein may vary substantially, ranging from a short peptide fragment to a polypeptide, which can exist as an autonomous folding unit. In particular these larger extensions are often observed to be strong inhibitors of the protease even after cleavage from the protease. It was observed that even after cleavage such pro-peptides could assist in proper folding of the proteases. As such pro-peptides can be considered to function as molecular chaperones and separate or additional co-expression of such pro-peptides could be advantageous for protease production.

There is substantial difference in the level of regulation between proteases that are secreted into the medium and proteases that remain intracellular. Proteases secreted into the medium are usually after activation no longer subject to control and therefore are usually relatively simple in their molecular architecture consisting of one globular module. Intracellular proteases are necessarily subject to continuous control in order to avoid damage to the cells. In contrast with zymogens of secreted proteases in more complex regulatory proteases very large polypeptide segments may be inserted between the signal and the zymogen activation domain of the proteolytic module. Structure-function studies indicate that such non-protease parts may be involved in interactions with macroscopic structures, membranes, cofactors, substrates, effectors, inhibitors, ions, that regulate activity and activation of the proteolytic module(s) or its (their) zymogens. The non-proteolytic modules exhibit remarkable variation in size and structure. Many of the modules can exist as such independently from the proteolytic module. Therefore such modules can be considered to correspond to independent structural and functional units that are autonomous with respect to folding. The value of such a modular organization is that acquisition of new modules can endow the recipient protease with new novel binding specificities and can lead to dramatic changes in its activity, regulation and targeting. The principle of modular organized proteolytic enzymes may also be exploited by applying molecular biology tools in order to create novel interactions, regulation, specificity, and/or targeting by shuffling of modules. Although in general such additional modules are observed as N or C terminal extension, also large insertions within the exterior loops of the catalytic domain have been observed. It is believed that also in this case the principal fold of the protease represents still the essential topology to form a functional proteolytic entity and that the insertion can be regarded as substructure folded onto the surface of the proteolytic module.

Molecular Structure

In principle the modular organization of larger proteins is a general theme in nature. In particular within the larger multimodular frameworks typical proteolytic modules show sizes of 100 to 400 amino acids on the average. This corresponds with the average size of most of the globular proteolytic enzymes that are secreted into the medium. As discussed above polypeptide modules are polypeptide fragments, which can fold and function as independent entities. Another term for such modules is domains. However domain is used in a broader context than module. The term domain as used herein refers usually to a part of the polypeptide chain that depicts in the three-dimensional structure a typical folding topology. In a protein domains interact to varying extents, but less extensively than do the structural elements within domains. Other terms such as subdomain and folding unit are also used in literature. As such it is observed that many proteins that share a particular functionality may share the same domains. Such domains can be recognized from the primary structure that may show certain sequence patterns, which are typical for a particular domain. Typical examples are the mononucleotide binding fold, cellulose binding domains, helix-turn-helix DNA binding motif, zinc fingers, EF hands, membrane anchors. Modules refer to those domains which are expected to be able to fold and function autonomously. A person skilled in the art knows how to identify particular domains in a primary structure by applying commonly available computer software to said structure and homologous sequences from other organisms or species.

Although multimodular or multidomain proteins may appear as a string of beads, assemblies of substantial more complex architecture have been observed. In case the various beads reside on the same polypeptide chain the beads are generally called modules or domains. When the beads do not reside on one and same polypeptide chain but form assemblies via non-covalent interactions then the term subunit is used to designate the bead. Subunits may be transcribed by one and the same gene or by different genes. The multimodular protein may become proteolytically processed after transcription leading to multiple subunits. Individual subunits may consist of multiple domains. Typically the smaller globular proteins of 100-300 amino acids usually consist only of one domain.

Molecular Classification of Proteolytic Enzymes

In general proteases are classified according to their molecular properties or according to their functional properties. The molecular classification is based on the primary structure of the protease. The primary structure of a protein represents its amino acid sequence, which can be derived from the nucleotide sequence of the corresponding gene. Tracing extensively the similarities in the primary structures may allow for the notice of similarities in catalytic mechanism and other properties, which even may extend to functional properties. The term family is used to describe a group of proteases that show evolutionary relationship based on similarity between their primary structures. The members of such a family are believed to have arisen by divergent evolution from the same ancestor. Within a family further sub-grouping of the primary structures based on more detailed refinement of sequence comparisons results in sub-families. Classification according to three-dimensional fold of the proteases may comprise secondary structure, tertiary structure and quarternary structure. In general the classification on secondary structure is limited to content and gross orientation of secondary structure elements. Similarities in tertiary structure have led to the recognition of superfamilies or clans. A superfamily or a clan is a group of families that are thought to have common ancestry as they show a common 3-dimensional fold. In general tertiary structure is more conserved than the primary structure. As a consequence similarity of the primary structure does not always reflect similar functional properties. In fact functional properties may have diverged substantially resulting in interesting new properties. At present quarternary structure has not been applied to classify various proteases. This might be due to a certain bias of the structural databases towards simple globular proteases. Many proteolytic systems that are subject to activation, regulation, or complex reaction cascades are likely to consist of multiple domains or subunits. General themes in the structural organization of such protease systems may lead to new types of classification.

Classification According to Specificity.

In absence of sequence information proteases haven been subject to various type of functional classification. The classification and naming of enzymes by reference to the reactions which are catalyzed is a general principle in enzyme nomenclature. This approach is also the underlying principle of the EC numbering of enzymes (*Enzyme Nomenclature* 1992 Academic Press, Orlando). Two types of proteases (EC 3.4) can be recognized within *Enzyme Nomenclature* 1992, those of the exo-peptidases (EC 3.4.11-19) and those of the endo-peptidases (EC 3.4.21-24, 3.4.99). Endo-peptidases cleave peptide bonds in the inner regions of the peptide chain, away from the termini. Exo-peptidases cleave only residues from the ends of the peptide chain. The exo-peptidases acting at the free N-terminus may liberate a single amino acid residue, a dipeptide or a tripeptide and are called respectively amino peptidases (EC 3.4.11), dipeptidyl peptidases (EC 3.4.14) and tripeptidyl peptidase (EC 3.3.14). Proteases starting peptide processing from the carboxyl terminus liberating a single amino acid are called carboxy peptidase (EC 3.4.16-18). Peptidyl-dipeptidases (EC 3.4.15) remove a dipeptide from the carboxyl terminus. Exo- and endo-peptidase in one are the dipeptidases (EC 3.4.13), which cleave specifically only dipeptides in their two amino acid halves. Omega peptidases (EC 3.4.19) remove terminal residues that are either substituted, cyclic, or linked by isopeptide bonds Apart from the position where the protease cleaves a peptide chain, for each type of protease a further division is possible based on the nature of the preferred amino acid residues in the substrate. In general one can distinguish proteases with broad, medium and narrow specificity. Some proteases are simply named after the specific proteins or polypeptides that they hydrolyze, e.g. keratinase, collagenase, elastase. A narrow specificity may pin down to one particular amino acid or one particular sequence which is removed or which is cleaved respectively. When the protease shows a particular preference for one aminoacid in the P1 or P1' position the name of this amino acid may be a qualifier. For example prolyl amino peptidase removes proline from the amino terminus of a peptide (proline is the P1 residue). X-Pro or proline is used when the bond on the imino side of the proline is cleaved (proline is P1' residue), eg proline carboxypeptidase removes proline from the carboxyl terminus. Prolyl endopeptidase (or Pro-X) cleaves behind proline while proline endopeptidase (X-Pro) cleaves in front of a proline. Amino acid residue in front of the scissile peptide bond refers to the amino acid residue that contributes the carboxyl group to the peptide bond. The amino acids residue behind the scissile peptide bond refers to the amino acid residue that contributes the amino group to the peptide bond. According to the general convention an amino acid chain runs from amino terminus (the start) to the carboxyl terminus (the end) and is numbered accordingly. Endo proteases may also show clear preference for a particular amino acid in the P1 or P1' position, eg glycyl endopeptidase, peptidyl-lysine endopeptidase, glutamyl endopeptidase. In addition proteases may show a preference for a certain group of amino acids that share a certain resemblance. Such a group of preferred amino acids may comprise the hydrophobic amino acids, only the bulky hydrophobic amino acids, small hydrophobic, or just small amino acids, large positively charged amino acids, etc, etc. Apart from preferences for P1 and P1' residues also particular preferences or exclusions may exist for residues preferred by other subsites on the protease. Such multiple preferences can result in proteases that are very specific for only those sequences that satisfy multiple binding requirements at the same time. In general it should be realized that protease are rather promiscuous enzymes. Even very specific protease may cleave peptides that do not comply with the generally observed preference of the protease. In addition it should be realized that environmental conditions such as pH, temperature, ionic strength, water activity, presence of solvents, presence of competing substrates or inhibitors may influence the preferences of the proteases. Environmental condition may not only influence the protease but also influence the way the proteinacious substrate is presented to the protease.

Classification by Catalytic Mechanism.

Proteases can be subdivided on the basis of their catalytic mechanism. It should be understood that for each catalytic mechanism the above classification based on specificity leads to further subdivision for each type of mechanism. Four major classes of proteases are known and are designated by the principal functional group in the active site: the serine proteases (EC 3.4.21 endo peptidase, EC 3.4.16 carboxy peptidase), the thiol or cysteine proteases (EC 3.4.22 endo peptidase, EC 3.4.18 carboxy peptidase), the carboxyl or aspartic proteases (EC 3.4.23 endo peptidase) and metallo proteases (EC 3.4.24 endo peptidase, EC 3.4.18 carboxy peptidase). There are characteristic inhibitors of the members of each catalytic type of protease. These small inhibitors irreversibly modify an amino acid residue of the protease active site. For example, the serine protease are inactivated by Phenyl Methane Sulfonyl Fluoride (PMSF) and Diisopropyl Fluoro Phosphate (DFP), which react with the active Serine whereas the chloromethylketone derivatives react with the Histidine of the catalytic triad. Phosphoramidon and 1,10 Phenanthroline typically inhibit metallo proteases. Inhibition by Pepstatin generally indicates an aspartic protease. E64 inhibits thiol protease specifically. Amastatin and Bestatin inhibit various aminopeptidases. Substantial variations in susceptibility of the proteases to the inhibitors are observed, even within one catalytic class. To a certain extent this might be related to the specificity of the protease. In case binding site architecture prevents a mechanism based inhibitor to approach the catalytic site, then such a protease escapes from inhibition and identification of the type of mechanism based on inhibition is prohibited. Chymostation for example is a potent inhibitor for serine protease with chymotrypsin like specificity, Elastatinal inhibits elastase like serine proteases and does not react with trypsin or chymostrypsin, 4 amido PMSF (APMSF) inhibits only serine proteases with trypsin like specificity. Extensive accounts of the use of inhibitors in the classification of proteases include Barret and Salvesen, *Proteinase Inhibitors*, Elsevier Amsterdam, 1986; Bond and Beynon (eds), *Proteolytic Enzymes, A Practical Approach*, IRL Press, Oxford, 1989; Methods in Enzymology, eds E. J. Barret, volume 244, 1994 and volume 248, 1995; E. Shaw, *Cysteinyl proteinases and their selective inactivation*, Adv Enzymol. 63:271-347 (1990)

Classification According to Optimal Performance Conditions.

The catalytic mechanism of a proteases and the requirement for its conformational integrity determine mainly the conditions under which the protease can be utilized. Finding the protease that performs optimal under application conditions is a major challenge. Often conditions at which proteases have to perform are not optimal and do represent a compromise between the ideal conditions for a particular application and the conditions which would suit the protease best. Apart from the particular properties of the protease it should be realized that also the presentation of a proteinacious substrates is dependant on the conditions, and as such determines also which conditions are most effective for proteolysis. Specifications for the enzyme that are relevant for application comprise for example the pH dependence, the temperature dependence, sensitivity for or the dependence of metal ions, ionic strength, salt concentration, solvent compatibility. Another factor of major importance is the specific activity of a protease. The higher the enzyme's specific activity, the less enzyme is needed for a specific conversion. Lower enzyme requirements imply lower costs and lower protein contamination levels.

The pH is a major parameter that determines protease performance in an application. Therefor pH dependence is an important parameter to group proteases. The major groups that are recognized are the acid proteases, the neutral proteases, the alkaline proteases and the high alkaline proteases. The optimum pH matches only to some extent the proteolytic mechanism, eg aspartic protease show often an optimum at acidic pH, metalloproteases and thiol proteases often perform optimal around neutral pH to slightly alkaline, serine peptidases are mainly active in the alkaline and high alkaline region. For each class exceptions are known. In addition the overall water activity of the system plays a role. The pH optimum of a protease is defined as the pH range where the protease exhibits an optimal hydrolysis rate for the majority of its substrates in a particular environment under particular conditions. This range can be narrow, e.g. one pH unit, as well as quite broad, 3-4 pH units. In general the pH optimum is also dependant on the nature of the proteinacious substrate. Both the turnover rate as well as the specificity may vary as a function of pH. For a certain efficacy it can be desirable to use the protease far from its pH optimum because production of less desired peptides is avoided. Less desired peptides might be for example very short peptides or peptides causing a bitter taste. In addition a more narrow specificity can be a reason to choose conditions that deviate from optimal conditions with respect to turnover rate. Dependant on the pH the specificity may be narrow, e.g. only cleaving the peptide chain in one particular position or before or after one particular amino acid, or broader, e.g. cleaving a chain at multiple positions or cleaving before or after more different types of amino acids. In fact the pH dependence might be an important tool to regulate the proteolytic activity in an application. In case the pH shifts during the process the proteolysis might cease spontaneously without the need for further treatment to inactivate the protease. In some cases the proteolysis itself may be the driver of the pH shift.

Very crucial for application of proteases is their handling and operating stability. As protease stability is strongly affected by the working temperature, stability is often also referred to as thermostability. In general the stability of a protease indicates how long a protease retains its proteolytic activity under particular conditions. Particular conditions may comprise fermentation conditions, conditions during isolation and down stream processing of the enzyme, storage conditions, formulation and operating or application conditions. In case particular conditions encompass elevated temperatures stability in general refers to thermostability. Apart from the general causes for enzyme inactivation such as chemical modification, unfolding, aggregation etc, main problem with proteases is that they are easy subject to autodegradation. Especially for the utilization of proteases the temperature optimum is a relevant criterion to group proteases. Although there are different definitions, economically the most useful definition is the temperature or the temperature range in which the protease is most productive in a certain application. Protease productivity is a function of both the stability and the turnover rate. Where elevated temperature in general will increase the turnover rate, rapid inactivation will counteract the increase in turnover rate and ultimately lead to low productivity. The conformational stability of the protease under a given process condition will determine its maximum operating temperature. The temperature at which the protease looses it active conformation, often indicated as unfolding or melting point, can be determined according various methods, for example NMR, Circular Dichroism Spectroscopy, Differential Scanning Calorimetry etc. For protease unfolding is usually accompanied by a tremendous increase in autodegradation rate.

In applications where low temperatures are required protease may be selected with emphasis on a high intrinsic activity at low to moderate temperature. As under such conditions inactivation is relatively slow, under these conditions activity might largely determine productivity. In processes where only during a short period protease activity is required, the stability of the protease might be used as a switch to turn the protease off. In such case more labile instead of very thermostable protease might be preferred.

Other environmental parameters which may play a role in selecting the appropriate protease may be its sensitivity to salts. The compatibility with metal ions which are found frequently at low concentrations in various natural materials can be crucial for certain applications. In particular with metallo proteases certain ions may replace the catalytic metal ion and reduce or even abolish activity completely. In some applications metal ions have to be added on purpose in order to prevent the washout of the metal ions coordinated to the protease. It is well known that for the sake of enzyme stability and life-time, calcium ions have to be supplied in order to prevent dissociation of protein bound calcium.

Most microorganisms show a certain tolerance with respect to adapting to changes in the environmental condition. As a consequence at least the proteolytic spectrum that the organism is able to produce are likely to show at least similar tolerances. Such a proteolyitic spectrum might be covered by many proteases covering together the hole spectrum or by only a few proteases of a broad spectrum. Taking into account the whole proteolytic spectrum of a microorganism it can be very important to take the location into account.

Cellular Localisation and Characterization of Proteolytic Processing and Degradation From an industrial point of view the proteases which are excreted from the cell have specific advantages with respect to producibility at a large scale and stress tolerance as they have to survive without protection of the cell. The large group of cellular protease can be further subdivided in soluble and membrane bound. Membrane bound may comprise protease at the inside as well the outside of the membrane. Intracellular soluble protease may be subdivided further according to specific compartments of the cell where they do occur. As the cell shields the proteases to some extent from the environment and because the cell controls the conditions in the cell, intracellular protease might be more sensitive to large environmental changes and their optima might correlate better with the specific intacellualr conditions. Knowing the conditions of the cellular department where the protease resides might indicate their preferences. Where extracellular protease in general do not require any regulation any more once excreted from the cell, intracellular proteases are often subject to more complicated control and regulation.

With respect to the function of a particular protease, its localisation is often very important; for example, a lot of the vacuolar and periplasmic proteases are involved in protein degradation, while many of the membrane-bound proteases are important in protein processing (Suarez Rendueles and Wolf, 1988).

A comprehensive review on the biological properties and evolution of proteases has been published in van den Hombergh: Thesis Landbouwuniversiteit Wageningen: An analysis of the proteolytic system in *Aspergillus* in order to improve protein production ISBN 90-5485-545-2, which is hereby incorporated by reference herein.

The Protease Problem

An important reason for the interest in microbial proteases are protease related expression problems observed in several expression hosts used in bioprocess industry. The increasing use of heterologous hosts for the production of proteins, by recombinant DNA technology, has recently brought this problem into focus, since it seems that heterologous proteins are more prone to proteolysis (Archer et al., 1992; van den Hombergh et al., 1996b).

In *S. cerevisiae*, already in the early eighties the protease problem and the involvement of several proteases, thus complicating targetted gene disruption approaches to overcome this problem, was recognised. During secretion a protein is exposed to several proteolytic activities residing in the secretory pathway. Additionally, in a prototrophic microorganism as *Aspergillus* secreted proteins can be exposed to several extracellular proteolytic activities The problem of degradation of heterologously expressed proteins is well documented in *Aspergillus* (van den Hombergh Thesis Landbouwuniversiteit Wageningen: An analysis of the proteolytic system in *Aspergillus* in order to improve protein production ISBN 90-5485-545-2) and has been reported in the expression of cow prochymosin, human interferon α-2 tPA, GMCSF, IL6, lactoferrin, chicken eggwhite lysosyme, porcine pIA2, *A. niger* pectin lyase B, *E. coli* enterotoxin B and β-glucoronidase, and *Erwinia carotovora* pectate lyase 3.

The problem of proteolysis may be addressed at several stages in protein production. Bioprocess engineers may address the problem of proteolysis by downstream processing at low temperatures, by early separation of product and protease(s) or by use of protease inhibitors. These may all lead to successful reduction of the problem. However it is certainly not eliminated, because much of the degradation occurs in vivo during the production of the protein.

In understanding how proteolysis is controlled in the cell, a major question concerns the recognition mechanism by which proteolysis is triggered. Into what extent are proteolytically susceptable (heterologous) proteins recognised as aberrant because of misfolding or, if correctly folded, as 'foreign', because they do not posses features essential for stability which are specific to the host. Various types of stress can cause the overall proteolysis in a cell to increase significantly. Factors known to increase rate of proteolysis include nutrient starvation and various other types of stress (i.e. elevation of temperature, osmotic stress, toxic substances and expression of certain heterologous proteins). To deal with proteolysis-related expression problems in vivo, several approaches have been proven succesfull as will be discussed below. However, we have to keep in mind that true 'non-proteolytic cells' cannot exist, since proteolysis by intracellular proteases is involved in many essential metabolic and 'housekeeping' reactions. Reducing proteolysis will therefore always be a process in which the changed genetical background which results in decreased proteolytic has to be analysed for potential secundary effects which could lead to reduced protein production (e.g. reduced growth rate or sporulation).

Disruption of Proteases in Filamentous Fungal Expression Hosts

Berka and coworkers (1990) describe the cloning and disruption of the *A. awamori* pepA gene. More recently, three disrupted aspartyl proteases in *A. niger* have been described. Disruptants for both the major extracellular aspartyl proteases and the major vacuolar aspartyl protease were described. Double and triple disruptants were generated via recombination and tested for protease spectra and expression and secretion of the *A. niger* pectin lyase PELB protein, which is very susceptable to proteolytic degradation (van den Hombergh et al., 1995). Disruption of pepA and pepB resulted both in reduction of extracellular protease activities, 80% and 6%, respectively. In the ΔpepE disruptant also other (vacuolar) protease activities were severely affected caused by inactivating of the proteolytic cascade for other vacuolar proteases. Reduced extracellular activities correlated with reduced in vitro degradation of PELB and improved in vivo expression of pelB (van den Hombergh et al., 1996f).

Protease Deficient (prt) Mutants Filamentous Fungi

Several *Aspergillus* protease deficient mutants have been studied whether protein production is improved. Archer and coworkers describe the reduced proteolysis of Hen egg white lysozyme in supernatants of an *A. niger* double prt mutant generated by Mattern and coworkers (1992) and conclude that although the degradation is not absent, it is significantly reduced. Van den Hombergh et al. (1995) show that the in vitro degradation of *A. niger* PELB is reduced in all seven prt complementation groups they have isolated. Virtually no degradation is observed in the prtB, prtF and prtG mutants. Recently, the expression of the pelB gene was shown to be improved in six complementation groups tested (prtA-F) and highest expression levels were observed in the prtB, prtF and prtG mutants. In addition to the single mutants, which contained residual extracellular proteolytic activities varying from 2-80% compared to wild type activity, double mutants were generated both by recombination and by additional rounds of mutagenesis. Via this approach several double prt mutants were selected and further characterised, which showed a further reduction of PELB degradation compared to their parental strains.

Instead of elimination of protease activities via disruption or mutagenesis, reduced proteolysis can also be achieved via down-regulation of the interfering proteolytic activities. This may be achieved by genetically altering the promoter or other regulatory sequences of the gene. As shown by Fraissinet-Tachet and coworkers (1996) the extracellular proteases in *A. niger* are all regulated by carbon catabolite repression and nitrogen metabolite repression. Nutrient starvation also causes the overall proteolysis rate in a cell to increase stromgly, which makes sense for a cell that lacks nutrients but posses proteins, that under starvation conditions are not needed or needed only in smaller amounts. In expression strategies which allow high expression on media containing high glucose and ammonium concentrations reduced proteolysis has been reported. Several constitutive glycolytic promoters (gpd and pkiA) are highly expressed under these conditions and can also be used to drive (heterologous) gene expression in continuous fermentations. The type of nutrient starvation imposed can influence different proteases to varying extent, which means that the importance of nutrient conditions in a given process depend on the type of proteolysis that is involved. Specific proteolysis may therefore be induced by conditions of substrate limitation which are frequently used in many large-scale fermentation processes.

The protease problem can nowadays be addressed in part by one or more of the above strategies. However, the residual proteolytic activity of yet unidentified proteolytic enzymes still constitutes a major problem in the art. In order to further reduce the level of unwanted proteolysis, there is a great need in the art to identify novel proteases responsible for degradation of homologously and heterologously expressed proteins. This invention provides such novel protease gene sequences encoding novel proteases. Once the primary sequence of a novel protease gene is known, one or more of the above recombinant DNA strategies may be employed to produce (knock-out) mutants with reduced proteolytic activity.

Despite the widespread applications of proteases in a great number of industrial processes, current enzymes also have significant shortcomings with respect to at least one of the following properties.

When added to animal feed, current proteases are not sufficiently resistant to digestive enzymes present in the gastrointestinal (GI) tract of e.g. pigs and poultry.

With respect to another aspect, the currently available enzymes are not sufficiently resistant to specific (high) temperatures and (high) pressure conditions that are applied during extrusion or pelleting operations.

Also, the current enzymes are not sufficiently active in a pH range of 3-7, conditions prevailing in many food, beverage products as well as in the GI tract of most animals.

According to yet another aspect the specificity of the currently available proteases is very limited which results in the inability of the existing enzymes to degrade or to dissolve certain "protease resistant" proteins thus resulting in low peptide or amino acid yields. Moreover proteases with new specificities allow the synthesis of new peptides.

Yet another drawback of the currently available enzymes is their low specific activity.

It is therefore clear that for a large number of applications a strong desire exists for proteases that are more resistant to digestive enzymes, high temperature and/or pressure and which exhibit novel specificities regarding their sites of hydrolysis. The present invention provides such enzymes.

OBJECT OF THE INVENTION

It is an object of the invention to provide novel polynucleotides encoding novel proteases. A further object is to provide naturally and recombinantly produced proteases as well as recombinant strains producing these. Such strains may also be used to produce classical fermentation products faster or with higher yields. Yet another object of the invention is to provide a filamentous fungus strain defective in producing a protease according to the invention. Such strains may be used for a more efficient production of heterologous or homologous proteins. Also antibodies and fusion polypeptides are part of the invention as well as methods of making and using the polynucleotides and polypeptides according to the invention.

SUMMARY OF THE INVENTION

The invention provides for novel polynucleotides encoding novel proteases.

More in particular, the invention provides for polynucleotides having a nucleotide sequence that hybridises (preferably under highly stringent conditions) to a sequence according to a sequence selected from the group consisting of SEQ ID NO: 1 to SEQ ID NO: 57 or to a sequence selected from the group consisting of SEQ ID NO: 58 to SEQ ID NO: 114. Consequently, the invention provides nucleic acids that are about 60%, preferably 65%, more preferably 70%, even more preferably 75%, 80%, 85%, 90%, 95%, 96%, 97%, 98% or 99% homologous to the sequences according to a sequence selected from the group consisting of SEQ ID NO: 1 to SEQ ID NO: 57 or a sequence selected from the group consisting of SEQ ID NO: 58 to SEQ ID NO: 114.

In a more preferred embodiment the invention provides for such an isolated polynucleotide obtainable from a filamentous fungus, preferably *Aspergilli*, in particular *A. niger* is preferred.

In one embodiment, the invention provides for an isolated polynucleotide comprising a nucleic acid sequence encoding a polypeptide with an amino acid sequence selected from the group consisting of SEQ ID NO: 115 to SEQ ID NO: 171 or functional equivalents thereof.

In a further preferred embodiment, the invention provides an isolated polynucleotide encoding at least one functional domain of a polypeptide according to a sequence selected from the group consisting of SEQ ID NO: 115 to SEQ ID NO: 171 or functional equivalents thereof.

In a preferred embodiment the invention provides a protease gene according to a sequence selected from the group consisting of SEQ ID NO: 1 to SEQ ID NO: 57. In another aspect the invention provides a polynucleotide, preferably a cDNA encoding an *A. niger* protease selected from the group consisting of SEQ ID NO: 115 to SEQ ID NO: 171 or variants or fragments of that polypeptide. In a preferred embodiment the cDNA has a sequence selected from the group consisting of SEQ ID NO: 58 to SEQ ID NO: 114 or functional equivalents thereof.

A genomic clone encoding a polypeptide according to the invention may also be obtained by selecting suitable probes to specifically amplify a genomic region corresponding to any of the sequences according to SEQ ID NO: 1 to SEQ ID NO: 57 or fragments thereof, hybridising that probe under suitable conditions to genomic DNA obtained from a suitable organism, such as *Aspergillus*, e.g. *A. niger*, amplifying the desired fragment e.g. by PCR (polymerase chain reaction) followed by purifying and cloning of the amplified fragment.

In an even further preferred embodiment, the invention provides for a polynucleotide comprising the coding sequence of the genomic polynucleotides according to the invention, preferred is a polynucleotide sequence selected from the group consisting of SEQ ID NO: 58 to SEQ ID NO: 114.

In another preferred embodiment, the invention provides a cDNA obtainable by cloning and expressing a sequence selected from the group consisting of SEQ ID NO: 1 to SEQ ID NO: 57 into a suitable host organism, such as *A. niger*.

A polypeptide according to the invention may also be obtained by cloning and expressing a sequence selected from the group consisting of SEQ ID NO: 1 to SEQ ID NO: 57 into a suitable host organism, such as *A. niger*.

The invention also relates to vectors comprising a polynucleotide sequence according to the invention and primers, probes and fragments that may be used to amplify or detect the DNA according to the invention.

In a further preferred embodiment, a vector is provided wherein the polynucleotide sequence according to the invention is functionally linked with regulatory sequences suitable for expression of the encoded amino acid sequence in a suitable host cell, such as *A. niger* or *A. oryzea*. The invention also provides methods for preparing polynucleotides and vectors according to the invention.

The invention also relates to recombinantly produced host cells that contain heterologous or homologous polynucleotides according to the invention.

In one embodiment, the invention provides recombinant host cells wherein the expression of a protease according to the invention is significantly reduced or wherein the activity of the protease is reduced or wherein the protease is even inactivated. Such recombinants are especially useful for the expression of homologous or heterologous proteins.

In another embodiment, the invention provides recombinant host cells wherein the expression of a protease according to the invention is significantly increased or wherein the activity of the protease is increased. Such recombinants are especially useful for the expression of homologous or heterologous proteins where maturation is seriously hampered in case the required proteolytic cleavage becomes the rate limiting step.

In another embodiment the invention provides for a recombinantly produced host cell that contains heterologous or homologous DNA according to the invention, preferably DNA encoding proteins bearing signal seqnnences and wherein the cell is capable of producing a functional protease according to the invention, preferably a cell capable of over-expressing the protease according to the invention, for example an *Aspergillus* strain comprising an increased copy number of a gene or cDNA according to the invention.

In another embodiment the invention provides for a recombinantly produced host cell that contains heterologous or homologous DNA according to the invention and wherein the cell is capable of secreting a functional protease according to the invention, preferably a cell capable of over-expressing and secreting the protease according to the invention, for example an *Aspergillus* strain comprising an increased copy number of a gene or cDNA according to the invention.

In yet another aspect of the invention, a purified polypeptide is provided. The polypeptides according to the invention include the polypeptides encoded by the polynucleotides according to the invention. Especially preferred is a polypeptide according to a sequence selected from the group consisting of SEQ ID NO: 115 to SEQ ID NO: 171 or functional equivalents thereof.

The invention also provides for antibodies reactive with a polypeptide according to the invention. These antibodies may be polyclonal, yet especially preferred are monoclonal antibodies. Such antibodies are particularly useful for purifying the polypeptides according to the invention.

Fusion proteins comprising a polypeptide according to the invention are also within the scope of the invention. The invention also provides methods of making the polypeptides according to the invention.

The invention further relates to a method for diagnosing aspergillosis either by detecting the presence of a polypeptide according to the invention or functional equivalents thereof, or by detecting the presence of a DNA according to the invention or fragments or functional equivalents thereof.

The invention also relates to the use of the protease according to the invention in an industrial process as described herein

DETAILED DESCRIPTION OF THE INVENTION

Polynucleotides

The present invention provides polynucleotides encoding proteases having an amino acid sequence selected from the group consisting of SEQ ID NO: 115 to SEQ ID NO: 171 or functional equivalents thereof. The sequence of these genes was determined by sequencing a genomic clone obtained from *Aspergillus niger*. The invention provides polynucleotide sequences comprising the gene encoding these proteases as well as their complete cDNA sequence and its coding sequence. Accordingly, the invention relates to an isolated polynucleotide comprising a nucleotide sequence selected from the group consisting of SEQ ID NO: 1 to SEQ ID NO: 57 or a sequence selected from the group consisting of SEQ ID NO: 58 to SEQ ID NO: 114 or functional equivalents thereof.

More in particular, the invention relates to an isolated polynucleotide hybridisable under stringent conditions to a polynucleotide selected from the group consisting of SEQ ID NO: 1 to SEQ ID NO: 57 or a sequence selected from the group consisting of SEQ ID NO: 58 to SEQ ID NO: 114 preferably under highly stringent conditions. Advantageously, such polynucleotides may be obtained from filamentous fungi, in particular from *Aspergillus niger*. More specifically, the invention relates to an isolated polynucleotide having a nucleotide sequence according to a sequence selected from the group consisting of SEQ ID NO: 1 to SEQ ID NO: 57 or a sequence selected from the group consisting of SEQ ID NO: 58 to SEQ ID NO: 114.

The invention also relates to an isolated polynucleotide encoding at least one functional domain of a polypeptide according to a sequence selected from the group consisting of SEQ ID NO: 115 to SEQ ID NO: 171 or functional equivalents thereof.

As used herein, the terms "gene" and "recombinant gene" refer to nucleic acid molecules which may be isolated from chromosomal DNA, which include an open reading frame encoding a protein, e.g. an *A. niger* protease. A gene may include coding sequences, non-coding sequences, introns and regulatory sequences. Moreover, a gene refers to an isolated nucleic acid molecule as defined herein.

A nucleic acid molecule of the present invention, such as a nucleic acid molecule having the nucleotide sequence of a sequence selected from the group consisting of SEQ ID NO: 1 to SEQ ID NO: 57 or a sequence selected from the group consisting of SEQ ID NO: 58 to SEQ ID NO: 114 or a functional equivalent thereof, can be isolated using standard molecular biology techniques and the sequence information provided herein. For example, using all or portion of the nucleic acid sequence of a sequence selected from the group consisting of SEQ ID NO: 1 to SEQ ID NO: 57 or the nucleotide sequence of a sequence selected from the group consisting of SEQ ID NO: 58 to SEQ ID NO: 114 as a hybridization probe, nucleic acid molecules according to the invention can be isolated using standard hybridization and cloning techniques (e. g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of a sequence selected from the group consisting of SEQ ID NO: 1 to SEQ ID NO: 57 or a sequence selected from the group consisting of SEQ ID NO: 58 to SEQ ID NO: 114 can be isolated by the polymerase chain reaction (PCR) using synthetic oligonucleotide primers designed based upon the sequence information contained in a sequence selected from the group consisting of SEQ ID NO: 1 to SEQ ID NO: 57 or a sequence selected from the group consisting of SEQ ID NO: 58 to SEQ ID NO: 114.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Furthermore, oligonucleotides corresponding to or hybridisable to nucleotide sequences according to the invention can be prepared by standard synthetic techniques, e.g., using an automated DNA synthesizer.

In a preferred embodiment, an isolated nucleic acid molecule of the invention comprises the nucleotide sequence shown in a sequence selected from the group consisting of SEQ ID NO: 58 to SEQ ID NO: 114. The sequence of a sequence selected from the group consisting of SEQ ID NO: 58 to SEQ ID NO: 114 corresponds to the coding region of the *A. niger* protease cDNA. This cDNA comprises sequences encoding the *A. niger* protease polypeptide according to a sequence selected from the group consisting of SEQ ID NO: 115 to SEQ ID NO: 171.

In another preferred embodiment, an isolated nucleic acid molecule of the invention comprises a nucleic acid molecule which is a complement of the nucleotide sequence shown in a sequence selected from the group consisting of SEQ ID NO: 1 to SEQ ID NO: 57 or a sequence selected from the group consisting of SEQ ID NO: 58 to SEQ ID NO: 114 or a functional equivalent of these nucleotide sequences.

A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a polypeptide of the invention or a functional equivalent thereof such as a biologically active fragment or domain, as well as nucleic acid molecules sufficient for use as hybridisation probes to identify nucleic acid molecules encoding a polypeptide of the invention and fragments of such nucleic acid molecules suitable for use as PCR primers for the amplification or mutation of nucleic acid molecules.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to a protease nucleic acid molecule, e.g., the coding strand of a protease nucleic acid molecule. Also included within the scope of the invention are the complement strands of the nucleic acid molecules described herein.

Sequencing Errors

The sequence information as provided herein should not be so narrowly construed as to require inclusion of erroneously identified bases. The specific sequences disclosed herein can be readily used to isolate the complete gene from filamentous fungi, in particular *A. niger* which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

Nucleic Acid Fragments, Probes and Primers

A nucleic acid molecule according to the invention may comprise only a portion or a fragment of the nucleic acid sequence shown in a sequence selected from the group consisting of SEQ ID NO: 1 to SEQ ID NO: 57 or a sequence selected from the group consisting of SEQ ID NO: 58 to SEQ ID NO: 114, for example a fragment which can be used as a probe or primer or a fragment encoding a portion of a protease protein. The nucleotide sequence determined from the cloning of the protease gene and cDNA allows for the generation of probes and primers designed for use in identifying and/or cloning other protease family members, as well as protease homologues from other species. The probe/primer typically comprises substantially purified oligonucleotide which typically comprises a region of nucleotide sequence that hybridizes preferably under highly stringent conditions to at least about 12 or 15, preferably about 18 or 20, preferably about 22 or 25, more preferably about 30, 35, 40, 45, 50, 55, 60, 65, or 75 or more consecutive nucleotides of a nucleotide sequence shown in a sequence selected from the group consisting of SEQ ID NO: 1 to SEQ ID NO: 57 or a sequence selected from the group consisting of SEQ ID NO: 58 to SEQ ID NO: 114 or of a functional equivalent thereof.

Probes based on the protease nucleotide sequences can be used to detect transcripts or genomic protease sequences encoding the same or homologous proteins for instance in other organisms. In preferred embodiments, the probe further comprises a label group attached thereto, e.g., the label group can be a radioisotope, a fluorescent compound, an enzyme, or an enzyme cofactor. Such probes can also be used as part of a diagnostic test kit for identifying cells which express a protease protein.

Identity & Homology

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100).

Preferably, the two sequences are the same length.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid sequences is determined using the Needleman and Wunsch (J. Mol. Biol. (48):444-453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity two amino acid or nucleotide sequence is determined using the algorithm of E. Meyers and W. Miller (CABIOS, 4:11-17 (1989) which has been incorporated into the ALIGN program (version 2.0) (available at *http://vega/igh.cnrs.fr/bin/align-guess.cgi*), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J.

Mol. Biol. 215:403-10. BLAST nucleotide searches can be performed with the NBLAST program, score=100, wordlength=12 to obtain nucleotide sequences homologous to protease nucleic acid molecules of the invention. BLAST protein searches can be performed with the XBLAST program, score=50, wordlength=3 to obtain amino acid sequences homologous to protease protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See http://www.ncbi.nlm.nih.gov.

Hybridisation

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, more preferably at least 95% homologous to each other typically remain hybridized to each other.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., preferably at 60° C. and even more preferably at 65° C.

Highly stringent conditions include, for example, hybridizing at 68° C. in 5×SSC/5× Denhardt's solution/1.0% SDS and washing in 0.2×SSC/0.1% SDS at room temperature. Alternatively washing may be performed at 42° C.

The skilled artisan will know which conditions to apply for stringent and highly stringent hybridisation conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule contain a poly (A) stretch or the complement thereof (e.g., practically any doublestanded cDNA clone).

Obtaining Full Length DNA from Other Organisms

In a typical approach, cDNA libraries constructed from other organisms, e.g. filamentous fungi, in particular from the species Aspergillus can be screened.

For example, Aspergillus strains can be screened for homologous protease polynucleotides by Northern blot analysis. Upon detection of transcripts homologous to polynucleotides according to the invention, cDNA libraries can be constructed from RNA isolated from the appropriate strain, utilizing standard techniques well known to those of skill in the art. Alternatively, a total genomic DNA library can be screened using a probe hybridisable to a protease polynucleotide according to the invention.

Homologous gene sequences can be isolated, for example, by performing PCR using two oligonucleotide primers or two degenerate oligonucleotide primer pools designed on the basis of nucleotide sequences as taught herein.

The template for the reaction can be cDNA obtained by reverse transcription of mRNA prepared from strains known or suspected to express a polynucleotide according to the invention. The PCR product can be subcloned and sequenced to ensure that the amplified sequences represent the sequences of a new protease nucleic acid sequence, or a functional equivalent thereof.

The PCR fragment can then be used to isolate a full length cDNA clone by a variety of known methods. For example, the amplified fragment can be labeled and used to screen a bacteriophage or cosmid cDNA library. Alternatively, the labeled fragment can be used to screen a genomic library.

PCR technology also can be used to isolate full length cDNA sequences from other organisms. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis.

The resulting RNA/DNA hybrid can then be "tailed" (e.g., with guanines) using a standard terminal transferase reaction, the hybrid can be digested with RNase H, and second strand synthesis can then be primed (e.g., with a poly-C primer). Thus, cDNA sequences upstream of the amplified fragment can easily be isolated. For a review of useful cloning strategies, see e.g., Sambrook et al., supra; and Ausubel et al., supra.

Vectors

Another aspect of the invention pertains to vectors, preferably expression vectors, containing a nucleic acid encoding a protease protein or a functional equivalent thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signal). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g. protease proteins, mutant forms of protease proteins, fragments, variants or functional equivalents thereof, fusion proteins, etc.).

The recombinant expression vectors of the invention can be designed for expression of protease proteins in prokaryotic or eukaryotic cells. For example, protease proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and 17 polymerase.

Expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled person. In a specific embodiment, promoters are preferred that are capable of directing a high expression level of proteases in filamentous fungi. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-percipitation, DEAE-dextran-mediated transfection, transduction, infection, lipofection, cationic lipid mediated transfection or electroporation. Suitable methods for transforming or transfecting host cells can be found in Sambrook, et al. (*Molecular Cloning: A Laboratory Manual, 2nd, ed. Cold Spring Harbor Laboratory*, Cold Spring Harbor Laboratory Press, Cold Spring Harbor, N.Y., 1989), Davis et al., *Basic Methods in Molecular Biology* (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methatrexate. Nucleic acid encoding a selectable marker can be introduced into a host cell on the same vector as that encoding a protease protein or can be introduced on a separate vector. Cells stably transfected with the introduced nucleic acid can be identified by drug selection (e.g. cells that have incorporated the selectable marker gene will survive, while the other cells die).

Expression of proteins in prokaryotes is often carried out in *E. coli* with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognation sequences, include Factor Xa, thrombin and enterokinase.

As indicated, the expression vectors will preferably contain selectable markers. Such markers include dihydrofolate reductase or neomycin resistance for eukarotic cell culture and tetracyline or ampicilling resistance for culturing in *E. coli* and other bacteria. Representative examples of appropriate host include bacterial cells, such as *E. coli, Streptomyces* and *Salmonella typhimurium*; fungal cells, such as yeast; insect cells such as *Drosophila* S2 and *Spodoptera* Sf9; animal cells such as CHO, COS and Bowes melanoma; and plant cells. Appropriate culture mediums and conditions for the above-described host cells are known in the art.

Among vectors preferred for use in bacteria are pQE70, pQE60 and PQE-9, available from Qiagen; pBS vectors, Phagescript vectors, Bluescript vectors, pNH8A, pNH16A, pNH18A, pNH46A, available from Stratagene; and ptrc99a, pKK223-3, pKK233-3, pDR540, pRIT5 available from Pharmacia. Among preferred eukaryotic vectors are PWL-NEO, pSV2CAT, pOG44, pZT1 and pSG available from Stratagene; and pSVK3, pBPV, pMSG and pSVL available from Pharmacia. Other suitable vectors will be readily apparent to the skilled artisan.

Among known bacterial promotors for use in the present invention include *E. coli* lacI and lacZ promoters, the T3 and T7 promoters, the gpt promoter, the lambda PR, PL promoters and the trp promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretation signal may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification.

Polypeptides According to the Invention

The invention provides an isolated polypeptide having an amino acid sequence selected from the group consisting of SEQ ID NO: 115 to SEQ ID NO: 171, an amino acid sequence obtainable by expressing a polynucleotide according to the invention or in a preferred embodiment of a sequence selected from the group consisting of SEQ ID NO: 1 to SEQ ID NO: 57 in an appropriate host, as well as an amino acid sequence obtainable by expressing a polynucleotide sequences selected from the group consisting of SEQ ID NO: 58 to SEQ ID NO: 114 in an appropriate host. Also, a peptide or polypeptide comprising a functional equivalent of the above polypeptides is comprised within the present invention. The above polypeptides are collectively comprised in the term "polypeptides according to the invention"

The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (*Molecular Cloning: A Laboratory Manual*, 2$^{nd}$, ed. Cold Spring Harbor Laboratory, Cold Spring Harbor Laboratory Press, Cold Spring Harbor, N.Y., 1989)

By "isolated" polypeptide or protein is intended a polypeptide or protein removed from its native environment. For example, recombinantly produced polypeptides and proteins expressed in host cells are considered isolated for purpose of the invention as are native or recombinant polypeptides which have been substantially purified by any suitable technique such as, for example, the single-step purification method disclosed in Smith and Johnson, Gene 67:31-40 (1988).

The protease according to the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. For analytical purposes most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Moreover, a protein according to the invention may be a precursor protein such as a zymogen, a hybrid protein, a protein obtained as a pro sequence or pre-pro sequence, or any other type of immature form.

Protein Fragments

The invention also features biologically active fragments of the polypeptides according to the invention.

Biologically active fragments of a polypeptide of the invention include polypeptides comprising amino acid sequences sufficiently identical to or derived from the amino acid sequence of the protease protein (e.g., the amino acid sequence of a sequence selected from the group consisting of SEQ ID NO: 115 to SEQ ID NO: 171), which include fewer amino acids than the full length protein, and exhibit at least one biological activity of the corresponding full-length protein. Typically, biologically active fragments comprise a domain or motif with at least one activity of the protease protein. A biologically active fragment of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

The invention also features nucleic acid fragments which encode the above biologically active fragments of the protease protein.

Fusion Proteins

The proteins of the present invention or functional equivalents thereof, e.g., biologically active portions thereof, can be operatively linked to a non-protease polypeptide (e.g., heterologous amino acid sequences) to form fusion proteins. As used herein, a protease "chimeric protein" or "fusion protein" comprises a protease polypeptide operatively linked to a non-protease polypeptide. A "protease polypeptide" refers to a polypeptide having an amino acid sequence corresponding to a polypeptide sequence according to the invention, whereas a "non-protease polypeptide" refers to a polypeptide having an amino acid sequence corresponding to a protein which is not substantially homologous to a protein according to the invention, e.g., a protein which is different from the protease protein and which is derived from the same or a different organism. Within a protease fusion protein the protease polypeptide can correspond to all or a portion of a protein according to the invention. In a preferred embodiment, a protease fusion protein comprises at least one biologically active fragment of a protein according to the invention. In another preferred embodiment, a protease fusion protein comprises at least two biologically active portions of a protein according to the invention. Within the fusion protein, the term "operatively linked" is intended to indicate that the protease polypeptide and the non-protease polypeptide are fused in-frame to each other. The non-protease polypeptide can be fused to the N-terminus or C-terminus of the protease polypeptide.

For example, in one embodiment, the fusion protein is a GST-protease fusion protein in which the protease sequences are fused to the C-terminus of the GST sequences. Such fusion proteins can facilitate the purification of recombinant protease. In another embodiment, the fusion protein is a protease protein containing a heterologous signal sequence at its N-terminus. In certain host cells (e.g., mammalian and Yeast host cells), expression and/or secretion of protease can be increased through use of a heterologous signal sequence.

In another example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokarytic heterologous signal sequences include the phoA secretory signal (Sambrook et al., supra) and the protein A secretory signal (Pharmacia Biotech; Piscataway, N.J.).

A signal sequence can be used to facilitate secretion and isolation of a protein or polypeptide of the invention. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain. Thus, for instance, the sequence encoding the polypeptide may be fused to a marker sequence, such as a sequence encoding a peptide, which facilitates purification of the fused polypeptide. In certain preferred embodiments of this aspect of the invention, the marker sequence is a hexa-histidine peptide, such as the tag provided in a pOE vector (Qiagen, Inc.), among others, many of which are commercially available. As described in Gentz et al, *Proc. Natl. Acad. Sci. USA* 86:821-824 (1989), for instance, hexa-histidine provides for convenient purificaton of the fusion protein. The HA tag is another peptide useful for purification which corresponds to an epitope derived of influenza hemaglutinin protein, which has been described by Wilson et al., *Cell* 37:767 (1984), for instance.

Preferably, a protease chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A protease-encoding nucleic acid can be cloned into such an expression vector such that the fusion moiety is linked in-frame to the protease protein.

Functional Equivalents

The terms "functional equivalents" and "functional variants" are used interchangeably herein. Functional equivalents of a DNA according to the invention are isolated DNA fragments that encode a polypeptide that exhibits a particular function of an *A. niger* protease as defined herein. A functional equivalent of a polypeptide according to the invention is a polypeptide that exhibits at least one function of an *A. niger* protease as defined herein.

Functional protein or polypeptide equivalents may contain only conservative substitutions of one or more amino acids of a sequence selected from the group consisting of SEQ ID NO: 115 to SEQ ID NO: 171 or substitutions, insertions or deletions of non-essential amino acids. Accordingly, a non-essential amino acid is a residue that can be altered in a sequence selected from the group consisting of SEQ ID NO: 115 to SEQ ID NO: 171 without substantially altering the biological function. For example, amino acid residues that are conserved among the protease proteins of the present invention, are predicted to be particularly unamenable to alteration. Furthermore, amino acids conserved among the protease proteins according to the present invention and other proteases are not likely to be amenable to alteration.

The term "conservative substitution" is intended to mean that a substitution in which the amino acid residue is replaced with an amino acid residue having a similar side chain. These families are known in the art and include amino acids with basic side chains (e.g. lysine, arginine and hystidine), acidic side chains (e.g. aspartic acid, glutamic acid), uncharged polar side chains (e.g., glycine, asparagines, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine tryptophan, histidine).

Functional nucleic acid equivalents may typically contain silent mutations or mutations that do not alter the biological function of encoded polypeptide. Accordingly, the invention provides nucleic acid molecules encoding protease proteins that contain changes in amino acid residues that are not essential for a particular biological activity. Such protease proteins differ in amino acid sequence from a sequence selected from the group consisting of SEQ ID NO: 115 to SEQ ID NO: 171 yet retain at least one biological activity. In one embodiment the isolated nucleic acid molecule comprises a nucleotide sequence encoding a protein, wherein the protein comprises a substantially homologous amino acid sequence of at least about 60%, 65%, 70%, 75%, 80%, 85%, 90%, 95%, 96%, 97%, 98%, 99% or more homologous to the amino acid sequence shown in a sequence selected from the group consisting of SEQ ID NO: 115 to SEQ ID NO: 171.

For example, guidance concerning how to make phenotypically silent amino acid substitutions is provided in Bowie, J. U. et al., Science 247:1306-1310 (1990) wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As the authors state, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, supra, and the references cited therein.

An isolated nucleic acid molecule encoding a protease protein homologous to the protein selected from the group consisting of SEQ ID NO: 115 to SEQ ID NO: 171 can be created by introducing one or more nucleotide substitutions, additions or deletions into the coding nucleotide sequences according to a sequence selected from the group consisting of SEQ ID NO: 1 to SEQ ID NO: 57 or a sequence selected from the group consisting of SEQ ID NO: 58 to SEQ ID NO: 114 such that one or more amino acid substitutions, deletions or insertions are introduced into the encoded protein. Such mutations may be introduced by standard techniques, such as site-directed mutagenesis and PCR-mediated mutagenesis.

The term "functional equivalents" also encompasses orthologues of the *A. niger* protease protein. Orthologues of the *A. niger* protease protein are proteins that can be isolated from other strains or species and possess a similar or identical biological activity. Such orthologues can readily be identified as comprising an amino acid sequence that is substantially homologous to a sequence selected from the group consisting of SEQ ID NO: 115 to SEQ ID NO: 171.

As defined herein, the term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain having about 60%, preferably 65%, more preferably 70%, even more preferably 75%, 80%, 85%, 90%, 95%, 96%, 97%, 98% or 99% identity or more are defined herein as sufficiently identical.

Also, nucleic acids encoding other protease family members, which thus have a nucleotide sequence that differs from a sequence selected from the group consisting of SEQ ID NO: 1 to SEQ ID NO: 57 or a sequence selected from the group consisting of SEQ ID NO: 58 to SEQ ID NO: 114, are within the scope of the invention. Moreover, nucleic acids encoding protease proteins from different species which thus have a nucleotide sequence which differs from a sequence selected from the group consisting of SEQ ID NO: 1 to SEQ ID NO: 57 or a sequence selected from the group consisting of SEQ ID NO: 58 to SEQ ID NO: 114 are within the scope of the invention.

Nucleic acid molecules corresponding to variants (e.g. natural allelic variants) and homologues of the protease DNA of the invention can be isolated based on their homology to the protease nucleic acids disclosed herein using the cDNAs disclosed herein or a suitable fragment thereof, as a hybridisation probe according to standard hybridisation techniques preferably under highly stringent hybridisation conditions.

In addition to naturally occurring allelic variants of the protease sequence, the skilled person will recognise that changes can be introduced by mutation into the nucleotide sequences of a sequence selected from the group consisting of SEQ ID NO: 1 to SEQ ID NO: 57 or a sequence selected from the group consisting of SEQ ID NO: 58 to SEQ ID NO: 114 thereby leading to changes in the amino acid sequence of the protease protein without substantially altering the function of the protease protein.

In another aspect of the invention, improved protease proteins are provided. Improved protease proteins are proteins wherein at least one biological activity is improved. Such proteins may be obtained by randomly introducing mutations along all or part of the protease coding sequence, such as by saturation mutagenesis, and the resulting mutants can be expressed recombinantly and screened for biological activity. For instance, the art provides for standard assays for measuring the enzymatic activity of proteases and thus improved proteins may easily be selected.

In a preferred embodiment the protease protein has an amino acid sequence according to a sequence selected from the group consisting of SEQ ID NO: 115 to SEQ ID NO: 171. In another embodiment, the protease polypeptide is substantially homologous to the amino acid sequence according to a sequence selected from the group consisting of SEQ ID NO: 115 to SEQ ID NO: 171 and retains at least one biological activity of a polypeptide according to a sequence selected from the group consisting of SEQ ID NO: 115 to SEQ ID NO: 171, yet differs in amino acid sequence due to natural variation or mutagenesis as described above.

In a further preferred embodiment, the protease protein has an amino acid sequence encoded by an isolated nucleic acid fragment capable of hybridising to a nucleic acid according to a sequence selected from the group consisting of SEQ ID NO: 1 to SEQ ID NO: 57 or a sequence selected from the group consisting of SEQ ID NO: 58 to SEQ ID NO: 114, preferably under highly stringent hybridisation conditions.

Accordingly, the protease protein is a protein which comprises an amino acid sequence at least about 60%, 65%, 70%, 75%, 80%, 85%, 90%, 95%, 96%, 97%, 98%, 99% or more homologous to the amino acid sequence shown in a sequence selected from the group consisting of SEQ ID NO: 115 to SEQ ID NO: 171 and retains at least one functional activity of the polypeptide according to a sequence selected from the group consisting of SEQ ID NO: 115 to SEQ ID NO: 171.

Functional equivalents of a protein according to the invention can also be identified e.g. by screening combinatorial libraries of mutants, e.g. truncation mutants, of the protein of the invention for protease activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the coding sequence of a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3):327-331).

In addition to the protease gene sequence shown in a sequence selected from the group consisting of SEQ ID NO: 1 to SEQ ID NO: 57, it will be apparent for the person skilled in the art that DNA sequence polymorphisms that may lead to changes in the amino acid sequence of the protease protein may exist within a given population. Such genetic polymorphisms may exist in cells from different populations or within a population due to natural allelic variation. Allelic variants may also include functional equivalents.

Fragments of a polynucleotide according to the invention may also comprise polynucleotides not encoding functional polypeptides. Such polynucleotides may function as probes or primers for a PCR reaction. Such polynucleotides may also be useful when it is desired to abolish the functional activity of a protease in a particular organism (knock-out mutants).

Nucleic acids according to the invention irrespective of whether they encode functional or non-functional polypeptides, can be used as hybridization probes or polymerase chain reaction (PCR) primers. Uses of the nucleic acid molecules of the present invention that do not encode a polypeptide having a protease activity include, inter alia, (1) isolating the gene encoding the protease protein, or allelic variants thereof from a cDNA library e.g. from other organisms than *A. niger*; (2) in situ hybridization (e.g. FISH) to metaphase chromosomal spreads to provide precise chromosomal location of the protease gene as described in Verma et al., Human Chromosomes: a Manual of Basic Techniques, Pergamon Press, New York (1988); (3) Northern blot analysis for detecting expression of protease mRNA in specific tissues and/or cells and 4) probes and primers that can be used as a diagnostic tool to analyse the presence of a nucleic acid hybridisable to the protease probe in a given biological (e.g. tissue) sample.

Also encompassed by the invention is a method of obtaining a functional equivalent of a protease gene or cDNA. Such a method entails obtaining a labelled probe that includes an isolated nucleic acid which encodes all or a portion of the sequence according to a sequence selected from the group consisting of SEQ ID NO: 115 to SEQ ID NO: 171 or a variant thereof; screening a nucleic acid fragment library with the labelled probe under conditions that allow hybridisation of the probe to nucleic acid fragments in the library, thereby forming nucleic acid duplexes, and preparing a full-length gene sequence from the nucleic acid fragments in any labelled duplex to obtain a gene related to the protease gene.

In one embodiment, a protease nucleic acid of the invention is at least 60%, 65%, 70%, 75%, 80%, 85%, 90%, 91%, 92%, 93%, 94%, 95%, 96%, 97%, 98%, 99%, or more homologous to a nucleic acid sequence shown in a sequence selected from the group consisting of SEQ ID NO: 1 to SEQ ID NO: 57, a sequence selected from the group consisting of SEQ ID NO: 58 to SEQ ID NO: 114 or the complement thereof.

In another preferred embodiment a protease polypeptide of the invention is at least 60%, 65%, 70%, 75%, 80%, 85%, 90%, 91%, 92%, 93%, 94%, 95%, 96%, 97%, 98%, 99%, or more homologous to the amino acid sequence shown in a sequence selected from the group consisting of SEQ ID NO: 115 to SEQ ID NO: 171.

Host Cells

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are cells from filamentous fungi, in particular *Aspergillus niger*.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

Host cells also include, but are not limited to, mammalian cell lines such as CHO, VERO, BHK, HeLa, COS, MDCK, 293, 3T3, W138, and choroid plexus cell lines.

If desired, the polypeptides according to the invention can be produced by a stably-transfected cell line. A number of

Antibodies

The invention further features antibodies, such as monoclonal or polyclonal antibodies, that specifically bind protease proteins according to the invention.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to protease protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)). Thus, these fragments are preferred.

The antibodies of the present invention may be prepared by any of a variety of methods. For example, cells expressing the protease protein or an antigenic fragment thereof can be administered to an animal in order to induce the production of sera containing polyclonal antibodies. In a preferred method, a preparation of protease protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protease protein binding fragments thereof). Such monoclonal antibodies can be prepared using hybridoma technology (Kohler et al., *Nature* 256:495 (1975); Kohler et al., *Eur. J. Immunol.* 6:511 (1976); Hammerling et al., In: *Monoclonal Antibodies and T-Cell Hybridomas*, Elsevier, N.Y., pp. 563-681 (1981)). In general, such procedures involve immunizing an animal (preferably a mouse) with a protease protein antigen or, with a protease protein expressing cell. The splenocytes of such mice are extracted and fused with a suitable myeloma cell line. Any suitable myeloma cell line may be employed in accordance with the present inventoin; however, it is preferably to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands et al. (*Gastroenterology* 8.225-232 (1981)). The hybridoma cells obtained through such a selection are then assayed to identify clones which secrete antibodies capable of binding the protease protein antigen. In general, the polypeptides can be coupled to a carrier protein, such as KLH, as described in Ausubel et al., supra, mixed with an adjuvant, and injected into a host mammal.

In particular, various host animals can be immunized by injection of a polypeptide of interest. Examples of suitable host animals include rabbits, mice, guinea pigs, and rats. Various adjuvants can be used to increase the immunological response, depending on the host species, including but not limited to Freund's (complete and incomplete), adjuvant mineral gels such as aluminum hydroxide, surface actve substances such as lysolecithin, pluronic polyols, polyanions, peptides, oil emulsions, keyhole limpet hemocyanin, dinitrophenol, BCG (bacille Calmette-Guerin) and *Corynebacterium parvum*. Polyclonal antibodies are heterogeneous populations of antibody molecules derived from the sera of the immunized animals.

Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies are tested for specific recognition of an protease polypeptide or functional equivalent thereof in an immunoassay, such as a Western blot or immunoprecipitation analysis using standard techniques, e.g., as described in Ausubel et al., supra. Antibodies that specifically bind to protease proteins or functional equivalents thereof are useful in the invention. For example, such antibodies can be used in an immunoassay to detect protease in pathogenic or non-pathogenic strains of *Aspergillus* (e.g., in *Aspergillus* extracts).

Preferably, antibodies of the invention are produced using fragments of the protease polypeptides that appear likely to be antigenic, by criteria such as high frequency of charged residues. For example, such fragments may be generated by standard techniques of PCR, and then cloned into the pGEX expression vector (Ausubel et al., supra). Fusion proteins may then be expressed in *E. coli* and purified using a glutathione agarose affinity matrix as described in Ausubel, et al., supra. If desired, several (e.g., two or three) fusions can be generated for each protein, and each fusion can be injected into at least two rabbits. Antisera can be raised by injections in a series, typically including at least three booster injections. Typically, the antisera are checked for their ability to immunoprecipitate a recombinant protease polypeptide or functional equivalents thereof whereas unrelated proteins may serve as a control for the specificity of the immune reaction.

Alternatively, techniques decribed for the production of single chain antibodies (U.S. Pat. Nos. 4,946,778 and 4,704,692) can be adapted to produce single chain antibodies against a protease polypeptide or functional equivalents thereof. Kits for generating and screening phage display libraries are commercially available e.g. from Pharmacia.

Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 20791; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246;1275-1281; Griffiths et al. (1993) *EMBO J.* 12:725-734.

Polyclonal and monoclonal antibodies that specifically bind protease polypeptides of functional equivalents thereof can be used, for example, to detect expression of a protease gene or a functional equivalent thereof e.g. in another strain of *Aspergillus*.

For example, protease polypeptide can be readily detected in conventional immunoassays of *Aspergillus* cells or extracts. Examples of suitable assays include, without limitation, Western blotting, ELISAs, radioimmune assays, and the like.

By "specifically binds" is meant that an antibody recognizes and binds a particular antigen, e.g., a protease polypeptide, but does not substantially recognize and bind other unrelated molecules in a sample.

Antibodies can be purified, for example, by affinity chromatography methods in which the polypeptide antigen is immobilized on a resin.

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in cells or tissue as part of a clinical testing procedure, e.g., to, for example, determine the efficacy of a given treatment regimen or in the diagnosis of Aspergillosis.

Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive materials include $^{125}$I, $^{131}$I, $^{35}$S or $^{3}$H.

Preferred epitopes encompassed by the antigenic peptide are regions that are located on the surface of the protein, e.g., hydrophilic regions. Hydrophobicity plots of the proteins of the invention can be used to identify hydrophilic regions.

The antigenic peptide of a protein of the invention comprises at least 7 (preferably 10, 15, 20, or 30) contiguous amino acid residues of the amino acid sequense of a sequence selected from the group consisting of SEQ ID NO: 115 to SEQ ID NO: 171 and encompasses an epitope of the protein such that an antibody raised against the peptide forms a specific immune complex with the protein.

Preferred epitopes encompassed by the antigenic peptide are regions of protease that are located on the surface of the protein, e.g., hydrophilic regions, hydrophobic regions, alpha regions, beta regions, coil regions, turn regions and flexible regions.

Immunoassays

Qualitative or quantitative determination of a polypeptide according to the present invention in a biological sample can occur using any art-known method. Antibody-based techniques provide special advantages for assaying specific polypeptide levels in a biological sample.

In these, the specific recognition is provided by the primary antibody (polyclonal or monoclonal) but the secondary detection system can utilize fluorescent, enzyme, or other conjugated secondary antibodies. As a result, an immunocomplex is obtained.

Accordingly, the invention provides a method for diagnosing whether a certain organism is infected with *Aspergillus* comprising the steps of:
 Isolating a biological sample from said organism suspected to be infected with *Aspergillus*,
 reacting said biological sample with an antibody according to the invention,
 determining whether immune complexes are formed.

Tissues can also be extracted, e.g., with urea and neutral detergent, for the liberation of protein for Western-blot or dot/slot assay. This technique can also be applied to body fluids.

Other antibody-based methods useful for detecting protease gene expression include immunoassays, such as the enzyme linked immunosorbent assay (ELISA) and the radioimmunoassay (RIA). For example, protease-specific monoclonal antibodies can be used both as an immunoabsorbent and as an enzyme-labeled probe to detect and quantify the protease protein. The amount of protease protein present in the sample can be calculated by reference to the amount present in a standard preparation using a linear regression computer algorithm. In another ELISA assay, two distinct specific monoclonal antibodies can be used to detect protease protein in a biological fluid. In this assay, one of the antibodies is used as the immuno-absorbent and the other as the enzyme-labeled probe.

The above techniques may be conducted essentially as a "one-step" or "two-step" assay. The "one-step" assay involves contacting protease protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Activity of an oxidase label may be assayed by measuring the concentration of hydrogen peroxide formed by the enzyme-labelled antibody/substrate reaction.

Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Specific binding of a test compound to a protease polypeptide can be detected, for example, in vitro by reversibly or irreversibly immobilizing the protease polypeptide on a substrate, e.g., the surface of a well of a 96-well polystyrene microtitre plate. Methods for immobilizing polypeptides and other small molecules are well known in the art. For example, the microtitre plates can be coated with a protease polypeptide by adding the polypeptide in a solution (typically, at a concentration of 0.05 to 1 mg/ml in a volume of 1-100 ul) to each well, and incubating the plates at room temperature to 37° C. for 0.1 to 36 hours. Polypeptides that are not bound to the plate can be removed by shaking the excess solution from the plate, and then washing the plate (once or repeatedly) with water or a buffer. Typically, the polypeptide is contained in water or a buffer. The plate is then washed with a buffer that lacks the bound polypeptide. To block the free protein-binding sites on the plates, the plates are blocked with a protein that is unrelated to the bound polypeptide. For example, 300 ul of bovine serum albumin (BSA) at a concentration of 2 mg/ml in Tris-HCl is suitable. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded sepharose, can be used as the substrate.

Binding of the test compound to the polypeptides according to the invention can be detected by any of a variety of art known methods. For example, a specific antibody can be used in an immunoassay. If desired, the antibody can be labeled (e.g., fluorescently or with a radioisotope) and detected directly (see, e.g., West and McMahon, J. Cell Biol.

74:264, 1977). Alternatively, a second antibody can be used for detection (e.g., a labeled antibody that binds the Fc portion of an anti-AN97 antibody). In an alternative detection method, the protease polypeptide is labeled, and the label is detected (e.g., by labeling a protease polypeptide with a radioisotope, fluorophore, chromophore, or the like). In still another method, the protease polypeptide is produced as a fusion protein with a protein that can be detected optically, e.g., green fluorescent protein (which can be detected under UV light). In an alternative method, the protease polypeptide can be covalently attached to or fused with an enzyme having a detectable enzymatic activity, such as horse radish peroxidase, alkaline phosphatase, a-galactosidase, or glucose oxidase. Genes encoding all of these enzymes have been cloned and are readily available for use by those of skill in the art. If desired, the fusion protein can include an antigen, and such an antigen can be detected and measured with a polyclonal or monoclonal antibody using conventional methods. Suitable antigens include enzymes (e.g., horse radish peroxidase, alkaline phosphatase, and a-galactosidase) and non-enzymatic polypeptides (e.g., serum proteins, such as BSA and globulins, and milk proteins, such as caseins).

Epitopes, Antigens and Immunogens.

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, H. M. et al., Proc. Natl. Acad. Sci. USA 81:3998-4002 (1984).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G. et al., Science 219:660-666 (1984). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra ?. For instance, 18 of 20 peptides designed according to these guidelines, containing 8-39 residues covering 75% of the sequence of the influenza virus hemagglutinin HAI polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope bearing peptides or polypeptides are useful to detect the mimicked protein, and antibodies to different peptides may be used for tracking the fate of various regions of a protein precursor which undergoes posttranslation processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson, I. A. et al., Cell 37:767-778 at 777 (1984). The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies.

Epitope-bearing peptides also may be synthesized using known methods of chemical synthesis. For instance, Houghten has described a simple method for synthesis of large numbers of peptides, such as 10-20 mg of 248 different 13 residue peptides representing single amino acid variants of a segment of the HAI polypeptide which were prepared and characterized (by ELISA-type binding studies) in less than four weeks. Houghten, R. A., Proc. Natl. Acad. Sci. USA 82:5131-5135 (1985). This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods.

A manual procedure allows 500-1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra;

Wilson et al., supra; Chow, M. et al., Proc. Natl. Acad. Sci. USA 82:910-914; and Bittle, F. J. et al., J. Gen. Virol. 66:2347-2354 (1985).

Generally, animals may be immunized with free peptide; however, anti-peptide antibody titer may be boosted by coupling of the peptide to a macromolecular carrier, such as keyhole limpet hemocyanin (KLH) or tetanus toxoid. For instance, peptides containing cysteine may be coupled to carrier using a linker such as maleimidobenzoyl-N-hydroxysuccinimide ester (MBS), while other peptides may be coupled to carrier using a more general linking agent such as glutaraldehyde.

Animals such as rabbits, rats and mice are immunized with either free or carrier coupled peptides, for instance, by intraperitoneal and/or intradermal injection of emulsions containing about 100 ug peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., 1984, supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1-C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Removal or Reduction of Protease Activity

The present invention also relates to methods for producing a mutant cell of a parent cell, which comprises disrupting or deleting a nucleic acid sequence encoding the protease or a control sequence thereof, which results in the mutant cell producing less of the protease than the parent cell.

The construction of strains which have reduced protease activity may be conveniently accomplished by modification or inactivation of a nucleic acid sequence necessary for expression of the protease activity in the cell. The nucleic acid sequence to be modified or inactivated may be, for example, a nucleic acid sequence encoding the protease or a part thereof essential for exhibiting protease activity, or the nucleic acid sequence may have a regulatory function required for the expression of the protease from the coding sequence of the nucleic acid sequence. An example of such a regulatory or control sequence may be a promoter sequence or a functional part thereof, i.e., a part which is sufficient for affecting expression of the protease. Other control sequences for possible modification include, but are not limited to, a leader, a polyadenylation sequence, a propeptide sequence, a signal sequence, and a termination site.

Modification or inactivation of the nucleic acid sequence may be performed by subjecting the cell to mutagenesis and selecting for cells in which the protease producing capability has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the cell to be mutagenized in the presence of the mutagenizing agent of choice under suitable conditions, and selecting for cells exhibiting reduced or no expression of protease activity.

Modification or inactivation of production of a protease of the present invention may be accomplished by introduction, substitution, or removal of one or more nucleotides in the nucleic acid sequence encoding the protease or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art.

Although, in principle, the modification may be performed in vivo, i.e., directly on the cell expressing the nucleic acid sequence to be modified, it is preferred that the modification be performed in vitro as exemplified below.

An example of a convenient way to inactivate or reduce production by a host cell of choice is based on techniques of gene replacement or gene interruption. For example, in the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the protease has been modified or destroyed.

Alternatively, modification or inactivation of the nucleic acid sequence encoding a protease of the present invention may be performed by established anti-sense techniques using a nucleotide sequence complementary to the protease encoding sequence. More specifically, production of the protease by a cell may be reduced or eliminated by introducing a nucleotide sequence complementary to the nucleic acid sequence encoding the protease which may be transcribed in the cell and is capable of hybridizing to the protease mRNA produced in the cell. Under conditions allowing the complementary antisense nucleotide sequence to hybridize to the protease mRNA, the amount of protease translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the protease or a control sequence thereof, which results in the mutant cell producing less of the protease than the parent cell.

The protease-deficient mutant cells so created are particularly useful as host cells for the expression of homologous and/or heterologous polypeptides. Therefore, the present invention further relates to methods for producing a homologous or heterologous polypeptide comprising (a) culturing the mutant cell under conditions conducive for production of the polypeptide; and (b) recovering the polypeptide. In the present context, the term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

The methods of the present invention for producing an essentially protease-free product is of particular interest in the production of eukaryotic polypeptides, in particular fungal proteins such as enzymes. The protease-deficient cells may also be used to express heterologous proteins of interest for the food industry, or of pharmaceutical interest.

Use of Proteases in Industrial Processes

The invention also relates to the use of the protease according to the invention in a selected number of industrial and pharmaceutical processes. Despite the long term experience obtained with these processes, the protease according to the invention features a number of significant advantages over the enzymes currently used. Depending on the specific application, these advantages can include aspects like lower production costs, higher specificity towards the substrate, less antigenic, less undesirable side activities, higher yields when produced in a suitable microorganism, more suitable pH and temperature ranges, better tastes of the final product as well as food grade and kosher aspects.

In large scale industrial applications aimed at food or feed production, proteolytic enzymes are commonly used to improve aspects like protein solubility, extraction yields, viscosity or taste, texture, nutritional value, minimalisation of antigenicity or antinutrional factors, colour or functionality as well as processing aspects like filterablity of the proteinaceous raw material. In these applications the proteinaceous raw material can be of animal or vegetable origin and examples include vegetable proteins such as soy protein, wheat gluten, rape seed protein, pea protein, alfalfa protein, sunflower protein, fabaceous bean protein, cotton or sesame seed protein, maize protein, barley protein, sorghum protein, potato protein, rice protein, coffee proteins, and animal derived protein such as milk protein (e.g. casein, whey protein), egg white, fish protein, meat protein including gelatin, collagen, blood protein (e.g. haemoglobin), hair, feathers and fish meal.

An important aspect of the proteases according to the invention is that they cover a whole range of pH and temperature optima which are ideally suited for a variety of applications. For example many large scale processes benefit from relatively high processing temperatures of 50 degrees C. or higher to control the risks of microbial infections. Several proteases according to the invention comply with this demand but at the same time exhibit no extreme heat stabilities so that they resist attempts to inactivate the enzyme by an additional heat treatment. The latter feature allows production routes that yield final products free of residual proteolytic activity. Similarly many feed and food products have slightly acidic pH values so that for their processing proteases with acidic or near neutral pH optima are preferred. A protease according to the invention complies with this requirement as well.

The specificity of endoproteases is usually defined in terms of preferential cleavages of bonds between the carboxyl of the amino acid residue in position P1 and the amino group of the residue in position P1' respectively. The preference may be conditioned predominantly either by P1 (e.g. positively charged residues in substrates for trypsin), by P1'(e.g. hydrophobic residues in cleavages by thermolysin) or by both P1 and P2 (e.g. specific cleavages between two positively charged residues by adrenal medulla serine endoprotease). In some cases more distant residues may determine the cleavage preference, e.g. P2 for streptococcal peptidase A. Some residues are known to influence cleavages negatively; it is well known that bonds with proline in position P1' are resistant to the action of many proteases. Most endoproteases cleave preferentially either in a hydrophobic environment or in the proximity of negatively charged residues. For example, industrially available endoproteases like chymotrypsin (obtained from bovine pancreas) or subtilisin, neutral metallo endoprotease or thermolysin (all obtained from *Bacillus* species) tend to favour cleavage "behind" hydrophobic amino acids like -Phe, -Leu and -Tyr. Other industrially available endoproteases are trypsin (obtained from bovine pancreas) preferring cleavage behind -Arg and -Lys and papain (a complex mixture of various enzymes including proteases obtained from papaya fruits) preferring cleavage behind -Arg.

In contrast, peptide bonds formed by small sized residues such as Ala, Gly, Ser, Thre as well as Ile and Pro are poor substrates (Keil, B et al.; Protein Seq Data Anal (1993) 5; 401-407). This situation has a profound implications for the pharmaceutical, the food and beverages, the agro and even the chemical industry. A protease according to the invention exhibits uncommon cleavage preferences.

The exopeptidases act only near the ends of polypeptide chains. Those acting at a free N-terminus liberate a single amino acid residue (socalled aminopeptidases) or a dipeptide or a tripeptide (socalled dipeptidyl-peptidases and tripeptidyl-peptidases) Those acting at a free C-terminus liberate a single residue (socalled carboxypeptidases) or a dipeptide (socalled peptidyl-dipeptidases) The carboxypeptidases are allocated to three groups on the basis of catalytic mechanism i.e. serine-type carboxypeptidases, metallocarboxypeptidases and cystein-type carboxypeptidases. Other exopeptidases are specific for dipeptides (socalled dipeptidases) or are able to cleave peptide linkages other than those of alpha-carboxyl or alpha-amino groups (socalled omega peptidases). Examples of such new omega peptidases are the pyroglutamyl-peptidase and the acylaminoacyl-peptidase as identified in the present invention (see Table 1, genes 18 and 45 respectively).

Typical examples of industrial application which depend on the use of pure endoproteases and in which the protease according to the invention can be expected to deliver a superior performance include the processing of materials of vegetable or animal origin. These processing steps can be-aimed at modifying a large array of characteristics of either the crude material or the (partially) purified protein fraction. For example, these processing steps can be aimed at maximising product solubilities, filterabilities, separabilities, protein extraction yields and digestibilities or minimising toxicities, off-tastes and viscosities. Furthermore the treatment can be directed at altering physico-chemical characteristics of the crude material or the purified (or partially purified) protein. These advantages apply not only if the endoprotease according to the invention is applied as a processing aid in industrial applications but also if applied as an active enzyme component in animal feed. Specifically the endoprotease according to the invention can be applied as bread improver in the bakery industry, e.g. to retard the staling of bread or to diminishing the viscosity of doughs. Or the endoprotease can be used in the beer and wine industry to prevent or to minimise the formation of undesirable protein hazes. Alternatively it can be used in the beer industry to optimise the protein extraction yields of cereals used in the preparation of the wort. Furthermore, it can also be advantageously used in the dairy industry as a milk clotting agent with superior characteristics or to optimise the texturising, foaming or setting characteristics of various milk components. Another application in the dairy industry is the use of the new protease in the preparation of Enzyme Modified Cheeses (EMC's).

Moreover, various proteinaceous substrates can be subjected to an endoprotease according to the invention, usually in combination with other proteolytic enzymes to obtain hydrolysates for medical or non-medical applications. Here the endoprotease according to the invention is surprisingly effective in achieving a complete hydrolysis of the proteinaceous substrate so that even protease resistant parts are fully hydrolysed, the endoprotease is also surprisingly active in minimising the allergenicity of the final hydrolysate or in suppressing the formation of bitter off-tastes.

More specifically the endoprotease according to the invention is characterised by its preference for cleaving proteins at unusual peptide bonds, especially with the small size amino acid residues of Ala, Gly, Ser and Thr, or the residues Ile and Pro in either the P1 or the P1' position (Keil, B et al.; Protein Seq Data Anal (1993) 5; 401-407). As the result those fractions of the proteinaceous starting materials that resist hydrolysis upon using prior art endoproteases, can be dissolved and hydrolysed using the endoprotease according to the invention. Non limiting examples of such protease resistant fractions include socalled extensins in plant materials and collagen, gelatin but also specific milk components in material of animal origen.

Various feedstuffs such as e.g. soybeans contain trypsin inhibitors. These proteins inhibit trypsin activity in the GI-tract of e.g. pigs and poultry. This trypsin inhibiting activity results in sub-optimal protein digestibility in these animals resulting in increased waste production and poor economics. This problem may partly be overcome by toasting soybeans at high temperatures. Two different types of trypsin inhibitors have been identified in soybeans, i.e. the Bowman-Birk type trypsin inhibitors and the Kunitz type trypsin inhibitors.

This invention now provides an alternative way to degrade trypsin inhibiting activity over toasting, in that it provides a cysteine proteases (EC 3.4.22, table 1) capable of cleaving at Leucine176-Aspartate177 peptide bond near the carboxyl-terminus of the Kunitz type trypsin inhibitor (as reviewed by Wilson (1988) in CRC Critical Reviews in Biotechnology 8 (3): 197-216). This results in inactivation of this trypsin inhibitor in soybean. It was surprisingly found that the cysteine proteases secreted by the fungus *Aspergillus niger* fulfilled these criteria far better than similar enzymes derived from other organisms.

Proteases are also widely used in the art of cheese-making. In the production of cheese it is necessary to coagulate the cheese milk to be able to separate the cheese matters e.g. casein from the whey. Several milk coagulating enzymes, also referred to as coagulants, have been described and include (bovine) chymosin, bovine pepsin, porcine pepsin as well as microbial enzymes like *Rhizomucor miehei* protease, *Rhizomucor pusillus* protease and *Cryptonectria parasitica* protease. Chymosin can be obtained from calf stomachs but can also be produced microbially by for example *Kluyveromyces lactis*. All these enzymes are characterized by having specificity for the peptide bond between residue 105 (phenylalanine) and residue 106 (methionine) or the bond adjacent to that in K-casein. This means that by employing these enzymes in cheese making, the K-casein is split at the junction between para-K-casein and the macropeptide moiety called glycomacropeptide (GMP) carrying the negative charges. When this occurs the macropeptide diffuses into the whey, its stabilizing effect on the solubility of the casein micelles is lost, and the casein micelles can start to aggregate once sufficient kappa-casein has been hydrolyzed. For further elaboration on the enzymatic coagulation of milk (e.g. *D. G. Dalgleish in Advanced Dairy Chemistry* vol. 1 ed by P. F. Fox, Elsevier, London, 1992.

The currently available coagulants allow for a rather high yield of cheese, however, it should be realised that due to the enormous volumes of cheese produced, an increased yield in the order of magnitude of tenths of percent points may constitute a substantial economical advantage. Consequently there is a great need in the art for coagulants with an (even slightly) improved yield.

Coagulants are characterized by their high substrate specificity, which is, however, dependent on pH and temperature. In a typical cheese making process the pH will change from the initial pH 6.3 to lower pH values in the range of 4.5-5.5, the end-value depends on the conditions used during the cheese production process. Some coagulants are more sensitive to pH changes than others. The *Rhizomucor pusillus* protease for example is more sensitive to pH changes than chymosin. Besides pH, also other parameters like temperature and water content may affect the protease specificity. It is well known that most coagulants show a changing substrate specificity with changing pH, resulting in altered proteolytic activity in later stages of the cheese making process. It is also well known that coagulants differ in the extent of casein proteolysis; they may also show differences in the peptide patterns produced during proteolysis. These are relevant factors during cheese ripening and may affect cheese properties like taste, flavor and texture. In some cases coagulants give rise to undesired effects like the formation of bitter tasting peptides or off-taste. In addition, changes in proteolytic specificity may lead to a reduction in yield. Pepsin, a well known component in many bovine chymosin preparations, is an example of a protease that gives rise to lower yields and taste effects as compared to pure chymosin. There is still a need for coagulants with give rise to new, improved cheese texture and taste. Such new coagulants result in the accelerated development of taste and texture profiles related to cheese aging, therewith providing a substantial economical benefit.

It is well known that free amino acids are very important in taste and flavour generation. Especially the amino acids leucine, phenylalanine, methionine and valine play an important role in the generation of typical cheese taste and flavor components. The free amino acids are converted via fermentation by micro organisms that are added during the cheese manufacturing process into the actual flavor and taste generating compounds like methanediol, dimethyldisulphide, methylpropanoic acid and methylpropanal. Exo-peptidases play an important role in the generation of free amino acids. They can only be effective, however, when they are combined with an endo-protease of appropriate specificity. Appropriate combinations of exo- and endo-peptidases can be used in cheese making, resulting in the manufacture of cheeses with new and improved taste profiles.

The enzymes according to the invention may be used to hydrolyze proteinaceous materials of animal origin such as whole milk, skim milk, casein, whey protein or mixtures of casein and whey protein. Such mixtures of casein and whey protein may be used, for example, in ratios similar to those found in human milk. Furthermore, the enzyme mixture according to the invention may be used to hydrolyze proteinaceous materials of plant origin such as, for example, wheat gluten malted or unmalted barley or other cereals used for making beer, soy milk, concentrates or isolates thereof, maize protein concentrates and isolates thereof, and rice proteins.

Within the area of large scale industrial processes, some applications rely on the use of endoproteases only whereas in other applications combinations of endoproteases with exoproteases are essential. Typical examples which depend on the use of pure endoproteases and in which the protease according to the invention can deliver a superior performance include applications like the processing of soy or peas or cereals proteins aimed at minimising viscosities or optimising foaming or other physics-chemical characteristics, bread improvers in the bakery industry also aimed at diminishing the viscosity of doughs, processing aids in the beer and wine industry aimed at the prevention of protein hazes or optimising the extraction yields of cereals, feed additives in the bio industry aimed at enhancing intestinal absorption or modulating microbial activities in the gut, processing aids in the dairy industry aimed at optimising the clotting, foaming or setting characteristics of various milk components. Moreover, v For specific market segments proteins derived from milk or soy or collagen are exposed to proteases to produce socalled protein hydrolysates. Although the main outlets for these protein hydrolysates are infant formula and food products for hospitalised persons, products intended for persons with non-medical needs, such as athletes or people on a slimming diet form a rapidly growing segment. In all of these applications protein hydrolysates offer attractive advantages such as lowered allergenicities, facilitated gastrointestinal uptake, less chemical deterioration of desirable amino acids like glutamine and cystein and finally, absence of proteinaceous precipitations in acid beverages during prolonged storage periods. All these advantages can be combined if the hydrolysate is offered as a mixture of di- and tripeptides. However, currently all commercially available hydrolysates are produced by combining several endoproteases. The latter approach implies a non-uniform and incomplete degradation of the protein. To obtain the desired mixture of di- and tripeptides, a hydrolysis process involving a combination of various di- and tripeptidylpeptidases would be ideal. Unfortunately, only few of these enzymes from food grade and industrially acceptable microorganisms are known, let alone industrially available. According to the invention several of highly useful di- and tripeptidylpeptidases are economically obtainable in a relatively pure state. Preferred are those di- or tripeptidylpeptidases that exhibit a low selectivity towards the substrate to be cleaved, i.e. exhibit minimal amino acid residue cleavage preferences only. Preferred are combinations of those di- or tripeptidylpeptidases that hydrolyse high percentage of the naturally occurring peptide bonds. Despite this high activity to naturally occurring peptide bonds, a total hydrolysis to free amino acids is prevented by the nature of the di- and tripeptidylpeptidases. Also preferred are those di- or tripeptidylpeptidases that are optimally active between pH 4 to 8 and exhibit adequate temperature stability. Adequate temperature stability implies that at least 40%, preferably at least 60%, more preferably between 70 and 100% of the initial hydrolytic activity survives after heating the enzyme together with the substrate for 1 hour at 50 degrees C.

Although the process towards an efficiebnt production of mixtures di-or tripeptides or di- and tripeptides hinges on the availability of the enzymes according to the invention, the first enzyme incubation with the proteinaceous substrate will usually be an endoprotease. Preferably an endoprotease with a broad spectrum endopeptidase suited for the situation, e.g. subtilisin (Delvolase from DSM), neutral metallo protease (Neutrase from NOVO) or thermolysin (Thermoase from Daiwa Kasei) for the near neutral conditions and pepsin or aspergillopepsin (e.g. Sumizyme AP from Shin Nihon, Japan) for the acidic conditions. Aim of this first digestion is to improve the solubility, to reduce the viscosity and to reduce the heat setting characteristics of the water/protein mixture. Furthermore this pretreatment with an endonuclease is essential to create enough starting points for the di- and tripeptidylpeptidases hereby accellerating the proces of di- or tripeptide formation. Optionally a protease intended for debittering of the hydrolysate can be included in this stage of the process or later, together with the di-or tripeptidylpeptidases.

Main aim of the latter hydrolysates is to minimize the allergenicity of the product or to facilitate gastrointestinal uptake. In the production of such hydrolysates the use of dipeptidyl- and tripeptidyl-peptidases is of special importance as these s offer an efficient way for producing hydrolysates.

Other applications in these food and feed industries totally rely upon combinations of one or more endoprotease(s) with one or more exoprotease(s). Such combinations of an endoprotease with an exoprotease are typically used in industries to improve aspects like taste and colour of the final product. The reason for this is that the development of taste and colour is largely dependent upon the presence of free amino acids. Free amino acids can not only be obtained by exoproteases such as carboxypeptidases and aminopeptidases but also by peptidyl-dipeptidases. If combined with endoproteases or even dipeptidyl-or tripeptidyl-peptidases, carboxypeptidases, aminopeptidases and peptidyl-dipeptidases can create larger quantities of free amino acids in less time. However, in all of these processes an uncontrolled release of amino acids or even non-proteinaceous components should be avoided to minimise undesirable side reactions.

Though free amino acids as such, can elicit a number of taste impressions, these taste impressions are very basic (bitter, sweet, sour and "umami") and the amino acid concentration required for perceiving these tastes are high. Despite these high threshold values, free amino acids are able to create major sensory effects at much lower concentration ranges through a number of flavour enhancing mechanisms. One of these mechanism involves the combination of free amino acids with sugars in so-called Maillard reactions. Compared with free amino acids, with these Maillard products overwhelmingly complex flavour and odour systems can develop with threshold values that are several orders of magnitude lower than those recorded for the free amino acids. Maillard products are formed at elevated temperatures usually during cooking, baking or roasting when preparing food or feed products. During these treatments both colour and a large array of aromas develop. In these reactions amino groups react with reducing compounds as a first step and ultimately leading to a whole family of reaction pathways. In foods or feeds the amino compounds involved are predominantly free amino acids which are released from the proteinaceous raw material by various proteases and the required reducing compounds primarily represent reducing sugars. The implication is that during the processsing of the raw material undesired release of free amino acids and sugars should be avoided to minimise off tastes that could be generated during subsequent heating steps as e.g. during spray drying or sterilisation. The latter notion emphasises once more the benefits of superior purity and low in-use costs of the enzyme according to the invention.

Apart from Maillard reactions, amino acids can also undergo important chemical transitions at ambient temperatures. The latter type of transitions are enzyme dependent and are quite common in fermented foods such as beer, yogurt, cheese ripening and meat and wine maturation processes. In these fermentation processes, free amino acids are liberated from the raw materials used by the proteases added or by proteolytic enzyme activity from the raw material or the microbial starters used. During the maturation phase microbial metabolic activity then converts the free amino acids into derivatives with increased sensoric properties. For example, L-leucine, L-isoleucine and L-valine lead to the formation of valuable fusel alcohols like amylalcohols and isobutanol in beer fermentation. Similarly cheese volatiles such as methanethiol and dimethyldisulphide have been traced back to the occurrence of methionine in cheese as well as methylpropanoic acid and methylpropanal to valine. Finally the free amino acid glutamate and can create strong savoury enhancing effects because of its synergy with the breakdown products of RNA, so-called 5'-ribonucleotides. If combined with proper concentrations of 5'-ribonucleotides such as 5'-IMP and 5'-GMP, the detection threshold of the umami taste generated by glutamate is known to be lowered by almost two orders of magnitude.

In order to obtain pronounced and precise taste effects in all of these processes, the proteinaceous substrates should be hydrolysed using a combination of an endo- and an exoprotease, wherein at least one of the endo or exoprotease, preferably both the endo- and exoprotease, are pure and preferably selective towards a specific set of amino acid(s) or preferentially release the preferred amino acid(s). So preferred proteases are characterised by a high selectivity towards the amino acid sequences that can be cleaved which notion makes the enzyme category in *Aspergillus* known as "maturases" of particular importance.

Apart from the food and feed industries, proteases are also commonly applied by the chemical, pharmaceutical, diagnostic and personal care industries.

In the personal care industry proteases are used to create peptides which are added to a variety of products to improve aspects like skin feel, gloss or protection. Moreover there is a new tendency towards direct topical application of the protease. Very similar to the enzyme use in the leather industry, the prime aim in the latter application is to clean, dehair and soften the skin.

In the chemical and pharmaceutical industry proteases are being developed as valuable tools in producing costly ingredients or intermediates. In these industries proteases are not only used because of their hydrolytic capacity but also because of their capacity to synthesise peptides from natural or non-natural amino acids. The latter option is clearly demonstrated by the possibility to synthesize aspartame from its amino acid based building blocks by using an endoprotease like thermolysin.

Unlike the situation in the food and feed industry, the stereo- and regioselectivity of proteases are also considered important assets although unusual reaction conditions may be needed to accomplish the desired chemical transformation. Typical examples of the application of proteases in this industry include the use of endoproteases, aminopeptidases as well as carboxypeptidases in the production of various intermediates for drugs like insulin, antibiotics, renin and ACE-inhibitors An overview of such uses is presented in Industrial Biotransformations, A. Liese, K. Seelbach, C. Wandrey, Wiley-VCH; ISBN 3-527-30094-5.

In view of the desired specificities, stereo- and regioselectivities, the absence of side activities and resistance to unusual reaction conditions such as high solvent concentrations, the improved performance of the protease according to the invention offers substantial advantages.

From a pharmaceutical point of view the role of proteases is illustrated by a substantial number of references in Martindale's, "The Extra Pharmacopoeia" (Pharmaceutical Press, London, UK). Moreover the important role of very specific proteases in regulating all kinds of biological processes is illustrated by the fact that many hormones become active only after the processing of an, mostly inactive, precursor molecule by such a very specific protease. Inhibitors active towards certain categories of such specific proteases have been implicated in the development of all kinds of new drugs. Therefore new and effective inhibitors for protease may now be identified using the sequences provided herein.

The entire disclosure of each document cited herein is hereby incorporated by reference

TABLE 1

| Gene | SEQ ID number cDNA | Protein | Function of encoded protein | EC number |
|---|---|---|---|---|
| 1 | 58 | 115 | Pepsin A$_3$ | EC3.4.23.1 |
| 2 | 59 | 116 | Metalloprotease | EC3.4.24.56 |
| 3 | 60 | 117 | acylaminoacyl-peptidase | EC3.4.19.1 |
| 4 | 61 | 118 | Tripeptidylaminopeptidase | EC3.4.14.- |
| 5 | 62 | 119 | serine carboxypeptidase | EC3.4.16.6 |
| 6 | 63 | 120 | Serine endoprotease | EC3.4.21.- |
| 7 | 64 | 121 | Carboxypeptidase Y | EC3.4.16.5 |
| 8 | 65 | 122 | aspergillopepsin II - hom | EC3.4.23.19 |
| 9 | 66 | 123 | Tripeptidyl peptidase | EC3.4.14.9 |
| 10 | 67 | 124 | Tripeptidyl peptidase | EC3.4.14.9 |
| 11 | 68 | 125 | aspergillopepsin II - hom | EC3.4.23.19 |
| 12 | 69 | 126 | Tripeptidyl peptidase | EC3.4.14.9 |
| 13 | 70 | 127 | Metalloprotease | EC3.4.24.- |
| 14 | 71 | 128 | aspergillopepsin I | EC3.4.23.18 |
| 15 | 72 | 129 | Pepsinogen E | EC3.4.23.25 |
| 16 | 73 | 130 | aspergillopepsin I - hom | EC3.4.23.18 |
| 17 | 74 | 131 | aspergillopepsin II | EC3.4.23.19 |
| 18 | 75 | 132 | Pyro-Glu peptidase | EC3.4.19.3 |
| 19 | 76 | 133 | dipeptidyl peptidase | EC3.4.14.2 |
| 20 | 77 | 134 | Secr. aminopeptidase | EC3.4.11.10 |
| 21 | 78 | 135 | alkaline D-peptidase | EC3.4.16.4 |
| 22 | 79 | 136 | Carboxypeptidase | EC3.4.16.1 |
| 23 | 80 | 137 | Carboxypeptidase | EC3.4.16.1 |
| 24 | 81 | 138 | Carboxypeptidase-II | EC3.4.16.1 |
| 25 | 82 | 139 | aspartic proteinase | EC3.4.23.- |
| 26 | 83 | 140 | Tripeptidyl peptidase | EC3.4.14.9 |
| 27 | 84 | 141 | Carboxypeptidase | EC3.4.16.1 |
| 28 | 85 | 142 | cysteine proteinase | EC3.4.22.- |
| 29 | 86 | 143 | Metallocarboxypeptidase | EC3.4.17.- |
| 30 | 87 | 144 | Subtilisin hom. | EC3.4.21.62 |
| 31 | 88 | 145 | Carboxypeptidase Y | EC3.4.16.5 |
| 32 | 89 | 146 | Metalloprotease | EC3.4.24.- |
| 33 | 90 | 147 | Carboxypeptidase Y | EC3.4.16.5 |
| 34 | 91 | 148 | Metalloprotease | EC3.4.24.- |
| 35 | 92 | 149 | Tripeptidyl peptidase | EC3.4.14.9 |
| 36 | 93 | 150 | Aspartic protease | EC3.4.23.24 |
| 37 | 94 | 151 | Aspartic protease | EC3.4.23.24 |
| 38 | 95 | 152 | Pepsin A$_3$ | EC3.4.23.1 |
| 39 | 96 | 153 | Aspartic protease | EC3.4.23.24 |
| 40 | 97 | 154 | Aspartic protease | EC3.4.23.24 |
| 41 | 98 | 155 | Kex | EC3.4.21.61 |
| 42 | 99 | 156 | Serine protease | EC3.4.21.- |
| 43 | 100 | 157 | Glutamyl endoprotease | EC3.4.21.82 |
| 44 | 101 | 158 | aspergillopepsin II - hom | EC3.4.23.19 |
| 45 | 102 | 159 | acylaminoacyl-peptidase | EC3.4.19.1 |
| 46 | 103 | 160 | Tripeptidylaminopeptidase | EC3.4.14.- |
| 47 | 104 | 161 | serine carboxypeptidase | EC3.4.16.6 |
| 48 | 105 | 162 | Gly-X carboxypeptidase | EC3.4.17.4 |
| 49 | 106 | 163 | aspartic proteinase | EC3.4.23.- |
| 50 | 107 | 164 | Tripeptidyl peptidase | EC3.4.14.9 |
| 51 | 108 | 165 | Carboxypeptidase-I | EC3.4.16.1 |
| 52 | 109 | 166 | serine carboxypeptidase | EC3.4.16.6 |
| 53 | 110 | 167 | serine carboxypeptidase | EC3.4.16.6 |
| 54 | 111 | 168 | Secr. aminopeptidase | EC3.4.11.10 |
| 55 | 112 | 169 | Prolyl endopeptidase | EC3.4.21.26 |
| 56 | 113 | 170 | aspergillopepsin I - hom | EC3.4.23.18 |
| 57 | 114 | 171 | Aminopeptidase | EC3.4.11.- |

EXAMPLES

Example 1

Assaying Proteolytic Activity and Specificity

Protease specificity may be explored by using various peptide substrates. Synthetic substrates are widely used to detect proteolytic enzymes in screening, in fermentation, during isolation, to assay enzyme activity, to determine enzyme concentrations, to investigate specificity and to explore interaction with inhibitors. Peptide p-nitroanilides are preferably used to assay protease activity as the activity can be followed continuously and therefore allow for kinetic measurement. The cleavage of peptide p-nitroanilides can be followed by measuring the increase in adsorption at 410 nm upon release of the 4-nitroanilide. Paranitroanilide substrates are generally used for serine and cysteine proteases. In addition peptide thioesters and 7-amino-p-methylcoumarin peptide derivates are used. Peptide thioesters are very sensitive substrates for serine and metalloproteases that exhibit relatively high turnover rate since the thioester bond is easier to cleave than the amide bond. Cleavage of thiolesters may be followed with a thiol reagent such 4,4-dithiopyridine (324 nm) or 5,5-dithiobis 2-nitrobenzoic acid (405 nm). The same increased turnover rate is usually observed for the cleavage of ester bonds relative to amide bond. The most well known substrates to assay the esterase activity of proteases are p-nitrophenol derivates. The release of p-nitrophenol can be monitored at different wavelength dependent on the pH that is used, eg around neutral pH a wavelength of 340 nm is used while above pH 9 monitoring is done around 405 nm. In addition the hydrolysis of esters can also be followed by titration using pH-stat equipment. In case of qualitative measurement of esterase activity pH sensitive dyes can be applied.

As an alternative, peptides may be attached to a fluorescent leaving group. Proteolysis is accompanied by an increase in fluorescence when monitored at the appropriate wavelengths. Peptidyl 2-naphtylamides and peptidyl 4-methyl-7-coumarylamides are commonly used. The release of for example 7-amino-4 methylcoumarin is measured using an excitation wavelength of 350 nm and an emission wavelength of 460 nm. The use of 7-amino-4 trifluoromethylcoumarin has the advantage of the leaving group being both chromogenic (absorbtion 380 nm) as well as flourogenic (excitation 400 nm, emission 505 nm). When it is essential that at both sides of the scissile bond an amino acid is present, the introduction of a group that quenches the fluorescence might be useful. The general characteristics of such substrates is that the peptide sequence separates a fluorescent donor group from an acceptor group that acts as a quencher of fluorescence. Cleavage of a peptide bond between the quenching group and the fluorophore will lead to substantial increase in fluorescence. Several donor-acceptor pairs have been reported, including o-aminobenzoic acid (Abz) as the donor and 2,4 dinitrophenyl (Dnp) as the acceptor, 5-[(2'aminoethyl)-amino]naphtalenesulfonic acid (EDANS) as the donor and 4-[[4'-(dimethylamino]phenyl] azo]-benzoic acid (DABCYL) as the acceptor. The Abz/EDDnp represents a very convenient donor-aceptor pair since after total hydrolysis, the fluorescence increases by a factor 7 to 100 and the absorption spectrum of EDDnp does not change with pH. Moreover, the peptide sequence may contain up to 10 residues without loss of the quenching effect. As the size of the connecting peptides increases, the position of the scissile bond may become less specific. Therefore in addition to establishing whether proteolysis occurred, additional analysis of the products may be required. This may be done by analysing and separating the produced peptides by HPLC and determining the amino acid sequence of the fragments. In addition the peptide composition of the digest may be directly analysed by using combined HPLC/mass-spectroscopy technique.

Apart from using peptides of a defined sequence also synthetic peptide libraries can be used to study protease specificity. Peptides are synthesised by solid phase synthesis in random or semi-random fashion. E.g. Meldal et al. (PNAS USA 91,3314,1994) report the preparation of a family of protease substrates by starting with H-Lys(Abz)-resin, extending the resin with peptides to a length of six amino acids, and finally coupling Tyr(NO2) to the peptides. Each resin bead has a unique sequence and on treatment with the proteases the most susceptible becomes fluorescent as the Tyr(NO2) containing peptide is released. Sequence analysis of the peptides on the susceptible will give information on the specificity of the protease.

Protease activity is usually expressed in units. Generally the international standard unit (IU) is defined as the amount of enzyme, which under defined conditions transfers one micromole of substrate per minute. Specifically with proteases the IU would relate to the hydrolysis of one micromole peptide bond per minute. However in the case of protease units deviations of the international definition are more rule than exception. Where with the model peptides, which are cleaved specifically at one bond the calculation of IU's is strait-forward, for proteinacious substrates where the protease can cleave at various positions to a various degree many deviating unit definition are used. Apart from a definition of the unit used, any hydrolysis experiment requires an adequate description of the conditions under which the units are measured. Such conditions comprise e.g. the substrate concentration, the enzyme-substrate ratio, the pH and temperature. Typical assays for determining the specific activity of a proteases comprise a proteinacious substrate such as for example denatured hemoglobin, insulin or casein. The polypeptide substrate is digested by a protease at fixed conditions during a fixed time interval. Undigested and large polypeptides are precipitated with TCA and TCA soluble product is determined by measuring absorbance at 220 or 280 nm, or by titrating the soluble peptides with folin reagent, ninhydrin, fluro 2,4, dinitrobenzene/dansylchloride, TNBS method or fluorescein. Instead of labeling the product after hydrolysis, also polypeptide substrates may be used which are already labeled by specific dyes or fluorophores such as for example fluorescein. In addition standard methods of amino acid analysis may be applied using standard laboratory analyzers. In order to hget insight in the size distribution of the peptides generated by a protease, gel chromatography experiments may be performed. In addition to this HPLC using reverse phase techniques is applied in order to get better resolution of the peptide patterns generated by the protease. The course of the hydrolysis of proteinacious substrates is usually expressed in the degree of hydrolysis or DH. In case pH-stat is used to follow the course of hydrolysis, DH can be derived from the base consumption during hydrolysis (Enzymatic Hydrolysis of Food Protein, J. Adler-Nissen, 1986, Elsevier Apilied Science Publishers LTD). The DH is related to various useful functional properties of the hydrolysate such as solubility, emulsifying capacity, foaming and foam stability, whipping expansion, organoleptic quality. In addition taste is an important aspect of food grade hydrolysates. Bitterness can be a major problem in protein hydrolysates. Termination of the hydrolysis reaction may be done by changing the pH, heat inactivation, denaruring agents such as SDS, acetonitril etc.

Polypeptides shown in Tabel 1 were expressed and at least partially purified according to standard procedures known in the art. They were analysed according to al least one of the methods described above and found to have the activities listed in Table 1.

Example 2

Direct Determination of the kcat/Km Ratio for Protease Substrates.

Synthetic substrates can be used to monitor the enzymatic activity during purification, to determine enzyme concentration, to determine inhibition constants or to investigate the substrate specificity. Determination of the kcat/Km ratio gives a measurement of the substrate specificity. It allows to compare the specificity of different substrates for a same enzyme or the comparison of hydrolysis rates with different enzymes cleaving the same substrate. This ratio has a unit of a second order rate constant and is then expressed as 1/(concentration·time). Substrates having a kcat/Km ratio in the range 10.5-10.6 M-1·sec-1 are considered to be very good substrates i.e good affinity and rapid turn-over. However, some substrates may be very specific with kcat/Km values in the 10.4 M-1·sec-1 range.

The kcat/Km ratio may be calculated after determination of individual parameters. In that case, Km and Vm may be obtained from various linear plots (e.g Hanes or Cornish-Bowden method) or by a non-linear regression method. Knowing that Vm=kcat·Et (where Et is the final active enzyme concentration then kcat=Vm/Et·Determination of the kcat/Km ratio by the previous method may be prevented when product or substrate inhibition occur, or when Substrate precipitates at high concentration. It is however possible to obtain an accurate value of the kcat/Km ratio working under first-order conditions i.e at a substrate concentration far below the estimated Km. In these conditions, the Michaelis-Menten equation: v=(Vm·S)/(Km+S) becomes:

$v=(Vm·S)/Km$ since S<<Km or $v=(Vm/Km)·S=kobs·S=-dS/dt$ which integrates as InS=-kobs·t+InSo where So is the starting substrate concentration and S the substrate concentration at a given time. The velocity is proportionnal to the substrate concentration. In other words, the substrate hydrolysis obeys a first order process with kobs as the first-order rate constant. kobs=Vm/Km=(kcat·Et)/Km since Vm=kcat·Et A continuously recording of the substrate hydrolysis will allow the graphical determination of kobs from the InS vs time graph. The kcat/Km ratio is simply inferred from kobs providing the active enzyme concentration is known:

$kcat/Km=kobs/Et$

Assay method: Use a starting substrate concentration far below the estimated Km and a low enzyme concentration to allow the substrate hydrolysis to be recorded. You will obtain a first-order curve for the product generation:

After total hydrolysis of the substrate, the absorbance (or fluorescence units) of the product will allow the accurate determination of So, since Pt=So. kobs is determined from the slope of the InS vs time graph or alternatively using a fitting software (Enzfitter, SigmaPlot . . . ).

NB: Do not forget to calculate the substrate concentration for any given time from the product concentration (S=So–P) since plotting P vs time would not provide the correct kobs (dP/dt=kobs·S does not integrate in the same way).

Alternatively, one can measure successive t½ (half-time) from the product apparition curve since in a first order process:

$t½=In2/kobs=0.693/kobs$ then $kobs=0.693/t½$

Using this method allows to check that you have a true first order decay (identical values for the successive t½).

Example 3

Inactivating Protease Genes in *Aspergillus*

The most conveniant way of inactivating protease genes in the genome of *Aspergillus* is the technique of gene replacement (also called "one step gene disruption"). The basics of this technique have been described by Rothstein R J in Meth. Enzymol. 101, p202, 1983. Essentially the technique is based on homologous recombination of transformed DNA fragments with the genomic DNA of a fungal cell. Via double crossover the gene to be inactivated is (partly) replaced by the DNA fragment with which the cell is transformed. Preverably the transformed DNA fragment contains a selectable marker gene for *Aspergillus niger*. Basically the manipulation of DNA and generation of a inactivation construct are done using general molecular biological techniques. First, genomic DNA is isolated from the *Aspergillus niger* strain that is later on used for the inactivation of the protease gene. Genomic DNA of *A. niger* can be isolated by any of the techniques described, e.g. by the method described by de Graaff et al. (1988) Curr. Genet. 13, 315-321, and known to the person skilled in the art. This genomic DNA is used as template for amplification of the flanking regions of the protease gene by using the polymerase chain reaction (PCR; Sambrook et al. (1989) Molecular cloning, a laboratory manual, 2nd edition, Cold Spring Harbor Laboratory Press, New York). With flanking regions is meant here the non-coding regions upstream and downstream of the protease gene that will be inactivated. Preferably the flanking regions should each be more than 1.0 kb in length.

Two single stranded DNA oligonucleotides are used for the priming of the PCR amplification of each flanking region. For the 5'-flanking region, one primer is homologous to a DNA sequence upstream of the start of the coding sequence of the protease gene. Preferably the homologous region is located more than 1.0 kb upstream of the translation start site. The second primer is homologous to the complementary and inverse DNA sequence located immediately upstream of the coding sequence of the protease gene.

For the 3'-flanking region, one primer is homologous to the DNA sequence immediately downstream of the coding sequence of the protease gene. The second primer is homologous to a complementary and inverse DNA sequence located preferably more than 1.0 kb downstream of the coding sequence of the protease gene.

The DNA sequence included in all primers and homologous to the *A. niger* genome should be minimally 15 nucleotides in length, preferably more than 18 nucleotides in length. Most conveniently, all primers should contain a DNA sequence coding for the recognition site of suitable restriction enzymes upstream of the sequence that is homologous to the *A. niger* genome. These extra recognition sites facilitate the cloning process.

Both primers and the genomic DNA of *A. niger* are used in a PCR reaction under conditions known to those skilled in the art. The annealing temperature of the primers can be calculated from the part of the DNA sequence that is homologous to the *A. niger* genome. Both fragments containing the 5'-flanking region and the 3'-flanking region are cloned into a vector that can be propagated in *E. coli* using general molecular biological techniques. A gene that can be used as selection marker in *Aspergillus niger* is then cloned in between the two flanking regions. Most conveniantly the marker gene is under control of a promoter that comes to expression in *A. niger*, preferably an endogenous *A. niger* promoter. The orientation of the insertion of the marker gene is preferably in the same direction as the original protease gene. The final inactivation fragment contains the 5'-flanking region, a selection marker gene preferably under control of a *A. niger* endogenous promoter, and the 3'-flanking region, all in this direction and orientation. DNA of the final construct is cloned into a vector that can be propagated in *E. coli*.

The inactivation construct is digested with suitable restriction enzymes to remove the *E. coli* vector sequences and the inactivation fragment is isolated using standard techniques (Sambrook et al. (1989) Molecular cloning, a laboratory manual, 2nd edition, Cold Spring Harbor Laboratory Press, New York). Finally *Aspergillus niger* is transformed with the inactivation fragment using a method described in literature, e.g. by the method described by Kusters-van Someren et al. (1991) Curr. Genet. 20, 293-299. Transformed cells are selected by plating the transformation mixture on agar plates that are selective for growth of *Aspergillus niger* strains that do express the marker gene. After purification of the transformed *Aspergillus* strains by replica plating, a representative number of strains is analysed by Southern blotting using standard methods (Sambrook et al. (1989) Molecular cloning, a laboratory manual, 2nd edition, Cold Spring Harbor Laboratory Press, New York). Therefore, genomic DNA of mycelium of transformed strains is isolated and digested with suitable restriction enzymes. Restriction fragments are separated using agarose gel electrophoresis, blotted to nitrocellulose membranes and probed with a labeled fragment of the marker gene. Hybridization and washing is under stringent conditions. Strains that contain labeled restriction fragments of the correct length are considered correct.

Using this method *A. niger* strains can be selected with an inactivated protease gene of choice.

Example 4

Isolating Proteases by Ion Exchange Chromatography

Small quanties of the protease encoded by the nucleotide sequence as provided herein are obtained by constructing an expression plasmid containing the relevant DNA sequence, transforming an *A. niger* strain with this plasmid and growing the *A. niger* strain in a suitable medium. After collecting the broth free of contaminating cells, the protease sought can be purified.

To isolate the protease as encoded by the provided nucleotide sequence in an essentially pure form several strategies can be followed. All of these strategies have been adequately described in the relevant scientific literature (see for example the Protein Purification Handbook, 18-1132-29 Edition AA as published by Amersham Pharmacia Biotech, Uppsala, Sweden). A procedure which is applicable to purify proteases from complex mixtures is provided hereunder. Essential is that a suitable assay is available that is selective towards the enzyme characteristics sought. For proteases typically a chromogenic, synthetic peptide substrate is used as described in Example 1. Such peptide substrates can be selective towards endoproteases, carboxypeptidases, aminopeptidases or omegapeptidases. In Example 11 the selectivity towards a specific tripeptidylpeptidase is described. By choosing the right amino acid residues in the relevant synthetic peptide, proteases with the desired specificity can be selected.

First it should be determined whether the protease is excreted into the medium, depending on the expression system chosen to produce the protease, it may be excreted or contained in the cell. If the protease is excreted into the fermentation medium, the producing cells or fragments of these cells have to be removed by centrifugation or filtration and the resulting clear or clarified medium is the starting point for further purification. In those cases in which the protease sought is not excreted, the producing cells have to be disrupted to enable purification of the protease. In such cases the collected cell mass is best ground with an abrasive, milled with beads, ultrasonicated or subjected to a French press or a Manton-Gaulin homogeniser and then filtered or centrifuged. In case the protease is hydrophobic or membrane bound, the addition of a non-ionic detergent to solubilise the protease before the filtering or centrifugation step may be necessary.

After the clarification step, a three phase purification strategy can be applied to obtain the unknown proteases in an essentially pure state. In all or some of these three phases addition of a detergent may be necessary.

In the first or capture phase the target protease is isolated, partly purified and concentrated. During the subsequent intermediate purification phase most of the bulk impurities are removed and in the final polishing phase trace amounts of remaining impurities of larger amounts of closely related substances are removed and the enzyme is dissolved in the desired buffer. Depending upon the nature and physical properties of the protease at hand, a person skilled in the art is capable of optimising the three phases using slightly modified versions of the different protein binding materials and apply these under somewhat changed conditions. However, in all cases a selective analytical assay is indispensible as it will enable the continuous monotoring of the increasingly purified proteolytic activity. Analytical assays suitable for the purpose include the use of chromogenic peptide substrates as has been mentioned before.

In the first capturing phase of the purification a strong ion exchange resin of the anionic type is preferably used to apply the clarified and desalted enzyme containing medium. To guarantee binding of the desired proteolytic activity to the resin, three or four different pH values of medium and resin are tested under low conductivity conditions. In these tests the resin is always equilibrated with a buffer of the same pH value and conductivity as the enzyme containing medium. The medium is then applied to the column under pH conditions which has been shown to allow adequate binding of the protease to the resin i.e. none of the desired enzymatic activity can be traced back in the run-through medium. Subsequently the desired enzymatic activity is eluted from the ion exchange resin using a continuous salt gradient which starts with the resin equilibration buffer and ends with this buffer to which 1 molliter of NaCl has been added. Eluted fractions containing the desired activity according to the assay are pooled and then prepared for an additional purification step. This additional purification step depends on the purity of the desired enzyme in the pooled fraction: if almost pure, an additional gel filtration step will proof to be adequate; if not almost pure, chromatography over a hydrophobic interaction resin is applied followed by a gel filtration step.

Chromatography over a hydrophobic interaction resin is carried out by first increasing the salt content of the pooled fraction obtained from the ion exchange resin to 4 mol/liter of NaCl and by removing any precipitate formed. If the resulting clear fraction does not contain the desired activity, this activity is obviously present in the precipitate and can be recovered in an essentially pure state. If the resulting clear fraction still exhibits the desired activity in the assay, then the liquid is applied as such to a phenyl sepharose resin (Pharmacia) equilibrated in this high salt buffer with an identical pH and conductivity. If the desired enzymatic activity binds to the phenyl sepharose resin, the activity is eluted with a continuous gradient of decreasing salt content followed by a salt free wash and, if nesessary, with a chaotropic agent. Like before those fractions from the gradient that exhibit activity in the assay are pooled and finally subjected to a gel filtration step. If the desired enzymatic activity does not bind to the phenyl sepharose resin, many of the contaminants will, so the desired proteolytic activity as present in the void volume of the column requires only an additional ultrafiltration step to obtain the activity in a more concentrated form before applying it to the gel filtration column. The gel filtration column does not only remove trace contaminations but also brings the enzyme in the buffer which is required by subsequent use.

Although this method is generally applicable for the isolation and purification of proteases according to the invention, a more specific isolation technique is described in Example 4. In that Example the isolation of an *Aspergillus* protease is described by using immobilised bacitracin, a peptide antibiotic known for its selective interaction with various types of proteases.

Example 5

Isolating Proteases by Affinity Chromatography

An alternative method for purifying small quantities of protease is by affinity chromatography. To obtain the protease in a purified form, a 100 milliliter culture is grown in a well aerated shake flask. After centrifugation to remove any non-soluble matter, the supernatant is applied to a 40 milliliter bacitracin-Sepharose column equilibrated with 0.05 mol/liter sodium acetate pH 5.0. Proteases bound to the column are eluted using the acetate buffer supplemented with 1 mol/liter of NaCl and 10% (v/v) isopropanol (J. Appl. Biochem., 1983 pp420-428). Active fractions are collected, dialysed against distilled water and applied on a 20 milliliter bacitracin-Sepharose column, again equilibrated with acetate buffer. As before, elution is carried out using the acetate buffer supplemented with NaCl and isopropanol. Active fractions, i.e. fractions displaying the activities sought, are collected, dialysed against a 5 millimol/liter acetate buffer pH 5.0 and then concentrated by means of ultrafiltration with a Amicon PM-10 membrane. To obtain the protease in an essentially pure state, the concentrated liquid is chromatographed over a Superdex 75 column equilibrated with the 0.05 mol/liter sodium acetate buffer pH 5.0 and supplemented with 0.5 mol/liter NaCl.

Further experiments carried out with the purified enzyme on PAGE may confirm if the molecular weight is in line with what can be expected on the basis of the available sequence data. Final confirmation can be obtained by carrying out a partial, N-terminal amino acid analysis.

Example 6

Properties of a Novel Cysteine Protease from *A. niger*.

In this Example *Aspergillus* gene nr 28 was cloned and overexpressed in *A. niger* as described before. The enzyme obtained was purified according to procedures described in Example 4 and used to destroy trypsin inhibiting activity from soybeans under various conditions. As reference materials papain and bromelain were used. Bromelain was obtained from Sigma, papain was obtained from DSM Food Specialties Business Unit Beverage Ingredients, PO Box 1, 2600 MA Delft, the Netherlands.

Trypsin inhibition was measured according to the method of Kakade, M. L., Rackis, J. J., McGhee, J. E. and Puski, G. (1974): J. Cereal Chemistry 51: 376-382.

Degradation of the substrate N-benzoyl-L-arghinine-p-nitroaniline to N-benzoyl-L-arginine and p-nitroaniline was taken as a measure of trypsin activity. Trypsin was obtained from British Drug Houses Ltd and was derived from cow's pancreas containing more than 0.54 Anson Units per gram of product.

The Kunitz inhibitor for soybeans was also obtained from Sigma.

The trypsin inhibitor was pre-incubated at a concentration of 2 mg/ml with the above mentioned cysteine protease enzymes at pH 3 in 50 mM Na-acetate buffer prior to measuring trypsin inhibition. Enzymes were added at a ratio of enzyme protein to trypsin inhibitor of 1:100 (w/w). Albumin served as a negative control for the enzymes. Remaining trypsin activity was measured after incubation during 3 hours at 37° C. Results are shown in Table 2.

TABLE 2

Effects of various cysteine proteases on the enzymatic inactivation of the Kunitz trypsin inhibitor from soybeans.

| 1<br>Enzyme<br>tested | 2<br>Remaining<br>TI<br>activity<br>(%) | 3<br>Remaining TI<br>activity after<br>pepsin<br>treatment | 4<br>Remaining TI<br>activity after<br>heat treatment<br>at 75° C. | 5<br>Remaining TI<br>activity after<br>heat treatment<br>at 90° C. |
|---|---|---|---|---|
| Papain | 25 | 55 | 78 | 95 |
| Bromelain | 30 | 62 | 86 | 99 |
| *A. niger* | 26 | 26 | 28 | 35 |
| Albumin (control) | 100 | 100 | 100 | 100 |

TI: Trypsin Inhibitor activity

Experiments were repeated in the presence of pepsin during the pre-incubation of cysteine proteases with the trypsin inhibitor. Pepsin was added at final concentration of 1.3 mg/ml. Results are shown in column 3.

Another series of experiments were conducted to check for heat stability. The cysteine proteases were incubated at 75 and 90° C. during 5 minutes prior to the addition of these enzymes to the pre-incubation with the trypsin inhibitors. Results are shown in columns 4 and 5.

These results clearly demonstrate the superior activity of these novel cysteine proteases from *Aspergillus niger* over currently available cysteine proteases for the inactivation of trypsin inhibitors in animal feed.

Example 7

Exo-Peptidases Promoting Cheese Ripening and Cheese Taste.

The amino-peptidases encoded by genes nr 20 and 54 (see Table 1) were overexpressed in *A. niger* according to methods described earlier. Purification of these enzymes was carried out according to procedures as described in Example 4. The activity of the purified enzyme samples was determined at pH7.2 in an aqueous phosphate buffer (50 mM) containing the para-nitro anilide derivative of a number of hydrophobic amino acids (3 mM) as the substrate. The conversion of the substate by the amino peptidase was determined by monitoring the change in optical density at 400 nm as a result of substrate conversion, using a solution not contaning the enzyme as the reference. Activity (A) was calculated as the change in OD per minute and expressed as e.g. Phe-AP, Leu-AP or Val-AP units, depending on the substrate used. Normal cheese milk was inoculated with starter culture of the Delvo-tec™ DX 31 range (DSM Food Specialities Delft, The Netherlands) to obtain a Gouda-type cheese and coagulating was executed with an average dosis of coagulant (50 IMCU per liter of cheese milk). In addition, 25 Phe-units of each exo-protease was added to two experimental cheeses whereas the control did not contain either one of the exo-proteases. Cheese making parameters were used conform the procedure applied for semi-hard cheese for both cheeses. A difference was noted in terms of flavor and aroma development between the experimental cheeses and control cheese to such an extent that the experimental cheeses has obtained most of its organoleptical properties after three (3) weeks whereas the control cheese has obtained a similar qualification after six (6) weeks. The level of free amino acids after three weeks was shown to be twice as high in the experimental cheeses; after six weeks of ripening the levels were comparable again. Amino acid analysis was carried out according to the Picotag method of Waters (Milford Mass., USA).

These data suggests that the product is ready for sale three weeks earlier without decreasing the keeping quality of the cheese. The organoleptic character of the experimental cheeses differed from the control to the extent that the bland cheese flavor with a slight tendency to bitterness of the control cheese was overcome in the experimental cheese in the presence of the amino-peptidase. The texture of the cheeses was found to be somewhat smoother as well.

Example 8

Novel Specificity of a Protease Encoded by Gene 55

As explained earlier, certain proteins can resist enzymatic hydrolysis as the result of specific amino acid compositions or specific tertiary structures. In such cases the quantity of peptides that can be solubilised from protease resistant proteins can be dramatically improved by using proteases exhibiting novel specificities.

Beta-casein is a protein with very limited tertiary structure but with an extraordinary high level of proline residues. Many proteases have difficulties in cleaving proline containing sequences so that the hydrolysis of beta-casein with commonly available proteases yields a hydrolysate that is relatively rich in large, protease-resistant peptides. The latter resistant peptides can attribute to a number of undesirable properties of the hydrolysate. For example, it is well known that these larger peptides have a relatively strong effect on allergenicity and bitterness. Moreover, these peptides withstand a further degradation into free amino acids so that in certain processes the occurrence of these large, protease resistant peptides are synonymous with yield losses. Therefore, the availability and use of proteases that are capable of cleaving the protease-resistant parts of the proteins, translate into serious technical and economical benefits.

Beta-casein represents one of the major casein fractions of bovine milk. The protein has been well characterised in terms of its amino acid sequence and is commercially available in an almost pure form. As such, beta-casein offers an excellent test substrate for studying the relationship between enzyme cleavage sites and the length of various peptides formed during enzyme hydrolysis.

This Example demonstrates that despite the broad spectrum cleavage character of the endoprotease subtilisin, the addition of a very specific enzyme like a prolyl endopeptidase as encoded by gene 55 (see Table 1) has a major impact on the size of the beta-casein fragments formed.

Beta-casein from bovine milk (lyophilised, essentially salt-free powder) with a minimum 90% beta-casein was obtained from Sigma. Subtilisin from *B. licheniformis* (Delvolase®, 560 000 DU per gram) was obtained from DSM Food Specialities (Seclin, France). The proline-specific endoprotease as encoded by gene 55 was overexpressed in *A. niger* and purified using procedures described in Example 4.

Beta-casein powder was dissolved at a concentration of 10% (w/w) together with 0.1% (w/w) Delvolase™ powder in a 0.1 mol/liter phosphate buffer pH7.0. After an incubation of 24 hours at 45° C. in a shaking waterbath, the reaction was stopped by heating the solution for 15 minutes at 90° C. To one half of the solution (1 ml containing 100 milligrams of beta-casein) 100 microliter of the proline-specific protease was added and the reaction was continued for another 24 hours at 45° C. After another heat shock at 90° C., samples of both the Delvolase™ and the Delvolase™+ proline-specific endoprotease treated beta-casein material were analysed by LC/MS equipment to study the precise peptide size distributions in the two samples.

LC/MS Analysis

HPLC using an ion trap mass spectrometer (Thermoquest™, Breda, the Netherlands) coupled to a P4000 pump (Thermoquest™, Breda, the Netherlands) was used in characterising the enzymatic protein hydrolysates produced by the inventive enzyme mixture. The peptides formed were separated using a PEPMAP C18 300A (MIC-15-03-C18-PM, LC Packings, Amsterdam, The Netherlands) column in combination with a gradient of 0.1% formic acid in Milli Q water (Millipore, Bedford, Mass., USA; Solution A) and 0.1% formic acid in acetonitrile (Solution B) for elution. The gradient started at 100% of Solution A and increased to 70% of solution B in 45 minutes and was kept at the latter ratio for another 5 minutes. The injection volume used was 50 microliters, the flow rate was 50 microliter per minute and the column temperature was maintained at 30° C. The protein concentration of the injected sample was approx. 50 micrograms/milliliter.

Detailed information on the individual peptides was obtained by using the "scan dependent" MS/MS algorithm which is a characteristic algorithm for an ion trap mass spectrometer. Full scan analysis was followed by zoom scan analysis for the determination of the charge state of the most intense ion in the full scan mass range. Subsequent MS/MS analysis of the latter ion resulted in partial peptide sequence information, which could be used for database searching using the SEQUEST application from Xcalibur Bioworks (Thermoquest™, Breda, The Netherlands). Databanks used were extracted from the OWL.fasta databank, available at the NCBI (National Centre for Biotechnology informatics), containing the proteins of interest for the application used.

By using this technique as a screening method only peptides with a mass ranging from approx. 400 to 2000 Daltons were considered suitable for further analysis by MS sequencing.

Angiotensin (M=1295.6) was used to tune for optimal sensitivity in MS mode and for optimal fragmentation in MS/MS mode, performing constant infusion of 60 µg/ml, resulting in mainly doubly and triply charged species in MS mode, and an optimal collision energy of about 35% in MS/MS mode.

In the sample digested with Delvolase alone, the LC/MS/MS analysis identified 40 peptides covering various parts of the beta-casein molecule. Together these peptides accounted for 79% of the total beta-casein sequence. Different retention times of the peptides on the C18 column could be traced back to peptide lengths ranging from 2 to 23 amino acid residues. Together <15% of the peptides found were smaller than 6 amino acids. The sample digested with Delvolase™ and the proline-specific protease also generated a large number ofl identifiable peptides from beta-casein. Together these peptides covered >50% of the total beta-casein protein sequence. In this sample the peptide size distribution was remarkably homogeneous, as the peptides ranged in length only between 2 and 6 residues. The results show that in the hydrolysate made with the proline-specific protease contain a large fraction of di-, tri-, up to 6 AA peptides, showing the distinct beneficial effect of the co-incubation with an endoprotease featuring an unusual specificity. It is also clear from these experiments that the endoprotease according to gene 55 encodes an endoprotease that cleaves the peptide chain at the carboxy terminus of the proline residue.

Example 9

The Selective Release of Specic Amino Acids to Promote Flavour Formation.

Free amino acids like leucine and phenylalanine have not only been implicated in Maillard reactions but also as precursor for desirable aromas in various food fermentations. To promote the formation of such aromas in food fermentations or during the heating, roasting or baking phase of food, it would be advantageous to incorporate into these products a protein hydrolysate that contains relatively high levels of these specific amino acids in a free form. In this Example we describe the production of yeast extracts selectively enriched t in leucine and phenylalanine. This enrichment is obtained by combining an endoprotease with a cleavage preference for a selected set of amino acid residues with an exoprotease favouring the release of a similar set of amino acid residues. The preference of the endoprotease should match with the preference of the exoprotease used. For example we have established that the aminopeptidases encoded by genes 20 and 54 (see Table 1) feature a definite preference for releasing leucine and phenylalanine residues which matches with the cleavage preferences of thermolysin. The carboxypeptidases encoded by genes 23 and 24 have a preference for releasing arginine and lysine residues which matches the cleavage preferences of trypsin. Carboxypeptidase encoded by gene 5 features a highly unusual preference for releasing glycine which could be combined with certain endoproteases present in papaine. The carboxypeptidase encoded by gene 51 is capable of removing glutamate residues which matches the glutamate specific protease encoded by gene 43.

The endoprotease thermolysin (commercially available as Thermoase)C 180 from Daiwa Kasei KK (Osaka, Japan) is known to cleave peptide bonds at the amino terminal side of bulky, hydrophobic amino acids like Leu and Phe. To liberate the thus exposed amino acids from the newly formed peptides, we used the amino-peptidases encoded by genes nr 20 and 54 (see Table 1). These genes were overexpressed in *A. niger* according to methods described earlier and purification of these enzymes was carried out according to procedures as described in Example 4.

To release as much leucine and phenylalanine as possible without concomitant release of undesired amino acids with this combination of enzymes, it is evident that the conditions used during enzymatic hydrolysis should be carefully selected. Moreover, the yeasts own endogeneous (and probably a specific) proteases have to be inactivated. After a number of test incubations, a protocol was worked out that leads to a surprisingly selective and effective release of leucine and phenylalanine from the yeast proteins using these two new enzymes.

To inactivate the yeasts endogeneous proteases, the yeast suspension was kept for 5 minutes at 95 degrees C. Then the suspension was quickly cooled down to the required temperature and the pH was adjusted to 7.0 using 4N NaOH. The yeast, the thermolysin and one of the aminopeptidases were all incubated simultaneously under the following conditions. After the heat shock, the pH of the 2000 milliliters yeast suspension was adjusted to 7.0 after which 680 milligrams of Thermoase were added and, after stirring, the purified aminopeptidase. The mixture was incubated with stirring at 50 degrees C. for 3 hours and centrifuged. To stop all enzymatic activities the pH of the supernatant was adjusted to 4 and subjected to another heat treatment of 45 minutes at 95 degrees C. After another centrifugation a sample for amino acid analysis was obtained from the supernatant. Precipitated or non-dissolved matter was removed by centrifugation for 15 minutes at 3500 rpm in an Hereaus Megafuge 2.0 R centrifuge. Supernatant was removed and kept frozen at −20° C.

Samples of the supernatant, were analysed for amino acid content according to the Picotag method of Waters (Milford Mass., USA) immediately after thawing.

In the amino acid analysis Trp and Cys values were omitted And Asp and Asn values were summed as one value. According to the data obtained, in the resulting hydrolysate the ratio between alanine and leucine (21.3:11.7) was 1:0.5 Commercially available yeast hydrolysates typically exhibit alanine versus leucine ratio's of 1:0.3.

In a second experiment a yeast extract was prepared that was enriched in free glutamate. To achieve this, use was made of an endoprotease exhibiting a preference for cleaving at the C-terminal end of glutamate residues (encoded by gene nr 43 in Table 1) and a carboxypeptidase (encoded by gene nr 51 in Table 1) capable of removing these glutamate residues thus exposed. The endoprotease encoded by gene nr 43 and the carboxypeptidase encoded by gene 51 (see Table 1) were overexpressed in *A. niger* according to methods described earlier. Purification of these enzymes was carried out according to procedures as described in Example 4.

The essential role of free glutamate in a number of aroma forming processes is well documented and MSG, the sodium salt of glutamic acid, is recognized as the single most important taste enhancing component.

In this Example the pH of the 200 ml heat shocked yeast suspension is adjusted to 8.0, then the purified enzyme product encoded by gene 43 is added and the mixture was incubated for 4 hours at 50 degrees C. Then the pH was lowered to 5.0 and the suspension was centrifuged. To 100 milliliters of supernatant the purified gene product of gene 51 is added. Incubation with this carboxypeptidase took place for 30 minutes at 50 degrees C. with continuous pH adjustments. After stopping the enzyme incubation by a heat treatment of 5 minutes by 95 degrees C., the material was again centrifuged (see above) and a sample was obtained for amino acid analysis.

According to the amino acid data obtained (see above), in the resulting hydrolysate the ratio between alanine and glutamate (30.0:48.7) was 1:1.6. Commercially available yeast hydrolysates typically exhibit alanine versus glutamate ratio's of 1:1.

Example 10

Flavour Evaluation of Yeast Hydrolysates Enriched in Specific Amino Acids.

To prove that a protein hydrolysate enriched in specific amino acids according to the invention can generate specific aroma's, a number of experiments were carried out with the yeast hydrolysates described in an earlier Example. To that end larger portions of these hydrolysates were prepared and lyophilised. The performance of the resulting powders were compared with the performance of a commercially availble yeast extract (Gistex LS, obtainable from DSM Food Specialties, Delft, The Netherlands) in a standardised mixture under several reaction conditions. The standardised mixture consisted of one of the hydrolysates, base mixture and water.

The base mixture contained 22 grams of Maxarome Plus Powder (a specialised yeast extract with a high content of natural nucleotides, also obtainable from DSM Food Specialties), 29.2 grams of glucose, 9 grams of REFEL-F fat (hydrogenated soy oil, obtainable from Barentz, Hoofddorp, The Netherlands) and 0.2 grams of calcium stearoyl lactylate (emulsifyer, obtainable from Abitec, Northampton, UK) thoroughly mixed in a mortar.

All standardised mixtures contained 5 grams of yeast hydrolysate powder (i.e. either the leucine or the glumate enriched material or the commercial yeast extract), 3 grams of the base mixture and 3 grams of water. After thorough mixing, these three slurries were subjected to different heating regimes i.e. either 65 minutes at 90-95 degrees C. in a reaction vial (liquid reaction) or dried at 20 millibar at 120 degrees C. in a vacuum oven (vacuum roast reaction) or heated in an open reaction vial at 120 degrees C. for 10 minutes after the dissipation of all water (roast reaction).

After the heat treatment all three products Shad assumed colours ranging from dark brown to almost black. In case of the vacuum roast reaction only the light coloured top layers were used. Taste evaluation of the heated products was carried out by grinding the blackened cakes into fine powders and dissolving these powders to a concentration of 2% (w/w) in water containing 0.6% (w/w) NaCl. The observations of the taste panel are specified in Table 3.

TABLE 3

| | Reference | Leucine | Glutamate |
|---|---|---|---|
| Liquid | Bouillon, slightly roast | Cold tea, slightly flowery, yeasty | More bouillon, meaty, yeasty |
| Vacuum roast | Burnt, fried potatoes | Astringent, beans, yeasty | Burnt, bouillon, yeasty |
| Roast | Dark roast, bouillon, umami | Less roast, flowery, umami | Roast, more bouillon, more umami |

Example 11

Non-Allergenic Whey Protein Hydrolysates Formed with Tripeptidylpeptidases.

The dipeptidylpeptidases encoded by the genes 19 and 55 as well as the tripeptidylpeptidases encoded by the genes 4, 9, 10, 12, 26, 35, 46, and 50 (see Table 1) may be overproduced as described and may be purified according to the methods provided in Example 4. After purification the pH optimum and the temperature stability of each individual enzyme may be established by any of the methods available and known by the skilled person. Furthermore, the specificity of each individual enzyme may be determined using the methods outlined in Example 1. The selectivity exhibited by tripeptidylpeptidases is illustrated in the following experiment.

The enzyme encoded by gene 12 was overproduced in an *Aspergillus niger* host cell and purified by procedures described in Example 4. The enzyme thus obtained was incubated at pH 5 and 50 degrees C. with different synthetic chromogenic substrates i.e. Ala-Ala-Phe-pNA and Ala-Phe-pNA (both from Bachem, Switserland). The incubation with the Ala-Ala-Phe-pNA substrate led to a significant increase of the absorbance at 410 nm whereas the incubation with Ala-Phe-pNA did not. This observation clearly demonstrates that tripeptidylpeptidases cleave off tripeptides and do not exhibit aminopeptidase activity that can lead to an undesirable increase of free amino acids.

Moreover, the enzyme encoded by gene 12 shows favourable enzyme stability characteristics as shown in the following experiment. Four samples of the enzyme were incubated at pH 5 for one hour at 0, 40, 50 and 60 degrees C. respectively. Then each enzyme sample was incubated with the above mentioned Ala-Ala-Phe-pNA substrate in a citrate buffer at pH5 and the residual activity in each individual sample was determined by measuring the increase in absorbance at 410 nm. With the 0 degrees C. sample showing 100% activity, the 40 degrees sample showed 96% residual activity, the 50 degrees sample 92% residual activity and the 60 degrees sample 88% residual activity.

In a typical process aimed at producing a hydrolysate with a high proportion of tripeptides, whey protein (WPC 75) may be dissolved/suspended in a concentration of 100 grams of protein/liter, in an aqueous medium having a pH of 8.5. The first enzyme incubation is with the broad spectrum endoprotease subtilisin (Delvolase®, 560 000 DU per gram from DSM). After a predigestion of the whey with this enzyme in a concentration of 0.5% enzyme concentrate per gram of protein for 2 hours at 60 degrees C., the mixture is heat-treated to inactivate the endoprotease used. Then the temperature is adjusted to 50 degrees C. and the tripeptidylpeptidase is added and the whole mixture is incubated until the desired level of tripeptides is reached. Further processing steps of the hydrolysate thus obtained depend on the specific application but may incorporate microfiltration or centrfugation followed by evaporation and spray drying.

The invention claimed is:

1. A isolated polynucleotide that encodes a tripeptidyl peptidase wherein said polynucleotide hybridizes to the full length complement of SEQ ID NO: 9; SEQ ID NO: 10; SEQ ID NO: 12; SEQ ID NO: 35; SEQ ID NO: 50; SEQ ID NO: 66; SEQ ID NO: 67; SEQ ID NO: 69; SEQ ID NO: 92; or SEQ ID NO: 107 under hybridization conditions of 5×SSC, 5× Denhardt's solution, and 1.0% SDS at 68° C. and wash conditions of 0.2×SSC and 0.1% SDS at room temperature.

2. An isolated polynucleotide encoding a tripeptidyl peptidase, which comprises a nucleotide sequence selected from the group consisting of SEQ ID NO: 9; SEQ ID NO: 10; SEQ ID NO: 12; SEQ ID NO: 35; SEQ ID NO: 50; SEQ ID NO: 66; SEQ ID NO: 67; SEQ ID NO: 69, SEQ ID NO: 92; and SEQ ID NO: 107.

3. The isolated polynucleotide of claim 1 obtainable from a filamentous fungus.

4. The isolated polynucleotide of claim 3 obtainable from *Aspergillus niger*.

5. An isolated polynucleotide encoding a polypeptide having tripeptidyl peptidase activity, said polypeptide comprising an amino acid sequence of SEQ ID NO:123; SEQ ID NO:124; SEQ ID NO:126; SEQ ID NO:149; or SEQ ID NO:164.

6. An isolated polynucleotide encoding a polypeptide having tripeptidyl peptidase activity, which is at least 95% identical to SEQ ID NO: 123; SEQ ID NO: 124; SEQ ID NO: 126; SEQ ID NO: 149; or SEQ ID NO: 164.

7. The isolated polynucleotide of claim 1, which hybridizes to the full-length complement of SEQ ID NO: 66; SEQ ID NO: 67; SEQ ID NO: 69; SEQ ID NO: 92; or SEQ ID NO: 107.

8. A vector comprising the polynucleotide sequence of claim 1.

9. The vector of claim 8 wherein said polynucleotide sequence is operatively linked with regulatory sequences suitable for expression of said polynucleotide sequence in a suitable host cell.

10. The vector of claim 9 wherein said suitable host cell is a filamentous fungus.

11. A method to prepare a tripeptidyl peptidase comprising the steps of culturing a host cell comprising the vector of claim 9 and isolating said tripeptidyl peptidase from said host cell.

12. An isolated polypeptide having tripeptidyl peptidase activity, which comprises an amino acid sequence selected from the group consisting of SEQ ID NO:123; SEQ ID NO:124; SEQ ID NO:126; SEQ ID NO:149; and SEQ ID NO:164.

13. An isolated polypeptide obtainable by expressing the polynucleotide of claim 1 in a host cell.

14. An isolated polypeptide having tripeptidyl peptidase activity, which comprises an amino acid sequence at least 95% identical to SEQ ID NO: 123; SEQ ID NO: 124; SEQ ID NO: 126; SEQ ID NO: 149; or SEQ ID NO: 164.

15. An isolated recombinant host cell comprising the vector of claim 9.

16. An isolated recombinant host cell expressing the polypeptide of claim 14.

17. The isolated recombinant host cell of claim 15 wherein said host cell is from an *Aspergillus* species.

18. A fusion protein comprising the amino acid sequence according to claim 14.

19. A fusion protein comprising the amino acid sequence according to claim 12.

20. A vector comprising the polynucleotide sequence of claim 6.

21. The vector of claim 20 wherein said polynucleotide sequence is operatively linked with regulatory sequences suitable for expression of said polynucleotide sequence in a suitable host cell.

22. A method to prepare a tripeptidyl peptidase comprising the steps of culturing a host cell comprising the vector of claim 21 and isolating said tripeptidyl peptidase from said host cell.

23. An isolated recombinant host cell comprising the vector of claim 21.

24. The isolated polynucleotide of claim 6 wherein said polypeptide is at least 98% identical to SEQ ID NO: 123; SEQ ID NO: 124; SEQ ID NO: 126; SEQ ID NO: 149; or SEQ ID NO: 164.

25. The isolated polypeptide of claim 14 wherein said polypeptide comprises an amino acid sequence at least 98% identical to SEQ ID NO: 123; SEQ ID NO: 124; SEQ ID NO: 126; SEQ ID NO: 149; or SEQ ID NO: 164.

* * * * *